United States Patent
Kanouni et al.

(10) Patent No.: US 11,390,618 B2
(45) Date of Patent: *Jul. 19, 2022

(54) INHIBITORS OF CYCLIN-DEPENDENT KINASES

(71) Applicant: Kinnate Biopharma Inc., San Diego, CA (US)

(72) Inventors: Toufike Kanouni, Rancho Santa Fe, CA (US); Lee D. Arnold, Rancho Santa Fe, CA (US); Stephen W. Kaldor, San Diego, CA (US); Eric A. Murphy, San Marcos, CA (US); John Tyhonas, San Diego, CA (US)

(73) Assignee: KINNATE BIOPHARMA INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/095,672

(22) Filed: Nov. 11, 2020

(65) Prior Publication Data

US 2021/0130340 A1    May 6, 2021

Related U.S. Application Data

(63) Continuation of application No. 16/457,400, filed on Jun. 28, 2019, now Pat. No. 10,894,788.

(60) Provisional application No. 62/691,879, filed on Jun. 29, 2018.

(51) Int. Cl.

| | | |
|---|---|---|
| *C07D 403/14* | (2006.01) | |
| *C07D 413/14* | (2006.01) | |
| *C07D 403/12* | (2006.01) | |
| *C07D 405/14* | (2006.01) | |
| *C07D 417/14* | (2006.01) | |
| *C07D 401/14* | (2006.01) | |

(52) U.S. Cl.
CPC ......... *C07D 413/14* (2013.01); *C07D 401/14* (2013.01); *C07D 403/12* (2013.01); *C07D 403/14* (2013.01); *C07D 405/14* (2013.01); *C07D 417/14* (2013.01)

(58) Field of Classification Search
CPC ... C07D 401/14; C07D 403/14; A61K 31/505
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 10,894,788 B2 * | 1/2021 | Kanouni | C07D 413/14 |
| 2007/0004763 A1 | 1/2007 | Baindur et al. | |
| 2014/0309184 A1 | 10/2014 | Rocconi et al. | |
| 2014/0309249 A1 | 10/2014 | Gray et al. | |
| 2015/0087664 A1 | 3/2015 | Blake et al. | |
| 2016/0264552 A1 | 9/2016 | Ciblat et al. | |
| 2020/0024266 A1 | 1/2020 | Kanouni et al. | |
| 2021/0053969 A1 | 2/2021 | Kanouni et al. | |

FOREIGN PATENT DOCUMENTS

| | | |
|---|---|---|
| WO | WO-2015058126 A1 | 4/2015 |
| WO | WO-2015058163 A2 | 4/2015 |
| WO | WO-2015124941 A1 | 8/2015 |
| WO | WO-2016105528 A2 | 6/2016 |
| WO | WO-2016160617 A2 | 10/2016 |
| WO | WO-2016193939 A1 | 12/2016 |
| WO | WO-2016201370 A1 | 12/2016 |
| WO | WO-2016210296 A1 | 12/2016 |
| WO | WO-2017044858 A2 | 3/2017 |
| WO | WO-2017163076 A1 | 9/2017 |
| WO | WO-2018118793 A1 | 6/2018 |
| WO | WO-2019035866 A1 | 2/2019 |
| WO | WO-2019058132 A1 | 3/2019 |
| WO | WO-2019213403 A1 | 11/2019 |
| WO | WO-2020006497 A1 | 1/2020 |
| WO | WO-2021011796 A1 | 1/2021 |
| WO | WO-2021138215 A1 | 7/2021 |

OTHER PUBLICATIONS

Ali et al. The development of a selective cyclin-dependent kinase inhibitor that shows antitumor activity. Cancer Res. 69(15):6208-6215 (2009).
Bajrami et al. Genome-wide profiling of genetic synthetic lethality identifies CDK12 as a novel determinant of PARP1/2 inhibitor sensitivity. Cancer Res. 74(1):287-297 (2014).
Berge et al. Pharmaceutical Salts. Journal of Pharmaceutical Sciences 66(1):1-19 (Jan. 1977).
Berro et al. CDK13, a new potential human immunodeficiency virus type 1 inhibitory factor regulating viral mRNA splicing. J. Virol. 82:7155-7166 (2008).
Brägelmann et al. Systematic Kinase Inhibitor Profiling Identifies CDK9 as a Synthetic Lethal Target in NUT Midline Carcinoma. Cell Rep. 20(12):2833-2845 (2017).
Cancer Genome Atlas Network, Comprehensive molecular portraits of human breast tumours, Nature, 490:61-70 (2012).
Cancer Genome Atlas Research Network, Integrated genomic analyses of ovarian carcinoma, Nature, 474:609-615 (2011).
Cao et al. Phylogenetic analysis of CDK and cyclin proteins in premetazoan lineages. BMC Evol. Biol. 14:10-26 (2014).
Cayrol et al. THZ1 targeting CDK7 suppresses STAT transcriptional activity and sensitizes T-cell lymphomas to BCL2 inhibitors. Nature Commun. 8:14290 (2017).
Cerami et al. The cBio cancer genomics portal: an open platform for exploring multidimensional cancer genomics data. Cancer Discov. 2:401-404 (2012).
Chemical Structure Search. (51 pgs.) (2018).
Chen et al. Cdk12 and Cdk13 regulate axonal elongation through a common signaling pathway that modulates Cdk5 expression. Exp. Neurol. 261:10-21 (2014).

(Continued)

*Primary Examiner* — Deepak R Rao
(74) *Attorney, Agent, or Firm* — Wilson Sonsini Goodrich & Rosati

(57) ABSTRACT

Provided herein are inhibitors of cyclin-dependent kinases (CDKs), pharmaceutical compositions comprising said compounds, and methods for using said compounds for the treatment of diseases.

20 Claims, No Drawings

Specification includes a Sequence Listing.

(56) References Cited

OTHER PUBLICATIONS

Christensen et al. Targeting transcriptional addictions in small cell lung cancer with a covalent CDK7 inhibitor. Cancer Cell 26(6):909-922 (2014).
Coleman et al. Chapter 17. Chemical Inhibitors of Cyclin-dependent Kinases. Annual Reports in Medicinal Chemistry 32:171-179 (1997).
Dey et al. Voruciclib, a clinical stage oral CDK9 inhibitor, represses MCL-1 and sensitizes high-risk Diffuse Large B-cell Lymphoma to BCL2 inhibition. Sci. Rep. 7(1):18007 (2017).
Enke et al. The CDK-activating kinase (Cak1p) from budding yeast has an unusual ATP-binding pocket. J. Biol. Chem. 274(4):1949-1956 (1999).
Evan et al. Re-engineering the Pancreas Tumor Microenvironment: A "Regenerative Program" Hacked. Clin. Cancer Res. 23(7):1647-1655 (2017).
Evans. Synthesis of radiolabeled compounds. J Radioanal Chem 64(1-2):9-32 (1981).
Ficarra et al. Leveraging Gas-Phase Fragmentation Pathways for Improved Identification and Selective Detection of Targets Modified by Covalent Probes. Anal. Chem. 88(24):12248-12254.
Gao et al. Overcoming Resistance to the THZ Series of Covalent Transcriptional CDK Inhibitors. Cell Chem. Biol. 25(2):135-142.
Greenall et al. Cyclin-dependent kinase 7 is a therapeutic target in high-grade glioma. Oncogenesis 6(5):e336 (2017).
Greifenberg et al. Structural and Functional Analysis of the Cdk13/Cyclin K Complex. Cell Rep. 14:320-331 (2016).
Hamilton et al. Heterozygous mutations affecting the protein kinase domain of CDK13 cause a syndromic form of developmental delay and intellectual disability. J. Med. Genet. 55(1):28-38 (2017).
He et al. Cdk7 Is Required for Activity-Dependent Neuronal Gene Expression, Long-Lasting Synaptic Plasticity and Long-Term Memory. Front. Mol. Neurosci. 10:365-377 (2017).
Hong et al. CDK7 inhibition suppresses rheumatoid arthritis inflammation via blockage of NF-κB activation and IL-1 β/IL-6 secretion. J. Cell. Mol. Med. 22:1292-1301 (2017).
Iniguez et al. EWS/FLI Confers Tumor Cell Synthetic Lethality to CDK12 Inhibition in Ewing Sarcoma. Cancer Cell 33(2):202-216 (2018).
Iversen et al. A comparison of assay performance measures in screening assays: signal window, Z' factor, and assay variability ratio. J. Biomol. Screen. 3:247-252 (2006).
Johnson et al. CDK12 Inhibition Reverses De Novo and Acquired PARP Inhibitor Resistance in BRCA Wild-Type and Mutated Models of Triple-Negative Breast Cancer. Cell Rep. 17(9):2367-2381 (2016).
Kabalka et al. The Synthesis of Radiolabeled Compounds via Organometallic Intermediates. Tetrahedron 45(21):6601-6621 (1989).
Kalan et al. Activation of the p53 Transcriptional Program Sensitizes Cancer Cells to Cdk7 Inhibitors. Cell Reports 21(2):467-481 (2017).
Kandoth et al. Mutational landscape and significance across 12 major cancer types. Nature 502(7471):333-339 (2013).
Kwiatkowski et al. Targeting transcription regulation in cancer with a covalent CDK7 inhibitor. Nature 511(7511):616-620 (2014).
Lam et al. Targeting RNA transcription and translation in ovarian cancer cells with pharmacological inhibitor CDKI-73. Oncotarget 5:7691-7704 (2014).
Li et al. Therapeutic Rationale to Target Highly Expressed CDK7 Conferring Poor Outcomes in Triple-Negative Breast Cancer. Cancer Res. 77(14):3834-3845 (2017).
Lim et al. Cdks, cyclins and CKIs: roles beyond cell cycle regulation. Development 140:3079-3093 (2013).
Lucking. Identification of Atuveciclib (BAY 1143572), the First Highly Selective, Clinical PTEFb/CDK9 Inhibitor for the Treatment of Cancer. ChemMedChem. 12(21):1776-1793 (2017).
Malumbres. Cyclin-dependent kinases. Genome Biol. 15(6):122-132 (2014).
Mertins et al. Proteogenomics connects somatic mutations to signalling in breast cancer. Nature 534(7605):55-62 (2016).
Nagaraja et al. Transcriptional Dependencies in Diffuse Intrinsic Pontine Glioma. Cancer Cell31(5):635-652 (2017).
Naidoo et al. Evaluation of CDK12 Protein Expression as a Potential Novel Biomarker for DNA Damage Response-Targeted Therapies in Breast Cancer. Mol. Cancer Ther. 17(1):306-315 (2017).
Paculova et al. The emerging roles ofCDK12 in tumorigenesis. Cell Div. 12 :7-17 (2017).
Pang et al. miR-206 inhibits the growth of hepatocellular carcinoma cells via targeting CDK9. Cancer Med. 6(10):2398-2409 (2017).
PCT/US2019/030409 International Search Report and Written Opinion dated Jul. 2, 2019.
PCT/US2019/039959 International Invitation to Pay Additional Fees dated Aug. 19, 2019.
PCT/US2019/039959 International Search Report and Written Opinion dated Oct. 29, 2019.
PCT/US2020/042371 International Search Report and Written Opinion dated Oct. 16, 2020.
PubChem CID 118976958 https://pubchem.ncbi.nlm.nih.gov/compound/118976958 (2016).
PubChem CID 153314224 https://pubchem.ncbi.nlm.nih.gov/compound/153314224 (2020).
PubChem CID 68429631. Create date Nov. 30, 2012 (7 pgs).
Tien et al. CDK12 regulates alternative last exon mRNA splicing and promotes breast cancer cell invasion. Nucleic Acids Res. 45(11):6698-6716 (2017).
U.S. Appl. No. 16/457,400 Office Action dated Apr. 17, 2020.
U.S. Appl. No. 16/457,400 Office Action dated Nov. 27, 2019.
Zhang et al. A Simple Statistical Parameter for Use in Evaluation and Validation of High Throughput Screening Assays. J. Biomol. Screen. 2:67-73 (1999).
Zhang et al. Covalent targeting of remote cysteine residues to develop CDK12 and CDK13 inhibitors. Nature Chem. Biol. 12(10):876-884 (2016).
PCT/US2020/066967 International Search Report and Written Opinion dated Mar. 15, 2021.
PubChem SID 325943755 [https://pubchem.ncbi.nlm.nih.gov/substance/325943755] (2017).

* cited by examiner

SEQUENCE LISTING

<160> NUMBER OF SEQ ID NOS: 16

<210> SEQ ID NO 1
<211> LENGTH: 1490
<212> TYPE: PRT
<213> ORGANISM: Homo sapiens

<400> SEQUENCE: 1

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Val Ser Ser Lys Ser Gly Ser Met Lys
130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
                180                 185                 190

Gly His Lys Asp Arg Ser Lys Ser His Arg Lys Arg Glu Thr Pro Lys
                195                 200                 205

Ser Tyr Lys Thr Val Asp Ser Pro Lys Arg Arg Ser Arg Ser Pro His
210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
                260                 265                 270

Gln Ser Val Ser Pro Pro Tyr Lys Glu Pro Ser Ala Tyr Gln Ser Ser
                275                 280                 285

Thr Arg Ser Pro Ser Pro Tyr Ser Arg Arg Gln Arg Ser Val Ser Pro
290                 295                 300

Tyr Ser Arg Arg Arg Ser Ser Ser Tyr Glu Arg Ser Gly Ser Tyr Ser
305                 310                 315                 320

Gly Arg Ser Pro Ser Pro Tyr Gly Arg Arg Arg Ser Ser Ser Pro Phe
                325                 330                 335

Leu Ser Lys Arg Ser Leu Ser Arg Ser Pro Leu Pro Ser Arg Lys Ser
                340                 345                 350

Met Lys Ser Arg Ser Arg Ser Pro Ala Tyr Ser Arg His Ser Ser Ser
                355                 360                 365

His Ser Lys Lys Lys Arg Ser Ser Arg Ser Arg His Ser Ser Ile
                370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                405                 410                 415

Gly Lys Glu Ser Lys Gly Ser Pro Val Phe Leu Pro Arg Lys Glu Asn
                420                 425                 430

Ser Ser Val Glu Ala Lys Asp Ser Gly Leu Glu Ser Lys Lys Leu Pro
                435                 440                 445

Arg Ser Val Lys Leu Glu Lys Ser Ala Pro Asp Thr Glu Leu Val Asn
450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

Ala Gln Gly Thr Arg Asp Ser Lys Pro Ile Ala Leu Lys Glu Glu Ile
                500                 505                 510

Val Thr Pro Lys Glu Thr Glu Thr Ser Glu Lys Glu Thr Pro Pro
                515                 520                 525

Leu Pro Thr Ile Ala Ser Pro Pro Pro Leu Pro Thr Thr Thr Pro
530                 535                 540

-continued

```
Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
            565                 570                 575

Pro Ala Ser Ser Thr Ser Thr Leu Pro Pro Ser Thr His Ser Lys Thr
            580                 585                 590

Ser Ala Val Ser Ser Gln Ala Asn Ser Gln Pro Pro Val Gln Val Ser
            595                 600                 605

Val Lys Thr Gln Val Ser Val Thr Ala Ala Ile Pro His Leu Lys Thr
            610                 615                 620

Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
                    645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Asp Ser Pro Glu Pro
            675                 680                 685

Lys Ala Ile Thr Pro Pro Gln Gln Pro Tyr Lys Lys Arg Pro Lys Ile
690                 695                 700

Cys Cys Pro Arg Tyr Gly Glu Arg Gln Thr Glu Ser Asp Trp Gly
705                 710                 715                 720

Lys Arg Cys Val Asp Lys Phe Asp Ile Ile Gly Ile Ile Gly Glu Gly
                725                 730                 735

Thr Tyr Gly Gln Val Tyr Lys Ala Lys Asp Lys Asp Thr Gly Glu Leu
            740                 745                 750

Val Ala Leu Lys Lys Val Arg Leu Asp Asn Glu Lys Glu Gly Phe Pro
755                 760                 765

Ile Thr Ala Ile Arg Glu Ile Lys Ile Leu Arg Gln Leu Ile His Arg
770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
            820                 825                 830

Glu Asp His Ile Lys Ser Phe Met Lys Gln Leu Met Glu Gly Leu Glu
            835                 840                 845

Tyr Cys His Lys Lys Asn Phe Leu His Arg Asp Ile Lys Cys Ser Asn
850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Leu Gly Glu Glu Arg
            900                 905                 910

Tyr Thr Pro Ala Ile Asp Val Trp Ser Cys Gly Cys Ile Leu Gly Glu
            915                 920                 925

Leu Phe Thr Lys Lys Pro Ile Phe Gln Ala Asn Leu Glu Leu Ala Gln
            930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
```

```
                965                 970                 975
Gln Tyr Arg Arg Arg Leu Arg Glu Glu Phe Ser Phe Ile Pro Ser Ala
                980                 985                 990
Ala Leu Asp Leu Leu Asp His Met Leu Thr Leu Asp Pro Ser Lys Arg
                995                1000                1005
Cys Thr Ala Glu Gln Thr Leu Gln Ser Asp Phe Leu Lys Asp Val
   1010                1015                1020
Glu Leu Ser Lys Met Ala Pro Pro Asp Leu Pro His Trp Gln Asp
   1025                1030                1035
Cys His Glu Leu Trp Ser Lys Lys Arg Arg Gln Arg Gln Ser
   1040                1045                1050
Gly Val Val Glu Glu Pro Pro Ser Lys Thr Ser Arg Lys
   1055                1060                1065
Glu Thr Thr Ser Gly Thr Ser Thr Glu Pro Val Lys Asn Ser Ser
   1070                1075                1080
Pro Ala Pro Pro Gln Pro Ala Pro Gly Lys Val Glu Ser Gly Ala
   1085                1090                1095
Gly Asp Ala Ile Gly Leu Ala Asp Ile Thr Gln Gln Leu Asn Gln
   1100                1105                1110
Ser Glu Leu Ala Val Leu Leu Asn Leu Leu Gln Ser Gln Thr Asp
   1115                1120                1125
Leu Ser Ile Pro Gln Met Ala Gln Leu Leu Asn Ile His Ser Asn
   1130                1135                1140
Pro Glu Met Gln Gln Leu Glu Ala Leu Asn Gln Ser Ile Ser
   1145                1150                1155
Ala Leu Thr Glu Ala Thr Ser Gln Gln Gln Asp Ser Glu Thr Met
   1160                1165                1170
Ala Pro Glu Glu Ser Leu Lys Glu Ala Pro Ser Ala Pro Val Ile
   1175                1180                1185
Leu Pro Ser Ala Glu Gln Thr Thr Leu Glu Ala Ser Ser Thr Pro
   1190                1195                1200
Ala Asp Met Gln Asn Ile Leu Ala Val Leu Leu Ser Gln Leu Met
   1205                1210                1215
Lys Thr Gln Glu Pro Ala Gly Ser Leu Glu Glu Asn Asn Ser Asp
   1220                1225                1230
Lys Asn Ser Gly Pro Gln Gly Pro Arg Arg Thr Pro Thr Met Pro
   1235                1240                1245
Gln Glu Glu Ala Ala Ala Cys Pro Pro His Ile Leu Pro Pro Glu
   1250                1255                1260
Lys Arg Pro Pro Glu Pro Pro Gly Pro Pro Pro Pro Pro Pro
   1265                1270                1275
Pro Pro Leu Val Glu Gly Asp Leu Ser Ser Ala Pro Gln Glu Leu
   1280                1285                1290
Asn Pro Ala Val Thr Ala Ala Leu Leu Gln Leu Leu Ser Gln Pro
   1295                1300                1305
Glu Ala Glu Pro Pro Gly His Leu Pro His Glu His Gln Ala Leu
   1310                1315                1320
Arg Pro Met Glu Tyr Ser Thr Arg Pro Arg Pro Asn Arg Thr Tyr
   1325                1330                1335
Gly Asn Thr Asp Gly Pro Glu Thr Gly Phe Ser Ala Ile Asp Thr
   1340                1345                1350
Asp Glu Arg Asn Ser Gly Pro Ala Leu Thr Glu Ser Leu Val Gln
   1355                1360                1365
```

```
Thr Leu Val Lys Asn Arg Thr Phe Ser Gly Ser Leu Ser His Leu
    1370                1375                1380

Gly Glu Ser Ser Ser Tyr Gln Gly Thr Gly Ser Val Gln Phe Pro
    1385                1390                1395

Gly Asp Gln Asp Leu Arg Phe Ala Arg Val Pro Leu Ala Leu His
    1400                1405                1410

Pro Val Val Gly Gln Pro Phe Leu Lys Ala Glu Gly Ser Ser Asn
    1415                1420                1425

Ser Val Val His Ala Glu Thr Lys Leu Gln Asn Tyr Gly Glu Leu
    1430                1435                1440

Gly Pro Gly Thr Thr Gly Ala Ser Ser Gly Ala Gly Leu His
    1445                1450                1455

Trp Gly Gly Pro Thr Gln Ser Ser Ala Tyr Gly Lys Leu Tyr Arg
    1460                1465                1470

Gly Pro Thr Arg Val Pro Pro Arg Gly Gly Arg Gly Arg Gly Val
    1475                1480                1485

Pro Tyr
    1490

<210> SEQ ID NO 2
<211> LENGTH: 1481
<212> TYPE: PRT
<213> ORGANISM: Homo sapiens

<400> SEQUENCE: 2

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
                20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
    210                 215                 220

Arg Lys Trp Ser Asp Ser Ser Lys Gln Asp Asp Ser Pro Ser Gly Ala
```

-continued

```
            225                 230                 235                 240
Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
                260                 265                 270

Gln Ser Val Ser Pro Pro Tyr Lys Glu Pro Ser Ala Tyr Gln Ser Ser
                275                 280                 285

Thr Arg Ser Pro Ser Pro Tyr Ser Arg Arg Gln Arg Ser Val Ser Pro
                290                 295                 300

Tyr Ser Arg Arg Arg Ser Ser Tyr Glu Arg Ser Gly Ser Tyr Ser
305                 310                 315                 320

Gly Arg Ser Pro Ser Pro Tyr Gly Arg Arg Arg Ser Ser Pro Phe
                325                 330                 335

Leu Ser Lys Arg Ser Leu Ser Arg Ser Pro Leu Pro Ser Arg Lys Ser
                340                 345                 350

Met Lys Ser Arg Ser Arg Ser Pro Ala Tyr Ser Arg His Ser Ser Ser
                355                 360                 365

His Ser Lys Lys Lys Arg Ser Ser Arg Ser Arg His Ser Ser Ile
        370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                405                 410                 415

Gly Lys Glu Ser Lys Gly Ser Pro Val Phe Leu Pro Arg Lys Glu Asn
                420                 425                 430

Ser Ser Val Glu Ala Lys Asp Ser Gly Leu Glu Ser Lys Lys Leu Pro
                435                 440                 445

Arg Ser Val Lys Leu Glu Lys Ser Ala Pro Asp Thr Glu Leu Val Asn
                450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

Ala Gln Gly Thr Arg Asp Ser Lys Pro Ile Ala Leu Lys Glu Glu Ile
                500                 505                 510

Val Thr Pro Lys Glu Thr Glu Thr Ser Glu Lys Glu Thr Pro Pro Pro
                515                 520                 525

Leu Pro Thr Ile Ala Ser Pro Pro Pro Leu Pro Thr Thr Pro
                530                 535                 540

Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
                565                 570                 575

Pro Ala Ser Ser Thr Ser Thr Leu Pro Pro Ser Thr His Ser Lys Thr
                580                 585                 590

Ser Ala Val Ser Ser Gln Ala Asn Ser Gln Pro Pro Val Gln Val Ser
                595                 600                 605

Val Lys Thr Gln Val Ser Val Thr Ala Ala Ile Pro His Leu Lys Thr
                610                 615                 620

Ser Thr Leu Pro Pro Leu Pro Leu Pro Leu Leu Pro Gly Asp Asp
625                 630                 635                 640

Asp Met Asp Ser Pro Lys Glu Thr Leu Pro Ser Lys Pro Val Lys Lys
                645                 650                 655
```

```
Glu Lys Glu Gln Arg Thr Arg His Leu Leu Thr Asp Leu Pro Leu Pro
            660                 665                 670

Pro Glu Leu Pro Gly Gly Asp Leu Ser Pro Pro Asp Ser Pro Glu Pro
            675                 680                 685

Lys Ala Ile Thr Pro Pro Gln Gln Pro Tyr Lys Lys Arg Pro Lys Ile
            690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Ile Gly Ile Gly Glu Gly
                725                 730                 735

Thr Tyr Gly Gln Val Tyr Lys Ala Lys Asp Lys Asp Thr Gly Glu Leu
            740                 745                 750

Val Ala Leu Lys Lys Val Arg Leu Asp Asn Glu Lys Glu Gly Phe Pro
755                 760                 765

Ile Thr Ala Ile Arg Glu Ile Lys Ile Leu Arg Gln Leu Ile His Arg
            770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
            820                 825                 830

Glu Asp His Ile Lys Ser Phe Met Lys Gln Leu Met Glu Gly Leu Glu
            835                 840                 845

Tyr Cys His Lys Lys Asn Phe Leu His Arg Asp Ile Lys Cys Ser Asn
            850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Leu Gly Glu Glu Arg
            900                 905                 910

Tyr Thr Pro Ala Ile Asp Val Trp Ser Cys Gly Cys Ile Leu Gly Glu
            915                 920                 925

Leu Phe Thr Lys Lys Pro Ile Phe Gln Ala Asn Leu Glu Leu Ala Gln
            930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
                965                 970                 975

Gln Tyr Arg Arg Arg Leu Arg Glu Glu Phe Ser Phe Ile Pro Ser Ala
            980                 985                 990

Ala Leu Asp Leu Leu Asp His Met Leu Thr Leu Asp Pro Ser Lys Arg
            995                 1000                1005

Cys Thr Ala Glu Gln Thr Leu Gln Ser Asp Phe Leu Lys Asp Val
    1010                1015                1020

Glu Leu Ser Lys Met Ala Pro Pro Asp Leu Pro His Trp Gln Asp
    1025                1030                1035

Cys His Glu Leu Trp Ser Lys Lys Arg Arg Arg Gln Arg Gln Ser
    1040                1045                1050

Gly Val Val Val Glu Glu Pro Pro Pro Ser Lys Thr Ser Arg Lys
    1055                1060                1065
```

```
Glu Thr Thr Ser Gly Thr Ser Thr Glu Pro Val Lys Asn Ser Ser
1070                1075                1080

Pro Ala Pro Pro Gln Pro Ala Pro Gly Lys Val Glu Ser Gly Ala
1085                1090                1095

Gly Asp Ala Ile Gly Leu Ala Asp Ile Thr Gln Gln Leu Asn Gln
1100                1105                1110

Ser Glu Leu Ala Val Leu Leu Asn Leu Leu Gln Ser Gln Thr Asp
1115                1120                1125

Leu Ser Ile Pro Gln Met Ala Gln Leu Leu Asn Ile His Ser Asn
1130                1135                1140

Pro Glu Met Gln Gln Leu Glu Ala Leu Asn Gln Ser Ile Ser
1145                1150                1155

Ala Leu Thr Glu Ala Thr Ser Gln Gln Gln Asp Ser Glu Thr Met
1160                1165                1170

Ala Pro Glu Glu Ser Leu Lys Glu Ala Pro Ser Ala Pro Val Ile
1175                1180                1185

Leu Pro Ser Ala Glu Gln Thr Thr Leu Glu Ala Ser Ser Thr Pro
1190                1195                1200

Ala Asp Met Gln Asn Ile Leu Ala Val Leu Leu Ser Gln Leu Met
1205                1210                1215

Lys Thr Gln Glu Pro Ala Gly Ser Leu Glu Glu Asn Asn Ser Asp
1220                1225                1230

Lys Asn Ser Gly Pro Gln Gly Pro Arg Arg Thr Pro Thr Met Pro
1235                1240                1245

Gln Glu Glu Ala Ala Glu Lys Arg Pro Pro Glu Pro Pro Gly Pro
1250                1255                1260

Pro Pro Pro Pro Pro Pro Pro Leu Val Glu Gly Asp Leu Ser
1265                1270                1275

Ser Ala Pro Gln Glu Leu Asn Pro Ala Val Thr Ala Ala Leu Leu
1280                1285                1290

Gln Leu Leu Ser Gln Pro Glu Ala Glu Pro Pro Gly His Leu Pro
1295                1300                1305

His Glu His Gln Ala Leu Arg Pro Met Glu Tyr Ser Thr Arg Pro
1310                1315                1320

Arg Pro Asn Arg Thr Tyr Gly Asn Thr Asp Gly Pro Glu Thr Gly
1325                1330                1335

Phe Ser Ala Ile Asp Thr Asp Glu Arg Asn Ser Gly Pro Ala Leu
1340                1345                1350

Thr Glu Ser Leu Val Gln Thr Leu Val Lys Asn Arg Thr Phe Ser
1355                1360                1365

Gly Ser Leu Ser His Leu Gly Glu Ser Ser Ser Tyr Gln Gly Thr
1370                1375                1380

Gly Ser Val Gln Phe Pro Gly Asp Gln Asp Leu Arg Phe Ala Arg
1385                1390                1395

Val Pro Leu Ala Leu His Pro Val Val Gly Gln Pro Phe Leu Lys
1400                1405                1410

Ala Glu Gly Ser Ser Asn Ser Val Val His Ala Glu Thr Lys Leu
1415                1420                1425

Gln Asn Tyr Gly Glu Leu Gly Pro Gly Thr Thr Gly Ala Ser Ser
1430                1435                1440

Ser Gly Ala Gly Leu His Trp Gly Gly Pro Thr Gln Ser Ser Ala
1445                1450                1455

Tyr Gly Lys Leu Tyr Arg Gly Pro Thr Arg Val Pro Pro Arg Gly
```

```
                    1460                1465                1470
Gly Arg  Gly Arg Gly Val Pro  Tyr
       1475                1480

<210> SEQ ID NO 3
<211> LENGTH: 1201
<212> TYPE: PRT
<213> ORGANISM: Homo sapiens

<400> SEQUENCE: 3

Met Pro Asn Ser Glu Arg His Gly Gly Lys Lys Asp Gly Ser Gly Gly
1               5                   10                  15

Ala Ser Gly Thr Leu Gln Pro Ser Gly Gly Ser Ser Asn Ser
            20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270

Gln Ser Val Ser Pro Pro Tyr Lys Glu Pro Ser Ala Tyr Gln Ser Ser
        275                 280                 285

Thr Arg Ser Pro Ser Pro Tyr Ser Arg Arg Gln Arg Ser Val Ser Pro
290                 295                 300

Tyr Ser Arg Arg Arg Ser Ser Ser Tyr Glu Arg Ser Gly Ser Tyr Ser
305                 310                 315                 320

Gly Arg Ser Pro Ser Pro Tyr Gly Arg Arg Ser Ser Ser Pro Phe
                325                 330                 335

Leu Ser Lys Arg Ser Leu Ser Arg Ser Pro Leu Pro Arg Lys Ser Met
            340                 345                 350
```

```
Lys Ser Arg Ser Arg Ser Pro Ala Tyr Ser Arg His Ser Ser His
            355                 360                 365
Ser Lys Lys Lys Arg Ser Ser Arg Ser Arg His Ser Ser Ile Ser
    370                 375                 380
Pro Val Arg Leu Pro Leu Asn Ser Ser Leu Gly Ala Glu Leu Ser Arg
385                 390                 395                 400
Lys Lys Lys Glu Arg Ala Ala Ala Ala Ala Ala Lys Met Asp Gly
                405                 410                 415
Lys Glu Ser Lys Gly Ser Pro Val Phe Leu Pro Arg Lys Glu Asn Ser
            420                 425                 430
Ser Val Glu Ala Lys Asp Ser Gly Leu Glu Ser Lys Lys Leu Pro Arg
        435                 440                 445
Ser Val Lys Leu Glu Lys Ser Ala Pro Asp Thr Glu Leu Val Asn Val
    450                 455                 460
Thr His Leu Asn Thr Glu Val Lys Asn Ser Ser Asp Thr Gly Lys Val
465                 470                 475                 480
Lys Leu Asp Glu Asn Ser Glu Lys His Leu Val Lys Asp Leu Lys Ala
                485                 490                 495
Gln Gly Thr Arg Asp Ser Lys Pro Ile Ala Leu Lys Glu Glu Ile Val
            500                 505                 510
Thr Pro Lys Glu Thr Glu Thr Ser Glu Lys Glu Thr Pro Pro Pro Leu
        515                 520                 525
Pro Thr Ile Ala Ser Pro Pro Pro Leu Pro Thr Thr Thr Pro Pro
    530                 535                 540
Pro Gln Thr Pro Pro Leu Pro Pro Leu Pro Ile Pro Ala Leu Pro
545                 550                 555                 560
Gln Gln Pro Pro Leu Pro Pro Ser Gln Pro Ala Phe Ser Gln Val Pro
                565                 570                 575
Ala Ser Ser Thr Ser Thr Leu Pro Pro Ser Thr His Ser Lys Thr Ser
            580                 585                 590
Ala Val Ser Ser Gln Ala Asn Ser Gln Pro Pro Val Gln Val Ser Val
        595                 600                 605
Lys Thr Gln Val Ser Val Thr Ala Ala Ile Pro His Leu Lys Thr Ser
    610                 615                 620
Thr Leu Pro Pro Leu Pro Leu Pro Leu Leu Pro Gly Asp Asp Asp
625                 630                 635                 640
Met Asp Ser Pro Lys Glu Thr Leu Pro Ser Lys Pro Val Lys Lys Glu
                645                 650                 655
Lys Glu Gln Arg Thr Arg His Leu Leu Thr Asp Leu Pro Leu Pro Pro
            660                 665                 670
Glu Leu Pro Gly Gly Asp Leu Ser Pro Asp Ser Pro Glu Pro Lys
        675                 680                 685
Ala Ile Thr Pro Pro Gln Gln Pro Tyr Lys Lys Arg Pro Lys Ile Cys
    690                 695                 700
Cys Pro Arg Tyr Gly Glu Arg Arg Gln Thr Glu Ser Asp Trp Gly Lys
705                 710                 715                 720
Arg Cys Val Asp Lys Phe Asp Ile Ile Gly Ile Ile Gly Glu Gly Thr
                725                 730                 735
Tyr Gly Gln Val Tyr Lys Ala Lys Asp Lys Asp Thr Gly Glu Leu Val
            740                 745                 750
Ala Leu Lys Lys Val Arg Leu Asp Asn Glu Lys Glu Gly Phe Pro Ile
        755                 760                 765
Thr Ala Ile Arg Glu Ile Lys Ile Leu Arg Gln Leu Ile His Arg Ser
```

```
                770              775              780
Val Val Asn Met Lys Glu Ile Val Thr Asp Lys Gln Asp Ala Leu Asp
785              790              795              800
Phe Lys Lys Asp Lys Gly Ala Phe Tyr Leu Val Phe Glu Tyr Met Asp
             805              810              815
His Asp Leu Met Gly Leu Leu Glu Ser Gly Leu Val His Phe Ser Glu
             820              825              830
Asp His Ile Lys Ser Phe Met Lys Gln Leu Met Glu Gly Leu Glu Tyr
             835              840              845
Cys His Lys Lys Asn Phe Leu His Arg Asp Ile Lys Cys Ser Asn Ile
             850              855              860
Leu Leu Asn Asn Ser Gly Gln Ile Lys Leu Ala Asp Phe Gly Leu Ala
865              870              875              880
Arg Leu Tyr Asn Ser Glu Glu Ser Arg Pro Tyr Thr Asn Lys Val Ile
             885              890              895
Thr Leu Trp Tyr Arg Pro Pro Glu Leu Leu Gly Glu Arg Tyr
             900              905              910
Thr Pro Ala Ile Asp Val Trp Ser Cys Gly Cys Ile Leu Gly Glu Leu
             915              920              925
Phe Thr Lys Lys Pro Ile Phe Gln Ala Asn Leu Glu Leu Ala Gln Leu
             930              935              940
Glu Leu Ile Ser Arg Leu Cys Gly Ser Pro Cys Pro Ala Val Trp Pro
945              950              955              960
Asp Val Ile Lys Leu Pro Tyr Phe Asn Thr Met Lys Pro Lys Lys Gln
             965              970              975
Tyr Arg Arg Arg Leu Arg Glu Glu Phe Ser Phe Ile Pro Ser Ala Ala
             980              985              990
Leu Asp Leu Leu Asp His Met Leu Thr Leu Asp Pro Ser Lys Arg Cys
             995             1000             1005
Thr Ala Glu Gln Thr Leu Gln Ser Asp Phe Leu Lys Asp Val Glu
            1010             1015             1020
Leu Ser Lys Met Ala Pro Pro Asp Leu Pro His Trp Gln Asp Cys
            1025             1030             1035
His Glu Leu Trp Ser Lys Lys Arg Arg Arg Gln Arg Gln Ser Gly
            1040             1045             1050
Val Val Val Glu Glu Pro Pro Ser Lys Thr Ser Arg Lys Glu
            1055             1060             1065
Thr Thr Ser Gly Thr Ser Thr Glu Pro Val Lys Asn Ser Ser Pro
            1070             1075             1080
Ala Pro Pro Gln Pro Ala Pro Gly Lys Val Glu Ser Gly Ala Gly
            1085             1090             1095
Asp Ala Ile Gly Leu Ala Asp Ile Thr Gln Gln Leu Asn Gln Ser
            1100             1105             1110
Glu Leu Ala Val Leu Leu Asn Leu Leu Gln Ser Gln Thr Asp Leu
            1115             1120             1125
Ser Ile Pro Gln Met Ala Gln Leu Leu Asn Ile His Ser Asn Pro
            1130             1135             1140
Glu Met Gln Gln Gln Leu Glu Ala Leu Asn Gln Ser Ile Ser Ala
            1145             1150             1155
Leu Thr Glu Ala Thr Ser Gln Gln Gln Asp Ser Glu Thr Met Ala
            1160             1165             1170
Pro Glu Glu Ser Leu Lys Glu Ala Pro Ser Ala Pro Val Ile Leu
            1175             1180             1185
```

```
Pro Ser Ala Glu Gln Thr Thr Leu Glu Ala Ser Ser Thr
    1190                1195                1200

<210> SEQ ID NO 4
<211> LENGTH: 159
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid

<400> SEQUENCE: 4

Xaa Ala Asp Ile Thr Gln Gln Leu Asn Gln Ser Glu Leu Ala Val Leu
1               5                   10                  15

Leu Asn Leu Leu Gln Ser Gln Thr Asp Leu Ser Ile Pro Gln Met Ala
            20                  25                  30

Gln Leu Leu Asn Ile His Ser Asn Pro Glu Met Gln Gln Gln Leu Glu
        35                  40                  45

Ala Leu Asn Gln Ser Ile Ser Ala Leu Thr Glu Ala Thr Ser Gln Gln
    50                  55                  60

Gln Asp Ser Glu Thr Met Ala Pro Glu Glu Ser Leu Lys Glu Ala Pro
65                  70                  75                  80

Ser Ala Pro Val Ile Leu Pro Ser Ala Glu Gln Thr Thr Leu Glu Ala
                85                  90                  95

Ser Ser Thr Pro Ala Asp Met Gln Asn Ile Leu Ala Val Leu Leu Ser
            100                 105                 110

Gln Leu Met Lys Thr Gln Glu Pro Ala Gly Ser Leu Glu Glu Asn Asn
        115                 120                 125

Ser Asp Lys Asn Ser Gly Pro Gln Gly Pro Arg Arg Thr Pro Thr Met
    130                 135                 140

Pro Gln Glu Glu Ala Ala Gly Arg Ser Asn Gly Gly Asn Ala Leu
145                 150                 155

<210> SEQ ID NO 5
<211> LENGTH: 1490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Pro Asn Ser Glu Arg His Gly Gly Lys Asp Gly Ser Gly Gly
1               5                   10                  15

Ala Ser Gly Thr Leu Gln Pro Ser Ser Gly Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
```

-continued

```
            115                 120                 125
Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
                180                 185                 190

Gly His Lys Asp Arg Ser Lys Ser His Arg Lys Arg Glu Thr Pro Lys
                195                 200                 205

Ser Tyr Lys Thr Val Asp Ser Pro Lys Arg Ser Arg Ser Pro His
    210                 215                 220

Arg Lys Trp Ser Asp Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
                260                 265                 270

Gln Ser Val Ser Pro Pro Tyr Lys Glu Pro Ser Ala Tyr Gln Ser Ser
                275                 280                 285

Thr Arg Ser Pro Ser Pro Tyr Ser Arg Arg Gln Arg Ser Val Ser Pro
    290                 295                 300

Tyr Ser Arg Arg Arg Ser Ser Tyr Glu Arg Ser Gly Ser Tyr Ser
305                 310                 315                 320

Gly Arg Ser Pro Ser Pro Tyr Gly Arg Arg Ser Ser Pro Phe
                325                 330                 335

Leu Ser Lys Arg Ser Leu Ser Arg Ser Pro Leu Pro Ser Arg Lys Ser
                340                 345                 350

Met Lys Ser Arg Ser Arg Ser Pro Ala Tyr Ser Arg His Ser Ser Ser
                355                 360                 365

His Ser Lys Lys Lys Arg Ser Ser Arg Ser Arg His Ser Ser Ile
    370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Lys Met Asp
                405                 410                 415

Gly Lys Glu Ser Lys Gly Ser Pro Val Phe Leu Pro Arg Lys Glu Asn
                420                 425                 430

Ser Ser Val Glu Ala Lys Asp Ser Gly Leu Glu Ser Lys Lys Leu Pro
                435                 440                 445

Arg Ser Val Lys Leu Glu Lys Ser Ala Pro Asp Thr Glu Leu Val Asn
    450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

Ala Gln Gly Thr Arg Asp Ser Lys Pro Ile Ala Leu Lys Glu Glu Ile
                500                 505                 510

Val Thr Pro Lys Glu Thr Glu Thr Ser Glu Lys Glu Thr Pro Pro Pro
                515                 520                 525

Leu Pro Thr Ile Ala Ser Pro Pro Pro Leu Pro Thr Thr Pro
                530                 535                 540
```

```
Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
                565                 570                 575

Pro Ala Ser Ser Thr Ser Thr Leu Pro Pro Ser Thr His Ser Lys Thr
            580                 585                 590

Ser Ala Val Ser Ser Gln Ala Asn Ser Gln Pro Pro Val Gln Val Ser
        595                 600                 605

Val Lys Thr Gln Val Ser Val Thr Ala Ala Ile Pro His Leu Lys Thr
    610                 615                 620

Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
                645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Pro Asp Ser Pro Glu Pro
            675                 680                 685

Lys Ala Ile Thr Pro Pro Gln Gln Pro Tyr Lys Lys Arg Pro Lys Ile
            690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Ile Gly Ile Gly Glu Gly
                725                 730                 735

Thr Tyr Gly Gln Val Tyr Lys Ala Lys Asp Lys Asp Thr Gly Glu Leu
            740                 745                 750

Val Ala Leu Lys Lys Val Arg Leu Asp Asn Glu Lys Glu Gly Phe Pro
            755                 760                 765

Ile Thr Ala Ile Arg Glu Ile Lys Ile Leu Arg Gln Leu Ile His Arg
    770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
            820                 825                 830

Glu Asp His Ile Lys Ser Phe Met Lys Gln Leu Met Glu Gly Leu Glu
        835                 840                 845

Tyr Cys His Lys Lys Asn Phe Leu His Arg Asp Ile Lys Cys Ser Asn
    850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Leu Gly Glu Glu Arg
                900                 905                 910

Tyr Thr Pro Ala Ile Asp Val Trp Ser Cys Gly Cys Ile Leu Gly Glu
            915                 920                 925

Leu Phe Thr Lys Lys Pro Ile Phe Gln Ala Asn Leu Glu Leu Ala Gln
            930                 935                 940

Leu Glu Leu Ile Ser Arg Leu Cys Gly Ser Pro Cys Pro Ala Val Trp
945                 950                 955                 960
```

```
Pro Asp Val Ile Lys Leu Pro Tyr Phe Asn Thr Met Lys Pro Lys Lys
            965                 970                 975

Gln Tyr Arg Arg Arg Leu Arg Glu Glu Phe Ser Phe Ile Pro Ser Ala
            980                 985                 990

Ala Leu Asp Leu Leu Asp His Met Leu Thr Leu Asp Pro Ser Lys Arg
        995                 1000                1005

Cys Thr Ala Glu Gln Thr Leu Gln Ser Asp Phe Leu Lys Asp Val
    1010                1015                1020

Glu Leu Ser Lys Met Ala Pro Pro Asp Leu Pro His Trp Gln Asp
    1025                1030                1035

Cys His Glu Leu Trp Ser Lys Lys Arg Arg Arg Gln Arg Gln Ser
    1040                1045                1050

Gly Val Val Val Glu Glu Pro Pro Pro Ser Lys Thr Ser Arg Lys
    1055                1060                1065

Glu Thr Thr Ser Gly Thr Ser Thr Glu Pro Val Lys Asn Ser Ser
    1070                1075                1080

Pro Ala Pro Pro Gln Pro Ala Pro Gly Lys Val Glu Ser Gly Ala
    1085                1090                1095

Gly Asp Ala Ile Gly Leu Ala Asp Ile Thr Gln Gln Leu Asn Gln
    1100                1105                1110

Ser Glu Leu Ala Val Leu Leu Asn Leu Leu Gln Ser Gln Thr Asp
    1115                1120                1125

Leu Ser Val Pro Gln Met Ala Gln Leu Leu Asn Ile His Ser Asn
    1130                1135                1140

Pro Glu Met Gln Gln Gln Leu Glu Ala Leu Asn Gln Ser Ile Ser
    1145                1150                1155

Ala Leu Thr Glu Ala Thr Ser Gln Gln Gln Asp Ser Glu Thr Met
    1160                1165                1170

Ala Pro Glu Glu Ser Leu Lys Glu Ala Pro Ser Ala Pro Val Ile
    1175                1180                1185

Leu Pro Ser Ala Glu Gln Thr Thr Leu Glu Ala Ser Ser Thr Pro
    1190                1195                1200

Ala Asp Met Gln Asn Ile Leu Ala Val Leu Leu Ser Gln Leu Met
    1205                1210                1215

Lys Thr Gln Glu Pro Ala Gly Ser Leu Glu Glu Asn Asn Ser Asp
    1220                1225                1230

Lys Asn Ser Gly Pro Gln Gly Pro Arg Arg Thr Pro Thr Met Pro
    1235                1240                1245

Gln Glu Glu Ala Ala Ala Cys Pro Pro His Ile Leu Pro Pro Glu
    1250                1255                1260

Lys Arg Pro Pro Glu Pro Pro Gly Pro Pro Pro Pro Pro Pro Pro
    1265                1270                1275

Pro Pro Leu Val Glu Gly Asp Leu Ser Ser Ala Pro Gln Glu Leu
    1280                1285                1290

Asn Pro Ala Val Thr Ala Ala Leu Leu Gln Leu Leu Ser Gln Pro
    1295                1300                1305

Glu Ala Glu Pro Pro Gly His Leu Pro His Glu His Gln Ala Leu
    1310                1315                1320

Arg Pro Met Glu Tyr Ser Thr Arg Pro Arg Pro Asn Arg Thr Tyr
    1325                1330                1335

Gly Asn Thr Asp Gly Pro Glu Thr Gly Phe Ser Ala Ile Asp Thr
    1340                1345                1350

Asp Glu Arg Asn Ser Gly Pro Ala Leu Thr Glu Ser Leu Val Gln
```

```
                    1355                1360                1365

Thr Leu Val Lys Asn Arg Thr Phe Ser Gly Ser Leu Ser His Leu
                1370                1375                1380

Gly Glu Ser Ser Ser Tyr Gln Gly Thr Gly Ser Val Gln Phe Pro
            1385                1390                1395

Gly Asp Gln Asp Leu Arg Phe Ala Arg Val Pro Leu Ala Leu His
        1400                1405                1410

Pro Val Val Gly Gln Pro Phe Leu Lys Ala Glu Gly Ser Ser Asn
    1415                1420                1425

Ser Val Val His Ala Glu Thr Lys Leu Gln Asn Tyr Gly Glu Leu
1430                1435                1440

Gly Pro Gly Thr Thr Gly Ala Ser Ser Ser Gly Ala Gly Leu His
    1445                1450                1455

Trp Gly Gly Pro Thr Gln Ser Ser Ala Tyr Gly Lys Leu Tyr Arg
    1460                1465                1470

Gly Pro Thr Arg Val Pro Pro Arg Gly Gly Arg Gly Arg Gly Val
    1475                1480                1485

Pro Tyr
    1490

<210> SEQ ID NO 6
<211> LENGTH: 1490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
                20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205
```

-continued

```
Ser Tyr Lys Thr Val Asp Ser Pro Lys Arg Arg Ser Arg Ser Pro His
    210                 215                 220
Arg Lys Trp Ser Asp Ser Lys Gln Asp Asp Ser Pro Ser Gly Ala
225                 230                 235                 240
Ser Tyr Gly Gln Asp Tyr Asp Leu Ser Pro Ser Arg Ser His Thr Ser
                245                 250                 255
Ser Asn Tyr Asp Ser Tyr Lys Lys Ser Pro Gly Ser Thr Ser Arg Arg
            260                 265                 270
Gln Ser Val Ser Pro Tyr Lys Glu Pro Ser Ala Tyr Gln Ser Ser
        275                 280                 285
Thr Arg Ser Pro Ser Pro Tyr Ser Arg Arg Gln Arg Ser Val Ser Pro
    290                 295                 300
Tyr Ser Arg Arg Ser Ser Tyr Glu Arg Ser Gly Ser Tyr Ser
305                 310                 315                 320
Gly Arg Ser Pro Ser Pro Tyr Gly Arg Arg Ser Ser Pro Phe
                325                 330                 335
Leu Ser Lys Arg Ser Leu Ser Arg Ser Pro Leu Pro Ser Arg Lys Ser
            340                 345                 350
Met Lys Ser Arg Ser Arg Ser Pro Ala Tyr Ser Arg His Ser Ser Ser
        355                 360                 365
His Ser Lys Lys Lys Arg Ser Ser Arg Ser Arg His Ser Ser Ile
    370                 375                 380
Ser Pro Val Arg Leu Pro Leu Asn Ser Ser Leu Gly Ala Glu Leu Ser
385                 390                 395                 400
Arg Lys Lys Lys Glu Arg Ala Ala Ala Ala Ala Ala Lys Met Asp
                405                 410                 415
Gly Lys Glu Ser Lys Gly Ser Pro Val Phe Leu Pro Arg Lys Glu Asn
            420                 425                 430
Ser Ser Val Glu Ala Lys Asp Ser Gly Leu Glu Ser Lys Lys Leu Pro
        435                 440                 445
Arg Ser Val Lys Leu Glu Lys Ser Ala Pro Asp Thr Glu Leu Val Asn
    450                 455                 460
Val Thr His Leu Asn Thr Glu Val Lys Asn Ser Ser Asp Thr Gly Lys
465                 470                 475                 480
Val Lys Leu Asp Glu Asn Ser Glu Lys His Leu Val Lys Asp Leu Lys
                485                 490                 495
Ala Gln Gly Thr Arg Asp Ser Lys Pro Ile Ala Leu Lys Glu Glu Ile
            500                 505                 510
Val Thr Pro Lys Glu Thr Glu Thr Ser Glu Lys Glu Thr Pro Pro
        515                 520                 525
Leu Pro Thr Ile Ala Ser Pro Pro Pro Leu Pro Thr Thr Thr Pro
    530                 535                 540
Pro Pro Gln Thr Pro Pro Leu Pro Pro Leu Pro Ile Pro Ala Leu
545                 550                 555                 560
Pro Gln Gln Pro Pro Leu Pro Pro Ser Gln Pro Ala Phe Ser Gln Val
                565                 570                 575
Pro Ala Ser Ser Thr Ser Thr Leu Pro Pro Ser Thr His Ser Lys Thr
            580                 585                 590
Ser Ala Val Ser Ser Gln Ala Asn Ser Gln Pro Val Gln Val Ser
        595                 600                 605
Val Lys Thr Gln Val Ser Val Thr Ala Ala Ile Pro His Leu Lys Thr
    610                 615                 620
Ser Thr Leu Pro Pro Leu Pro Leu Pro Pro Leu Leu Pro Gly Asp Asp
```

-continued

```
            625                 630                 635                 640
Asp Met Asp Ser Pro Lys Glu Thr Leu Pro Ser Lys Pro Val Lys Lys
                645                 650                 655
Glu Lys Glu Gln Arg Thr Arg His Leu Leu Thr Asp Leu Pro Leu Pro
                660                 665                 670
Pro Glu Leu Pro Gly Gly Asp Leu Ser Pro Pro Asp Ser Pro Glu Pro
                675                 680                 685
Lys Ala Ile Thr Pro Pro Gln Gln Pro Tyr Lys Lys Arg Pro Lys Ile
                690                 695                 700
Cys Cys Pro Arg Tyr Gly Glu Arg Arg Gln Thr Glu Ser Asp Trp Gly
705                 710                 715                 720
Lys Arg Cys Val Asp Lys Phe Asp Ile Ile Gly Ile Ile Gly Glu Gly
                725                 730                 735
Thr Tyr Gly Gln Val Tyr Lys Ala Lys Asp Lys Asp Thr Gly Glu Leu
                740                 745                 750
Val Ala Leu Lys Lys Val Arg Leu Asp Asn Glu Lys Glu Gly Phe Pro
                755                 760                 765
Ile Thr Ala Ile Arg Glu Ile Lys Ile Leu Arg Gln Leu Ile His Arg
                770                 775                 780
Ser Val Val Asn Met Lys Glu Ile Val Thr Asp Lys Gln Asp Ala Leu
785                 790                 795                 800
Asp Phe Lys Lys Asp Lys Gly Ala Phe Tyr Leu Val Phe Glu Tyr Met
                805                 810                 815
Asp His Asp Leu Met Gly Leu Leu Glu Ser Gly Leu Val His Phe Ser
                820                 825                 830
Glu Asp His Ile Lys Ser Phe Met Lys Gln Leu Met Glu Gly Leu Glu
                835                 840                 845
Tyr Cys His Lys Lys Asn Phe Leu His Arg Asp Ile Lys Cys Ser Asn
                850                 855                 860
Ile Leu Leu Asn Asn Ser Gly Gln Ile Lys Leu Ala Asp Phe Gly Leu
865                 870                 875                 880
Ala Arg Leu Tyr Asn Ser Glu Glu Ser Arg Pro Tyr Thr Asn Lys Val
                885                 890                 895
Ile Thr Leu Trp Tyr Arg Pro Pro Glu Leu Leu Leu Gly Glu Glu Arg
                900                 905                 910
Tyr Thr Pro Ala Ile Asp Val Trp Ser Cys Gly Cys Ile Leu Gly Glu
                915                 920                 925
Leu Phe Thr Lys Lys Pro Ile Phe Gln Ala Asn Leu Glu Leu Ala Gln
930                 935                 940
Leu Glu Leu Ile Ser Arg Leu Cys Gly Ser Pro Cys Pro Ala Val Trp
945                 950                 955                 960
Pro Asp Val Ile Lys Leu Pro Tyr Phe Asn Thr Met Lys Pro Lys Lys
                965                 970                 975
Gln Tyr Arg Arg Arg Leu Arg Glu Glu Phe Ser Phe Ile Pro Ser Ala
                980                 985                 990
Ala Leu Asp Leu Leu Asp His Met Leu Thr Leu Asp Pro Ser Lys Arg
                995                 1000                1005
Cys Thr Ala Glu Gln Thr Leu Gln Ser Asp Phe Leu Lys Asp Val
                1010                1015                1020
Glu Leu Ser Lys Met Ala Pro Pro Asp Leu Pro His Trp Gln Asp
                1025                1030                1035
Cys His Glu Leu Trp Ser Lys Lys Arg Arg Arg Gln Arg Gln Ser
                1040                1045                1050
```

```
Gly Val Val Val Glu Glu Pro Pro Ser Lys Thr Ser Arg Lys
    1055                1060                1065

Glu Thr Thr Ser Gly Thr Ser Thr Glu Pro Val Lys Asn Ser Ser
    1070                1075                1080

Pro Ala Pro Pro Gln Pro Ala Pro Gly Lys Val Glu Ser Gly Ala
    1085                1090                1095

Gly Asp Ala Ile Gly Leu Ala Asp Ile Thr Gln Gln Leu Asn Gln
    1100                1105                1110

Ser Glu Leu Ala Val Leu Leu Asn Leu Leu Gln Ser Gln Thr Asp
    1115                1120                1125

Leu Ser Ile Pro Gln Met Ala Gln Leu Leu Asn Ile His Ser Asn
    1130                1135                1140

Pro Glu Met Gln Gln Leu Glu Ala Leu Asn Gln Ser Ile Ser
    1145                1150                1155

Ala Leu Thr Glu Ala Thr Ser Gln Gln Gln Asp Ser Glu Thr Met
    1160                1165                1170

Ala Pro Glu Glu Ser Leu Lys Glu Ala Pro Ser Ala Pro Val Ile
    1175                1180                1185

Gln Pro Ser Ala Glu Gln Thr Thr Leu Glu Ala Ser Ser Thr Pro
    1190                1195                1200

Ala Asp Met Gln Asn Ile Leu Ala Val Leu Leu Ser Gln Leu Met
    1205                1210                1215

Lys Thr Gln Glu Pro Ala Gly Ser Leu Glu Glu Asn Asn Ser Asp
    1220                1225                1230

Lys Asn Ser Gly Pro Gln Gly Pro Arg Arg Thr Pro Thr Met Pro
    1235                1240                1245

Gln Glu Glu Ala Ala Ala Cys Pro Pro His Ile Leu Pro Pro Glu
    1250                1255                1260

Lys Arg Pro Pro Glu Pro Pro Gly Pro Pro Pro Pro Pro Pro Pro
    1265                1270                1275

Pro Pro Leu Val Glu Gly Asp Leu Ser Ser Ala Pro Gln Glu Leu
    1280                1285                1290

Asn Pro Ala Val Thr Ala Ala Leu Leu Gln Leu Leu Ser Gln Pro
    1295                1300                1305

Glu Ala Glu Pro Pro Gly His Leu Pro His Glu His Gln Ala Leu
    1310                1315                1320

Arg Pro Met Glu Tyr Ser Thr Arg Pro Arg Pro Asn Arg Thr Tyr
    1325                1330                1335

Gly Asn Thr Asp Gly Pro Glu Thr Gly Phe Ser Ala Ile Asp Thr
    1340                1345                1350

Asp Glu Arg Asn Ser Gly Pro Ala Leu Thr Glu Ser Leu Val Gln
    1355                1360                1365

Thr Leu Val Lys Asn Arg Thr Phe Ser Gly Ser Leu Ser His Leu
    1370                1375                1380

Gly Glu Ser Ser Ser Tyr Gln Gly Thr Gly Ser Val Gln Phe Pro
    1385                1390                1395

Gly Asp Gln Asp Leu Arg Phe Ala Arg Val Pro Leu Ala Leu His
    1400                1405                1410

Pro Val Val Gly Gln Pro Phe Leu Lys Ala Glu Gly Ser Ser Asn
    1415                1420                1425

Ser Val Val His Ala Glu Thr Lys Leu Gln Asn Tyr Gly Glu Leu
    1430                1435                1440
```

-continued

```
Gly Pro Gly Thr Thr Gly Ala Ser Ser Ser Gly Ala Gly Leu His
    1445              1450                1455

Trp Gly Gly Pro Thr Gln Ser Ser Ala Tyr Gly Lys Leu Tyr Arg
1460                 1465                1470

Gly Pro Thr Arg Val Pro Pro Arg Gly Gly Arg Gly Arg Gly Val
    1475                1480                1485

Pro Tyr
    1490

<210> SEQ ID NO 7
<211> LENGTH: 1490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
    210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270

Gln Ser Val Ser Pro Pro Tyr Lys Glu Pro Ser Ala Tyr Gln Ser Ser
        275                 280                 285

Thr Arg Ser Pro Ser Pro Tyr Ser Arg Arg Gln Arg Ser Val Ser Pro
    290                 295                 300
```

```
Tyr Ser Arg Arg Arg Ser Ser Tyr Glu Arg Ser Gly Tyr Ser
305                 310                 315                 320

Gly Arg Ser Pro Ser Pro Tyr Gly Arg Arg Ser Ser Pro Phe
                325                 330                 335

Leu Ser Lys Arg Ser Leu Ser Arg Ser Pro Leu Pro Ser Arg Lys Ser
                340                 345                 350

Met Lys Ser Arg Ser Arg Ser Pro Ala Tyr Ser Arg His Ser Ser Ser
                355                 360                 365

His Ser Lys Lys Lys Arg Ser Ser Arg Ser Arg His Ser Ser Ile
    370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                405                 410                 415

Gly Lys Glu Ser Lys Gly Ser Pro Val Phe Leu Pro Arg Lys Glu Asn
                420                 425                 430

Ser Ser Val Glu Ala Lys Asp Ser Gly Leu Glu Ser Lys Lys Leu Pro
                435                 440                 445

Arg Ser Val Lys Leu Glu Lys Ser Ala Pro Asp Thr Glu Leu Val Asn
450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

Ala Gln Gly Thr Arg Asp Ser Lys Pro Ile Ala Leu Lys Glu Glu Ile
                500                 505                 510

Val Thr Pro Lys Glu Thr Glu Thr Ser Glu Lys Glu Thr Pro Pro Pro
                515                 520                 525

Leu Pro Thr Ile Ala Ser Pro Pro Pro Leu Pro Thr Thr Thr Pro
530                 535                 540

Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
                565                 570                 575

Pro Ala Ser Ser Thr Ser Thr Leu Pro Pro Ser Thr His Ser Lys Thr
                580                 585                 590

Ser Ala Val Ser Ser Gln Ala Asn Ser Gln Pro Pro Val Gln Val Ser
                595                 600                 605

Val Lys Thr Gln Val Ser Val Thr Ala Ala Ile Pro His Leu Lys Thr
                610                 615                 620

Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
                645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Asp Ser Pro Glu Pro
                675                 680                 685

Lys Ala Ile Thr Pro Pro Gln Gln Pro Tyr Lys Lys Arg Pro Lys Ile
                690                 695                 700

Cys Cys Pro Arg Tyr Gly Glu Arg Arg Gln Thr Glu Ser Asp Trp Gly
705                 710                 715                 720
```

-continued

```
Lys Arg Cys Val Asp Lys Phe Asp Ile Ile Gly Ile Ile Gly Glu Gly
                    725                 730                 735

Thr Tyr Gly Gln Val Tyr Lys Ala Lys Asp Lys Asp Thr Gly Glu Leu
                740                 745                 750

Val Ala Leu Lys Lys Val Arg Leu Asp Asn Glu Lys Glu Gly Phe Pro
            755                 760                 765

Ile Thr Ala Ile Arg Glu Ile Lys Ile Leu Arg Gln Leu Ile His Arg
        770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
                820                 825                 830

Glu Asp His Ile Lys Ser Phe Met Lys Gln Leu Met Glu Gly Leu Glu
                835                 840                 845

Tyr Cys His Lys Lys Asn Phe Leu His Arg Asp Ile Lys Cys Ser Asn
            850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Leu Gly Glu Glu Arg
                900                 905                 910

Tyr Thr Pro Ala Ile Asp Val Trp Ser Cys Gly Cys Ile Leu Gly Glu
            915                 920                 925

Leu Phe Thr Lys Lys Pro Ile Phe Gln Ala Asn Leu Glu Leu Ala Gln
        930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
                965                 970                 975

Gln Tyr Arg Arg Arg Leu Arg Glu Glu Phe Ser Phe Ile Pro Ser Ala
            980                 985                 990

Ala Leu Asp Leu Leu Asp His Met Leu Thr Leu Asp Pro Ser Lys Arg
        995                 1000                1005

Cys Thr Ala Glu Gln Thr Leu Gln Ser Asp Phe Leu Lys Asp Val
    1010                1015                1020

Glu Leu Ser Lys Met Ala Pro Pro Asp Leu Pro His Trp Gln Asp
    1025                1030                1035

Cys His Glu Leu Trp Ser Lys Lys Arg Arg Arg Gln Arg Gln Ser
    1040                1045                1050

Gly Val Val Val Glu Glu Pro Pro Pro Ser Lys Thr Ser Arg Lys
    1055                1060                1065

Glu Thr Thr Ser Gly Thr Ser Thr Glu Pro Val Lys Asn Ser Ser
    1070                1075                1080

Pro Ala Pro Pro Gln Pro Ala Pro Gly Lys Val Glu Ser Gly Ala
    1085                1090                1095

Gly Asp Ala Ile Gly Leu Ala Asp Ile Thr Gln Gln Leu Asn Gln
    1100                1105                1110

Ser Glu Leu Ala Val Leu Leu Asn Leu Leu Gln Ser Gln Thr Asp
    1115                1120                1125

Leu Ser Ile Pro Gln Met Ala Gln Leu Leu Asn Ile His Ser Asn
```

```
                    1130                1135                1140

Pro  Glu  Met  Gln  Gln  Gln  Leu  Glu  Ala  Leu  Asn  Gln  Ser  Ile  Ser
     1145                1150                1155

Ala  Leu  Thr  Glu  Ala  Thr  Ser  Gln  Gln  Gln  Asp  Ser  Glu  Thr  Met
     1160                1165                1170

Ala  Pro  Glu  Glu  Ser  Leu  Lys  Glu  Ala  Pro  Ser  Ala  Pro  Val  Ile
     1175                1180                1185

Leu  Pro  Ser  Ala  Glu  Gln  Met  Thr  Leu  Glu  Ala  Ser  Ser  Thr  Pro
     1190                1195                1200

Ala  Asp  Met  Gln  Asn  Ile  Leu  Ala  Val  Leu  Leu  Ser  Gln  Leu  Met
     1205                1210                1215

Lys  Thr  Gln  Glu  Pro  Ala  Gly  Ser  Leu  Glu  Glu  Asn  Asn  Ser  Asp
     1220                1225                1230

Lys  Asn  Ser  Gly  Pro  Gln  Gly  Pro  Arg  Arg  Thr  Pro  Thr  Met  Pro
     1235                1240                1245

Gln  Glu  Glu  Ala  Ala  Ala  Cys  Pro  Pro  His  Ile  Leu  Pro  Pro  Glu
     1250                1255                1260

Lys  Arg  Pro  Pro  Glu  Pro  Pro  Gly  Pro  Pro  Pro  Pro  Pro  Pro  Pro
     1265                1270                1275

Pro  Pro  Leu  Val  Glu  Gly  Asp  Leu  Ser  Ser  Ala  Pro  Gln  Glu  Leu
     1280                1285                1290

Asn  Pro  Ala  Val  Thr  Ala  Ala  Leu  Leu  Gln  Leu  Leu  Ser  Gln  Pro
     1295                1300                1305

Glu  Ala  Glu  Pro  Pro  Gly  His  Leu  Pro  His  Glu  His  Gln  Ala  Leu
     1310                1315                1320

Arg  Pro  Met  Glu  Tyr  Ser  Thr  Arg  Pro  Arg  Pro  Asn  Arg  Thr  Tyr
     1325                1330                1335

Gly  Asn  Thr  Asp  Gly  Pro  Glu  Thr  Gly  Phe  Ser  Ala  Ile  Asp  Thr
     1340                1345                1350

Asp  Glu  Arg  Asn  Ser  Gly  Pro  Ala  Leu  Thr  Glu  Ser  Leu  Val  Gln
     1355                1360                1365

Thr  Leu  Val  Lys  Asn  Arg  Thr  Phe  Ser  Gly  Ser  Leu  Ser  His  Leu
     1370                1375                1380

Gly  Glu  Ser  Ser  Ser  Tyr  Gln  Gly  Thr  Gly  Ser  Val  Gln  Phe  Pro
     1385                1390                1395

Gly  Asp  Gln  Asp  Leu  Arg  Phe  Ala  Arg  Val  Pro  Leu  Ala  Leu  His
     1400                1405                1410

Pro  Val  Val  Gly  Gln  Pro  Phe  Leu  Lys  Ala  Glu  Gly  Ser  Ser  Asn
     1415                1420                1425

Ser  Val  Val  His  Ala  Glu  Thr  Lys  Leu  Gln  Asn  Tyr  Gly  Glu  Leu
     1430                1435                1440

Gly  Pro  Gly  Thr  Thr  Gly  Ala  Ser  Ser  Ser  Gly  Ala  Gly  Leu  His
     1445                1450                1455

Trp  Gly  Gly  Pro  Thr  Gln  Ser  Ser  Ala  Tyr  Gly  Lys  Leu  Tyr  Arg
     1460                1465                1470

Gly  Pro  Thr  Arg  Val  Pro  Pro  Arg  Gly  Gly  Arg  Gly  Arg  Gly  Val
     1475                1480                1485

Pro  Tyr
     1490

<210> SEQ ID NO 8
<211> LENGTH: 1481
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 8

Met Pro Asn Ser Glu Arg His Gly Gly Lys Lys Asp Gly Ser Gly Gly
1               5                   10                  15

Ala Ser Gly Thr Leu Gln Pro Ser Gly Gly Ser Ser Asn Ser
            20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
    115                 120                 125

Glu Lys Glu Lys Ser Gln Glu Val Ser Ser Lys Ser Gly Ser Met Lys
130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
    195                 200                 205

Ser Tyr Lys Thr Val Asp Ser Pro Lys Arg Arg Ser Arg Ser Pro His
210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270

Gln Ser Val Ser Pro Pro Tyr Lys Glu Pro Ser Ala Tyr Gln Ser Ser
    275                 280                 285

Thr Arg Ser Pro Ser Pro Tyr Ser Arg Arg Gln Arg Ser Val Ser Pro
290                 295                 300

Tyr Ser Arg Arg Arg Ser Ser Ser Tyr Glu Arg Ser Gly Ser Tyr Ser
305                 310                 315                 320

Gly Arg Ser Pro Ser Pro Tyr Gly Arg Arg Arg Ser Ser Ser Pro Phe
                325                 330                 335

Leu Ser Lys Arg Ser Leu Ser Arg Ser Pro Leu Pro Ser Arg Lys Ser
            340                 345                 350

Met Lys Ser Arg Ser Arg Ser Pro Ala Tyr Ser Arg His Ser Ser Ser
    355                 360                 365

His Ser Lys Lys Lys Arg Ser Ser Ser Arg Ser Arg His Ser Ser Ile
370                 375                 380

Ser Pro Val Arg Leu Pro Leu Asn Ser Ser Leu Gly Ala Glu Leu Ser

```
                385                 390                 395                 400
        Arg Lys Lys Lys Glu Arg Ala Ala Ala Ala Ala Ala Lys Met Asp
                        405                 410                 415

Gly Lys Glu Ser Lys Gly Ser Pro Val Phe Leu Pro Arg Lys Glu Asn
                        420                 425                 430

Ser Ser Val Glu Ala Lys Asp Ser Gly Leu Glu Ser Lys Lys Leu Pro
                        435                 440                 445

Arg Ser Val Lys Leu Glu Lys Ser Ala Pro Asp Thr Glu Leu Val Asn
                        450                 455                 460

Val Thr His Leu Asn Thr Glu Val Lys Asn Ser Ser Asp Thr Gly Lys
                        465                 470                 475                 480

Val Lys Leu Asp Glu Asn Ser Glu Lys His Leu Val Lys Asp Leu Lys
                        485                 490                 495

Ala Gln Gly Thr Arg Asp Ser Lys Pro Ile Ala Leu Lys Glu Glu Ile
                        500                 505                 510

Val Thr Pro Lys Glu Thr Glu Thr Ser Glu Lys Glu Thr Pro Pro Pro
                        515                 520                 525

Leu Pro Thr Ile Ala Ser Pro Pro Pro Leu Pro Thr Thr Thr Pro
                        530                 535                 540

Pro Pro Gln Thr Pro Pro Leu Pro Pro Leu Pro Ile Pro Ala Leu
        545                 550                 555                 560

Pro Gln Gln Pro Pro Leu Pro Pro Ser Gln Pro Ala Phe Ser Gln Val
                        565                 570                 575

Pro Ala Ser Ser Thr Ser Thr Leu Pro Pro Ser Thr His Ser Lys Thr
                        580                 585                 590

Ser Ala Val Ser Ser Gln Ala Asn Ser Gln Pro Pro Val Gln Val Ser
                        595                 600                 605

Val Lys Thr Gln Val Ser Val Thr Ala Ala Ile Pro His Leu Lys Thr
                        610                 615                 620

Ser Thr Leu Pro Pro Leu Pro Leu Pro Pro Leu Leu Pro Gly Asp Asp
        625                 630                 635                 640

Asp Met Asp Ser Pro Lys Glu Thr Leu Pro Ser Lys Pro Val Lys Lys
                        645                 650                 655

Glu Lys Glu Gln Arg Thr Arg His Leu Leu Thr Asp Leu Pro Leu Pro
                        660                 665                 670

Pro Glu Leu Pro Gly Gly Asp Leu Ser Pro Pro Asp Ser Pro Glu Pro
                        675                 680                 685

Lys Ala Ile Thr Pro Pro Gln Gln Pro Tyr Lys Lys Arg Pro Lys Ile
                        690                 695                 700

Cys Cys Pro Arg Tyr Gly Glu Arg Arg Gln Thr Glu Ser Asp Trp Gly
        705                 710                 715                 720

Lys Arg Cys Val Asp Lys Phe Asp Ile Ile Gly Ile Ile Gly Glu Gly
                        725                 730                 735

Thr Tyr Gly Gln Val Tyr Lys Ala Lys Asp Lys Asp Thr Gly Glu Leu
                        740                 745                 750

Val Ala Leu Lys Lys Val Arg Leu Asp Asn Glu Lys Glu Gly Phe Pro
                        755                 760                 765

Ile Thr Ala Ile Arg Glu Ile Lys Ile Leu Arg Gln Leu Ile His Arg
                        770                 775                 780

Ser Val Val Asn Met Lys Glu Ile Val Thr Asp Lys Gln Asp Ala Leu
        785                 790                 795                 800

Asp Phe Lys Lys Asp Lys Gly Ala Phe Tyr Leu Val Phe Glu Tyr Met
                        805                 810                 815
```

```
Asp His Asp Leu Met Gly Leu Leu Glu Ser Gly Leu Val His Phe Ser
            820                 825                 830

Glu Asp His Ile Lys Ser Phe Met Lys Gln Leu Met Glu Gly Leu Glu
            835                 840                 845

Tyr Cys His Lys Lys Asn Phe Leu His Arg Asp Ile Lys Cys Ser Asn
            850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
            885                 890                 895

Ile Thr Leu Trp Tyr Arg Pro Pro Glu Leu Leu Leu Gly Glu Glu Arg
            900                 905                 910

Tyr Thr Pro Ala Ile Asp Val Trp Ser Cys Gly Cys Ile Leu Gly Glu
            915                 920                 925

Leu Phe Thr Lys Lys Pro Ile Phe Gln Ala Asn Leu Glu Leu Ala Gln
            930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
            965                 970                 975

Gln Tyr Arg Arg Arg Leu Arg Glu Glu Phe Ser Phe Ile Pro Ser Ala
            980                 985                 990

Ala Leu Asp Leu Leu Asp His Met Leu Thr Leu Asp Pro Ser Lys Arg
            995                 1000                1005

Cys Thr Ala Glu Gln Thr Leu Gln Ser Asp Phe Leu Lys Asp Val
            1010                1015                1020

Glu Leu Ser Lys Met Ala Pro Pro Asp Leu Pro His Trp Gln Asp
            1025                1030                1035

Cys His Glu Leu Trp Ser Lys Lys Arg Arg Arg Gln Arg Gln Ser
            1040                1045                1050

Gly Val Val Val Glu Glu Pro Pro Pro Ser Lys Thr Ser Arg Lys
            1055                1060                1065

Glu Thr Thr Ser Gly Thr Ser Thr Glu Pro Val Lys Asn Ser Ser
            1070                1075                1080

Pro Ala Pro Pro Gln Pro Ala Pro Gly Lys Val Glu Ser Gly Ala
            1085                1090                1095

Gly Asp Ala Ile Gly Leu Ala Asp Ile Thr Gln Gln Leu Asn Gln
            1100                1105                1110

Ser Glu Leu Ala Val Leu Leu Asn Leu Leu Gln Ser Gln Thr Asp
            1115                1120                1125

Leu Ser Val Pro Gln Met Ala Gln Leu Leu Asn Ile His Ser Asn
            1130                1135                1140

Pro Glu Met Gln Gln Gln Leu Glu Ala Leu Asn Gln Ser Ile Ser
            1145                1150                1155

Ala Leu Thr Glu Ala Thr Ser Gln Gln Gln Asp Ser Glu Thr Met
            1160                1165                1170

Ala Pro Glu Glu Ser Leu Lys Glu Ala Pro Ser Ala Pro Val Ile
            1175                1180                1185

Leu Pro Ser Ala Glu Gln Thr Thr Leu Glu Ala Ser Ser Thr Pro
            1190                1195                1200

Ala Asp Met Gln Asn Ile Leu Ala Val Leu Leu Ser Gln Leu Met
            1205                1210                1215
```

```
Lys Thr Gln Glu Pro Ala Gly Ser Leu Glu Glu Asn Asn Ser Asp
    1220                1225                1230

Lys Asn Ser Gly Pro Gln Gly Pro Arg Arg Thr Pro Thr Met Pro
    1235                1240                1245

Gln Glu Glu Ala Ala Glu Lys Arg Pro Pro Glu Pro Pro Gly Pro
    1250                1255                1260

Pro Pro Pro Pro Pro Pro Pro Leu Val Glu Gly Asp Leu Ser
    1265                1270                1275

Ser Ala Pro Gln Glu Leu Asn Pro Ala Val Thr Ala Ala Leu Leu
    1280                1285                1290

Gln Leu Leu Ser Gln Pro Glu Ala Glu Pro Pro Gly His Leu Pro
    1295                1300                1305

His Glu His Gln Ala Leu Arg Pro Met Glu Tyr Ser Thr Arg Pro
    1310                1315                1320

Arg Pro Asn Arg Thr Tyr Gly Asn Thr Asp Gly Pro Glu Thr Gly
    1325                1330                1335

Phe Ser Ala Ile Asp Thr Asp Glu Arg Asn Ser Gly Pro Ala Leu
    1340                1345                1350

Thr Glu Ser Leu Val Gln Thr Leu Val Lys Asn Arg Thr Phe Ser
    1355                1360                1365

Gly Ser Leu Ser His Leu Gly Glu Ser Ser Ser Tyr Gln Gly Thr
    1370                1375                1380

Gly Ser Val Gln Phe Pro Gly Asp Gln Asp Leu Arg Phe Ala Arg
    1385                1390                1395

Val Pro Leu Ala Leu His Pro Val Val Gly Gln Pro Phe Leu Lys
    1400                1405                1410

Ala Glu Gly Ser Ser Asn Ser Val Val His Ala Glu Thr Lys Leu
    1415                1420                1425

Gln Asn Tyr Gly Glu Leu Gly Pro Gly Thr Thr Gly Ala Ser Ser
    1430                1435                1440

Ser Gly Ala Gly Leu His Trp Gly Gly Pro Thr Gln Ser Ser Ala
    1445                1450                1455

Tyr Gly Lys Leu Tyr Arg Gly Pro Thr Arg Val Pro Pro Arg Gly
    1460                1465                1470

Gly Arg Gly Arg Gly Val Pro Tyr
    1475                1480

<210> SEQ ID NO 9
<211> LENGTH: 1481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
                20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Ser Asp Ser
65                  70                  75                  80
```

-continued

Asp Thr Phe Ser Asp Asp Met Ala Phe Lys Leu Asp Arg Arg Glu Asn
            85                  90                  95

Asp Glu Arg Arg Gly Ser Asp Arg Ser Asp Arg Leu His Lys His Arg
100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
            210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270

Gln Ser Val Ser Pro Pro Tyr Lys Glu Pro Ser Ala Tyr Gln Ser Ser
        275                 280                 285

Thr Arg Ser Pro Ser Pro Tyr Ser Arg Arg Gln Arg Ser Val Ser Pro
        290                 295                 300

Tyr Ser Arg Arg Arg Ser Ser Tyr Glu Arg Ser Gly Ser Tyr Ser
305                 310                 315                 320

Gly Arg Ser Pro Ser Pro Tyr Gly Arg Arg Arg Ser Ser Pro Phe
                325                 330                 335

Leu Ser Lys Arg Ser Leu Ser Arg Ser Pro Leu Pro Ser Arg Lys Ser
            340                 345                 350

Met Lys Ser Arg Ser Arg Ser Pro Ala Tyr Ser Arg His Ser Ser Ser
        355                 360                 365

His Ser Lys Lys Lys Arg Ser Ser Arg Ser Arg His Ser Ser Ile
    370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                405                 410                 415

Gly Lys Glu Ser Lys Gly Ser Pro Val Phe Leu Pro Arg Lys Glu Asn
            420                 425                 430

Ser Ser Val Glu Ala Lys Asp Ser Gly Leu Glu Ser Lys Lys Leu Pro
        435                 440                 445

Arg Ser Val Lys Leu Glu Lys Ser Ala Pro Asp Thr Glu Leu Val Asn
450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

```
Ala Gln Gly Thr Arg Asp Ser Lys Pro Ile Ala Leu Lys Glu Ile
            500                 505                 510

Val Thr Pro Lys Glu Thr Glu Thr Ser Glu Lys Glu Thr Pro Pro
            515                 520                 525

Leu Pro Thr Ile Ala Ser Pro Pro Pro Leu Pro Thr Thr Thr Pro
            530                 535                 540

Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
                    565                 570                 575

Pro Ala Ser Ser Thr Ser Thr Leu Pro Pro Ser Thr His Ser Lys Thr
                580                     585                 590

Ser Ala Val Ser Ser Gln Ala Asn Ser Gln Pro Pro Val Gln Val Ser
                    595                 600                 605

Val Lys Thr Gln Val Ser Val Thr Ala Ala Ile Pro His Leu Lys Thr
            610                 615                 620

Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
                    645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Pro Asp Ser Pro Glu Pro
                675                 680                 685

Lys Ala Ile Thr Pro Pro Gln Gln Pro Tyr Lys Lys Arg Pro Lys Ile
            690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Ile Gly Ile Gly Glu Gly
                    725                 730                 735

Thr Tyr Gly Gln Val Tyr Lys Ala Lys Asp Lys Asp Thr Gly Glu Leu
                740                 745                 750

Val Ala Leu Lys Lys Val Arg Leu Asp Asn Glu Lys Glu Gly Phe Pro
                755                 760                 765

Ile Thr Ala Ile Arg Glu Ile Lys Ile Leu Arg Gln Leu Ile His Arg
            770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                    805                 810                 815

Asp His Asp Leu Met Gly Leu Leu Glu Ser Gly Leu Val His Phe Ser
                820                 825                 830

Glu Asp His Ile Lys Ser Phe Met Lys Gln Leu Met Glu Gly Leu Glu
            835                 840                 845

Tyr Cys His Lys Lys Asn Phe Leu His Arg Asp Ile Lys Cys Ser Asn
850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                    885                 890                 895

Ile Thr Leu Trp Tyr Arg Pro Pro Glu Leu Leu Leu Gly Glu Glu Arg
                900                 905                 910

Tyr Thr Pro Ala Ile Asp Val Trp Ser Cys Gly Cys Ile Leu Gly Glu
```

```
                915                 920                 925
Leu Phe Thr Lys Lys Pro Ile Phe Gln Ala Asn Leu Glu Leu Ala Gln
    930                 935                 940
Leu Glu Leu Ile Ser Arg Leu Cys Gly Ser Pro Cys Pro Ala Val Trp
945                 950                 955                 960
Pro Asp Val Ile Lys Leu Pro Tyr Phe Asn Thr Met Lys Pro Lys Lys
                965                 970                 975
Gln Tyr Arg Arg Leu Arg Glu Glu Phe Ser Phe Ile Pro Ser Ala
            980                 985                 990
Ala Leu Asp Leu Leu Asp His Met Leu Thr Leu Asp Pro Ser Lys Arg
            995                 1000                1005
Cys Thr Ala Glu Gln Thr Leu Gln Ser Asp Phe Leu Lys Asp Val
    1010                1015                1020
Glu Leu Ser Lys Met Ala Pro Pro Asp Leu Pro His Trp Gln Asp
    1025                1030                1035
Cys His Glu Leu Trp Ser Lys Lys Arg Arg Arg Gln Arg Gln Ser
    1040                1045                1050
Gly Val Val Val Glu Glu Pro Pro Pro Ser Lys Thr Ser Arg Lys
    1055                1060                1065
Glu Thr Thr Ser Gly Thr Ser Thr Glu Pro Val Lys Asn Ser Ser
    1070                1075                1080
Pro Ala Pro Pro Gln Pro Ala Pro Gly Lys Val Glu Ser Gly Ala
    1085                1090                1095
Gly Asp Ala Ile Gly Leu Ala Asp Ile Thr Gln Gln Leu Asn Gln
    1100                1105                1110
Ser Glu Leu Ala Val Leu Leu Asn Leu Leu Gln Ser Gln Thr Asp
    1115                1120                1125
Leu Ser Ile Pro Gln Met Ala Gln Leu Leu Asn Ile His Ser Asn
    1130                1135                1140
Pro Glu Met Gln Gln Gln Leu Glu Ala Leu Asn Gln Ser Ile Ser
    1145                1150                1155
Ala Leu Thr Glu Ala Thr Ser Gln Gln Gln Asp Ser Glu Thr Met
    1160                1165                1170
Ala Pro Glu Glu Ser Leu Lys Glu Ala Pro Ser Ala Pro Val Ile
    1175                1180                1185
Gln Pro Ser Ala Glu Gln Thr Thr Leu Glu Ala Ser Ser Thr Pro
    1190                1195                1200
Ala Asp Met Gln Asn Ile Leu Ala Val Leu Leu Ser Gln Leu Met
    1205                1210                1215
Lys Thr Gln Glu Pro Ala Gly Ser Leu Glu Glu Asn Asn Ser Asp
    1220                1225                1230
Lys Asn Ser Gly Pro Gln Gly Pro Arg Arg Thr Pro Thr Met Pro
    1235                1240                1245
Gln Glu Glu Ala Ala Glu Lys Arg Pro Pro Glu Pro Pro Gly Pro
    1250                1255                1260
Pro Pro Pro Pro Pro Pro Pro Leu Val Glu Gly Asp Leu Ser
    1265                1270                1275
Ser Ala Pro Gln Glu Leu Asn Pro Ala Val Thr Ala Ala Leu Leu
    1280                1285                1290
Gln Leu Leu Ser Gln Pro Glu Ala Glu Pro Pro Gly His Leu Pro
    1295                1300                1305
His Glu His Gln Ala Leu Arg Pro Met Glu Tyr Ser Thr Arg Pro
    1310                1315                1320
```

-continued

```
Arg Pro Asn Arg Thr Tyr Gly Asn Thr Asp Gly Pro Glu Thr Gly
    1325                1330                1335

Phe Ser Ala Ile Asp Thr Asp Glu Arg Asn Ser Gly Pro Ala Leu
    1340                1345                1350

Thr Glu Ser Leu Val Gln Thr Leu Val Lys Asn Arg Thr Phe Ser
    1355                1360                1365

Gly Ser Leu Ser His Leu Gly Glu Ser Ser Tyr Gln Gly Thr
    1370                1375                1380

Gly Ser Val Gln Phe Pro Gly Asp Gln Asp Leu Arg Phe Ala Arg
    1385                1390                1395

Val Pro Leu Ala Leu His Pro Val Val Gly Gln Pro Phe Leu Lys
    1400                1405                1410

Ala Glu Gly Ser Ser Asn Ser Val Val His Ala Glu Thr Lys Leu
    1415                1420                1425

Gln Asn Tyr Gly Glu Leu Gly Pro Gly Thr Thr Gly Ala Ser Ser
    1430                1435                1440

Ser Gly Ala Gly Leu His Trp Gly Gly Pro Thr Gln Ser Ser Ala
    1445                1450                1455

Tyr Gly Lys Leu Tyr Arg Gly Pro Thr Arg Val Pro Pro Arg Gly
    1460                1465                1470

Gly Arg Gly Arg Gly Val Pro Tyr
    1475                1480
```

<210> SEQ ID NO 10
<211> LENGTH: 1481
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
                20                  25                  30

Arg Glu Arg His Arg Leu Val Ser Lys His Leu Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Ser Lys Glu Ser Arg Ser
                165                 170                 175

Ser Lys Leu His Lys Glu Lys Thr Arg Lys Glu Arg Glu Leu Lys Ser
```

```
                180                 185                 190
Gly His Lys Asp Arg Ser Lys Ser His Arg Lys Arg Glu Thr Pro Lys
                    195                 200                 205

Ser Tyr Lys Thr Val Asp Ser Pro Lys Arg Ser Arg Ser Pro His
210                 215                 220

Arg Lys Trp Ser Asp Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                    245                 250                 255

Ser Asn Tyr Asp Ser Tyr Lys Lys Ser Pro Gly Ser Thr Ser Arg Arg
                    260                 265                 270

Gln Ser Val Ser Pro Pro Tyr Lys Glu Pro Ser Ala Tyr Gln Ser Ser
                    275                 280                 285

Thr Arg Ser Pro Ser Pro Tyr Ser Arg Arg Gln Arg Ser Val Ser Pro
                    290                 295                 300

Tyr Ser Arg Arg Arg Ser Ser Ser Tyr Glu Arg Ser Gly Ser Tyr Ser
305                 310                 315                 320

Gly Arg Ser Pro Ser Pro Tyr Gly Arg Arg Ser Ser Pro Phe
                    325                 330                 335

Leu Ser Lys Arg Ser Leu Ser Arg Ser Pro Leu Pro Ser Arg Lys Ser
                    340                 345                 350

Met Lys Ser Arg Ser Arg Ser Pro Ala Tyr Ser Arg His Ser Ser Ser
                    355                 360                 365

His Ser Lys Lys Lys Arg Ser Ser Arg Ser Arg His Ser Ser Ile
                    370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                    405                 410                 415

Gly Lys Glu Ser Lys Gly Ser Pro Val Phe Leu Pro Arg Lys Glu Asn
                    420                 425                 430

Ser Ser Val Glu Ala Lys Asp Ser Gly Leu Glu Ser Lys Lys Leu Pro
                    435                 440                 445

Arg Ser Val Lys Leu Glu Lys Ser Ala Pro Asp Thr Glu Leu Val Asn
                    450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                    485                 490                 495

Ala Gln Gly Thr Arg Asp Ser Lys Pro Ile Ala Leu Lys Glu Glu Ile
                    500                 505                 510

Val Thr Pro Lys Glu Thr Glu Thr Ser Glu Lys Glu Thr Pro Pro
                    515                 520                 525

Leu Pro Thr Ile Ala Ser Pro Pro Pro Leu Pro Thr Thr Thr Pro
                    530                 535                 540

Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
                    565                 570                 575

Pro Ala Ser Ser Thr Ser Thr Leu Pro Pro Ser Thr His Ser Lys Thr
                    580                 585                 590

Ser Ala Val Ser Ser Gln Ala Asn Ser Gln Pro Pro Val Gln Val Ser
                    595                 600                 605
```

```
Val Lys Thr Gln Val Ser Val Thr Ala Ala Ile Pro His Leu Lys Thr
    610             615                 620
Ser Thr Leu Pro Pro Leu Pro Leu Pro Pro Leu Leu Pro Gly Asp Asp
625             630              635                 640
Asp Met Asp Ser Pro Lys Glu Thr Leu Pro Ser Lys Pro Val Lys Lys
                645             650                 655
Glu Lys Glu Gln Arg Thr Arg His Leu Leu Thr Asp Leu Pro Leu Pro
            660             665                 670
Pro Glu Leu Pro Gly Gly Asp Leu Ser Pro Pro Asp Ser Pro Glu Pro
        675             680             685
Lys Ala Ile Thr Pro Pro Gln Gln Pro Tyr Lys Arg Pro Lys Ile
690             695             700
Cys Cys Pro Arg Tyr Gly Glu Arg Arg Gln Thr Glu Ser Asp Trp Gly
705             710             715                 720
Lys Arg Cys Val Asp Lys Phe Asp Ile Ile Gly Ile Gly Glu Gly
                725             730             735
Thr Tyr Gly Gln Val Tyr Lys Ala Lys Asp Lys Asp Thr Gly Glu Leu
            740             745             750
Val Ala Leu Lys Lys Val Arg Leu Asp Asn Glu Lys Glu Gly Phe Pro
    755             760             765
Ile Thr Ala Ile Arg Glu Ile Lys Ile Leu Arg Gln Leu Ile His Arg
770             775             780
Ser Val Val Asn Met Lys Glu Ile Val Thr Asp Lys Gln Asp Ala Leu
785             790             795                 800
Asp Phe Lys Lys Asp Lys Gly Ala Phe Tyr Leu Val Phe Glu Tyr Met
                805             810             815
Asp His Asp Leu Met Gly Leu Leu Glu Ser Gly Leu Val His Phe Ser
        820             825             830
Glu Asp His Ile Lys Ser Phe Met Lys Gln Leu Met Glu Gly Leu Glu
            835             840             845
Tyr Cys His Lys Lys Asn Phe Leu His Arg Asp Ile Lys Cys Ser Asn
    850             855             860
Ile Leu Leu Asn Asn Ser Gly Gln Ile Lys Leu Ala Asp Phe Gly Leu
865             870             875             880
Ala Arg Leu Tyr Asn Ser Glu Glu Ser Arg Pro Tyr Thr Asn Lys Val
            885             890             895
Ile Thr Leu Trp Tyr Arg Pro Pro Glu Leu Leu Leu Gly Glu Glu Arg
        900             905             910
Tyr Thr Pro Ala Ile Asp Val Trp Ser Cys Gly Cys Ile Leu Gly Glu
            915             920             925
Leu Phe Thr Lys Lys Pro Ile Phe Gln Ala Asn Leu Glu Leu Ala Gln
    930             935             940
Leu Glu Leu Ile Ser Arg Leu Cys Gly Ser Pro Cys Pro Ala Val Trp
945             950             955             960
Pro Asp Val Ile Lys Leu Pro Tyr Phe Asn Thr Met Lys Pro Lys Lys
            965             970             975
Gln Tyr Arg Arg Arg Leu Arg Glu Glu Phe Ser Phe Ile Pro Ser Ala
        980             985             990
Ala Leu Asp Leu Leu Asp His Met Leu Thr Leu Asp Pro Ser Lys Arg
            995             1000            1005
Cys Thr Ala Glu Gln Thr Leu Gln Ser Asp Phe Leu Lys Asp Val
    1010            1015            1020
```

```
Glu Leu Ser Lys Met Ala Pro Pro Asp Leu Pro His Trp Gln Asp
    1025                1030                1035

Cys His Glu Leu Trp Ser Lys Lys Arg Arg Gln Arg Gln Ser
    1040                1045                1050

Gly Val Val Val Glu Glu Pro Pro Ser Lys Thr Ser Arg Lys
    1055                1060                1065

Glu Thr Thr Ser Gly Thr Ser Thr Glu Pro Val Lys Asn Ser Ser
    1070                1075                1080

Pro Ala Pro Pro Gln Pro Ala Pro Gly Lys Val Glu Ser Gly Ala
    1085                1090                1095

Gly Asp Ala Ile Gly Leu Ala Asp Ile Thr Gln Gln Leu Asn Gln
    1100                1105                1110

Ser Glu Leu Ala Val Leu Leu Asn Leu Leu Gln Ser Gln Thr Asp
    1115                1120                1125

Leu Ser Ile Pro Gln Met Ala Gln Leu Leu Asn Ile His Ser Asn
    1130                1135                1140

Pro Glu Met Gln Gln Gln Leu Glu Ala Leu Asn Gln Ser Ile Ser
    1145                1150                1155

Ala Leu Thr Glu Ala Thr Ser Gln Gln Gln Asp Ser Glu Thr Met
    1160                1165                1170

Ala Pro Glu Glu Ser Leu Lys Glu Ala Pro Ser Ala Pro Val Ile
    1175                1180                1185

Leu Pro Ser Ala Glu Gln Met Thr Leu Glu Ala Ser Ser Thr Pro
    1190                1195                1200

Ala Asp Met Gln Asn Ile Leu Ala Val Leu Leu Ser Gln Leu Met
    1205                1210                1215

Lys Thr Gln Glu Pro Ala Gly Ser Leu Glu Glu Asn Asn Ser Asp
    1220                1225                1230

Lys Asn Ser Gly Pro Gln Gly Pro Arg Arg Thr Pro Thr Met Pro
    1235                1240                1245

Gln Glu Glu Ala Ala Glu Lys Arg Pro Pro Glu Pro Pro Gly Pro
    1250                1255                1260

Pro Pro Pro Pro Pro Pro Pro Leu Val Glu Gly Asp Leu Ser
    1265                1270                1275

Ser Ala Pro Gln Glu Leu Asn Pro Ala Val Thr Ala Ala Leu Leu
    1280                1285                1290

Gln Leu Leu Ser Gln Pro Glu Ala Glu Pro Pro Gly His Leu Pro
    1295                1300                1305

His Glu His Gln Ala Leu Arg Pro Met Glu Tyr Ser Thr Arg Pro
    1310                1315                1320

Arg Pro Asn Arg Thr Tyr Gly Asn Thr Asp Gly Pro Glu Thr Gly
    1325                1330                1335

Phe Ser Ala Ile Asp Thr Asp Glu Arg Asn Ser Gly Pro Ala Leu
    1340                1345                1350

Thr Glu Ser Leu Val Gln Thr Leu Val Lys Asn Arg Thr Phe Ser
    1355                1360                1365

Gly Ser Leu Ser His Leu Gly Glu Ser Ser Ser Tyr Gln Gly Thr
    1370                1375                1380

Gly Ser Val Gln Phe Pro Gly Asp Gln Asp Leu Arg Phe Ala Arg
    1385                1390                1395

Val Pro Leu Ala Leu His Pro Val Val Gly Gln Pro Phe Leu Lys
    1400                1405                1410

Ala Glu Gly Ser Ser Asn Ser Val Val His Ala Glu Thr Lys Leu
```

-continued

```
                1415                1420                1425

Gln Asn Tyr Gly Glu Leu Gly Pro Gly Thr Thr Gly Ala Ser Ser
                1430                1435                1440

Ser Gly Ala Gly Leu His Trp Gly Gly Pro Thr Gln Ser Ser Ala
                1445                1450                1455

Tyr Gly Lys Leu Tyr Arg Gly Pro Thr Arg Val Pro Pro Arg Gly
                1460                1465                1470

Gly Arg Gly Arg Gly Val Pro Tyr
                1475                1480

<210> SEQ ID NO 11
<211> LENGTH: 1201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Ser Ser Asn Ser
                20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
    210                 215                 220

Arg Lys Trp Ser Asp Ser Ser Lys Gln Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270

Gln Ser Val Ser Pro Pro Tyr Lys Glu Pro Ser Ala Tyr Gln Ser Ser
        275                 280                 285
```

-continued

Thr Arg Ser Pro Ser Pro Tyr Ser Arg Arg Gln Arg Ser Val Ser Pro
    290                 295                 300

Tyr Ser Arg Arg Ser Ser Ser Tyr Glu Arg Ser Gly Ser Tyr Ser
305                 310                 315                 320

Gly Arg Ser Pro Ser Pro Tyr Gly Arg Arg Ser Ser Ser Pro Phe
                325                 330                 335

Leu Ser Lys Arg Ser Leu Ser Arg Ser Pro Leu Pro Arg Lys Ser Met
                340                 345                 350

Lys Ser Arg Ser Arg Ser Pro Ala Tyr Ser Arg His Ser Ser Ser His
                355                 360                 365

Ser Lys Lys Lys Arg Ser Ser Arg Ser Arg His Ser Ser Ile Ser
    370                 375                 380

Pro Val Arg Leu Pro Leu Asn Ser Ser Leu Gly Ala Glu Leu Ser Arg
385                 390                 395                 400

Lys Lys Lys Glu Arg Ala Ala Ala Ala Ala Ala Lys Met Asp Gly
                405                 410                 415

Lys Glu Ser Lys Gly Ser Pro Val Phe Leu Pro Arg Lys Glu Asn Ser
                420                 425                 430

Ser Val Glu Ala Lys Asp Ser Gly Leu Glu Ser Lys Lys Leu Pro Arg
                435                 440                 445

Ser Val Lys Leu Glu Lys Ser Ala Pro Asp Thr Glu Leu Val Asn Val
    450                 455                 460

Thr His Leu Asn Thr Glu Val Lys Asn Ser Ser Asp Thr Gly Lys Val
465                 470                 475                 480

Lys Leu Asp Glu Asn Ser Glu Lys His Leu Val Lys Asp Leu Lys Ala
                485                 490                 495

Gln Gly Thr Arg Asp Ser Lys Pro Ile Ala Leu Lys Glu Glu Ile Val
                500                 505                 510

Thr Pro Lys Glu Thr Glu Thr Ser Glu Lys Glu Thr Pro Pro Leu
    515                 520                 525

Pro Thr Ile Ala Ser Pro Pro Pro Leu Pro Thr Thr Thr Pro Pro
    530                 535                 540

Pro Gln Thr Pro Pro Leu Pro Pro Leu Pro Ile Pro Ala Leu Pro
545                 550                 555                 560

Gln Gln Pro Pro Leu Pro Pro Ser Gln Pro Ala Phe Ser Gln Val Pro
                565                 570                 575

Ala Ser Ser Thr Ser Thr Leu Pro Pro Ser Thr His Ser Lys Thr Ser
                580                 585                 590

Ala Val Ser Ser Gln Ala Asn Ser Gln Pro Pro Val Gln Val Ser Val
                595                 600                 605

Lys Thr Gln Val Ser Val Thr Ala Ala Ile Pro His Leu Lys Thr Ser
    610                 615                 620

Thr Leu Pro Pro Leu Pro Leu Pro Leu Leu Pro Gly Asp Asp Asp
625                 630                 635                 640

Met Asp Ser Pro Lys Glu Thr Leu Pro Ser Lys Pro Val Lys Lys Glu
                645                 650                 655

Lys Glu Gln Arg Thr Arg His Leu Leu Thr Asp Leu Pro Leu Pro Pro
                660                 665                 670

Glu Leu Pro Gly Gly Asp Leu Ser Pro Asp Ser Pro Glu Pro Lys
                675                 680                 685

Ala Ile Thr Pro Pro Gln Gln Pro Tyr Lys Lys Arg Pro Lys Ile Cys
    690                 695                 700

Cys Pro Arg Tyr Gly Glu Arg Arg Gln Thr Glu Ser Asp Trp Gly Lys

```
                705                 710                 715                 720
        Arg Cys Val Asp Lys Phe Asp Ile Ile Gly Ile Ile Gly Glu Gly Thr
                        725                 730                 735
        Tyr Gly Gln Val Tyr Lys Ala Lys Asp Lys Asp Thr Gly Glu Leu Val
                        740                 745                 750
        Ala Leu Lys Lys Val Arg Leu Asp Asn Glu Lys Glu Gly Phe Pro Ile
                        755                 760                 765
        Thr Ala Ile Arg Glu Ile Lys Ile Leu Arg Gln Leu Ile His Arg Ser
                770                 775                 780
        Val Val Asn Met Lys Glu Ile Val Thr Asp Lys Gln Asp Ala Leu Asp
        785                 790                 795                 800
        Phe Lys Lys Asp Lys Gly Ala Phe Tyr Leu Val Phe Glu Tyr Met Asp
                        805                 810                 815
        His Asp Leu Met Gly Leu Leu Glu Ser Gly Leu Val His Phe Ser Glu
                        820                 825                 830
        Asp His Ile Lys Ser Phe Met Lys Gln Leu Met Glu Gly Leu Glu Tyr
                        835                 840                 845
        Cys His Lys Lys Asn Phe Leu His Arg Asp Ile Lys Cys Ser Asn Ile
                850                 855                 860
        Leu Leu Asn Asn Ser Gly Gln Ile Lys Leu Ala Asp Phe Gly Leu Ala
        865                 870                 875                 880
        Arg Leu Tyr Asn Ser Glu Glu Ser Arg Pro Tyr Thr Asn Lys Val Ile
                        885                 890                 895
        Thr Leu Trp Tyr Arg Pro Pro Glu Leu Leu Leu Gly Glu Glu Arg Tyr
                        900                 905                 910
        Thr Pro Ala Ile Asp Val Trp Ser Cys Gly Cys Ile Leu Gly Glu Leu
                        915                 920                 925
        Phe Thr Lys Lys Pro Ile Phe Gln Ala Asn Leu Glu Leu Ala Gln Leu
                        930                 935                 940
        Glu Leu Ile Ser Arg Leu Cys Gly Ser Pro Cys Pro Ala Val Trp Pro
        945                 950                 955                 960
        Asp Val Ile Lys Leu Pro Tyr Phe Asn Thr Met Lys Pro Lys Lys Gln
                        965                 970                 975
        Tyr Arg Arg Arg Leu Arg Glu Glu Phe Ser Phe Ile Pro Ser Ala Ala
                        980                 985                 990
        Leu Asp Leu Leu Asp His Met Leu Thr Leu Asp Pro Ser Lys Arg Cys
                        995                 1000                1005
        Thr Ala Glu Gln Thr Leu Gln Ser Asp Phe Leu Lys Asp Val Glu
                1010                1015                1020
        Leu Ser Lys Met Ala Pro Pro Asp Leu Pro His Trp Gln Asp Cys
                1025                1030                1035
        His Glu Leu Trp Ser Lys Lys Arg Arg Arg Gln Arg Gln Ser Gly
                1040                1045                1050
        Val Val Val Glu Glu Pro Pro Ser Lys Thr Ser Arg Lys Glu
                1055                1060                1065
        Thr Thr Ser Gly Thr Ser Thr Glu Pro Val Lys Asn Ser Ser Pro
                1070                1075                1080
        Ala Pro Pro Gln Pro Ala Pro Gly Lys Val Glu Ser Gly Ala Gly
                1085                1090                1095
        Asp Ala Ile Gly Leu Ala Asp Ile Thr Gln Gln Leu Asn Gln Ser
                1100                1105                1110
        Glu Leu Ala Val Leu Leu Asn Leu Leu Gln Ser Gln Thr Asp Leu
                1115                1120                1125
```

```
Ser Val Pro Gln Met Ala Gln Leu Leu Asn Ile His Ser Asn Pro
    1130                1135                1140

Glu Met Gln Gln Gln Leu Glu Ala Leu Asn Gln Ser Ile Ser Ala
    1145                1150                1155

Leu Thr Glu Ala Thr Ser Gln Gln Gln Asp Ser Glu Thr Met Ala
    1160                1165                1170

Pro Glu Glu Ser Leu Lys Glu Ala Pro Ser Ala Pro Val Ile Leu
    1175                1180                1185

Pro Ser Ala Glu Gln Thr Thr Leu Glu Ala Ser Ser Thr
    1190                1195                1200

<210> SEQ ID NO 12
<211> LENGTH: 1201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Pro Asn Ser Glu Arg His Gly Gly Lys Lys Asp Gly Ser Gly Gly
1               5                   10                  15

Ala Ser Gly Thr Leu Gln Pro Ser Gly Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Leu Ser Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
    210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270

Gln Ser Val Ser Pro Pro Tyr Lys Glu Pro Ser Ala Tyr Gln Ser Ser
```

```
                275                 280                 285
Thr Arg Ser Pro Ser Pro Tyr Ser Arg Gln Arg Ser Val Ser Pro
        290                 295                 300
Tyr Ser Arg Arg Arg Ser Ser Ser Tyr Glu Arg Ser Gly Ser Tyr Ser
305                 310                 315                 320
Gly Arg Ser Pro Ser Pro Tyr Gly Arg Arg Arg Ser Ser Ser Pro Phe
                325                 330                 335
Leu Ser Lys Arg Ser Leu Ser Arg Ser Pro Leu Pro Arg Lys Ser Met
                340                 345                 350
Lys Ser Arg Ser Arg Ser Pro Ala Tyr Ser Arg His Ser Ser Ser His
                355                 360                 365
Ser Lys Lys Lys Arg Ser Ser Ser Arg Ser Arg His Ser Ser Ile Ser
        370                 375                 380
Pro Val Arg Leu Pro Leu Asn Ser Ser Leu Gly Ala Glu Leu Ser Arg
385                 390                 395                 400
Lys Lys Lys Glu Arg Ala Ala Ala Ala Ala Ala Lys Met Asp Gly
                405                 410                 415
Lys Glu Ser Lys Gly Ser Pro Val Phe Leu Pro Arg Lys Glu Asn Ser
                420                 425                 430
Ser Val Glu Ala Lys Asp Ser Gly Leu Glu Ser Lys Lys Leu Pro Arg
                435                 440                 445
Ser Val Lys Leu Glu Lys Ser Ala Pro Asp Thr Glu Leu Val Asn Val
        450                 455                 460
Thr His Leu Asn Thr Glu Val Lys Asn Ser Ser Asp Thr Gly Lys Val
465                 470                 475                 480
Lys Leu Asp Glu Asn Ser Glu Lys His Leu Val Lys Asp Leu Lys Ala
                    485                 490                 495
Gln Gly Thr Arg Asp Ser Lys Pro Ile Ala Leu Lys Glu Glu Ile Val
                500                 505                 510
Thr Pro Lys Glu Thr Glu Thr Ser Glu Lys Glu Thr Pro Pro Leu
        515                 520                 525
Pro Thr Ile Ala Ser Pro Pro Pro Leu Pro Thr Thr Thr Pro Pro
    530                 535                 540
Pro Gln Thr Pro Pro Leu Pro Pro Leu Pro Pro Ile Pro Ala Leu Pro
545                 550                 555                 560
Gln Gln Pro Pro Leu Pro Pro Ser Gln Pro Ala Phe Ser Gln Val Pro
                565                 570                 575
Ala Ser Ser Thr Ser Thr Leu Pro Pro Ser Thr His Ser Lys Thr Ser
                580                 585                 590
Ala Val Ser Ser Gln Ala Asn Ser Gln Pro Pro Val Gln Val Ser Val
                595                 600                 605
Lys Thr Gln Val Ser Val Thr Ala Ala Ile Pro His Leu Lys Thr Ser
        610                 615                 620
Thr Leu Pro Pro Leu Pro Leu Pro Pro Leu Pro Gly Asp Asp
625                 630                 635                 640
Met Asp Ser Pro Lys Glu Thr Leu Pro Ser Lys Pro Val Lys Glu
                645                 650                 655
Lys Glu Gln Arg Thr Arg His Leu Leu Thr Asp Leu Pro Leu Pro Pro
                660                 665                 670
Glu Leu Pro Gly Gly Asp Leu Ser Pro Asp Ser Pro Glu Pro Lys
            675                 680                 685
Ala Ile Thr Pro Pro Gln Gln Pro Tyr Lys Lys Arg Pro Lys Ile Cys
        690                 695                 700
```

```
Cys Pro Arg Tyr Gly Glu Arg Gln Thr Glu Ser Asp Trp Gly Lys
705                 710                 715                 720

Arg Cys Val Asp Lys Phe Asp Ile Ile Gly Ile Ile Gly Glu Gly Thr
            725                 730                 735

Tyr Gly Gln Val Tyr Lys Ala Lys Asp Lys Asp Thr Gly Glu Leu Val
        740                 745                 750

Ala Leu Lys Lys Val Arg Leu Asp Asn Glu Lys Glu Gly Phe Pro Ile
    755                 760                 765

Thr Ala Ile Arg Glu Ile Lys Ile Leu Arg Gln Leu Ile His Arg Ser
770                 775                 780

Val Val Asn Met Lys Glu Ile Val Thr Asp Lys Gln Asp Ala Leu Asp
785                 790                 795                 800

Phe Lys Lys Asp Lys Gly Ala Phe Tyr Leu Val Phe Glu Tyr Met Asp
                805                 810                 815

His Asp Leu Met Gly Leu Leu Glu Ser Gly Leu Val His Phe Ser Glu
            820                 825                 830

Asp His Ile Lys Ser Phe Met Lys Gln Leu Met Glu Gly Leu Glu Tyr
        835                 840                 845

Cys His Lys Lys Asn Phe Leu His Arg Asp Ile Lys Cys Ser Asn Ile
    850                 855                 860

Leu Leu Asn Asn Ser Gly Gln Ile Lys Leu Ala Asp Phe Gly Leu Ala
865                 870                 875                 880

Arg Leu Tyr Asn Ser Glu Glu Ser Arg Pro Tyr Thr Asn Lys Val Ile
                885                 890                 895

Thr Leu Trp Tyr Arg Pro Pro Glu Leu Leu Gly Glu Glu Arg Tyr
            900                 905                 910

Thr Pro Ala Ile Asp Val Trp Ser Cys Gly Cys Ile Leu Gly Glu Leu
        915                 920                 925

Phe Thr Lys Lys Pro Ile Phe Gln Ala Asn Leu Glu Leu Ala Gln Leu
    930                 935                 940

Glu Leu Ile Ser Arg Leu Cys Gly Ser Pro Cys Pro Ala Val Trp Pro
945                 950                 955                 960

Asp Val Ile Lys Leu Pro Tyr Phe Asn Thr Met Lys Pro Lys Lys Gln
                965                 970                 975

Tyr Arg Arg Arg Leu Arg Glu Glu Phe Ser Phe Ile Pro Ser Ala Ala
            980                 985                 990

Leu Asp Leu Leu Asp His Met Leu Thr Leu Asp Pro Ser Lys Arg Cys
        995                 1000                1005

Thr Ala Glu Gln Thr Leu Gln Ser Asp Phe Leu Lys Asp Val Glu
    1010                1015                1020

Leu Ser Lys Met Ala Pro Pro Asp Leu Pro His Trp Gln Asp Cys
    1025                1030                1035

His Glu Leu Trp Ser Lys Lys Arg Arg Arg Gln Arg Gln Ser Gly
    1040                1045                1050

Val Val Val Glu Glu Pro Pro Pro Ser Lys Thr Ser Arg Lys Glu
    1055                1060                1065

Thr Thr Ser Gly Thr Ser Thr Glu Pro Val Lys Asn Ser Ser Pro
    1070                1075                1080

Ala Pro Pro Gln Pro Ala Pro Gly Lys Val Glu Ser Gly Ala Gly
    1085                1090                1095

Asp Ala Ile Gly Leu Ala Asp Ile Thr Gln Gln Leu Asn Gln Ser
    1100                1105                1110
```

```
Glu Leu Ala Val Leu Leu Asn Leu Leu Gln Ser Gln Thr Asp Leu
    1115                1120                1125

Ser Ile Pro Gln Met Ala Gln Leu Leu Asn Ile His Ser Asn Pro
    1130                1135                1140

Glu Met Gln Gln Gln Leu Glu Ala Leu Asn Gln Ser Ile Ser Ala
    1145                1150                1155

Leu Thr Glu Ala Thr Ser Gln Gln Asp Ser Glu Thr Met Ala
    1160                1165                1170

Pro Glu Glu Ser Leu Lys Glu Ala Pro Ser Ala Pro Val Ile Gln
    1175                1180                1185

Pro Ser Ala Glu Gln Thr Thr Leu Glu Ala Ser Ser Thr
    1190                1195                1200
```

<210> SEQ ID NO 13
<211> LENGTH: 1201
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Pro Asn Ser Glu Arg His Gly Gly Lys Lys Asp Gly Ser Gly
1               5                   10                  15

Ala Ser Gly Thr Leu Gln Pro Ser Ser Gly Gly Gly Ser Ser Asn Ser
            20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
    210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270
```

```
Gln Ser Val Ser Pro Pro Tyr Lys Glu Pro Ser Ala Tyr Gln Ser Ser
        275                 280                 285

Thr Arg Ser Pro Ser Pro Tyr Ser Arg Arg Gln Arg Ser Val Ser Pro
290                 295                 300

Tyr Ser Arg Arg Ser Ser Ser Tyr Glu Arg Ser Gly Ser Tyr Ser
305                 310                 315                 320

Gly Arg Ser Pro Ser Pro Tyr Gly Arg Arg Ser Ser Ser Pro Phe
            325                 330                 335

Leu Ser Lys Arg Ser Leu Ser Arg Ser Pro Leu Pro Arg Lys Ser Met
            340                 345                 350

Lys Ser Arg Ser Arg Ser Pro Ala Tyr Ser Arg His Ser Ser Ser His
            355                 360                 365

Ser Lys Lys Lys Arg Ser Ser Ser Arg Ser Arg His Ser Ser Ile Ser
    370                 375                 380

Pro Val Arg Leu Pro Leu Asn Ser Ser Leu Gly Ala Glu Leu Ser Arg
385                 390                 395                 400

Lys Lys Lys Glu Arg Ala Ala Ala Ala Ala Ala Lys Met Asp Gly
                405                 410                 415

Lys Glu Ser Lys Gly Ser Pro Val Phe Leu Pro Arg Lys Glu Asn Ser
            420                 425                 430

Ser Val Glu Ala Lys Asp Ser Gly Leu Glu Ser Lys Lys Leu Pro Arg
            435                 440                 445

Ser Val Lys Leu Glu Lys Ser Ala Pro Asp Thr Glu Leu Val Asn Val
            450                 455                 460

Thr His Leu Asn Thr Glu Val Lys Asn Ser Ser Asp Thr Gly Lys Val
465                 470                 475                 480

Lys Leu Asp Glu Asn Ser Glu Lys His Leu Val Lys Asp Leu Lys Ala
            485                 490                 495

Gln Gly Thr Arg Asp Ser Lys Pro Ile Ala Leu Lys Glu Glu Ile Val
            500                 505                 510

Thr Pro Lys Glu Thr Glu Thr Ser Glu Lys Glu Thr Pro Pro Leu
        515                 520                 525

Pro Thr Ile Ala Ser Pro Pro Pro Leu Pro Thr Thr Thr Pro Pro
            530                 535                 540

Pro Gln Thr Pro Pro Leu Pro Pro Leu Pro Ile Pro Ala Leu Pro
545                 550                 555                 560

Gln Gln Pro Pro Leu Pro Pro Ser Gln Pro Ala Phe Ser Gln Val Pro
            565                 570                 575

Ala Ser Ser Thr Ser Thr Leu Pro Pro Ser Thr His Ser Lys Thr Ser
            580                 585                 590

Ala Val Ser Ser Gln Ala Asn Ser Gln Pro Pro Val Gln Val Ser Val
            595                 600                 605

Lys Thr Gln Val Ser Val Thr Ala Ala Ile Pro His Leu Lys Thr Ser
    610                 615                 620

Thr Leu Pro Pro Leu Pro Leu Pro Leu Leu Pro Gly Asp Asp Asp
625                 630                 635                 640

Met Asp Ser Pro Lys Glu Thr Leu Pro Ser Lys Pro Val Lys Lys Glu
            645                 650                 655

Lys Glu Gln Arg Thr Arg His Leu Leu Thr Asp Leu Pro Leu Pro Pro
            660                 665                 670

Glu Leu Pro Gly Gly Asp Leu Ser Pro Pro Asp Ser Pro Glu Pro Lys
            675                 680                 685
```

```
Ala Ile Thr Pro Pro Gln Gln Pro Tyr Lys Lys Arg Pro Lys Ile Cys
    690                 695                 700

Cys Pro Arg Tyr Gly Glu Arg Arg Gln Thr Glu Ser Asp Trp Gly Lys
705                 710                 715                 720

Arg Cys Val Asp Lys Phe Asp Ile Ile Gly Ile Ile Gly Glu Gly Thr
                725                 730                 735

Tyr Gly Gln Val Tyr Lys Ala Lys Asp Lys Asp Thr Gly Glu Leu Val
            740                 745                 750

Ala Leu Lys Lys Val Arg Leu Asp Asn Glu Lys Glu Gly Phe Pro Ile
        755                 760                 765

Thr Ala Ile Arg Glu Ile Lys Ile Leu Arg Gln Leu Ile His Arg Ser
770                 775                 780

Val Val Asn Met Lys Glu Ile Val Thr Asp Lys Gln Asp Ala Leu Asp
785                 790                 795                 800

Phe Lys Lys Asp Lys Gly Ala Phe Tyr Leu Val Phe Glu Tyr Met Asp
                805                 810                 815

His Asp Leu Met Gly Leu Leu Glu Ser Gly Leu Val His Phe Ser Glu
            820                 825                 830

Asp His Ile Lys Ser Phe Met Lys Gln Leu Met Glu Gly Leu Glu Tyr
        835                 840                 845

Cys His Lys Lys Asn Phe Leu His Arg Asp Ile Lys Cys Ser Asn Ile
850                 855                 860

Leu Leu Asn Asn Ser Gly Gln Ile Lys Leu Ala Asp Phe Gly Leu Ala
865                 870                 875                 880

Arg Leu Tyr Asn Ser Glu Glu Ser Arg Pro Tyr Thr Asn Lys Val Ile
                885                 890                 895

Thr Leu Trp Tyr Arg Pro Pro Glu Leu Leu Leu Gly Glu Glu Arg Tyr
            900                 905                 910

Thr Pro Ala Ile Asp Val Trp Ser Cys Gly Cys Ile Leu Gly Glu Leu
        915                 920                 925

Phe Thr Lys Lys Pro Ile Phe Gln Ala Asn Leu Glu Leu Ala Gln Leu
930                 935                 940

Glu Leu Ile Ser Arg Leu Cys Gly Ser Pro Cys Pro Ala Val Trp Pro
945                 950                 955                 960

Asp Val Ile Lys Leu Pro Tyr Phe Asn Thr Met Lys Pro Lys Lys Gln
                965                 970                 975

Tyr Arg Arg Arg Leu Arg Glu Glu Phe Ser Phe Ile Pro Ser Ala Ala
            980                 985                 990

Leu Asp Leu Leu Asp His Met Leu Thr Leu Asp Pro Ser Lys Arg Cys
        995                 1000                1005

Thr Ala Glu Gln Thr Leu Gln Ser Asp Phe Leu Lys Asp Val Glu
    1010                1015                1020

Leu Ser Lys Met Ala Pro Pro Asp Leu Pro His Trp Gln Asp Cys
    1025                1030                1035

His Glu Leu Trp Ser Lys Lys Arg Arg Arg Gln Arg Gln Ser Gly
    1040                1045                1050

Val Val Val Glu Glu Pro Pro Ser Lys Thr Ser Arg Lys Glu
    1055                1060                1065

Thr Thr Ser Gly Thr Ser Thr Glu Pro Val Lys Asn Ser Ser Pro
    1070                1075                1080

Ala Pro Pro Gln Pro Ala Pro Gly Lys Val Glu Ser Gly Ala Gly
    1085                1090                1095

Asp Ala Ile Gly Leu Ala Asp Ile Thr Gln Gln Leu Asn Gln Ser
```

```
                        1100                1105                1110

Glu  Leu  Ala  Val  Leu  Leu  Asn  Leu  Leu  Gln  Ser  Gln  Thr  Asp  Leu
         1115                1120                1125

Ser  Ile  Pro  Gln  Met  Ala  Gln  Leu  Leu  Asn  Ile  His  Ser  Asn  Pro
    1130                1135                1140

Glu  Met  Gln  Gln  Gln  Leu  Glu  Ala  Leu  Asn  Gln  Ser  Ile  Ser  Ala
        1145                1150                1155

Leu  Thr  Glu  Ala  Thr  Ser  Gln  Gln  Gln  Asp  Ser  Glu  Thr  Met  Ala
    1160                1165                1170

Pro  Glu  Glu  Ser  Leu  Lys  Glu  Ala  Pro  Ser  Ala  Pro  Val  Ile  Leu
        1175                1180                1185

Pro  Ser  Ala  Glu  Gln  Met  Thr  Leu  Glu  Ala  Ser  Ser  Thr
    1190                1195                1200

<210> SEQ ID NO 14
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid

<400> SEQUENCE: 14

Xaa  Ala  Asp  Ile  Thr  Gln  Gln  Leu  Asn  Gln  Ser  Glu  Leu  Ala  Val  Leu
1                  5                  10                 15

Leu  Asn  Leu  Leu  Gln  Ser  Gln  Thr  Asp  Leu  Ser  Val  Pro  Gln  Met  Ala
              20                  25                  30

Gln  Leu  Leu  Asn  Ile  His  Ser  Asn  Pro  Glu  Met  Gln  Gln  Gln  Leu  Glu
         35                  40                  45

Ala  Leu  Asn  Gln  Ser  Ile  Ser  Ala  Leu  Thr  Glu  Ala  Thr  Ser  Gln  Gln
     50                  55                  60

Gln  Asp  Ser  Glu  Thr  Met  Ala  Pro  Glu  Glu  Ser  Leu  Lys  Glu  Ala  Pro
65                  70                  75                  80

Ser  Ala  Pro  Val  Ile  Leu  Pro  Ser  Ala  Glu  Gln  Thr  Thr  Leu  Glu  Ala
                 85                  90                  95

Ser  Ser  Thr  Pro  Ala  Asp  Met  Gln  Asn  Ile  Leu  Ala  Val  Leu  Leu  Ser
             100                 105                 110

Gln  Leu  Met  Lys  Thr  Gln  Glu  Pro  Ala  Gly  Ser  Leu  Glu  Glu  Asn  Asn
         115                 120                 125

Ser  Asp  Lys  Asn  Ser  Gly  Pro  Gln  Gly  Pro  Arg  Arg  Thr  Pro  Thr  Met
    130                 135                 140

Pro  Gln  Glu  Glu  Ala  Ala  Gly  Arg  Ser  Asn  Gly  Gly  Asn  Ala  Leu
145                 150                 155

<210> SEQ ID NO 15
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid

<400> SEQUENCE: 15
```

Xaa Ala Asp Ile Thr Gln Gln Leu Asn Gln Ser Glu Leu Ala Val Leu
1               5                   10                  15

Leu Asn Leu Leu Gln Ser Gln Thr Asp Leu Ser Ile Pro Gln Met Ala
            20                  25                  30

Gln Leu Leu Asn Ile His Ser Asn Pro Glu Met Gln Gln Gln Leu Glu
        35                  40                  45

Ala Leu Asn Gln Ser Ile Ser Ala Leu Thr Glu Ala Thr Ser Gln Gln
    50                  55                  60

Gln Asp Ser Glu Thr Met Ala Pro Glu Glu Ser Leu Lys Glu Ala Pro
65                  70                  75                  80

Ser Ala Pro Val Ile Gln Pro Ser Ala Glu Gln Thr Thr Leu Glu Ala
                85                  90                  95

Ser Ser Thr Pro Ala Asp Met Gln Asn Ile Leu Ala Val Leu Leu Ser
            100                 105                 110

Gln Leu Met Lys Thr Gln Glu Pro Ala Gly Ser Leu Glu Glu Asn Asn
        115                 120                 125

Ser Asp Lys Asn Ser Gly Pro Gln Gly Pro Arg Arg Thr Pro Thr Met
    130                 135                 140

Pro Gln Glu Glu Ala Ala Gly Arg Ser Asn Gly Gly Asn Ala Leu
145                 150                 155

<210> SEQ ID NO 16
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid

<400> SEQUENCE: 16

Xaa Ala Asp Ile Thr Gln Gln Leu Asn Gln Ser Glu Leu Ala Val Leu
1               5                   10                  15

Leu Asn Leu Leu Gln Ser Gln Thr Asp Leu Ser Ile Pro Gln Met Ala
            20                  25                  30

Gln Leu Leu Asn Ile His Ser Asn Pro Glu Met Gln Gln Gln Leu Glu
        35                  40                  45

Ala Leu Asn Gln Ser Ile Ser Ala Leu Thr Glu Ala Thr Ser Gln Gln
    50                  55                  60

Gln Asp Ser Glu Thr Met Ala Pro Glu Glu Ser Leu Lys Glu Ala Pro
65                  70                  75                  80

Ser Ala Pro Val Ile Leu Pro Ser Ala Glu Gln Met Thr Leu Glu Ala
                85                  90                  95

Ser Ser Thr Pro Ala Asp Met Gln Asn Ile Leu Ala Val Leu Leu Ser
            100                 105                 110

Gln Leu Met Lys Thr Gln Glu Pro Ala Gly Ser Leu Glu Glu Asn Asn
        115                 120                 125

Ser Asp Lys Asn Ser Gly Pro Gln Gly Pro Arg Arg Thr Pro Thr Met
    130                 135                 140

Pro Gln Glu Glu Ala Ala Gly Arg Ser Asn Gly Gly Asn Ala Leu
145                 150                 155

INHIBITORS OF CYCLIN-DEPENDENT KINASES

CROSS REFERENCE TO RELATED APPLICATIONS

This application is a continuation application of U.S. patent application Ser. No. 16/457,400, filed Jun. 28, 2019, and claims the benefit of U.S. Provisional Application No. 62/691,879, filed Jun. 29, 2018, which is incorporated by reference in the disclosure of this application.

BACKGROUND

Cyclin-dependent kinases (CDKs) are a family of multifunctional enzymes that modify various protein substrates involved in cell cycle progression. Specifically, CDKs phosphorylate their substrates by transferring phosphate groups from ATP to specific stretches of amino acids in the substrates. The deregulation of CDKs is involved in the etiology of many human diseases, including cancers.

BRIEF SUMMARY OF THE INVENTION

Provided herein are inhibitors of cyclin-dependent kinases (CDKs), pharmaceutical compositions comprising said compounds, and methods for using said compounds for the treatment of diseases.

One embodiment provides a compound, or pharmaceutically acceptable salt or solvate thereof, having the structure of Formula (I):

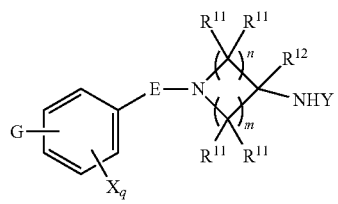

(I)

wherein,

E is selected from a bond, —SO$_2$—, —C(O)—, —CH$_2$—, —CH(R$^4$)—, or —C(R$^4$)$_2$—;

G is selected from a group having the structure:

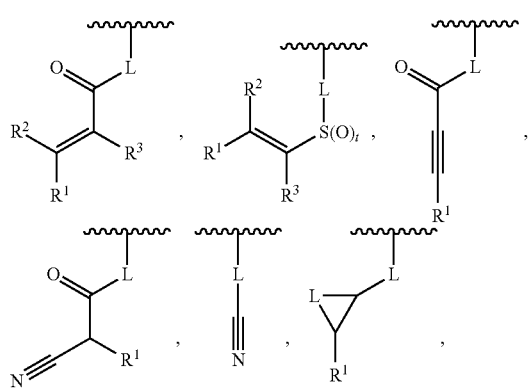

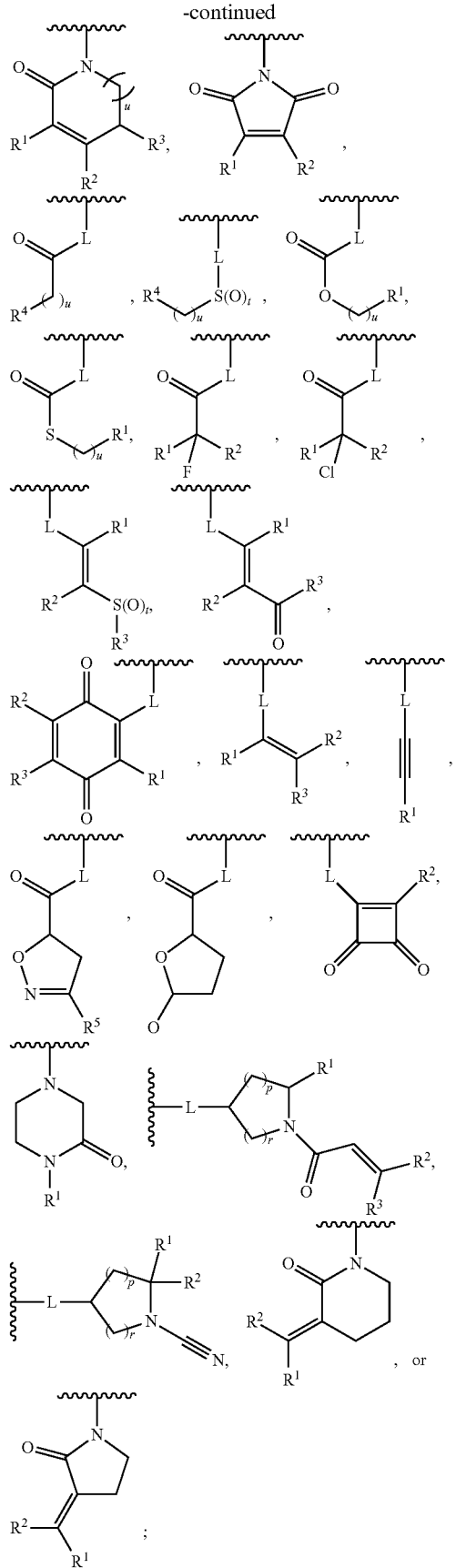

wherein,
L is O, NH, N (optionally substituted C1-C4 alkyl), or —NH—CH$_2$—* wherein the * denotes the point of attachment to the phenyl ring;

t is 0, 1, or 2;

u is 1, or 2;

p is 0, 1, or 2;

r is 0, 1, or 2;

R$^1$ is selected from hydrogen, optionally substituted C1-C4 alkyl, or optionally substituted heterocyclylalkyl;

R$^2$ is selected from hydrogen, or optionally substituted C1-C4 alkyl;

R$^3$ is selected from hydrogen, —CN, or optionally substituted C1-C4 alkyl;

each R$^4$ is independently selected from optionally substituted C1-C4 alkyl, or optionally substituted heterocyclylalkyl;

R$^5$ is optionally substituted C1-C4 alkyl, or optionally substituted heterocyclylalkyl;

each R$^{11}$ is independently hydrogen, halogen, optionally substituted C1-C6 alkyl, —OH, optionally substituted C1-C4 alkoxy, or two R$^{11}$ groups on the same carbon atom form an oxo;

R$^{12}$ is hydrogen or optionally substituted C1-C4 alkyl;

q is 0, 1, 2, or 3; n is 0, 1, 2, or 3; m is 0, 1, 2, or 3;

each X is independently halogen, optionally substituted C1-C4 alkyl, optionally substituted C1-C4 alkoxy, optionally substituted aminoalkyl, optionally substituted cycloalkyl, optionally substituted heterocyclyl, optionally substituted aryl, or optionally substituted heteroaryl;

Y is a group selected from:

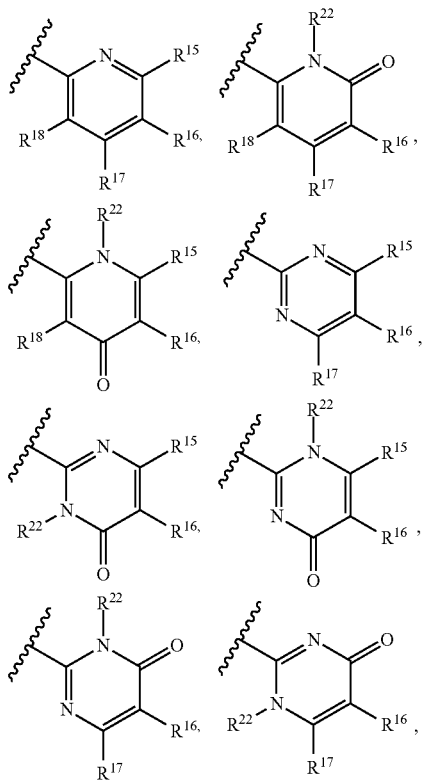

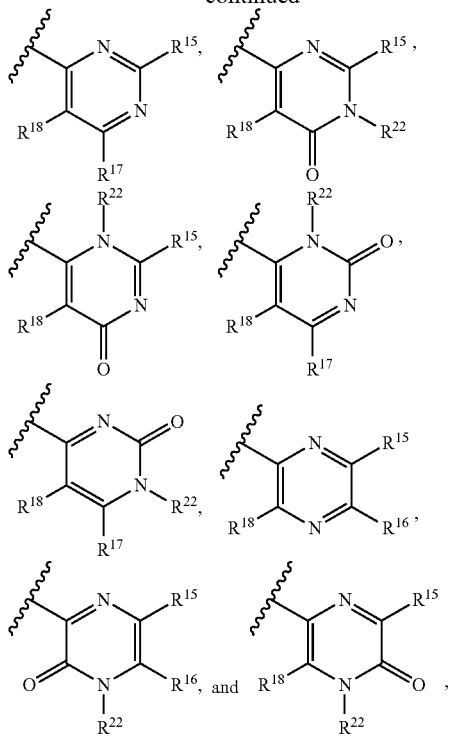

wherein,

R$^{15}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted aryloxy, optionally substituted aralkyloxy, optionally substituted heteroaryloxy, optionally substituted heteroaralkyloxy, —OR$^{22}$, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{16}$ is selected from hydrogen, halogen, —CN, optionally substituted alkyl, optionally substituted alkenyl, optionally substituted alkynyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —OR$^{22}$, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{17}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted aryloxy, optionally substituted aralkyloxy, optionally substituted heteroaryloxy, optionally substituted heteroaralkyloxy, —OR$^{22}$, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{18}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —OR$^{22}$, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound, or pharmaceutically acceptable salt or solvate thereof, having the structure of Formula (II):

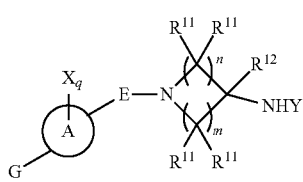

(II)

wherein,
ring A is a monocyclic heteroaryl;
E is selected from a bond, —SO$_2$—, —C(O)—, —CH$_2$—, —CH(R$^4$)—, or —C(R$^4$)$_2$—;
G is selected from a group having the structure:

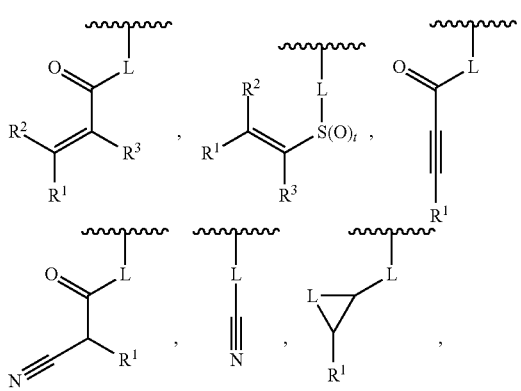

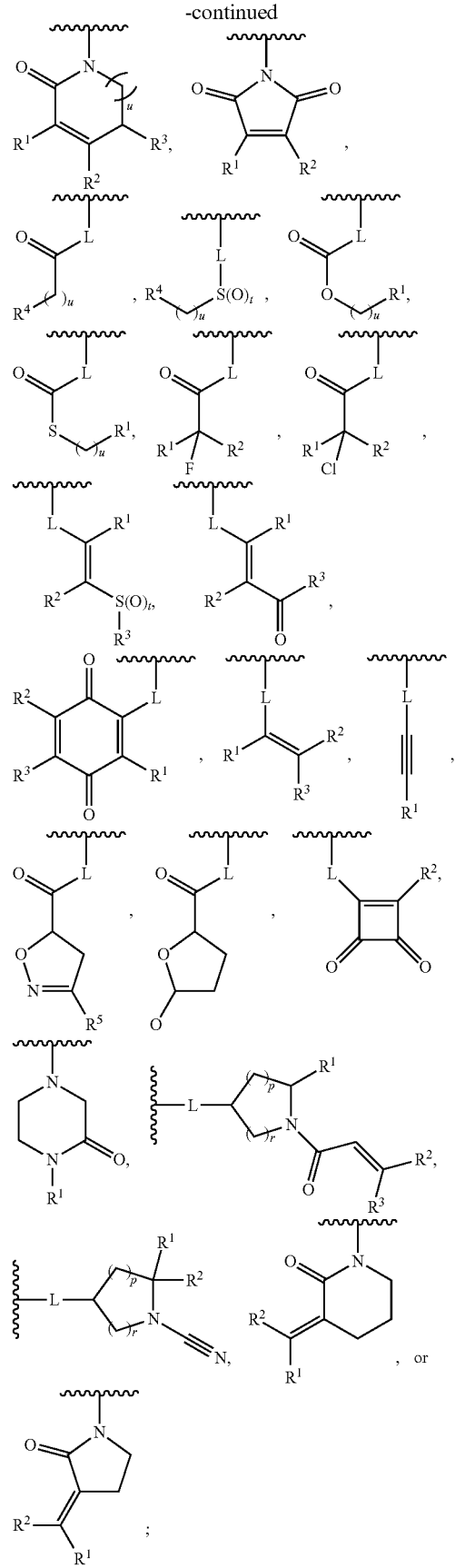

wherein,

L is, NH, or N (optionally substituted C1-C4 alkyl);

t is 0, 1, or 2;

u is 1, or 2;

p is 0, 1, or 2;

r is 0, 1, or 2;

$R^1$ is selected from hydrogen, optionally substituted C1-C4 alkyl, or optionally substituted heterocyclylalkyl;

$R^2$ is selected from hydrogen, or optionally substituted C1-C4 alkyl;

$R^3$ is selected from hydrogen, —CN, or optionally substituted C1-C4 alkyl;

each $R^4$ is independently selected from optionally substituted C1-C4 alkyl, or optionally substituted heterocyclylalkyl;

$R^5$ is optionally substituted C1-C4 alkyl, or optionally substituted heterocyclylalkyl;

each $R^{11}$ is independently hydrogen, halogen, optionally substituted C1-C6 alkyl, —OH, optionally substituted C1-C4 alkoxy, or two $R^{11}$ groups on the same carbon atom form an oxo;

$R^{12}$ is hydrogen or optionally substituted C1-C4 alkyl;

q is 0, 1, 2, or 3;

n is 0, 1, 2, or 3; m is 0, 1, 2, or 3;

each X is independently halogen, optionally substituted C1-C4 alkyl, optionally substituted C1-C4 alkoxy, optionally substituted aminoalkyl, optionally substituted cycloalkyl, optionally substituted heterocyclyl, optionally substituted aryl, or optionally substituted heteroaryl;

Y is a group selected from:

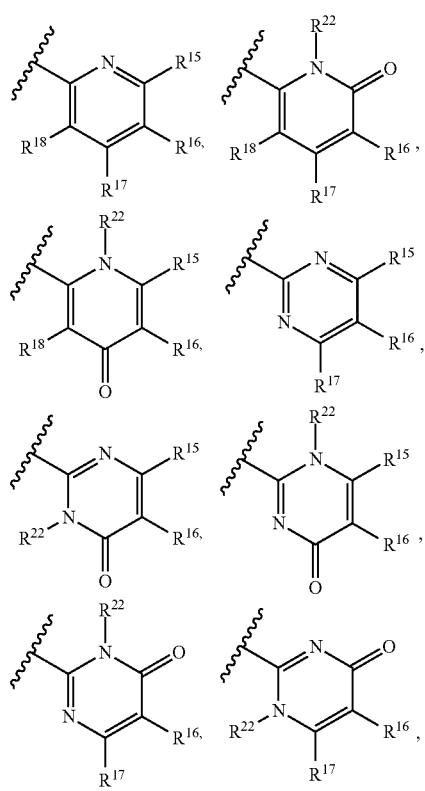

wherein, $R^{15}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{16}$ is selected from hydrogen, halogen, —CN, optionally substituted alkyl, optionally substituted fluoroalkyl, optionally substituted alkenyl, optionally substituted alkynyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{17}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —OR$^{22}$, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{18}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —OR$^{22}$, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound, or pharmaceutically acceptable salt or solvate thereof, having the structure of Formula (III):

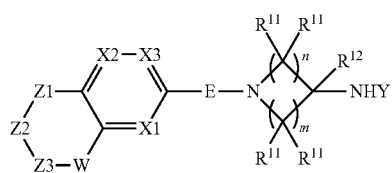

(III)

wherein,

Z1, Z2, and Z3 are selected from CH$_2$ or N-G, with the provision that only one of Z1, Z2, or Z3 is N-G;

X1, X2 and X3 are each independently N or C—R$^7$;

W is absent, O, S, SO$_2$, NH, NR$^{12}$, C(R$^{11}$)$_2$;

E is selected from a bond, —SO$_2$—, —C(O)—, —CH$_2$—, —CH(R$^4$)—, or —C(R$^4$)$_2$—;

G is selected from a group having the structure:

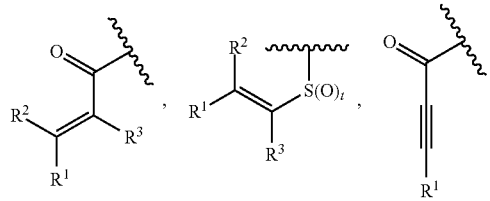

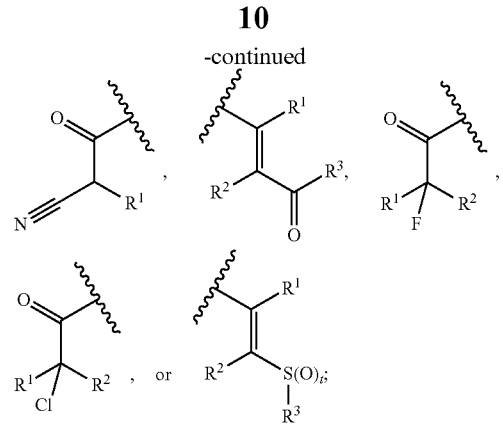

wherein, t is 0, 1, or 2;

R$^1$ is selected from hydrogen, optionally substituted C1-C4 alkyl, or optionally substituted heterocyclylalkyl;

R$^2$ is selected from hydrogen, or optionally substituted C1-C4 alkyl;

R$^3$ is selected from hydrogen, —CN, or optionally substituted C1-C4 alkyl;

each R$^4$ is independently selected from optionally substituted C1-C4 alkyl, or optionally substituted heterocyclylalkyl;

each R$^7$ is independently hydrogen, halogen, optionally substituted C1-C4 alkyl, optionally substituted C1-C4 alkoxy, optionally substituted cycloalkyl, optionally substituted heterocyclyl, optionally substituted aryl, or optionally substituted heteroaryl each R$^{11}$ is independently hydrogen, halogen, optionally substituted C1-C6 alkyl, or two R$^{11}$ groups on the same carbon atom form an oxo;

each R$^{12}$ is independently hydrogen or optionally substituted C1-C4 alkyl;

n is 0, 1, 2, or 3; m is 0, 1, 2, or 3;

Y is a group selected from:

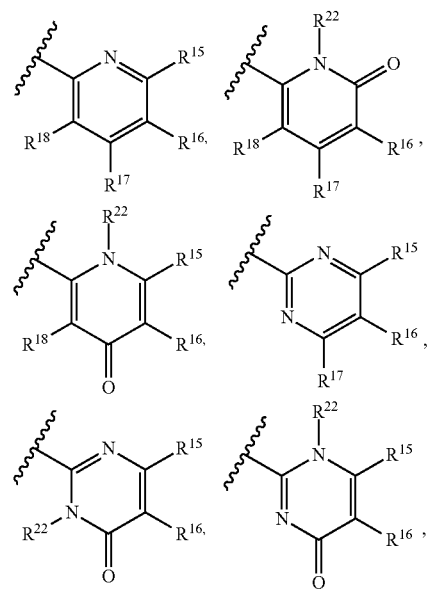

-continued

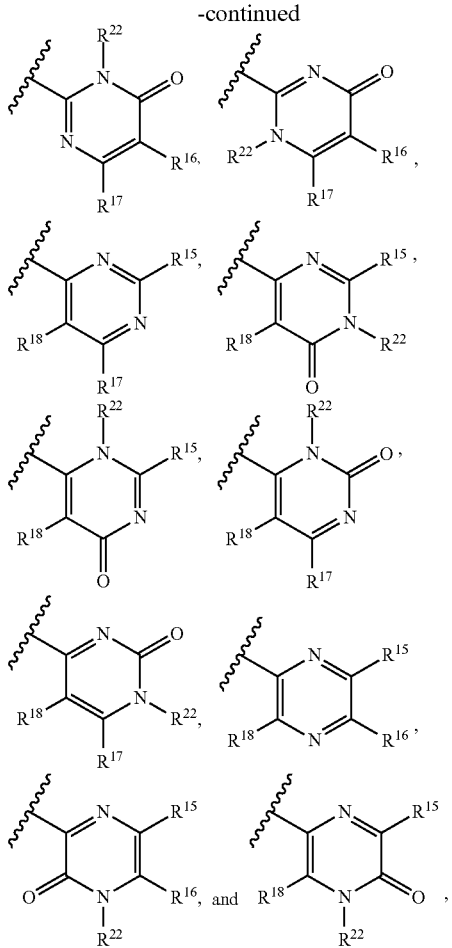

wherein,

R$^{15}$ is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{16}$ is selected from hydrogen, halogen, —CN, optionally substituted alkyl, optionally substituted alkenyl, optionally substituted alkynyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{17}$ is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{18}$ is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

One embodiment provides a method of treating cancer in a patient in need thereof comprising administering to the patient a compound of Formula (I), or pharmaceutically acceptable salt or solvate thereof. Another embodiment provides the method wherein the disease or disorder is cancer.

One embodiment provides a pharmaceutical composition comprising a compound of Formula (II), or pharmaceutically acceptable salt or solvate thereof, and at least one pharmaceutically acceptable excipient.

One embodiment provides a method of treating a disease or disorder in a patient in need thereof comprising administering to the patient a compound of Formula (II), or pharmaceutically acceptable salt or solvate thereof. Another embodiment provides the method wherein the disease or disorder is cancer.

One embodiment provides a method of treating cancer in a patient in need thereof comprising administering to the patient a compound of Formula (II), or pharmaceutically acceptable salt or solvate thereof. Another embodiment provides the method wherein the disease or disorder is cancer.

One embodiment provides a pharmaceutical composition comprising a compound of Formula (III), or pharmaceutically acceptable salt or solvate thereof, and at least one pharmaceutically acceptable excipient.

One embodiment provides a method of treating a disease or disorder in a patient in need thereof comprising administering to the patient a compound of Formula (III), or pharmaceutically acceptable salt or solvate thereof. Another embodiment provides the method wherein the disease or disorder is cancer.

One embodiment provides a method of treating cancer in a patient in need thereof comprising administering to the patient a compound of Formula (III), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), het- "Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Amionoalkyl" refers to a —N(alkyl)$_2$ radical, wherein each "alkyl" is independently as defined above, for example, dimethylamino, ethyl(methyl)amino, 2-aminoethyl)(methyl)amino, (2-(dimethylamino)ethyl)(methyl)amino, and the like. In some embodiments, the alkyl part of the aminoalkyl radical is optionally substituted as defined above for an alkyl group.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)R$^a$ (where t is 1 or 2), —R$^b$—S(O)OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

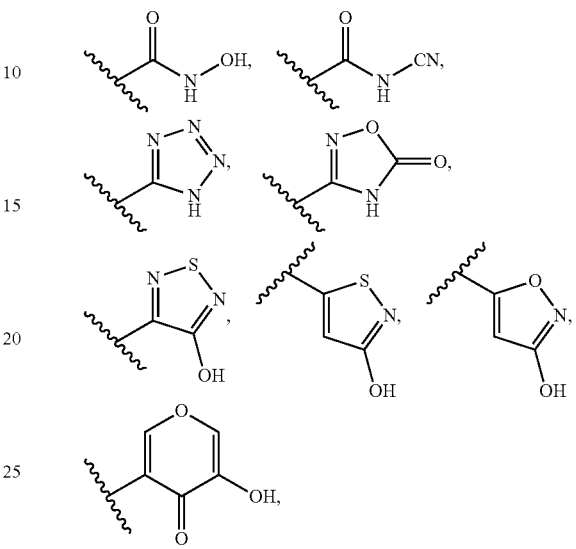

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$OR^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

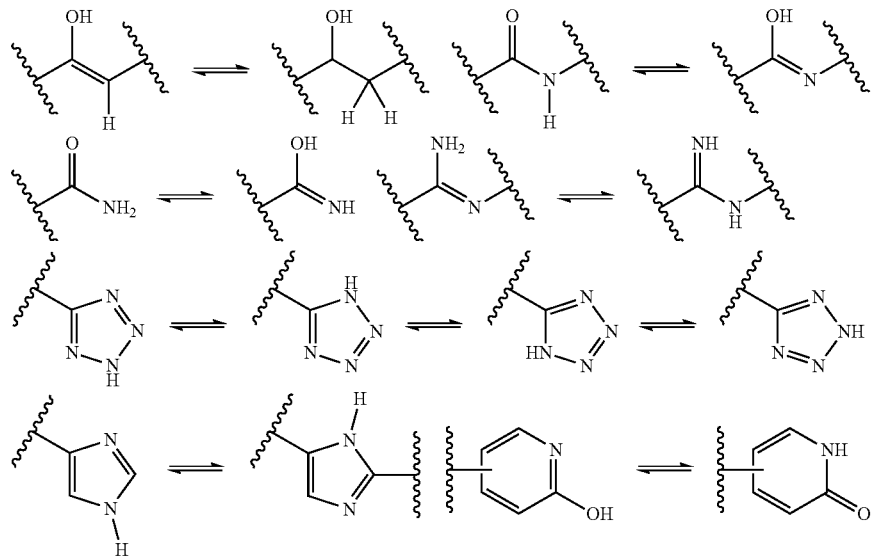

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334, 997. As described in U.S. Pat. Nos. 5,846,514 and 6,334, 997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}$H), tritium ($^{3}$H), iodine-125 ($^{125}$I) or carbon-14 ($^{14}$C). Isotopic substitution with $^{2}$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. In some embodiments, isotopic substitution with $^{18}$F is contemplated. All isotopic variations of the compounds of the present invention, whether radioactive or not, are encompassed within the scope of the present invention.

In certain embodiments, the compounds disclosed herein have some or all of the $^{1}$H atoms replaced with $^{2}$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

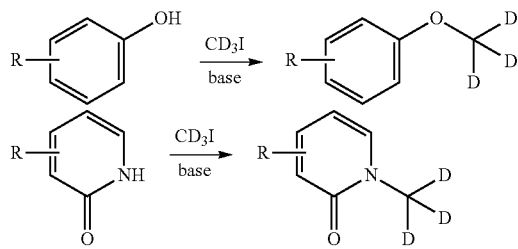

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

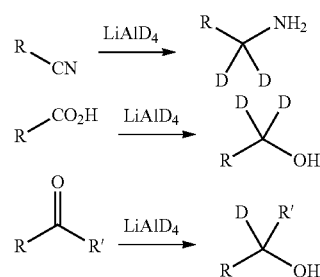

Deuterium gas and palladium catalyst are employed to reduce unsaturated carbon-carbon linkages and to perform a reductive substitution of aryl carbon-halogen bonds as illustrated, by way of example only, in the reaction schemes below.

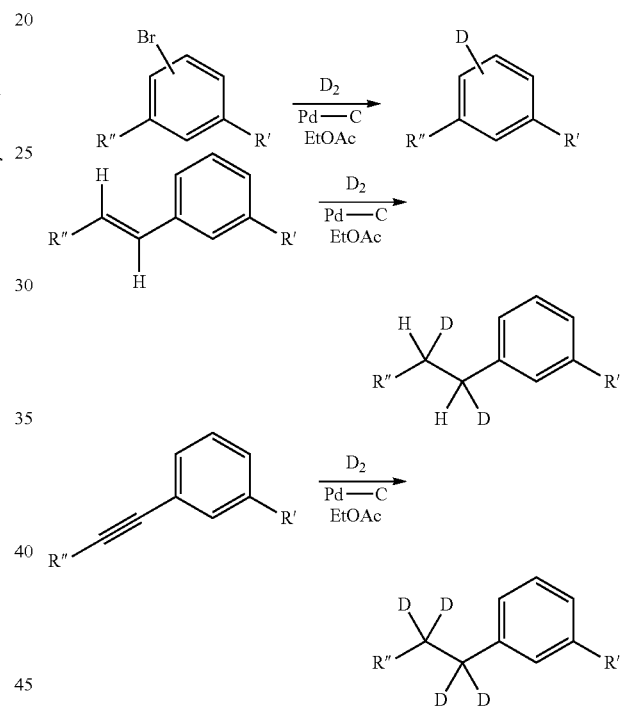

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^{1}$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the inhibitor of cyclin-dependent kinases (CDKs)

compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Cyclin-Dependent Kinases

Cyclin-dependent kinases (CDKs) are a family of serine/threonine protein kinases that are known to function in the processes of cell cycle regulation, metabolism, gene transcription, RNA processing, and DNA repair, with each CDK playing a distinct role (Malumbres, M., 2014, Genome Biol. 15(6), 122-132; Lim et al., 2013, Development 140, 3079-3093). Inhibition of CDKs has long been of therapeutic interest in the treatment of conditions characterized by cellular hyperproliferation, such as cancer, psoriasis, and fungal infections (Coleman, K. G. et al., 1997, Annual Reports in Medicinal Chemistry 32, 171-179).

CDKs are characterized by as being dependent on one or more separate catalytic cyclin subunits in order to carry out specific functions (Malumbres, 2014). Structurally, CDKs comprise a conserved catalytic core containing an ATP-binding pocket, a cyclin binding domain, and an activating T-loop motif (Coleman, 1997; Enke et al., 1999, J. Biol. Chem. 274(4), 1949-1956).

Human cells are known to have at least 20 CDKs and 29 cyclins, which can be grouped into 8 subfamilies (Lim, 2013; Cao et al., 2014, BMC Evol. Biol. 14, 10-26). Therapies known in the art include selective inhibition of specific CDKs.

CDK7 and CDK9 are part of the subfamily of transcriptional CDKs which regulate gene transcription via the phosphorylation of the carboxy-terminal domain of RNA polymerase II (Lucking, U., 2017, Chem Med Chem. 12(21), 1776-1793). Inhibitors of CDK7 and CDK9 are recognized in the art as being therapeutically beneficial against various types of cancers.

CDK7 is known to be required for activity-dependent neuronal gene expression, synaptic plasticity, and long-term memory (He et al., 2017, Front. Mol. Neurosci. 10, 365-377). CDK7 inhibition is known to suppress rheumatoid arthritis inflammation via blocking NF-kB activation and IL-1β/IL-6 secretion (Hong et al., 2017, J. Cell. Mol. Med. 22, 1292-1301), and has been shown to disrupt the cell cycle of high-grade glioma (Greenall et al., 2017, Oncogenesis 6(5), e336). The CDK7 inhibitor THZ1 has been shown to significantly affect transcription in T cell leukemia, neuroblastoma, small-cell lung cancer and triple-negative breast cancer cells in vitro (Gao et al., 2017, Cell Chem. Biol. 25, 1-8; Kwiatkowski et al., 2014, Nature 511(7511), 616-620). When screened against a panel of 1,151 cancer cell lines, a THZ1 concentration less than 200 nM exhibited an IC50 in 52% of those lines (Kwiatkowski, 2014, see Table 3a).

CDK9 is known to regulate the expression of antiapoptotic proteins for the survival of cancer cells (Pang et al., 2017, Cancer Med. 6(10), 2398-2409) and is known to regulate the DNA damage response in complex with cyclin-K (Lim, 2013). Inhibitors of CDK9 have been shown to repress transcription of genes associated with B-cell lymphoma, the most common form of non-Hodgkin lymphoma (Dey et al., 2017, Sci. Rep. 7(1), 18007), hepatocellular carcinoma (Pang, 2017), NUT midline carcinoma (Brägelmann et al., 2017, Cell Rep. 20(12), 2833-2845), ovarian cancer, epithelial carcinoma, colorectal carcinoma, cervical carcinoma, prostate adenocarcinoma, breast adenocarcinoma, and pancreatic carcinoma (Lam et al., 2014, Oncotarget 5, 7691-7704).

CDK12 and CDK13 are transcription-associated CDKs, and are known to regulate RNA polymerase II transcription in complex with cyclin K (Lim, 2013), as well as axonal and transcriptional elongation (Chen et al., 2014, Exp. Neurol. 261, 10-21; Paculová et al., 2017, Cell Div. 12, 7-17).

It has been suggested that CDK12 has oncogenic properties, and is mutated or overexpressed in various types of cancer, leading to dysregulation of cell proliferation (Paculová, 2017). CDK12 inhibitors have been found to reduce gene expression in BRCA cells (Johnson et al., 2016, Cell Rep. 17(9), 2367-2381). Mutations of CDK12 have been shown to disrupt DNA repair, contributing to hyperproliferation and the pathogenesis of breast tumor cells (Tien et al., 2017, Nucleic Acids Res. 45(11), 6698-6716). It is estimated that CDK12 mutations are present in 13% of breast cancers and 5% of ovarian cancers (Tien, 2017; Cerami et al., 2012, Cancer Discov. 2, 401-404; Cancer Genome Atlas Research Network, 2011, Nature, 474, 609-615; Kandoth et al., 2013, Nature 502, 333-339; Cancer Genome Atlas Network, 2012, Nature 490, 61-70).

CDK13 is known to regulate processes associated with growth signaling (Greifenberg et al., 2016, Cell Rep. 14, 320-331). CDK13 mutations affecting the protein kinase domain have been linked to congenital heart disease, developmental delay and intellectual disability (Hamilton et al., 2017, J. Med. Genet. 55(1), 28-38). CDK13 is known to interact with the splicing factor SRSF1 and regulate alternative splicing of HIV mRNA (Berro et al., 2008, J. Virol. 82, 7155-7166).

CDK inhibitory compounds have been described in the literature. See, for example: Gao et al., 2018, Cell Chem. Biol. 25(2), 135-142; WO 2017/044858; WO 2016/210296; WO 2016/201370; Ficarro et al., 2016, Anal. Chem. 88(24), 12248-12254; WO 2016/160617; Zhang et al., 2016, Nature Chem. Biol. 12(10), 876-884; WO 2016/105528; WO 2015/058126; and WO 2015/058163. Other examples include: WO 2015/124941; Ali et al., 2009, Cancer Res. 69(15), 6208-6215; WO 2016/193939; Bajrami et al., 2014, Cancer Res. 74(1), 287-297; Li et al., 2017, Cancer Res. 77(14), 3834-3845; Cayrol et al., 2017, Nature Commun. 8:14290, 1-11; Johnson et al., 2016, Cell Reports 17(9), 2367-2381; Kalan et al., 2017, Cell Reports 21(2), 467-481; Christensen et al., 2014, Cancer Cell 26(6), 909-922; Iniguez et al., 2018, Cancer Cell 33(2), 202-216; Mertins et al., 2016, Nature 534(7605), 55-62; Nagaraja et al., 2017, Cancer Cell 31(5), 635-652; Naidoo et al., 2017, Mol. Cancer Ther. 17(1), 306-315; Paculova et al., 2017, Cell Div. 12:7, 1-10; and Evan et al., 2017, Clin. Cancer Res. 23(7), 1647-1655.

Based on the role of CDKs in the processes of cell cycle regulation, metabolism, gene transcription, RNA processing, and DNA repair, compounds which alter CDKs activity are considered to be useful in treating or preventing various disorders, including cancer. In some embodiments, described herein is a small molecule inhibitor of cyclin-dependent kinases (CDKs). In some embodiments, described herein is a pharmaceutical composition comprising a small molecule inhibitor of cyclin-dependent kinases (CDKs). In other embodiments, a small molecule inhibitor of cyclin-dependent kinases (CDKs) is used to treat or prevent a disease or condition in a subject in need thereof.

In some embodiments, a heteroaromatic CDK inhibitory compound as described herein is used to treat or prevent cancer in a subject in need thereof. In some embodiments, a pharmaceutical composition comprising a heteroaromatic CDK inhibitory compound as described herein is used to treat or prevent cancer in a subject in need thereof. In some embodiments, disclosed herein is a method of treating cancer comprising administering to a subject in need thereof a therapeutically effective amount of a heteroaromatic CDK inhibitory compound as described herein. In some embodiments, disclosed herein is a method of treating cancer comprising administering to a subject in need thereof a therapeutically effective amount of a pharmaceutical composition comprising a heteroaromatic CDK inhibitory compound as described herein. In some embodiments, disclosed herein is a method of treating cancer comprising administering to a subject having been previously diagnosed with cancer a therapeutically effective amount of a heteroaromatic CDK inhibitory compound as described herein.

In some embodiments, a heteroaromatic CDK inhibitory compound is a heteroaromatic CDK7, CDK9, CDK12, and CDK13 inhibitory compound. In some embodiments, a heteroaromatic CDK inhibitory compound is a heteroaromatic CDK7 inhibitory compound. In some embodiments, a heteroaromatic CDK inhibitory compound is a heteroaromatic CDK9 inhibitory compound. In some embodiments, a heteroaromatic CDK inhibitory compound is a heteroaromatic CDK12 inhibitory compound. In some embodiments, a heteroaromatic CDK inhibitory compound is a heteroaromatic CDK13 inhibitory compound. In some embodiments, a heteroaromatic CDK inhibitory compound is a heteroaromatic CDK7 and CDK9 inhibitory compound. In some embodiments, a heteroaromatic CDK inhibitory compound is a heteroaromatic CDK7 and CDK12 inhibitory compound. In some embodiments, a heteroaromatic CDK inhibitory compound is a heteroaromatic CDK7 and CDK13 inhibitory compound. In some embodiments, a heteroaromatic CDK inhibitory compound is a heteroaromatic CDK9 and CDK12 inhibitory compound. In some embodiments, a heteroaromatic CDK inhibitory compound is a heteroaromatic CDK9 and CDK13 inhibitory compound. In some embodiments, a heteroaromatic CDK inhibitory compound is a heteroaromatic CDK12 and CDK13 inhibitory compound. In some embodiments, a heteroaromatic CDK inhibitory compound is a heteroaromatic CDK7, CDK9, and CDK12 inhibitory compound.

In some embodiments, a heteroaromatic CDK inhibitory compound is a heteroaromatic CDK7, CDK9, and CDK13 inhibitory compound. In some embodiments, a heteroaromatic CDK inhibitory compound is a heteroaromatic CDK7, CDK12, and CDK13 inhibitory compound. In some embodiments, a heteroaromatic CDK inhibitory compound is a heteroaromatic CDK9, CDK12, and CDK13 inhibitory compound.

Heteroaromatic CDK Inhibitory Compounds

In one aspect, provided herein is a heteroaromatic CDK inhibitory compound.

One embodiment provides a compound, or pharmaceutically acceptable salt or solvate thereof, having the structure of Formula (I):

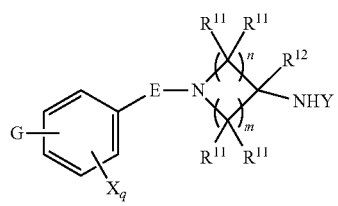

(I)

wherein,
E is selected from a bond, —SO$_2$—, —C(O)—, —CH$_2$—, —CH(R$^4$)—, or —C(R$^4$)$_2$—;
G is selected from a group having the structure:

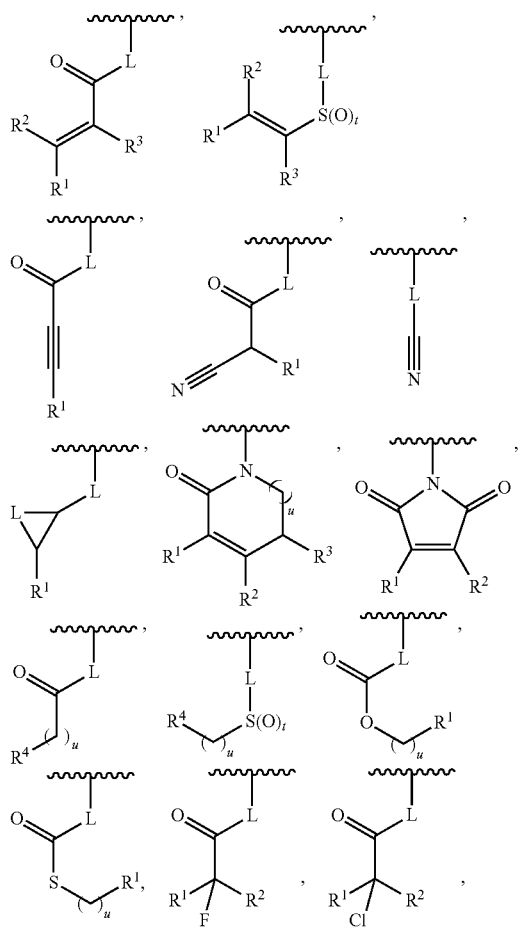

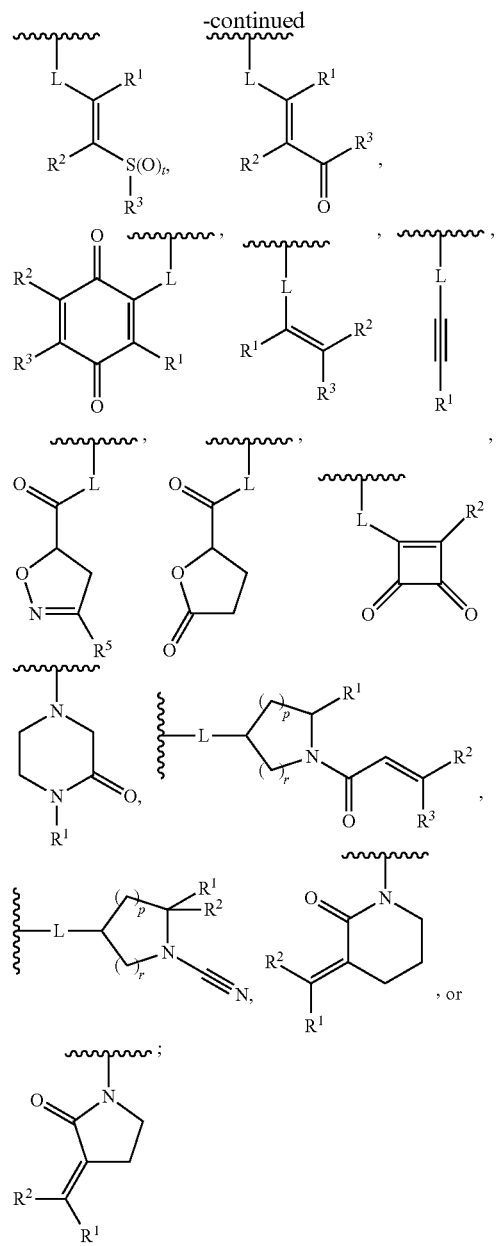

wherein,
L is O, NH, N (optionally substituted C1-C4 alkyl), or —NH—CH$_2$—* wherein the * denotes the point of attachment to the phenyl ring;
t is 0, 1, or 2;
u is 1, or 2;
p is 0, 1, or 2;
r is 0, 1, or 2;
R$^1$ is selected from hydrogen, optionally substituted C1-C4 alkyl, or optionally substituted heterocyclylalkyl;
R$^2$ is selected from hydrogen, or optionally substituted C1-C4 alkyl;
R$^3$ is selected from hydrogen, —CN, or optionally substituted C1-C4 alkyl;
each R$^4$ is independently selected from optionally substituted C1-C4 alkyl, or optionally substituted heterocyclylalkyl;
R$^5$ is optionally substituted C1-C4 alkyl, or optionally substituted heterocyclylalkyl;

each $R^{11}$ is independently hydrogen, halogen, optionally substituted C1-C6 alkyl, —OH, optionally substituted C1-C4 alkoxy, or two $R^{11}$ groups on the same carbon atom form an oxo;

$R^{12}$ is hydrogen or optionally substituted C1-C4 alkyl;

q is 0, 1, 2, or 3; n is 0, 1, 2, or 3; m is 0, 1, 2, or 3;

each X is independently halogen, optionally substituted C1-C4 alkyl, optionally substituted C1-C4 alkoxy, optionally substituted aminoalkyl, optionally substituted cycloalkyl, optionally substituted heterocyclyl, optionally substituted aryl, or optionally substituted heteroaryl;

Y is a group selected from:

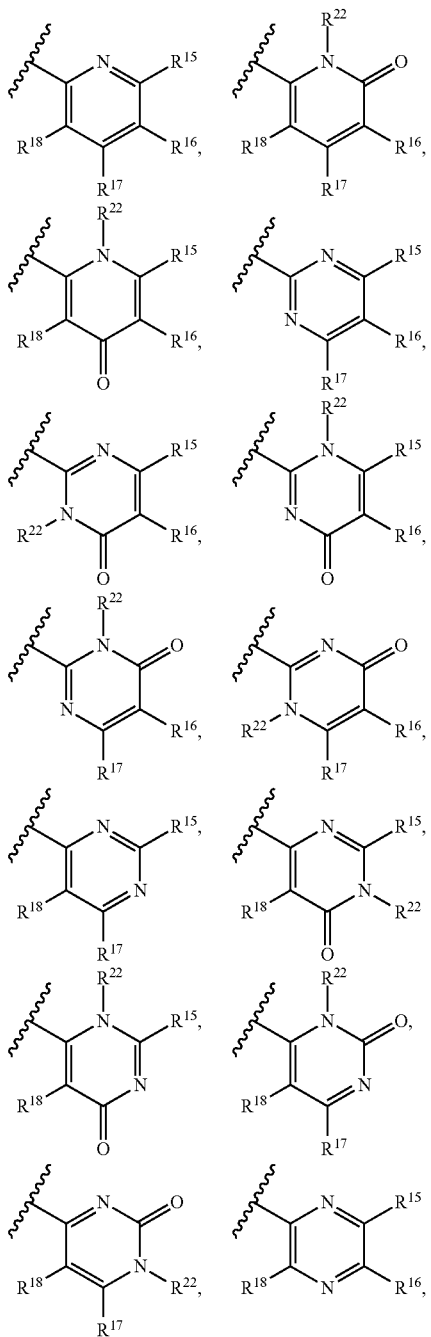

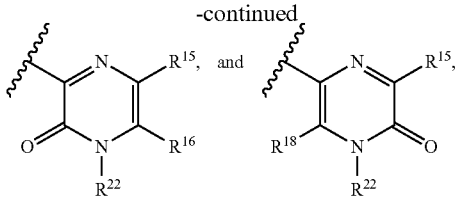

wherein, $R^{15}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{16}$ is selected from hydrogen, halogen, —CN, optionally substituted alkyl, optionally substituted alkenyl, optionally substituted alkynyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{17}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

In some embodiments,

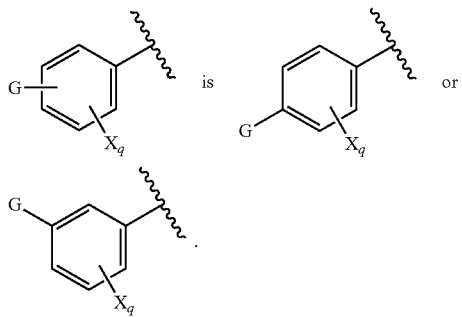

In some embodiments,

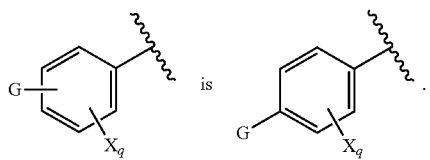

In some embodiments,

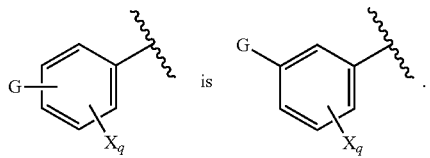

In some embodiments, G is

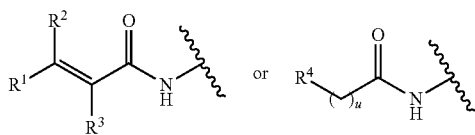

In some embodiments, G is

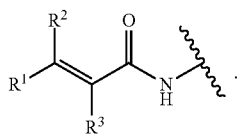

In some embodiments, G is

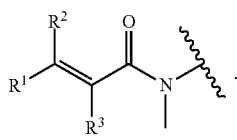

In some embodiments, G is

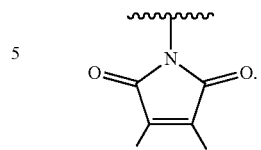

In some embodiments, G is

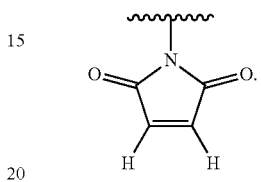

In some embodiments, $R^3$ is hydrogen or —CN.
In some embodiments, L is O, NH, or N (optionally substituted C1-C4 alkyl);
In some embodiments, L is NH. In some embodiments, L is $NCH_3$.
In some embodiments, t is 2.
In some embodiments, q is 0, 1, or 2.
In some embodiments, q is 0, or 1.
In some embodiments, q is 0.
In some embodiments, X is a halogen.
In some embodiments, $R^2$ is hydrogen.
In some embodiments, $R^3$ is hydrogen.
In some embodiments, $R^2$ and $R^3$ is hydrogen.
In some embodiments, $R^1$ is hydrogen. In some embodiments, $R^1$ is optionally substituted C1-C4 alkyl. In some embodiments, $R^1$ is optionally substituted C1-C2 alkyl. In some embodiments, $R^1$ is optionally substituted C1 alkyl. In some embodiments, the C1 alkyl is substituted with an optionally substituted amino group. In some embodiments, the optionally substituted amino group is a dimethylamino.
In some embodiments, $R^1$ is —$CH_2$—$N(Me)_2$.
In some embodiments, $R^1$ is optionally substituted heterocyclylalkyl. In some embodiments, the optionally substituted heterocyclylalkyl comprises an optionally substituted C1 alkyl. In some embodiments, the optionally substituted heterocyclylalkyl comprises an optionally substituted N-linked heterocyclyl. In some embodiments, the optionally substituted N-linked heterocyclyl is an N-linked pyrrolidine or piperidine.
In some embodiments, n is 1 and m is 1. In some embodiments, n is 1 and m is 2. In some embodiments, n is 1 and m is 3.
In some embodiments, $R^{11}$ is hydrogen. In some embodiments, n is 1 and m is 2; and $R^{11}$ is hydrogen.
In some embodiments, Y is selected from:

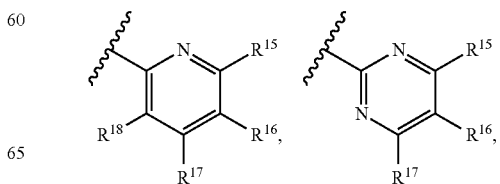

-continued

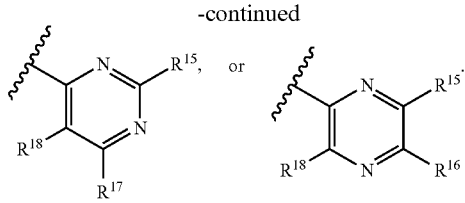

In some embodiments, Y is:

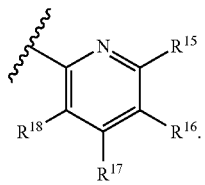

In some embodiments, Y is:

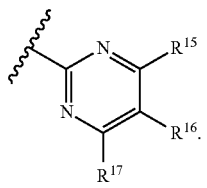

In some embodiments, $R^{15}$ is selected from hydrogen, halogen, —CN, and optionally substituted alkyl. In some embodiments, $R^{15}$ is hydrogen.

In some embodiments, $R^{16}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$.

In some embodiments, L is O, NH, or N (optionally substituted C1-C4 alkyl); and $R^{16}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$.

In some embodiments, $R^{16}$ is selected from hydrogen, halogen, —CN, and optionally substituted alkyl. In some embodiments, $R^{16}$ is hydrogen.

In some embodiments, $R^{16}$ is selected from optionally substituted alkyl, optionally substituted alkenyl, or optionally substituted alkynyl. In some embodiments, $R^{16}$ is selected from optionally substituted alkynyl.

In some embodiments, Y is:

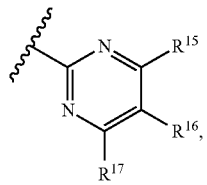

and $R^{16}$ is not hydrogen.

In some embodiments, Y is:

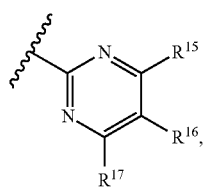

and $R^{16}$ is halogen.

In some embodiments, Y is:

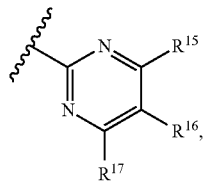

and $R^{16}$ is selected from optionally substituted alkyl, optionally substituted alkenyl, or optionally substituted alkynyl.

In some embodiments, Y is:

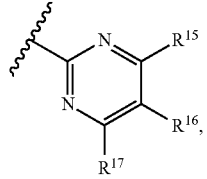

$R^{15}$ is hydrogen, $R^{16}$ is selected from optionally substituted alkynyl, and $R^{17}$ is hydrogen or optionally substituted alkoxy.

In some embodiments, Y is:

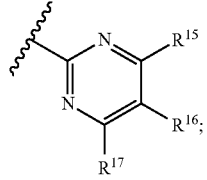

optionally substituted alkyl, optionally substituted alkenyl, or optionally substituted alkynyl In some embodiments, n is 1 and m is 2; Y is:

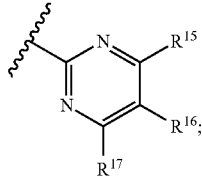

$R^{15}$ is hydrogen, $R^{16}$ is selected from halogen, —CN, optionally substituted alkyl, optionally substituted fluoroalkyl, optionally substituted alkenyl, optionally substituted alkynyl, and $R^{17}$ is hydrogen or optionally substituted alkoxy.

In some embodiments, $R^{17}$ is selected from hydrogen, halogen, —CN, and optionally substituted alkyl. In some embodiments, $R^{17}$ is hydrogen.

In some embodiments, $R^{18}$ is selected from hydrogen, halogen, —CN, and optionally substituted alkyl. In some embodiments, $R^{18}$ is hydrogen.

In some embodiments, $R^{15}$ and $R^{16}$ are hydrogen. In some embodiments, $R^{17}$ and $R^{18}$ are hydrogen.

In some embodiments, $R^{15}$ and $R^{17}$ are hydrogen.

In some embodiments, E is a bond. In some embodiments, E is —SO$_2$—. In some embodiments, E is —C(O)—. In some embodiments, E is —CH$_2$—. In some embodiments, E is —CH(R$^4$)—. In some embodiments, E is —C(R$^4$)$_2$—.

In some embodiments, $R^{12}$ is hydrogen. In some embodiments, $R^{12}$ is optionally substituted C1-C4 alkyl.

One embodiment provides the compound of Formula (I), or pharmaceutically acceptable salt or solvate thereof, wherein

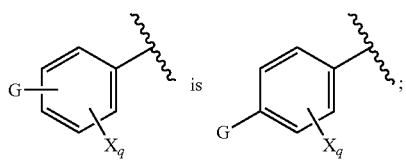

Y is:

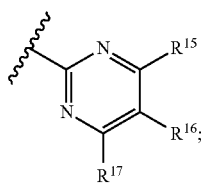

$R^{11}$ and $R^{12}$ are hydrogen; n is 1 and m is 2; and E is —C(O)—.

One embodiment provides the compound of Formula (I), or pharmaceutically acceptable salt or solvate thereof, wherein

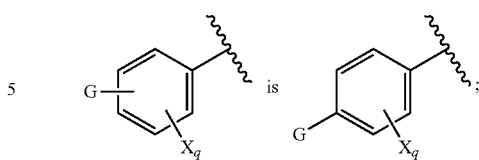

G is

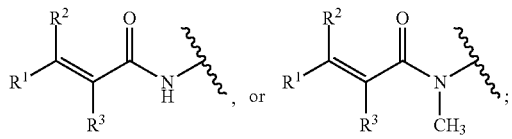

Y is:

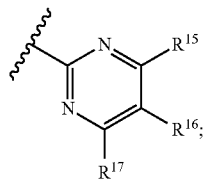

$R^{11}$ and $R^{12}$ are hydrogen; n is 1 and m is 2; and E is —C(O)—.

One embodiment provides the compound of Formula (I), or pharmaceutically acceptable salt or solvate thereof, wherein

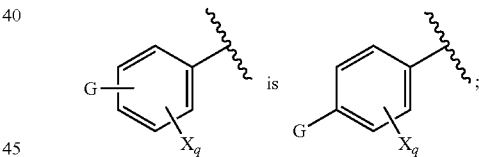

Y is:

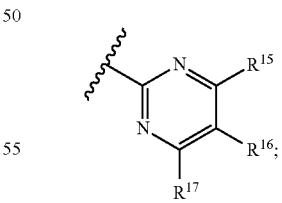

$R^{15}$ is hydrogen, $R^{16}$ is selected from halogen, —CN, optionally substituted alkyl, optionally substituted fluoroalkyl, optionally substituted alkynyl, and $R^{17}$ is hydrogen or optionally substituted alkoxy; $R^{11}$ and $R^{12}$ are hydrogen; n is 1 and m is 2; and E is —C(O)—.

One embodiment provides the compound of Formula (I), or pharmaceutically acceptable salt or solvate thereof, wherein

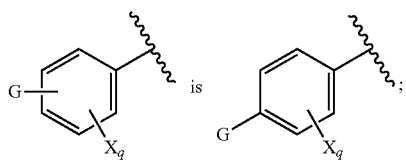 is q is 0; G is

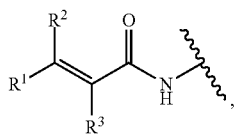

or

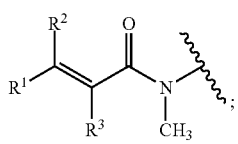

$R^1$, $R^2$ and $R^3$ are each hydrogen; Y is:

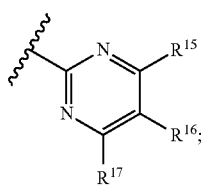

$R^{15}$ is hydrogen, $R^{16}$ is selected from halogen, —CN, optionally substituted alkyl, optionally substituted fluoroalkyl, optionally substituted alkynyl, and $R^{17}$ is hydrogen or optionally substituted alkoxy; $R^{11}$ and $R^{12}$ are hydrogen; n is 1 and m is 2; and E is —C(O)—.

One embodiment provides a compound, or pharmaceutically acceptable salt or solvate thereof, having the structure of Formula (II):

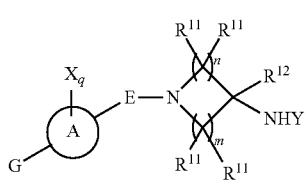

wherein, ring A is a monocyclic heteroaryl;

E is selected from a bond, —SO$_2$—, —C(O)—, —CH$_2$—, —CH(R$^4$)—, or —C(R$^4$)$_2$—;

G is selected from a group having the structure:

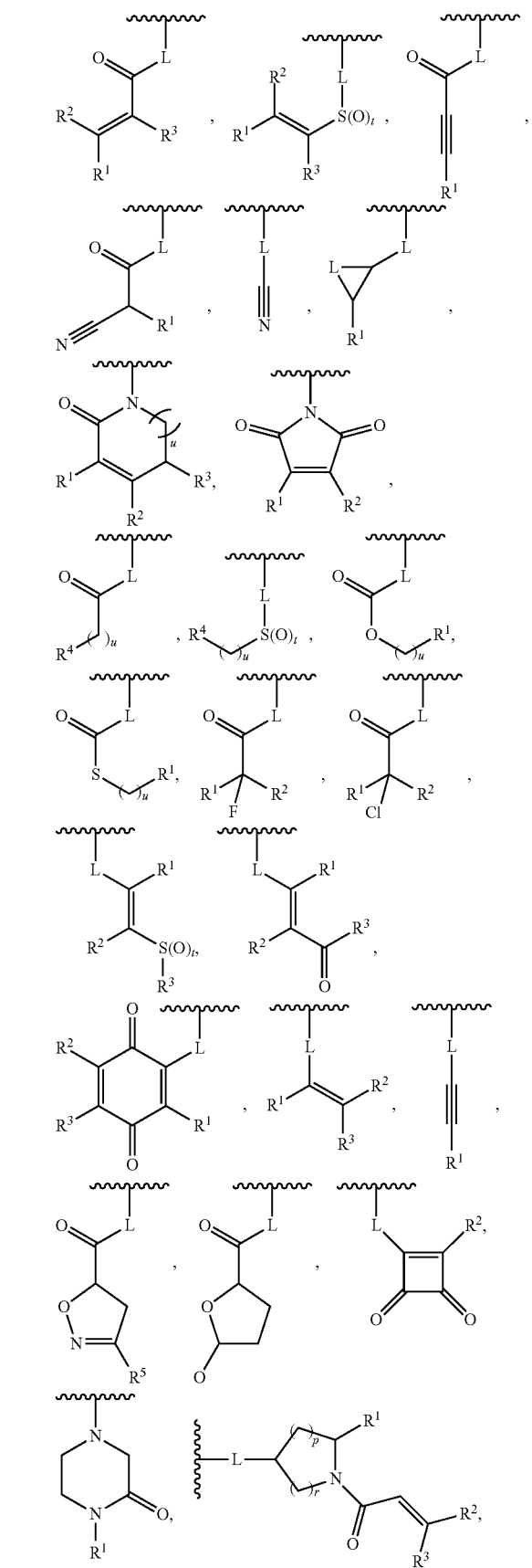

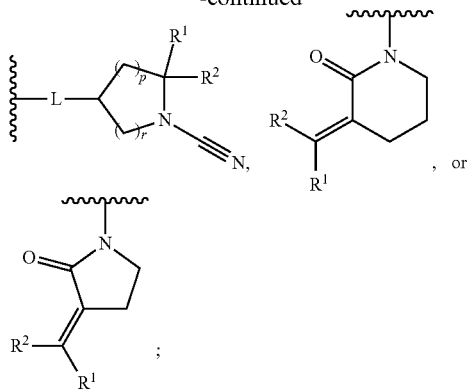

wherein,
L is O, NH, or N (optionally substituted C1-C4 alkyl);
t is 0, 1, or 2;
u is 1, or 2;
p is 0, 1, or 2;
r is 0, 1, or 2;
$R^1$ is selected from hydrogen, optionally substituted C1-C4 alkyl, or optionally substituted heterocyclylalkyl;
$R^2$ is selected from hydrogen, or optionally substituted C1-C4 alkyl;
$R^3$ is selected from hydrogen, —CN, or optionally substituted C1-C4 alkyl;
each $R^4$ is independently selected from optionally substituted C1-C4 alkyl, or optionally substituted heterocyclylalkyl;
$R^5$ is optionally substituted C1-C4 alkyl, or optionally substituted heterocyclylalkyl;
each $R^{11}$ is independently hydrogen, halogen, optionally substituted C1-C6 alkyl, —OH, optionally substituted C1-C4 alkoxy, or two $R^{11}$ groups on the same carbon atom form an oxo;
$R^{12}$ is hydrogen or optionally substituted C1-C4 alkyl;
q is 0, 1, 2, or 3;
n is 0, 1, 2, or 3; m is 0, 1, 2, or 3;
each X is independently halogen, optionally substituted C1-C4 alkyl, optionally substituted C1-C4 alkoxy, optionally substituted aminoalkyl, optionally substituted cycloalkyl, optionally substituted heterocyclyl, optionally substituted aryl, or optionally substituted heteroaryl;
Y is a group selected from:

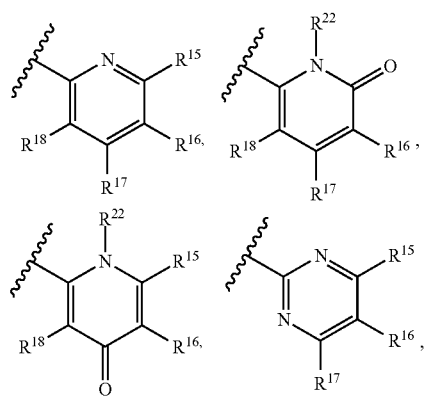

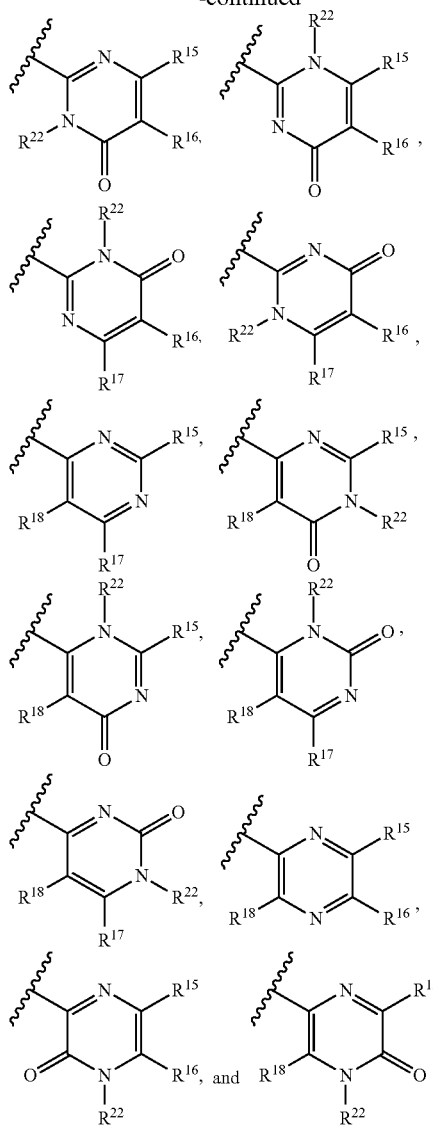

wherein,
$R^{15}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
$R^{16}$ is selected from hydrogen, halogen, —CN, optionally substituted alkyl, optionally substituted fluoroalkyl, optionally substituted alkenyl, optionally substituted alkynyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{17}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{18}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

In some embodiments,

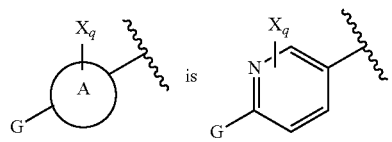

or

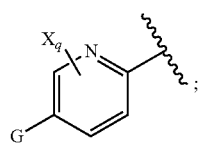

and q is 0, 1, 2, or 3. In some embodiments,

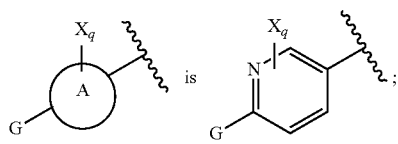

and q is 0, 1, 2, or 3. In some embodiments,

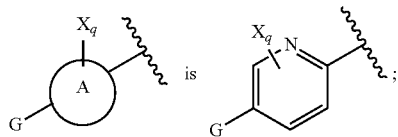

and q is 0, 1, 2, or 3.

In some embodiments,

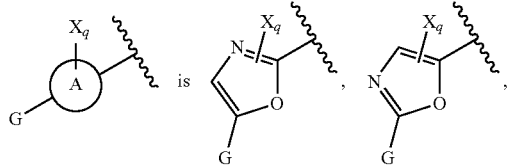

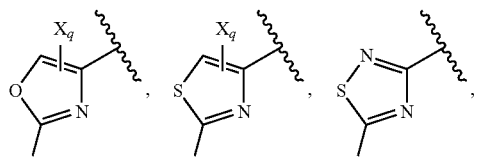

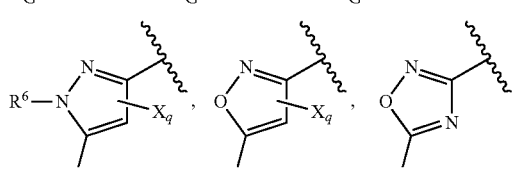

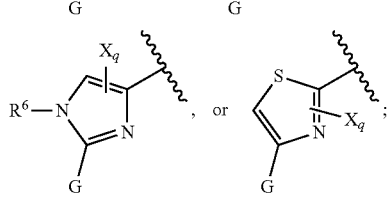

$R^6$ is hydrogen or optionally substituted C1-C4 alkyl; and q is 0 or 1.

In some embodiments,

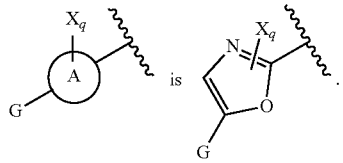

In some embodiments,

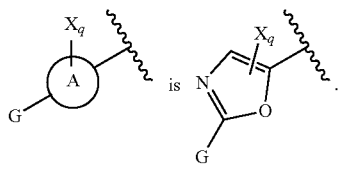

In some embodiments,

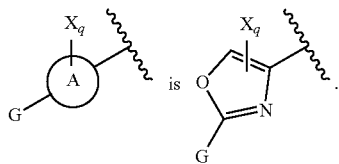

In some embodiments,

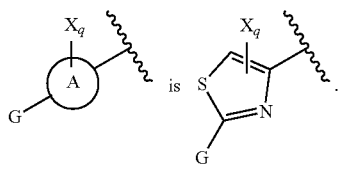

In some embodiments,

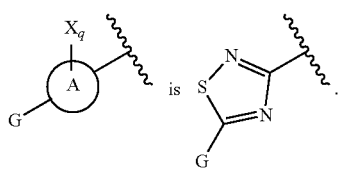

In some embodiments,

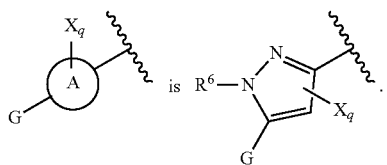

In some embodiments

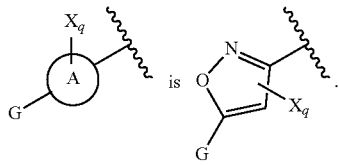

In some embodiments,

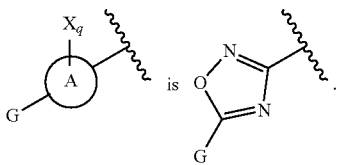

In some embodiments,

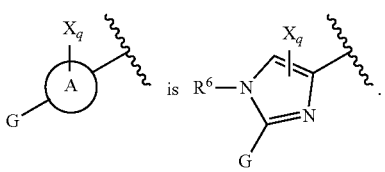

In some embodiments,

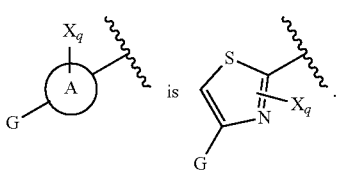

In some embodiments, G is

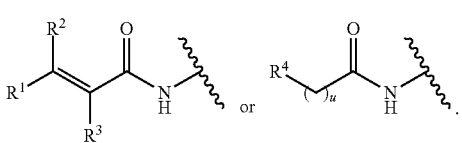

In some embodiments, G is

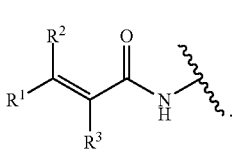

In some embodiments, G is

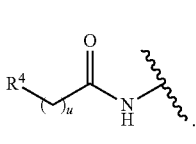

In some embodiments, $R^3$ is hydrogen or —CN.
In some embodiments, L is NH.
In some embodiments, t is 2.
In some embodiments, q is 0 or 1.
In some embodiments, q is 0.
In some embodiments, X is a halogen.
In some embodiments, $R^2$ is hydrogen.
In some embodiments, $R^3$ is hydrogen.
In some embodiments, $R^2$ and $R^3$ is hydrogen.

In some embodiments, $R^1$ is hydrogen. In some embodiments, $R^1$ is optionally substituted C1-C4 alkyl. In some embodiments, $R^1$ is optionally substituted C1-C2 alkyl. In some embodiments, $R^1$ is optionally substituted C1 alkyl. In some embodiments, the C1 alkyl is substituted with an optionally substituted amino group. In some embodiments, the optionally substituted amino group is a dimethylamino.

In some embodiments, $R^1$ is —CH$_2$—N(Me)$_2$.

In some embodiments, $R^1$ is optionally substituted heterocyclylalkyl. In some embodiments, the optionally substituted heterocyclylalkyl comprises an optionally substituted C1 alkyl. In some embodiments, the optionally substituted heterocyclylalkyl comprises an optionally substituted N-linked heterocyclyl. In some embodiments, the optionally substituted N-linked heterocyclyl is an N-linked pyrrolidine or piperidine.

In some embodiments, n is 1 and m is 1. In some embodiments, n is 1 and m is 2. In some embodiments, n is 1 and m is 3.

In some embodiments, Y is selected from:

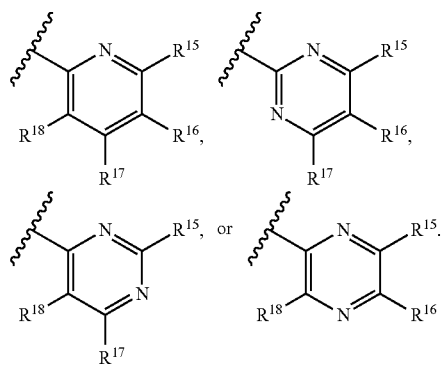

In some embodiments, Y is:

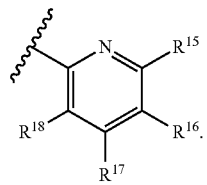

In some embodiments, Y is:

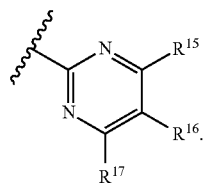

In some embodiments, $R^{15}$ is selected from hydrogen, halogen, —CN, and optionally substituted alkyl. In some embodiments, $R^{15}$ is hydrogen.

In some embodiments, $R^6$ is selected from hydrogen, halogen, —CN, optionally substituted alkyl, optionally substituted fluoroalkyl, optionally substituted alkenyl, optionally substituted alkynyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —OR$^{22}$, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$.

In some embodiments, $R^{16}$ is selected from optionally substituted alkenyl, optionally substituted alkynyl. In some embodiments, $R^{16}$ is selected from optionally substituted alkynyl.

In some embodiments, $R^{16}$ is selected from hydrogen, halogen, —CN, and optionally substituted alkyl. In some embodiments, $R^{16}$ is hydrogen.

In some embodiments, $R^{17}$ is selected from hydrogen, halogen, —CN, and optionally substituted alkyl. In some embodiments, $R^{17}$ is hydrogen.

In some embodiments, $R^{18}$ is selected from hydrogen, halogen, —CN, and optionally substituted alkyl. In some embodiments, $R^{18}$ is hydrogen.

In some embodiments, $R^{15}$ and $R^{16}$ are hydrogen. In some embodiments, $R^{17}$ and $R^{18}$ are hydrogen.

In some embodiments, E is a bond. In some embodiments, E is —SO$_2$—. In some embodiments, E is —C(O)—. In some embodiments, E is —CH$_2$—. In some embodiments, E is —CH(R$^4$)—. In some embodiments, E is —C(R$^4$)$_2$—.

In some embodiments, the heteroaromatic CDK inhibitory compound of Formula (I) or Formula (II) described herein has a structure provided in Table 1.

One embodiment provides a compound, or pharmaceutically acceptable salt or solvate thereof, having the structure of Formula (III):

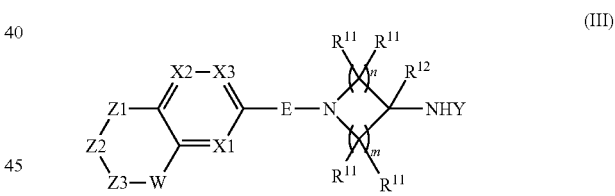

(III)

wherein,

Z1, Z2, and Z3 are selected from CH$_2$ or N-G, with the provision that only one of Z1, Z2, or Z3 is N-G;

X1, X2 and X3 are each independently N or C—R$^7$;

W is absent, O, S, SO$_2$, NH, NR$^{12}$, C(R$^{11}$)$_2$;

E is selected from a bond, —SO$_2$—, —C(O)—, —CH$_2$—, —CH(R$^4$)—, or —C(R$^4$)$_2$—;

G is selected from a group having the structure:

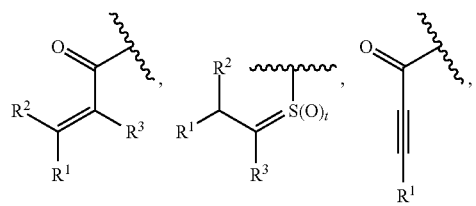

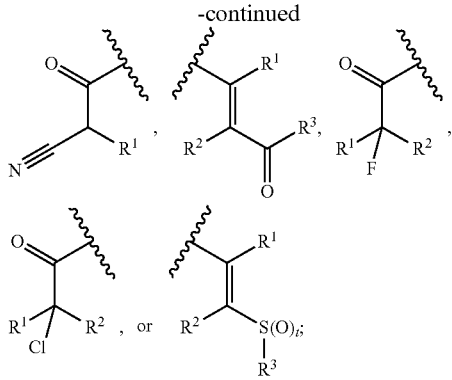

wherein, t is 0, 1, or 2;

$R^1$ is selected from hydrogen, optionally substituted C1-C4 alkyl, or optionally substituted heterocyclylalkyl;

$R^2$ is selected from hydrogen, or optionally substituted C1-C4 alkyl;

$R^3$ is selected from hydrogen, —CN, or optionally substituted C1-C4 alkyl;

each $R^4$ is independently selected from optionally substituted C1-C4 alkyl, or optionally substituted heterocyclylalkyl;

each $R^7$ is independently hydrogen, halogen, optionally substituted C1-C4 alkyl, optionally substituted C1-C4 alkoxy, optionally substituted cycloalkyl, optionally substituted heterocyclyl, optionally substituted aryl, or optionally substituted heteroaryl each $R^{11}$ is independently hydrogen, halogen, optionally substituted C1-C6 alkyl, or two $R^{11}$ groups on the same carbon atom form an oxo;

each $R^{12}$ is independently hydrogen or optionally substituted C1-C4 alkyl;

n is 0, 1, 2, or 3; m is 0, 1, 2, or 3;

Y is a group selected from:

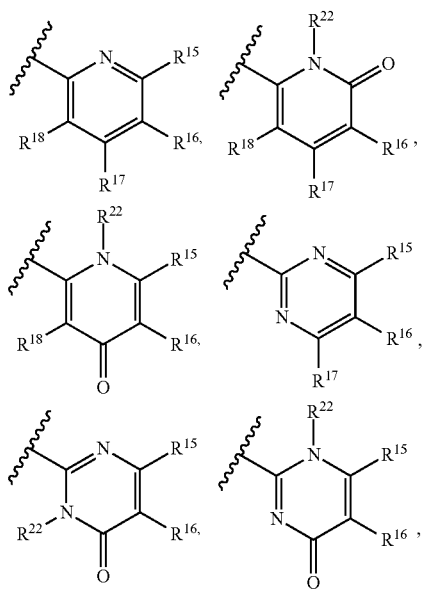

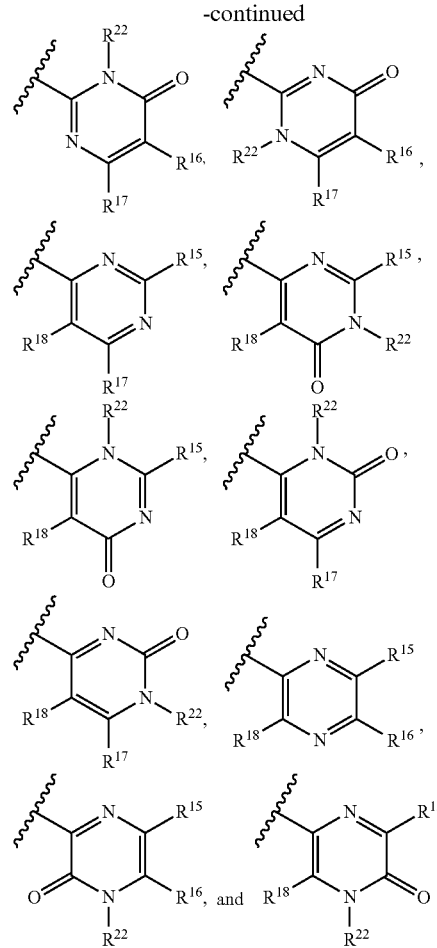

wherein, $R^{15}$ is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N$(R^{22})_2$, —SO$_2R^{21}$, —N$(R^{22})$SO$_2R^{21}$, —SO$_2$N$(R^{22})_2$, —N$(R^{22})$SO$_2$N$(R^{22})_2$, —CON$(R^{22})_2$, —N$(R^{22})$CO$_2R^{21}$, —N$(R^{22})$CON$(R^{22})_2$, —N$(R^{22})$COR$^{21}$, —OC(O)N$(R^{22})_2$, —OSO$_2$N$(R^{22})_2$, or —N$(R^{22})$SO$_3R^{21}$;

$R^{16}$ is selected from hydrogen, halogen, —CN, optionally substituted alkyl, optionally substituted alkenyl, optionally substituted alkynyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N$(R^{22})_2$, —SO$_2R^{21}$, —N$(R^{22})$SO$_2R^{21}$, —SO$_2$N$(R^{22})_2$, —N$(R^{22})$SO$_2$N$(R^{22})_2$, —CON$(R^{22})_2$, —N$(R^{22})$CO$_2R^{21}$, —N$(R^{22})$CON$(R^{22})_2$, —N$(R^{22})$COR$^{21}$, —OC(O)N$(R^{22})_2$, —OSO$_2$N$(R^{22})_2$, or —N$(R^{22})$SO$_3R^{21}$;

$R^{17}$ is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

$R^{18}$ is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

In some embodiments, Z1 is N-G.

In some embodiments, G is

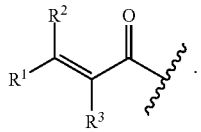

In some embodiments, G is

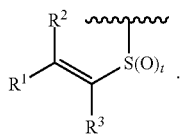

In some embodiments, $R^3$ is hydrogen or —CN.

In some embodiments, t is 2.

In some embodiments, W is O. In some embodiments, W is —CH$_2$—. In some embodiments, W is NH or NR$^{12}$. In some embodiments, W is SO$_2$. In some embodiments, W is absent.

In some embodiments, $R^2$ is hydrogen.

In some embodiments, $R^3$ is hydrogen.

In some embodiments, $R^2$ and $R^3$ is hydrogen.

In some embodiments, $R^1$ is hydrogen. In some embodiments, $R^1$ is optionally substituted C1-C4 alkyl. In some embodiments, $R^1$ is optionally substituted C1-C2 alkyl. In some embodiments, $R^1$ is optionally substituted C1 alkyl. In some embodiments, the C1 alkyl is substituted with an optionally substituted amino group. In some embodiments, the optionally substituted amino group is a dimethylamino.

In some embodiments, $R^1$ is —CH$_2$—N(Me)$_2$.

In some embodiments, $R^1$ is optionally substituted heterocyclylalkyl. In some embodiments, the optionally substituted heterocyclylalkyl comprises an optionally substituted C1 alkyl. In some embodiments, the optionally substituted heterocyclylalkyl comprises an optionally substituted N-linked heterocyclyl. In some embodiments, the optionally substituted N-linked heterocyclyl is an N-linked pyrrolidine or piperidine.

In some embodiments, n is 1 and m is 1. In some embodiments, n is 1 and m is 2. In some embodiments, n is 1 and m is 3.

In some embodiments, Y is selected from:

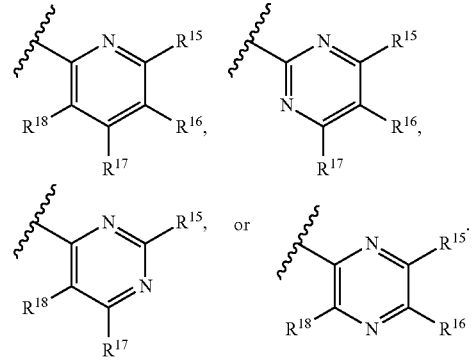

In some embodiments, Y is:

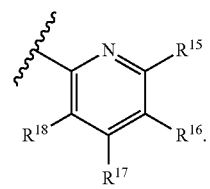

In some embodiments, Y is:

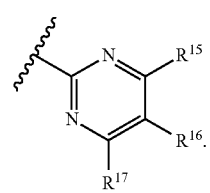

In some embodiments, $R^{15}$ is selected from hydrogen, halogen, —CN, and optionally substituted alkyl. In some embodiments, $R^{15}$ is hydrogen.

In some embodiments, $R^{16}$ is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$.

In some embodiments, $R^{16}$ is selected from optionally substituted alkenyl, optionally substituted alkynyl. In some embodiments, $R^{16}$ is selected from optionally substituted alkynyl.

In some embodiments, $R^{16}$ is selected from hydrogen, halogen, —CN, and optionally substituted alkyl. In some embodiments, $R^{16}$ is hydrogen.

In some embodiments, $R^{17}$ is selected from hydrogen, halogen, —CN, and optionally substituted alkyl. In some embodiments, $R^{17}$ is hydrogen.

In some embodiments, $R^{18}$ is selected from hydrogen, halogen, —CN, and optionally substituted alkyl. In some embodiments, $R^{18}$ is hydrogen.

In some embodiments, $R^{15}$ and $R^{16}$ are hydrogen. In some embodiments, $R^{17}$ and $R^{18}$ are hydrogen.

In some embodiments, E is a bond. In some embodiments, E is —SO$_2$—. In some embodiments, E is —C(O)—. In some embodiments, E is —CH$_2$—. In some embodiments, E is —CH($R^4$)—. In some embodiments, E is —C($R^4$)$_2$—.

In some embodiments, the heteroaromatic CDK inhibitory compound of Formula (III) described herein has a structure provided in Table 1.

TABLE 1

| Synthetic Chemistry Example | Compound Structure | Compound Name |
| --- | --- | --- |
| 1 | 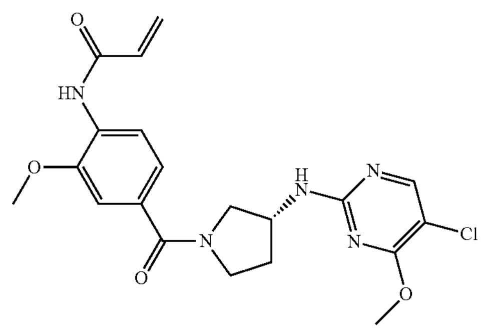 [SMILES: C=CC(=O)Nc1ccc(C(=O)N2CC[C@@H](Nc3ncc(Cl)c(OC)n3)C2)cc1OC] | (R)-N-(4-(3-((5-chloro-4-methoxypyrimidin-2-yl)amino)pyrrolidine-1-carbonyl)-2-methoxyphenyl)acrylamide |
| 2 | 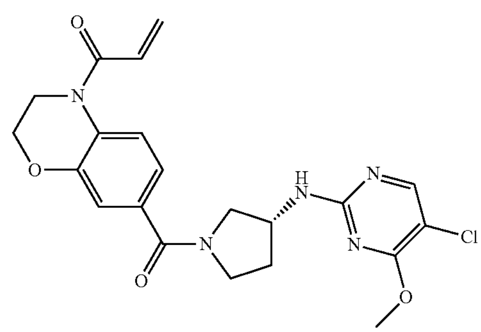 [SMILES: C=CC(=O)N1CCOc2cc(C(=O)N3CC[C@@H](Nc4ncc(Cl)c(OC)n4)C3)ccc21] | (R)-1-(7-(3-((5-chloro-4-methoxypyrimidin-2-yl)amino)pyrrolidine-1-carbonyl)-2H-benzo[b][1,4]oxazin-4(3H)-yl)prop-2-en-1-one |
| 3 | 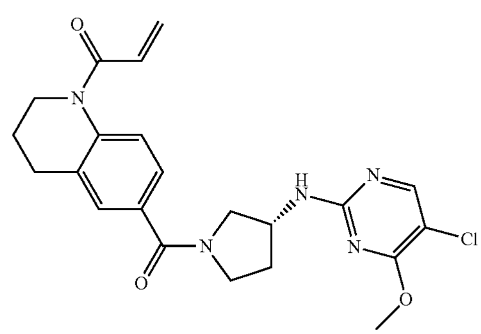 | (R)-1-(6-(3-((5-chloro-4-methoxypyrimidin-2-yl)amino)pyrrolidine-1-carbonyl)-3,4-dihydroquinolin-1(2H)-yl)prop-2-en-1-one |

TABLE 1-continued

| Synthetic Chemistry Example | Compound Structure | Compound Name |
|---|---|---|
| 4 | 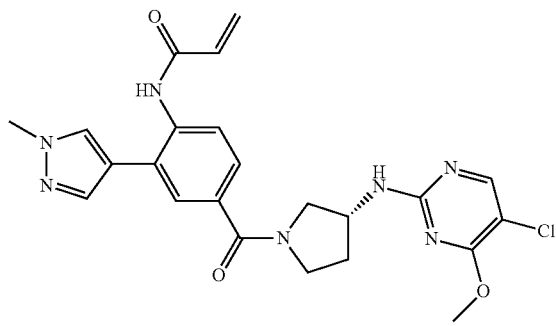 [SMILES: C=CC(=O)Nc1ccc(C(=O)N2CC[C@@H](Nc3ncc(Cl)c(OC)n3)C2)cc1-c1cnn(C)c1] | (R)-N-(4-(3-((5-chloro-4-methoxypyrimidin-2-yl)amino)pyrrolidine-1-carbonyl)-2-(1-methyl-1H-pyrazol-4-yl)phenyl)acrylamide |
| 5 | 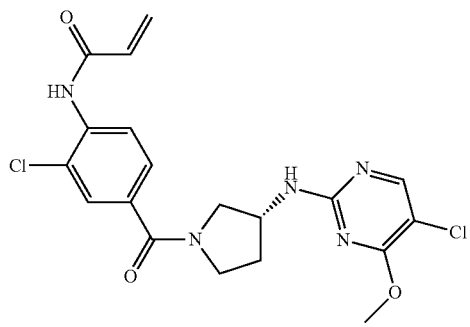 [SMILES: C=CC(=O)Nc1ccc(C(=O)N2CC[C@@H](Nc3ncc(Cl)c(OC)n3)C2)cc1Cl] | (R)-N-(2-chloro-4-(3-((5-chloro-4-methoxypyrimidin-2-yl)amino)pyrrolidine-1-carbonyl)phenyl)acrylamide |
| 6 | 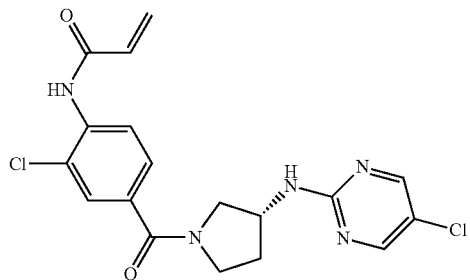 [SMILES: C=CC(=O)Nc1ccc(C(=O)N2CC[C@@H](Nc3ncc(Cl)cn3)C2)cc1Cl] | (R)-N-(2-chloro-4-(3-((5-chloropyrimidin-2-yl)amino)pyrrolidine-1-carbonyl)phenyl)acrylamide |
| 7 | 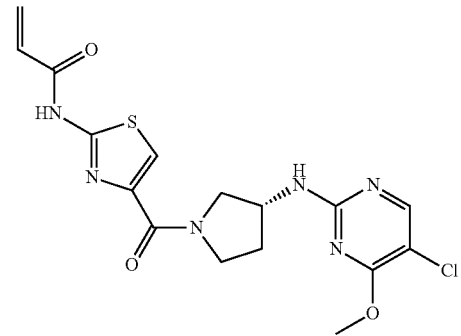 [SMILES: C=CC(=O)Nc1nc(C(=O)N2CC[C@@H](Nc3ncc(Cl)c(OC)n3)C2)cs1] | (R)-N-(4-(3-((5-chloro-4-methoxypyrimidin-2-yl)amino)pyrrolidine-1-carbonyl)thiazol-2-yl)acrylamide |

TABLE 1-continued

| Synthetic Chemistry Example | Compound Structure | Compound Name |
|---|---|---|
| 8 | 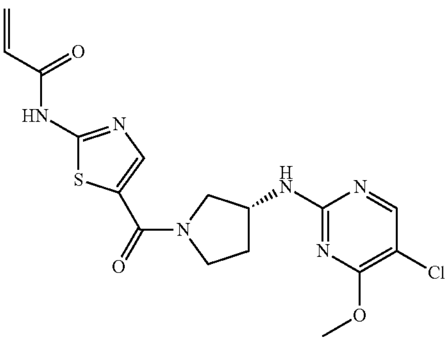 [SMILES: C=CC(=O)Nc1ncc(C(=O)N2CC[C@@H](Nc3ncc(Cl)c(OC)n3)C2)s1] | (R)-N-(4-(3-((5-chloro-4-methoxypyrimidin-2-yl)amino)pyrrolidine-1-carbonyl)-2-(4-methylpiperazin-1-yl)phenyl)acrylamide |
| 9 | 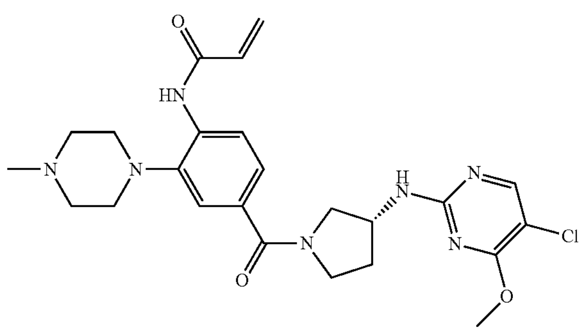 [SMILES: C=CC(=O)Nc1ccc(C(=O)N2CC[C@@H](Nc3ncc(Cl)c(OC)n3)C2)cc1N1CCN(C)CC1] | (R)-N-(4-(3-((5-chloro-4-methoxypyrimidin-2-yl)amino)pyrrolidine-1-carbonyl)-2-(4-methylpiperazin-1-yl)phenyl)acrylamide |
| 10 | 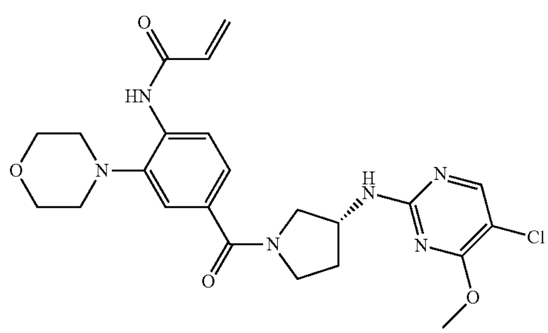 [SMILES: C=CC(=O)Nc1ccc(C(=O)N2CC[C@@H](Nc3ncc(Cl)c(OC)n3)C2)cc1N1CCOCC1] | (R)-N-(4-(3-((5-chloro-4-methoxypyrimidin-2-yl)amino)pyrrolidine-1-carbonyl)-2-morpholinophenyl)acrylamide |
| 11 | 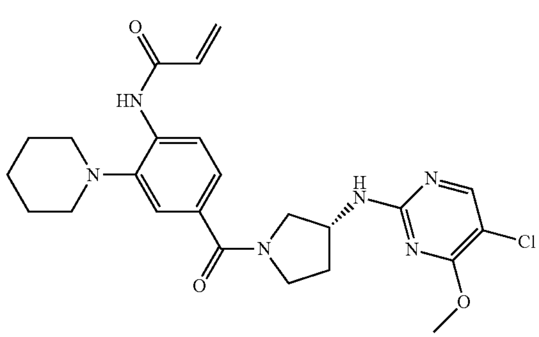 [SMILES: C=CC(=O)Nc1ccc(C(=O)N2CC[C@@H](Nc3ncc(Cl)c(OC)n3)C2)cc1N1CCCCC1] | (R)-N-(4-(3-((5-chloro-4-methoxypyrimidin-2-yl)amino)pyrrolidine-1-carbonyl)-2-(piperidin-1-yl)phenyl)acrylamide |

TABLE 1-continued

| Synthetic Chemistry Example | Compound Structure | Compound Name |
|---|---|---|
| 18 | 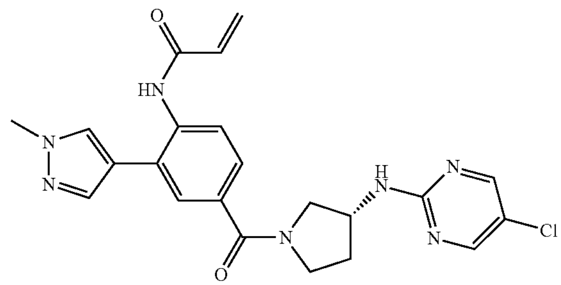 [SMILES: C=CC(=O)Nc1ccc(C(=O)N2CC[C@@H](Nc3ncc(Cl)cn3)C2)cc1-c1cnn(C)c1] | (R)-N-(4-(3-((5-chloropyrimidin-2-yl)amino)pyrrolidine-1-carbonyl)-2-(1-methyl-1H-pyrazol-4-yl)phenyl)acrylamide |
| 19 | 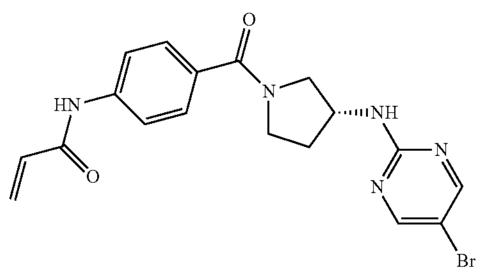 [SMILES: C=CC(=O)Nc1ccc(C(=O)N2CC[C@@H](Nc3ncc(Br)cn3)C2)cc1] | (R)-N-(4-(3-((5-bromopyrimidin-2-yl)amino)pyrrolidine-1-carbonyl)phenyl)acrylamide |
| 20 | 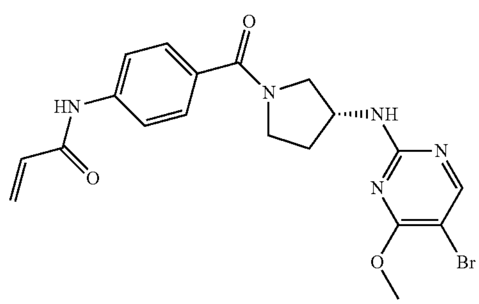 [SMILES: C=CC(=O)Nc1ccc(C(=O)N2CC[C@@H](Nc3ncc(Br)c(OC)n3)C2)cc1] | (R)-N-(4-(3-((5-bromo-4-methoxypyrimidin-2-yl)amino)pyrrolidine-1-carbonyl)phenyl)acrylamide |
| 21 | 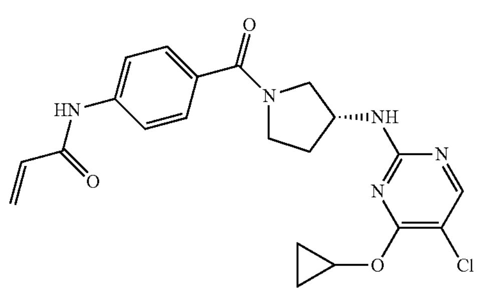 [SMILES: C=CC(=O)Nc1ccc(C(=O)N2CC[C@@H](Nc3ncc(Cl)c(OC4CC4)n3)C2)cc1] | (R)-N-(4-(3-((5-chloro-4-cyclopropoxypyrimidin-2-yl)amino)pyrrolidine-1-carbonyl)phenyl)acrylamide |
| 22 | 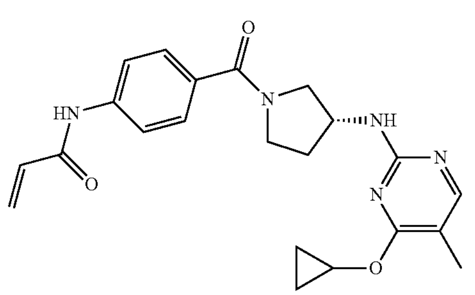 [SMILES: C=CC(=O)Nc1ccc(C(=O)N2CC[C@@H](Nc3ncc(C)c(OC4CC4)n3)C2)cc1] | (R)-N-(4-(3-((4-cyclopropoxy-5-methylpyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 23 | 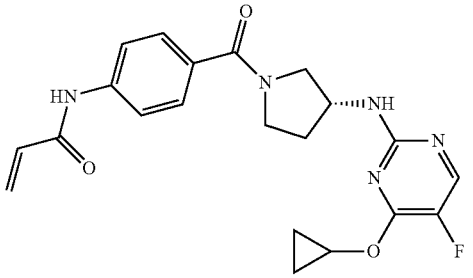 [SMILES: C=CC(=O)Nc1ccc(C(=O)N2CC[C@@H](Nc3ncc(F)c(OC4CC4)n3)C2)cc1] | (R)-N-(4-(3-((4-cyclopropoxy-5-fluoropyrimidin-2-yl)amino)pyrrolidine-1-carbonyl)phenyl)acrylamide |
| 24 | 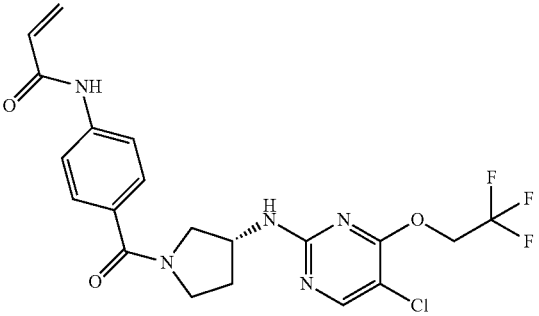 [SMILES: C=CC(=O)Nc1ccc(C(=O)N2CC[C@@H](Nc3ncc(Cl)c(OCC(F)(F)F)n3)C2)cc1] | (R)-N-(4-(3-((5-chloro-4-(2,2,2-trifluoroethoxy)pyrimidin-2-yl)amino)pyrrolidine-1-carbonyl)phenyl)acrylamide |
| 25 | 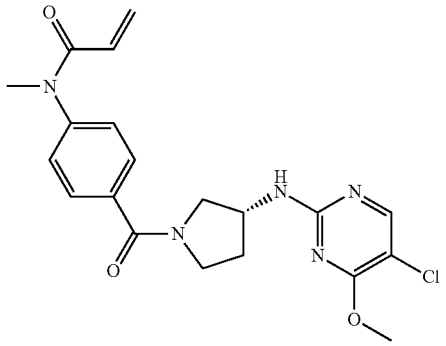 [SMILES: C=CC(=O)N(C)c1ccc(C(=O)N2CC[C@@H](Nc3ncc(Cl)c(OC)n3)C2)cc1] | (R)-N-(4-(3-((5-chloro-4-methoxypyrimidin-2-yl)amino)pyrrolidine-1-carbonyl)phenyl)-N-methylacrylamide |
| 26 | 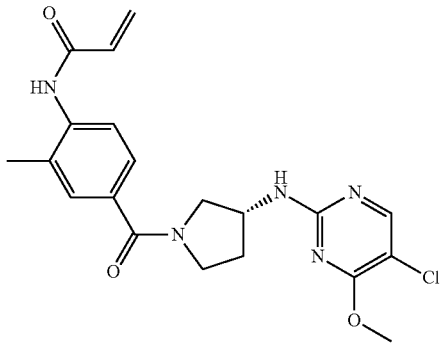 [SMILES: C=CC(=O)Nc1ccc(C(=O)N2CC[C@@H](Nc3ncc(Cl)c(OC)n3)C2)cc1C] | (R)-N-(4-(3-((5-chloro-4-methoxypyrimidin-2-yl)amino)pyrrolidine-1-carbonyl)-2-methylphenyl)acrylamide |

TABLE 1-continued

| Synthetic Chemistry Example | Compound Structure | Compound Name |
| --- | --- | --- |
| 27 | 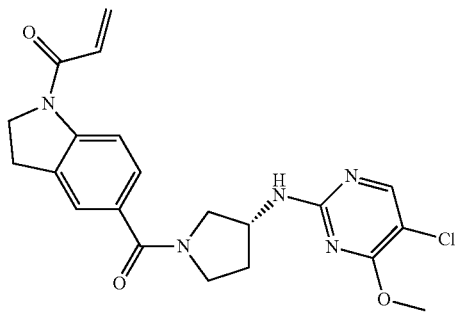 [SMILES: C=CC(=O)N1CCc2cc(C(=O)N3CC[C@@H](Nc4ncc(Cl)c(OC)n4)C3)ccc21] | (R)-1-(5-(3-((5-chloro-4-methoxypyrimidin-2-yl)amino)pyrrolidine-1-carbonyl)indolin-1-yl)prop-2-en-1-one |
| 28 | 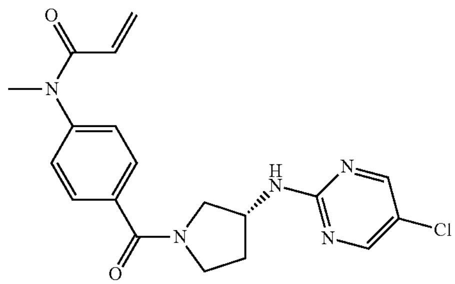 [SMILES: C=CC(=O)N(C)c1ccc(C(=O)N2CC[C@@H](Nc3ncc(Cl)cn3)C2)cc1] | (R)-N-(4-(3-((5-chloropyrimidin-2-yl)amino)pyrrolidine-1-carbonyl)phenyl)-N-methylacrylamide |
| 29 | 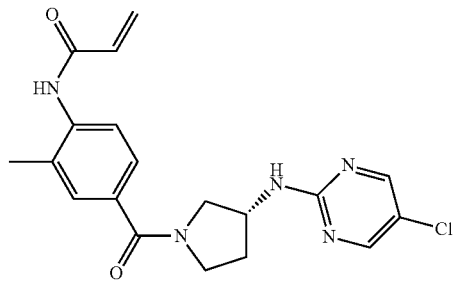 [SMILES: C=CC(=O)Nc1ccc(C(=O)N2CC[C@@H](Nc3ncc(Cl)cn3)C2)cc1C] | (R)-N-(4-(3-((5-chloropyrimidin-2-yl)amino)pyrrolidine-1-carbonyl)-2-methylphenyl)acrylamide |
| 30 | 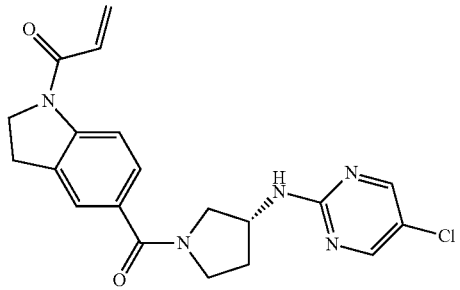 [SMILES: C=CC(=O)N1CCc2cc(C(=O)N3CC[C@@H](Nc4ncc(Cl)cn4)C3)ccc21] | (R)-1-(5-(3-((5-chloropyrimidin-2-yl)amino)pyrrolidine-1-carbonyl)indolin-1-yl)prop-2-en-1-one |
| 31 | 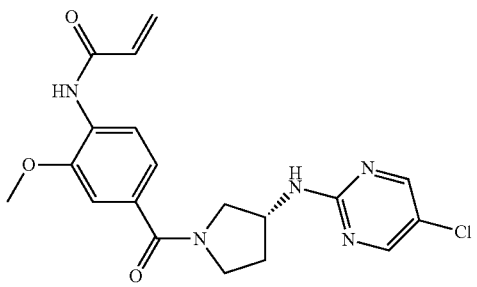 [SMILES: C=CC(=O)Nc1ccc(C(=O)N2CC[C@@H](Nc3ncc(Cl)cn3)C2)cc1OC] | (R)-N-(4-(3-((5-chloropyrimidin-2-yl)amino)pyrrolidine-1-carbonyl)-2-methoxyphenyl)acrylamide |

TABLE 1-continued

| Synthetic Chemistry Example | Compound Structure | Compound Name |
|---|---|---|
| 32 | 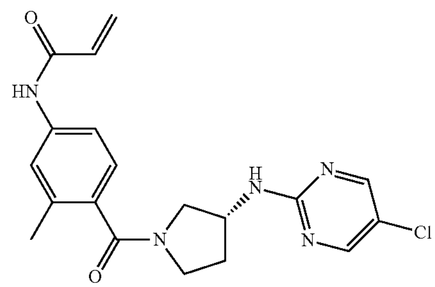 [SMILES: C=CC(=O)Nc1ccc(C(=O)N2CC[C@@H](Nc3ncc(Cl)cn3)C2)c(C)c1] | (R)-N-(4-(3-((5-chloropyrimidin-2-yl)amino)pyrrolidine-1-carbonyl)-3-methylphenyl)acrylamide |
| 33 | 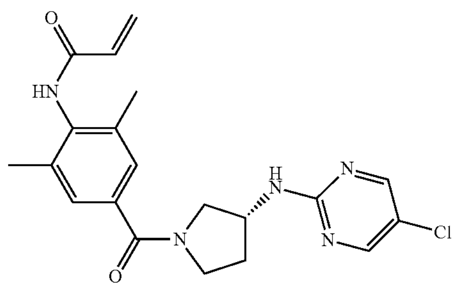 [SMILES: C=CC(=O)Nc1c(C)cc(C(=O)N2CC[C@@H](Nc3ncc(Cl)cn3)C2)cc1C] | (R)-N-(4-(3-((5-chloropyrimidin-2-yl)amino)pyrrolidine-1-carbonyl)-2,6-dimethylphenyl)acrylamide |
| 34 | 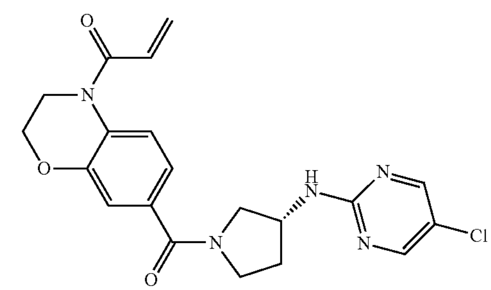 [SMILES: C=CC(=O)N1CCOc2cc(C(=O)N3CC[C@@H](Nc4ncc(Cl)cn4)C3)ccc21] | (R)-1-(7-(3-((5-chloropyrimidin-2-yl)amino)pyrrolidine-1-carbonyl)-2H-benzo[b][1,4]oxazin-4(3H)-yl)prop-2-en-1-one |
| 35 | 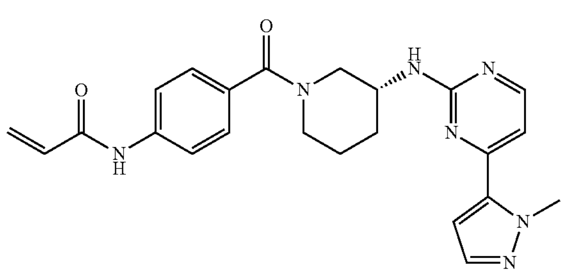 [SMILES: C=CC(=O)Nc1ccc(C(=O)N2CCC[C@@H](Nc3nccc(-c4ccnn4C)n3)C2)cc1] | (R)-N-(4-(3-((4-(1-methyl-1H-pyrazol-5-yl)pyrimidin-2-yl)amino)piperidine-1-carbonyl)phenyl)acrylamide |
| 36 | 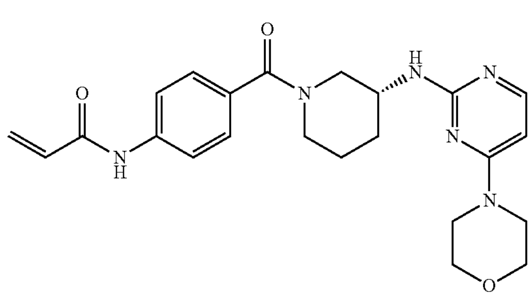 [SMILES: C=CC(=O)Nc1ccc(C(=O)N2CCC[C@@H](Nc3nccc(N4CCOCC4)n3)C2)cc1] | (R)-N-(4-(3-((4-morpholinopyrimidin-2-yl)amino)piperidine-1-carbonyl)phenyl)acrylamide |

TABLE 1-continued

| Synthetic Chemistry Example | Compound Structure | Compound Name |
|---|---|---|
| 37 | 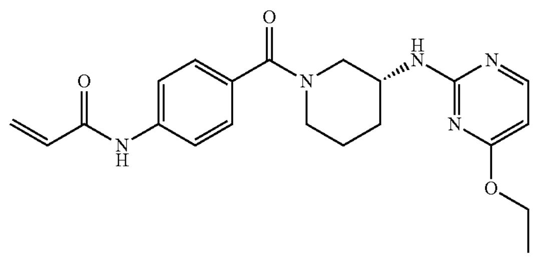 [SMILES: C=CC(=O)Nc1ccc(C(=O)N2CCC[C@@H](Nc3nccc(OCC)n3)C2)cc1] | (R)-N-(4-(3-((4-methoxypyrimidin-2-yl)amino)piperidine-1-carbonyl)phenyl)acrylamide |
| 38 | 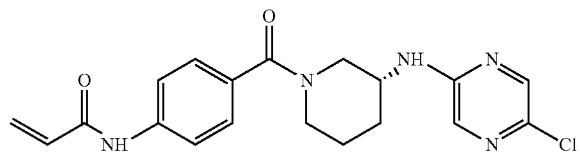 [SMILES: C=CC(=O)Nc1ccc(C(=O)N2CCC[C@@H](Nc3cnc(Cl)cn3)C2)cc1] | (R)-N-(4-(3-((5-chloropyrazin-2-yl)amino)piperidine-1-carbonyl)phenyl)acrylamide |
| 39 | 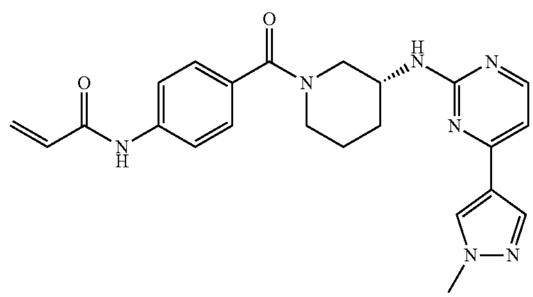 [SMILES: C=CC(=O)Nc1ccc(C(=O)N2CCC[C@@H](Nc3nccc(-c4cnn(C)c4)n3)C2)cc1] | (R)-N-(4-(3-((4-(1-methyl-1H-pyrazol-4-yl)pyrimidin-2-yl)amino)piperidine-1-carbonyl)phenyl)acrylamide |
| 40 | 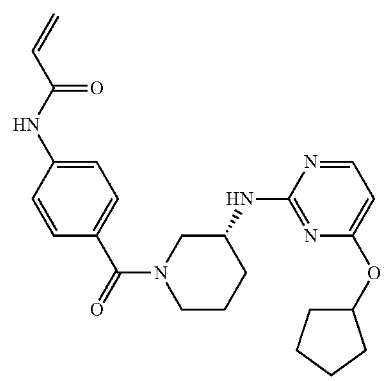 [SMILES: C=CC(=O)Nc1ccc(C(=O)N2CCC[C@@H](Nc3nccc(OC4CCCC4)n3)C2)cc1] | (R)-N-(4-(3-((4-(cyclopentyloxy)pyrimidin-2-yl)amino)piperidine-1-carbonyl)phenyl)acrylamide |
| 44 | 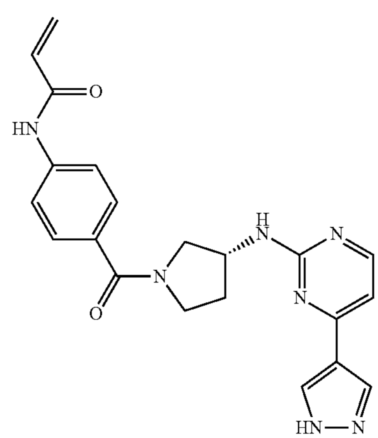 [SMILES: C=CC(=O)Nc1ccc(C(=O)N2CC[C@@H](Nc3nccc(-c4cn[nH]c4)n3)C2)cc1] | (R)-N-(4-(3-((4-(1H-pyrazol-4-yl)pyrimidin-2-yl)amino)pyrrolidine-1-carbonyl)phenyl)acrylamide |

TABLE 1-continued
| Synthetic Chemistry Example | Compound Structure | Compound Name |
|---|---|---|
| 45 | 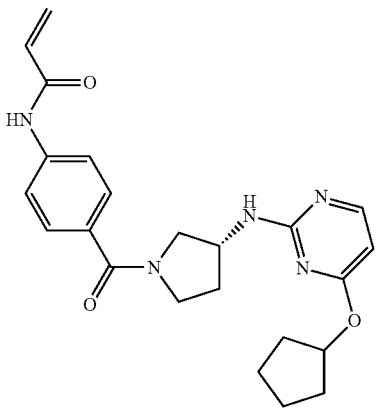 [SMILES: C=CC(=O)Nc1ccc(C(=O)N2CC[C@@H](Nc3nccc(OC4CCCC4)n3)C2)cc1] | (R)-N-(4-(3-((4-(cyclopentyloxy)pyrimidin-2-yl)amino)pyrrolidine-1-carbonyl)phenyl)acrylamide |
| 46 | 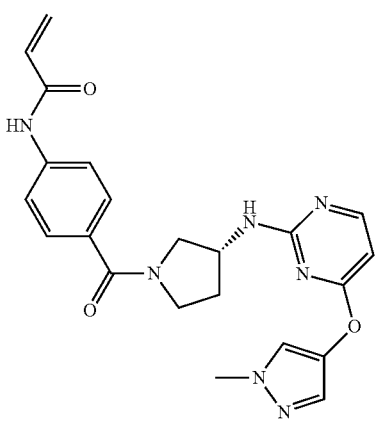 [SMILES: C=CC(=O)Nc1ccc(C(=O)N2CC[C@@H](Nc3nccc(Oc4cnn(C)c4)n3)C2)cc1] | (R)-N-(4-(3-((4-((1-methyl-1H-pyrazol-4-yl)oxy)pyrimidin-2-yl)amino)pyrrolidine-1-carbonyl)phenyl)acrylamide |
| 47 | 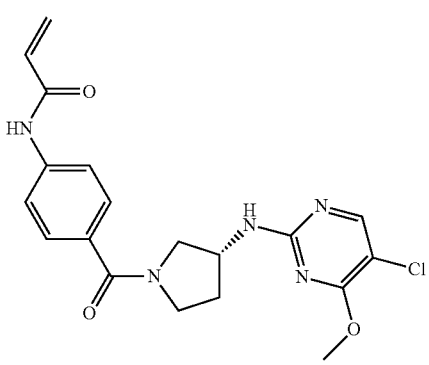 | (R)-N-(4-(3-((5-chloro-4-methoxypyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 48 | 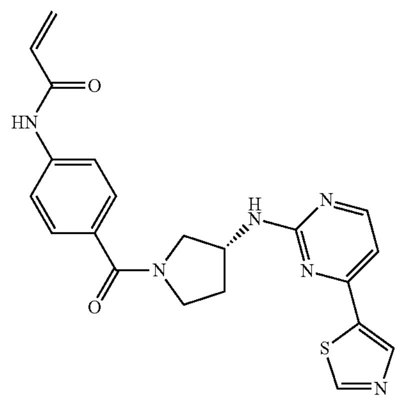 [SMILES: C=CC(=O)Nc1ccc(C(=O)N2CC[C@@H](Nc3nccc(-c4cncs4)n3)C2)cc1] | (R)-N-(4-(3-((4-(thiazol-5-yl)pyrimidin-2-yl)amino)pyrrolidine-1-carbonyl)phenyl)acrylamide |
| 49 | 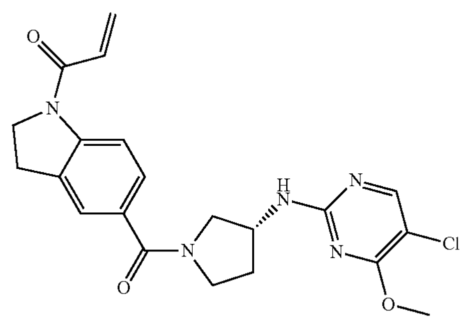 [SMILES: C=CC(=O)N1CCc2cc(C(=O)N3CC[C@@H](Nc4ncc(Cl)c(OC)n4)C3)ccc21] | (R)-1-(5-(3-((5-chloro-4-methoxypyrimidin-2-yl)amino)pyrrolidine-1-carbonyl)indolin-1-yl)prop-2-en-1-one |
| 50 | 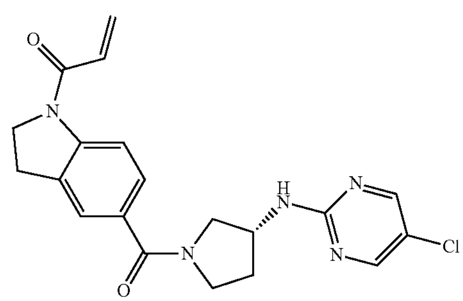 [SMILES: C=CC(=O)N1CCc2cc(C(=O)N3CC[C@@H](Nc4ncc(Cl)cn4)C3)ccc21] | (R)-1-(5-(3-((5-chloropyrimidin-2-yl)amino)pyrrolidine-1-carbonyl)indolin-1-yl)prop-2-en-1-one |
| 51 | 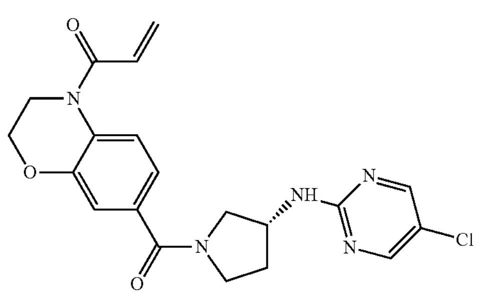 [SMILES: C=CC(=O)N1CCOc2cc(C(=O)N3CC[C@@H](Nc4ncc(Cl)cn4)C3)ccc21] | (R)-1-(7-(3-((5-chloropyrimidin-2-yl)amino)pyrrolidine-1-carbonyl)-2H-benzo[b][1,4]oxazin-4(3H)-yl)prop-2-en-1-one |

TABLE 1-continued

| Synthetic Chemistry Example | Compound Structure | Compound Name |
|---|---|---|
| 52 | 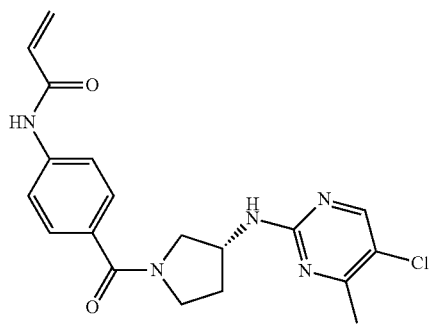 | (R)-N-(4-(3-((5-chloro-4-methylpyrimidin-2-yl)amino)pyrrolidine-1-carbonyl)phenyl)acrylamide |
| 53 | 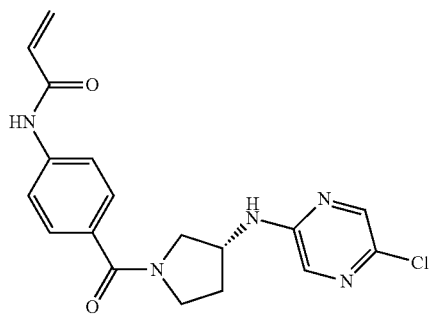 [SMILES: C=CC(=O)Nc1ccc(C(=O)N2CC[C@@H](Nc3cnc(Cl)cn3)C2)cc1] | (R)-N-(4-(3-((5-chloropyrazin-2-yl)amino)pyrrolidine-1-carbonyl)phenyl)acrylamide |
| 54 | 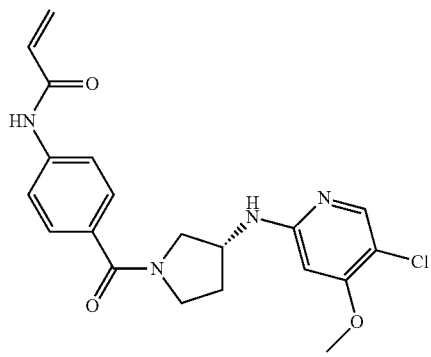 [SMILES: C=CC(=O)Nc1ccc(C(=O)N2CC[C@@H](Nc3cc(OC)c(Cl)cn3)C2)cc1] | (R)-N-(4-(3-((5-chloro-4-methoxypyridin-2-yl)amino)pyrrolidine-1-carbonyl)phenyl)acrylamide |
| 55 | 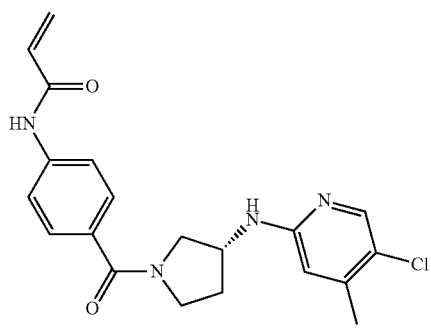 | (R)-N-(4-(3-((5-chloro-4-methylpyridin-2-yl)amino)pyrrolidine-1-carbonyl)phenyl)acrylamide |

TABLE 1-continued

| Synthetic Chemistry Example | Compound Structure | Compound Name |
|---|---|---|
| 56 | 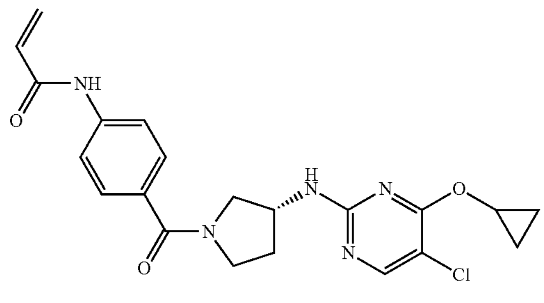 [SMILES: C=CC(=O)Nc1ccc(C(=O)N2CC[C@@H](Nc3ncc(Cl)c(OC4CC4)n3)C2)cc1] | (R)-N-(4-(3-((5-chloro-4-cyclopropoxypyrimidin-2-yl)amino)pyrrolidine-1-carbonyl)phenyl)acrylamide |
| 57 | 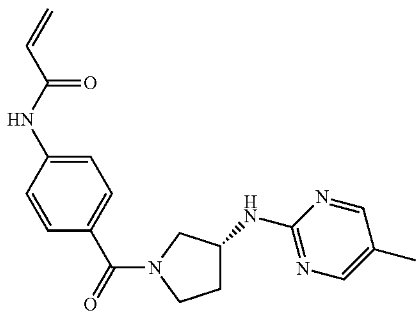 | (R)-N-(4-(3-((5-methylpyrimidin-2-yl)amino)pyrrolidine-1-carbonyl)phenyl)acrylamide |
| 58 | 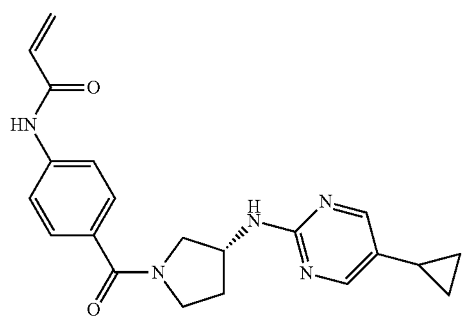 | (R)-N-(4-(3-((5-cyclopropylpyrimidin-2-yl)amino)pyrrolidine-1-carbonyl)phenyl)acrylamide |
| 59 | 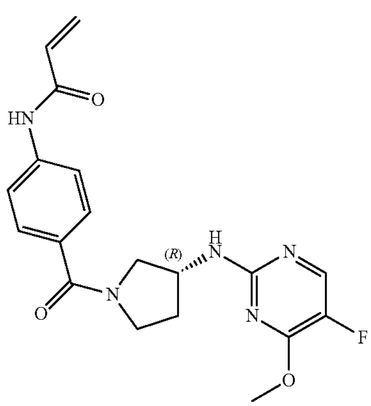 | (R)-N-(4-(3-((5-fluoro-4-methoxypyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 60 | 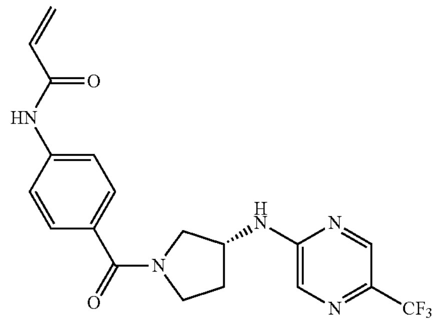 [SMILES: C=CC(=O)Nc1ccc(C(=O)N2CC[C@@H](Nc3cnc(C(F)(F)F)cn3)C2)cc1] | (R)-N-(4-(3-((5-(trifluoromethyl)pyrazin-2-yl)amino)pyrrolidine-1-carbonyl)phenyl)acrylamide |
| 61 | 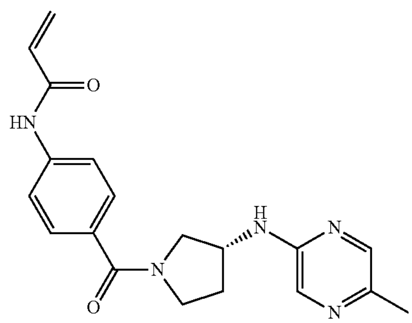 [SMILES: C=CC(=O)Nc1ccc(C(=O)N2CC[C@@H](Nc3cnc(C)cn3)C2)cc1] | (R)-N-(4-(3-((5-methylpyrazin-2-yl)amino)pyrrolidine-1-carbonyl)phenyl)acrylamide |
| 62 | 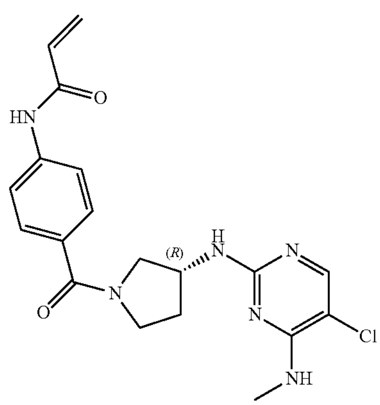 | (R)-N-(4-(3-((5-chloro-4-(methylamino)pyrimidin-2-yl)amino)pyrrolidine-1-carbonyl)phenyl)acrylamide |
| 63 | 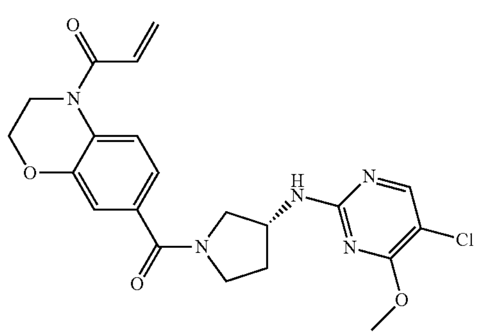 [SMILES: C=CC(=O)N1CCOc2cc(C(=O)N3CC[C@@H](Nc4ncc(Cl)c(OC)n4)C3)ccc21] | (R)-1-(7-(3-((5-chloro-4-methoxypyrimidin-2-yl)amino)pyrrolidine-1-carbonyl)-2H-benzo[b][1,4]oxazin-4(3H)-yl)prop-2-en-1-one |

TABLE 1-continued

| Synthetic Chemistry Example | Compound Structure | Compound Name |
|---|---|---|
| 64 | 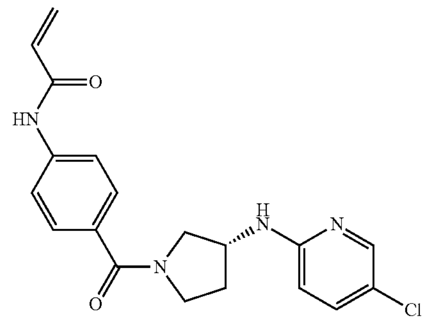 [SMILES: C=CC(=O)Nc1ccc(C(=O)N2CC[C@@H](Nc3ccc(Cl)cn3)C2)cc1] | (R)-N-(4-(3-((5-chloropyridin-2-yl)amino)pyrrolidine-1-carbonyl)phenyl)acrylamide |
| 65 | 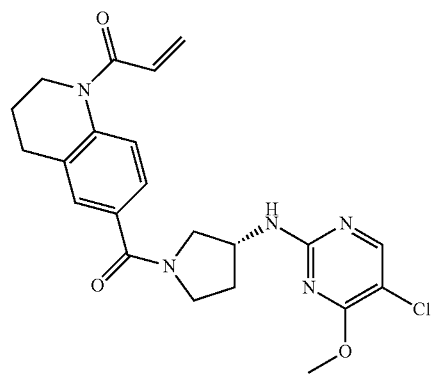 [SMILES: C=CC(=O)N1CCCc2cc(C(=O)N3CC[C@@H](Nc4ncc(Cl)c(OC)n4)C3)ccc21] | Synthesis of (R)-1-(6-(3-((5-chloro-4-methoxypyrimidin-2-yl)amino)pyrrolidine-1-carbonyl)-3,4-dihydroquinolin-1(2H)-yl)prop-2-en-1-one |
| 66 | 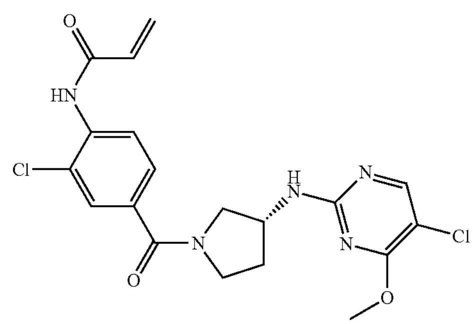 [SMILES: C=CC(=O)Nc1ccc(C(=O)N2CC[C@@H](Nc3ncc(Cl)c(OC)n3)C2)cc1Cl] | (R)-N-(2-chloro-4-(3-((5-chloro-4-methoxypyrimidin-2-yl)amino)pyrrolidine-1-carbonyl)phenyl)acrylamide |
| 67 | 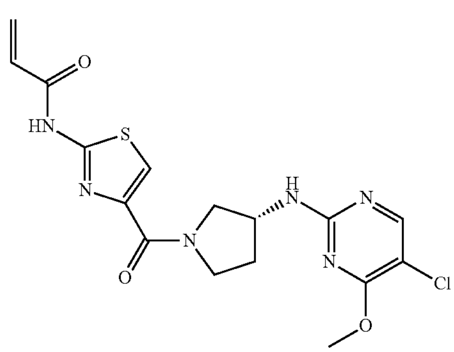 [SMILES: C=CC(=O)Nc1nc(C(=O)N2CC[C@@H](Nc3ncc(Cl)c(OC)n3)C2)cs1] | (R)-N-(4-(3-((5-chloro-4-methoxypyrimidin-2-yl)amino)pyrrolidine-1-carbonyl)thiazol-2-yl)acrylamide |

TABLE 1-continued

| Synthetic Chemistry Example | Compound Structure | Compound Name |
|---|---|---|
| 68 | 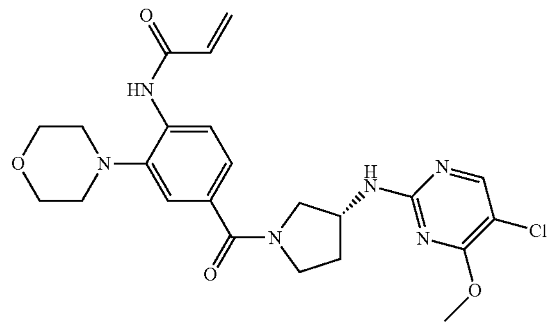 [SMILES: C=CC(=O)Nc1ccc(C(=O)N2CC[C@@H](Nc3ncc(Cl)c(OC)n3)C2)cc1N1CCOCC1] | (R)-N-(4-(3-((5-chloro-4-methoxypyrimidin-2-yl)amino)pyrrolidine-1-carbonyl)-2-morpholinophenyl)acrylamide |
| 69 | 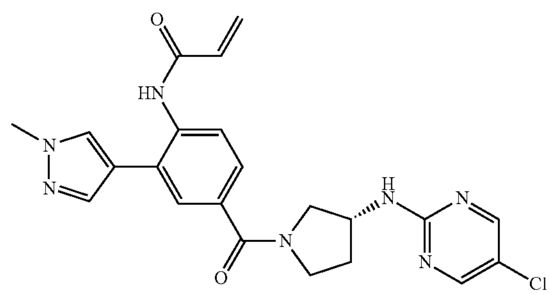 [SMILES: C=CC(=O)Nc1ccc(C(=O)N2CC[C@@H](Nc3ncc(Cl)cn3)C2)cc1-c1cnn(C)c1] | (R)-N-(4-(3-((5-chloropyrimidin-2-yl)amino)pyrrolidine-1-carbonyl)-2-(1-methyl-1H-pyrazol-4-yl)phenyl)acrylamide |
| 70 | 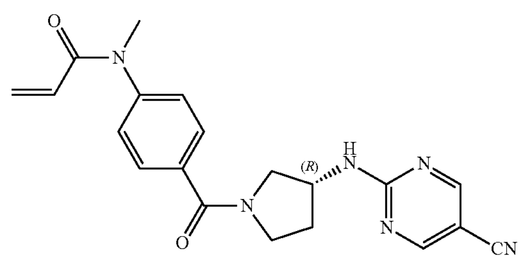 | (R)-N-(4-(3-((5-cyanopyrimidin-2-yl)amino)pyrrolidine-1-carbonyl)phenyl)-N-methylacrylamide |
| 71 | 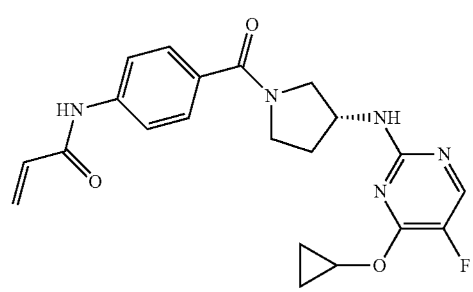 [SMILES: C=CC(=O)Nc1ccc(C(=O)N2CC[C@@H](Nc3ncc(F)c(OC4CC4)n3)C2)cc1] | (R)-N-(4-(3-((4-cyclopropoxy-5-fluoropyrimidin-2-yl)amino)pyrrolidine-1-carbonyl)phenyl)acrylamide |
| 72 | 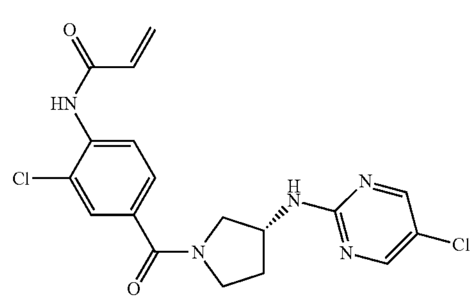 [SMILES: C=CC(=O)Nc1ccc(C(=O)N2CC[C@@H](Nc3ncc(Cl)cn3)C2)cc1Cl] | (R)-N-(2-chloro-4-(3-((5-chloropyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 73 | 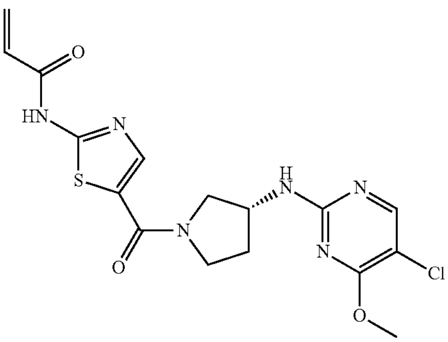 [SMILES: C=CC(=O)Nc1ncc(C(=O)N2CC[C@@H](Nc3ncc(Cl)c(OC)n3)C2)s1] | (R)-N-(5-(3-((5-chloro-4-methoxypyrimidin-2-yl)amino)pyrrolidine-1-carbonyl)thiazol-2-yl)acrylamide |
| 74 | 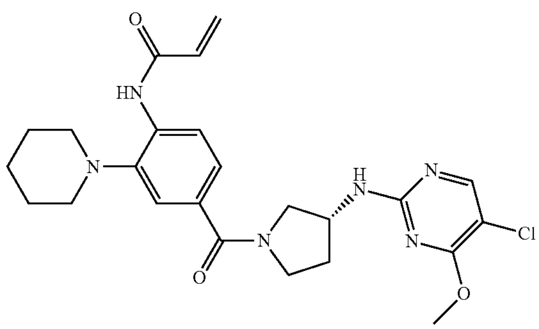 [SMILES: C=CC(=O)Nc1ccc(C(=O)N2CC[C@@H](Nc3ncc(Cl)c(OC)n3)C2)cc1N1CCCCC1] | (R)-N-(4-(3-((5-chloro-4-methoxypyrimidin-2-yl)amino)pyrrolidine-1-carbonyl)-2-(piperidin-1-yl)phenyl)acrylamide |
| 75 | 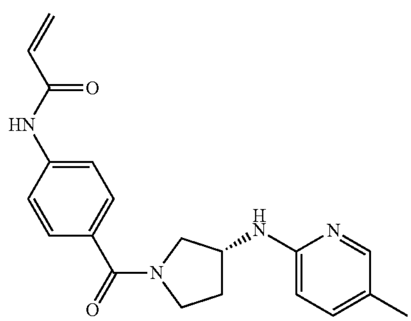 [SMILES: C=CC(=O)Nc1ccc(C(=O)N2CC[C@@H](Nc3ccc(C)cn3)C2)cc1] | (R)-N-(4-(3-((5-methylpyridin-2-yl)amino)pyrrolidine-1-carbonyl)phenyl)acrylamide |
| 76 | 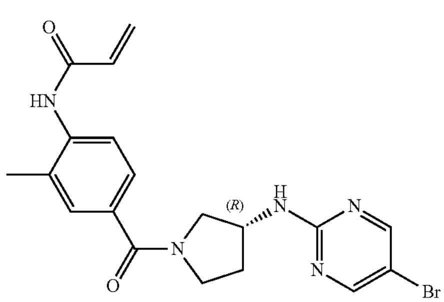 | (R)-N-(4-(3-((5-bromopyrimidin-2-yl)amino)pyrrolidine-1-carbonyl)-2-methylphenyl)acrylamide |

TABLE 1-continued

| Synthetic Chemistry Example | Compound Structure | Compound Name |
|---|---|---|
| 77 | 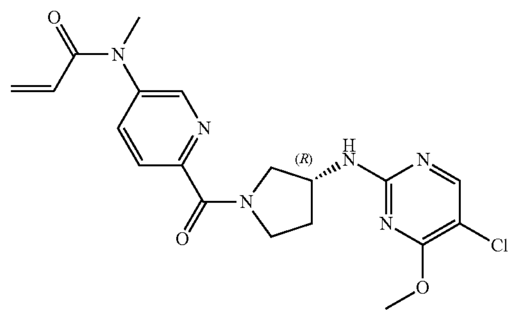 | (R)-N-(6-(3-((5-chloro-4-methoxypyrimidin-2-yl)amino)pyrrolidine-1-carbonyl)pyridin-3-yl)-N-methylacrylamide |
| 78 | 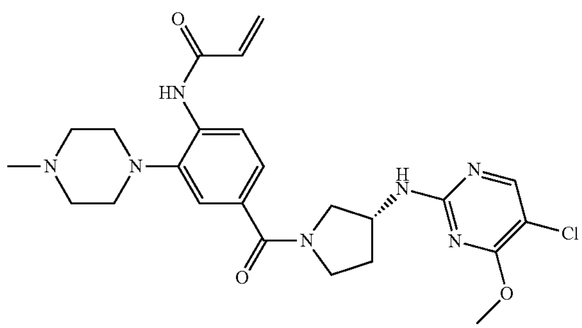 [SMILES: C=CC(=O)Nc1ccc(C(=O)N2CC[C@@H](Nc3ncc(Cl)c(OC)n3)C2)cc1N1CCN(C)CC1] | (R)-N-(4-(3-((5-chloro-4-methoxypyrimidin-2-yl)amino)pyrrolidine-1-carbonyl)-2-(4-methylpiperazin-1-yl)phenyl)acrylamide |
| 79 | 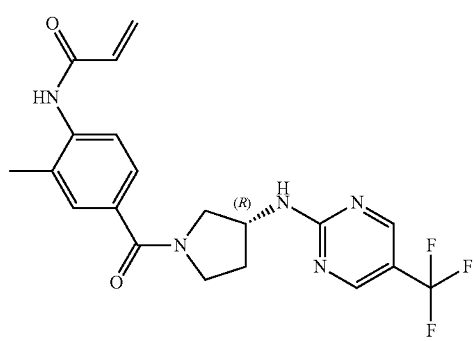 | (R)-N-(2-methyl-4-(3-((5-(trifluoromethyl)pyrimidin-2-yl)amino)pyrrolidine-1-carbonyl)phenyl)acrylamide |
| 80 | 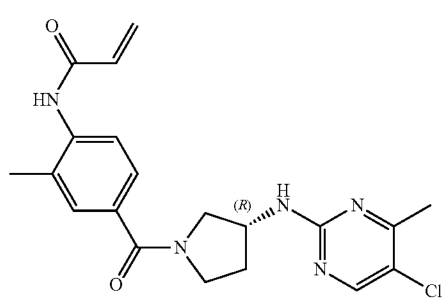 | (R)-N-(4-(3-((5-chloro-4-methylpyrimidin-2-yl)amino)pyrrolidine-1-carbonyl)-2-methylphenyl)acrylamide |

TABLE 1-continued

| Synthetic Chemistry Example | Compound Structure | Compound Name |
|---|---|---|
| 81 | 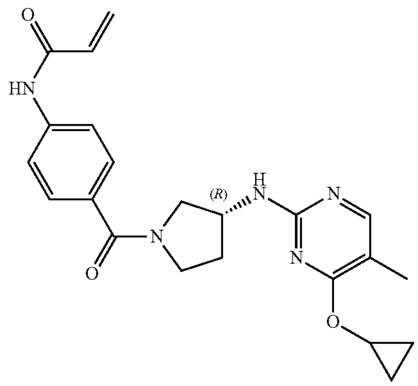 | (R)-N-(4-(3-((4-cyclopropoxy-5-methylpyrimidin-2-yl)amino)pyrrolidine-1-carbonyl)phenyl)acrylamide |
| 82 | 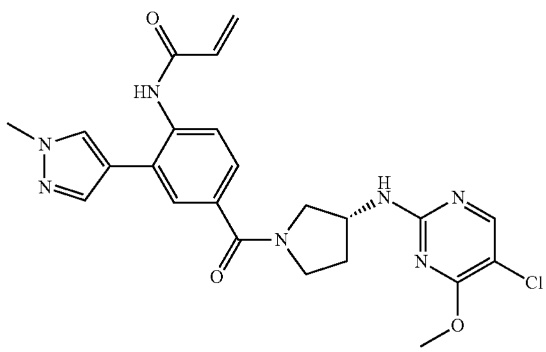 [SMILES: C=CC(=O)Nc1ccc(C(=O)N2CC[C@@H](Nc3ncc(Cl)c(OC)n3)C2)cc1-c1cnn(C)c1] | (R)-N-(4-(3-((5-chloro-4-methoxypyrimidin-2-yl)amino)pyrrolidine-1-carbonyl)-2-(1-methyl-1H-pyrazol-4-yl)phenyl)acrylamide |
| 83 | 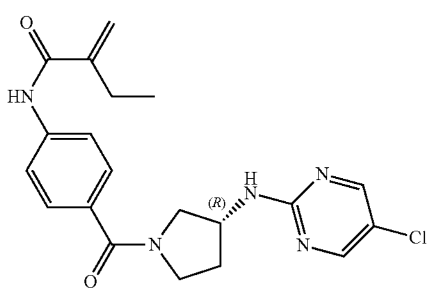 | (R)-N-(4-(3-((5-chloropyrimidin-2-yl)amino)pyrrolidine-1-carbonyl)phenyl)-2-methylenebutanamide |
| 84 | 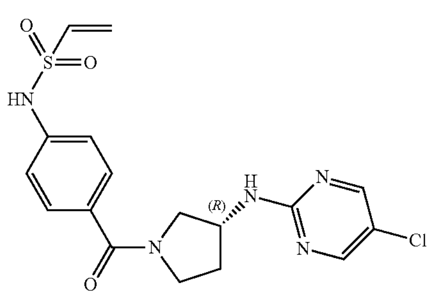 | (R)-N-(4-(3-((5-chloropyrimidin-2-yl)amino)pyrrolidine-1-carbonyl)phenyl)ethenesulfonamide |

TABLE 1-continued

| Synthetic Chemistry Example | Compound Structure | Compound Name |
|---|---|---|
| 85 | 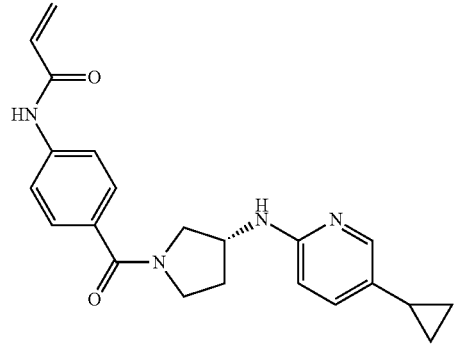 [SMILES: C=CC(=O)Nc1ccc(C(=O)N2CC[C@@H](Nc3ccc(C4CC4)cn3)C2)cc1] | (R)-N-(4-(3-((5-cyclopropylpyridin-2-yl)amino)pyrrolidine-1-carbonyl)phenyl)acrylamide |
| 86 | 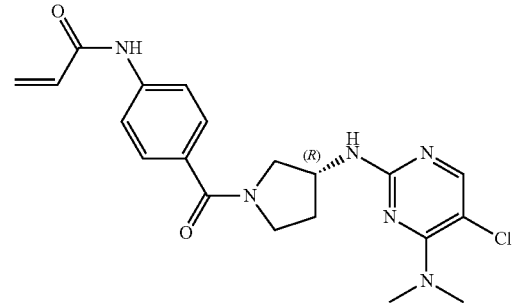 | (R)-N-(4-(3-((5-chloro-4-(dimethylamino)pyrimidin-2-yl)amino)pyrrolidine-1-carbonyl)phenyl)acrylamide |
| 87 | 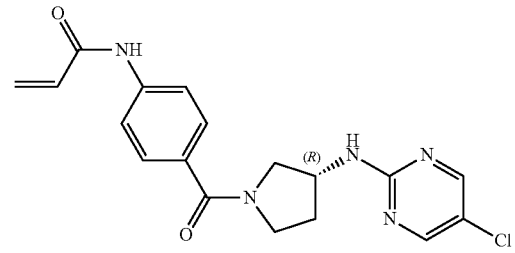 | (R)-N-(4-(3-((5-chloropyrimidin-2-yl)amino)pyrrolidine-1-carbonyl)phenyl)acrylamide |
| 88 | 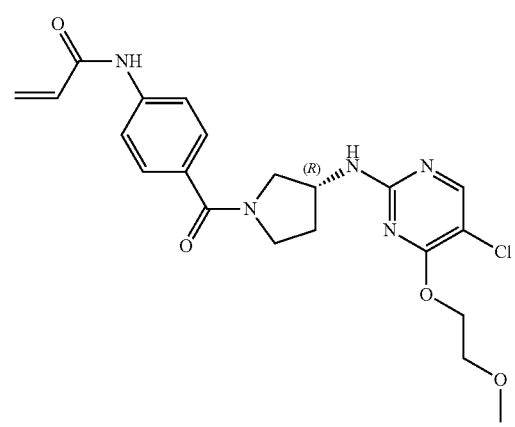 | (R)-N-(4-(3-((5-chloro-4-(2-methoxyethoxy)pyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 89 | 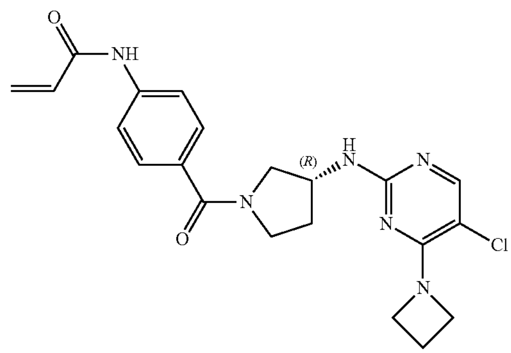 | (R)-N-(4-(3-((4-(azetidin-1-yl)-5-chloropyrimidin-2-yl)amino)pyrrolidine-1-carbonyl)phenyl)acrylamide |
| 90 | 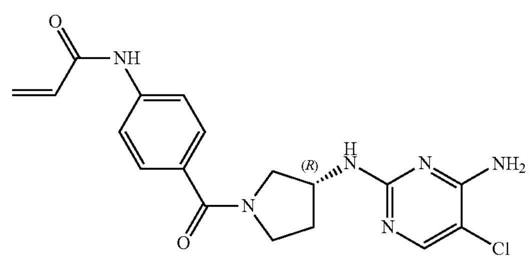 | (R)-N-(4-(3-((4-amino-5-chloropyrimidin-2-yl)amino)pyrrolidine-1-carbonyl)phenyl)acrylamide |
| 91 | 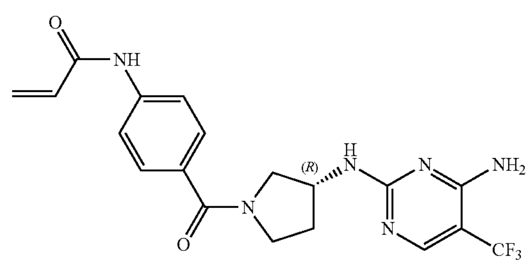 | (R)-N-(4-(3-((4-amino-5-(trifluoromethyl)pyrimidin-2-yl)amino)pyrrolidine-1-carbonyl)phenyl)acrylamide |
| 92 | 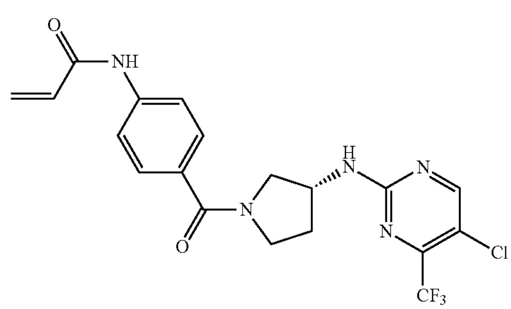 [SMILES: C=CC(=O)Nc1ccc(C(=O)N2CC[C@@H](Nc3ncc(Cl)c(C(F)(F)F)n3)C2)cc1] | (R)-N-(4-(3-((5-chloro-4-(trifluoromethyl)pyrimidin-2-yl)amino)pyrrolidine-1-carbonyl)phenyl)acrylamide |
| 93 | 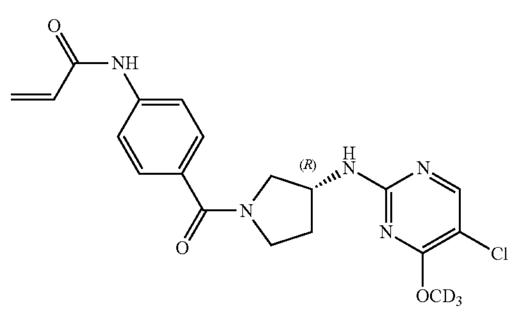 | (R)-N-(4-(3-((5-chloro-4-(trideuteromethoxy)pyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 94 | 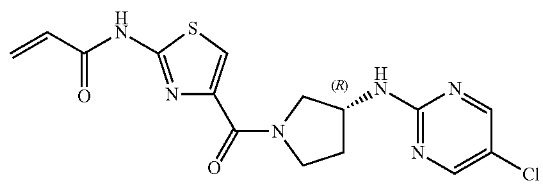 | (R)-N-(4-(3-((5-chloropyrimidin-2-yl)amino)pyrrolidine-1-carbonyl)thiazol-2-yl)acrylamide |
| 95 | 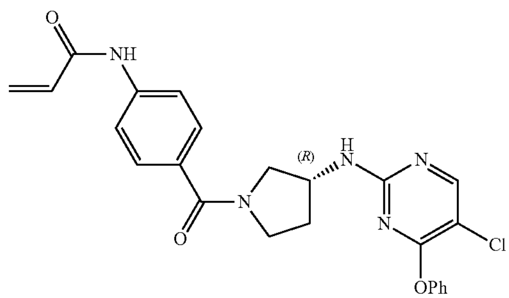 | (R)-N-(4-(3-((5-chloro-4-phenoxypyrimidin-2-yl)amino)pyrrolidine-1-carbonyl)phenyl)acrylamide |
| 96 | 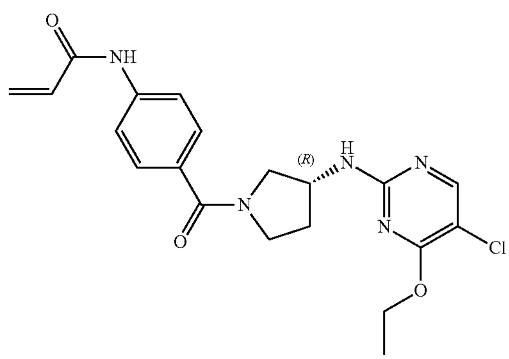 | (R)-N-(4-(3-((5-chloro-4-ethoxypyrimidin-2-yl)amino)pyrrolidine-1-carbonyl)phenyl)acrylamide |
| 97 | 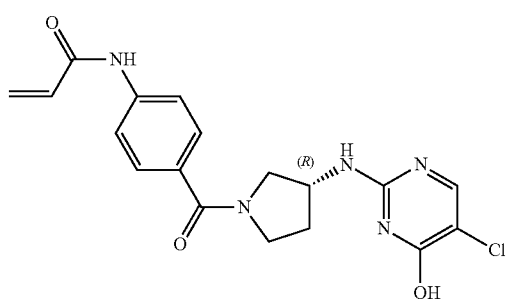 | (R)-N-(4-(3-((5-chloro-4-hydroxypyrimidin-2-yl)amino)pyrrolidine-1-carbonyl)phenyl)acrylamide |
| 98 | 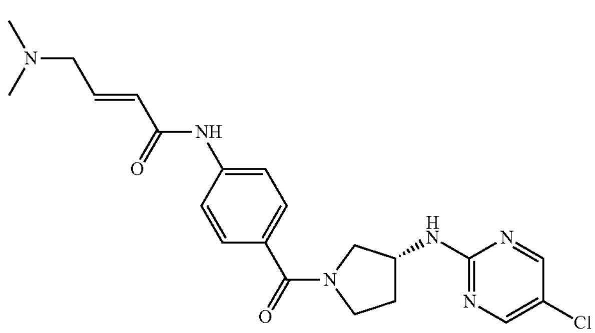 [SMILES: CN(C)C/C=C/C(=O)Nc1ccc(C(=O)N2CC[C@@H](Nc3ncc(Cl)cn3)C2)cc1] | (R,E)-N-(4-(3-((5-chloropyrimidin-2-yl)amino)pyrrolidine-1-carbonyl)phenyl)-4-(dimethylamino)but-2-enamide |

TABLE 1-continued

| Synthetic Chemistry Example | Compound Structure | Compound Name |
|---|---|---|
| 99 | 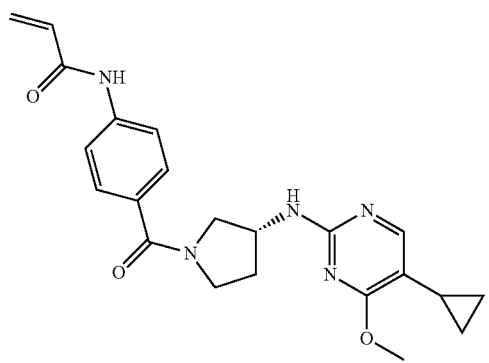 [SMILES: C=CC(=O)Nc1ccc(C(=O)N2CC[C@@H](Nc3ncc(C4CC4)c(OC)n3)C2)cc1] | (R)-N-(4-(3-((5-cyclopropyl-4-methoxypyrimidin-2-yl)amino)pyrrolidine-1-carbonyl)phenyl)acrylamide |
| 100 | 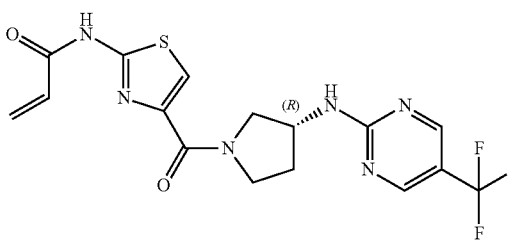 | (R)-N-(4-(3-((5-(trifluoromethyl)pyrimidin-2-yl)amino)pyrrolidine-1-carbonyl)thiazol-2-yl)acrylamide |
| 101 | 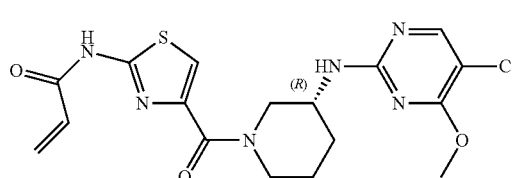 | (R)-N-(4-(3-((5-chloro-4-methoxypyrimidin-2-yl)amino)piperidine-1-carbonyl)thiazol-2-yl)acrylamide |
| 102 | 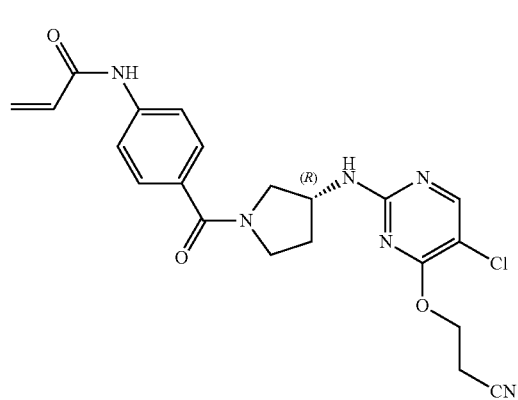 | (R)-N-(4-(3-((5-chloro-4-(2-cyanoethoxy)pyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 103 | 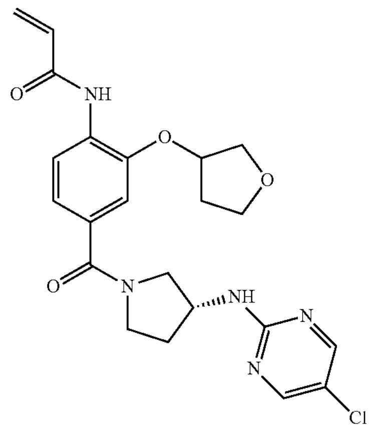 [SMILES: C=CC(=O)Nc1ccc(C(=O)N2CC[C@@H](Nc3ncc(Cl)cn3)C2)cc1OC1CCOC1] | N-(4-((R)-3-((5-chloropyrimidin-2-yl)amino)pyrrolidine-1-carbonyl)-2-((tetrahydrofuran-3-yl)oxy)phenyl)acrylamide |
| 104 | 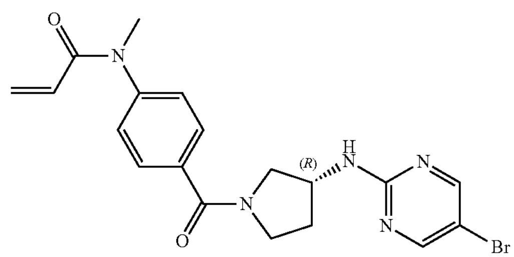 | (R)-N-(4-(3-((5-bromopyrimidin-2-yl)amino)pyrrolidine-1-carbonyl)phenyl)-N-methylacrylamide |
| 105 | 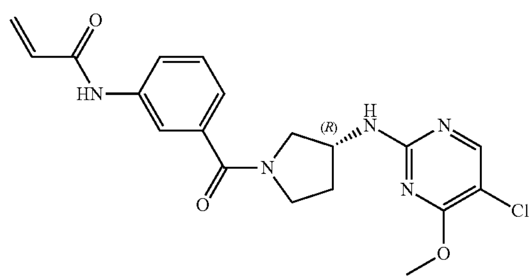 | (R)-N-(3-(3-((5-chloro-4-methoxypyrimidin-2-yl)amino)pyrrolidine-1-carbonyl)phenyl)acrylamide |
| 106 | 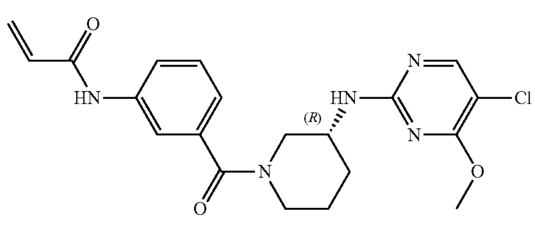 | (R)-N-(3-(3-((5-chloro-4-methoxypyrimidin-2-yl)amino)piperidine-1-carbonyl)phenyl)acrylamide |
| 107 | 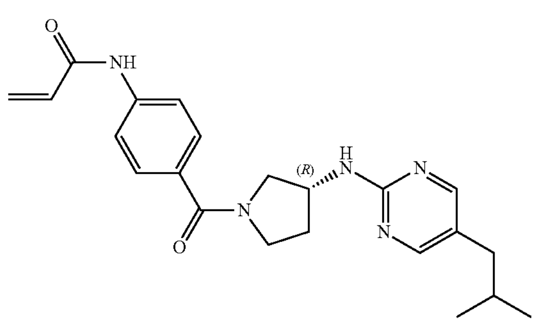 | (R)-N-(4-(3-((5-isobutylpyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 108 | 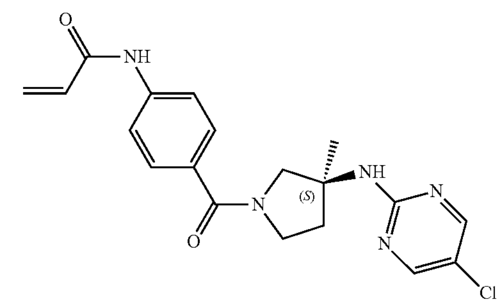 | (S)-N-(4-(3-((5-chloropyrimidin-2-yl)amino)-3-methylpyrrolidine-1-carbonyl)phenyl)acrylamide |
| 109 | 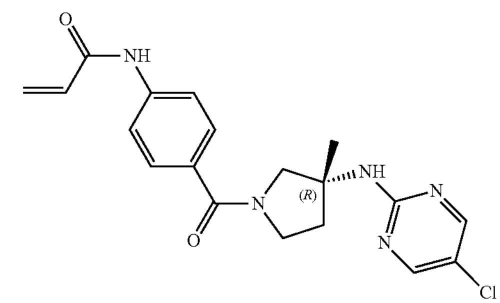 | (R)-N-(4-(3-((5-cyanopyrimidin-2-yl)amino)pyrrolidine-1-carbonyl)-2-(2-(dimethylamino)ethoxy)phenyl)acrylamide |
| 110 | 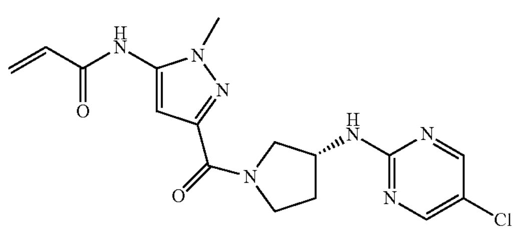 [SMILES: C=CC(=O)Nc1cc(C(=O)N2CC[C@@H](Nc3ncc(Cl)cn3)C2)nn1C] | (R)-N-(3-(3-((5-chloropyrimidin-2-yl)amino)pyrrolidine-1-carbonyl)-1-methyl-1H-pyrazol-5-yl)acrylamide |
| 111 | 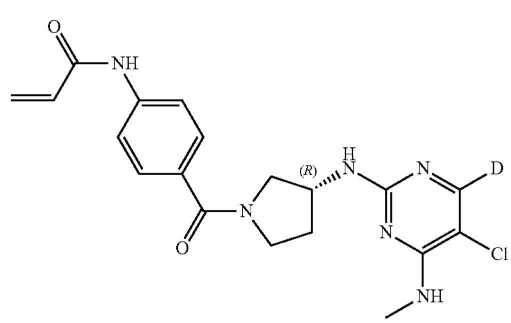 | (R)-N-(4-(3-((4-deutero-5-chloro-6-(methylamino)pyrimidin-2-yl)amino)pyrrolidine-1-carbonyl)phenyl)acrylamide |
| 112 | 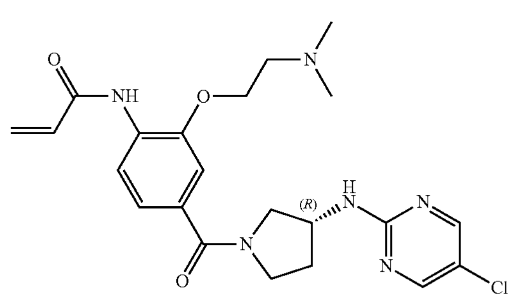 | (R)-N-(4-(3-((5-chloropyrimidin-2-yl)amino)pyrrolidine-1-carbonyl)-2-(2-(dimethylamino)ethoxy)phenyl)acrylamide |

TABLE 1-continued

| Synthetic Chemistry Example | Compound Structure | Compound Name |
|---|---|---|
| 113 | 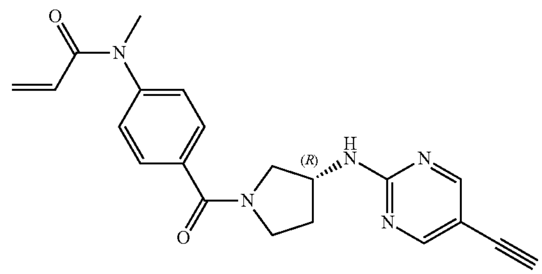 | (R)-N-(4-(3-((5-ethynylpyrimidin-2-yl)amino)pyrrolidine-1-carbonyl)phenyl)-N-methylacrylamide |
| 114 | 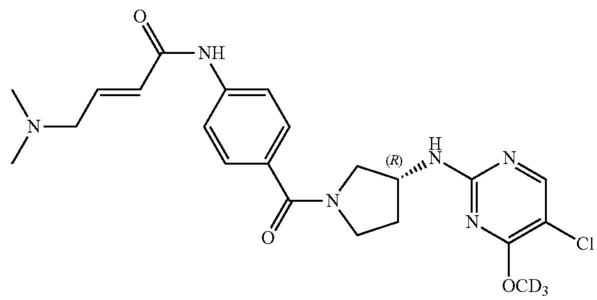 | (R,E)-N-(4-(3-((5-chloro-4-(trideuteromethoxy)pyrimidin-2-yl)amino)pyrrolidine-1-carbonyl)phenyl)-4-(dimethylamino)but-2-enamide |
| 115 | 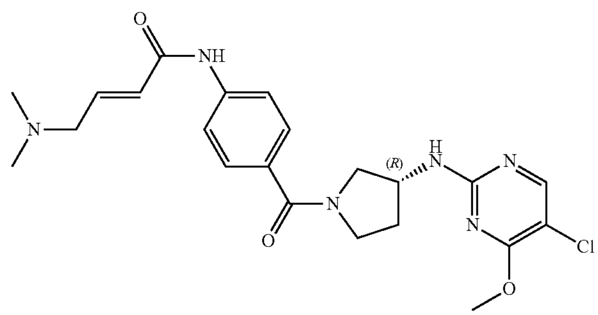 | (R,E)-N-(4-(3-((5-chloro-4-methoxypyrimidin-2-yl)amino)pyrrolidine-1-carbonyl)phenyl)-4-(dimethylamino)but-2-enamide |
| 116 | 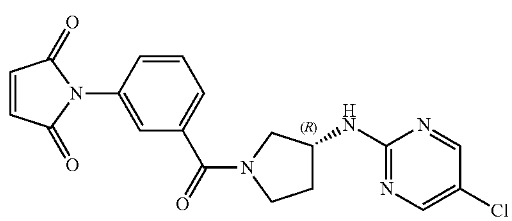 | (R)-1-(3-(3-((5-chloropyrimidin-2-yl)amino)pyrrolidine-1-carbonyl)phenyl)-1H-pyrrole-2,5-dione |
| 117 | 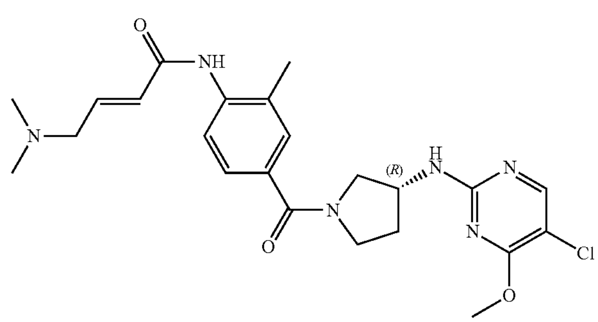 | (R,E)-N-(4-(3-((5-chloro-4-methoxypyrimidin-2-yl)amino)pyrrolidine-1-carbonyl)-2-methylphenyl)-4-(dimethylamino)but-2-enamide |

TABLE 1-continued

| Synthetic Chemistry Example | Compound Structure | Compound Name |
|---|---|---|
| 118 | 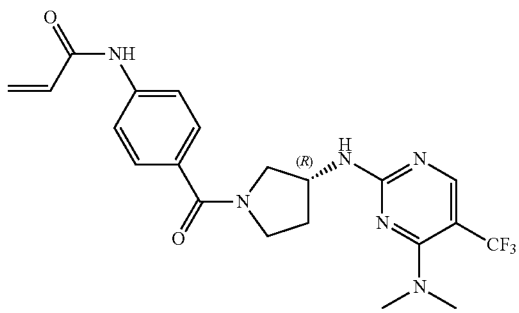 | (R)-N-(4-(3-((4-(dimethylamino)-5-(trifluoromethyl)pyrimidin-2-yl)amino)pyrrolidine-1-carbonyl)phenyl)acrylamide |
| 119 | 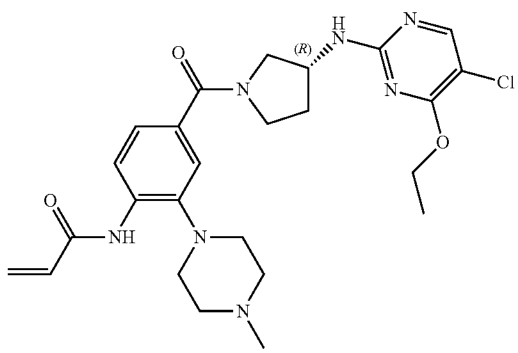 | (R)-N-(4-(3-((5-chloro-4-ethoxypyrimidin-2-yl)amino)pyrrolidine-1-carbonyl)-2-(4-methylpiperazin-1-yl)phenyl)acrylamide |
| 120 | 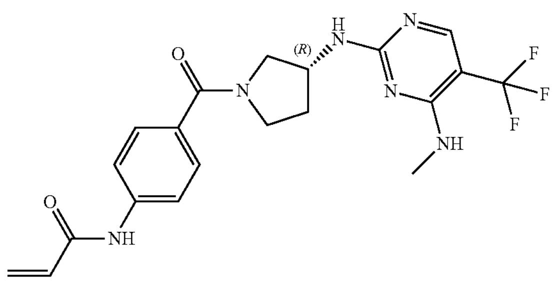 | (R)-N-(4-(3-((4-(methylamino)-5-(trifluoromethyl)pyrimidin-2-yl)amino)pyrrolidine-1-carbonyl)phenyl)acrylamide |
| 121 | 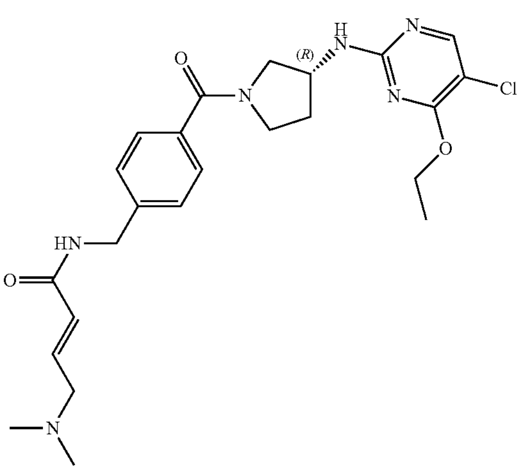 | (R,E)-N-(4-(3-((5-chloro-4-ethoxypyrimidin-2-yl)amino)pyrrolidine-1-carbonyl)benzyl)-4-(dimethylamino)but-2-enamide |

TABLE 1-continued

| Synthetic Chemistry Example | Compound Structure | Compound Name |
|---|---|---|
| 122 | 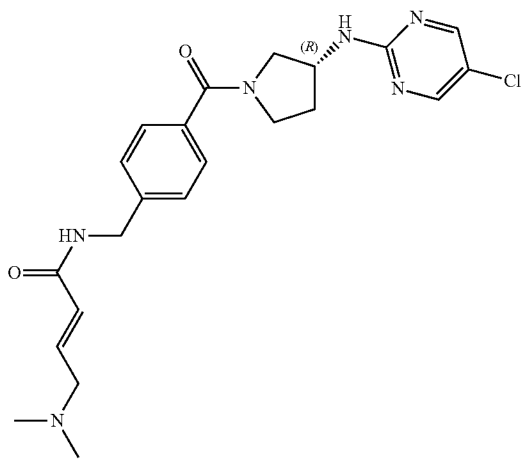 | (R,E)-N-(4-(3-((5-chloropyrimidin-2-yl)amino)pyrrolidine-1-carbonyl)benzyl)-4-(dimethylamino)but-2-enamide |
| 123 | 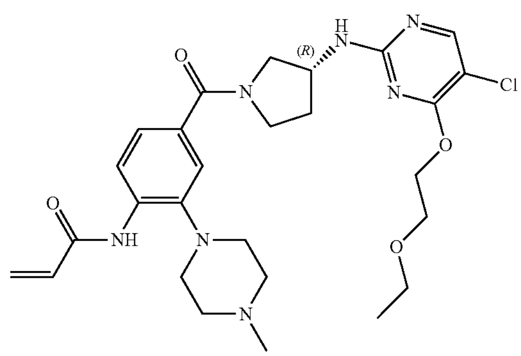 | (R)-N-(4-(3-((5-chloro-4-(2-ethoxyethoxy)pyrimidin-2-yl)amino)pyrrolidine-1-carbonyl)-2-(4-methylpiperazin-1-yl)phenyl)acrylamide |
| 124 | 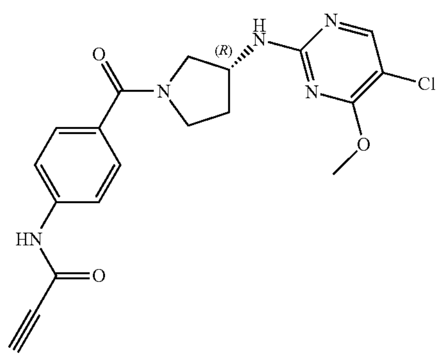 | (R)-N-(4-(3-((5-chloro-4-methoxypyrimidin-2-yl)amino)pyrrolidine-1-carbonyl)phenyl)propiolamide |
| 125 | 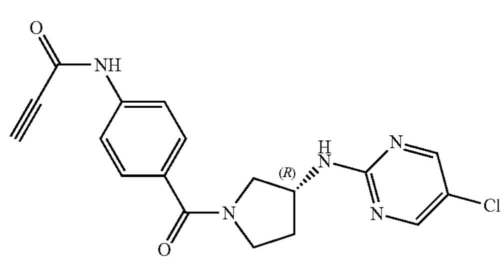 | (R)-N-(4-(3-((5-chloropyrimidin-2-yl)amino)pyrrolidine-1-carbonyl)phenyl)propiolamide |

TABLE 1-continued

| Synthetic Chemistry Example | Compound Structure | Compound Name |
|---|---|---|
| 126 | 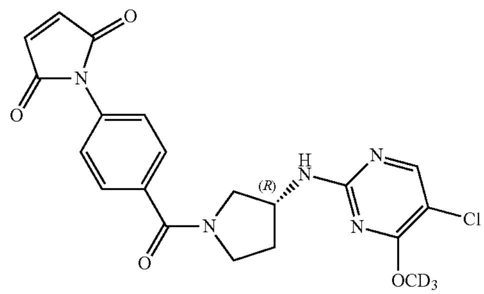 | (R)-1-(4-(3-((5-chloro-4-(trideuteromethoxy)pyrimidin-2-yl)amino)pyrrolidine-1-carbonyl)phenyl)-1H-pyrrole-2,5-dione |
| 127 | 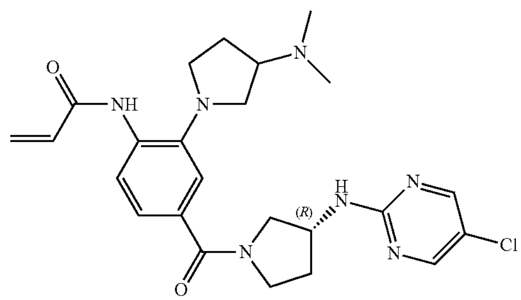 | N-(4-((R)-3-((5-chloropyrimidin-2-yl)amino)pyrrolidine-1-carbonyl)-2-(3-(dimethylamino)pyrrolidin-1-yl)phenyl)acrylamide |
| 128 | 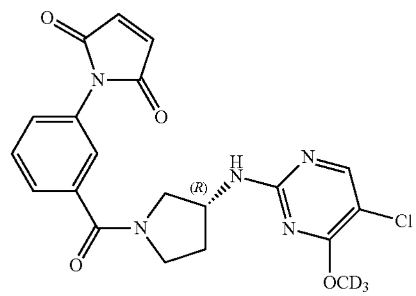 | (R)-1-(3-(3-((5-chloro-4-(trideuteriomethoxy)pyrimidin-2-yl)amino)pyrrolidine-1-carbonyl)phenyl)-1H-pyrrole-2,5-dione |
| 129 | 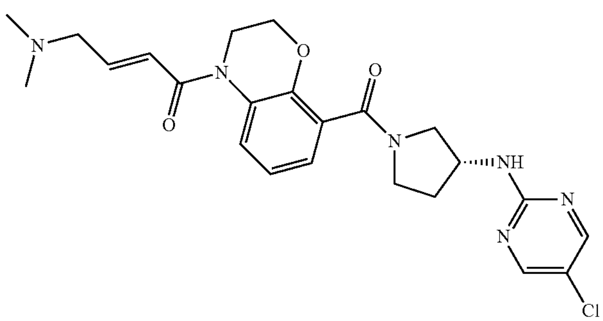 [SMILES: CN(C)C/C=C/C(=O)N1CCOc2c(C(=O)N3CC[C@@H](Nc4ncc(Cl)cn4)C3)cccc21] | (R,E)-1-(8-(3-((5-chloropyrimidin-2-yl)amino)pyrrolidine-1-carbonyl)-2H-benzo[b][1,4]oxazin-4(3H)-yl)-4-(dimethylamino)but-2-en-1-one |
| 130 | 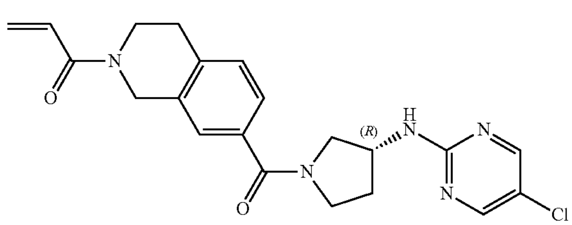 | (R)-1-(7-(3-((5-chloropyrimidin-2-yl)amino)pyrrolidine-1-carbonyl)-3,4-dihydroisoquinolin-2(1H)-yl)prop-2-en-1-one |

TABLE 1-continued

| Synthetic Chemistry Example | Compound Structure | Compound Name |
|---|---|---|
| 131 | 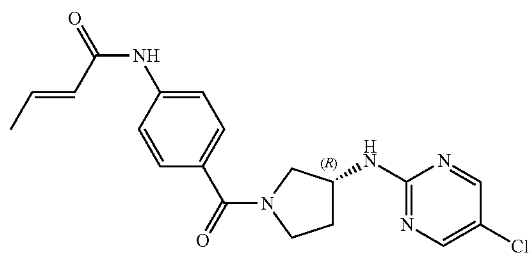 | (R,E)-N-(4-(3-((5-chloropyrimidin-2-yl)amino)pyrrolidine-1-carbonyl)phenyl)but-2-enamide |
| 132 | 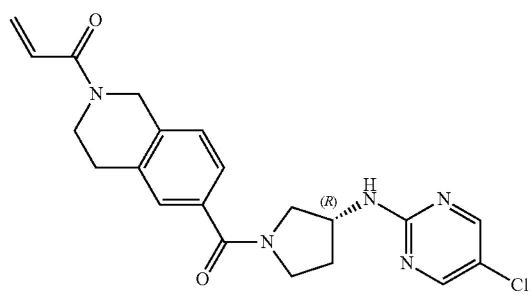 | (R)-1-(6-(3-((5-chloropyrimidin-2-yl)amino)pyrrolidine-1-carbonyl)-3,4-dihydroisoquinolin-2(1H)-yl)prop-2-en-1-one |
| 133 | 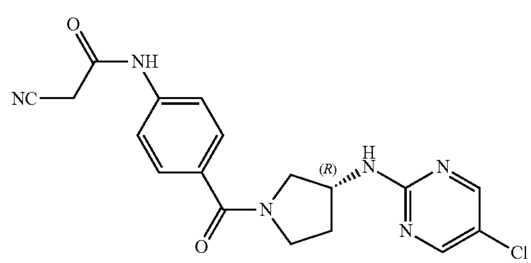 | (R)-N-(4-(3-((5-chloropyrimidin-2-yl)amino)pyrrolidine-1-carbonyl)phenyl)-2-cyanoacetamide |
| 134 | 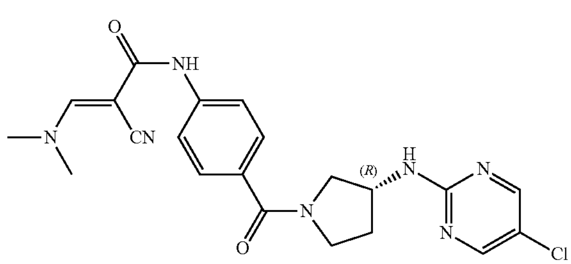 | (R)-N-(4-(3-((5-chloropyrimidin-2-yl)amino)pyrrolidine-1-carbonyl)phenyl)-2-cyano-3-(dimethylamino)acrylamide |
| 135 | 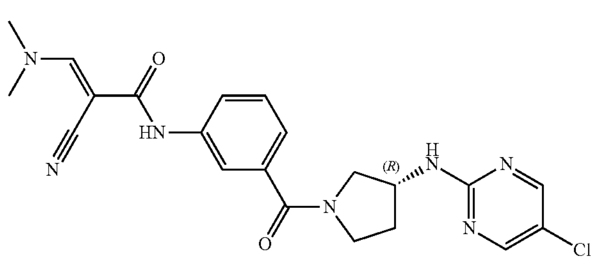 | (R)-N-(3-(3-((5-chloropyrimidin-2-yl)amino)pyrrolidine-1-carbonyl)phenyl)-2-cyano-3-(dimethylamino)acrylamide |

TABLE 1-continued

| Synthetic Chemistry Example | Compound Structure | Compound Name |
|---|---|---|
| 136 | 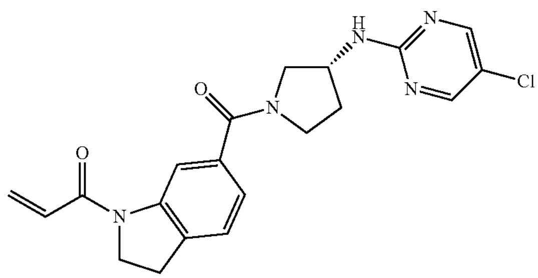 [SMILES: C=CC(=O)N1CCc2ccc(C(=O)N3CC[C@@H](Nc4ncc(Cl)cn4)C3)cc21] | (R)-1-(6-(3-((5-chloropyrimidin-2-yl)amino)pyrrolidine-1-carbonyl)indolin-1-yl)prop-2-en-1-one |
| 137 | 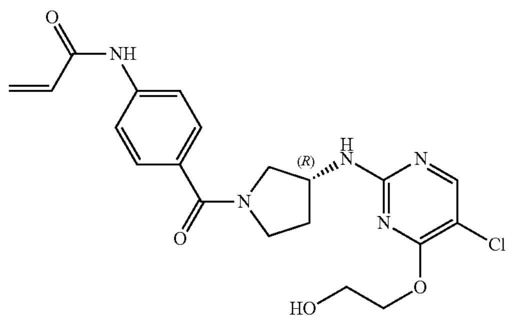 | (R)-N-(4-(3-((5-chloro-4-(2-hydroxyethoxy)pyrimidin-2-yl)amino)pyrrolidine-1-carbonyl)phenyl)acrylamide |
| 138 | 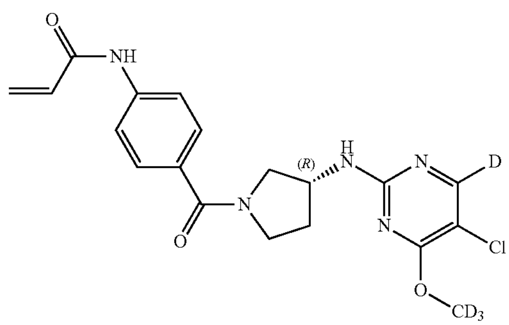 | (R)-N-(4-(3-((4-deutero-5-chloro-6-(trideuteromethoxy)pyrimidin-2-yl)amino)pyrrolidine-1-carbonyl)phenyl)acrylamide |
| 139 | 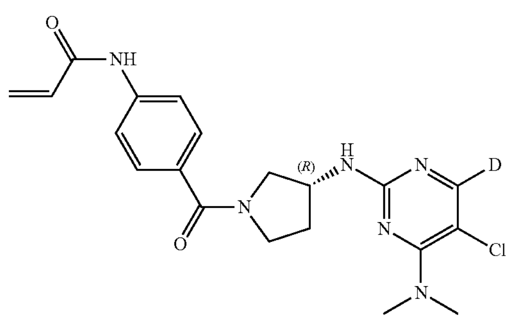 | (R)-N-(4-(3-((4-deutero-5-chloro-6-(dimethylamino)pyrimidin-2-yl)amino)pyrrolidine-1-carbonyl)phenyl)acrylamide |
| 140 | 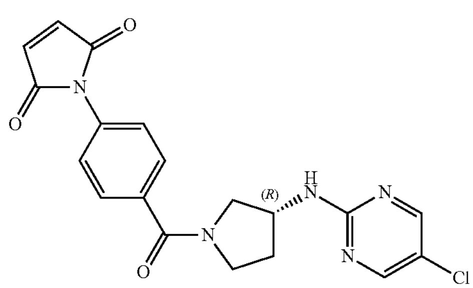 | (R)-1-(4-(3-((5-chloropyrimidin-2-yl)amino)pyrrolidine-1-carbonyl)phenyl)-1H-pyrrole-2,5-dione |

TABLE 1-continued

| Synthetic Chemistry Example | Compound Structure | Compound Name |
|---|---|---|
| 141 | 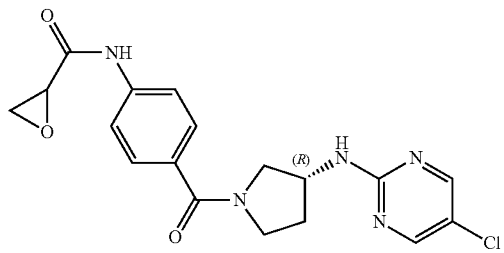 | N-(4-((R)-3-((5-chloropyrimidin-2-yl)amino)pyrrolidine-1-carbonyl)phenyl)oxirane-2-carboxamide |
| 142 | 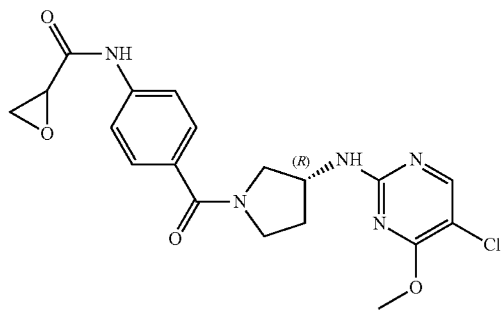 | N-(4-((R)-3-((5-chloro-4-methoxypyrimidin-2-yl)amino)pyrrolidine-1-carbonyl)phenyl)oxirane-2-carboxamide |
| 143 | 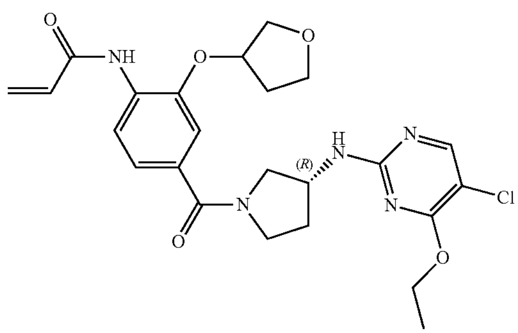 | N-(4-((R)-3-((5-chloro-4-ethoxypyrimidin-2-yl)amino)pyrrolidine-1-carbonyl)-2-((tetrahydrofuran-3-yl)oxy)phenyl)acrylamide |
| 144 | 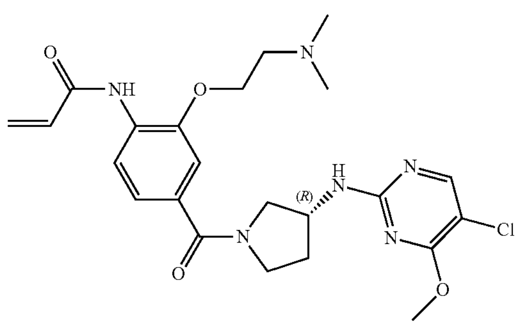 | (R)-N-(4-(3-((5-chloro-4-ethoxypyrimidin-2-yl)amino)pyrrolidine-1-carbonyl)-2-(2-(dimethylamino)ethoxy)phenyl)acrylamide |
| 145 | 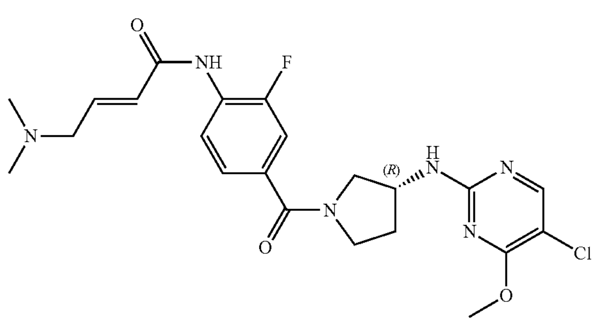 | (R,E)-N-(4-(3-((5-chloro-4-methoxypyrimidin-2-yl)amino)pyrrolidine-1-carbonyl)-2-fluorophenyl)-4-(dimethylamino)but-2-enamide |

TABLE 1-continued

| Synthetic Chemistry Example | Compound Structure | Compound Name |
|---|---|---|
| 146 | 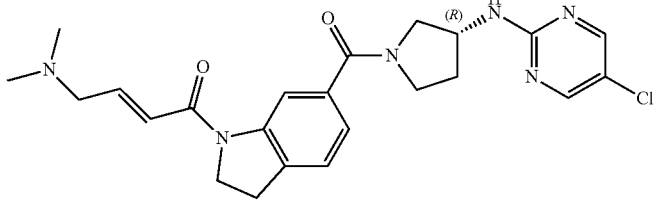 | (R,E)-1-(6-(3-((5-chloropyrimidin-2-yl)amino)pyrrolidine-1-carbonyl)indolin-1-yl)-4-(dimethylamino)but-2-en-1-one |
| 147 | 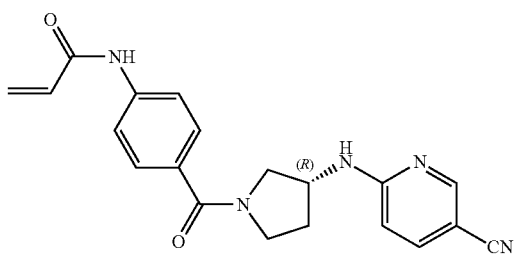 | (R)-N-(4-(3-((5-cyanopyridin-2-yl)amino)pyrrolidine-1-carbonyl)phenyl)acrylamide |
| 148 | 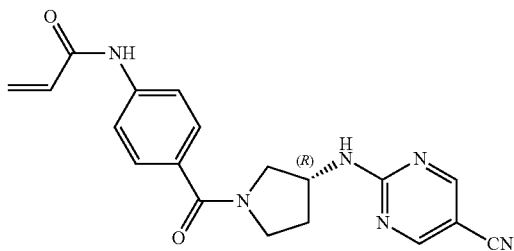 | (R)-N-(4-(3-((5-cyanopyrimidin-2-yl)amino)pyrrolidine-1-carbonyl)phenyl)acrylamide |
| 149 | 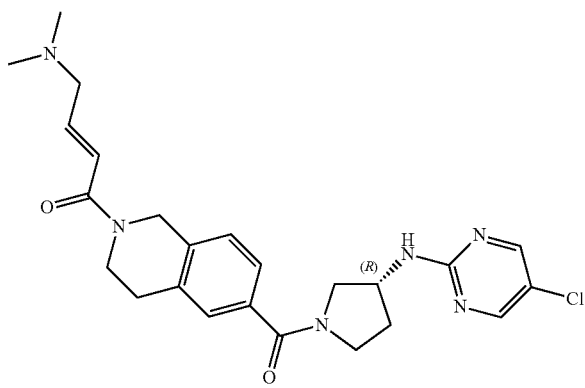 | (R,E)-1-(6-(3-((5-chloropyrimidin-2-yl)amino)pyrrolidine-1-carbonyl)-3,4-dihydroisoquinolin-2(1H)-yl)-4-(dimethylamino)but-2-en-1-one |
| 150 | 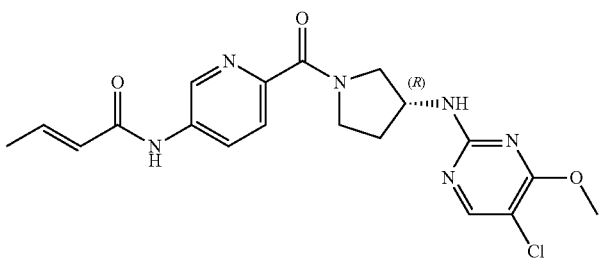 | (R,E)-N-(6-(3-((5-chloro-4-methoxypyrimidin-2-yl)amino)pyrrolidine-1-carbonyl)pyridin-3-yl)but-2-enamide |

TABLE 1-continued

| Synthetic Chemistry Example | Compound Structure | Compound Name |
|---|---|---|
| 151 | 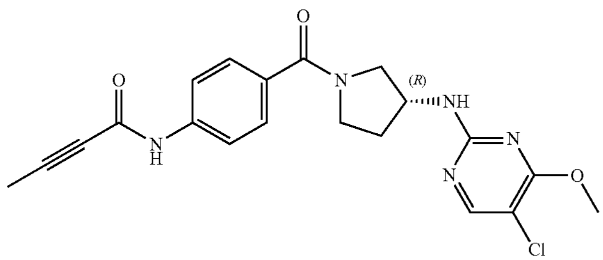 | (R)-N-(4-(3-((5-chloro-4-methoxypyrimidin-2-yl)amino)pyrrolidine-1-carbonyl)phenyl)but-2-ynamide |
| 152 | 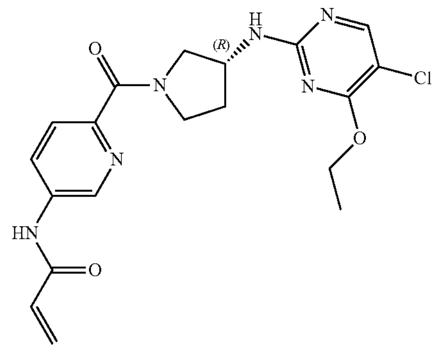 | (R)-N-(6-(3-((5-chloro-4-ethoxypyrimidin-2-yl)amino)pyrrolidine-1-carbonyl)pyridin-3-yl)acrylamide |
| 153 | 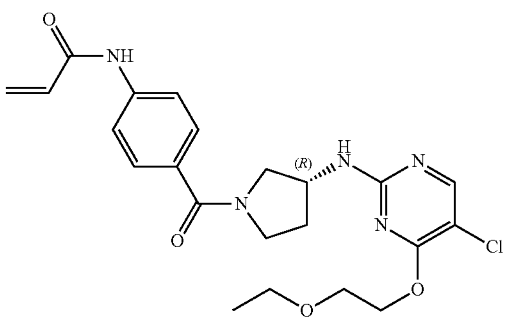 | (R)-N-(4-(3-((5-chloro-4-(2-ethoxyethoxy)pyrimidin-2-yl)amino)pyrrolidine-1-carbonyl)phenyl)acrylamide |
| 154 | 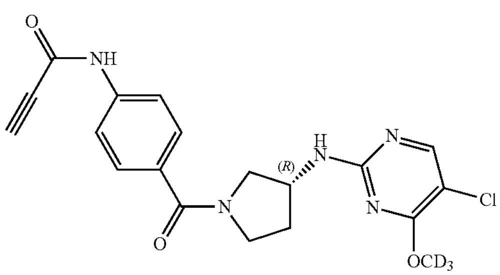 | (R)-N-(4-(3-((5-chloro-4-(trideuteromethoxy)pyrimidin-2-yl)amino)pyrrolidine-1-carbonyl)phenyl)propiolamide |
| 155 | 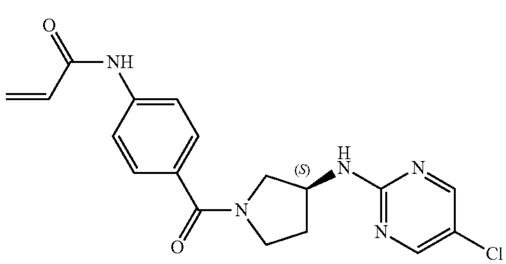 | (S)-N-(4-(3-((5-chloropyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 156 | 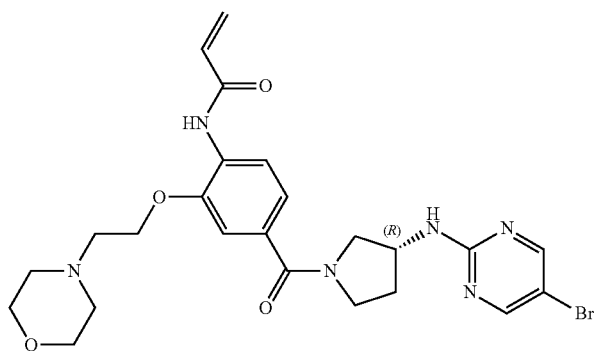 | (R)-N-(4-(3-((5-bromopyrimidin-2-yl)amino)pyrrolidine-1-carbonyl)-2-(2-morpholinoethoxy)phenyl)acrylamide |
| 157 | 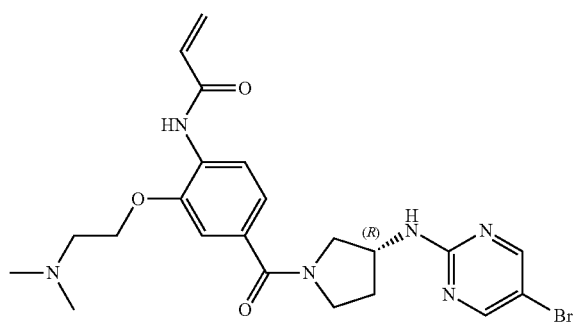 | (R)-N-(4-(3-((5-bromopyrimidin-2-yl)amino)pyrrolidine-1-carbonyl)-2-(2-(dimethylamino)ethoxy)phenyl)acrylamide |
| 158 | 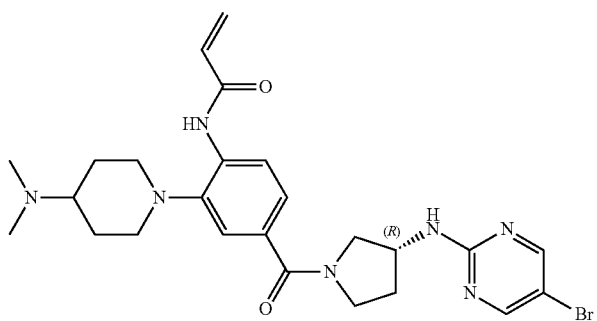 | (R)-N-(4-(3-((5-bromopyrimidin-2-yl)amino)pyrrolidine-1-carbonyl)-2-(4-(dimethylamino)piperidin-1-yl)phenyl)acrylamide |
| 159 | 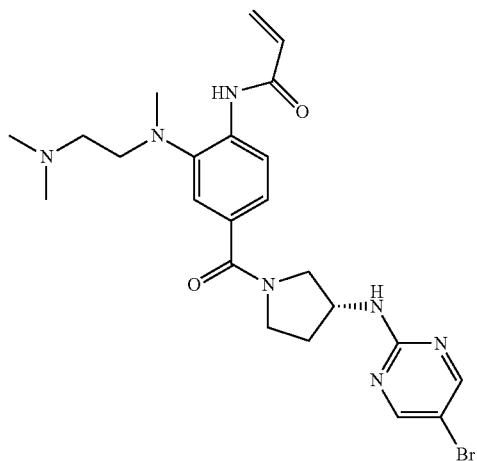 [SMILES: C=CC(=O)Nc1ccc(C(=O)N2CC[C@@H](Nc3ncc(Br)cn3)C2)cc1N(C)CCN(C)C] | (R)-N-(4-(3-((5-bromopyrimidin-2-yl)amino)pyrrolidine-1-carbonyl)-2-((2-(dimethylamino)ethyl)(methyl)amino)phenyl)acrylamide |

TABLE 1-continued

| Synthetic Chemistry Example | Compound Structure | Compound Name |
|---|---|---|
| 160 | 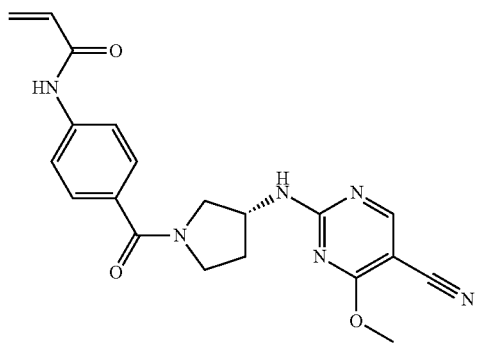 [SMILES: C=CC(=O)Nc1ccc(C(=O)N2CC[C@@H](Nc3ncc(C#N)c(OC)n3)C2)cc1] | (R)-N-(4-(3-((5-cyano-4-methoxypyrimidin-2-yl)amino)pyrrolidine-1-carbonyl)phenyl)acrylamide |
| 161 | 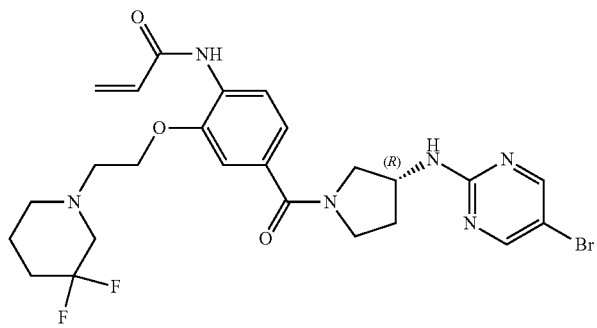 | (R)-N-(4-(3-((5-bromopyrimidin-2-yl)amino)pyrrolidine-1-carbonyl)-2-(2-(3,3-difluoropiperidin-1-yl)ethoxy)phenyl)acrylamide |
| 162 | 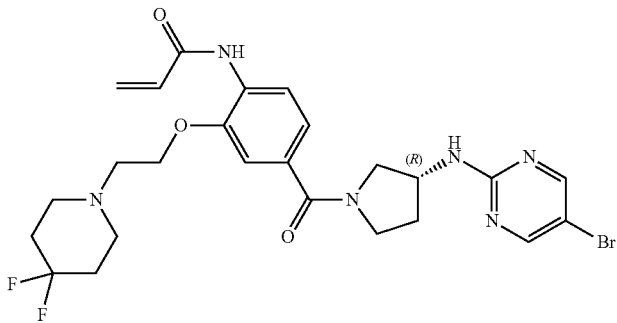 | (R)-N-(4-(3-((5-bromopyrimidin-2-yl)amino)pyrrolidine-1-carbonyl)-2-(2-(4,4-difluoropiperidin-1-yl)ethoxy)phenyl)acrylamide |
| 163 | 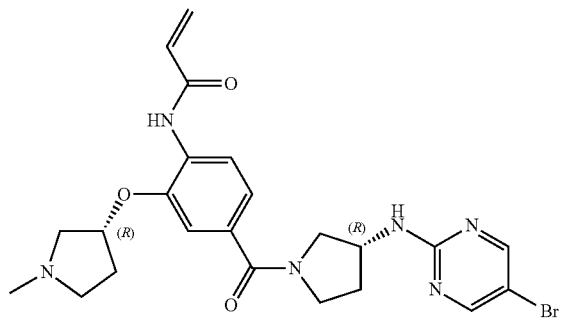 | N-(4-((R)-3-((5-bromopyrimidin-2-yl)amino)pyrrolidine-1-carbonyl)-2-(((R)-1-methylpyrrolidin-3-yl)oxy)phenyl)acrylamide |

| Synthetic Chemistry Example | Compound Structure | Compound Name |
|---|---|---|
| 164 | 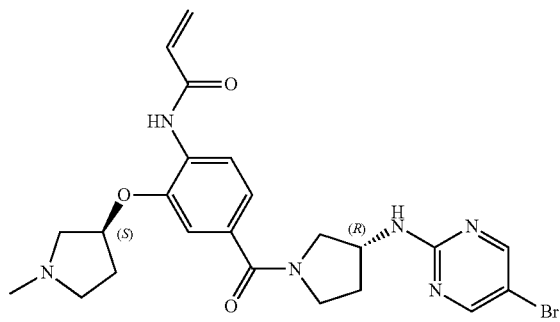 | N-(4-((R)-3-((5-bromopyrimidin-2-yl)amino)pyrrolidine-1-carbonyl)-2-(((S)-1-methylpyrrolidin-3-yl)oxy)phenyl)acrylamide |
| 165 | 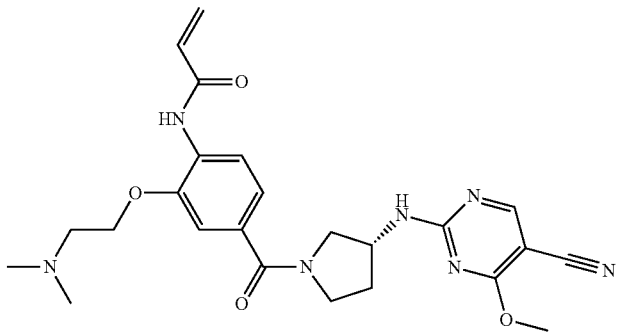 [SMILES: C=CC(=O)Nc1ccc(C(=O)N2CC[C@@H](Nc3ncc(C#N)c(OC)n3)C2)cc1OCCN(C)C] | (R)-N-(4-(3-((5-cyano-4-methoxypyrimidin-2-yl)amino)pyrrolidine-1-carbonyl)-2-(2-(dimethylamino)ethoxy)phenyl)acrylamide |
| 166 | 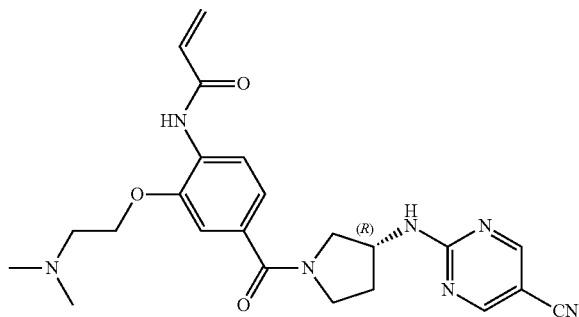 | (R)-N-(4-(3-((5-cyanopyrimidin-2-yl)amino)pyrrolidine-1-carbonyl)-2-(2-(dimethylamino)ethoxy)phenyl)acrylamide |
| 167 | 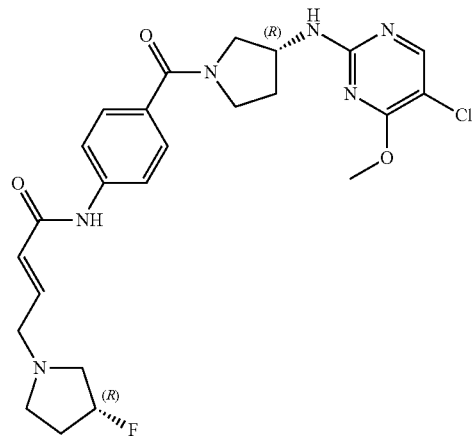 | (E)-N-(4-((R)-3-((5-chloro-4-methoxypyrimidin-2-yl)amino)pyrrolidine-1-carbonyl)phenyl)-4-((R)-3-fluoropyrrolidin-1-yl)but-2-enamide |

TABLE 1-continued

| Synthetic Chemistry Example | Compound Structure | Compound Name |
|---|---|---|
| 168 | 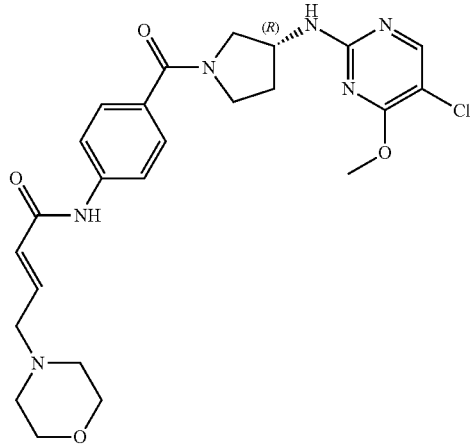 | (R,E)-N-(4-(3-((5-chloro-4-methoxypyrimidin-2-yl)amino)pyrrolidine-1-carbonyl)phenyl)-4-morpholinobut-2-enamide |
| 169 | 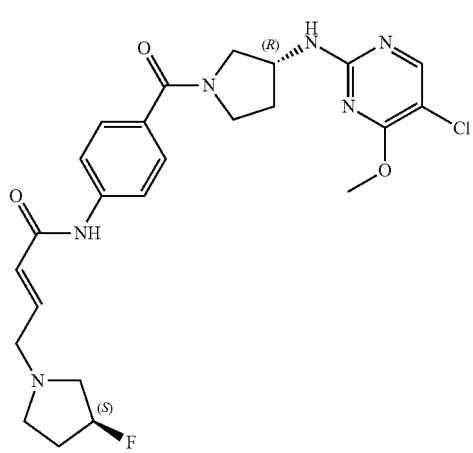 | (E)-N-(4-((R)-3-((5-chloro-4-methoxypyrimidin-2-yl)amino)pyrrolidine-1-carbonyl)phenyl)-4-((S)-3-fluoropyrrolidin-1-yl)but-2-enamide |
| 170 | 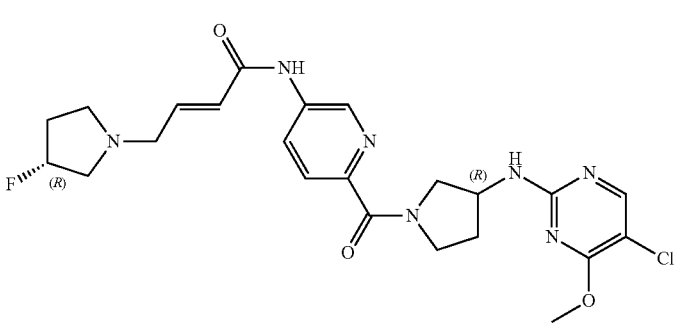 | (E)-N-(6-((R)-3-((5-chloro-4-methoxypyrimidin-2-yl)amino)pyrrolidine-1-carbonyl)pyridin-3-yl)-4-((R)-3-fluoropyrrolidin-1-yl)but-2-enamide |
| 171 | 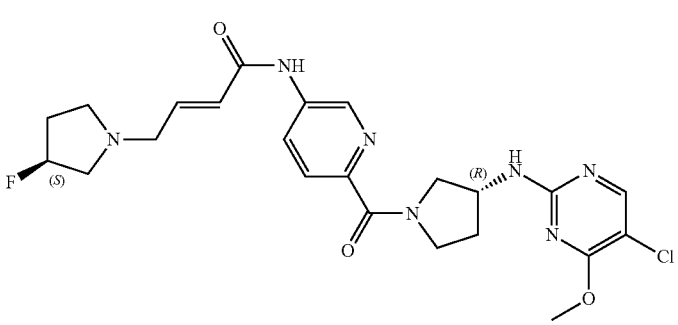 | (E)-N-(6-((R)-3-((5-chloro-4-methoxypyrimidin-2-yl)amino)pyrrolidine-1-carbonyl)pyridin-3-yl)-4-((S)-3-fluoropyrrolidin-1-yl)but-2-enamide |

TABLE 1-continued

| Synthetic Chemistry Example | Compound Structure | Compound Name |
|---|---|---|
| 172 | 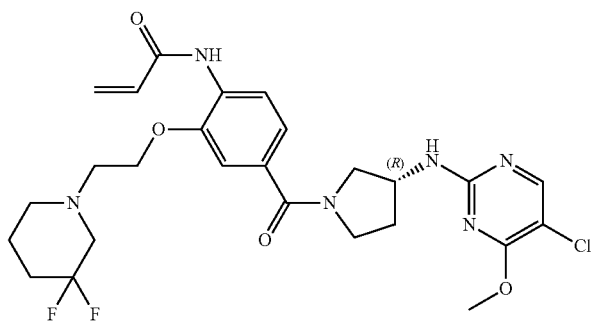 | (R,E)-N-(6-(3-((5-chloro-4-methoxypyrimidin-2-yl)amino)pyrrolidine-1-carbonyl)pyridin-3-yl)-4-(3,3-difluoropiperidin-1-yl)but-2-enamide |
| 173 | 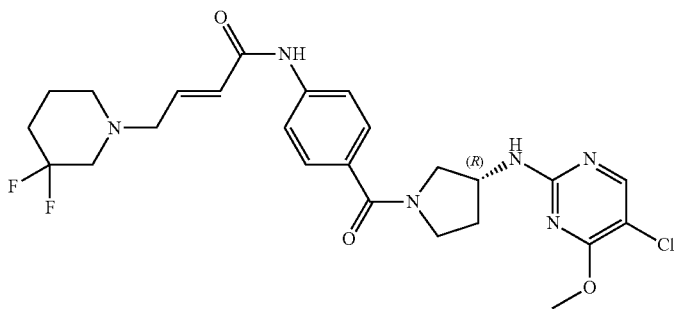 | (R,E)-N-(4-(3-((5-chloro-4-methoxypyrimidin-2-yl)amino)pyrrolidine-1-carbonyl)phenyl)-4-(3,3-difluoropiperidin-1-yl)but-2-enamide |
| 174 | 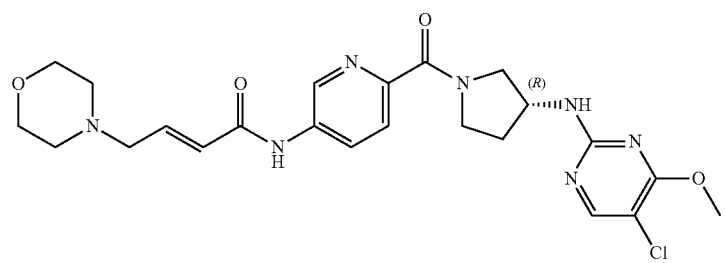 | (R,E)-N-(6-(3-((5-chloro-4-methoxypyrimidin-2-yl)amino)pyrrolidine-1-carbonyl)pyridin-3-yl)-4-morpholinobut-2-enamide |
| 175 | 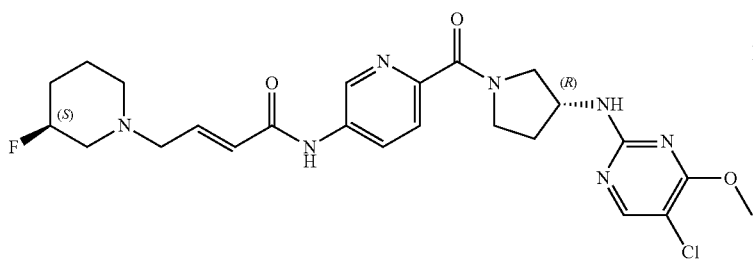 | (E)-N-(6-((R)-3-((5-chloro-4-methoxypyrimidin-2-yl)amino)pyrrolidine-1-carbonyl)pyridin-3-yl)-4-((S)-3-fluoropiperidin-1-yl)but-2-enamide |
| 176 | 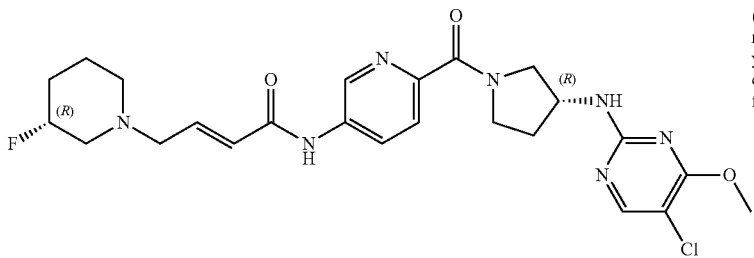 | (E)-N-(6-((R)-3-((5-chloro-4-methoxypyrimidin-2-yl)amino)pyrrolidine-1-carbonyl)pyridin-3-yl)-4-((R)-3-fluoropiperidin-1-yl)but-2-enamide |

TABLE 1-continued

| Synthetic Chemistry Example | Compound Structure | Compound Name |
|---|---|---|
| 177 | 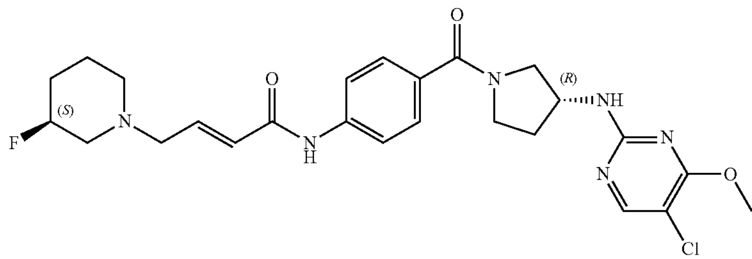 | (E)-N-(4-((R)-3-((5-chloro-4-methoxypyrimidin-2-yl)amino)pyrrolidine-1-carbonyl)phenyl)-4-((S)-3-fluoropiperidin-1-yl)but-2-enamide |
| 178 | 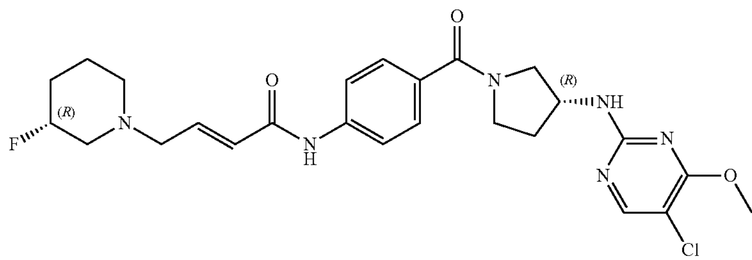 | (E)-N-(4-((R)-3-((5-chloro-4-methoxypyrimidin-2-yl)amino)pyrrolidine-1-carbonyl)phenyl)-4-((R)-3-fluoropiperidin-1-yl)but-2-enamide |
| 179 | 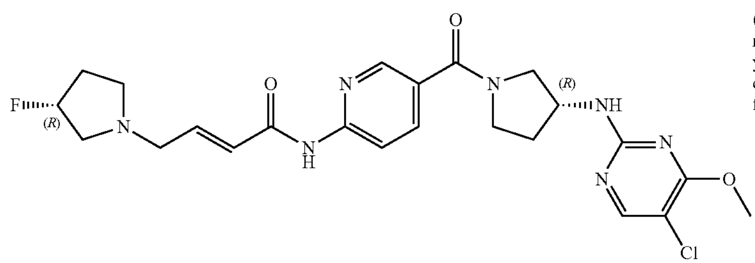 | (E)-N-(5-((R)-3-((5-chloro-4-methoxypyrimidin-2-yl)amino)pyrrolidine-1-carbonyl)pyridin-2-yl)-4-((R)-3-fluoropyrrolidin-1-yl)but-2-enamide |
| 180 | 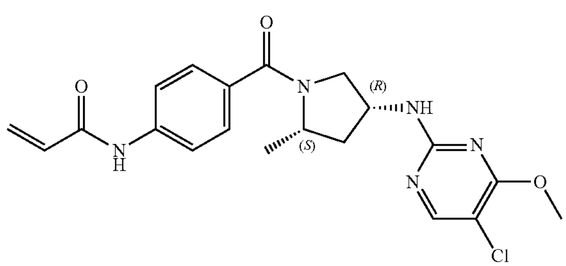 | N-(4-((2S,4R)-4-((5-chloro-4-methoxypyrimidin-2-yl)amino)-2-methylpyrrolidine-1-carbonyl)phenyl)acrylamide |
| 181 | 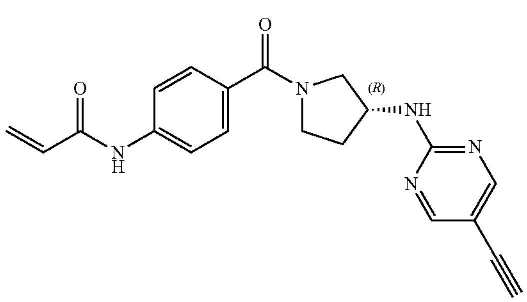 | (R)-N-(4-(3-((5-ethynylpyrimidin-2-yl)amino)pyrrolidine-1-carbonyl)phenyl)acrylamide |

TABLE 1-continued

| Synthetic Chemistry Example | Compound Structure | Compound Name |
|---|---|---|
| 182 | 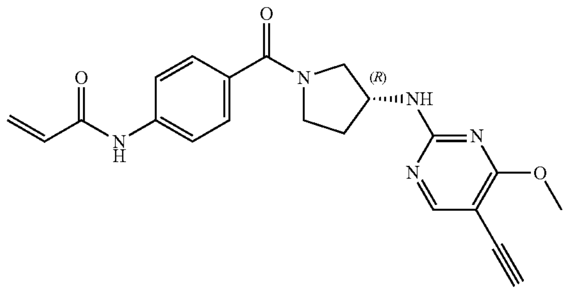 | (R)-N-(4-(3-((5-ethynyl-4-methoxypyrimidin-2-yl)amino)pyrrolidine-1-carbonyl)phenyl)acrylamide |
| 183 | 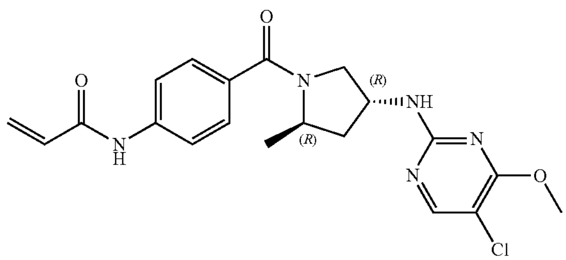 | N-(4-((2R,4R)-4-((5-chloro-4-methoxypyrimidin-2-yl)amino)-2-methylpyrrolidine-1-carbonyl)phenyl)acrylamide |
| 184 | 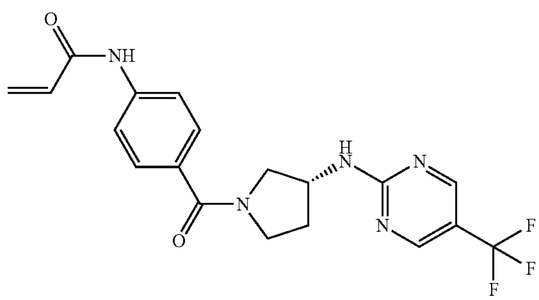 [SMILES: C=CC(=O)Nc1ccc(C(=O)N2CC[C@@H](Nc3ncc(C(F)(F)F)cn3)C2)cc1] | (R)-N-(4-(3-((5-(trifluoromethyl)pyrimidin-2-yl)amino)pyrrolidine-1-carbonyl)phenyl)acrylamide |

In some embodiments, the heteroaromatic CDK inhibitory compound of Formula (I) or Formula (II) described herein has a structure provided in Table 2.

TABLE 2

| Compound Structure | Compound Name |
|---|---|
| 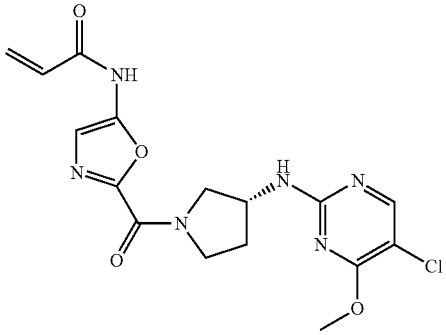 [SMILES: C=CC(=O)Nc1cnc(C(=O)N2CC[C@@H](Nc3ncc(Cl)c(OC)n3)C2)o1] | (R)-N-(2-(3-((5-chloro-4-methoxypyrimidin-2-yl)amino)pyrrolidine-1-carbonyl)oxazol-5-yl)acrylamide |

TABLE 2-continued

| Compound Structure | Compound Name |
|---|---|
| 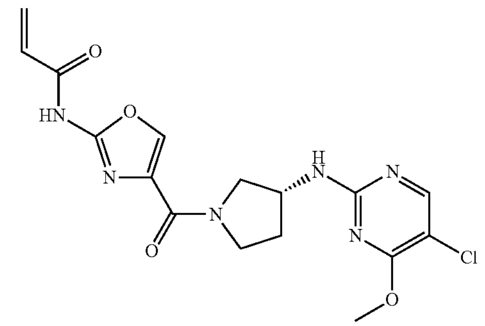 [SMILES: C=CC(=O)Nc1nc(C(=O)N2CC[C@@H](Nc3ncc(Cl)c(OC)n3)C2)co1] | (R)-N-(4-(3-((5-chloro-4-methoxypyrimidin-2-yl)amino)pyrrolidine-1-carbonyl)oxazol-2-yl)acrylamide |
| 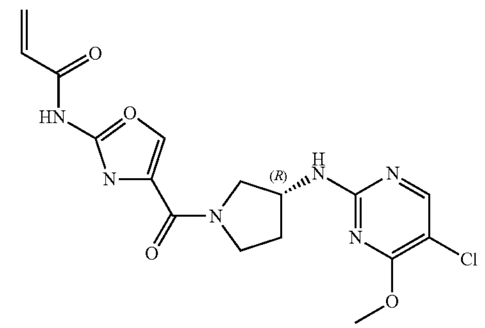 | (R)-N-(5-(3-((5-chloro-4-methoxypyrimidin-2-yl)amino)pyrrolidine-1-carbonyl)oxazol-2-yl)acrylamide |
| 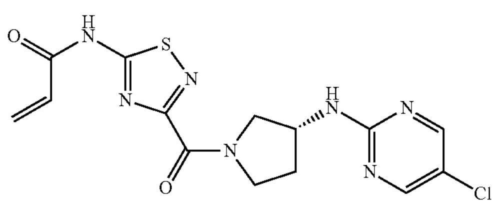 [SMILES: C=CC(=O)Nc1nc(C(=O)N2CC[C@@H](Nc3ncc(Cl)cn3)C2)ns1] | (R)-N-(3-(3-((5-chloropyrimidin-2-yl)amino)pyrrolidine-1-carbonyl)-1,2,4-thiadiazol-5-yl)acrylamide |
| 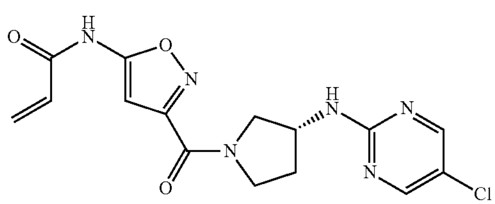 [SMILES: C=CC(=O)Nc1cc(C(=O)N2CC[C@@H](Nc3ncc(Cl)cn3)C2)no1] | (R)-N-(3-(3-((5-chloropyrimidin-2-yl)amino)pyrrolidine-1-carbonyl)isoxazol-5-yl)acrylamide |
| 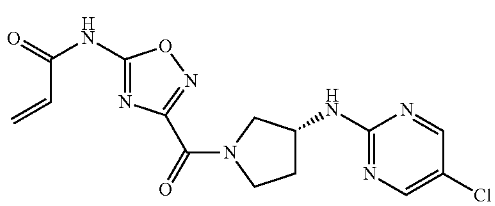 [SMILES: C=CC(=O)Nc1nc(C(=O)N2CC[C@@H](Nc3ncc(Cl)cn3)C2)no1] | (R)-N-(3-(3-((5-chloropyrimidin-2-yl)amino)pyrrolidine-1-carbonyl)-1,2,4-oxadiazol-5-yl)acrylamide |
| 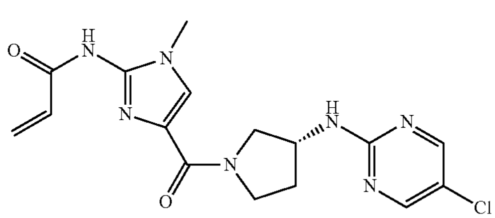 [SMILES: C=CC(=O)Nc1nc(C(=O)N2CC[C@@H](Nc3ncc(Cl)cn3)C2)cn1C] | (R)-N-(4-(3-((5-chloropyrimidin-2-yl)amino)pyrrolidine-1-carbonyl)-1-methyl-1H-imidazol-2-yl)acrylamide |

TABLE 2-continued

| Compound Structure | Compound Name |
|---|---|
| 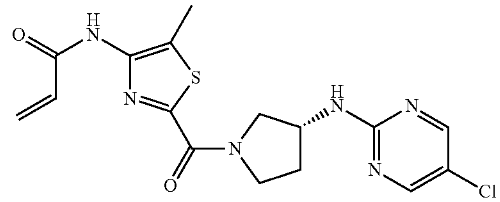 [SMILES: C=CC(=O)Nc1nc(C(=O)N2CC[C@@H](Nc3ncc(Cl)cn3)C2)sc1C] | (R)-N-(2-(3-((5-chloropyrimidin-2-yl)amino)pyrrolidine-1-carbonyl)-5-methylthiazol-4-yl)acrylamide |
| 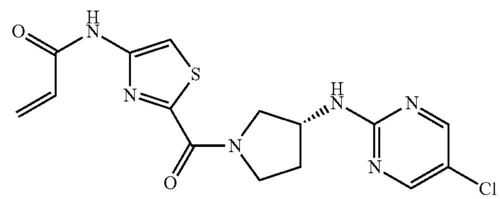 [SMILES: C=CC(=O)Nc1csc(C(=O)N2CC[C@@H](Nc3ncc(Cl)cn3)C2)n1] | (R)-N-(2-(3-((5-chloropyrimidin-2-yl)amino)pyrrolidine-1-carbonyl)thiazol-4-yl)acrylamide |
| 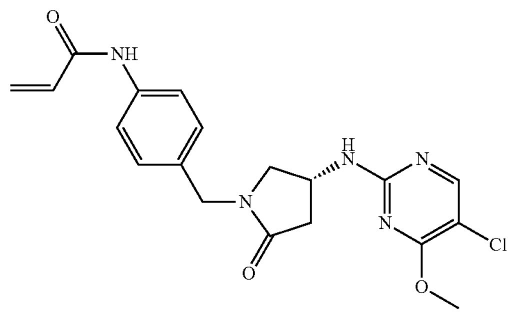 [SMILES: C=CC(=O)Nc1ccc(CN2C[C@H](Nc3ncc(Cl)c(OC)n3)CC2=O)cc1] | (R)-N-(4-((4-((5-chloro-4-methoxypyrimidin-2-yl)amino)-2-oxopyrrolidin-1-yl)methyl)phenyl)acrylamide |
| 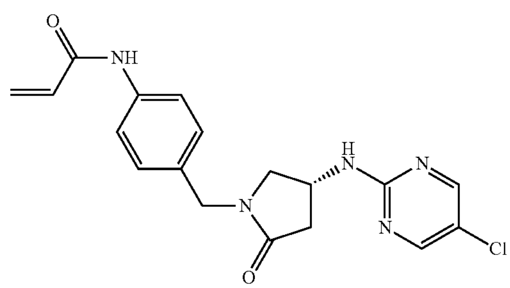 [SMILES: C=CC(=O)Nc1ccc(CN2C[C@H](Nc3ncc(Cl)cn3)CC2=O)cc1] | (R)-N-(4-((4-((5-chloropyrimidin-2-yl)amino)-2-oxopyrrolidin-1-yl)methyl)phenyl)acrylamide |
| 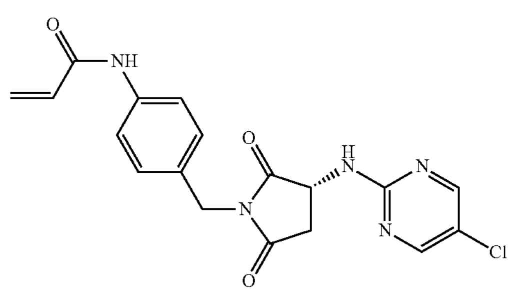 [SMILES: C=CC(=O)Nc1ccc(CN2C(=O)C[C@@H](Nc3ncc(Cl)cn3)C2=O)cc1] | (R)-N-(4-((3-((5-chloropyrimidin-2-yl)amino)-2,5-dioxopyrrolidin-1-yl)methyl)phenyl)acrylamide |
| 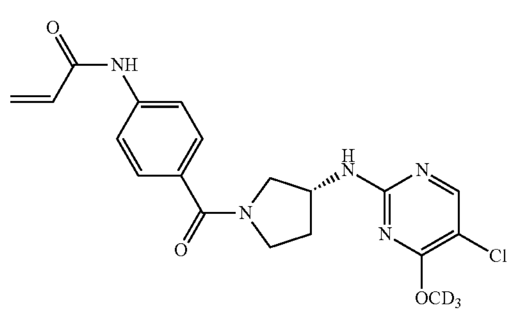 | (R)-N-(4-(3-((5-chloro-4-(methoxy-d3)pyrimidin-2-yl)amino)pyrrolidine-1-carbonyl)phenyl)acrylamide |

TABLE 2-continued

| Compound Structure | Compound Name |
|---|---|
| 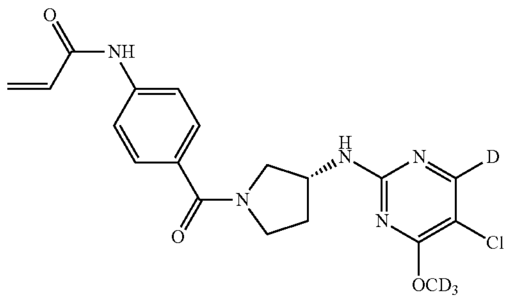 | (R)-N-(4-(3-((5-chloro-4-(methoxy-d3)pyrimidin-2-yl-6-d)amino)pyrrolidine-1-carbonyl)phenyl)acrylamide |
| 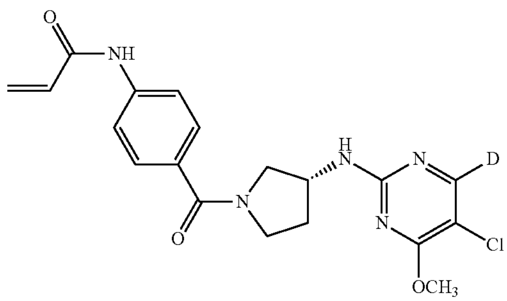 | (R)-N-(4-(3-((5-chloro-4-methoxypyrimidin-2-yl-6-d)amino)pyrrolidine-1-carbonyl)phenyl)acrylamide |
| 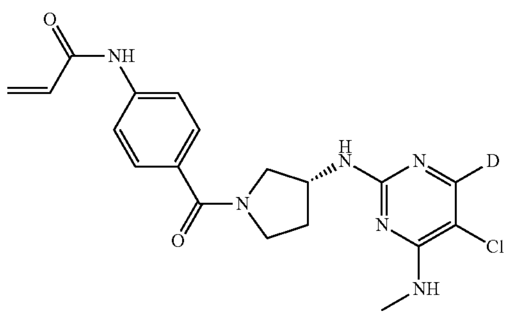 [SMILES: [2H]c1nc(N[C@@H]2CCN(C(=O)c3ccc(NC(=O)C=C)cc3)C2)nc(NC)c1Cl] | (R)-N-(4-(3-((5-chloro-4-(methylamino)pyrimidin-2-yl-6-d)amino)pyrrolidine-1-carbonyl)phenyl)acrylamide |
| 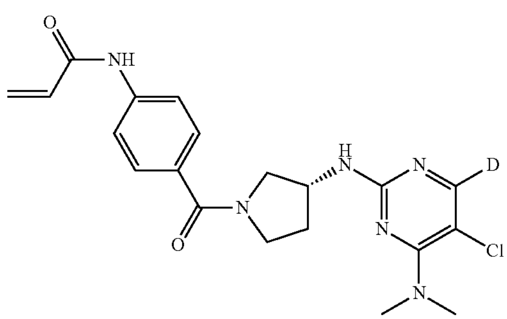 [SMILES: [2H]c1nc(N[C@@H]2CCN(C(=O)c3ccc(NC(=O)C=C)cc3)C2)nc(N(C)C)c1Cl] | (R)-N-(4-(3-((5-chloro-4-(dimethylamino)pyrimidin-2-yl-6-d)amino)pyrrolidine-1-carbonyl)phenyl)acrylamide |
| 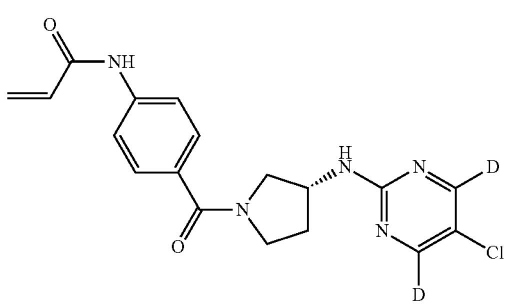 [SMILES: [2H]c1nc(N[C@@H]2CCN(C(=O)c3ccc(NC(=O)C=C)cc3)C2)nc([2H])c1Cl] | (R)-N-(4-(3-((5-chloropyrimidin-2-yl-4,6-d2)amino)pyrrolidine-1-carbonyl)phenyl)acrylamide |

TABLE 2-continued

| Compound Structure | Compound Name |
| --- | --- |
| 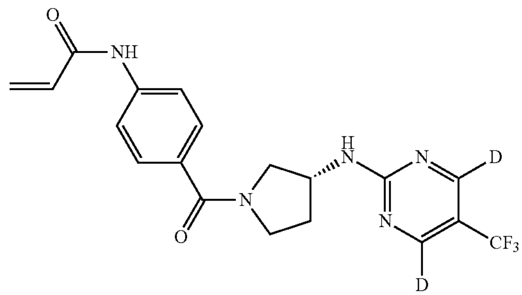 [SMILES: [2H]c1nc(N[C@@H]2CCN(C(=O)c3ccc(NC(=O)C=C)cc3)C2)nc([2H])c1C(F)(F)F] | (R)-N-(4-(3-((5-(trifluoromethyl)pyrimidin-2-yl-4,6-d2)amino)pyrrolidine-1-carbonyl)phenyl)acrylamide |
| 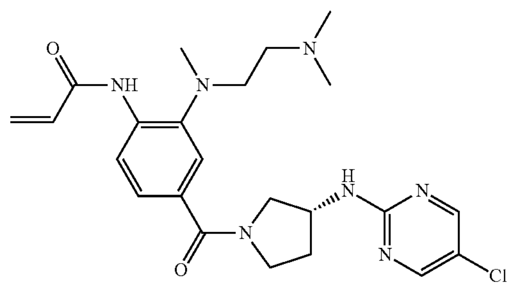 [SMILES: C=CC(=O)Nc1ccc(C(=O)N2CC[C@@H](Nc3ncc(Cl)cn3)C2)cc1N(C)CCN(C)C] | (R)-N-(4-(3-((5-chloropyrimidin-2-yl)amino)pyrrolidine-1-carbonyl)-2-((2-(dimethylamino)ethyl)(methyl)amino)phenyl)acrylamide |
| 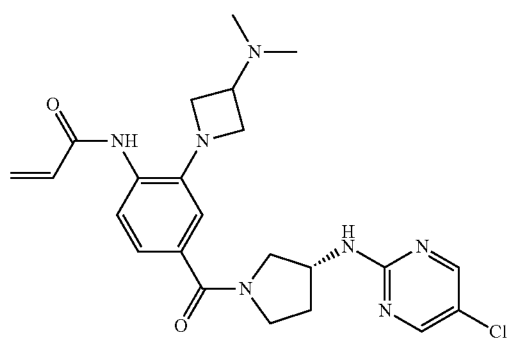 [SMILES: C=CC(=O)Nc1ccc(C(=O)N2CC[C@@H](Nc3ncc(Cl)cn3)C2)cc1N1CC(N(C)C)C1] | (R)-N-(4-(3-((5-chloropyrimidin-2-yl)amino)pyrrolidine-1-carbonyl)-2-(3-(dimethylamino)azetidin-1-yl)phenyl)acrylamide |
| 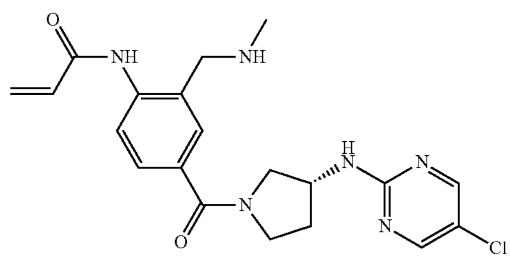 [SMILES: C=CC(=O)Nc1ccc(C(=O)N2CC[C@@H](Nc3ncc(Cl)cn3)C2)cc1CNC] | (R)-N-(4-(3-((5-chloropyrimidin-2-yl)amino)pyrrolidine-1-carbonyl)-2-((methylamino)methyl)phenyl)acrylamide |
| 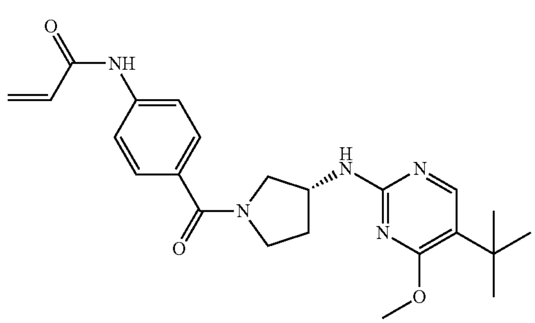 [SMILES: C=CC(=O)Nc1ccc(C(=O)N2CC[C@@H](Nc3ncc(C(C)(C)C)c(OC)n3)C2)cc1] | (R)-N-(4-(3-((5-tert-butyl)-4-methoxypyrimidin-2-yl)amino)pyrrolidine-1-carbonyl)phenyl)acrylamide |

TABLE 2-continued

| Compound Structure | Compound Name |
|---|---|
| 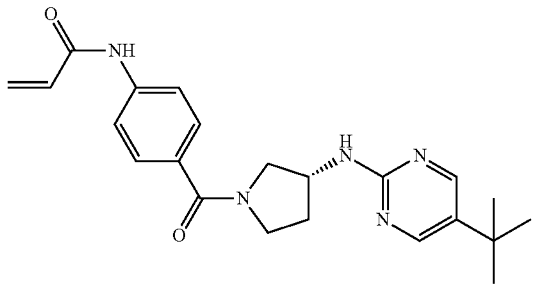 [SMILES: C=CC(=O)Nc1ccc(C(=O)N2CC[C@@H](Nc3ncc(C(C)(C)C)cn3)C2)cc1] | (R)-N-(4-(3-((5-(tert-butyl)pyrimidin-2-yl)amino)pyrrolidine-1-carbonyl)phenyl)acrylamide |
| 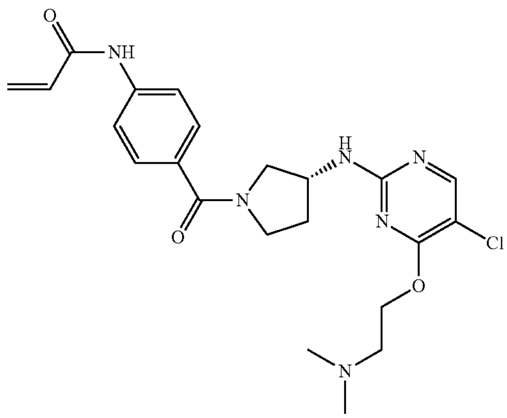 [SMILES: C=CC(=O)Nc1ccc(C(=O)N2CC[C@@H](Nc3ncc(Cl)c(OCCN(C)C)n3)C2)cc1] | (R)-N-(4-(3-((5-chloro-4-(2-(dimethylamino)ethoxy)pyrimidin-2-yl)amino)pyrrolidine-1-carbonyl)phenyl)acrylamide |
| 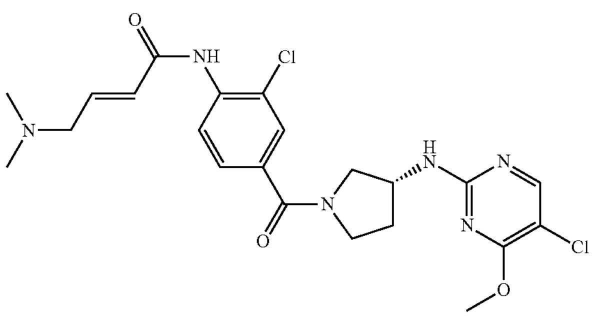 [SMILES: COc1nc(N[C@@H]2CCN(C(=O)c3ccc(NC(=O)/C=C/CN(C)C)c(Cl)c3)C2)ncc1Cl] | (R,E)-N-(2-chloro-4-(3-((5-chloro-4-methoxypyrimidin-2-yl)amino)pyrrolidine-1-carbonyl)phenyl)-4-(dimethylamino)but-2-enamide |
| 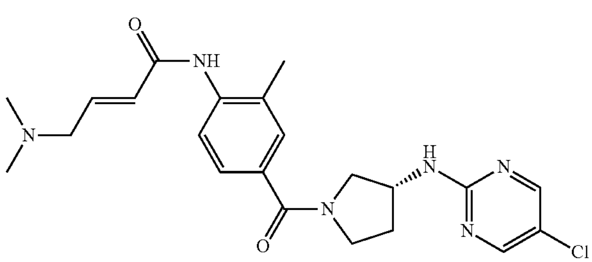 [SMILES: Cc1cc(C(=O)N2CC[C@@H](Nc3ncc(Cl)cn3)C2)ccc1NC(=O)/C=C/CN(C)C] | (R,E)-N-(4-(3-((5-chloropyrimidin-2-yl)amino)pyrrolidine-1-carbonyl)-2-methylphenyl)-4-(dimethylamino)but-2-enamide |
| 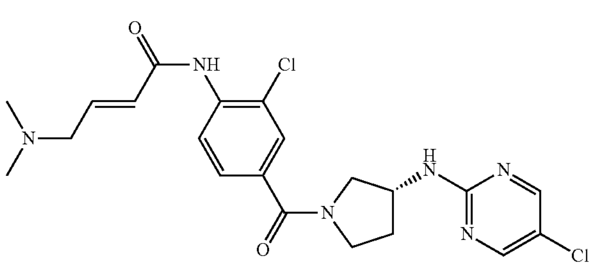 [SMILES: CN(C)C/C=C/C(=O)Nc1ccc(C(=O)N2CC[C@@H](Nc3ncc(Cl)cn3)C2)cc1Cl] | (R,E)-N-(2-chloro-4-(3-((5-chloropyrimidin-2-yl)amino)pyrrolidine-1-carbonyl)phenyl)-4-(dimethylamino)but-2-enamide |

TABLE 2-continued

| Compound Structure | Compound Name |
| --- | --- |
| 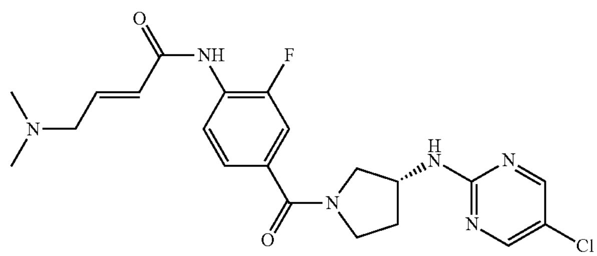 [SMILES: CN(C)C/C=C/C(=O)Nc1ccc(C(=O)N2CC[C@@H](Nc3ncc(Cl)cn3)C2)cc1F] | (R,E)-N-(4-(3-((5-chloropyrimidin-2-yl)amino)pyrrolidine-1-carbonyl)-2-fluorophenyl)-4-(dimethylamino)but-2-enamide |
| 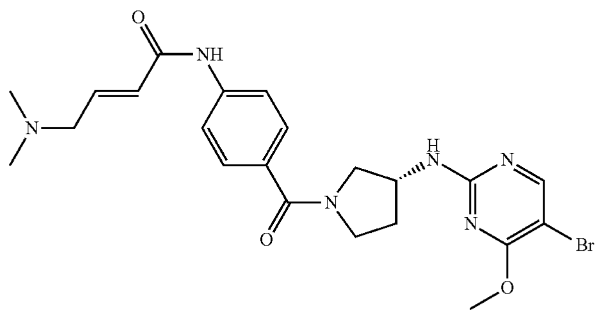 [SMILES: COc1nc(N[C@@H]2CCN(C(=O)c3ccc(NC(=O)/C=C/CN(C)C)cc3)C2)ncc1Br] | (R,E)-N-(4-(3-((5-bromo-4-methoxypyrimidin-2-yl)amino)pyrrolidine-1-carbonyl)phenyl)-4-(dimethylamino)but-2-enamide |
| 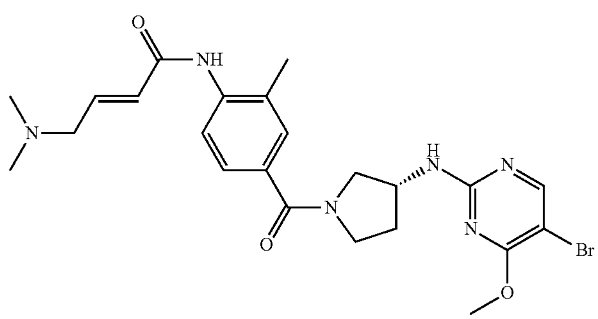 [SMILES: COc1nc(N[C@@H]2CCN(C(=O)c3ccc(NC(=O)/C=C/CN(C)C)c(C)c3)C2)ncc1Br] | (R,E)-N-(4-(3-((5-bromo-4-methoxypyrimidin-2-yl)amino)pyrrolidine-1-carbonyl)-2-methylphenyl)-4-(dimethylamino)but-2-enamide |
| 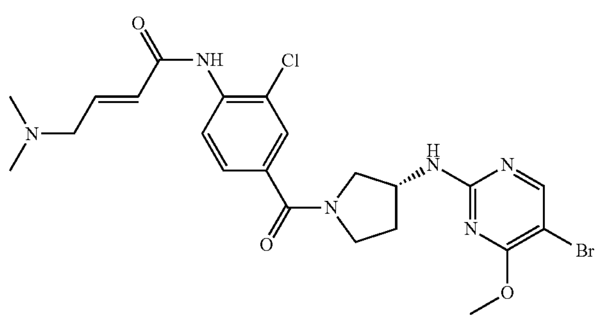 [SMILES: COc1nc(N[C@@H]2CCN(C(=O)c3ccc(NC(=O)/C=C/CN(C)C)c(Cl)c3)C2)ncc1Br] | (R,E)-N-(4-(3-((5-bromo-4-methoxypyrimidin-2-yl)amino)pyrrolidine-1-carbonyl)-2-chlorophenyl)-4-(dimethylamino)but-2-enamide |
| 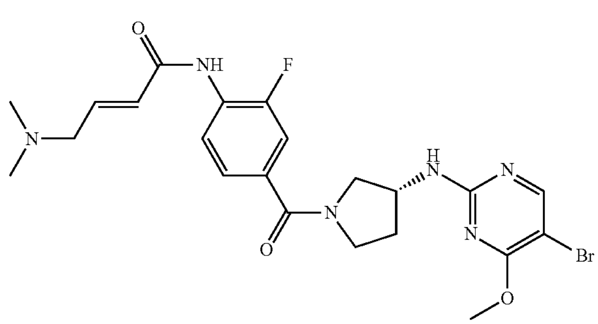 [SMILES: COc1nc(N[C@@H]2CCN(C(=O)c3ccc(NC(=O)/C=C/CN(C)C)c(F)c3)C2)ncc1Br] | (R,E)-N-(4-(3-((5-bromo-4-methoxypyrimidin-2-yl)amino)pyrrolidine-1-carbonyl)-2-fluorophenyl)-4-(dimethylamino)but-2-enamide |

TABLE 2-continued

| Compound Structure | Compound Name |
|---|---|
| 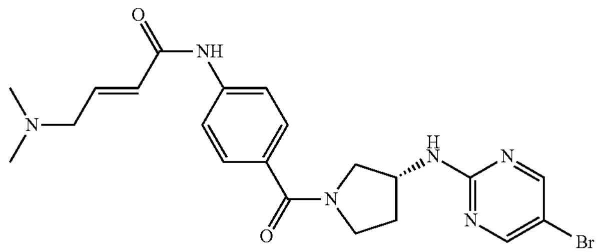 [SMILES: CN(C)C/C=C/C(=O)Nc1ccc(C(=O)N2CC[C@@H](Nc3ncc(Br)cn3)C2)cc1] | (R,E)-N-(4-(3-((5-bromopyrimidin-2-yl)amino)pyrrolidine-1-carbonyl)phenyl)-4-(dimethylamino)but-2-enamide |
| 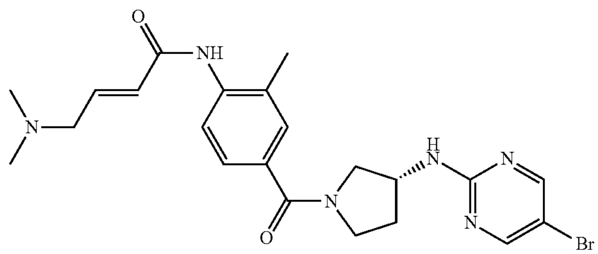 [SMILES: Cc1cc(C(=O)N2CC[C@@H](Nc3ncc(Br)cn3)C2)ccc1NC(=O)/C=C/CN(C)C] | (R,E)-N-(4-(3-((5-bromopyrimidin-2-yl)amino)pyrrolidine-1-carbonyl)-2-methylphenyl)-4-(dimethylamino)but-2-enamide |
| 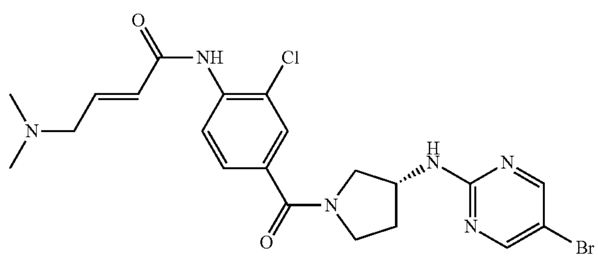 [SMILES: CN(C)C/C=C/C(=O)Nc1ccc(C(=O)N2CC[C@@H](Nc3ncc(Br)cn3)C2)cc1Cl] | (R,E)-N-(4-(3-((5-bromopyrimidin-2-yl)amino)pyrrolidine-1-carbonyl)-2-chlorophenyl)-4-(dimethylamino)but-2-enamide |
| 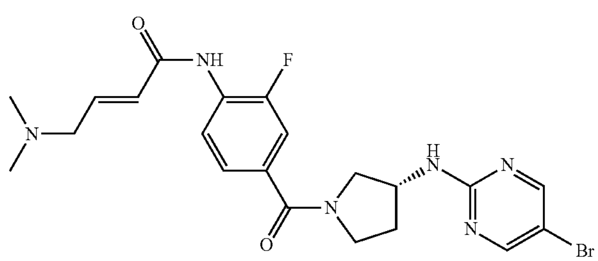 [SMILES: CN(C)C/C=C/C(=O)Nc1ccc(C(=O)N2CC[C@@H](Nc3ncc(Br)cn3)C2)cc1F] | (R,E)-N-(4-(3-((5-bromopyrimidin-2-yl)amino)pyrrolidine-1-carbonyl)-2-fluorophenyl)-4-(dimethylamino)but-2-enamide |
| 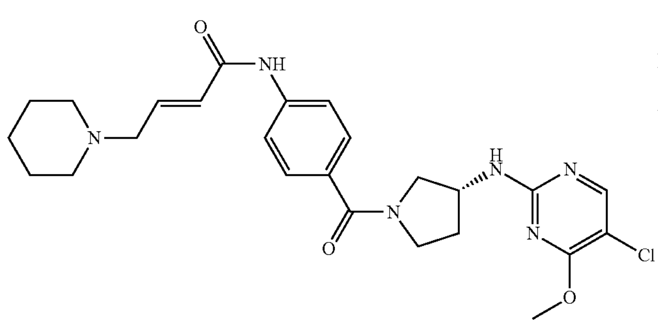 [SMILES: COc1nc(N[C@@H]2CCN(C(=O)c3ccc(NC(=O)/C=C/CN4CCCCC4)cc3)C2)ncc1Cl] | (R,E)-N-(4-(3-((5-chloro-4-methoxpyrimidin-2-yl)amino)pyrrolidine-1-carbonyl)phenyl)-4-(piperidin-1-yl)but-2-enamide |

TABLE 2-continued

| Compound Structure | Compound Name |
|---|---|
| 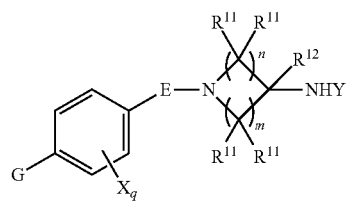 | (R)-N-(4-((3-((5-chloro-4-methoxypyrimidin-2-yl)amino)-2-oxopyrrolidin-1-yl)methyl)phenyl)acrylamide |

One embodiment provides a compound, or pharmaceutically acceptable salt or solvate thereof, having the structure of Formula (IV):

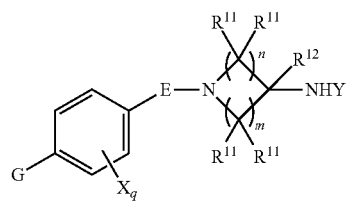

(IV)

wherein,

E is selected from a bond, —SO$_2$—, —C(O)—, —CH$_2$—, —CH(R$^4$)—, or —C(R$^4$)$_2$—;

G is:

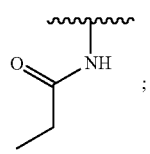

wherein, r is 0, 1, or 2;

each R$^4$ is independently selected from optionally substituted C1-C4 alkyl, or optionally substituted heterocyclylalkyl;

each R$^{11}$ is independently hydrogen, halogen, optionally substituted C1-C6 alkyl, or both R$^{11}$ groups form an oxo;

R$^{12}$ is hydrogen or optionally substituted C1-C4 alkyl;

q is 0, 1, 2, or 3; n is 0, 1, 2, or 3; m is 0, 1, 2, or 3;

X is halogen, optionally substituted C1-C4 alkyl, optionally substituted C1-C4 alkoxy, optionally substituted cycloalkyl, optionally substituted heterocyclyl, optionally substituted aryl, or optionally substituted heteroaryl;

Y is a group selected from:

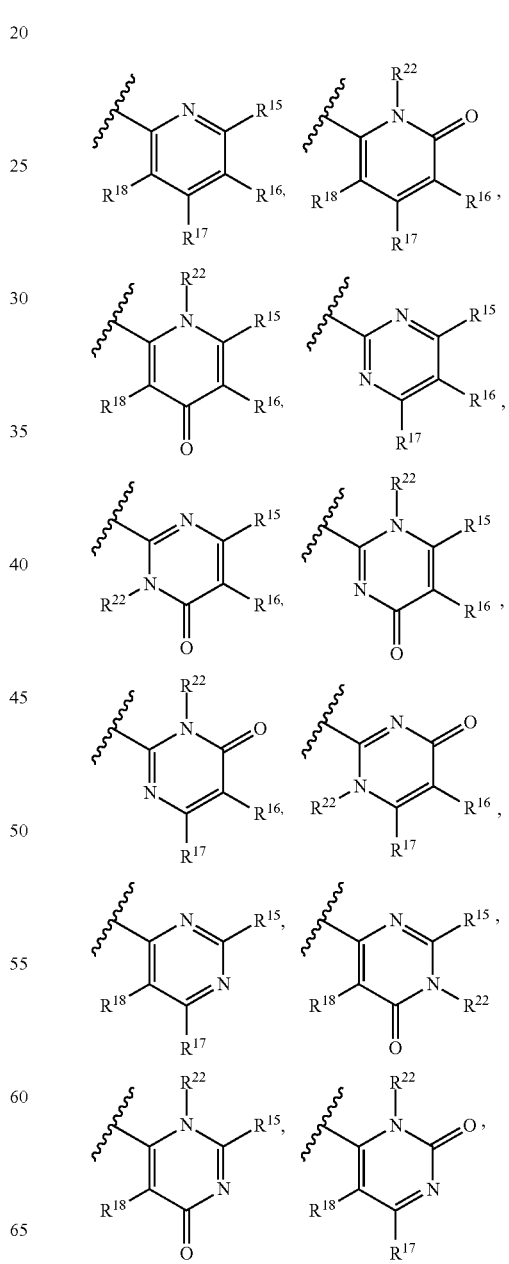

-continued

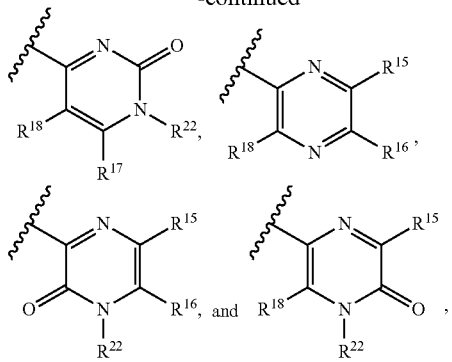

wherein,

R[15] is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R[22])$_2$, —SO$_2$R[21], —N(R[22])SO$_2$R[21], —SO$_2$N(R[22])$_2$, —N(R[22])SO$_2$N(R[22])$_2$, —CON(R[22])$_2$, —N(R[22])CO$_2$R[21], —N(R[22])CON(R[22])$_2$, —N(R[22])COR[21], —OC(O)N(R[22])$_2$, —OSO$_2$N(R[22])$_2$, or —N(R[22])SO$_3$R[21];

R[16] is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R[22])$_2$, —SO$_2$R[21], —N(R[22])SO$_2$R[21], —SO$_2$N(R[22])$_2$, —N(R[22])SO$_2$N(R[22])$_2$, —CON(R[22])$_2$, —N(R[22])CO$_2$R[21], —N(R[22])CON(R[22])$_2$, —N(R[22])COR[21], —OC(O)N(R[22])$_2$, —OSO$_2$N(R[22])$_2$, or —N(R[22])SO$_3$R[21];

R[17] is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R[22])$_2$, —SO$_2$R[21], —N(R[22])SO$_2$R[21], —SO$_2$N(R[22])$_2$, —N(R[22])SO$_2$N(R[22])$_2$, —CON(R[22])$_2$, —N(R[22])CO$_2$R[21], —N(R[22])CON(R[22])$_2$, —N(R[22])COR[21], —OC(O)N(R[22])$_2$, —OSO$_2$N(R[22])$_2$, or —N(R[22])SO$_3$R[21];

R[18] is selected from hydrogen, halogen, —CN, optionally substituted alkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R[22])$_2$, —SO$_2$R[21], —N(R[22])SO$_2$R[21], —SO$_2$N(R[22])$_2$, —N(R[22])SO$_2$N(R[22])$_2$, —CON(R[22])$_2$, —N(R[22])CO$_2$R[21], —N(R[22])CON(R[22])$_2$, —N(R[22])COR[21], —OC(O)N(R[22])$_2$, —OSO$_2$N(R[22])$_2$, or —N(R[22])SO$_3$R[21];

each R[21] is independently selected from alkyl, cycloalkyl, cycloalkylalkyl, aryl, aralkyl, heterocyclyl, heterocyclylalkyl, heteroaryl, or heteroarylalkyl; and each R[22] is independently selected from hydrogen, alkyl, cycloalkyl, cycloalkylalkyl, aryl, aralkyl, heterocyclyl, heterocyclylalkyl, heteroaryl, or heteroarylalkyl.

In some embodiments, the heteroaromatic CDK inhibitory compound of Formula (IV) as described herein has a structure provided in Table 3.

TABLE 3

| Synthetic Chemistry Example | Compound Structure | Compound Name |
|---|---|---|
| 13 | 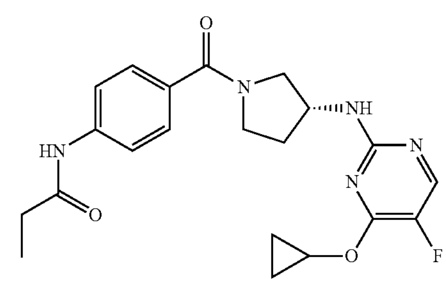 [SMILES: CCC(=O)Nc1ccc(C(=O)N2CC[C@@H](Nc3ncc(F)c(OC4CC4)n3)C2)cc1] | (R)-N-(4-(3-((4-cyclopropoxy-5-fluoropyrimidin-2-yl)amino)pyrrolidine-1-carbonyl)phenyl)propionamide |

TABLE 3-continued

| Synthetic Chemistry Example | Compound Structure | Compound Name |
|---|---|---|
| 14 | 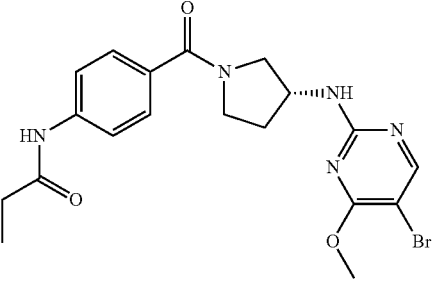 [SMILES: CCC(=O)Nc1ccc(C(=O)N2CC[C@@H](Nc3ncc(Br)c(OC)n3)C2)cc1] | (R)-N-(4-(3-((5-bromo-4-methoxypyrimidin-2-yl)amino)pyrrolidine-1-carbonyl)phenyl)propionamide |
| 15 | 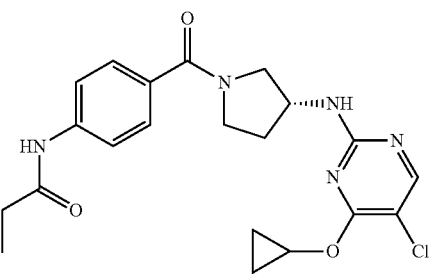 [SMILES: CCC(=O)Nc1ccc(C(=O)N2CC[C@@H](Nc3ncc(Cl)c(OC4CC4)n3)C2)cc1] | (R)-N-(4-(3-((5-chloro-4-cyclopropoxypyrimidin-2-yl)amino)pyrrolidine-1-carbonyl)phenyl)propionamide |
| 16 | 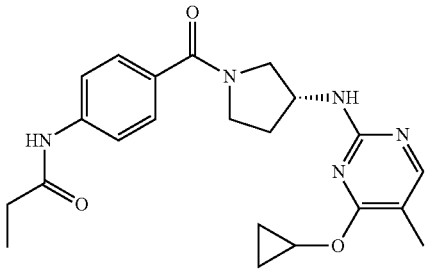 [SMILES: CCC(=O)Nc1ccc(C(=O)N2CC[C@@H](Nc3ncc(C)c(OC4CC4)n3)C2)cc1] | (R)-N-(4-(3-((4-cyclopropoxy-5-methylpyrimidin-2-yl)amino)pyrrolidine-1-carbonyl)phenyl)propionamide |
| 17 | 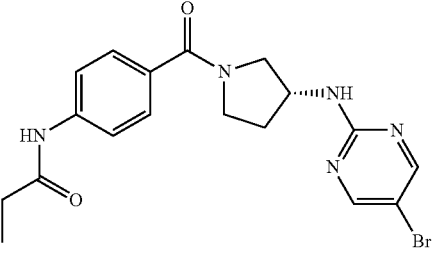 [SMILES: CCC(=O)Nc1ccc(C(=O)N2CC[C@@H](Nc3ncc(Br)cn3)C2)cc1] | (R)-N-(4-(3-((5-bromopyrimidin-2-yl)amino)pyrrolidine-1-carbonyl)phenyl)propionamide |
| 18 | 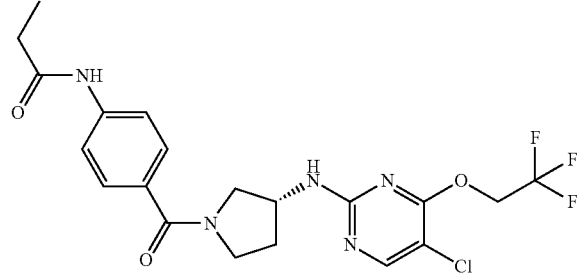 [SMILES: CCC(=O)Nc1ccc(C(=O)N2CC[C@@H](Nc3ncc(Cl)c(OCC(F)(F)F)n3)C2)cc1] | (R)-N-(4-(3-((5-chloro-4-(2,2,2-trifluoroethoxy)pyrimidin-2-yl)amino)pyrrolidine-1-carbonyl)phenyl)propionamide |

TABLE 3-continued

| Synthetic Chemistry Example | Compound Structure | Compound Name |
|---|---|---|
| 41 | 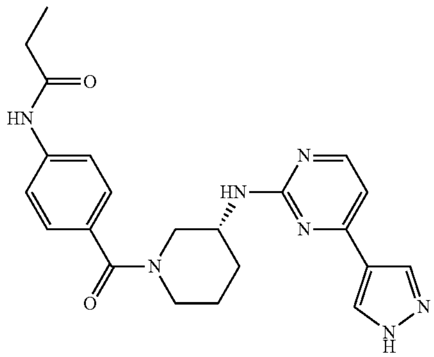 [SMILES: CCC(=O)Nc1ccc(C(=O)N2CCC[C@@H](Nc3nccc(-c4cn[nH]c4)n3)C2)cc1] | (R)-N-(4-(3-((4-(1H-pyrazol-4-yl)pyrimidin-2-yl)amino)piperidine-1-carbonyl)phenyl)propionamide |
| 42 | 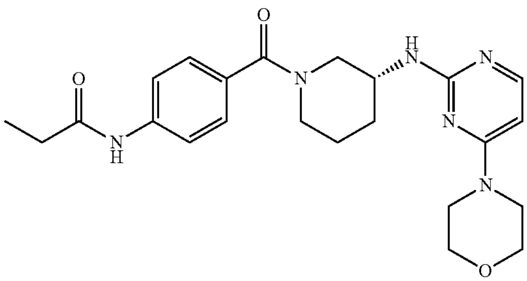 [SMILES: CCC(=O)Nc1ccc(C(=O)N2CCC[C@@H](Nc3nccc(N4CCOCC4)n3)C2)cc1] | (R)-N-(4-(3-((4-morpholinopyrimidin-2-yl)amino)piperidine-1-carobnyl)phenyl)propionamide |
| 43 | 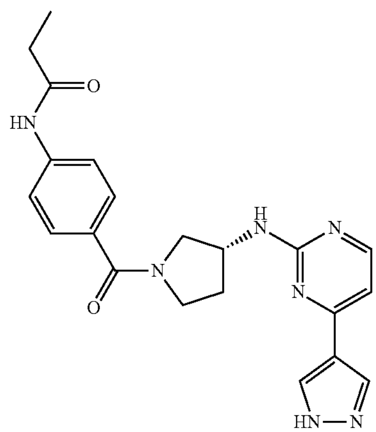 [SMILES: CCC(=O)Nc1ccc(C(=O)N2CC[C@@H](Nc3nccc(-c4cn[nH]c4)n3)C2)cc1] | (R)-N-(4-(3-((4-(1H-pyrazol-4-yl)pyrimidin-2-yl)amino)pyrrolidine-1-carbonyl)phenyl)propionamide |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the heteroaromatic CDK inhibitory compounds described herein is P. H. Stahl & C. G. Wermuth "Handbook of Pharmaceutical Salts", Verlag Helvetica Chimica Acta, Zurich, 2002.

Modification of Cyclin-Dependent Kinase

One embodiment provides a method of inhibiting a CDK enzyme comprising contacting the enzyme with a compound of Formula (I), (II), (III) or a compound disclosed in Table 1 or 2. One embodiment provides the method wherein the CDK enzyme is CDK12.

One embodiment provides a modified CDK12 polypeptide wherein the active site cysteine of an unmodified CDK12 has been modified with a substituent having the structure of Formula (V):

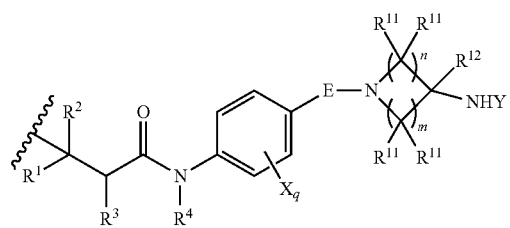

(V)

wherein,

E is selected from a bond, —SO$_2$—, —C(O)—, —CH$_2$—, —CH(R$^4$)—, or —C(R$^4$)$_2$—;

R$^1$ is selected from hydrogen, optionally substituted C1-C4 alkyl, or optionally substituted heterocyclylalkyl;

R$^2$ is selected from hydrogen, or optionally substituted C1-C4 alkyl;

R$^3$ is selected from hydrogen, —CN, or optionally substituted C1-C4 alkyl;

R$^4$ is selected from hydrogen, or optionally substituted C1-C4 alkyl;

each R$^{11}$ is independently hydrogen, halogen, optionally substituted C1-C6 alkyl, —OH, optionally substituted C1-C4 alkoxy, or two R$^{11}$ groups on the same carbon atom form an oxo;

R$^{12}$ is hydrogen or optionally substituted C1-C4 alkyl;

q is 0, 1, 2, or 3; n is 0, 1, 2, or 3; m is 0, 1, 2, or 3;

each X is independently halogen, optionally substituted C1-C4 alkyl, optionally substituted C1-C4 alkoxy, optionally substituted aminoalkyl, optionally substituted cycloalkyl, optionally substituted heterocyclyl, optionally substituted aryl, or optionally substituted heteroaryl;

Y is a group selected from:

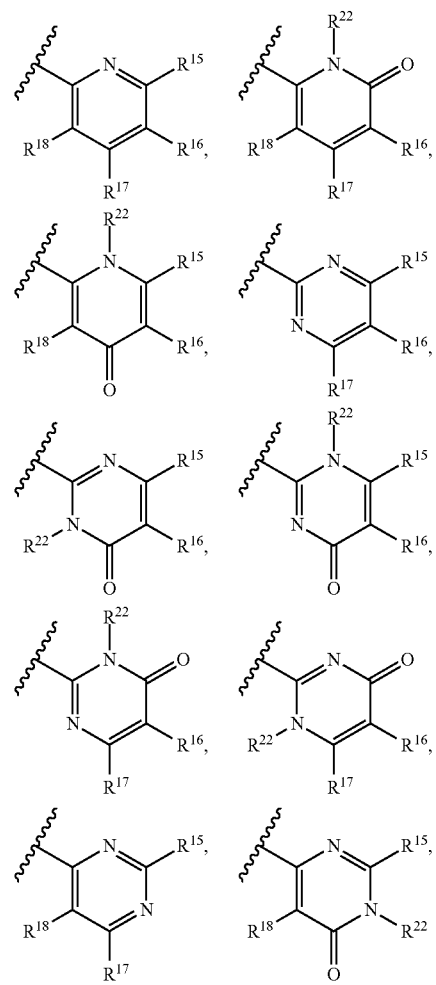

-continued

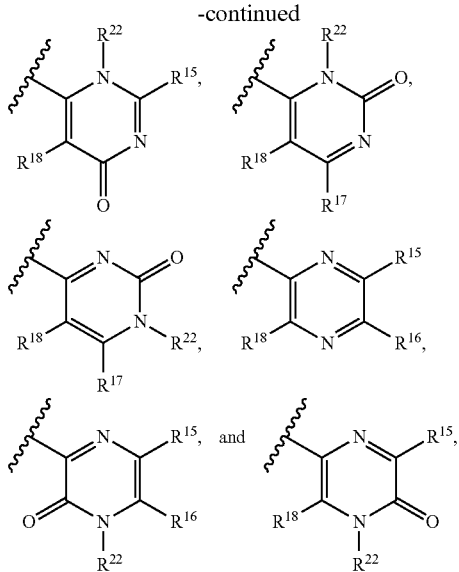

wherein,
$R^{15}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{16}$ is selected from hydrogen, halogen, —CN, optionally substituted alkyl, optionally substituted alkenyl, optionally substituted alkynyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

$R^{17}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

In some embodiments, q is 0, 1, or 2.

In some embodiments, q is 0, or 1.

In some embodiments, q is 0.

In some embodiments, X is a halogen. In some embodiments, X is an optionally substituted C1-C4 alkyl.

In some embodiments, $R^2$ is hydrogen.

In some embodiments, $R^3$ is hydrogen. In some embodiments, $R^3$ is hydrogen or —CN.

In some embodiments, $R^2$ and $R^3$ are hydrogen.

In some embodiments, $R^1$ is hydrogen. In some embodiments, $R^1$ is optionally substituted C1-C4 alkyl. In some embodiments, $R^1$ is optionally substituted C1-C2 alkyl. In some embodiments, $R^1$ is optionally substituted C1 alkyl. In some embodiments, the C1 alkyl is substituted with an optionally substituted amino group. In some embodiments, the optionally substituted amino group is a dimethylamino.

In some embodiments, $R^1$ is —$CH_2$—$N(Me)_2$.

In some embodiments, $R^1$ is optionally substituted heterocyclylalkyl. In some embodiments, the optionally substituted heterocyclylalkyl comprises an optionally substituted C1 alkyl. In some embodiments, the optionally substituted heterocyclylalkyl comprises an optionally substituted N-linked heterocyclyl. In some embodiments, the optionally substituted N-linked heterocyclyl is an N-linked pyrrolidine or piperidine.

In some embodiments, $R^4$ is hydrogen. In some embodiments, $R^4$ is optionally substituted C1-C4 alkyl. In some embodiments, $R^4$ is $CH_3$.

In some embodiments, n is 1 and m is 1. In some embodiments, n is 1 and m is 2. In some embodiments, n is 1 and m is 3.

In some embodiments, Y is selected from:

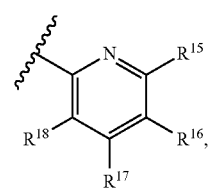 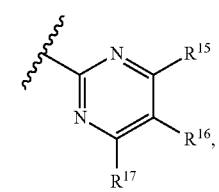

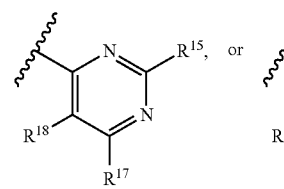 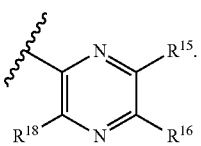

In some embodiments, Y is:

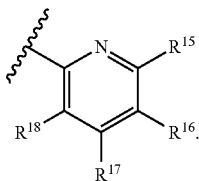

In some embodiments, Y is:

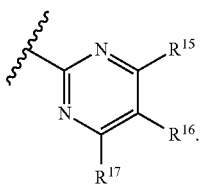

In some embodiments, $R^{15}$ is selected from hydrogen, halogen, —CN, and optionally substituted alkyl. In some embodiments, $R^{15}$ is hydrogen.

In some embodiments, $R^{16}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$S_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$.

In some embodiments, L is O, NH, or N (optionally substituted C1-C4 alkyl); and $R^{16}$ is selected from hydrogen, halogen, —CN, optionally substituted alkyl, optionally substituted fluoroalkyl, optionally substituted alkoxy, optionally substituted cycloalkyl, optionally substituted heterocyclyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —$OR^{22}$, —$N(R^{22})_2$, —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$.

In some embodiments, $R^{16}$ is selected from hydrogen, halogen, —CN, and optionally substituted alkyl. In some embodiments, $R^{16}$ is hydrogen.

In some embodiments, $R^{16}$ is selected from optionally substituted alkyl, optionally substituted alkenyl, or optionally substituted alkynyl. In some embodiments, $R^{16}$ is selected from optionally substituted alkynyl.

In some embodiments, Y is:

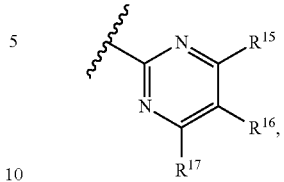

and $R^{16}$ is not hydrogen.

In some embodiments, Y is:

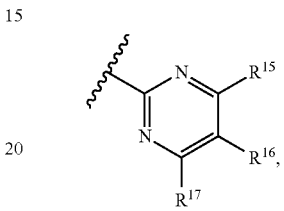

and $R^{16}$ is halogen.

In some embodiments, Y is:

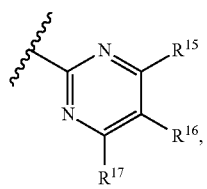

and $R^{16}$ is selected from optionally substituted alkyl, optionally substituted alkenyl, or optionally substituted alkynyl.

In some embodiments, Y is:

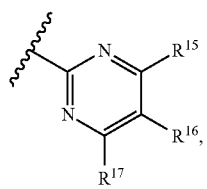

$R^{15}$ is hydrogen, $R^{16}$ is selected from optionally substituted alkynyl, and $R^{17}$ is hydrogen or optionally substituted alkoxy.

In some embodiments, Y is:

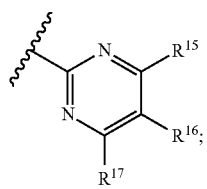

$R^{15}$ is hydrogen, $R^{16}$ is selected from halogen, —CN, optionally substituted alkyl, optionally substituted fluoroalkyl, optionally substituted alkenyl, optionally substituted alkynyl, and $R^{17}$ is hydrogen or optionally substituted alkoxy.

In some embodiments, n is 1 and m is 2; Y is:

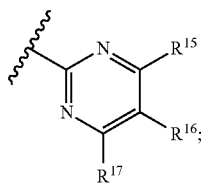

$R^{15}$ is hydrogen, $R^{16}$ is selected from halogen, —CN, optionally substituted alkyl, optionally substituted fluoroalkyl, optionally substituted alkenyl, optionally substituted alkynyl, and $R^{17}$ is hydrogen or optionally substituted alkoxy.

In some embodiments, $R^{17}$ is selected from hydrogen, halogen, —CN, and optionally substituted alkyl. In some embodiments, $R^{17}$ is hydrogen.

In some embodiments, $R^{18}$ is selected from hydrogen, halogen, —CN, and optionally substituted alkyl. In some embodiments, $R^{18}$ is hydrogen.

In some embodiments, $R^{15}$ and $R^{16}$ are hydrogen. In some embodiments, $R^{17}$ and $R^{18}$ are hydrogen.

In some embodiments, $R^{15}$ and $R^{17}$ are hydrogen.

In some embodiments, E is a bond. In some embodiments, E is —SO$_2$—. In some embodiments, E is —C(O)—. In some embodiments, E is —CH$_2$—. In some embodiments, E is —CH(R$^4$)—. In some embodiments, E is —C(R$^4$)$_2$—.

Another embodiment provides the modified CDK12 polypeptide wherein the unmodified CDK12 polypeptide is isoform 1 (*Homo sapiens*).

Another embodiment provides the modified CDK12 polypeptide wherein the unmodified CDK12 polypeptide is isoform 2 (*Homo sapiens*).

Another embodiment provides the modified CDK12 polypeptide wherein the unmodified CDK12 polypeptide is an isoform 1 (*Homo sapiens*) variant. Another embodiment provides the modified CDK12 polypeptide wherein the unmodified CDK12 polypeptide is isoform 1 (*Homo sapiens*) variant I1131V. Another embodiment provides the modified CDK12 polypeptide wherein the unmodified CDK12 polypeptide is isoform 1 (*Homo sapiens*) variant L1189Q. Another embodiment provides the modified CDK12 polypeptide wherein the unmodified CDK12 polypeptide is isoform 1 (*Homo sapiens*) variant T1195M.

Another embodiment provides the modified CDK12 polypeptide wherein the unmodified CDK12 polypeptide is a SEQID selected from a SEQID provided in Table 4 or 5.

TABLE 4

CDK12 Sequences

| SEQ ID NO | Ensembl Protein ID (Accession Number) | Amino Acid Sequence |
|---|---|---|
| 1 | ENSP00000398880 (NP_057591.2) | MPNSERHGGKKDGSGGASGTLQPSSGGGSSNSRERHRLVSKHKRHK SKHSKDMGLVTPEAASLGTVIKPLVEYDDISSDSDTFSDDMAFKLDR RENDERRGSDRSDRLHKHRHHQHRRSRDLLKAKQTEKEKSQEVSSK SGSMKDRISGSSKRSNEETDDYGKAQVAKSSSKESRSSKLHKEKTRK ERELKSGHKDRSKSHRKRETPKSYKTVDSPKRRSRSPHRKWSDSSKQ DDSPSGASYGQDYDLSPSRSHTSSNYDSYKKSPGSTSRRQSVSPPYKE PSAYQSSTRSPSPYSRRQRSVSPYSRRSSSYERSGSYSGRSPSPYGRR RSSSPFLSKRSLSRSPLPSRKSMKSRSRSPAYSRHSSSHSKKKRSSSRS RHSSISPVRLPLNSSLGAELSRKKKERAAAAAAAKMDGKESKGSPVF LPRKENSSVEAKDSGLESKKLPRSVKLEKSAPDTELVNVTHLNTEVK NSSDTGKVKLDENSEKHLVKDLKAQGTRDSKPIALKEEIVTPKETETS EKETPPPLPTIASPPPPLPTTTPPPQTPPLPPLPPIPALPQQPPLPPSQPAF SQVPASSTSTLPPSTHSKTSAVSSQANSQPPVQVSVKTQVSVTAAIPH LKTSTLPPLPLPPLLPGDDDMDSPKETLPSKPVKKEKEQRTRHLLTDL PLPPELPGGDLSPPDSPEPKAITPPQQPYKKRPKICCPRYGERRQTESD WGKRCVDKFDIIGIIGEGTYGQVYKAKDKDTGELVALKKVRLDNEK EGFPITAIREIKILRQLIHRSVVNMKEIVTDKQDALDFKKDKGAFYLV FEYMDHDLMGLLESGLVHFSEDHIKSFMKQLMEGLEYCHKKNFLHR DIKCSNILLNNSGQIKLADFGLARLYNSEESRPYTNKVITLWYRPPEL LLGEERYTPAIDVWSCGCILGELFTKKPIFQANLELAQLELISRLCGSP CPAVWPDVIKLPYFNTMKPKKQYRRRLREEFSFIPSAALDLLDHMLT LDPSKRCTAEQTLQSDFLKDVELSKMAPPDLPHWQDCHELWSKKRR RQRQSGVVVEEPPPSKTSRKETTSGTSTEPVKNSSPAPPQPAPGKVES GAGDAIGLADITQQLNQSELAVLLNLLQSQTDLSIPQMAQLLNIHSNP EMQQQLEALNQSISALTEATSQQQDSETMAPEESLKEAPSAPVILPSA EQTTLEASSTPADMQNILAVLLSQLMKTQEPAGSLEENNSDKNSGPQ GPRRTPT1VIPQEEAAACPPHILPPEKRPPEPPGPPPPPPPPLVEGDLSSA PQELNPAVTAALLQLLSQPEAEPPGHLPHEHQALRPMEYSTRPRPNR TYGNTDGPETGESAIDTDERNSGPALTESLVQTLVKNRTFSGSLSHLG ESSSYQGTGSVQFPGDQDLRFARVPLALHPVVGQPFLKAEGSSNSVV HAETKLQNYGELGPTTGASSSGAGLHWGGPTQSSAYGKLYRGPTR VPPRGGRGRGVPY |
| 2 | ENSP00000407720 (NP_055898.1) | MPNSERHGGKKDGSGGASGTLQPSSGGGSSNSRERHRLVSKHKRHK SKHSKDMGLVTPEAASLGTVIKPLVEYDDISSDSDTFSDDMAFKLDR RENDERRGSDRSDRLHKHRHHQHRRSRDLLKAKQTEKEKSQEVSSK SGSMKDRISGSSKRSNEETDDYGKAQVAKSSSKESRSSKLHKEKTRK ERELKSGHKDRSKSHRKRETPKSYKTVDSPKRRSRSPHRKWSDSSKQ DDSPSGASYGQDYDLSPSRSHTSSNYDSYKKSPGSTSRRQSVSPPYKE PSAYQSSTRSPSPYSRRQRSVSPYSRRSSSYERSGSYSGRSPSPYGRR RSSSPFLSKRSLSRSPLPSRKSMKSRSRSPAYSRHSSSHSKKKRSSSRS RHSSISPVRLPLNSSLGAELSRKKKERAAAAAAAKMDGKESKGSPVF |

TABLE 4-continued

CDK12 Sequences

| SEQ ID NO | Ensembl Protein ID (Accession Number) | Amino Acid Sequence |
|---|---|---|
| | | LPRKENSSVEAKDSGLESKKLPRSVKLEKSAPDTELVNVTHLNTEVK<br>NSSDTGKVKLDENSEKHLVKDLKAQGTRDSKPIALKEEIVTPKETETS<br>EKETPPPLPTIASPPPPLPTTTPPPQTPPLPPLPPIPALPQQPPLPPSQPAF<br>SQVPASSTSTLPPSTHSKTSAVSSQANSQPPVQVSVKTQVSVTAAIPH<br>LKTSTLPPLPLPPLLPGDDDMDSPKETLPSKPVKKEKEQRTRHLLTDL<br>PLPPELPGGDLSPPDSPEPKAITPPQQPYKKRPKICCPRYGERRQTESD<br>WGKRCVDKEDIIGIIGEGTYGQVYKAKDKDTGELVALKKVRLDNEK<br>EGFPITAIREIKILRQLIHRSVVNMKEIVTDKQDALDEKKDKGAFYLV<br>FEYMDHDLMGLLESGLVHFSEDHIKSEMKQLMEGLEYCHKKNELHR<br>DIKCSNILLNNSGQIKLADFGLARLYNSEESRPYTNKVITLWYRPPEL<br>LLGEERYTPAIDVWSCGCILGELFTKKPIFQANLELAQLELISRLCGSP<br>CPAVWPDVIKLPYENTMKPKKQYRRRLREEFSFIPSAALDLLDHMLT<br>LDPSKRCTAEQTLQSDFLKDVELSKMAPPDLPHWQDCHELWSKKRR<br>RQRQSGVVVEEPPPSKTSRKETTSGTSTEPVKNSSPAPPQPAPGKVES<br>GAGDAIGLADITQQLNQSELAVLLNLLQSQTDLSIPMAQLLNIHSNP<br>EMQQQLEALNQSISALTEATSQQQDSETMAPEESLKEAPSAPVILPSA<br>EQTTLEASSTPADMQNILAVLLSQLMKTQEPAGSLEENNSDKNSGPQ<br>GPRRTPTMPQEEAAEKRPPEPPGPPPPPPPPLVEGDLSSAPQELNPAV<br>TAALLQLLSQPEAEPPGHLPHEHQALRPMEYSTRPRPNRTYGNTDGP<br>ETGFSAIDTDERNSGPALTESLVQTLVKNRTFSGSLSHLGESSSYQGT<br>GSVQFPGDQDLRFARVPLALHPVVGQPFLKAEGSSNSVVHAETKLQ<br>NYGELGPGTTGASSSGAGLHWGGPTQSSAYGKLYRGPTRVPPRGGR<br>GRGVPY |
| 3 | ENSP00000464641 | MPNSERHGGKKDGSGGASGTLQPSSGGGSSNSRERHRLVSKHKRHK<br>SKHSKDMGLVTPEAASLGTVIKPLVEYDDISSDSDTFSDDMAFKLDR<br>RENDERRGSDRSDRLHKHRHHQHRRSRDLLKAKQTEKEKSQEVSSK<br>SGSMKDRISGSSKRSNEETDDYGKAQVAKSSSKESRSSKLHKEKTRK<br>ERELKSGHKDRSKSHRKRETPKSYKTVDSPKRRSRSPHRKWSDSSKQ<br>DDSPSGASYGQDYDLSPSRSHTSSNYDSYKKSPGSTSRRQSVSPPYKE<br>PSAYQSSTRSPSPYSRRQRSVSPYSRRRSSSYERSGSYSGRSPSPYGRR<br>RSSSPFLSKRSLSRSPLPRKSMKSRSRSPAYSRHSSSHSKKKRSSSRSR<br>HSSISPVRLPLNSSLGAELSRKKKERAAAAAAAKMDGKESKGSPVFL<br>PRKENSSVEAKDSGLESKKLPRSVKLEKSAPDTELVNVTHLNTEVKN<br>SSDTGKVKLDENSEKHLVKDLKAQGTRDSKPIALKEEIVTPKETETSE<br>KETPPPLPTIASPPPPLPTTTPPPQTPPLPPLPPIPALPQQPPLPPSQPAFS<br>QVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLP<br>LPPELPGGDLSPPDSPEPKAITPPQQPYKKRPKICCPRYGERRQTESDW<br>GKRCVDKEDIIGIIGEGTYGQVYKAKDKDTGELVALKKVRLDNEKE<br>GEPITAIREIKILRQLIHRSVVNMKEIVTDKQDALDEKKDKGAFYLVE<br>EYMDHDLMGLLESGLVHFSEDHIKSEMKQLMEGLEYCHKKNELHR<br>DIKCSNILLNNSGQIKLADFGLARLYNSEESRPYTNKVITLWYRPPEL<br>LLGEERYTPAIDVWSCGCILGELFTKKPIFQANLELAQLELISRLCGSP<br>CPAVWPDVIKLPYENTMKPKKQYRRRLREEFSFIPSAALDLLDHMLT<br>LDPSKRCTAEQTLQSDFLKDVELSKMAPPDLPHWQDCHELWSKKRR<br>RQRQSGVVVEEPPPSKTSRKETTSGTSTEPVKNSSPAPPQPAPGKVES<br>GAGDAIGLADITQQLNQSELAVLLNLLQSQTDLSIPMAQLLNIHSNP<br>EMQQQLEALNQSISALTEATSQQQDSETMAPEESLKEAPSAPVILPSA<br>EQTTLEASST |
| 4 | ENSP00000453329 | XADITQQLNQSELAVLLNLLQSQTDLSIPMAQLLNIHSNPEMQQQL<br>EALNQSISALTEATSQQQDSETMAPEESLKEAPSAPVILPSAEQTTLEA<br>SSTPADMQNILAVLLSQLMKTQEPAGSLEENNSDKNSGPQGPRRTPT<br>MPQEEAAGRSNGGNAL |

TABLE 5

Variant CDK12 Sequences

| SEQ ID NO | Amino Acid Sequence |
|---|---|
| 5 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS |

TABLE 5-continued

Variant CDK12 Sequences

| SEQ ID NO | Amino Acid Sequence |
|---|---|
| | LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSVPQMAQLLNIHSNPEMQQQLEALNQSISALTEATSQQQDSETMAPEESLKEAP<br>SAPVILPSAEQTTLEASSTPADMQNILAVLLSQLMKTQEPAGSLEENNSDKNSGPQ<br>GPRRTPTMPQEEAAACPPHILPPEKRPPEPPGPPPPPPPPPLVEGDLSSAPQELNPAV<br>TAALLQLLSQPEAEPPGHLPHEHQALRPMEYSTRPRPNRTYGNTDGPETGFSAIDT<br>DERNSGPALTESLVQTLVKNRTFSGSLSHLGESSSYQGTGSVQFPGDQDLRFARVP<br>LALHPVVGQPFLKAEGSSNSVVHAETKLQNYGELGPGTTGASSSGAGLHWGGPT<br>QSSAYGKLYRGPTRVPPRGGRGRGVPY |
| 6 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSIPQMAQLLNIHSNPEMQQQLEALNQSISALTEATSQQQDSETMAPEESLKEAP<br>SAPVIQPSAEQTTLEASSTPADMQNILAVLLSQLMKTQEPAGSLEENNSDKNSGPQ<br>GPRRTPTMPQEEAAACPPHILPPEKRPPEPPGPPPPPPPPPLVEGDLSSAPQELNPAV<br>TAALLQLLSQPEAEPPGHLPHEHQALRPMEYSTRPRPNRTYGNTDGPETGFSAIDT<br>DERNSGPALTESLVQTLVKNRTFSGSLSHLGESSSYQGTGSVQFPGDQDLRFARVP<br>LALHPVVGQPFLKAEGSSNSVVHAETKLQNYGELGPGTTGASSSGAGLHWGGPT<br>QSSAYGKLYRGPTRVPPRGGRGRGVPY |
| 7 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSIPQMAQLLNIHSNPEMQQQLEALNQSISALTEATSQQQDSETMAPEESLKEAP<br>SAPVILPSAEQMTLEASSTPADMQNILAVLLSQLMKTQEPAGSLEENNSDKNSGPQ<br>GPRRTPTMPQEEAAACPPHILPPEKRPPEPPGPPPPPPPPPLVEGDLSSAPQELNPAV<br>TAALLQLLSQPEAEPPGHLPHEHQALRPMEYSTRPRPNRTYGNTDGPETGFSAIDT |

TABLE 5-continued

Variant CDK12 Sequences

| SEQ ID NO | Amino Acid Sequence |
|---|---|
| | DERNSGPALTESLVQTLVKNRTFSGSLSHLGESSSYQGTGSVQFPGDQDLRFARVP<br>LALHPVVGQPFLKAEGSSNSVVHAETKLQNYGELGPGTTGASSSGAGLHWGGPT<br>QSSAYGKLYRGPTRVPPRGGRGRGVPY |
| 8 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSVPQMAQLLNIHSNPEMQQQLEALNQSISALTEATSQQQDSETMAPEESLKEAP<br>SAPVILPSAEQTTLEASSTPADMQNILAVLLSQLMKTQEPAGSLEENNSDKNSGPQ<br>GPRRTPTMPQEEAAEKRPPEPPGPPPPPPPPPLVEGDLSSAPQELNPAVTAALLQLL<br>SQPEAEPPGHLPHEHQALRPMEYSTRPRPNRTYGNTDGPETGFSAIDTDERNSGPA<br>LTESLVQTLVKNRTFSGSLSHLGESSSYQGTGSVQFPGDQDLRFARVPLALHPVVG<br>QPFLKAEGSSNSVVHAETKLQNYGELGPGTTGASSSGAGLHWGGPTQSSAYGKL<br>YRGPTRVPPRGGRGRGVPY |
| 9 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSIPQMAQLLNIHSNPEMQQQLEALNQSISALTEATSQQQDSETMAPEESLKEAP<br>SAPVIQPSAEQTTLEASSTPADMQNILAVLLSQLMKTQEPAGSLEENNSDKNSGPQ<br>GPRRTPTMPQEEAAEKRPPEPPGPPPPPPPPPLVEGDLSSAPQELNPAVTAALLQLL<br>SQPEAEPPGHLPHEHQALRPMEYSTRPRPNRTYGNTDGPETGFSAIDTDERNSGPA<br>LTESLVQTLVKNRTFSGSLSHLGESSSYQGTGSVQFPGDQDLRFARVPLALHPVVG<br>QPFLKAEGSSNSVVHAETKLQNYGELGPGTTGASSSGAGLHWGGPTQSSAYGKL<br>YRGPTRVPPRGGRGRGVPY |
| 10 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL |

TABLE 5-continued

Variant CDK12 Sequences

SEQ
ID NO Amino Acid Sequence

EYCHKKNFLHRDIKCSNILLNNSGQIKLADFGLARLYNSEESRPYTNKVITLWYRP
PELLLGEERYTPAIDVWSCGCILGELFTKKPIFQANLELAQLELISRLCGSPCAVW
PDVIKLPYFNTMKPKKQYRRRLREEFSFIPSAALDLLDHMLTLDPSKRCTAEQTLQ
SDFLKDVELSKMAPPDLPHWQDCHELWSKKRRQRQSGVVVEEPPPSKTSRKETT
SGTSTEPVKNSSPAPPQPAPGKVESGAGDAIGLADITQQLNQSELAVLLNLLQSQT
DLSIPQMAQLLNIHSNPEMQQQLEALNQSISALTEATSQQQDSETMAPEESLKEAP
SAPVILPSAEQMTLEASSTPADMQNILAVLLSQLMKTQEPAGSLEENNSDKNSGPQ
GPRRTPTMPQEEAAEKRPPEPPGPPPPPPPPLVEGDLSSAPQELNPAVTAALLQLL
SQPEAEPPGHLPHEHQALRPMEYSTRPRPNRTYGNTDGPETGFSAIDTDERNSGPA
LTESLVQTLVKNRTFSGSLSHLGESSSYQGTGSVQFPGDQDLRFARVPLALHPVVG
QPFLKAEGSSNSVVHAETKLQNYGELGPGTTGASSSGAGLHWGGPTQSSAYGKL
YRGPTRVPPRGGRGRGVPY

11  MPNSERHGGKKDGSGGASGTLQPSSGGGSSNSRERHRLVSKHKRHKSKHSKDMG
LVTPEAASLGTVIKPLVEYDDISSDSDTFSDDMAFKLDRRENDERRGSDRSDRLHK
HRHHQHRRSRDLLKAKQTEKEKSQEVSSKSGSMKDRISGSSKRSNEETDDYGKAQ
VAKSSSKESRSSKLHKEKTRKERELKSGHKDRSKSHRKRETPKSYKTVDSPKRRSR
SPHRKWSDSSKQDDSPSGASYGQDYDLSPSRSHTSSNYDSYKKSPGSTSRRQSVSP
PYKEPSAYQSSTRSPSPYSRRQRSVSPYSRRRSSSYERSGSYSGRSPSPYGRRRSSSP
FLSKRSLSRSPLPRKSMKSRSRSPAYSRHSSSHSKKKRSSSRSHSSISPVRLPLNSSL
GAELSRKKKERAAAAAAAKMDGKESKGSPVFLPRKENSSVEAKDSGLESKKLPRS
VKLEKSAPDTELVNVTHLNTEVKNSSDTGKVKLDENSEKHLVKDLKAQGTRDSK
PIALKEEIVTPKETETSEKETPPPLPTIASPPPPLPTTTPPPQTPPLPPLPPIPALPQQPPL
PPSQPAFSQVPASSTSTLPPSTHSKTSAVSSQANSQPPVQVSVKTQVSVTAAIPHLK
TSTLPPLPLPPLLPGDDDMDSPKETLPSKPVKKEKEQRTRHLLTDLPLPPELPGGDL
SPPDSPEPKAITPPQQPYKKRPKICCPRYGERRQTESDWGKRCVDKFDIIGIIGEGTY
GQVYKAKDKDTGELVALKKVRLDNEKEGFPITAIREIKILRQLIHRSVVNMKEIVT
DKQDALDFKKDKGAFYLVFEYMDHDLMGLLESGLVHFSEDHIKSFMKQLMEGLE
YCHKKNFLHRDIKCSNILLNNSGQIKLADFGLARLYNSEESRPYTNKVITLWYRPP
ELLLGEERYTPAIDVWSCGCILGELFTKKPIFQANLELAQLELISRLCGSPCAVWP
DVIKLPYENTMKPKKQYRRRLREEFSFIPSAALDLLDHMLTLDPSKRCTAEQTLQS
DFLKDVELSKMAPPDLPHWQDCHELWSKKRRQRQSGVVVEEPPPSKTSRKETTS
GTSTEPVKNSSPAPPQPAPGKVESGAGDAIGLADITQQLNQSELAVLLNLLQSQTD
LSVPQMAQLLNIHSNPEMQQQLEALNQSISALTEATSQQQDSETMAPEESLKEAPS
APVILPSAEQTTLEASST

12  MPNSERHGGKKDGSGGASGTLQPSSGGGSSNSRERHRLVSKHKRHKSKHSKDMG
LVTPEAASLGTVIKPLVEYDDISSDSDTFSDDMAFKLDRRENDERRGSDRSDRLHK
HRHHQHRRSRDLLKAKQTEKEKSQEVSSKSGSMKDRISGSSKRSNEETDDYGKAQ
VAKSSSKESRSSKLHKEKTRKERELKSGHKDRSKSHRKRETPKSYKTVDSPKRRSR
SPHRKWSDSSKQDDSPSGASYGQDYDLSPSRSHTSSNYDSYKKSPGSTSRRQSVSP
PYKEPSAYQSSTRSPSPYSRRQRSVSPYSRRRSSSYERSGSYSGRSPSPYGRRRSSSP
FLSKRSLSRSPLPRKSMKSRSRSPAYSRHSSSHSKKKRSSSRSHSSISPVRLPLNSSL
GAELSRKKKERAAAAAAAKMDGKESKGSPVFLPRKENSSVEAKDSGLESKKLPRS
VKLEKSAPDTELVNVTHLNTEVKNSSDTGKVKLDENSEKHLVKDLKAQGTRDSK
PIALKEEIVTPKETETSEKETPPPLPTIASPPPPLPTTTPPPQTPPLPPLPPIPALPQQPPL
PPSQPAFSQVPASSTSTLPPSTHSKTSAVSSQANSQPPVQVSVKTQVSVTAAIPHLK
TSTLPPLPLPPLLPGDDDMDSPKETLPSKPVKKEKEQRTRHLLTDLPLPPELPGGDL
SPPDSPEPKAITPPQQPYKKRPKICCPRYGERRQTESDWGKRCVDKFDIIGIIGEGTY
GQVYKAKDKDTGELVALKKVRLDNEKEGFPITAIREIKILRQLIHRSVVNMKEIVT
DKQDALDFKKDKGAFYLVFEYMDHDLMGLLESGLVHFSEDHIKSFMKQLMEGLE
YCHKKNELHRDIKCSNILLNNSGQIKLADEGLARLYNSEESRPYTNKVITLWYRPP
ELLLGEERYTPAIDVWSCGCILGELFTKKPIFQANLELAQLELISRLCGSPCAVWP
DVIKLPYENTMKPKKQYRRRLREEFSFIPSAALDLLDHMLTLDPSKRCTAEQTLQS
DFLKDVELSKMAPPDLPHWQDCHELWSKKRRQRQSGVVVEEPPPSKTSRKETTS
GTSTEPVKNSSPAPPQPAPGKVESGAGDAIGLADITQQLNQSELAVLLNLLQSQTD
LSIPQMAQLLNIHSNPEMQQQLEALNQSISALTEATSQQQDSETMAPEESLKEAPS
APVIQPSAEQTTLEASST

13  MPNSERHGGKKDGSGGASGTLQPSSGGGSSNSRERHRLVSKHKRHKSKHSKDMG
LVTPEAASLGTVIKPLVEYDDISSDSDTFSDDMAFKLDRRENDERRGSDRSDRLHK
HRHHQHRRSRDLLKAKQTEKEKSQEVSSKSGSMKDRISGSSKRSNEETDDYGKAQ
VAKSSSKESRSSKLHKEKTRKERELKSGHKDRSKSHRKRETPKSYKTVDSPKRRSR
SPHRKWSDSSKQDDSPSGASYGQDYDLSPSRSHTSSNYDSYKKSPGSTSRRQSVSP
PYKEPSAYQSSTRSPSPYSRRQRSVSPYSRRRSSSYERSGSYSGRSPSPYGRRRSSSP
FLSKRSLSRSPLPRKSMKSRSRSPAYSRHSSSHSKKKRSSSRSHSSISPVRLPLNSSL
GAELSRKKKERAAAAAAAKMDGKESKGSPVFLPRKENSSVEAKDSGLESKKLPRS
VKLEKSAPDTELVNVTHLNTEVKNSSDTGKVKLDENSEKHLVKDLKAQGTRDSK
PIALKEEIVTPKETETSEKETPPPLPTIASPPPPLPTTTPPPQTPPLPPLPPIPALPQQPPL
PPSQPAFSQVPASSTSTLPPSTHSKTSAVSSQANSQPPVQVSVKTQVSVTAAIPHLK
TSTLPPLPLPPLLPGDDDMDSPKETLPSKPVKKEKEQRTRHLLTDLPLPPELPGGDL
SPPDSPEPKAITPPQQPYKKRPKICCPRYGERRQTESDWGKRCVDKFDIIGIIGEGTY
GQVYKAKDKDTGELVALKKVRLDNEKEGFPITAIREIKILRQLIHRSVVNMKEIVT
DKQDALDFKKDKGAFYLVFEYMDHDLMGLLESGLVHFSEDHIKSFMKQLMEGLE
YCHKKNFLHRDIKCSNILLNNSGQIKLADFGLARLYNSEESRPYTNKVITLWYRPP

TABLE 5-continued

Variant CDK12 Sequences

| SEQ ID NO | Amino Acid Sequence |
|---|---|
|  | ELLLGEERYTPAIDVWSCGCILGELFTKKPIFQANLELAQLELISRLCGSPCPAVWP<br>DVIKLPYFNTMKPKKQYRRRLREEFSFIPSAALDLLDHMLTLDPSKRCTAEQTLQS<br>DFLKDVELSKMAPPDLPHWQDCHELWSKKRRRQRQSGVVVEEPPPSKTSRKETTS<br>GTSTEPVKNSSPAPPQPAPGKVESGAGDAIGLADITQQLNQSELAVLLNLLQSQTD<br>LSIPQMAQLLNIHSNPEMQQQLEALNQSISALTEATSQQQDSETMAPEESLKEAPS<br>APVILPSAEQMTLEASST |
| 14 | XADITQQLNQSELAVLLNLLQSQTDLSVPQMAQLLNIHSNPEMQQQLEALNQSISA<br>LTEATSQQQDSETMAPEESLKEAPSAPVILPSAEQTTLEASSTPADMQNILAVLLSQ<br>LMKTQEPAGSLEENNSDKNSGPQGPRRTPTMPQEEAAGRSNGGNAL |
| 15 | XADITQQLNQSELAVLLNLLQSQTDLSIPQMAQLLNIHSNPEMQQQLEALNQSISA<br>LTEATSQQQDSETMAPEESLKEAPSAPVIQPSAEQTTLEASSTPADMQNILAVLLSQ<br>LMKTQEPAGSLEENNSDKNSGPQGPRRTPTMPQEEAAGRSNGGNAL |
| 16 | XADITQQLNQSELAVLLNLLQSQTDLSIPQMAQLLNIHSNPEMQQQLEALNQSISA<br>LTEATSQQQDSETMAPEESLKEAPSAPVILPSAEQMTLEASSTPADMQNILAVLLS<br>QLMKTQEPAGSLEENNSDKNSGPQGPRRTPTMPQEEAAGRSNGGNAL |

Pharmaceutical Compositions

In certain embodiments, the heteroaromatic CDK inhibitory compound described herein is administered as a pure chemical. In other embodiments, the heteroaromatic CDK inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Provided herein is a pharmaceutical composition comprising at least one heteroaromatic CDK inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), (II), (III), or (IV) or a compound disclosed in Tables 1-3, or a pharmaceutically acceptable salt or solvate thereof.

One embodiment provides a method of preparing a pharmaceutical composition comprising mixing a compound of Formula (I), (II), (III), or (IV), or a pharmaceutically acceptable salt or solvate thereof, and a pharmaceutically acceptable carrier.

In certain embodiments, the heteroaromatic CDK inhibitory compound as described by Formula (I), (II), (III), or (IV) or a compound disclosed in Tables 1-3, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

In some embodiments, the heteroaromatic CDK inhibitory compound as described by Formula (I), (II), (III), or (IV) or a compound disclosed in Tables 1-3, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heteroaromatic CDK inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), (II), (III), or (IV) or a compound disclosed in Tables 1-3, or a pharmaceutically acceptable salt or solvate thereof, for use in a method of treatment of the human or animal body.

One embodiment provides a compound of Formula (I), (II), (III), or (IV) or a compound disclosed in Tables 1-3, or a pharmaceutically acceptable salt or solvate thereof, for use in a method of treatment of cancer, neoplastic disease, or hyperproliferative disorder.

One embodiment provides a use of a compound of Formula (I), (II), (III), or (IV) or a compound disclosed in Tables 1-3, or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I), or a pharmaceutically acceptable salt or solvate thereof. In some embodiments, described herein is a method of treating cancer in a patient in need thereof comprising administering to the patient a compound of Formula (II), or a pharmaceutically acceptable salt or solvate thereof. In some embodiments, described herein is a method of treating cancer in a patient in need thereof comprising administering to the patient a compound of Formula (III), or a pharmaceutically acceptable salt or solvate thereof. In some embodiments, described herein is a method of treating cancer in a patient in need thereof comprising administering to the patient a compound of Formula (IV), or a pharmaceutically acceptable salt or solvate thereof. In some embodiments, described herein is a method of treating cancer in a patient in need thereof comprising administering to the patient a compound disclosed in Table 1-3, or a pharmaceutically acceptable salt or solvate thereof. In some embodiments, also described herein is a method of treating cancer in a patient in need thereof comprising administering to the patient a pharmaceutical composition comprising a compound of Formula (I), or a pharmaceutically acceptable salt or solvate thereof, and a pharmaceutically acceptable excipient. In some embodiments, also described herein is a method of treating cancer in a patient in need thereof comprising administering to the patient a pharmaceutical composition comprising a compound of Formula (II), or a pharmaceutically acceptable salt or solvate thereof, and a pharmaceutically acceptable excipient. In some embodiments, also described herein is a method of treating cancer in a patient in need thereof comprising administering to the patient a pharmaceutical composition comprising a compound of Formula (III), or a pharmaceutically acceptable salt or solvate thereof, and a pharmaceutically acceptable excipient. In some embodiments, also described herein is a method of treating cancer in a patient in need thereof comprising administering to the patient a pharmaceutical composition comprising a compound of Formula (IV), or a pharmaceutically acceptable salt or solvate thereof, and a pharmaceutically acceptable excipient. In some embodiments, also described herein is a method of treating cancer in a patient in need thereof comprising administering to the patient a pharmaceutical composition comprising a compound disclosed in Table 1-3, or a pharmaceutically acceptable salt or solvate thereof, and a pharmaceutically acceptable excipient. In some embodiments, the cancer is breast cancer, colorectal cancer, ovarian cancer, pancreatic cancer, prostate cancer, or lung cancer.

Provided herein is the method wherein the pharmaceutical composition is administered orally. Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heteroaromatic CDK inhibitory compounds disclosed herein are synthesized according to the following examples. As used below, and throughout the description of the invention, the following abbreviations, unless otherwise indicated, shall be understood to have the following meanings:

° C. degrees Celsius
$\delta_H$ chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THE tetrahydrofuran Example A1: Synthesis of Intermediate 1 (4-acrylamidobenzoic Acid)

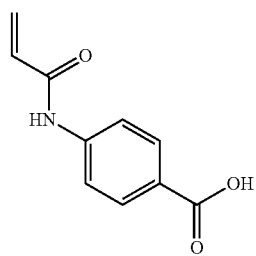

A mixture of 4-amino-benzoic acid (25 g, 181.9 mmol) and pyridine (10 mL) in DMF (200 mL) was cooled to 0° C. Acryloyl chloride (22 mL, 272.8 mmol) was added and the solution was stirred at RT for 3 h. The reaction mixture was poured into water (200 mL) and the precipitate was filtered, washed with water, washed with PE, dried under high vacuum to give 4-acrylamidobenzoic acid as a white solid (22 g, 63%). MS Calcd.: 191, MS Found: 192 ([M+H]$^+$).

Example A2: Synthesis of Intermediate 2 (4-propionamidobenzoic acid)

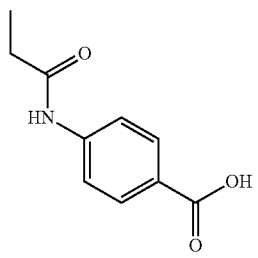

A mixture of 4-amino-benzoic acid (25 g, 181.9 mmol) and pyridine (10 mL) in DMF (200 mL) was cooled to 0° C. Propionyl chloride (23.8 mL, 272.9 mmol) was added and the solution was stirred at RT for 16 h. The reaction mixture was poured into water (200 mL) and the precipitate was filtered, washed with water, washed with PE, dried under high vacuum to give 4-propionamidobenzoic acid as a white solid (22 g, 63%). MS Calcd.: 193, MS Found: 194 ([M+H]$^+$).

Example A3: Synthesis of 4-(N-methylacrylamido)benzoic Acid

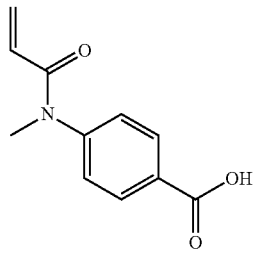

A solution of 4-(methylamino)benzoic acid (1.5 g, 10.0 mmol) in DMF (20 mL) and Pyridine (1.0 mL) was cooled to 0° C. To this cooled solution was added acryloyl chloride (1.4 g, 15.5 mmol). The reaction mixture was stirred at room temperature for 3 h then poured into 20 mL of water. The resultant white solid was collected by filtration, washed with water and Petroleum Ether then dried under high vacuum to give 4-(N-methylacrylamido)benzoic acid (500 mg, 24%). MS Calcd.: 205, MS Found: 206 ([M+H]+).

Example 1: Synthesis of (R)—N-(4-(3-((5-chloro-4-methoxypyrimidin-2-yl)amino)pyrrolidine-1-carbonyl)-2-methoxyphenyl)acrylamide

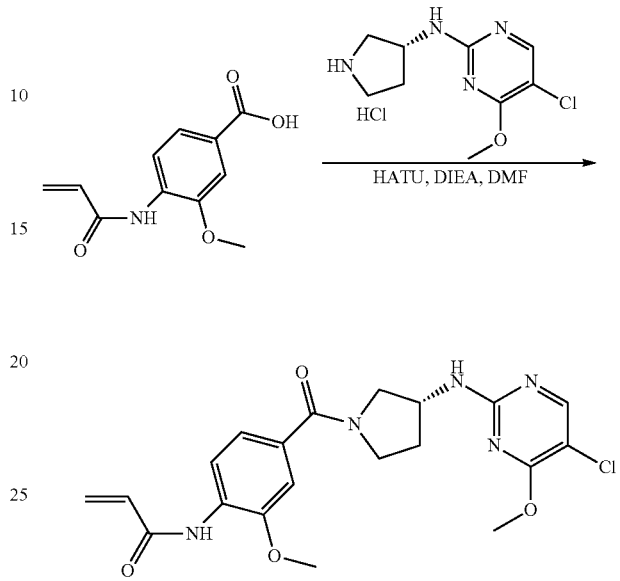

A mixture of 4-acrylamido-3-methoxybenzoic acid (100 mg, 0.45 mmol), (R)-5-chloro-4-methoxy-N-(pyrrolidin-3-yl)pyrimidin-2-amine hydrochloride (112 mg, 0.49 mmol), HATU (256 mg, 0.67 mmol) and DIEA (145 mg, 1.12 mmol) in DMF (10 mL) was stirred at 25° C. overnight. The mixture was diluted with H$_2$O (30 mL) and extracted with DCM (30 mL*2). The combined organic phases were concentrated in vacuo. The residue was purified by prep-HPLC to afford (R)—N-(4-(3-((5-chloro-4-methoxypyrimidin-2-yl)amino)pyrrolidine-1-carbonyl)-2-methoxyphenyl)acrylamide (13 mg, 7%). $^1$H NMR (400 MHz, DMSO-d$_6$): δ 1.89-2.11 (m, 1H), 2.12-2.29 (m, 1H), 3.42-3.55 (m, 4H), 3.64-3.94 (m, 6H), 4.30-4.52 (m, 1H), 5.73-5.75 (m, 1H), 6.23-6.27 (m, 1H), 6.75-6.79 (m, 1H), 7.12-7.19 (m, 2H), 7.73-7.75 (m, 1H), 8.09-8.16 (m, 2H), 9.51 (m, 1H). MS Calcd.: 431, MS Found: 432 ([M+H]$^+$).

Example 2: Synthesis of (R)-1-(7-(3-((5-chloro-4-methoxypyrimidin-2-yl)amino)pyrrolidine-1-carbonyl)-2H-benzo[b][1,4]oxazin-4(3H)-yl)prop-2-en-1-one

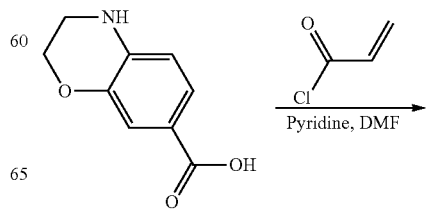

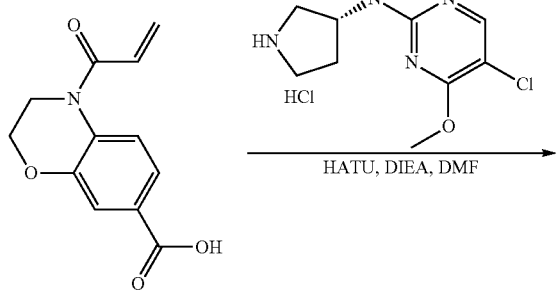

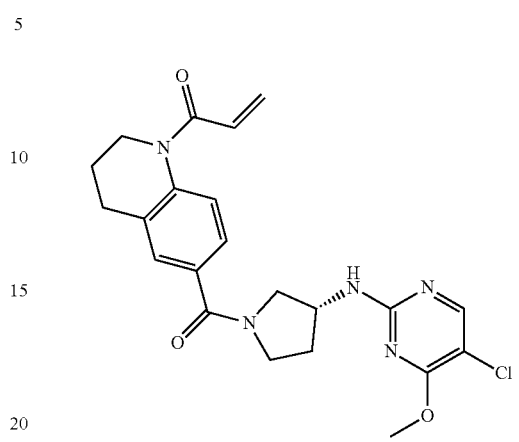

Example 3: Synthesis of (R)-1-(6-(3-((5-chloro-4-methoxypyrimidin-2-yl)amino)pyrrolidine-1-carbonyl)-3,4-dihydroquinolin-1(2H)-yl)prop-2-en-1-one The title compound was prepared in 18% yield from 1-acryloyl-1,2,3,4-tetrahydro-quinoline-6-carboxylic acid using general procedure of N-{4-[3-(5-choro-4-methoxy-pyrimidin-2-ylamino)-piperidine-1-carbonyl]-2-methoxy-phenyl}-acrylamide. $^1$H NMR (400 MHz, DMSO-d$_6$): δ 1.88-2.15 (m, 4H), 2.72-2.73 (m, 2H), 3.28-3.94 (m, 9H), 4.29-4.45 (m, 1H), 5.72 (d, J=12.0 Hz, 1H), 6.22 (d, J=8.8 Hz, 1H), 6.57 (d, J=16.8 Hz, 1H), 7.35 (m, 3H), 7.67 (m, 1H), 8.11 (s, 1H). MS Calcd.: 441, MS Found: 442 ([M+H]$^+$).

Step 1:

To a solution of 3,4-dihydro-2H-benzo[b][1,4]oxazine-7-carboxylic acid (500 mg, 2.82 mmol) in DMF (20 mL) was added pyridine (663 mg, 8.40 mmol) at 0° C. To the mixture was then added acryloyl chloride (510 mg, 5.64 mmol) dropwise over 5 min. The mixture was then stirred at room temperature for overnight. The reaction mixture was concentrated in vacuo and the residue was purified by flash chromatography on silica gel (Petroleum Ether/Ethyl Acetate=1/1) to afford 4-acryloyl-3,4-dihydro-2H-benzo[b][1,4]oxazine-7-carboxylic acid (150 mg, 23%). MS Calcd.: 233, MS Found: 234 ([M+H]$^+$).

Step 2:

The title compound was prepared in 32% yield from 4-acryloyl-3,4-dihydro-2H-benzo[b][1,4]oxazine-7-carboxylic acid using general procedure of N-{4-[3-(5-choro-4-methoxy-pyrimidin-2-ylamino)-piperidine-1-carbonyl]-2-methoxy-phenyl}-acrylamide. $^1$H NMR (400 MHz, DMSO-d$_6$): δ 1.91-2.13 (m, 2H), 3.50-3.95 (m, 9H), 4.30-4.31 (m, 3H), 5.83-5.85 (d, J=8.0 Hz, 1H), 6.25-6.30 (d, J=24.0 Hz, 1H), 6.78 (m, 1H), 7.02-7.08 (m, 2H), 7.49-7.67 (m, 2H), 8.08-8.14 (m, 1H). MS Calcd.: 443, MS Found: 444 ([M+H]$^+$)

Example 4: Synthesis of (R)—N-(4-(3-((5-chloro-4-methoxypyrimidin-2-yl)amino)pyrrolidine-1-carbonyl)-2-(1-methyl-1H-pyrazol-4-yl)phenyl)acrylamide

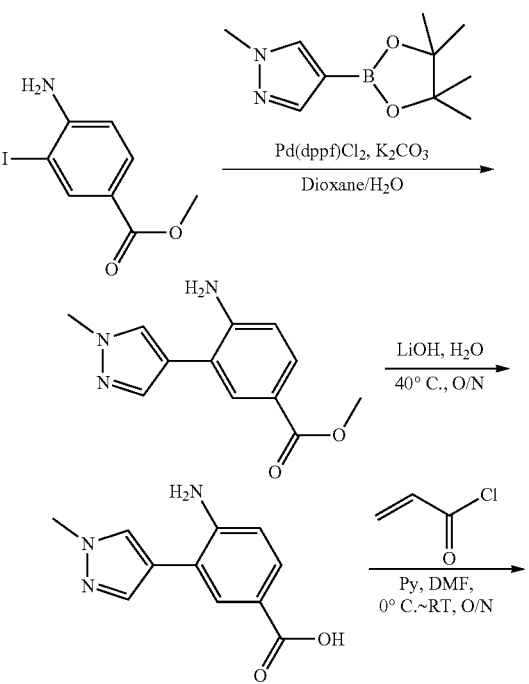

-continued

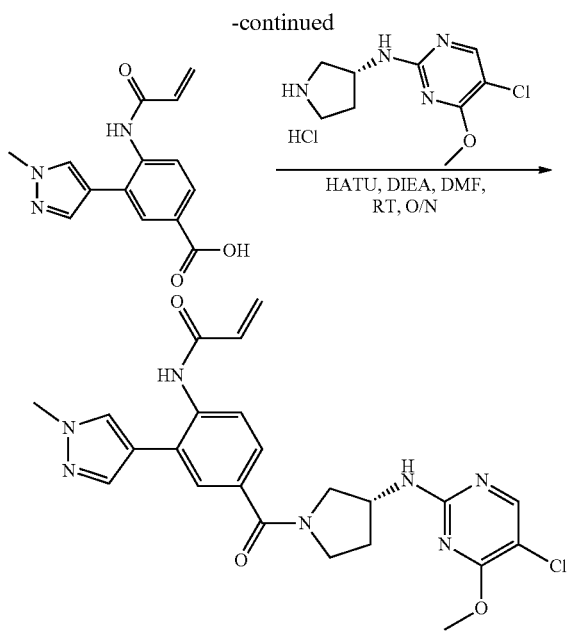

Step 1:

A suspension of methyl 4-amino-3-iodobenzoate (500 mg, 1.81 mmol), 1-methyl-4-(4,4,5,5-tetramethyl-1,3,2-dioxaborolan-2-yl)-1H-pyrazole (563 mg, 2.71 mmol), Pd(dppf)Cl$_2$ (132 mg, 0.18 mmol) and Cs$_2$CO$_3$ (1177 mg, 3.61 mmol) in Dioxane/H$_2$O (10 mL/2 mL) was stirred at 90° C. for 8 h under Nitrogen. The mixture was then diluted with H$_2$O (30 mL) and extracted with DCM (30 mL*2). The combined organic phases were concentrated in vacuo and the residue was purified by flash chromatography on silica gel (Petroleum Ether/Ethyl Acetate=1/1) to afford methyl 4-amino-3-(1-methyl-1H-pyrazol-4-yl)benzoate (417 mg, 100%) as a brown solid. MS Calcd.: 231, MS Found: 232 ([M+H]$^+$).

Step 2:

A solution of 4-amino-3-(1-methyl-1H-pyrazol-4-yl)benzoate (417 mg, 1.81 mmol) and LiOH.H$_2$O (235 mg, 5.60 mmol) in THF/H$_2$O (20 mL/10 mL) was stirred at RT for 1 day. The reaction mixture was adjusted to pH=3 with HCl (2 M) and then extracted with DCM (30 mL). The organic layer was concentrated in vacuo to afford 4-amino-3-(1-methyl-1H-pyrazol-4-yl)benzoic acid (300 mg, 76%) as a brown solid. MS Calcd.: 217, MS Found: 218 ([M+H]$^+$).

Step 3:

To a solution of 4-amino-3-(1-methyl-1H-pyrazol-4-yl)benzoic acid (300 mg, 1.38 mmol) in DMF (15 mL) was added pyridine (328 mg, 4.15 mmol) at 0° C. To the mixture was then added acryloyl chloride (250 mg, 2.76 mmol) dropwise over 5 min. The mixture was then stirred at RT overnight. Water (30 mL) was added and adjusted the pH to 3 with HCl (2 M), extracted with DCM (30 mL*2). The combined organic phases were concentrated in vacuo to afford 4-acrylamido-3-(1-methyl-1H-pyrazol-4-yl)benzoic acid (150 mg, 40%) as a brown solid. MS Calcd.: 271, MS Found: 272 ([M+H]+).

Step 4:

The title compound was prepared in 18% yield from 4-acrylamido-3-(1-methyl-1H-pyrazol-4-yl)benzoic acid using the general procedure of N-{4-[3-(5-choro-4-methoxy-pyrimidin-2-ylamino)-piperidine-1-carbonyl]-2-methoxy-phenyl}-acrylamide. $^1$H NMR (400 MHz, DMSO-d$_6$): δ 1.95-2.17 (m, 2H), 3.39-3.70 (m, 3H), 3.82-3.95 (m, 7H), 4.27-4.45 (m, 1H), 5.75 (d, J=10.4 Hz, 1H), 6.24 (d, J=17.2 Hz, 1H), 6.49-6.53 (m, 1H), 7.35-7.41 (m, 1H), 7.55-7.69 (m, 4H), 7.98 (d, J=10.0 Hz, 1H), 8.08-8.16 (m, 1H), 9.62 (s, 1H). MS Calcd.: 481, MS Found: 482 ([M+H]+).

Example 5: Synthesis of (R)—N-(2-chloro-4-(3-((5-chloro-4-methoxypyrimidin-2-yl)amino)pyrrolidine-1-carbonyl)phenyl)acrylamide

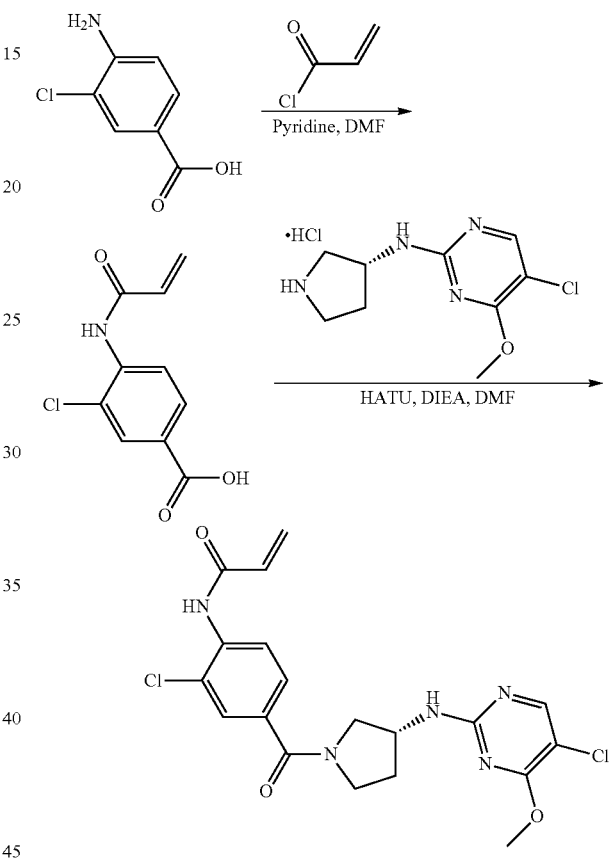

Step 1:

To a solution of 4-amino-3-chlorobenzoic acid (4.0 g, 23.3 mmol) in DMF (35 mL) was added pyridine (3.6 g, 45.6 mmol) at 0° C. To the mixture was then added acryloyl chloride (2.1 g, 23.2 mmol) dropwise over 3 min. The mixture was then stirred at RT overnight. The reaction was quenched with ice water (50 mL) and extracted with Ethyl Acetate (50 mL*2). The combined organic layers were collected, dried over Na$_2$SO$_4$, filtered, concentrated in vacuo and purified by column (Petroleum Ether/Ethyl Acetate=1/1) to give 4-acrylamido-3-chlorobenzoic acid (700 mg, 11%). MS Calcd.: 225, MS Found: 226 ([M+H]$^+$).

Step 2:

To a solution of 4-acrylamido-3-chlorobenzoic acid (150 mg, 0.67 mmol), (R)-5-chloro-4-methoxy-N-(pyrrolidin-3-yl)pyrimidin-2-amine hydrochloride (235 mg, 0.73 mmol) in DMF (15 mL) was added HATU (305 mg, 0.80 mmol) and DIEA (260 mg, 2.01 mmol) at 0° C. The mixture was stirred at RT overnight. The reaction was concentrated in-vacuo and purified by prep-HPLC to give (R)—N-(2-chloro-4-(3-((5-chloro-4-methoxypyrimidin-2-yl)amino)

pyrrolidine-1-carbonyl)phenyl)acrylamide (130 mg, 44%). $^1$H NMR (400 MHz, DMSO-d$_6$): δ 1.90-2.14 (m, 2H), 3.39-3.94 (m, 7H), 4.27-4.44 (m, 1H), 5.79-5.82 (m, 1H), 6.27-6.32 (m, 1H), 6.62-6.69 (m, 1H), 7.50 (m, 1H), 7.62-7.67 (m, 2H), 7.89-7.91 (m, 1H), 8.08-8.14 (m, 1H), 9.79-9.80 (m, 1H). MS Calcd.: 435, MS Found: 436 ([M+H]$^+$).

Example 6: Synthesis of (R)—N-(2-chloro-4-(3-((5-chloropyrimidin-2-yl)amino)pyrrolidine-1-carbonyl)phenyl)acrylamide

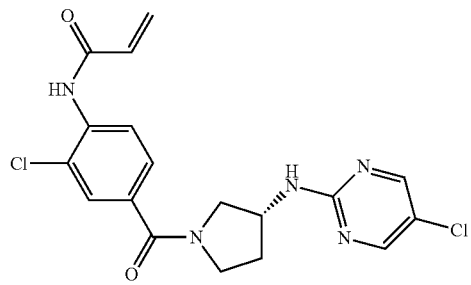 [SMILES: C=CC(=O)Nc1ccc(C(=O)N2CC[C@@H](Nc3ncc(Cl)cn3)C2)cc1Cl]

The title compound was prepared in 6% yield from 4-acrylamido-3-chlorobenzoic acid using general procedure of (R)—N-(2-chloro-4-(3-((5-chloro-4-methoxypyrimidin-2-yl)amino)pyrrolidine-1-carbonyl)phenyl)acrylamide. $^1$H NMR (400 MHz, DMSO-d$_6$): δ 1.98-2.14 (m, 2H), 3.38-3.74 (m, 4H), 4.27-4.42 (m, 1H), 5.90-5.82 (m, 1H), 6.27-6.32 (d, J=20 Hz, 1H), 6.64-6.69 (m, 1H), 7.48-7.49 (m, 1H), 7.62-7.66 (m, 1H), 7.82 (m, 1H), 7.91 (m, 1H), 8.32-8.38 (m, 1H), 9.78-9.80 (m, 1H). MS Calcd.: 405, MS Found: 406 ([M+H]$^+$).

Example 7: Synthesis of (R)—N-(4-(3-((5-chloro-4-methoxypyrimidin-2-yl)amino)pyrrolidine-1-carbonyl)thiazol-2-yl)acrylamide

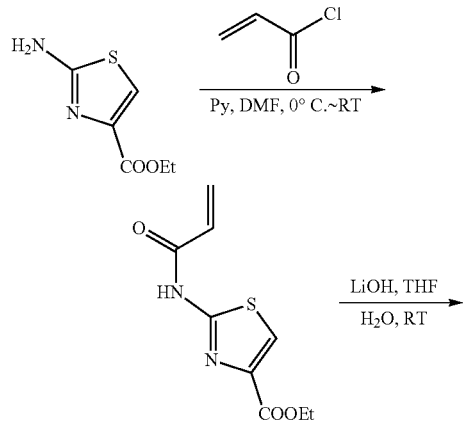

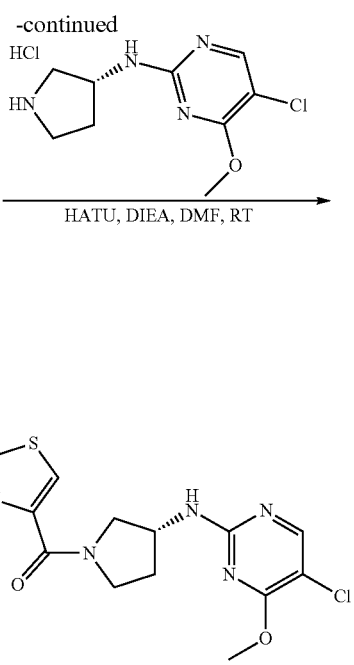

Step 1:
To a solution of ethyl 2-aminothiazole-4-carboxylate (5.0 g, 29.0 mmol) in DMF (35 mL) was added pyridine (2.5 mL) at 0° C. Then to the mixture was added acryloyl chloride (3.5 mL, 43.6 mmol) dropwise over 3 min and the mixture was then stirred at RT overnight. The reaction mixture was quenched with water (50 mL) and extracted with Ethyl Acetate (50 mL*3). The combined organic layers were washed with water (100 mL*2) and brine (100 mL). The organic layer was collected, dried over Na$_2$SO$_4$, filtered, concentrated in vacuo and purified by flash chromatography on silica gel (Petroleum Ether/Ethyl Acetate=1/1) to give ethyl 2-acrylamidothiazole-4-carboxylate (1.5 g, 23%). MS Calcd.: 226, MS Found: 227 ([M+H]$^+$).

Step 2:
To a solution of 2-acrylamidothiazole-4-carboxylate (500 mg, 2.22 mmol) in THF (15 mL) and water (15 mL) was added LiOH.H$_2$O (93 mg, 2.22 mmol). The mixture was then stirred at RT overnight. The reaction progress was monitored by LCMS (50% starting material and 50% product was formed). To the reaction was then added LiOH.H$_2$O (46 mg, 1.10 mmol) and the mixture was stirred at RT overnight. The reaction mixture was concentrated in-vacuo to afford lithium 2-acrylamidothiazole-4-carboxylate (400 mg, 23%). MS Calcd.: 198, MS Found: 199 ([M+H]$^+$).

Step 3:
The title compound was prepared in 14% yield from lithium salt of 2-acryloylamino-thiazole-4-carboxylic acid using general procedure of N-{4-[3-(5-Chloro-4-methoxy-pyrimidin-2-ylamino)-pyrrolidine-1-carbonyl]-thiazol-2-yl}-acrylamide. $^1$H NMR (400 MHz, DMSO-d$_6$): δ 1.99-2.0 (m, 1H), 2.1-2.15 (m, 1H), 3.67-3.69 (m, 3H), 3.97-4.0 (m, 3H), 4.1-4.4 (m, 2H), 5.89-5.92 (m, 1H), 6.40 (d, J=12.0 Hz, 1H), 6.51-6.52 (m, 1H), 7.67 (s, 1H), 7.7 (s, 1H), 8.12 (d, J=16.0 Hz, 1H), 12.39 (s, 1H). MS Calcd.: 408, MS Found: 409 ([M+H]$^+$).

Example 8: Synthesis of (R)—N-(5-(3-((5-chloro-4-methoxypyrimidin-2-yl)amino)pyrrolidine-1-carbonyl)thiazol-2-yl)acrylamide

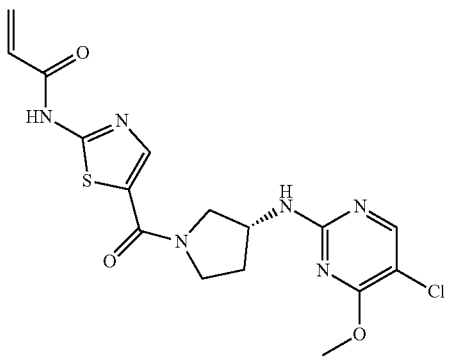 [SMILES: C=CC(=O)Nc1ncc(C(=O)N2CC[C@@H](Nc3ncc(Cl)c(OC)n3)C2)s1]

The title compound was prepared in 2% yield from 2-acrylamidothiazole-5-carboxylic acid using general procedure of N-{4-[3-(4-Cyclopentyloxy-pyrimidin-2-ylamino)-piperidine-1-carbonyl]-phenyl}-acrylamide. $^1$H NMR (400 MHz, DMSO-$d_6$): δ 1.98-1.99 (m, 1H), 2.07-2.25 (m, 1H), 3.52-3.69 (m, 3H), 3.85-3.92 (m, 3H), 4.08 (s, 1H), 4.38-4.43 (m, 1H), 5.93-5.95 (m, 1H), 6.40-6.44 (m, 1H), 6.50-6.53 (m, 1H), 7.75 (s, 1H), 7.94-7.99 (m, 1H), 8.14 (s, 1H), 12.58 (s, 1H). MS Calcd.: 408, MS Found: 409 ([M+H]$^+$).

Example 9: Synthesis of (R)—N-(4-(3-((5-chloro-4-methoxypyrimidin-2-yl)amino)pyrrolidine-1-carbonyl)-2-(4-methylpiperazin-1-yl)phenyl)acrylamide

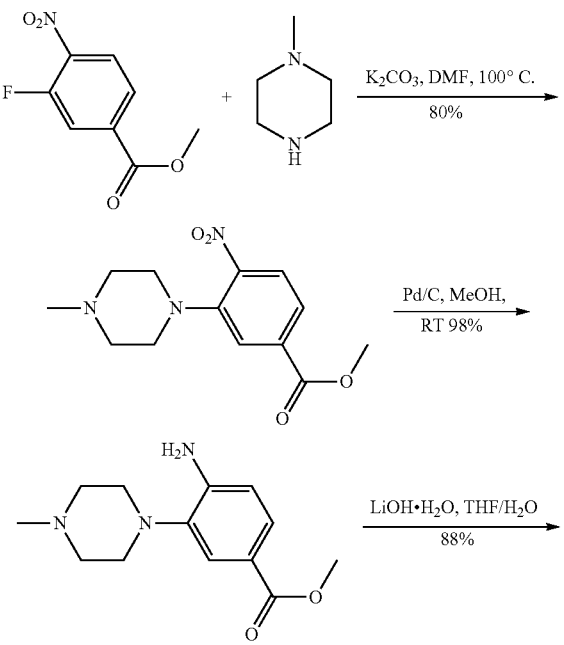

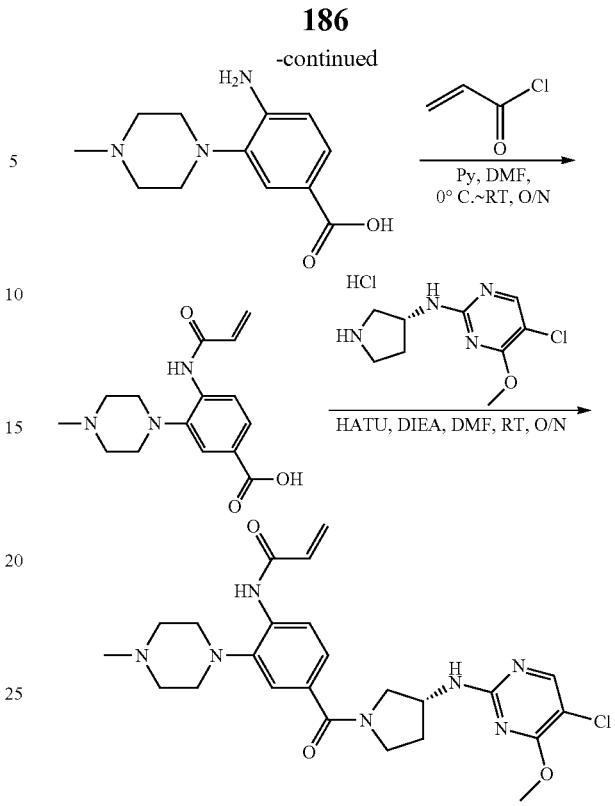

Step 1:
A suspension of methyl 3-fluoro-4-nitrobenzoate (1.1 g, 5.4 mmol), 1-methyl-piperazine (0.6 g, 5.9 mmol) and $K_2CO_3$ (1.5 g, 1.1 mmol) in DMF (30 mL) was stirred at 100° C. overnight. The reaction mixture was diluted with water (100 mL) and extracted with Ethyl Acetate (50 mL*3). The combined organic layers were washed with water (100 mL*2) and brine (100 mL), dried over $Na_2SO_4$, filtered and concentrated in vacuo to give methyl 3-(4-methylpiperazin-1-yl)-4-nitrobenzoate (1.2 g, 80%). MS Calcd.: 279, MS Found: 280 ([M+H]$^+$).

Step 2:
A suspension of methyl 3-(4-methylpiperazin-1-yl)-4-nitrobenzoate (1.5 g, 5.7 mmol) and Pd/C (400 mg, 5%) in MeOH (30 mL) was stirred at room temperature for overnight under 1 atm $H_2$. The reaction was filtered and concentrated in vacuo to give methyl 4-amino-3-(4-methylpiperazin-1-yl)benzoate (1.3 g, 98%). MS Calcd.: 249, MS Found: 250 ([M+H]$^+$).

Step 3:
A suspension of methyl 4-amino-3-(4-methylpiperazin-1-yl)benzoate (1.8 g, 6.5 mmol) and LiOH.$H_2O$ (540 mg, 12.9 mmol) in THF (30 mL) and water (10 mL) was stirred at RT overnight. The reaction was concentrated to remove THF, acidified to pH 5, filtered and then dried in vacuo to afford 4-amino-3-(4-methylpiperazin-1-yl)benzoic acid (1.5 g, 88%). MS Calcd.: 235, MS Found: 236 ([M+H]$^+$).

Step 4:
The title compound was prepared in 40% yield from 4-amino-3-(4-methylpiperazin-1-yl)benzoic acid using general procedure of 4-acrylamido-3-chlorobenzoic acid. MS Calcd.: 289, MS Found: 290 ([M+H]$^+$).

Step 5:
The title compound was prepared in 6% yield from 4-acrylamido-3-(4-methylpiperazin-1-yl)benzoic acid using general procedure of (R)—N-(4-(3-((5-chloro-4-methoxypyrimidin-2-yl)amino)pyrrolidine-1-carbonyl)-2-(4-methylpiperazin-1-yl)phenyl)acrylamide. $^1$H NMR (400 MHz, DMSO-d$_6$): δ 1.90-2.12 (m, 1H), 2.12-2.20 (m, 1H), 2.25 (s, 3H), 2.51-2.54 (m, 4H), 2.79-2.84 (m, 4H), 3.40-3.43 (m, 1H), 3.50-3.54 (m, 1H), 3.62-3.66 (m, 1H), 3.75-3.76 (m, 1H), 3.86 (s, 1.55H), 3.94 (s, 1.45H), 4.25-4.42 (m, 1H), 5.78 (d, J=10.4 Hz, 1H), 6.26 (d, J=16.8 Hz, 1H), 6.60-6.67 (m, 1H), 7.22-7.32 (m, 2H), 7.68 (br s, 1H), 8.00-8.14 (s, 2H), 9.08 (s, 0.55H), 9.10 (s, 0.45H). MS Calcd.: 499, MS Found: 500 ([M+H]+).

Example 10: Synthesis of (R)—N-(4-(3-((5-chloro-4-methoxypyrimidin-2-yl)amino)pyrrolidine-1-carbonyl)-2-morpholinophenyl)acrylamide

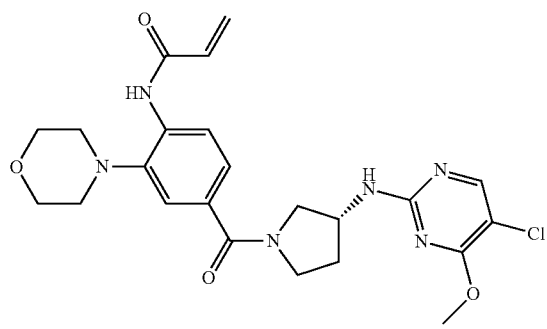 [SMILES: C=CC(=O)Nc1ccc(C(=O)N2CC[C@@H](Nc3ncc(Cl)c(OC)n3)C2)cc1N1CCOCC1]

The title compound was prepared in 38% yield from 4-acrylamido-3-morpholinobenzoic acid using general procedure of N-{4-[3-(4-cyclopentyloxy-pyrimidin-2-ylamino)-piperidine-1-carbonyl]-phenyl}-acrylamide. $^1$H NMR (400 MHz, DMSO-d$_6$): δ 1.90-2.12 (m, 1H), 2.12-2.20 (m, 1H), 2.79-2.83 (m, 4H), 3.40-3.50 (m, 1H), 3.50-3.54 (m, 1H), 3.62-3.66 (m, 1H), 3.79-3.95 (m, 8H), 4.26-4.30 (m, 1H), 5.79 (d, J=10.0 Hz, 1H), 6.27 (d, J=16.4 Hz, 1H), 6.60-6.67 (m, 1H), 7.27-7.34 (m, 2H), 7.69 (br s, 1H), 8.07-8.16 (s, 2H), 9.20 (s, 0.55H), 9.22 (s, 0.45H). MS Calcd.: 486, MS Found: 487 ([M+H]$^+$).

Example 11: Synthesis of (R)—N-(4-(3-((5-chloro-4-methoxypyrimidin-2-yl)amino)pyrrolidine-1-carbonyl)-2-(piperidin-1-yl)phenyl)acrylamide

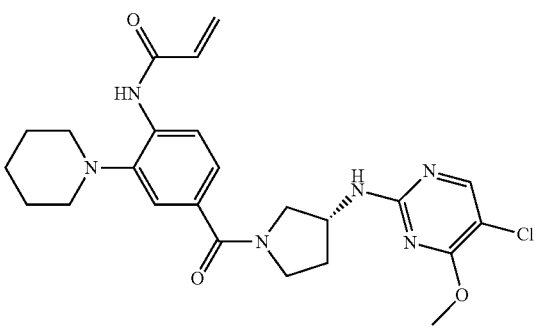 [SMILES: C=CC(=O)Nc1ccc(C(=O)N2CC[C@@H](Nc3ncc(Cl)c(OC)n3)C2)cc1N1CCCCC1]

The title compound was prepared in 6% yield from 4-acrylamido-3-(piperidin-1-yl)benzoic acid using general procedure of N-{4-[3-(4-cyclopentyloxy-pyrimidin-2-ylamino)-piperidine-1-carbonyl]-phenyl}-acrylamide. $^1$H NMR (400 MHz, DMSO-d$_6$): δ 1.53 (s, 2H), 1.70 (s, 4H), 1.98-2.01 (m, 1H), 2.14-2.16 (m, 1H), 2.71-2.77 (m, 4H), 3.40-3.44 (m, 2H), 3.65-3.94 (m, 5H), 4.24-4.50 (m, 1H), 5.79 (d, J=10.0 Hz, 1H), 6.26 (d, J=16.4 Hz, 1H), 6.63-6.70 (m, 1H), 7.21-7.31 (m, 2H), 7.71 (br s, 1H), 8.02-8.15 (s, 2H), 9.09 (s, 0.55H), 9.11 (s, 0.45H). MS Calcd.: 484, MS Found: 485 ([M+H]$^+$).

Example 12: Synthesis of (R)—N-(4-(3-((5-chloropyrimidin-2-yl)amino)pyrrolidine-1-carbonyl)-2-(1-methyl-1H-pyrazol-4-yl)phenyl)acrylamide

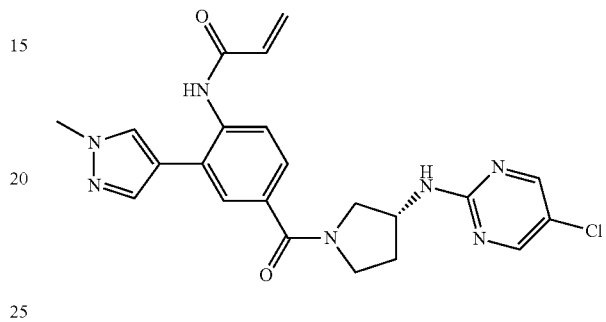

The title compound was prepared in 39% yield from 4-acrylamido-3-(1-methyl-1H-pyrazol-4-yl)benzoic acid using general procedure of N-{4-[3-(4-Cyclopentyloxy-pyrimidin-2-ylamino)-piperidine-1-carbonyl]-phenyl}-acrylamide. $^1$H NMR (400 MHz, DMSO-d$_6$): δ 1.90-2.12 (m, 1H), 2.12-2.20 (m, 1H), 3.37-3.45 (m, 1H), 3.54-3.67 (m, 1H), 3.74-3.80 (m, 2H), 3.86 (s, 3H), 4.23-4.42 (m, 1H), 5.75 (d, J=10.0 Hz, 1H), 6.24 (d, J=16.4 Hz, 1H), 6.51-6.67 (m, 1H), 7.35-7.40 (m, 1H), 7.55-7.68 (m, 3H), 7.81 (br s, 1H), 7.98 (d, J=8.4 Hz, 1H), 8.31-8.38 (m, 2H), 9.20 (s, 0.55H), 9.22 (s, 0.45H). MS Calcd.: 451, MS Found: 452 ([M+H]$^+$).

Example 13: Synthesis of (R)—N-(4-(3-((4-cyclopropoxy-5-fluoropyrimidin-2-yl)amino)pyrrolidine-1-carbonyl)phenyl)propionamide

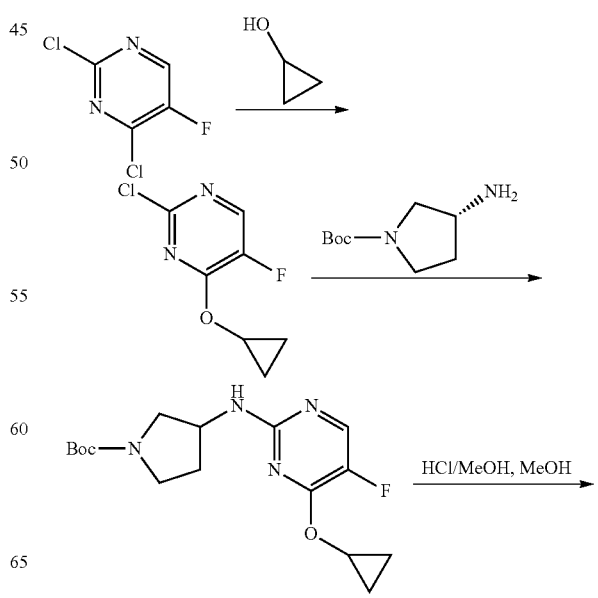

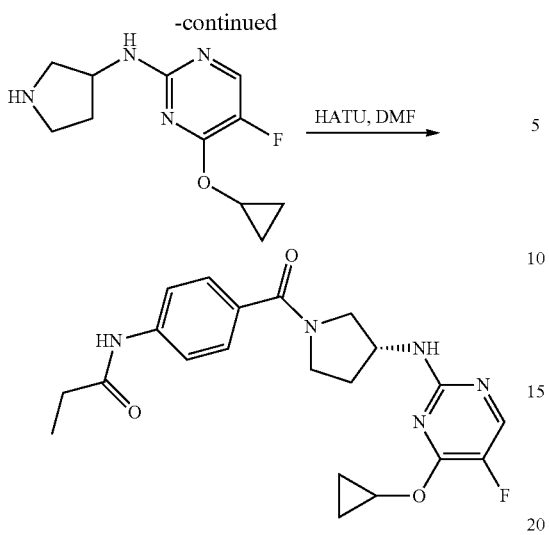

Step 1:
To a solution of cyclopropanol (3.3 g, 20.0 mmol) in THF (60 mL) was added NaH (880 mg, 22.0 mmol, 60% in oil) at 0° C. The reaction mixture was then stirred at 0° C. for 20 min. A solution of 2,4-dichloro-5-fluoropyrimidine in THF (10 mL) was then added and the mixture was stirred at 0° C. for 4 hours. Sat. NH$_4$Cl (20 mL) was added to quench the reaction and the mixture was extracted with Ethyl Acetate (500 mL). The organic layer was washed with water (500 mL*3) and concentrated in vacuo to afford 2-chloro-4-cyclopropoxy-5-fluoropyrimidine (3.76 g, 100%) as yellow oil. $^1$H NMR (400 MHz, CDCl$_3$): δ 0.89 (s, 4H), 4.49-4.54 (m, 1H), 8.15 (d, J=2.0 Hz, 1H).

Step 2:
A solution of 2-chloro-4-cyclopropoxy-5-fluoropyrimidine (1.9 g, 10 mmol), (R)-tert-butyl 3-aminopyrrolidine-1-carboxylate (1.9 g, 10.0 mmol) and DIEA (3.9 g, 30.0 mmol) in NMP (30 mL) was stirred at 130° C. for 8 hours. The mixture was cooled to room temperature and diluted with Ethyl Acetate (500 mL). The organic layer was then washed with water (500 mL*2) and brine (100 mL), dried over Na$_2$SO$_4$, then filtered and concentrated in vacuo. The residue was purified by reverse-chromatography column ACN/H$_2$O (5-95%, RT=30 min), to afford (R)-tert-butyl 3-((4-cyclopropoxy-5-fluoropyrimidin-2-yl)amino)pyrrolidine-1-carboxylate (1.8 g, 53%) as black oil. $^1$H NMR (400 MHz, CDCl$_3$): δ 0.79-0.86 (m, 4H), 1.46 (s, 9H), 1.90 (br s, 1H), 2.19-2.24 (m, 1H), 3.20-3.49 (m, 3H), 3.70-3.74 (m, 1H), 4.32-4.41 (m, 2H), 5.03-5.05 (m, 1H), 7.91 (d, J=2.8 Hz, 1H).

Step 3:
To a solution of (R)-tert-butyl 3-((4-cyclopropoxy-5-fluoropyrimidin-2-yl)amino)pyrrolidine-1-carboxylate (1.5 g, 4.48 mmol) in MeOH (2 mL) was added HCl/MeOH (8 mL, 1M). The mixture was stirred at room temperature for 8 hours. The mixture was concentrated to afford (R)-4-cyclopropoxy-5-fluoro-N-(pyrrolidin-3-yl)pyrimidin-2-amine (1.0 g, 100%). MS Calcd.: 238, MS Found: 239 ([M+H]$^+$).

Step 4:
The title compound was prepared in 21.4% yield from (R)-4-cyclopropoxy-5-fluoro-N-(pyrrolidin-3-yl)pyrimidin-2-amine according to the procedure for the preparation of N-{4-[3-(4-Cyclopropoxy-5-fluoro-pyrimidin-2-ylamino)-pyrrolidine-1-carbonyl]-phenyl}-propionamide. $^1$H NMR (400 MHz, DMSO-d$_6$): δ 0.56-0.79 (m, 4H), 1.06-1.10 (m, 3H), 1.86-2.17 (m, 2H), 2.31-2.37 (m, 2H), 3.39-3.84 (m, 4H), 4.18-4.37 (m, 2H), 7.46-7.51 (m, 3H), 7.61-7.66 (m, 2H), 8.06-8.15 (m, 1H), 10.05 (s, 1H). MS Calcd.: 413; Found: 414 ([M+H]$^+$).

Example 14: Synthesis of (R)—N-(4-(3-((5-bromo-4-methoxypyrimidin-2-yl)amino)pyrrolidine-1-carbonyl)phenyl)propionamide

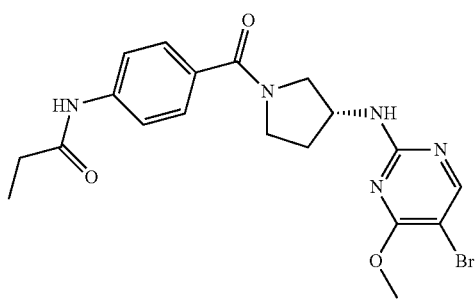 [SMILES: CCC(=O)Nc1ccc(C(=O)N2CC[C@@H](Nc3ncc(Br)c(OC)n3)C2)cc1]

The title compound was prepared in 17.9% yield from (R)-5-bromo-4-methoxy-N-(pyrrolidin-3-yl)pyrimidin-2-amine according to the procedure for the preparation of (R)—N-(4-(3-((4-cyclopropoxy-5-fluoropyrimidin-2-yl)amino)pyrrolidine-1-carbonyl)phenyl)propionamide. $^1$H NMR (400 MHz, DMSO-d$_6$): δ 1.06-1.10 (m, 3H), 1.90-2.14 (m, 2H), 2.31-2.36 (m, 2H), 3.37-3.64 (m, 3H), 3.74-3.93 (m, 4H), 4.25-4.42 (m, 1H), 7.46-7.51 (m, 2H), 7.61-7.74 (m, 3H), 8.14-8.21 (m, 1H), 10.04 (s, 1H). MS Calcd.: 447; Found: 448 ([M+H]$^+$).

Example 15: Synthesis of (R)—N-(4-(3-((5-chloro-4-cyclopropoxypyrimidin-2-yl)amino)pyrrolidine-1-carbonyl)phenyl)propionamide

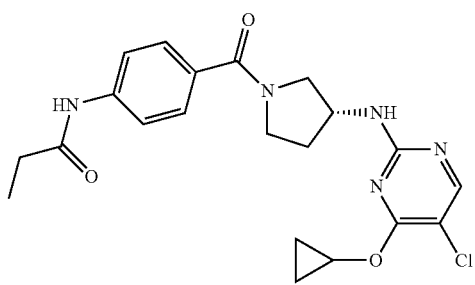 [SMILES: CCC(=O)Nc1ccc(C(=O)N2CC[C@@H](Nc3ncc(Cl)c(OC4CC4)n3)C2)cc1]

The title compound was prepared in 29% yield from (5-Chloro-4-cyclopropoxy-pyrimidin-2-yl)-pyrrolidin-3-yl-amine according to the procedure for the preparation of (R)—N-(4-(3-((4-cyclopropoxy-5-fluoropyrimidin-2-yl)amino)pyrrolidine-1-carbonyl)phenyl)propionamide; $^1$H NMR (400 MHz, DMSO-d$_6$): δ 0.68-0.80 (m, 4H), 1.08 (t, J=7.2 Hz, 3H), 1.91-2.07 (m, 1H), 2.13-2.18 (m, 1H), 2.31-2.36 (m, 2H), 3.34-3.47 (m, 1H), 3.49-3.55 (m, 1H), 3.59-3.67 (m, 1H), 3.74-3.88 (m, 1H), 4.15-4.27 (m, 1H), 4.32-4.37 (m, 1H), 7.45-7.50 (m, 2H), 7.61-7.71 (m, 3H), 8.07-8.15 (m, 1H), 10.02 (s, 1H). MS Calcd.: 429; Found: 430 ([M+H]$^+$).

Example 16: Synthesis of (R)—N-(4-(3-((4-cyclopropoxy-5-methylpyrimidin-2-yl)amino)pyrrolidine-1-carbonyl)phenyl)propionamide

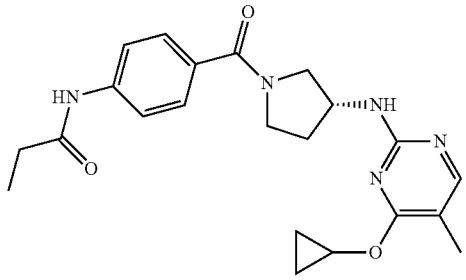 [SMILES: CCC(=O)Nc1ccc(C(=O)N2CC[C@@H](Nc3ncc(C)c(OC4CC4)n3)C2)cc1]

The title compound was prepared in 20.9% yield from (R)-4-cyclopropoxy-5-methyl-N-(pyrrolidin-3-yl)pyrimidin-2-amine according to the procedure for the preparation of (R)—N-(4-(3-((4-cyclopropoxy-5-fluoropyrimidin-2-yl)amino)pyrrolidine-1-carbonyl)phenyl)propionamide $^1$H NMR (400 MHz, DMSO-$d_6$): 0.54-0.85 (m, 4H), 1.06-1.10 (m, 3H), 1.81-1.86 (m, 3H), 1.91-2.16 (m, 2H), 2.30-2.36 (m, 2H), 3.35-3.87 (m, 4H), 4.19-4.41 (m, 2H), 7.16 (s, 1H), 7.44-7.48 (m, 2H), 7.50-7.65 (m, 2H), 7.80-7.88 (m, 1H), 10.01 (s, 1H). [M+H] Calcd.: 409; Found: 410 ([M+H]$^+$).

Example 17: Synthesis of (R)—N-(4-(3-((5-bromopyrimidin-2-yl)amino)pyrrolidine-1-carbonyl)phenyl)propionamide

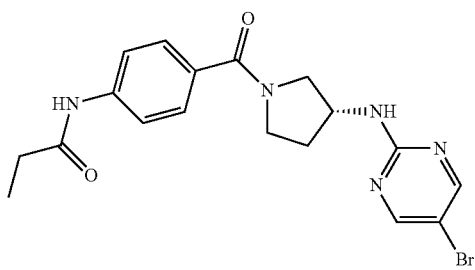 [SMILES: CCC(=O)Nc1ccc(C(=O)N2CC[C@@H](Nc3ncc(Br)cn3)C2)cc1]

The title compound was prepared in 16.5% yield from (R)-5-bromo-N-(pyrrolidin-3-yl)pyrimidin-2-amine according to the procedure for the preparation of (R)—N-(4-(3-((5-bromopyrimidin-2-yl)amino)pyrrolidine-1-carbonyl) phenyl)propionamide. $^1$H NMR (400 MHz, DMSO-$d_6$): δ 1.06-1.13 (m, 3H), 1.86-2.26 (m, 2H), 2.32-2.38 (m, 2H), 3.40-3.77 (m, 4H), 4.16-4.40 (m, 1H), 7.45-7.50 (m, 2H), 7.61-7.65 (m, 2H), 7.78-7.80 (m, 1H), 8.34-8.42 (m, 2H), 9.98-10.01 (m, 1H). Calcd.: 417; Found: 418 ([M+H]$^+$).

Example 18: Synthesis of (R)—N-(4-(3-((5-chloro-4-(2,2,2-trifluoroethoxy)pyrimidin-2-yl)amino)pyrrolidine-1-carbonyl)phenyl)propionamide

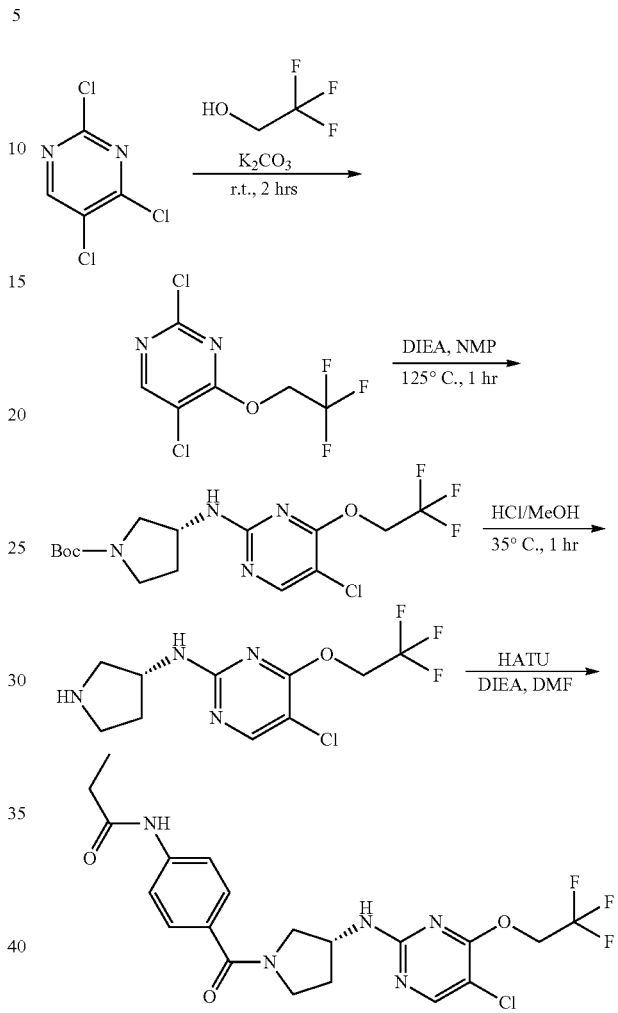

Step 1:
A mixture of 2,4,5-trichloropyrimidine (1.0 g, 5.46 mmol) and K$_2$CO$_3$ (753 mg, 5.46 mmol) in 2,2,2-trifluoroethanol (5 mL) was stirred at room temperature for 2 hrs. The mixture was diluted with Ethyl Acetate (100 mL) and filtered. The filtrate was concentrated in-vacuo to afford 2,5-dichloro-4-(2,2,2-trifluoroethoxy)pyrimidine (1.35 g, 100%) as colorless oil. $^1$H NMR (400 MHz, CD$_3$C): δ 4.84-4.90 (m, 2H), 8.44 (s, 1H).

Step 2:
A solution of 2,5-dichloro-4-(2,2,2-trifluoroethoxy)pyrimidine (1.4 g, 5.4 mmol), (R)-tert-butyl 3-aminopyrrolidine-1-carboxylate (1.0 g, 5.4 mmol) and DIEA (1.4 g, 10.8 mmol) in NMP (6 mL) was stirred at 125° C. for 1 hour. The mixture was cooled to rt and diluted with Ethyl Acetate (500 mL). The organic layer was washed with water (500 mL*2) and brine (100 mL), dried over Na$_2$SO$_4$, filtered and concentrated in vacuo. The residue was purified by reverse-chromatography column ACN/H$_2$O (5-95%, RT=30 min), to afford (R)-tert-butyl 3-((5-chloro-4-(2,2,2-trifluoroethoxy) pyrimidin-2-yl)amino)pyrrolidine-1-carboxylate (1.4 g, 64%) as colorless oil. MS Calcd.: 396, MS Found: 397 ([M+H]$^+$).

Step 3:

To a solution of (R)-tert-butyl 3-((5-chloro-4-(2,2,2-trifluoroethoxy)pyrimidin-2-yl)amino)pyrrolidine-1-carboxylate (1.4 g, 3.5 mmol) in MeOH (2 mL) was added HCl/MeOH (8 mL, 1M). The mixture was stirred at 35° C. for 2 hours. The mixture was concentrated to afford (R)-5-chloro-N-(pyrrolidin-3-yl)-4-(2,2,2-trifluoroethoxy)pyrimidin-2-amine (730 mg, 69%). MS Calcd.: 296, MS Found: 297 ([M+H]+).

Step 4:

The title compound was prepared in 46% yield from (R)-5-chloro-N-(pyrrolidin-3-yl)-4-(2,2,2-trifluoroethoxy)pyrimidin-2-amine according to the procedure for the preparation of (R)—N-(4-(3-((4-cyclopropoxy-5-fluoropyrimidin-2-yl)amino)pyrrolidine-1-carbonyl)phenyl)propionamide. $^1$H NMR (400 MHz, DMSO-d$_6$): δ 1.08 (t, J=7.2 Hz, 3H), 1.88-1.99 (m, 1H), 2.11-2.16 (m, 1H), 2.31-2.34 (m, 2H), 3.41-3.44 (m, 1H), 3.51-3.53 (m, 1H), 3.62-3.64 (m, 1H), 3.77-3.78 (m, 1H), 4.28-4.24 (m, 1H), 4.99-5.11 (m, 2H), 7.46-7.51 (m, 2H), 7.61-7.66 (m, 2H), 7.84-7.93 (m, 1H), 8.20-8.27 (m, 1H), 10.03 (s, 1H). MS Calcd.: 471; Found, 472 ([M+H]+).

Example 19: Synthesis of (R)—N-(4-(3-((5-bromopyrimidin-2-yl)amino)pyrrolidine-1-carbonyl)phenyl)acrylamide

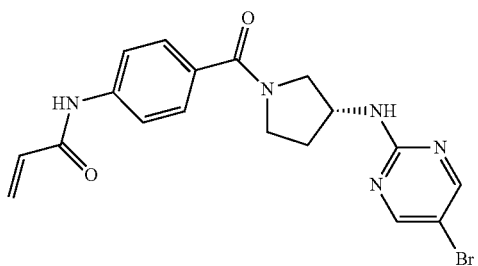 [SMILES: C=CC(=O)Nc1ccc(C(=O)N2CC[C@@H](Nc3ncc(Br)cn3)C2)cc1]

The title compound was prepared in 18% yield from (R)-5-bromo-N-(pyrrolidin-3-yl)pyrimidin-2-amine according to the procedure for the preparation of (R)—N-(4-(3-((4-cyclopropoxy-5-fluoropyrimidin-2-yl)amino)pyrrolidine-1-carbonyl)phenyl)propionamide. $^1$H NMR (400 MHz, DMSO-d$_6$): δ 1.87-2.16 (m, 2H), 3.41-3.80 (m, 4H), 4.23-4.39 (m, 1H), 5.78-5.80 (m, 1H), 6.26-6.48 (m, 2H), 7.49-7.54 (m, 2H), 7.69-7.86 (m, 3H), 8.36-8.43 (m, 2H), 10.33 (s, 1H). Calcd.: 416; Found, 417 ([M+H]+).

Example 20: Synthesis of (R)—N-(4-(3-((5-bromo-4-methoxypyrimidin-2-yl)amino)pyrrolidine-1-carbonyl)phenyl)acrylamide

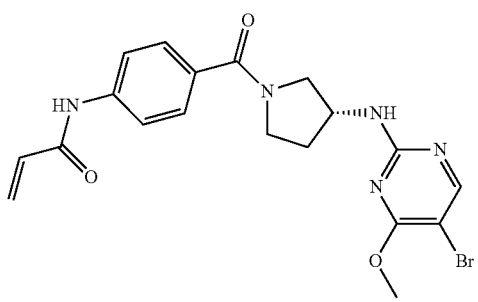 [SMILES: C=CC(=O)Nc1ccc(C(=O)N2CC[C@@H](Nc3ncc(Br)c(OC)n3)C2)cc1]

The title compound was prepared in 10.4% yield from (R)-5-bromo-4-methoxy-N-(pyrrolidin-3-yl)pyrimidin-2-amine according to the procedure for the preparation of (R)—N-(4-(3-((4-cyclopropoxy-5-fluoropyrimidin-2-yl)amino)pyrrolidine-1-carbonyl)phenyl)propionamide. $^1$H NMR (400 MHz, DMSO-d$_6$): δ 1.88-2.14 (m, 2H), 3.41-3.93 (m, 7H), 4.26-4.22 (m, 1H), 5.80-5.78 (m, 1H), 6.26-6.30 (m, 1H), 6.41-6.48 (m, 1H), 7.50-7.54 (m, 2H), 7.69-7.74 (m, 3H), 8.14-8.21 (m, 1H), 10.33 (s, 1H). Calcd.: 445; Found, 447 ([M+H]+).

Example 21: Synthesis of (R)—N-(4-(3-((5-chloro-4-cyclopropoxypyrimidin-2-yl)amino)pyrrolidine-1-carbonyl)phenyl)acrylamide

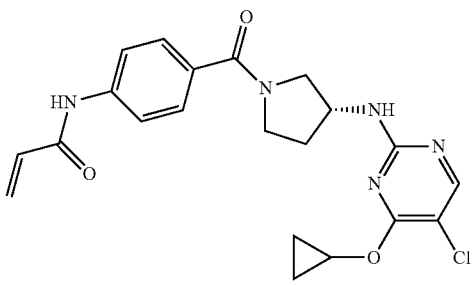 [SMILES: C=CC(=O)Nc1ccc(C(=O)N2CC[C@@H](Nc3ncc(Cl)c(OC4CC4)n3)C2)cc1]

The title compound was prepared in 23% yield from (5-Chloro-4-cyclopropoxy-pyrimidin-2-yl)-pyrrolidin-3-yl-amine according to the procedure for the preparation of (R)—N-(4-(3-((4-cyclopropoxy-5-fluoropyrimidin-2-yl)amino)pyrrolidine-1-carbonyl)phenyl)propionamide; $^1$H NMR (400 MHz, DMSO-d$_6$): δ 0.68-0.80 (m, 4H), 1.91-2.17 (m, 1H), 2.19-2.21 (m, 1H), 3.38-3.48 (m, 1H), 3.52-3.58 (m, 1H), 3.64-3.68 (m, 1H), 3.77-3.81 (m, 1H), 4.18-4.35 (m, 1H), 4.37-4.41 (m, 1H), 5.77-5.80 (m, 1H), 6.26-6.30 (m, 1H), 6.41-6.48 (m, 1H), 7.49-7.54 (m, 2H), 7.69-7.73 (m, 3H), 8.07-8.15 (m, 1H), 10.29 (s, 1H). MS Calcd.: 427; Found, 428 ([M+H]+).

Example 22: Synthesis of (R)—N-(4-(3-((4-cyclopropoxy-5-methylpyrimidin-2-yl)amino)pyrrolidine-1-carbonyl)phenyl)acrylamide

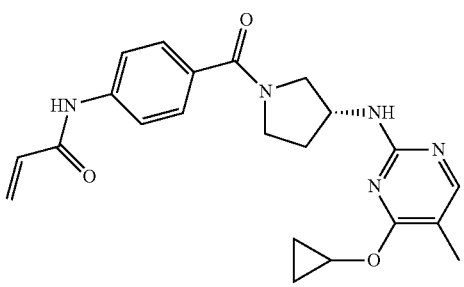 [SMILES: C=CC(=O)Nc1ccc(C(=O)N2CC[C@@H](Nc3ncc(C)c(OC4CC4)n3)C2)cc1]

The title compound was prepared in 21% yield from (R)-4-cyclopropoxy-5-methyl-N-(pyrrolidin-3-yl)pyrimidin-2-amine according to the procedure for the preparation of (R)—N-(4-(3-((4-cyclopropoxy-5-fluoropyrimidin-2-yl)amino)pyrrolidine-1-carbonyl)phenyl)propionamide. $^1$H NMR (400 MHz, DMSO-d$_6$): δ 0.52-0.76 (m, 4H), 1.81-1.91 (m, 3H), 1.97-2.15 (m, 2H), 3.36-3.64 (m, 4H), 3.86-

4.19 (m, 2H), 5.77-5.80 (m, 1H), 6.26-6.30 (m, 1H), 6.41-6.48 (m, 1H), 7.18 (m, 1H), 7.48-7.54 (m, 2H), 7.68-7.89 (m, 3H), 10.29 (s, 1H). Calcd.: 407; Found, 408 ([M+H]$^+$).

Example 23: Synthesis of (R)—N-(4-(3-((4-cyclopropoxy-5-fluoropyrimidin-2-yl)amino)pyrrolidine-1-carbonyl)phenyl)acrylamide

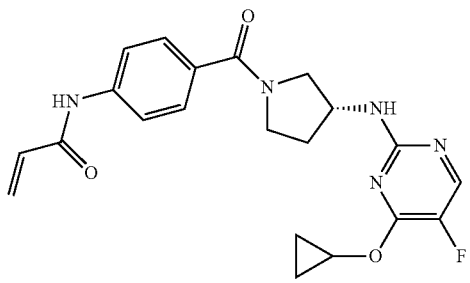 [SMILES: C=CC(=O)Nc1ccc(C(=O)N2CC[C@@H](Nc3ncc(F)c(OC4CC4)n3)C2)cc1]

The title compound was prepared in 20.6% yield from (R)-4-cyclopropoxy-5-fluoro-N-(pyrrolidin-3-yl)pyrimidin-2-amine according to the procedure for the preparation of (R)—N-(4-(3-((4-cyclopropoxy-5-fluoropyrimidin-2-yl)amino)pyrrolidine-1-carbonyl)phenyl)propionamide. $^1$H NMR (400 MHz, DMSO-d$_6$): δ 0.62-0.79 (m, 4H), 1.99-2.18 (m, 2H), 3.43-3.86 (m, 4H), 4.19-4.38 (m, 2H), 5.78-5.80 (m, 1H), 6.26-6.31 (m, 1H), 6.42-6.48 (m, 1H), 7.45-7.54 (m, 3H), 7.69-7.74 (m, 2H), 8.06-8.14 (m, 1H), 10.32 (s, 1H). Calcd.: 411; Found, 412 ([M+H]$^+$).

Example 24: Synthesis of (R)—N-(4-(3-((5-chloro-4-(2,2,2-trifluoroethoxy)pyrimidin-2-yl)amino)pyrrolidine-1-carbonyl)phenyl)acrylamide

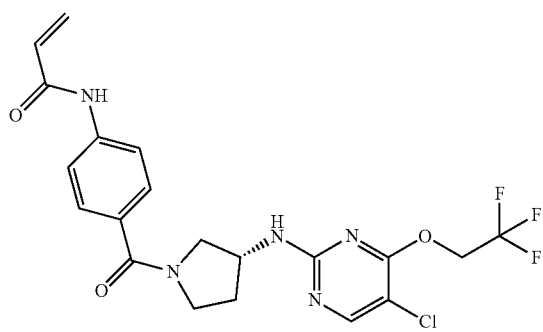 [SMILES: C=CC(=O)Nc1ccc(C(=O)N2CC[C@@H](Nc3ncc(Cl)c(OCC(F)(F)F)n3)C2)cc1]

The title compound was prepared in 21% yield from [5-chloro-4-(2,2,2-trifluoro-ethoxy)-pyrimidin-2-yl]-pyrrolidin-3-yl-amine according to the procedure for the preparation of (R)—N-(4-(3-((5-chloro-4-(2,2,2-trifluoroethoxy)pyrimidin-2-yl)amino)pyrrolidine-1-carbonyl)phenyl) propionamide. $^1$H NMR (400 MHz, DMSO-d$_6$): δ 1.88-2.02 (m, 1H), 2.15-2.18 (m, 1H), 3.39-3.47 (m, 1H), 3.51-3.57 (m, 1H), 3.62-3.71 (m, 1H), 3.75-3.81 (m, 1H), 4.30-4.47 (m, 1H), 5.01-5.13 (m, 2H), 5.78 (d, J=10.0 Hz, 1H), 6.27-6.32 (m, 1H), 6.43-6.50 (m, 1H), 7.50-7.56 (m, 2H), 7.71-7.75 (m, 2H), 7.85-7.97 (m, 1H), 8.22-8.29 (m, 1H), 10.33 (s, 1H). MS Calcd.: 469; Found, 470 ([M+H]$^+$).

Example 25: Synthesis of (R)—N-(4-(3-((5-chloro-4-methoxypyrimidin-2-yl)amino)pyrrolidine-1-carbonyl)phenyl)-N-methylacrylamide

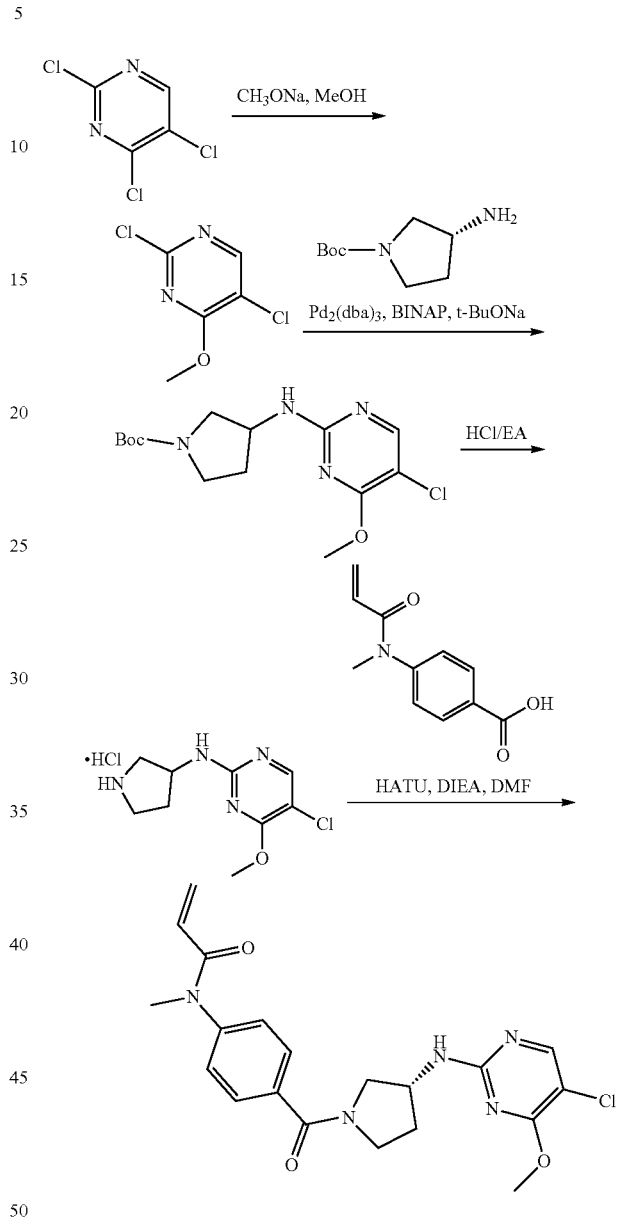

Step 1:
To a solution of 2,4,5-trichloropyrimidine (7.0 g, 38.2 mmol) in MeOH (100 mL) was added sodium methoxide (4.1 g, 76.5 mmol) and the mixture was stirred at RT for 12 h. The reaction mixture was evaporated to dryness and the residue purified by silica gel chromatography (Petroleum Ether/Ethyl Acetate=20/1) to give 2,5-dichloro-4-methoxypyrimidine (5.1 g, 75%). MS Calcd.: 178, MS Found: 179 ([M+H]$^+$).
Step 2:
To a solution of 2,5-dichloro-4-methoxypyrimidine (2.6 g, 14.5 mmol) in toluene (60 mL) was added (R)-tert-butyl 3-aminopyrrolidine-1-carboxylate (3.0 g, 16.0 mmol), t-BuONa (2.1 g, 21.7 mmol), Pd$_2$(dba)$_3$ (1.7 g, 2.9 mmol) and BINAP (3.6 g, 5.8 mmol) at room temperature under N$_2$. The mixture was stirred at 100° C. for 12 h and then concentrated in vacuo. The residue was then purified by silica gel chromatography (Petroleum Ether/Ethyl Acetate=1/1) to afford (R)-tert-butyl 3-((5-chloro-4-methoxypyrimidin-2-yl)amino)pyrrolidine-1-carboxylate (2.4 g, 51%). MS Calcd.: 328, MS Found: 329 ([M+H]⁺).

Step 3:
A solution of (R)-tert-butyl 3-((5-chloro-4-methoxypyrimidin-2-yl)amino)pyrrolidine-1-carboxylate (2.4 g, 7.3 mmol) in HCl/Ethyl Acetate (10 mL, 2.0 M) was stirred at RT for 3 h. The reaction mixture was then filtered to give (R)-5-chloro-4-methoxy-N-(pyrrolidin-3-yl)pyrimidin-2-amine hydrochloride (1.7 g, 88%). MS Calcd.: 228, MS Found: 229 ([M+H]⁺).

Step 4:
A mixture of (R)-5-chloro-4-methoxy-N-(pyrrolidin-3-yl)pyrimidin-2-amine hydrochloride (129 mg, 0.49 mmol), 4-(N-methylacrylamido)benzoic acid (100 mg, 0.49 mmol), HATU (205 mg, 0.54 mmol) and DIEA (189 mg, 1.47 mmol) in DMF (10 mL) was stirred at 25° C. for overnight. The mixture was diluted with H₂O (30 mL) and extracted with DCM (30 mL*2). The combined organic phases were concentrated in vacuo. The residue was then purified by prep-HPLC to afford (R)—N-(4-(3-((5-chloro-4-methoxypyrimidin-2-yl)amino)pyrrolidine-1-carbonyl)phenyl)-N-methylacrylamide (58 mg, 29%). $^1$H NMR (400 MHz, DMSO-d₆): δ 1.80-2.05 (m, 1H), 2.06-2.18 (m, 1H), 3.26 (s, 1.45H), 3.27 (s, 1.55H), 3.35-3.90 (m, 7H), 4.27-4.46 (m, 1H), 5.58-5.62 (m, 1H), 6.11-6.20 (m, 2H), 7.31-7.36 (m, 2H), 7.56-7.69 (m, 3H). 8.08 (m, 0.55H), 8.14 (m, 0.45H). MS Calcd.: 415 Found: 416 ([M+H]⁺).

Example 26: Synthesis of (R)—N-(4-(3-((5-chloro-4-methoxypyrimidin-2-yl)amino)pyrrolidine-1-carbonyl)-2-methylphenyl)acrylamide

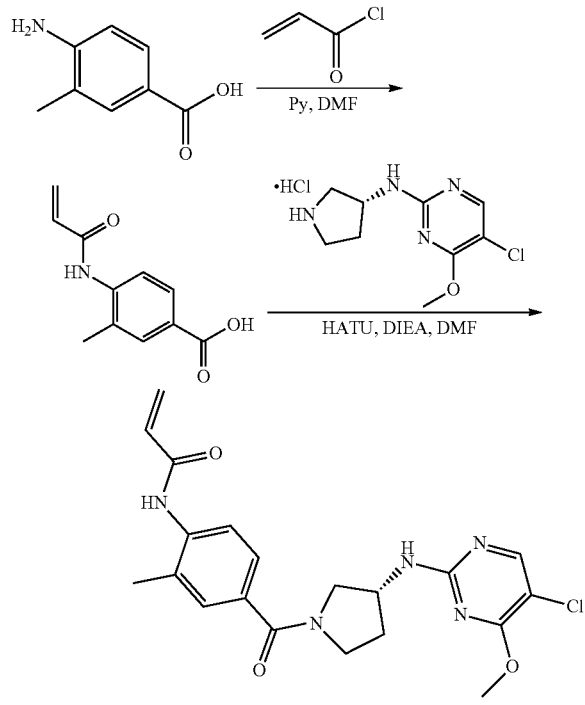

Step 1:
The title compound was prepared in 29% yield from 4-amino-3-methylbenzoic acid using general procedure of 4-(N-methylacrylamido)benzoic acid. MS Calcd.: 205, MS Found: 206 ([M+H]⁺).

Step 2:
The title compound was prepared in 18% yield from 4-acrylamido-3-methylbenzoic acid using general procedure of (R)—N-(4-(3-((5-chloro-4-methoxypyrimidin-2-yl)amino)pyrrolidine-1-carbonyl)phenyl)-N-methylacrylamide. $^1$H NMR (400 MHz, DMSO-d₆): δ 1.88-2.02 (m, 1H), 2.09-2.20 (m, 1H), 2.23 (s, 1.65H), 2.25 (s, 1.35H), 3.35-3.94 (m, 7H), 4.24-4.44 (m, 1H), 5.77 (d, J=10.4 Hz, 1H), 6.26 (d, J=17.2 Hz, 1H), 6.53-6.60 (m, 1H), 7.31-7.40 (m, 2H), 7.59-7.67 (m, 2H), 8.07 (s, 0.56H), 8.14 (s, 0.44H), 9.51 (s, 1H). MS Calcd.: 415 MS Found: 416 ([M+H]⁺).

Example 27: Synthesis of (R)-1-(5-(3-((5-chloro-4-methoxypyrimidin-2-yl)amino)pyrrolidine-1-carbonyl)indolin-1-yl)prop-2-en-1-one

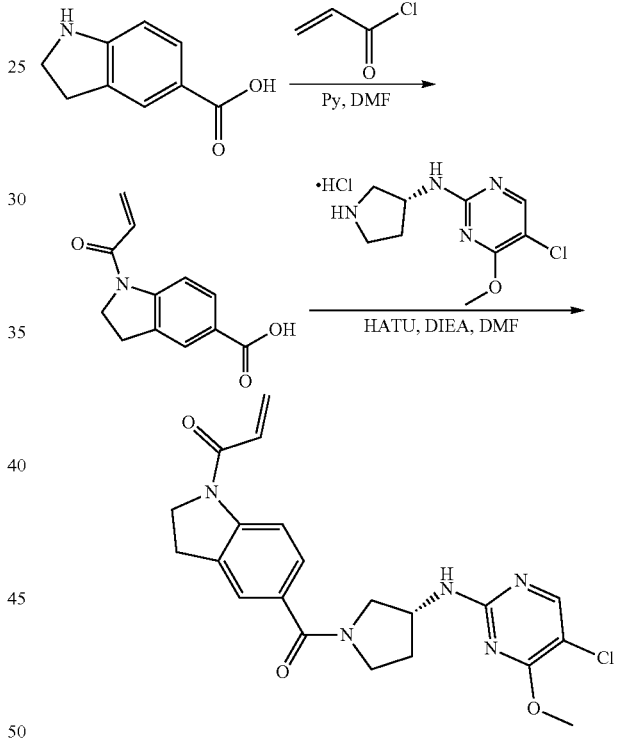

Step 1:
The title compound was prepared in 42% yield from indoline-5-carboxylic acid using general procedure of 4-(N-methylacrylamido)benzoic acid. MS Calcd.: 217, MS Found: 218 ([M+H]⁺).

Step 2:
The title compound was prepared in 10% yield from 1-acryloylindoline-5-carboxylic acid using general procedure of (R)—N-(4-(3-((5-chloro-4-methoxypyrimidin-2-yl)amino)pyrrolidine-1-carbonyl)phenyl)-N-methylacrylamide. $^1$H NMR (400 MHz, CD₃OD): δ 2.00-2.10 (m, 1H), 2.22-2.33 (m, 1H), 3.22-3.27 (m, 2H), 3.31-4.00 (m, 7H), 4.25-4.55 (m, 3H), 5.85-5.88 (m, 1H), 6.39 (s, 0.43H), 6.43 (s, 0.57H), 6.72-6.79 (m, 1H), 7.34-7.46 (m, 2H), 7.94 (s, 0.52H), 8.00 (s, 0.48H), 8.23 (s, 1H). MS Calcd.: 427 Found: 428 ([M+H]⁺).

Example 28: Synthesis of (R)—N-(4-(3-((5-chloro-pyrimidin-2-yl)amino)pyrrolidine-1-carbonyl)phenyl)-N-methylacrylamide

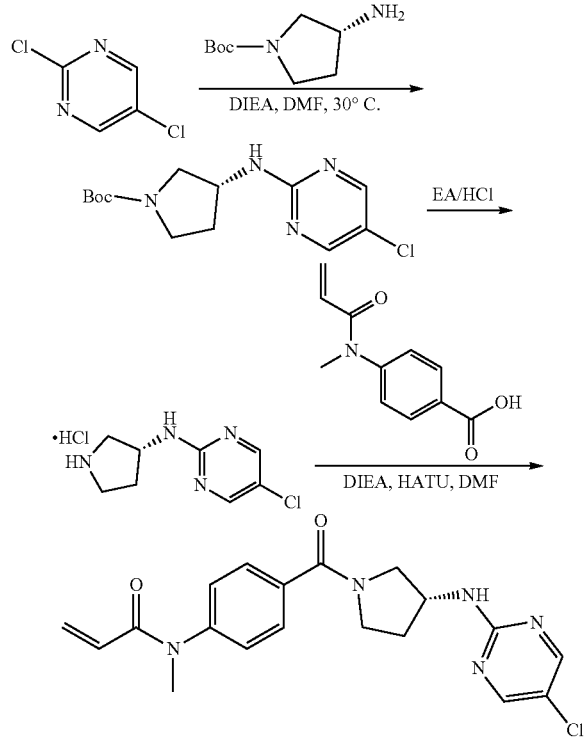

Step 1:

A mixture of 2,5-dichloropyrimidine (6.1 g, 40.9 mmol), (R)-tert-butyl 3-aminopyrrolidine-1-carboxylate (9.9 g, 53.2 mmol) and DIEA (7.9 g, 61.2 mmol) in DMF (30 mL) was stirred at 30° C. for overnight. The reaction was then quenched with water (100 mL) and extracted with DCM (50 mL*3). The combined organic layers were washed with water (100 mL*2) and brine (100 mL), dried over Na₂SO₄, filtered and then concentrated in vacuo. The residue was washed with Petroleum Ether to afford (R)-tert-butyl 3-((5-chloropyrimidin-2-yl)amino)pyrrolidine-1-carboxylate (9.9 g, 81%). MS Calcd.: 298, MS Found: 299 ([M+H]⁺).

Step 2:

A solution of (R)-tert-butyl 3-((5-chloropyrimidin-2-yl)amino)pyrrolidine-1-carboxylate (9.9 g, 33.2 mmol) in HCl/Ethyl Acetate (50 mL, 2.0 M) was stirred at RT for 3 h. The reaction mixture was filtered to afford (R)-5-chloro-N-(pyrrolidin-3-yl)pyrimidin-2-amine hydrochloride (6.9 g, 89%). MS Calcd.: 198, MS Found: 199 ([M+H]+)

Step 3:

The title compound was prepared in 48% yield from 4-(N-methylacrylamido)benzoic acid using general procedure of (R)—N-(4-(3-((5-chloro-4-methoxypyrimidin-2-yl)amino)pyrrolidine-1-carbonyl)phenyl)-N-methylacrylamide. ¹H NMR (400 MHz, DMSO-d₆): δ 1.87-2.03 (m, 1H), 110-2.20 (m, 1H), 3.26-3.27 (m, 3H), 3.33-3.81 (m, 4H), 4.25-4.44 (m, 1H), 5.58-5.61 (m, 1H), 6.09-6.19 (m, 2H), 7.31-7.36 (m, 2H), 7.56-7.61 (m, 2H), 7.81-7.84 (m, 1H), 8.32 (s, 1H), 8.38 (s, 1H). MS Calcd.: 385 Found: 386 ([M+H]⁺).

Example 29: Synthesis of (R)—N-(4-(3-((5-chloro-pyrimidin-2-yl)amino)pyrrolidine-1-carbonyl)-2-methylphenyl)acrylamide

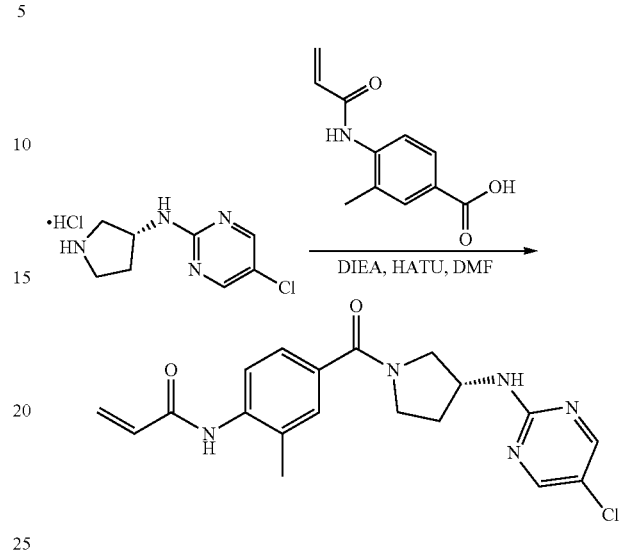

The title compound was prepared in 43% yield from 4-acrylamido-3-methylbenzoic acid using general procedure of (R)—N-(4-(3-((5-chloro-4-methoxypyrimidin-2-yl)amino)pyrrolidine-1-carbonyl)phenyl)-N-methylacrylamide. ¹H NMR (400 MHz, DMSO-d₆): δ 1.86-2.01 (m, 1H), 2.10-2.19 (m, 1H), 2.23 (s, 1.65H), 2.25 (s, 1.35H), 3.28-3.78 (m, 4H), 4.22-4.42 (m, 1H), 5.77 (d, J=10.0 Hz, 1H), 6.26 (d, J=17.2 Hz, 1H), 6.53-6.60 (m, 1H), 7.30-7.40 (m, 2H), 7.59-7.64 (m, 1H), 7.79-7.82 (m, 1H), 8.32 (s, 1H), 8.38 (s, 1H), 9.51 (s, 1H). MS Calcd.: 385 MS Found: 386 ([M+H]⁺).

Example 30: Synthesis of (R)-1-(5-(3-((5-chloropyrimidin-2-yl)amino)pyrrolidine-1-carbonyl)indolin-1-yl)prop-2-en-1-one

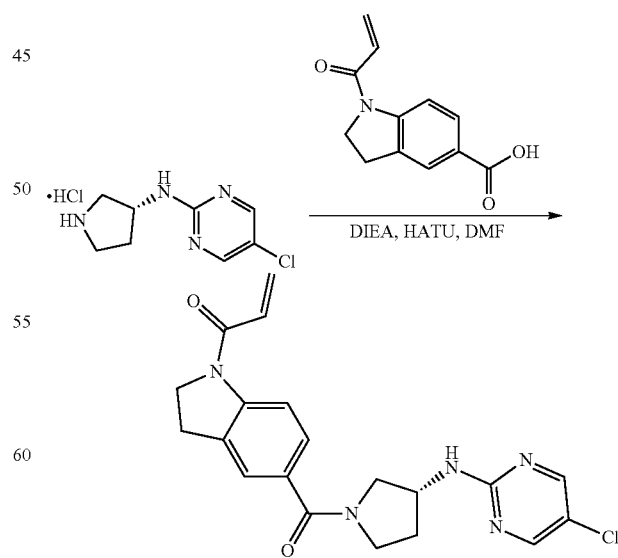

The title compound was prepared in 5% yield from (R)-5-chloro-N-(pyrrolidin-3-yl)pyrimidin-2-amine hydrochloride using general procedure of (R)-1-(5-(3-((5-chloro-pyrimidin-2-yl)amino)pyrrolidine-1-carbonyl)indolin-1-yl)prop-2-en-1-one. $^1$H NMR (400 MHz, CD$_3$OD): δ 2.00-2.10 (m, 1H), 2.22-2.33 (m, 1H), 3.24-3.31 (m, 2H), 3.44-3.94 (m, 4H), 4.25-4.55 (m, 3H), 5.85-5.88 (m, 1H), 6.39 (s, 0.44H), 6.43 (s, 0.57H), 6.73-6.79 (m, 1H), 7.35-7.45 (m, 2H), 8.21-8.23 (m, 3H). MS Calcd.: 397 Found: 398 ([M+H]+).

Example 31: Synthesis of (R)—N-(4-(3-((5-chloro-pyrimidin-2-yl)amino)pyrrolidine-1-carbonyl)-2-methoxyphenyl)acrylamide

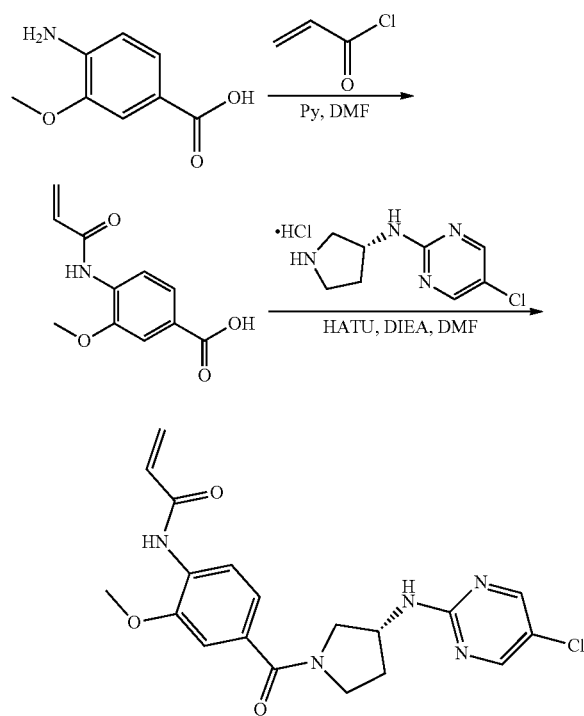

Step 1:

The title compound was prepared in 30% yield from 4-amino-3-methoxybenzoic acid using general procedure of 4-(N-methoxyacrylamido)benzoic acid. MS Calcd.: 221, MS Found: 222 ([M+H]$^+$).

Step 2:

The title compound was prepared in 15% yield from 4-acrylamido-3-methoxybenzoic acid using general procedure of (R)—N-(4-(3-((5-chloropyrimidin-2-yl)amino)pyrrolidine-1-carbonyl)-2-methoxyphenyl)acrylamide. $^1$H NMR (400 MHz, DMSO-d$_6$): δ 1.88-2.08 (m, 1H), 2.14-2.16 (m, 1H), 3.35-3.89 (m, 7H), 4.24-4.45 (m, 1H), 5.74 (d, J=10.4 Hz, 1H), 6.27 (d, J=16.8 Hz, 1H), 6.69-6.76 (m, 1H), 7.07-7.19 (m, 2H), 7.79-7.83 (m, 1H), 8.11 (s, 0.56H), 8.14 (s, 0.44H), 8.32-8.38 (m, 2H), 9.47 (s, 1H). MS Calcd.: 401 MS Found: 402 ([M+H]$^+$).

Example 32: Synthesis of (R)—N-(4-(3-((5-chloro-pyrimidin-2-yl)amino)pyrrolidine-1-carbonyl)-3-methylphenyl)acrylamide

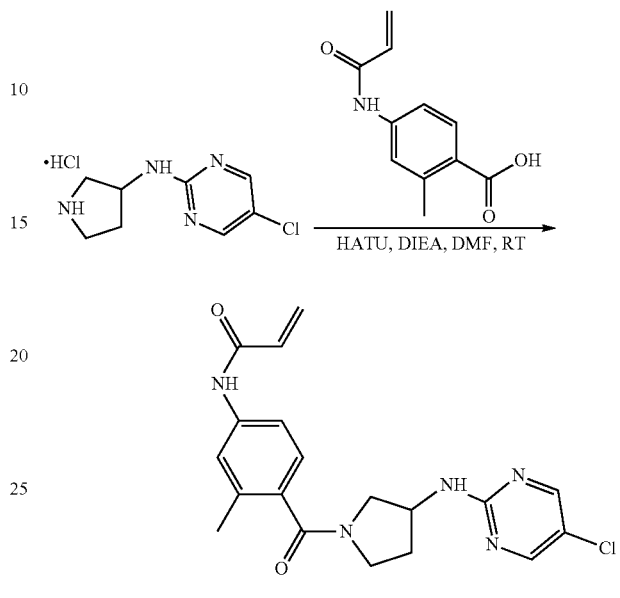

The title compound was prepared in 35% yield from (R)-5-chloro-N-(pyrrolidin-3-yl)pyrimidin-2-amine hydrochloride using general procedure of (R)—N-(4-(3-((5-chloropyrimidin-2-yl)amino)pyrrolidine-1-carbonyl)-3-methylphenyl)acrylamide. $^1$H NMR (400 MHz, DMSO-d$_6$): δ 1.88-1.98 (m, 1H), 2.07-2.22 (m, 4H), 3.07-3.16 (m, 1H), 3.42-3.51 (m, 2H), 3.68-3.77 (m, 1H), 4.23-4.37 (m, 1H), 5.74-5.77 (m, 1H), 6.23-6.28 (m, 1H), 6.38-6.43 (m, 1H), 7.12-7.20 (m, 1H), 7.49-7.54 (m, 1H), 7.76-7.83 (m, 1H), 8.31 (s, 1H), 8.38 (s, 1H), 10.14-10.16 (m, 1H). MS Calcd.: 385 Found: 386 ([M+H]$^+$).

Example 33: Synthesis of (R)—N-(4-(3-((5-chloro-pyrimidin-2-yl)amino)pyrrolidine-1-carbonyl)-2,6-dimethylphenyl)acrylamide

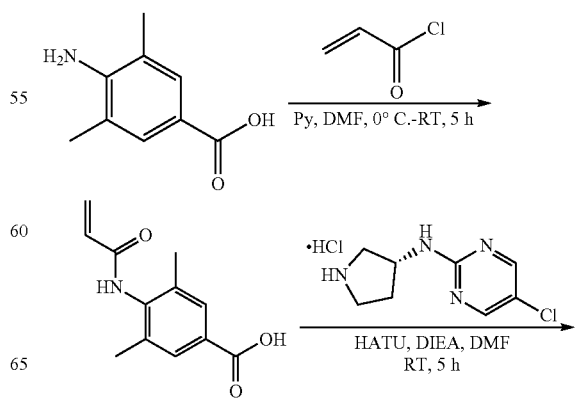

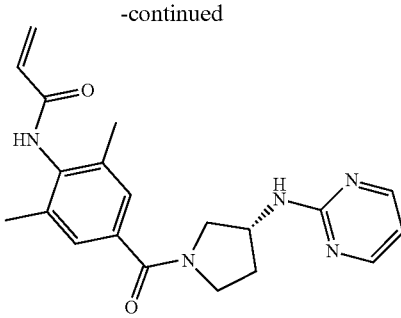

Step 1:
The title compound was prepared in 31% yield from 4-amino-3,5-dimethylbenzoic acid using general procedure of 4-(N-methoxyacrylamido)benzoic acid. MS Calcd.: 219, MS Found: 220 ([M+H]+)

Step 2:
The title compound was prepared in 25% yield from 4-amino-3,5-dimethylbenzoic acid using general procedure of N-{4-[3-(5-Chloro-pyrimidin-2-ylamino)-pyrrolidine-1-carbonyl]-2,6-dimethyl-phenyl}-acrylamide. ¹H NMR (400 MHz, DMSO-d₆): δ 1.87-1.99 (m, 1H), 2.13-2.19 (m, 7H), 3.41-3.52 (m, 2H), 3.67-3.78 (m, 2H), 4.22-4.40 (m, 1H), 5.75 (d, J=10.4 Hz, 1H), 6.22 (d, J=17.2 Hz, 1H), 6.48-6.51 (m, 1H), 7.19 (s, 1H), 7.24 (s, 1H), 7.79-7.82 (m, 1H), 8.33 (s, 1H), 8.38 (s, 1H), 9.54 (d, J=3.6 Hz, 1H). MS Calcd.: 399 MS Found: 400 ([M+H]+).

Example 34: Synthesis of (R)-1-(7-(3-((5-chloropyrimidin-2-yl)amino)pyrrolidine-1-carbonyl)-2H-benzo[b][1,4]oxazin-4(3H)-yl)prop-2-en-1-one

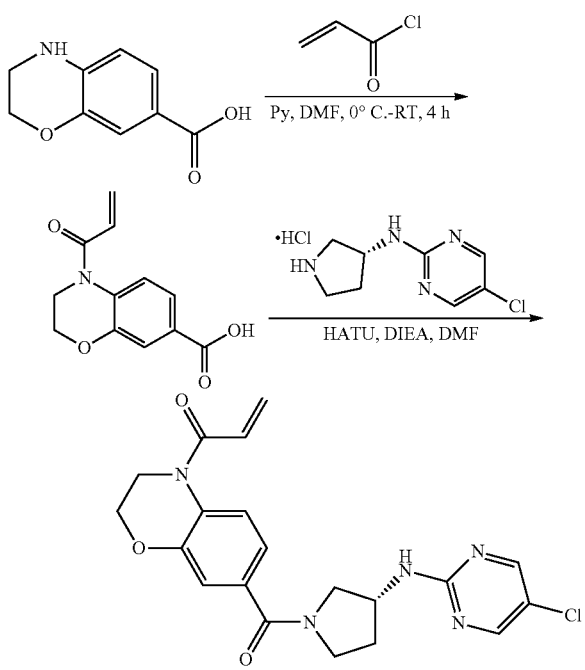

Step 1:
The title compound was prepared in 44% yield from 3,4-dihydro-2H-benzo[b][1,4]oxazine-7-carboxylic acid using general procedure of 4-(N-methoxyacrylamido)benzoic acid MS Calcd.: 233, MS Found: 234 ([M+H]+)

Step 2:
The title compound was prepared in 8% yield from 4-acryloyl-3,4-dihydro-2H-benzo[b][1,4]oxazine-7-carboxylic acid using general procedure of N-{4-[3-(5-chloro-pyrimidin-2-ylamino)-pyrrolidine-1-carbonyl]-2,6-dimethyl-phenyl}-acrylamide. ¹H NMR (400 MHz, DMSO-d₆): δ 1.86-2.13 (m, 2H), 3.34 (m, 2H), 3.64 (m, 2H), 3.95 (m, 2H), 4.31-4.40 (m, 3H), 5.82-5.85 (m, 1H), 6.25-6.30 (m, 1H), 6.782 (m, 1H), 7.02-7.07 (m, 2H), 7.49 (m, 1H), 7.81 (m, 1H), 8.32-8.38 (m, 2H). MS Calcd.: 413 MS Found: 414 ([M+H]+).

Example 35: Synthesis of (R)—N-(4-(3-((4-(1-methyl-1H-pyrazol-5-yl)pyrimidin-2-yl)amino)piperidine-1-carbonyl)phenyl)acrylamide

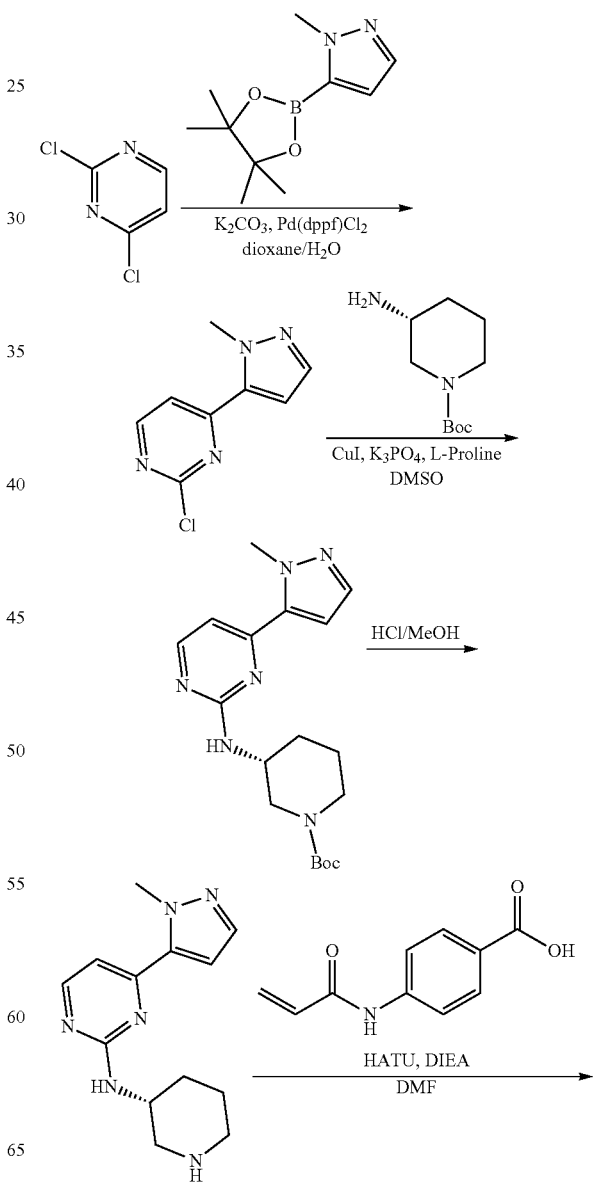

-continued

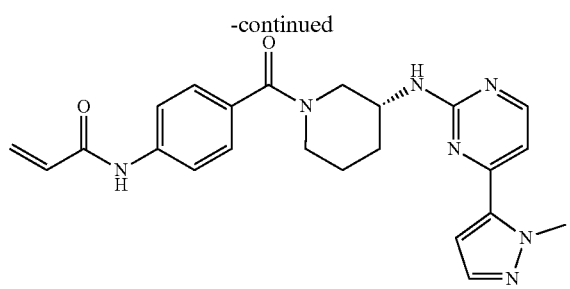

Step 1:

A mixture of 2,4-dichloropyrimidine (1.04 g, 7 mmol), 1-methyl-5-(4,4,5,5-tetramethyl-1,3,2-dioxaborolan-2-yl)-1H-pyrazole (1.46 g, 7 mmol), $K_2CO_3$ (1.93 g, 14 mmol) and Pd(dppf)Cl$_2$ (512 mg, 0.7 mmol) in Dioxane/$H_2O$ (20 mL/5 mL) was stirred at 120° C. for 2 hours. The mixture was concentrated in-vacuo and the residue was purified by flash chromatography on silica gel (Petroleum Ether/Ethyl Acetate=2/1) to afford 2-chloro-4-(1-methyl-1H-pyrazol-5-yl)pyrimidine (1.3 g, 96%). $^1$H NMR (400 MHz, CDCl$_3$): δ 4.33 (s, 3H), 6.82 (d, J=2.0 Hz, 1H), 7.48 (d, J=5.2 Hz, 1H), 7.55 (d, J=2.0 Hz, 1H), 8.63 (d, J=5.2 Hz, 1H).

Step 2:

A mixture of 2-chloro-4-(1-methyl-1H-pyrazol-5-yl)pyrimidine (600 mg, 3.1 mmol), (R)-tert-butyl 3-aminopiperidine-1-carboxylate (619 mg, 3.1 mmol), CuI (285 mg, 1.5 mmol), $K_3PO_4$ (1.3 g, 6.2 mmol) and L-Proline (356 mg, 3.1 mmol) in DMSO (10 mL) was stirred at 35° C. for overnight. To the mixture was then added $H_2O$ (50 mL) and extracted with EtOAc (50 mL*2). The combined organic layers were washed with $NH_3.H_2O$ (50 mL*2, 1M) and concentrated in-vacuo. The residue was purified by column ACN/$H_2O$ (5-95%) to afford (R)-tert-butyl 3-((4-(1-methyl-1H-pyrazol-5-yl)pyrimidin-2-yl)amino)piperidine-1-carboxylate (180 mg, 16%). MS Calcd.: 358 Found: 359 ([M+H]+).

Step 3:

To a solution of (R)-tert-butyl 3-((4-(1-methyl-H-pyrazol-5-yl)pyrimidin-2-yl)amino)piperidine-1-carboxylate (180 mg, 0.5 mmol) in MeOH (1 mL) was added HCl/MeOH (1 mL, 1M) and then stirred at room temperature for 2 hours. The reaction mixture was concentrated to afford (R)-4-(1-methyl-1H-pyrazol-5-yl)-N-(piperidin-3-yl)pyrimidin-2-amine (130 mg, 100%). MS Calcd.: 258 Found: 259 ([M+H]$^+$).

Step 4:

A mixture of (R)-4-(1-methyl-1H-pyrazol-5-yl)-N-(piperidin-3-yl)pyrimidin-2-amine (130 mg, 0.5 mmol), 4-acrylamidobenzoic acid (105 mg, 0.55 mmol), HATU (228 mg, 0.6 mmol) and DIPEA (258 mg, 2 mmol) in DMF (2 mL) was stirred at 25° C. for overnight. The reaction mixture was then diluted with $H_2O$ (30 mL), extracted with Ethyl Acetate (30 mL*2), and the combined organic layers were concentrated in vacuo. The residue was purified by prep-TLC (DCM/MeOH=20/1) to afford (R)—N-(4-(3-((4-(1-methyl-H-pyrazol-5-yl)pyrimidin-2-yl)amino)piperidine-1-carbonyl)phenyl)acrylamide (26 mg, 12%). $^1$H NMR (400 MHz, CD$_3$OD): δ 1.67-2.12 (m, 4H), 3.10-3.33 (m, 1H), 3.47-4.36 (m, 7H), 5.76-5.80 (m, 1H), 6.37 (s, 2H), 6.59-6.86 (m, 2H), 6.95-7.79 (m, 5H), 8.21-8.33 (m, 1H). MS Calcd.: 431 Found: 432 ([M+H]$^+$).

Example 36: (R)—N-(4-(3-((4-morpholinopyrimidin-2-yl)amino)piperidine-1-carbonyl)phenyl)acrylamide

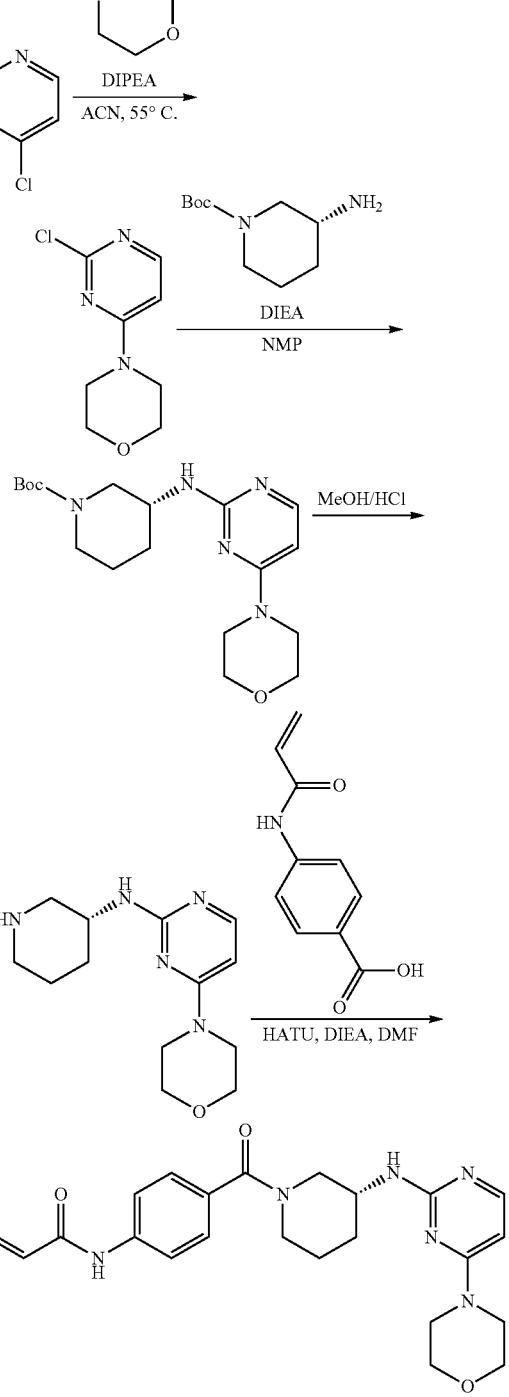

Step 1:

A mixture of 2,4-dichloropyrimidine (500 mg, 3.35 mmol), morpholine (292 mg, 3.35 mmol) and DIPEA (1.3 g, 10.05 mmol) in ACN (3 mL) was stirred at 55° C. for 2 hours. The mixture was then concentrated in-vacuo and purified by flash chromatography on silica gel (Petroleum Ether/Ethyl Acetate=2/1) to afford 4-(2-chloropyrimidin-4-yl)morpholine (660 mg, 98%) as a white solid.

¹H NMR (300 MHz, CDCl₃): δ 3.66 (br s, 4H), 3.77-3.80 (m, 4H), 6.38-6.41 (m, 1H), 8.07-8.10 (m, 1H).

Step 2 to 4

The title compound was prepared in 11% yield from (R)-tert-butyl 3-((4-morpholinopyrimidin-2-yl)amino)piperidine-1-carboxylate using general procedure of (R)—N-(4-(3-((4-(1-methyl-1H-pyrazol-5-yl)pyrimidin-2-yl)amino)piperidine-1-carbonyl)phenyl)acrylamide. ¹H NMR (400 MHz, DMSO-d₆): δ 1.47-1.94 (m, 4H), 2.50-3.04 (m, 1H), 3.45-3.83 (m, 11H), 4.28-4.42 (m, 1H), 5.78-5.80 (m, 1H), 6.06-6.09 (m, 1H), 6.26-6.30 (m, 1H), 6.41-6.48 (m, 1H), 7.24-7.40 (m, 2H), 7.59-7.80 (m, 4H), 10.30 (br s, 1H). MS Calcd.: 436 MS Found: 437 ([M+H]⁺).

Example 37: Synthesis of (R)—N-(4-(3-((4-methoxypyrimidin-2-yl)amino)piperidine-1-carbonyl)phenyl)acrylamide

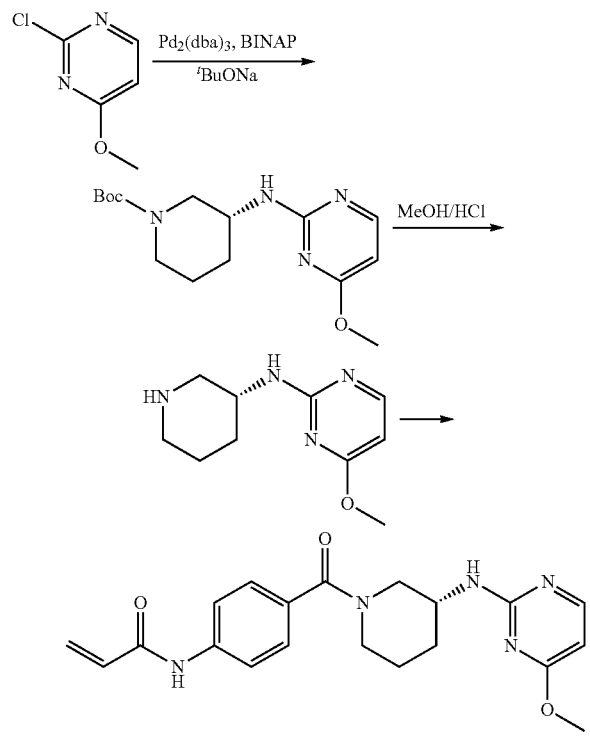

Step 1:

A mixture of 2-chloro-4-methoxypyrimidine (144 mg, 1 mmol), (R)-tert-butyl 3-aminopiperidine-1-carboxylate (200 mg, 1 mmol), tBuONa (144 mg g, 1.5 mmol), Pd₂(dba)₃ (183 mg, 0.2 mmol) and BINAP (249 mg, 0.4 mmol) in 4 mL of toluene was stirred at 50° C. for 3 hours. The mixture was diluted with 10 mL of water and extracted with Ethyl Acetate (10 mL*2). The combined organic layers were dried over Na₂SO₄, filtered and concentrated in vacuo. The residue was purified by flash chromatography on silica gel (Petroleum ether/Ethyl Acetate=2/1) to afford (R)-tert-butyl 3-((4-methoxypyrimidin-2-yl)amino)piperidine-1-carboxylate (1.3 g, 29%). [M+H]MS Calcd.: 381 Found: 382 ([M+H]⁺).

Step 2 to Step 3:

The title compound was prepared in 4% yield from (R)-4-methoxy-N-(piperidin-3-yl)pyrimidin-2-amine using general procedure of (R)—N-(4-(3-((4-(1-methyl-H-pyrazol-5-yl)pyrimidin-2-yl)amino)piperidine-1-carbonyl)phenyl)acrylamide. ¹H NMR (400 MHz, DMSO-d₆): δ 1.25-1.31 (m, 2H), 1.47-1.64 (m, 1H), 1.81-1.98 (m, 1H), 2.94-3.22 (m, 2H), 3.52-3.86 (m, 6H), 5.77-5.83 (m, 1H), 6.27-6.54 (m, 2H), 6.80-6.83 (m, 1H), 7.319-7.407 (m, 2H), 7.64-7.75 (m, 2H), 7.99-8.08 (m, 2H), 10.31-10.32 (m, 1H). MS Calcd.: 381 Found: 382 ([M+H]⁺).

Example 38: Synthesis of (R)—N-(4-(3-((5-chloropyrazin-2-yl)amino)piperidine-1-carbonyl)phenyl)acrylamide

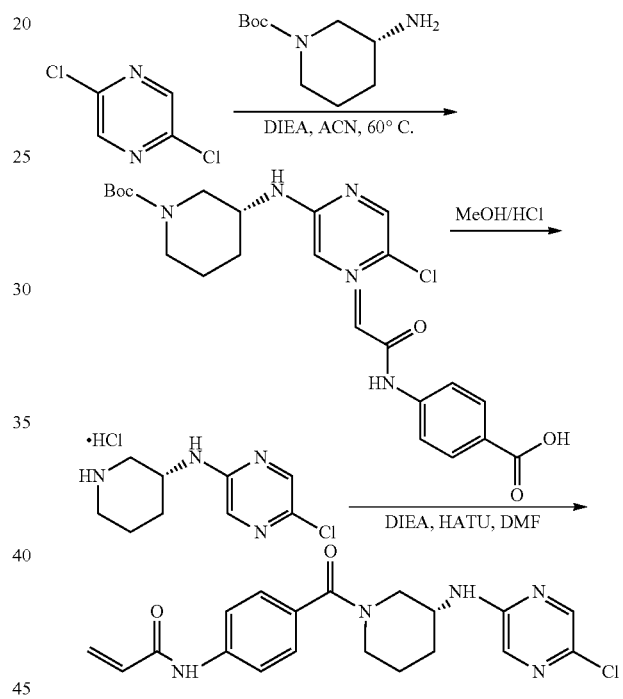

Step 1:

A mixture of 2,5-dichloropyrazine (367 mg, 2.5 mmol), (R)-tert-butyl 3-aminopiperidine-1-carboxylate (500 mg, 2.5 mmol) and DIEA (645 mg, 5 mmol) in ACN (5 mL) was stirred at 60° C. for overnight. After cooling to room temperature, the reaction mixture was concentrated and purified by silica gel chromatography (Petroleum Ether/Ethyl Acetate=1/1) to afford (R)-tert-butyl 3-((5-chloropyrazin-2-yl)amino)piperidine-1-carboxylate (530 mg, 68%). MS Calcd.: 312, MS Found: 313 ([M+H]⁺).

Step 2 to 3:

The title compound was prepared in 21% yield from (R)-5-chloro-N-(piperidin-3-yl)pyrazin-2-amine hydrochloride using general procedure of (R)—N-(4-(3-((4-(1-methyl-H-pyrazol-5-yl)pyrimidin-2-yl)amino)piperidine-1-carbonyl)phenyl)acrylamide. ¹H NMR (400 MHz, CDCl₃): δ 1.73-2.05 (m, 4H), 3.18-4.22 (m, 5H), 5.08-5.70 (m, 1H), 5.79 (d, J=10.0 Hz, 1H), 6.26-6.30 (m, 1H), 6.43-6.48 (m, 1H), 7.37-7.57 (m, 4H), 7.80 (s, 1H), 8.17-8.43 (m, 1H). MS Calcd.: 385 MS Found: 386 ([M+H]⁺).

Example 39: Synthesis of (R)—N-(4-(3-((4-(1-methyl-1H-pyrazol-4-yl)pyrimidin-2-yl)amino)piperidine-1-carbonyl)phenyl)acrylamide

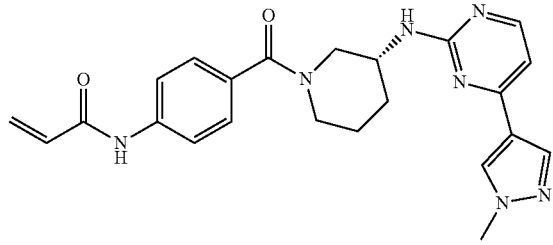 [SMILES: C=CC(=O)Nc1ccc(C(=O)N2CCC[C@@H](Nc3nccc(-c4cnn(C)c4)n3)C2)cc1]

The title compound was prepared in 21% yield from 4-(1-methyl-1H-pyrazol-4-yl)-N-(piperidin-3-yl)pyrimidin-2-amine using general procedure of (R)—N-(4-(3-((4-(1-methyl-H-pyrazol-5-yl)pyrimidin-2-yl)amino)piperidine-1-carbonyl)phenyl)acrylamide. 1H NMR (400 MHz, DMSO-$d_6$): δ1.47-1.67 (m, 2H), 1.78-1.88 (m, 1H), 1.96-2.03 (m, 1H), 2.78-3.16 (m, 2H), 3.67-4.15 (m, 6H), 5.74-5.82 (m, 1H), 6.22-6.49 (m, 2H), 6.79-6.87 (m, 1H), 7.07-8.32 (m, 8H), 10.13-10.46 (m, 1H). MS Calcd.: 431 MS Found: 432 ([M+H]$^+$).

Example 40: Synthesis of (R)—N-(4-(3-((4-(cyclopentyloxy)pyrimidin-2-yl)amino)piperidine-1-carbonyl)phenyl)acrylamide

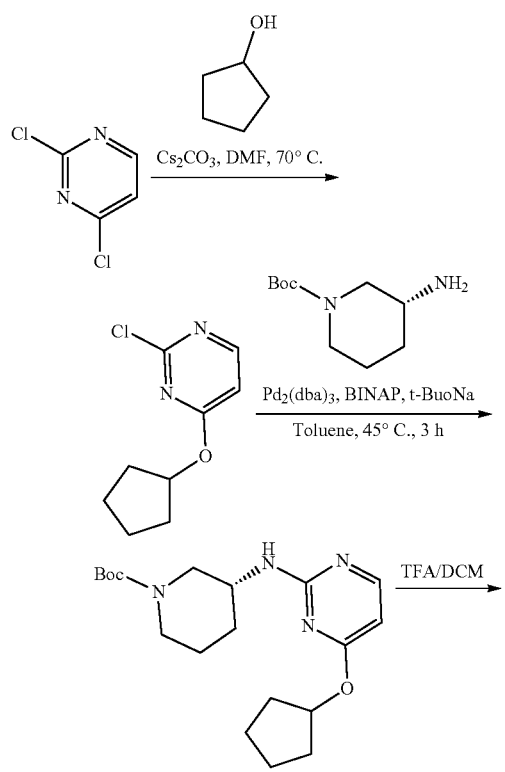

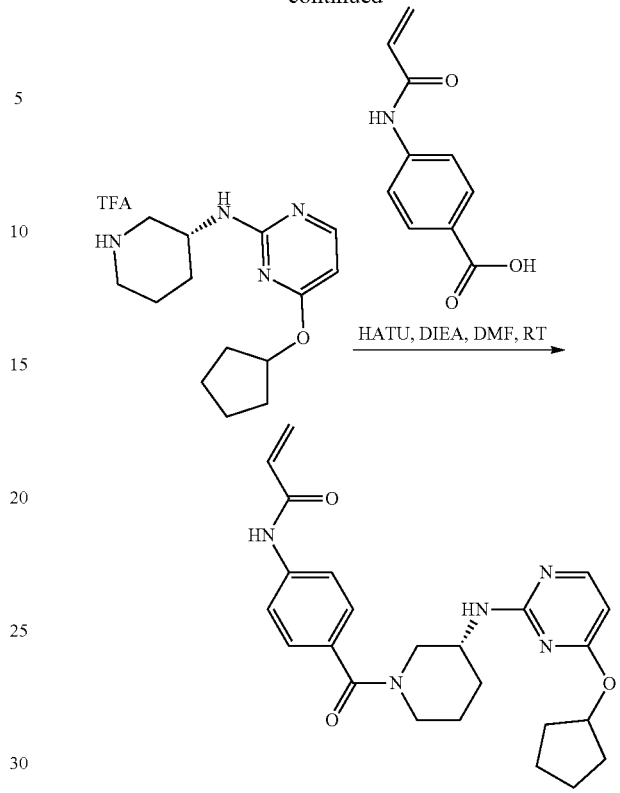

Step 1:
To a solution of 2,4-dichloropyrimidine (2.0 g, 13.40 mmol) in DMF (50 mL) was added cyclopentanol (1.5 mL, 16.10 mmol) and cesium carbonate (8.8 g, 26.84 mmol) at room temperature. The mixture was then heated to 80° C. for 1 h followed by stirring at 70° C. for 16 h. The reaction mixture was then cooled to RT, quenched with water (100 mL), and extracted with Ethyl Acetate (50 mL*3). The combined organic layers were washed with water (100 mL*2) and brine (100 mL), dried over Na$_2$SO$_4$, filtered and then concentrated in vacuo. The residue was purified by silica gel chromatography (Petroleum Ether/Ethyl Acetate=1/1) to give 2-chloro-4-(cyclopentyloxy)pyrimidine (1.2 g, 46%). MS Calcd.: 198, MS Found: 199 ([M+H]$^+$).

Step 2:
To a solution of 2-chloro-4-(cyclopentyloxy)pyrimidine (1.1 g, 5.55 mmol) in toluene (12 mL) was added (R)-tert-butyl 3-aminopiperidine-1-carboxylate (1.1 g, 5.55 mmol), t-BuONa (800 mg, 8.33 mmol), Pd$_2$(dba)$_3$ (638 mg, 1.11 mmol) and BINAP (1.38 g, 2.22 mmol) at room temperature. This mixture was stirred at 45° C. for 3 h. The reaction was filtered and concentrated in-vacuo. The residue was purified by silica gel chromatography (Petroleum Ether/Ethyl Acetate=1/1) to afford (R)-tert-butyl 3-((4-(cyclopentyloxy)pyrimidin-2-yl)amino)piperidine-1-carboxylate (275 mg, 14%). MS Calcd.: 362, MS Found: 363 ([M+H]$^+$).

Step 3:
A solution of (R)-tert-butyl 3-((4-(cyclopentyloxy)pyrimidin-2-yl)amino)piperidine-1-carboxylate (275 mg, 0.76 mmol) in DCM (15 mL) and TFA (5 mL) was stirred at rt for 2 h. The reaction mixture was concentrated to give the crude (R)-4-(cyclopentyloxy)-N-(piperidin-3-yl)pyrimidin-2-amine (286 mg, 100%). MS Calcd.: 262, MS Found: 263 ([M+H]$^+$).

Step 4:

To a solution of (R)-4-(cyclopentyloxy)-N-(piperidin-3-yl)pyrimidin-2-amine (280 mg, 0.74 mmol), 4-acrylamidobenzoic acid (156 mg, 0.82 mmol) and DIEA (0.36 mL, 2.23 mmol) in DMF (15 mL) was added HATU (340 mg, 0.89 mmol) at rt. The reaction mixture was stirred at rt for 12 h. The reaction was concentrated. The residue was purified by prep-HPLC to give (R)—N-(4-(3-((4-(cyclopentyloxy)pyrimidin-2-yl)amino)piperidine-1-carbonyl)phenyl)acrylamide (127 mg, 39%). $^1$H NMR (400 MHz, DMSO-d$_6$): δ 1.53-1.64 (m, 8H), 1.82-1.92 (m, 4H), 2.51-2.62 (m, 1H), 3.29-3.32 (m, 3H), 4.51-4.62 (m, 1H), 5.32-5.42 (m, 1H), 5.76-5.79 (m, 1H), 5.92 (br s, 1H), 6.25 (d, J=2.0 Hz, 1H), 6.43-6.47 (m, 1H), 7.02-7.08 (m, 1H), 7.33-7.34 (m, 1H), 7.61-7.64 (m, 2H), 7.93 (m, 1H), 10.25 (s, 1H). MS Calcd.: 435, MS Found: 436 ([M+H]$^+$).

Example 41: Synthesis of (R)—N-(4-(3-((4-(1H-pyrazol-4-yl)pyrimidin-2-yl)amino)piperidine-1-carbonyl)phenyl)propionamide

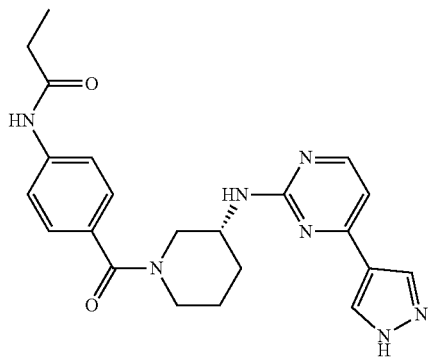 [SMILES: CCC(=O)Nc1ccc(C(=O)N2CCC[C@@H](Nc3nccc(-c4cn[nH]c4)n3)C2)cc1]

The title compound was prepared in 3% yield from (R)—N-(piperidin-3-yl)-4-(1H-pyrazol-4-yl)pyrimidin-2-amine using general procedure of (R)—N-(4-(3-((4-(1-methyl-1H-pyrazol-5-yl)pyrimidin-2-yl)amino)piperidine-1-carbonyl)phenyl)acrylamide. $^1$H NMR (400 MHz, CD$_3$OD): δ 1.5 (s, 3H), 1.71-1.84 (m, 2H), 1.98-2.11 (m, 2H), 2.36 (s, 2H), 3.05-3.20 (m, 1H), 3.72-3.90 (m, 4H), 6.71-6.85 (m, 1H), 7.25-7.41 (m, 4H), 7.99-8.19 (m, 3H). MS Calcd.: 419 MS Found: 420 ([M+H]$^+$).

Example 42: Synthesis of (R)—N-(4-(3-((4-morpholinopyrimidin-2-yl)amino)piperidine-1-carbonyl)phenyl)propionamide

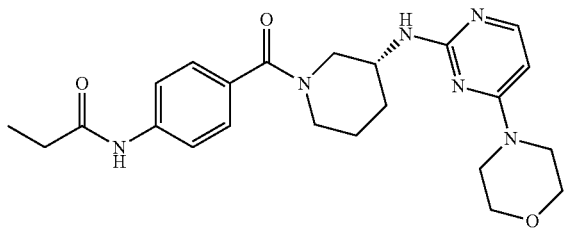 [SMILES: CCC(=O)Nc1ccc(C(=O)N2CCC[C@@H](Nc3nccc(N4CCOCC4)n3)C2)cc1]

The title compound was prepared in 4% yield from (R)-4-morpholino-N-(piperidin-3-yl)pyrimidin-2-amine using general procedure of (R)—N-(4-(3-((4-(1-methyl-1H-pyrazol-5-yl)pyrimidin-2-yl)amino)piperidine-1-carbonyl)phenyl)acrylamide. $^1$H NMR (400 MHz, CD$_3$OD): δ 1.18-1.22 (m, 3H), 1.28-1.32 (m, 1H), 1.59-2.07 (m, 4H), 2.37-2.43 (m, 2H), 3.35-3.47 (m, 3H), 3.59-3.65 (m, 7H), 3.94-4.50 (m, 2H), 6.10-6.14 (m, 1H), 7.15-7.16 (m, 1H), 7.41-7.49 (m, 2H), 7.67-7.75 (m, 2H). MS Calcd.: 438 MS Found: 439 ([M+H]$^+$).

Example 43: Synthesis of (R)—N-(4-(3-(4-(1H-pyrazol-4-yl)pyrimidin-2-yl)pyrrolidine-1-carbonyl)phenyl)propionamide

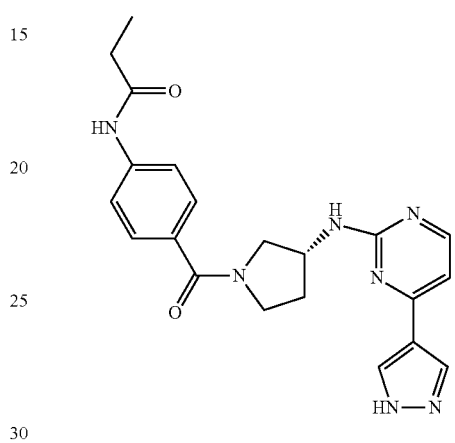

The title compound was prepared in 1% yield from (R)-4-(1H-pyrazol-4-yl)-2-(pyrrolidin-3-yl)pyrimidine using general procedure of (R)—N-(4-(3-((4-(1-methyl-1H-pyrazol-5-yl)pyrimidin-2-yl)amino)piperidine-1-carbonyl)phenyl)acrylamide. $^1$H NMR (400 MHz, DMSO-d$_6$): δ 1.07-1.11 (m, 3H), 1.88-2.37 (m, 4H), 3.43-3.82 (m, 4H), 4.34-4.51 (m, 1H), 6.87-6.94 (m, 1H), 7.33-7.67 (m, 5H), 8.16-8.25 (m, 3H), 10.03-10.06 (m, 1H), 13.17-13.20 (m, 1H). MS Calcd.: 405 MS Found: 406 ([M+H]$^+$).

Example 44: Synthesis of (R)—N-(4-(3-((4-(1H-pyrazol-4-yl)pyrimidin-2-yl)amino)pyrrolidine-1-carbonyl)phenyl)acrylamide

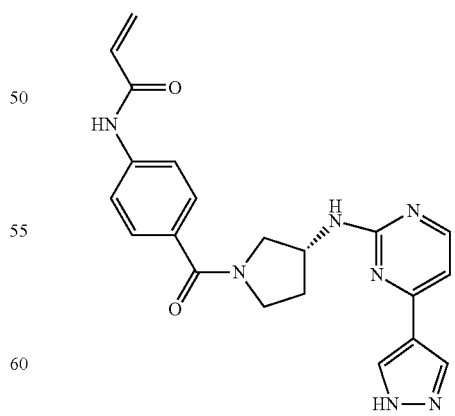

The title compound was prepared in 5% yield from (R)-4-(1H-pyrazol-4-yl)-N-(pyrrolidin-3-yl)pyrimidin-2-amine hydrochloride using general procedure of (R)—N-(4-(3-((4-(1-methyl-1H-pyrazol-5-yl)pyrimidin-2-yl)amino)piperidine-1-carbonyl)phenyl)acrylamide. $^1$H NMR (400 MHz, CD$_3$OD): δ 2.03-2.38 (m, 2H), 3.49-4.02 (m, 4H), 4.41-4.66 (m, 2H), 5.76-5.81 (m, 1H), 6.36-6.46 (m, 2H), 6.87-6.94 (m, 1H), 7.52-7.77 (m, 4H), 8.09-8.22 (m, 3H). MS Calcd.: 403 MS Found: 404 ([M+H]$^+$).

Example 45: Synthesis of N-{4-[3-(4-Cyclopentyloxy-pyrimidin-2-ylamino)-pyrrolidine-1-carbonyl]-phenyl}-acrylamide

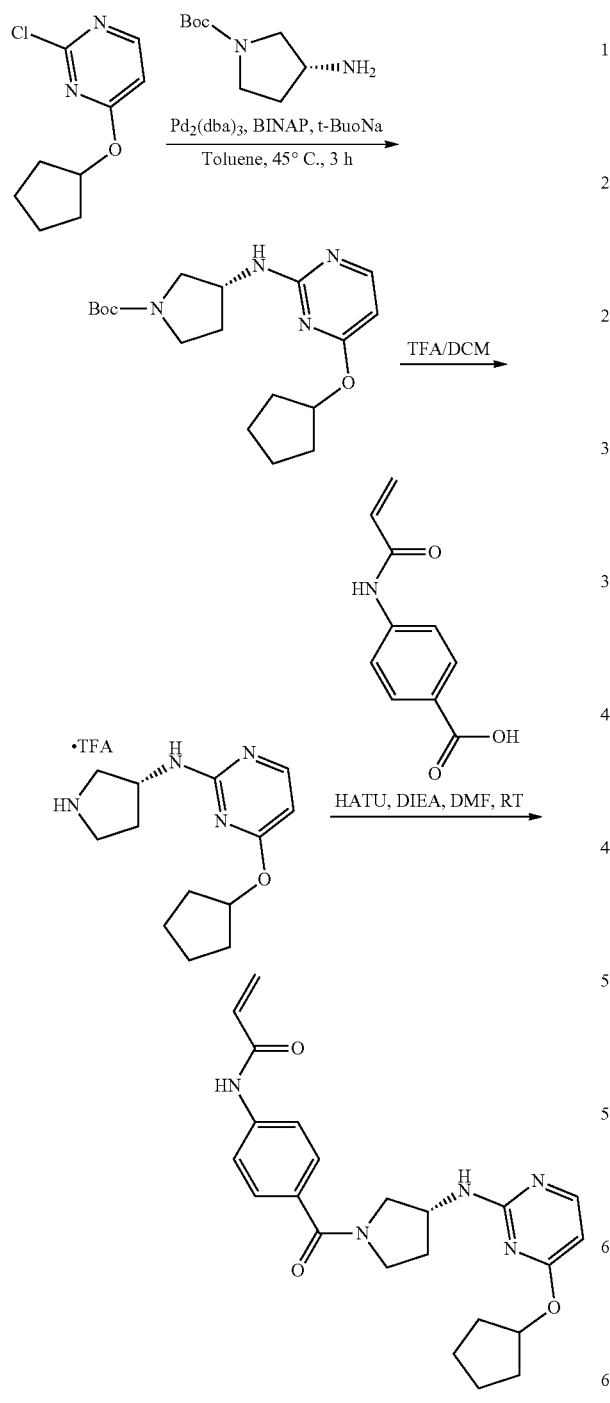

Step 1:

The title compound was prepared in 12% yield from 2-chloro-4-(cyclopentyloxy)pyrimidine using general procedure of 3-(4-cyclopentyloxy-pyrimidin-2-ylamino)-piperidine-1-carboxylic acid tert-butyl ester. MS Calcd.: 348.1, MS Found: 349.1 ([M+H]$^+$).

Step 2:

The title compound was prepared in 100% yield from 3-(4-cyclopentyloxy-pyrimidin-2-ylamino)-pyrrolidine-1-carboxylic acid tert-butyl ester using general procedure of (4-cyclopentyloxy-pyrimidin-2-yl)-piperidin-3-yl-amine. MS Calcd.: 248, MS Found: 249 ([M+H]$^+$).

Step 3:

The title compound was prepared in 27% yield from (4-cyclopentyloxy-pyrimidin-2-yl)-pyrrolidin-3-yl-amine using general procedure of N-{4-[3-(4-cyclopentyloxy-pyrimidin-2-ylamino)-piperidine-1-carbonyl]-phenyl}-acrylamide. $^1$H NMR (400 MHz, DMSO-d$_6$): δ 1.44-1.64 (m, 7H), 1.92-2.00 (m, 3H), 3.31-3.34 (m, 1H), 3.34-3.56 (m, 2H), 3.61-3.64 (m, 1H), 4.05-4.43 (m, 1H), 5.09-5.42 (m, 1H), 5.77-5.79 (m, 1H), 5.93-5.94 (m, 1H), 6.25-6.30 (m, 1H), 6.43-6.47 (m, 1H) 7.47-7.49 (m, 1H), 7.68-7.73 (m, 2H) 7.93-7.95 (m, 2H), 7.84-8.02 (m, 1H), 10.35 (s, 1H). MS Calcd.: 421, MS Found: 422 ([M+H]$^+$).

Example 46: Synthesis of N-(4-{3-[4-(1-Methyl-1H-pyrazol-4-yloxy)-pyrimidin-2-ylamino]-pyrrolidine-1-carbonyl}-phenyl)-acrylamide

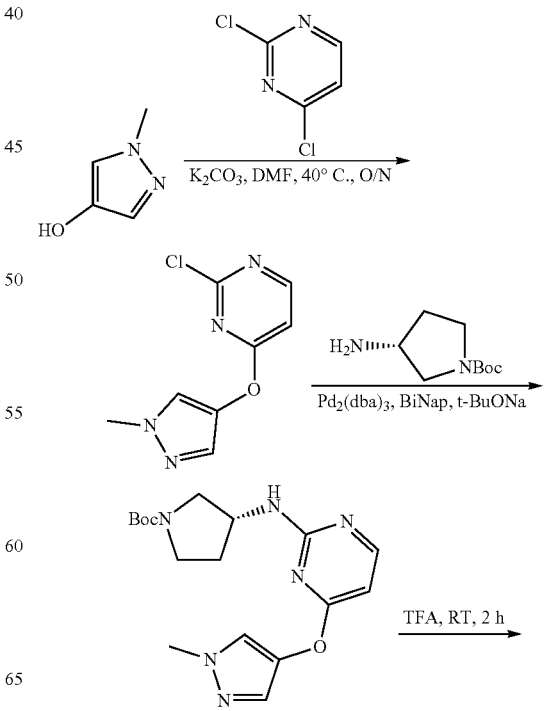

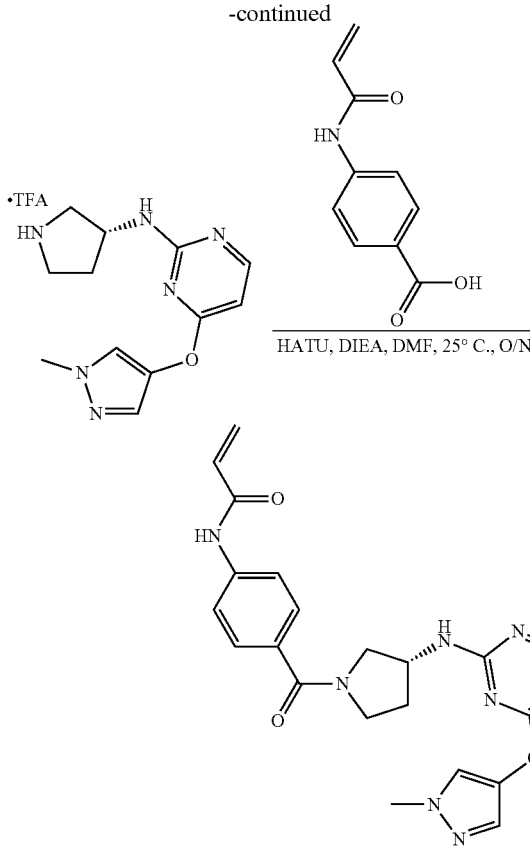

Step 1:

To a solution of 1-methyl-1H-pyrazol-4-ol (1.0 g, 11.0 mmol) and 2,4-dichloropyrimidine (1.6 g, 11.0 mmol) in DMF (20 mL) was added K$_2$CO$_3$ (3.0 g, 22.0 mmol) at room temperature. The mixture was stirred at 40° C. overnight. The mixture was water (100 mL) and extracted with DCM (50 mL*3). The combined organic layers were washed with water (100 mL*2) and brine (100 mL), dried over Na$_2$SO$_4$, filtered and concentrated in vacuo to give 2-chloro-4-((1-methyl-1H-pyrazol-4-yl)oxy)pyrimidine (2.2 g, 97%). MS Calcd.: 210, MS Found: 211 ([M+H]+).

Step 2:

To a solution of 2-chloro-4-((1-methyl-1H-pyrazol-4-yl)oxy)pyrimidine (800 mg, 3.8 mmol) and (R)-tert-butyl 3-aminopyrrolidine-1-carboxylate (1.1 g, 5.7 mmol) in toluene (20 mL) was added Pd$_2$(dba)$_3$ (696 mg, 0.8 mmol), BINAP (472 mg, 0.8 mmol) and t-BuONa (729 mg, 7.6 mmol) at room temperature under N$_2$. The mixture was stirred at 60° C. for 5 h under N$_2$. The mixture was then diluted with DCM (50 mL), washed with brine (50 mL), dried over Na$_2$SO$_4$, filtered and concentrated in vacuo. The residue was purified by flash chromatography on silica gel (Petroleum Ether/Ethyl Acetate=1/1) to afford (R)-tert-butyl 3-((4-((1-methyl-1H-pyrazol-4-yl)oxy)pyrimidin-2-yl)amino)pyrrolidine-1-carboxylate (720 mg, 52%). MS Calcd.: 360, MS Found: 361 ([M+H]+).

Step 3:

The title compound was prepared in 99% yield from 3-[4-(1-methyl-1H-pyrazol-4-yloxy)-pyrimidin-2-ylamino]-pyrrolidine-1-carboxylic acid tert-butyl ester using general procedure of (4-Cyclopentyloxy-pyrimidin-2-yl)-piperidin-3-yl-amine. MS Calcd.: 260, MS Found: 261 ([M+H]+).

Step 4:

The title compound was prepared in 11% yield from (R)-4-((1-methyl-H-pyrazol-4-yl)oxy)-N-(pyrrolidin-3-yl)pyrimidin-2-amine using general procedure of N-{4-[3-(4-Cyclopentyloxy-pyrimidin-2-ylamino)-piperidine-1-carbonyl]-phenyl}-acrylamide. $^1$H NMR (400 MHz, CD$_3$OD): δ 2.01-2.29 (m, 2H), 3.46-3.90 (m, 7H), 4.33-4.51 (m, 1H), 5.81 (d, J=9.6 Hz, 1H), 6.22 (d, J=6.0 Hz, 0.6H), 6.28 (d, J=6.0 Hz, 0.4H), 6.37-6.46 (m, 2H), 7.44-7.59 (m, 3H), 7.73-7.83 (m, 3H), 7.81 (d, J=5.6 Hz, 0.6H), 8.16 (d, J=5.6 Hz, 0.4H). MS Calcd.: 433, MS Found: 434 ([M+H]+).

Example 47: Synthesis of (R)—N-(4-(3-((5-chloro-4-methoxypyrimidin-2-yl)amino)pyrrolidine-1-carbonyl)phenyl)acrylamide

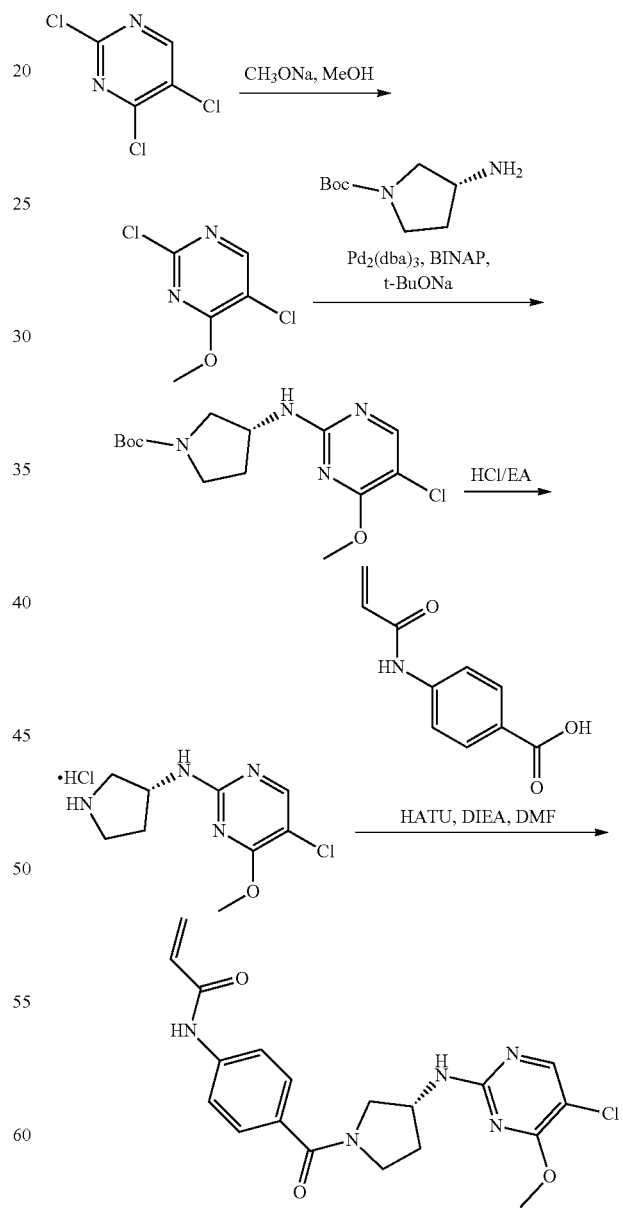

Step 1:

To a solution of 2,4,5-trichloropyrimidine (2.0 g, 10.9 mmol) in MeOH (30 mL) was added sodium methoxide (590 mg, 10.9 mmol) at room temperature. The mixture was stirred at rt for 12 h then concentrated in vacuo. The residue was purified by silica gel chromatography (Petroleum Ether/Ethyl Acetate=20/1) to give 2,5-dichloro-4-methoxypyrimidine (1.0 g, 51%). MS Calcd.: 178, MS Found: 179 ([M+H]$^+$).

Step 2:

To a solution of 2,5-dichloro-4-methoxypyrimidine (400 mg, 2.27 mmol) in toluene (20 mL) was added (R)-tert-butyl 3-aminopyrrolidine-1-carboxylate (465 mg, 2.49 mmol), t-BuONa (326 mg, 3.40 mmol), Pd$_2$(dba)$_3$ (261 mg, 0.45 mmol) and BINAP (564 mg, 0.91 mmol) at RT under N$_2$. The mixture was stirred at 100° C. for 12 h and concentrated in-vacuo. The residue was purified by silica gel chromatography (Petroleum Ether/Ethyl Acetate=1/1) to afford (R)-tert-butyl 3-((5-chloro-4-methoxypyrimidin-2-yl)amino)pyrrolidine-1-carboxylate (260 mg, 35%). MS Calcd.: 328, MS Found: 329 ([M+H]$^+$).

Step 3:

A solution of 3-((5-chloro-4-methoxypyrimidin-2-yl)amino)pyrrolidine-1-carboxylate (260 mg, 0.79 mmol) in HCl/Ethyl Acetate (10 mL, 2.0 M) was stirred at rt for 3 h. The reaction mixture was then filtered to give (R)-5-chloro-4-methoxy-N-(pyrrolidin-3-yl)pyrimidin-2-amine hydrochloride (180 mg, 100%). MS Calcd.: 228, MS Found: 229 ([M+H]$^+$).

Step 4:

The title compound was prepared in 23% yield from (R)-5-chloro-4-methoxy-N-(pyrrolidin-3-yl)pyrimidin-2-amine hydrochloride using general procedure of N-{4-[3-(4-Cyclopentyloxy-pyrimidin-2-ylamino)-piperidine-1-carbonyl]-phenyl}-acrylamide. $^1$H NMR (400 MHz, CD$_3$OD): δ 1.91-2.15 (m, 2H), 3.32-3.41 (m, 1H), 3.44-3.64 (m, 2H), 3.79 (m, 1H), 3.86-3.94 (m, 3H), 4.26 (m, 1H), 5.78 (d, J=10.0 Hz, 1H), 6.28 (d, J=14.8 Hz, 1H), 6.41-6.48 (m, 1H), 7.49-7.54 (m, 2H), 7.69-7.73 (m, 3H), 8.07-8.14 (m, 1H), 10.31 (s, 1H). MS Calcd.: 401, MS Found: 402 ([M+H]$^+$).

Example 48: Synthesis of N-{4-[3-(4-Thiazol-5-yl-pyrimidin-2-ylamino)-pyrrolidine-1-carbonyl]-phenyl}-acrylamide

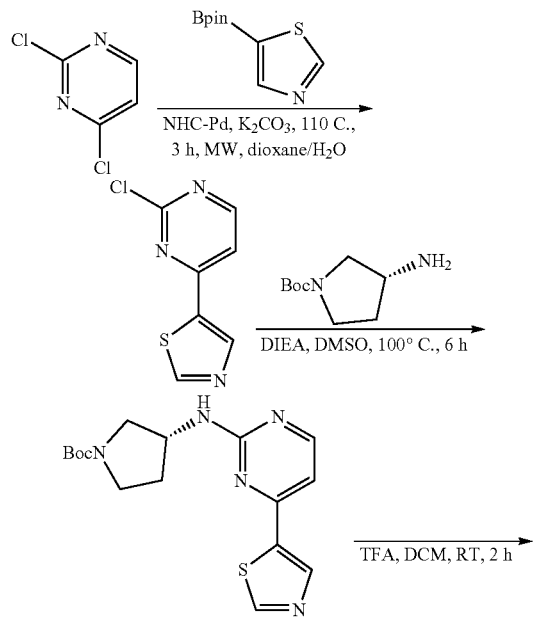

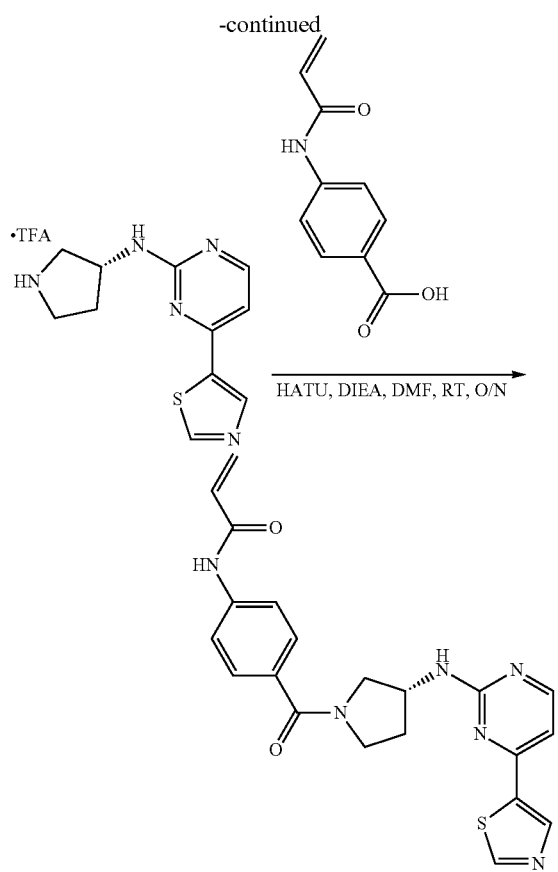

Step 1:

To a solution of 5-(4,4,5,5-tetramethyl-1,3,2-dioxaborolan-2-yl)thiazole (200 mg, 0.95 mmol) and 2,4-dichloropyrimidine (95 mg, 0.63 mmol) in dioxane (5 mL) and H$_2$O (1 mL) was added NHC—Pd (20 mg, 0.06 mmol) and K$_2$CO$_3$ (174 mg, 1.26 mmol) at room temperature under N$_2$. The mixture was stirred at 110° C. for 3 h in microwave. The solution was diluted with DCM (50 mL) and washed with brine (20 mL). The organic layer was dried over Na$_2$SO$_4$, filtered and concentrated in vacuo. The residue was purified by prep-TLC (Petroleum Ether/Ethyl Acetate=1/1) to give 5-(2-chloropyrimidin-4-yl)thiazole (40 mg, 35%). MS Calcd.: 197, MS Found: 198 ([M+H]$^+$).

Step 2:

To a solution of 5-(2-chloropyrimidin-4-yl)thiazole (40 mg, 0.2 mmol) and (R)-tert-butyl 3-aminopyrrolidine-1-carboxylate (57 mg, 0.3 mmol) in DMSO (5 mL) was added DIEA (52 mg, 0.4 mmol) at room temperature. The mixture was stirred at 100° C. for then was diluted with water and filtered to give (R)-tert-butyl 3-((4-(thiazol-5-yl)pyrimidin-2-yl)amino)pyrrolidine-1-carboxylate (60 mg, 87%). MS Calcd.: 347, MS Found: 348 ([M+H]$^+$).

Step 3:

The title compound was prepared in 99% yield from (R)-tert-butyl 3-((4-(thiazol-5-yl)pyrimidin-2-yl)amino)pyrrolidine-1-carboxylate using general procedure of (4-Cyclopentyloxy-pyrimidin-2-yl)-piperidin-3-yl-amine. MS Calcd.: 247, MS Found: 248 ([M+H]$^+$).

Step 4:

The title compound was prepared in 7% yield from (R)—N-(pyrrolidin-3-yl)-4-(thiazol-5-yl)pyrimidin-2-amine using general procedure of N-{4-[3-(4-Cyclopentyloxy-pyrimidin-2-ylamino)-piperidine-1-carbonyl]-phenyl}-acrylamide. $^1$H NMR (400 MHz, CD$_3$OD): δ 1.89-2.11 (m, 1H), 2.12-2.29 (m, 1H), 3.39-3.71 (m, 3H), 3.89-3.90 (m, 1H), 4.30-4.52 (m, 1H), 5.67-5.71 (m, 1H), 6.28-6.34 (m, 2H), 7.00 (d, J=5.2 Hz, 0.6H), 7.06 (d, J=5.2 Hz, 0.4H), 7.42-7.49 (m, 2H), 7.61-7.67 (m, 2H), 8.17 (d, J=5.6 Hz, 0.6H), 8.25 (d, J=5.6 Hz, 0.4H), 8.41 (s, 0.6H), 8.48 (s, 0.4H), 8.94 (s, 0.4H), 9.00 (s, 0.6H). MS Calcd.: 420, MS Found: 421 ([M+H]$^+$).

Example 49: Synthesis of (R)-1-(5-(3-((5-chloro-4-methoxypyrimidin-2-yl)amino)pyrrolidine-1-carbonyl)indolin-1-yl)prop-2-en-1-one

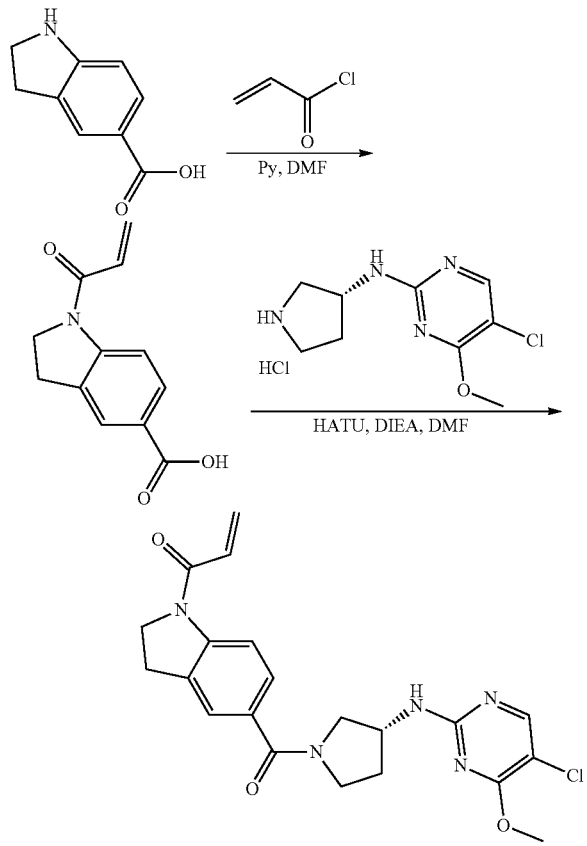

Step 1: 1-acryloylindoline-5-carboxylic acid

To a mixture of indoline-5-carboxylic acid (500 mg, 3.07 mmol) in DMF (3 mL) was added Pyridine (0.2 mL) at 0° C. followed by acryloyl chloride (555 mg, 6.13 mmol). The reaction mixture was stirred at RT for 5 h. The mixture was then concentrated, DCM was added (20 mL), washed with 0.5N HCl (10 mL), dried over Na$_2$SO$_4$, filtered and concentrated in vacuo to afford 1-acryloylindoline-5-carboxylic acid (280 mg, 42%) as a yellow solid. [M+H] Calc'd for C$_{12}$H$_{11}$NO$_3$: 218.1; Found: 218.1

Step 2: (R)-1-(5-(3-((5-chloro-4-methoxypyrimidin-2-yl)amino)pyrrolidine-1-carbonyl)indolin-1-yl)prop-2-en-1-one A mixture of 1-acryloylindoline-5-carboxylic acid (140 mg, 0.65 mmol), (R)-5-chloro-4-methoxy-N-(pyrrolidin-3-yl)pyrimidin-2-amine hydrochloride (221 mg, 0.84 mmol), HATU (368 mg, 0.97 mmol) and DIEA (416 mg, 3.22 mmol) in DMF (5 mL) was stirred at RT overnight. The mixture was diluted with water (20 mL) and extracted with DCM (10 mL*3). The combined organic layer was washed with brine (20 mL), dried over Na$_2$SO$_4$, filtered and concentrated in-vacuo. The residue was purified by prep-HPLC to afford (R)-1-(5-(3-((5-chloro-4-methoxypyrimidin-2-yl)amino)pyrrolidine-1-carbonyl)indolin-1-yl)prop-2-en-1-one (27 mg, 10%) as a yellow solid. $^1$H NMR (400 MHz, CD$_3$OD): δ 2.00-2.10 (m, 1H), 2.21-2.35 (m, 1H), 3.22-3.27 (m, 2H), 3.46-3.96 (m, 6H), 4.00 (s, 1H), 4.25-4.29 (m, 2H), 4.37-4.55 (m, 1H), 5.86 (d, J=10.4 Hz, 1H), 6.39-6.44 (m, 1H), 6.73-6.79 (m, 1H), 7.37-7.46 (m, 2H), 7.93 (s, 0.5H), 8.01 (s, 0.5H), 8.22 (br s, 1H). [M+H] Calc'd for C$_{21}$H$_{22}$ClN$_5$O$_3$: 428.2; Found: 428.2.

Example 50: Synthesis of (R)-1-(5-(3-((5-chloropyrimidin-2-yl)amino)pyrrolidine-1-carbonyl)indolin-1-yl)prop-2-en-1-one

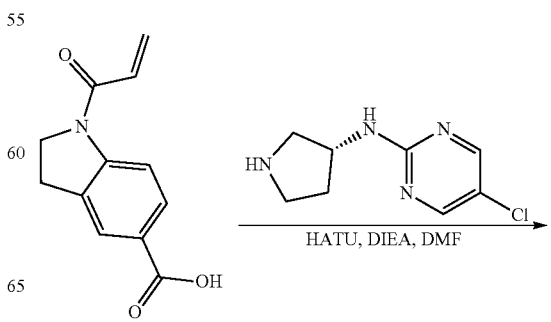

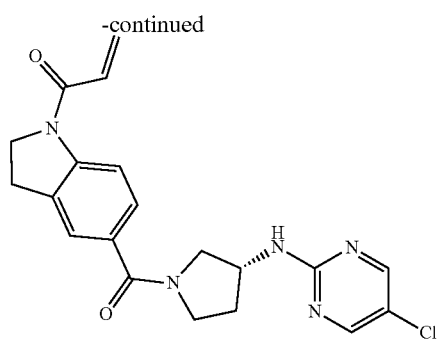

A mixture of 1-acryloylindoline-5-carboxylic acid (140 mg, 0.65 mmol), (R)-5-chloro-N-(pyrrolidin-3-yl)pyrimidin-2-amine (HCl salt) (196 mg, 0.84 mmol), HATU (368 mg, 0.97 mmol) and DIEA (416 mg, 3.22 mmol) in DMF (5 mL) was stirred at RT overnight. The mixture was diluted with water (20 mL) and extracted with DCM (10 mL*3). The combined organic layer was washed with brine (20 mL), dried over Na$_2$SO$_4$, filtered and concentrated in-vacuo. The residue was purified by prep-HPLC to afford (R)-1-(5-(3-((5-chloropyrimidin-2-yl)amino)pyrrolidine-1-carbonyl)indolin-1-yl)prop-2-en-1-one (12 mg, 5%) as a white solid. $^1$H NMR (400 MHz, CD$_3$OD): δ 1.99-2.10 (m, 1H), 2.21-2.35 (m, 1H), 3.22-3.29 (m, 2H), 3.44-3.95 (m, 4H), 4.25-4.31 (m, 2H), 4.36-4.55 (m, 1H), 5.86 (d, J=10.4 Hz, 1H), 6.39-6.43 (m, 1H), 6.73-6.79 (m, 1H), 7.37-7.45 (m, 2H), 8.21 (s, 2H), 8.28 (s, 1H). [M+H] Calc'd for C$_{20}$H$_{20}$ClN$_5$O$_2$, 398.1; Found, 398.1

Example 51: Synthesis of (R)-1-(7-(3-((5-chloropyrimidin-2-yl)amino)pyrrolidine-1-carbonyl)-2H-benzo[b][1,4]oxazin-4(3H)-yl)prop-2-en-1-one

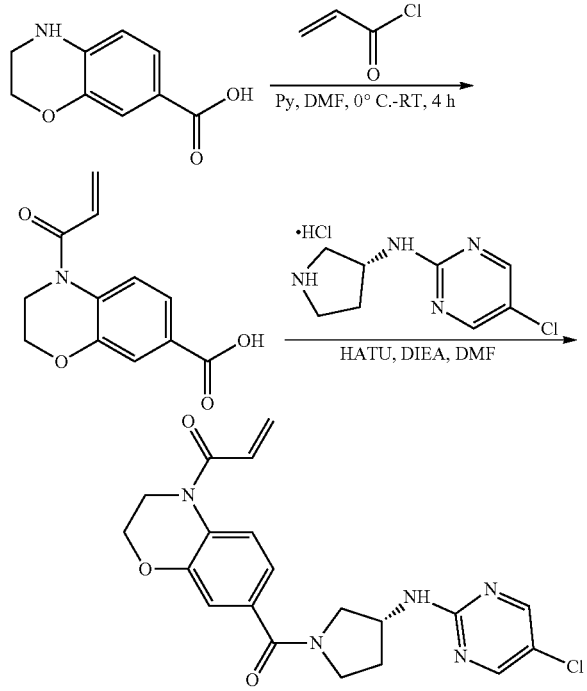

Step 1: 4-acryloyl-3,4-dihydro-2H-benzo[b][1,4]oxazine-7-carboxylic acid

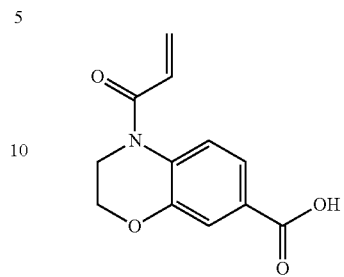

A mixture of 3,4-dihydro-2H-benzo[b][1,4]oxazine-7-carboxylic acid (800 mg, 4.47 mmol) in DMF (15 mL) was added Pyridine (1.0 mL) at 0° C., then added acryloyl chloride (603 mg, 6.66 mmol). The mixture was stirred at RT for 4 h. The mixture was concentrated and added DCM, washed with 1N HCl, dried over Na$_2$SO$_4$, filtered, concentrated in vacuo to afford 4-acryloyl-3,4-dihydro-2H-benzo[b][1,4]oxazine-7-carboxylic acid (460 mg, 44%) as yellow solid. [M+H]Calc'd for C$_{12}$H$_{11}$NO$_4$: 234.1; Found: 234.1

Step 2: (R)-1-(7-(3-((5-chloropyrimidin-2-yl)amino) pyrrolidine-1-carbonyl)-2H-benzo[b][1,4]oxazin-4(3H)-yl)prop-2-en-1-one

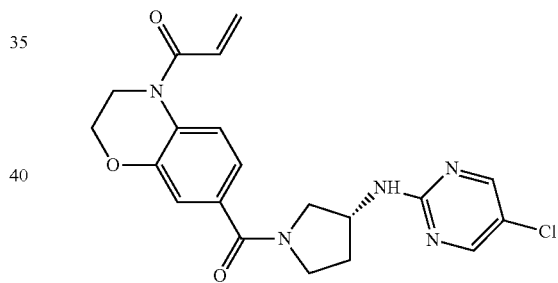

A mixture of 4-acryloyl-3,4-dihydro-2H-benzo[b][1,4]oxazine-7-carboxylic acid (200 mg, 0.86 mmol), (R)-5-chloro-N-(pyrrolidin-3-yl)pyrimidin-2-amine hydrochloride (200 mg, 0.86 mmol), HATU (653 mg, 1.72 mmol) and DIEA (553 mg, 4.29 mmol) in DMF (20 mL) was stirred at RT overnight. The mixture was diluted with water (20 mL) and extracted with DCM (20 mL*3). The combined organic layer was washed with brine (20 mL), dried over Na$_2$SO$_4$, filtered and concentrated in-vacuo. The residue was purified by prep-HPLC to afford (R)-1-(7-(3-((5-chloropyrimidin-2-yl)amino)pyrrolidine-1-carbonyl)-2H-benzo[b][1,4]oxazin-4(3H)-yl)prop-2-en-1-one (34.6 mg, 8%) as a white solid. $^1$H NMR (400 MHz, DMSO-d$_6$): δ 1.86-2.13 (m, 2H), 3.34-3.77 (m, 4H), 3.92-3.95 (m, 2H), 4.31-4.09 (m, 3H), 5.82-5.85 (m, 1H), 6.25-6.30 (m, 1H), 6.74-6.82 (m, 1H), 7.02-7.07 (m, 2H), 7.49 (br s, 1H), 7.81 (s, 1H), 8.32-8.38 (m, 2H). [M+H]Calc'd for C$_2$H$_{20}$ClN$_5$O$_3$, 414.1; Found, 414.1

Example 52: Synthesis of (R)—N-(4-(3-((5-chloro-4-methylpyrimidin-2-yl)amino)pyrrolidine-1-carbonyl)phenyl)acrylamide

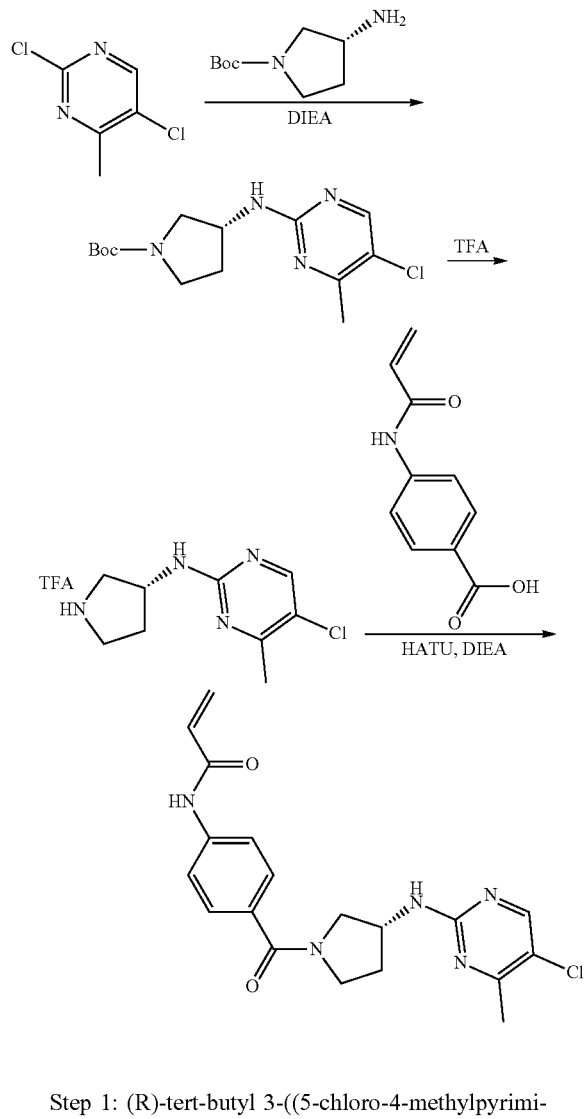

Step 1: (R)-tert-butyl 3-((5-chloro-4-methylpyrimidin-2-yl)amino)pyrrolidine-1-carboxylate

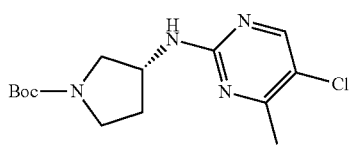 [SMILES: Cc1nc(N[C@@H]2CCN(C(=O)OC(C)(C)C)C2)ncc1Cl]

A mixture of 2,5-dichloro-4-methylpyrimidine (300 mg, 1.6 mmol), (R)-tert-butyl 3-aminopyrrolidine-1-carboxylate (263 mg, 1.6 mmol) and DIEA (619 mg, 4.8 mmol) in DMF (5 mL) was stirred at 120° C. for 5 hours. The mixture was cooled to RT, diluted with water (20 mL) and extracted with EtOAc (20 mL*3). The combined organic phase was washed with brine (20 mL), dried over Na$_2$SO$_4$, filtered and concentrated. The residue was purified by flash chromatography on silica gel (petroleum ether/EtOAc=20/1) to afford (R)-tert-butyl 3-((5-chloro-4-methylpyrimidin-2-yl)amino)pyrrolidine-1-carboxylate (250 mg, 50%) as a yellow solid. [M+H] Calc'd for C$_{14}$H$_{21}$ClN$_4$O$_2$, 313.1; Found, 313.1.

Step 2: (R)-5-chloro-4-methyl-N-(pyrrolidin-3-yl)pyrimidin-2-amine 2,2,2-trifluoroacetate

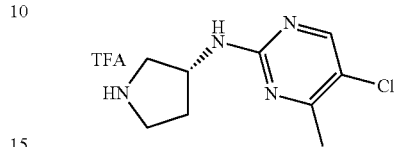

To a mixture of (R)-tert-butyl 3-((5-chloro-4-methylpyrimidin-2-yl)amino)pyrrolidine-1-carboxylate (120 mg, 0.38 mmol) in DCM (2 mL) was added TFA (1.5 mL). The mixture was stirred at RT for 15 minutes. The mixture was concentrated to afford (R)-5-chloro-4-methyl-N-(pyrrolidin-3-yl)pyrimidin-2-amine 2,2,2-trifluoroacetate (320 mg, crude, 100%) as yellow oil. [M+H] Calc'd for C$_9$H$_{13}$ClN$_4$, 213.6; Found, 213.6.

Step 3: (R)—N-(4-(3-((5-chloro-4-methylpyrimidin-2-yl)amino)pyrrolidine-1-carbonyl)phenyl)acrylamide

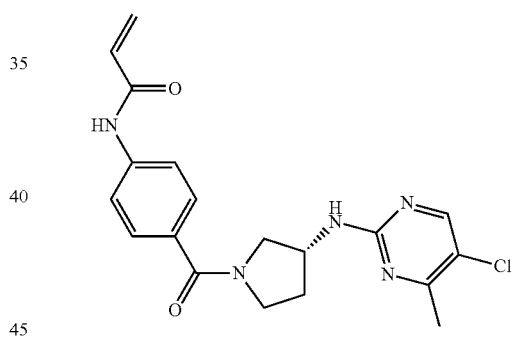

A mixture of (R)-5-chloro-4-methyl-N-(pyrrolidin-3-yl)pyrimidin-2-amine 2,2,2-trifluoroacetate (300 mg, crude, 0.38 mmol), 4-acrylamidobenzoic acid (73 mg, 0.38 mmol), HATU (174 mg, 0.46 mmol) and DIEA (147 mg, 1.14 mmol) in DMF (2 mL) was stirred at RT overnight. The mixture was diluted with water (20 mL) and extracted with EtOAc (20 mL*3). The combined organic phase was washed with brine (20 mL), dried over Na$_2$SO$_4$, filtered and concentrated. The residue was purified by prep-HPLC to afford (R)—N-(4-(3-((5-chloro-4-methylpyrimidin-2-yl)amino)pyrrolidine-1-carbonyl)phenyl)acrylamide (40 mg, 27%) as a white solid. $^1$H NMR (400 MHz, CDCl$_3$): δ 1.95-2.00 (m, 1H), 2.24-2.42 (m, 4H), 3.35-3.88 (m, 4H), 4.47-4.58 (m, 1H), 5.13-5.29 (m, 1H), 5.78 (d, J=11.2 Hz, 1H), 6.25-6.32 (m, 1H), 6.42-6.47 (m, 1H), 7.45-7.48 (m, 2H), 7.56 (m, 2H), 7.88 (s, 1H), 8.08 (s, 0.5H), 8.14 (s, 0.5H). [M+H] Calc'd for C$_{19}$H$_{20}$ClN$_5$O$_2$, 386.1; Found, 386.1.

Example 53: Synthesis of (R)—N-(4-(3-((5-chloropyrazin-2-yl)amino)pyrrolidine-1-carbonyl)phenyl)acrylamide

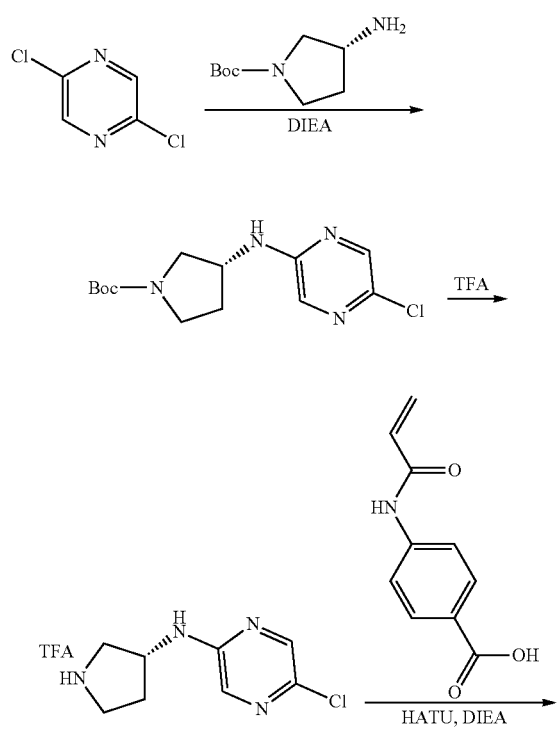

Step 1: (R)-tert-butyl 3-((5-chloropyrazin-2-yl)amino)pyrrolidine-1-carboxylate

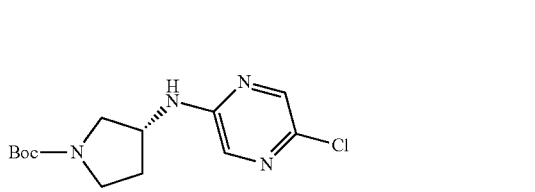 [SMILES: CC(C)(C)OC(=O)N1CC[C@@H](Nc2cnc(Cl)cn2)C1]

The title compound was prepared in 16% yield from 2,5-dichloropyrazine using general procedure of (R)-tert-butyl 3-((5-chloro-4-methylpyrimidin-2-yl)amino)pyrrolidine-1-carboxylate. [M+H] Calc'd for $C_{13}H_9ClN_4O_2$, 299.1; Found, 299.1.

Step 2: (R)-5-chloro-N-(pyrrolidin-3-yl)pyrazin-2-amine 2,2,2-trifluoroacetate

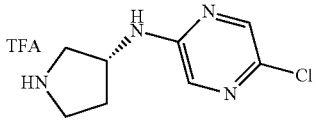 [SMILES: Clc1cnc(N[C@@H]2CCNC2)cn1]

The title compound was prepared in 100% yield from (R)-tert-butyl 3-((5-chloropyrazin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_8H_{11}ClN_4$, 199.0; Found, 199.0.

Step 3: (R)—N-(4-(3-((5-chloropyrazin-2-yl)amino)pyrrolidine-1-carbonyl)phenyl)acrylamide

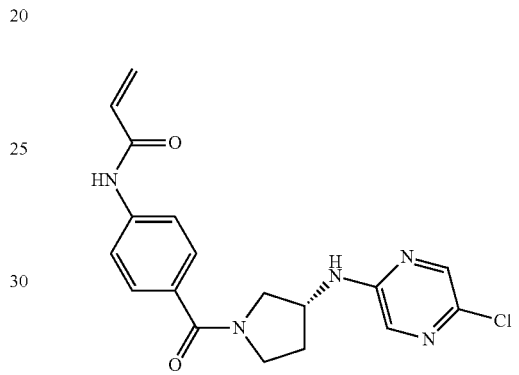

The title compound was prepared in 28% yield from (R)-5-chloro-N-(pyrrolidin-3-yl)pyrazin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, CDCl$_3$): δ 1.99-2.00 (m, 1H), 2.21-2.37 (m, 1H), 3.60-3.84 (m, 4H), 4.40-4.41 (m, 1H), 5.27-5.44 (m, 1H), 5.78 (d, J=11.2 Hz, 1H), 6.26-6.33 (m, 1H), 6.42-6.46 (m, 1H), 7.40-7.42 (m, 2H), 7.53-7.55 (m, 2H), 7.66 (s, 0.5H), 7.75 (s, 0.5H), 7.95-8.10 (m, 2H). [M+H] Calc'd for $C_{18}H_{18}ClN_5O_2$, 372.1; Found, 372.1.

Example 54: Synthesis of (R)—N-(4-(3-((5-chloro-4-methoxypyridin-2-yl)amino)pyrrolidine-1-carbonyl)phenyl)acrylamide

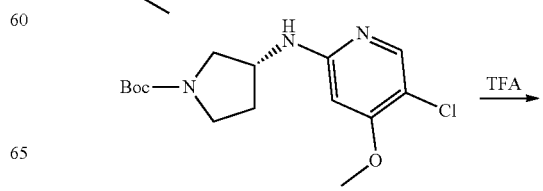

227
-continued

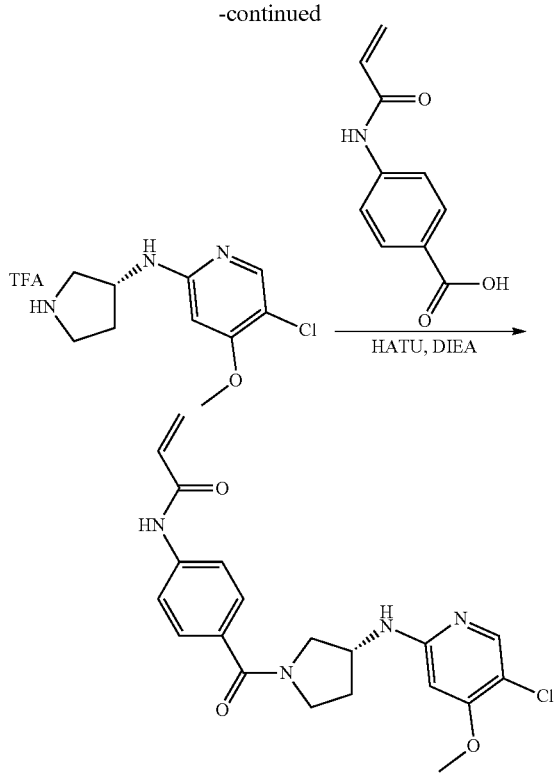

Step 1: (R)-tert-butyl 3-((5-chloro-4-methoxypyridin-2-yl)amino)pyrrolidine-1-carboxylate

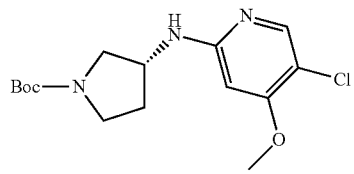 [SMILES: COc1cc(N[C@@H]2CCN(C(=O)OC(C)(C)C)C2)ncc1Cl]

The title compound was prepared in 53% yield from 2,5-dichloro-4-methoxypyridine using general procedure of (R)-tert-butyl 3-((5-chloro-4-methylpyrimidin-2-yl)amino)pyrrolidine-1-carboxylate. [M+H] Calc'd for $C_{15}H_{22}ClN_3O_3$, 328.1; Found, 328.1.

Step 2: (R)-5-chloro-4-methoxy-N-(pyrrolidin-3-yl)pyridin-2-amine 2,2,2-trifluoroacetate

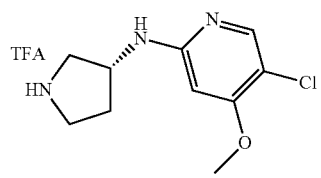

The title compound was prepared in 100% yield from (R)-tert-butyl 3-((5-chloro-4-methoxypyridin-2-yl)amino)

228 pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{10}H_{14}ClN_3O$, 228.0; Found, 228.0.

Step 3: (R)—N-(4-(3-((5-chloro-4-methoxypyridin-2-yl)amino)pyrrolidine-1-carbonyl)phenyl)acrylamide

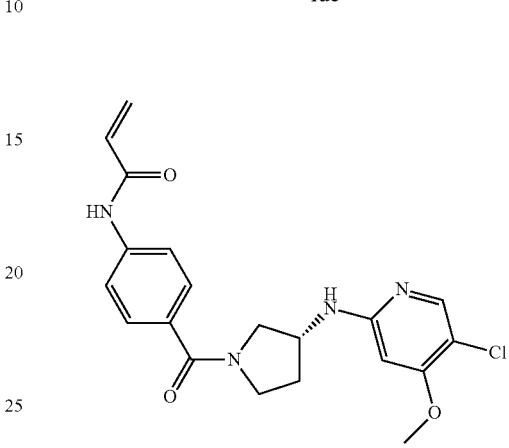

The title compound was prepared in 14% yield from (R)-5-chloro-4-methoxy-N-(pyrrolidin-3-yl)pyridin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.80-1.90 (m, 1H), 2.07-2.20 (m, 1H), 3.35-3.39 (m, 1H), 3.51-3.63 (m, 2H), 3.68-3.82 (m, 4H), 4.25-4.41 (m, 1H), 5.78 (d, J=10.0 Hz, 1H), 6.14-6.18 (m, 1H), 6.26-6.30 (m, 1H), 6.40-6.47 (m, 1H), 6.92-6.99 (m, 1H), 7.49-7.54 (m, 2H), 7.69-7.77 (m, 2H), 7.78 (s, 0.5H), 7.88 (s, 0.5H), 10.30 (s, 1H). [M+H] Calc'd for $C_{20}H_{21}ClN_4O_3$, 401.1; Found, 401.1.

Example 55: Synthesis of (R)—N-(4-(3-((5-chloro-4-methylpyridin-2-yl)amino)pyrrolidine-1-carbonyl)phenyl)acrylamide

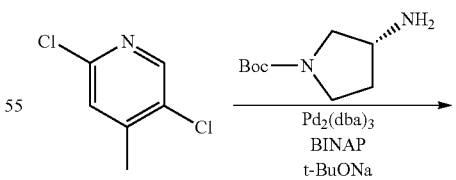

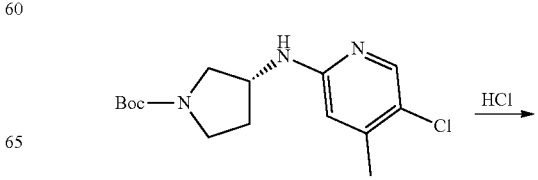

229
-continued

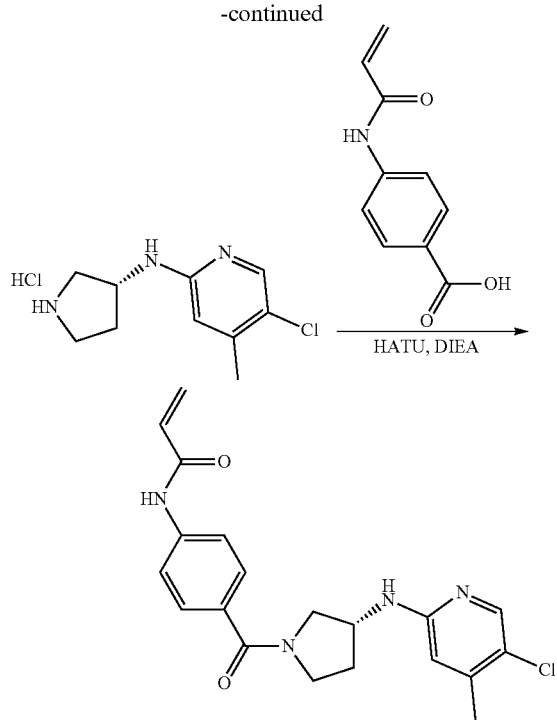

Step 1: (R)-tert-butyl 3-((5-chloro-4-methylpyridin-2-yl)amino)pyrrolidine-1-carboxylate

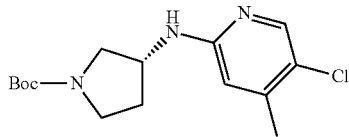 [SMILES: Cc1cc(N[C@@H]2CCN(C(=O)OC(C)(C)C)C2)ncc1Cl]

The title compound was prepared in 87% yield from 2,5-dichloro-4-methylpyridine using general procedure of (R)-tert-butyl 3-((5-chloro-4-methylpyrimidin-2-yl)amino) pyrrolidine-1-carboxylate. [M+H] Calc'd for $C_{15}H_{22}ClN_3O_2$, 312.1; Found, 312.1.

Step 2: (R)-5-chloro-4-methyl-N-(pyrrolidin-3-yl)pyridin-2-amine hydrochloride

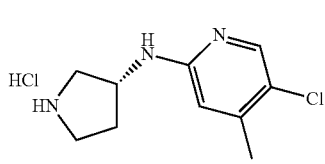

A mixture of (R)-tert-butyl 3-((5-chloro-4-methylpyridin-2-yl)amino)pyrrolidine-1-carboxylate (500 mg, 1.64 mmol) in HCl/EtOAc (4M, 10 mL) was stirred at 15° C. for 30 minutes. The mixture was concentrated to afford (R)-5-chloro-4-methyl-N-(pyrrolidin-3-yl)pyridin-2-amine hydrochloride (480 mg, crude, 100%) as a yellow solid. [M+H] Calc'd for $C_{10}H_{14}ClN_3$, 212.0; Found, 212.0.

230

Step 3: (R)—N-(4-(3-((5-chloro-4-methylpyridin-2-yl)amino)pyrrolidine-1-carbonyl)phenyl)acrylamide

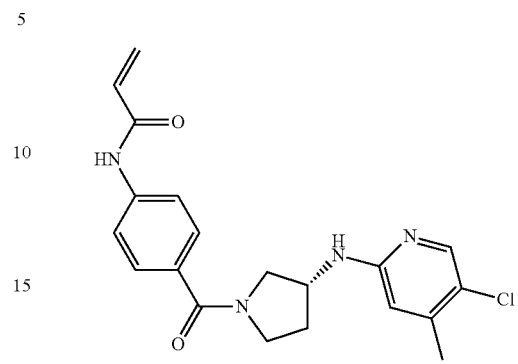

The title compound was prepared in 8% yield from (R)-5-chloro-4-methyl-N-(pyrrolidin-3-yl)pyridin-2-amine hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.81-1.91 (m, 1H), 2.15-2.20 (m, 4H), 3.26-3.32 (m, 1H), 3.50-3.64 (m, 2H), 3.77-3.79 (m, 1H), 4.21-4.35 (m, 1H), 5.78 (d, J=9.6 Hz, 1H), 6.26-6.30 (m, 1H), 6.40-6.48 (m, 2H), 6.91-6.96 (m, 1H), 7.49-7.54 (m, 2H), 7.69-7.74 (m, 2H), 7.86 (s, 0.6H), 7.96 (s, 0.4H), 10.33 (br s, 1H). [M+H] Calc'd for $C_{20}H_{21}ClN_4O_2$, 385.1; Found, 385.1.

Example 56: Synthesis of (R)—N-(4-(3-((5-chloro-4-cyclopropoxypyrimidin-2-yl)amino)pyrrolidine-1-carbonyl)phenyl)acrylamide

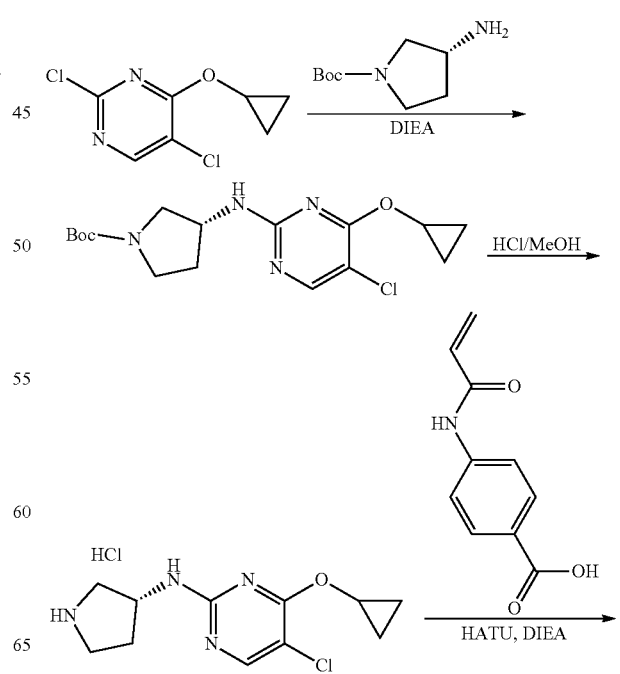

-continued

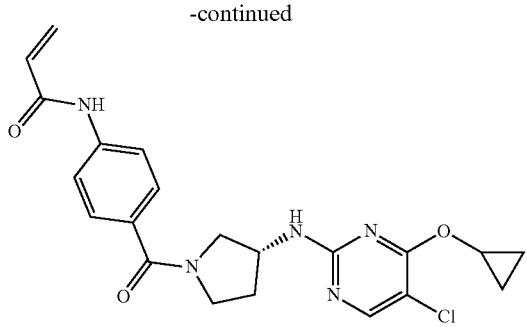

Step 1: (R)-tert-butyl 3-((5-chloro-4-cyclopropoxy-pyrimidin-2-yl)amino)pyrrolidine-1-carboxylate

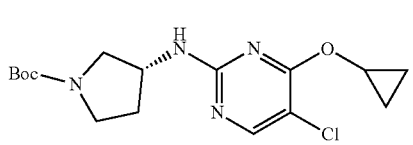 [SMILES: CC(C)(C)OC(=O)N1CC[C@@H](Nc2ncc(Cl)c(OC3CC3)n2)C1]

The title compound was prepared in 42% yield from 2,5-dichloro-4-cyclopropoxypyrimidine using general procedure of (R)-tert-butyl 3-((5-chloro-4-methylpyrimidin-2-yl)amino)pyrrolidine-1-carboxylate. [M+H] Calc'd for $C_{16}H_{23}ClN_4O_3$, 355.1; Found, 355.1.

Step 2: (R)-5-chloro-4-cyclopropoxy-N-(pyrrolidin-3-yl)pyrimidin-2-amine hydrochloride

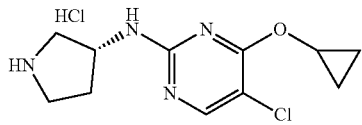 [SMILES: Cl ; Clc1cnc(N[C@@H]2CCNC2)nc1OC1CC1]

A mixture of (R)-tert-butyl 3-((5-chloro-4-cyclopropoxy-pyrimidin-2-yl)amino)pyrrolidine-1-carboxylate (800 mg, 2.26 mmol) in MeOH (4 mL) was added HCl/MeOH (2M, 2 mL). The mixture was stirred at 35° C. for 3 hours. The mixture was concentrated to afford (R)-5-chloro-4-cyclopropoxy-N-(pyrrolidin-3-yl)pyrimidin-2-amine hydrochloride (574 mg, crude, 100%) as a white solid. [M+H] Calc'd for $C_{11}H_{15}ClN_4O$, 255.0; Found, 255.0.

Step 3: (R)—N-(4-(3-((5-chloro-4-cyclopropoxypyrimidin-2-yl)amino)pyrrolidine-1-carbonyl)phenyl)acrylamide

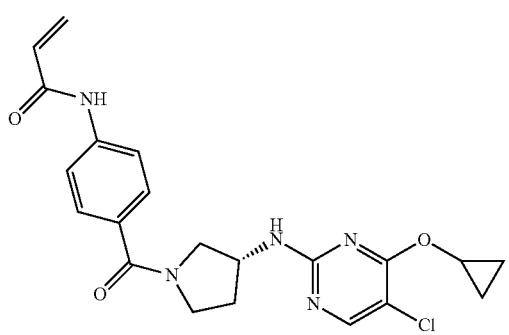 [SMILES: C=CC(=O)Nc1ccc(C(=O)N2CC[C@@H](Nc3ncc(Cl)c(OC4CC4)n3)C2)cc1]

The title compound was prepared in 23% yield from (R)-5-chloro-4-cyclopropoxy-N-(pyrrolidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 0.61-0.80 (m, 4H), 1.90-2.04 (m, 1H), 2.07-2.15 (m, 1H), 3.38-3.47 (m, 1H), 3.51-3.57 (m, 1H), 3.63-3.65 (m, 1H), 3.77-3.80 (m, 1H), 4.20-4.25 (m, 1H), 4.34-4.41 (m, 1H), 5.77-5.80 (m, 1H), 6.25-6.30 (m, 1H), 6.41-6.47 (m, 1H), 7.48-7.53 (m, 2H), 7.68-7.73 (m, 3H), 8.07-8.14 (m, 1H), 10.29 (s, 1H). [M+H] Calc'd for $C_{21}H_{22}ClN_5O_3$, 428.1; Found, 428.1.

Example 57: Synthesis of (R)—N-(4-(3-((5-methylpyrimidin-2-yl)amino)pyrrolidine-1-carbonyl)phenyl)acrylamide

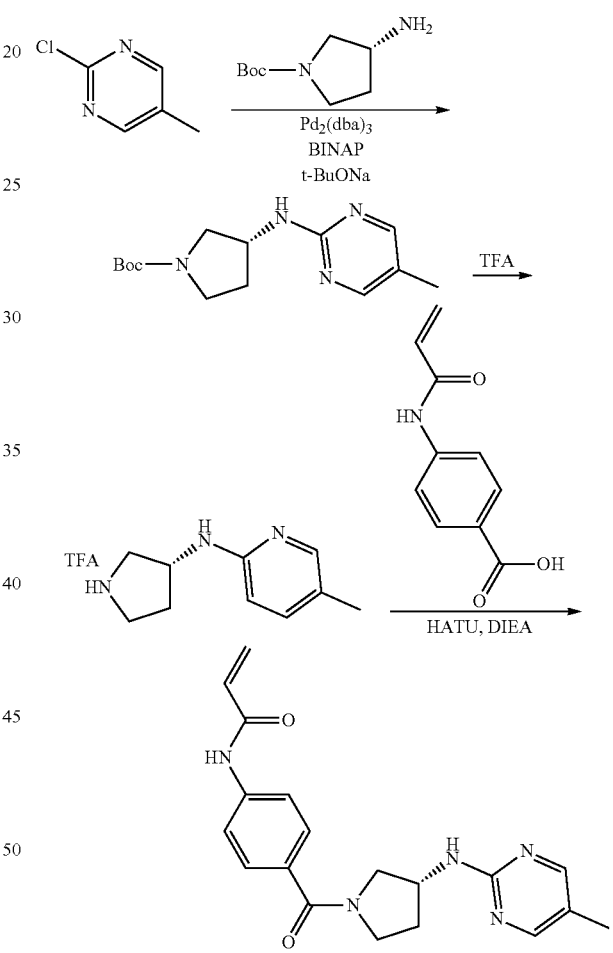

Step 1: (R)-tert-butyl 3-((5-methylpyrimidin-2-yl)amino)pyrrolidine-1-carboxylate

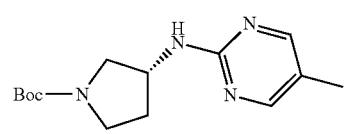

The title compound was prepared in 32% yield from 2-chloro-5-methylpyrimidine using general procedure of (R)-tert-butyl 3-((5-chloro-4-methylpyrimidin-2-yl)amino)pyrrolidine-1-carboxylate. [M+H] Calc'd for $C_{14}H_{22}N_4O_2$, 279.1; Found, 279.1.

Step 2: (R)-5-methyl-N-(pyrrolidin-3-yl)pyridin-2-amine 2,2,2-trifluoroacetate

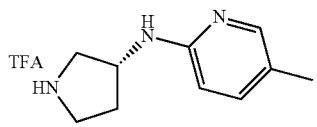

The title compound was prepared in 100% yield from (R)-tert-butyl 3-((5-methylpyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{10}H_{15}N_3$, 178.1; Found, 178.1.

Step 3: (R)—N-(4-(3-((5-methylpyrimidin-2-yl)amino)pyrrolidine-1-carbonyl)phenyl)acrylamide

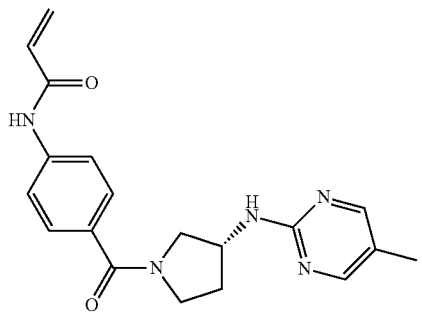

The title compound was prepared in 34% yield from (R)-5-methyl-N-(pyrrolidin-3-yl)pyridin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.82-2.19 (m, 5H), 3.35-3.42 (m, 1H), 3.47-3.55 (m, 1H), 3.62-3.69 (m, 1H), 3.73-3.78 (m, 1H), 4.22-4.44 (m, 1H), 5.78 (d, J=10.4 Hz, 1H), 6.26-6.30 (m, 1H), 6.40-6.47 (m, 1H), 7.22-7.25 (m, 1H), 7.47-7.53 (m, 2H), 7.67-7.73 (m, 2H), 8.09 (s, 1H), 8.17 (s, 1H), 10.29 (s, 1H). [M+H] Calc'd for $C_{19}H_{21}N_5O_2$, 352.1; Found, 352.1.

Example 58: Synthesis of (R)—N-(4-(3-((5-cyclopropylpyrimidin-2-yl)amino)pyrrolidine-1-carbonyl)phenyl)acrylamide

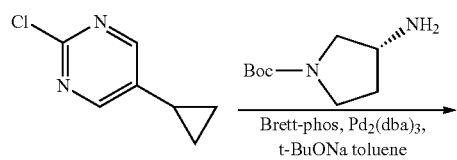

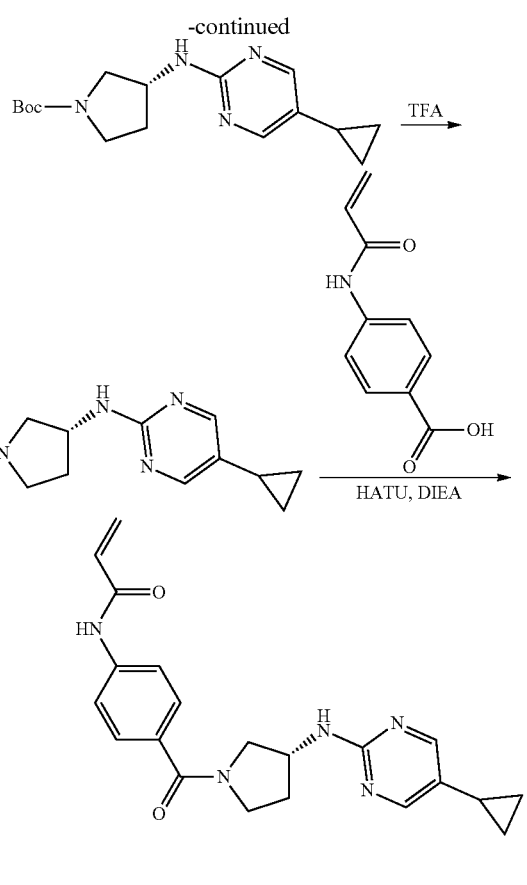

Step 1: (R)-tert-butyl 3-((5-cyclopropylpyrimidin-2-yl)amino)pyrrolidine-1-carboxylate

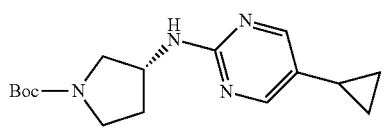 [SMILES: CC(C)(C)OC(=O)N1CC[C@@H](Nc2ncc(C3CC3)cn2)C1]

A mixture of 2-chloro-5-cyclopropylpyrimidine (200 mg, 1.3 mmol), (R)-tert-butyl 3-aminopyrrolidine-1-carboxylate (242 mg, 1.3 mmol), Brett-phos (107 mg, 0.2 mmol), Pd$_2$(dba)$_3$ (59 mg, 0.07 mmol) and t-BuONa (250 mg, 2.6 mmol) in toluene (5 mL) was stirred at 100° C. under N$_2$ overnight. The mixture was cooled to RT and concentrated. The residue was purified by flash chromatography on silica gel (petroleum ether/EtOAc=50/1 to petroleum ether/EtOAc=1/1) to afford (R)-tert-butyl 3-((5-cyclopropylpyrimidin-2-yl)amino)pyrrolidine-1-carboxylate (50 mg, 11%) as yellow oil. [M+H] Calc'd for $C_{16}H_{24}N_4O_2$, 305.1; Found, 305.1.

Step 2: (R)-5-cyclopropyl-N-(pyrrolidin-3-yl)pyrimidin-2-amine 2,2,2-trifluoroacetate

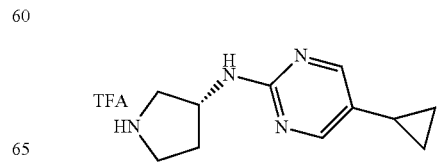

The title compound was prepared in 100% yield from (R)-tert-butyl 3-((5-cyclopropylpyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{11}H_{16}N_4$, 205.1; Found, 205.1.

Step 3: (R)—N-(4-(3-((5-cyclopropylpyrimidin-2-yl)amino)pyrrolidine-1-carbonyl)phenyl)acrylamide

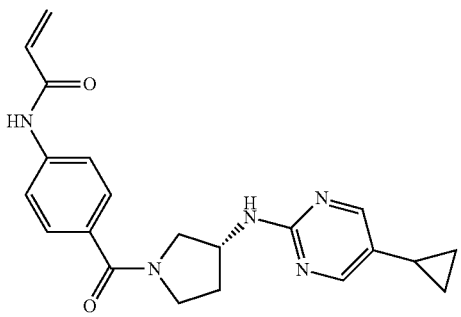 [SMILES: C=CC(=O)Nc1ccc(C(=O)N2CC[C@@H](Nc3ncc(C4CC4)cn3)C2)cc1]

The title compound was prepared in 29% yield from (R)-5-cyclopropyl-N-(pyrrolidin-3-yl)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 0.57-0.62 (m, 2H), 0.81-0.86 (m, 2H), 1.68-2.17 (m, 3H), 3.37-3.79 (m, 4H), 4.22-4.24 (m, 0.5H), 4.39-4.41 (m, 0.5H), 5.78 (d, J=10.8 Hz, 1H), 6.25-6.30 (m, 1H), 6.40-6.47 (m, 1H), 7.28 (s, 1H), 7.48-7.53 (m, 2H), 7.68-7.73 (m, 2H), 8.05 (s, 1H), 8.12 (s, 1H), 10.31 (s, 1H). [M+H] Calc'd for $C_{21}H_{23}N_5O_2$, 378.1; Found, 378.1.

Example 59: Synthesis of (R)—N-(4-(3-((5-fluoro-4-methoxypyrimidin-2-yl)amino)pyrrolidine-1-carbonyl)phenyl)acrylamide

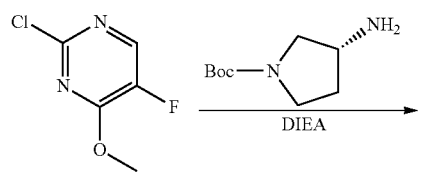

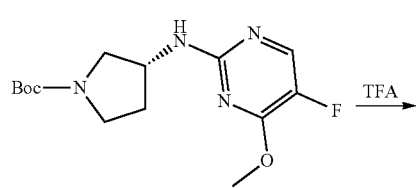

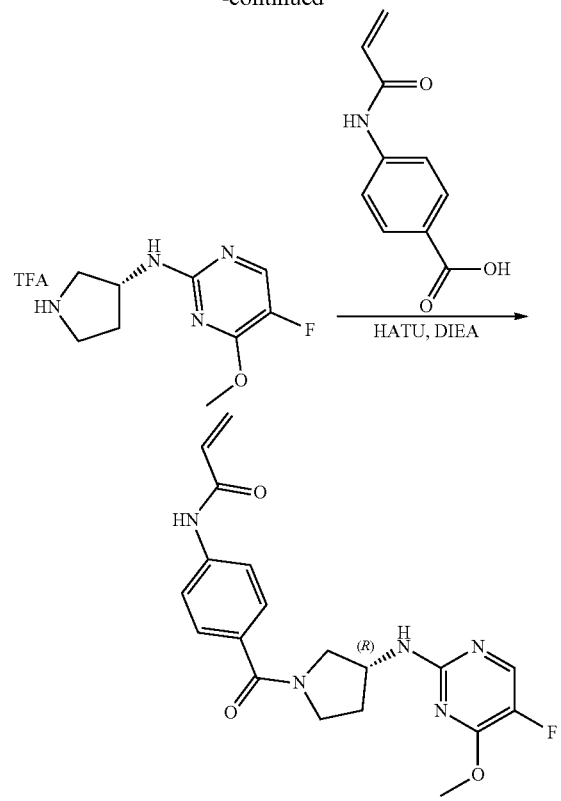

Step 1: (R)-tert-butyl 3-((5-fluoro-4-methoxypyrimidin-2-yl)amino)pyrrolidine-1-carboxylate

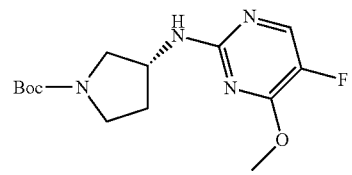 [SMILES: COc1nc(N[C@@H]2CCN(C(=O)OC(C)(C)C)C2)ncc1F]

The title compound was prepared in 32% yield from 2-chloro-5-fluoro-4-methoxypyrimidine using general procedure of (R)-tert-butyl 3-((5-chloro-4-methylpyrimidin-2-yl)amino)pyrrolidine-1-carboxylate. [M+H] Calc'd for $C_{14}H_{21}FN_4O_3$, 313.1; Found, 313.1.

Step 2: (R)-5-fluoro-4-methoxy-N-(pyrrolidin-3-yl)pyrimidin-2-amine 2,2,2-trifluoroacetate

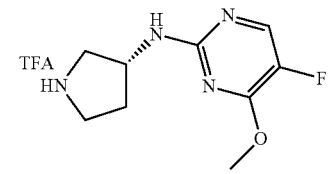

The title compound was prepared in 90% yield from (R)-tert-butyl 3-((5-fluoro-4-methoxypyrimidin-2-yl)

amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_9H_{13}FN_4O$, 213.1; Found, 213.1.

Step 3: (R)—N-(4-(3-((5-fluoro-4-methoxypyrimidin-2-yl)amino)pyrrolidine-1-carbonyl)phenyl)acrylamide

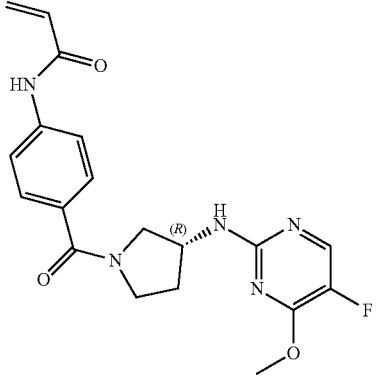

The title compound was prepared in 7.5% yield from (R)-5-fluoro-4-methoxy-N-(pyrrolidin-3-yl)pyrimidin-2-amine 2,2,2-trifluoroacetate using general procedure of (R)—N-(4-(3-((5-chloro-4-methylpyrimidin-2-yl)amino) pyrrolidine-1-carbonyl)phenyl)acrylamide. $^1$H NMR (400 MHz, DMSO-$d_6$): δ 1.86-2.00 (m, 1H), 2.07-2.17 (m, 1H), 3.35-3.44 (m, 1H), 3.47-3.56 (m, 1H), 3.60-3.79 (m, 2H), 3.86 (s, 1.5H), 3.94 (s, 1.5H), 4.20-4.22 (m, 0.5H), 4.37-4.39 (m, 0.5H), 5.78 (d, J=12.0 Hz, 1H), 6.27 (d, J=16.8 Hz, 1H), 6.41-6.47 (m, 1H), 7.41-7.45 (m, 1H), 7.48-7.53 (m, 2H), 7.68-7.73 (m, 2H), 8.05 (d, J=2.8 Hz, 0.5H), 8.12 (d, J=2.8 Hz, 0.5H), 10.30 (s, 1H). [M+H] Calc'd for $C_{19}H_{20}FN_5O_3$, 386.1; Found, 386.1.

Example 60: Synthesis of (R)—N-(4-(3-((5-(trifluoromethyl)pyrazin-2-yl)amino)pyrrolidine-1-carbonyl)phenyl)acrylamide

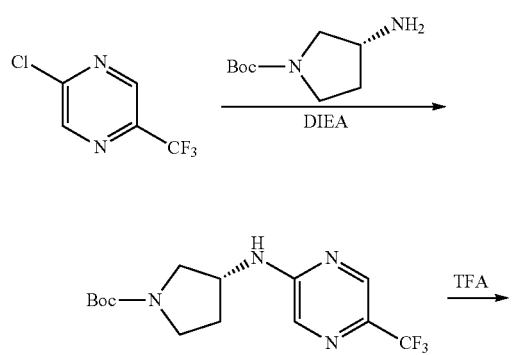

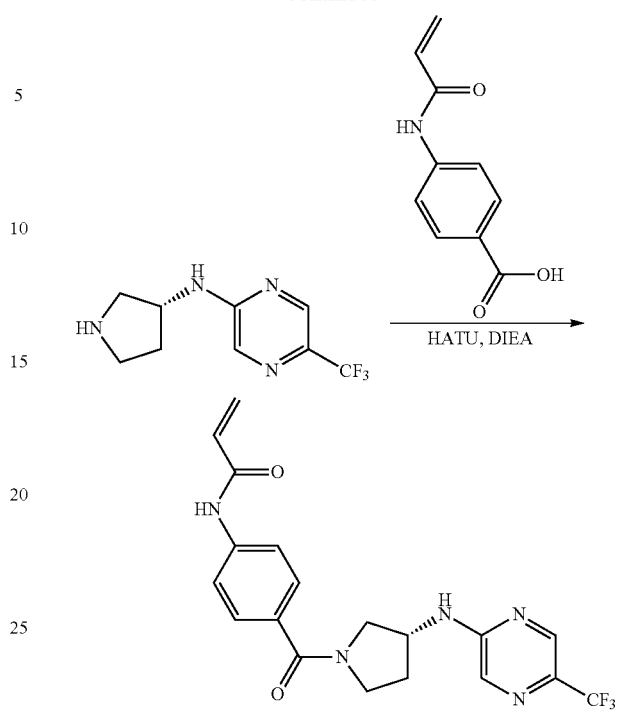

Step 1: (R)-tert-butyl 3-((5-(trifluoromethyl)pyrazin-2-yl)amino)pyrrolidine-1-carboxylate

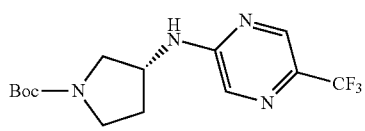 [SMILES: CC(C)(C)OC(=O)N1CC[C@@H](Nc2cnc(C(F)(F)F)cn2)C1]

The title compound was prepared in 43% yield from 2-chloro-5-(trifluoromethyl)pyrazine using general procedure of (R)-tert-butyl 3-((5-chloro-4-methylpyrimidin-2-yl) amino)pyrrolidine-1-carboxylate. [M+H] Calc'd for $C_{14}H_{19}F_3N_4O_2$, 333.1; Found, 333.1.

Step 2: (R)—N-(pyrrolidin-3-yl)-5-(trifluoromethyl) pyrazin-2-amine 2,2,2-trifluoroacetate

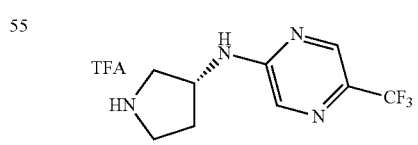

The title compound was prepared in 100% yield from (R)-tert-butyl 3-((5-(trifluoromethyl)pyrazin-2-yl)amino) pyrrolidine-1-carboxylate using general procedure of (R)-5-chloro-4-methyl-N-(pyrrolidin-3-yl)pyrimidin-2-amine 2,2, 2-trifluoroacetate. [M+H] Calc'd for $C_9H_{11}F_3N_4$, 233.0; Found, 233.0.

Step 3: (R)—N-(4-(3-((5-(trifluoromethyl)pyrazin-2-yl)amino)pyrrolidine-1-carbonyl)phenyl)acrylamide

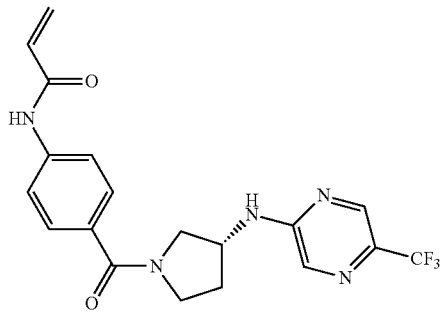 [SMILES: C=CC(=O)Nc1ccc(C(=O)N2CC[C@@H](Nc3cnc(C(F)(F)F)cn3)C2)cc1]

The title compound was prepared in 26% yield from (R)—N-(pyrrolidin-3-yl)-5-(trifluoromethyl)pyrazin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.91-1.98 (m, 1H), 2.19-2.22 (m, 1H), 3.37-3.48 (m, 1H), 3.56-3.65 (m, 2H), 3.80-3.86 (m, 1H), 4.37-4.47 (m, 1H), 5.78 (d, J=10.8 Hz, 1H), 6.28 (d, J=16.8 Hz, 1H), 6.41-6.47 (m, 1H), 7.50-7.54 (m, 2H), 7.69-7.74 (m, 2H), 8.00 (s, 0.5H), 8.04 (s, 0.5H), 8.18-8.26 (m, 1H), 8.35 (s, 0.5H), 8.44 (s, 0.5H), 10.30 (s, 1H). [M+H] Calc'd for $C_{19}H_{18}F_3N_5O_2$, 406.1; Found, 406.1.

Example 61: Synthesis of (R)—N-(4-(3-((5-methylpyrazin-2-yl)amino)pyrrolidine-1-carbonyl)phenyl)acrylamide

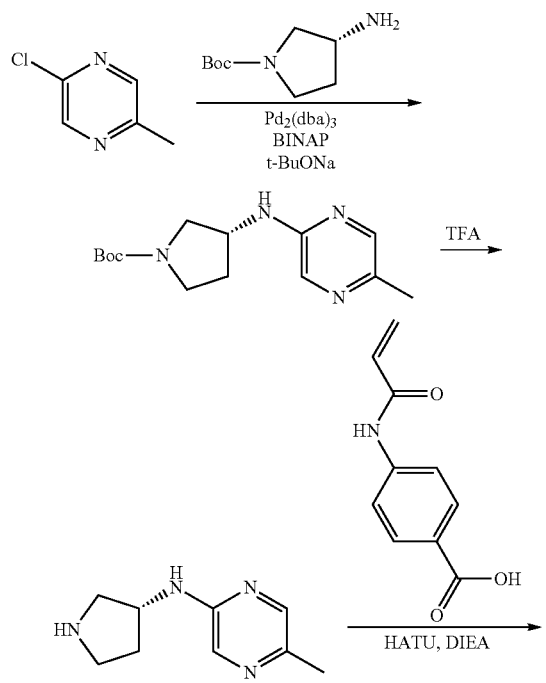

Step 1: (R)-tert-butyl 3-((5-methylpyrazin-2-yl)amino)pyrrolidine-1-carboxylate

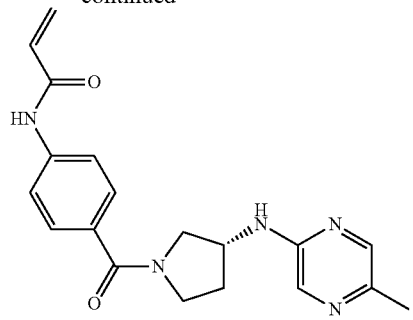

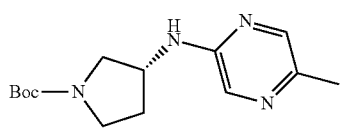 [SMILES: Cc1cnc(N[C@@H]2CCN(C(=O)OC(C)(C)C)C2)cn1]

A mixture of 2-chloro-5-methylpyrazine (300 mg, 1.6 mmol), (R)-tert-butyl 3-aminopyrrolidine-1-carboxylate (206 mg, 1.6 mmol), BINAP (199 mg, 0.3 mmol), Pd$_2$(dba)$_3$ (73 mg, 0.08 mmol) and t-BuONa (307 mg, 3.2 mmol) in toluene (10 mL) was stirred at 80° C. under N$_2$ for 3 hours. The mixture was cooled to RT and concentrated. The residue was purified by reverse phase chromatography to afford (R)-tert-butyl 3-((5-methylpyrazin-2-yl)amino)pyrrolidine-1-carboxylate (240 mg, 54%) as yellow oil. [M+H] Calc'd for $C_{14}H_{22}N_4O_2$, 279.1; Found, 279.1.

Step 2: (R)-5-methyl-N-(pyrrolidin-3-yl)pyrazin-2-amine 2,2,2-trifluoroacetate

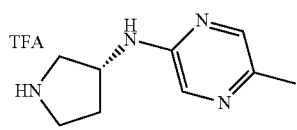

The title compound was prepared in 100 yield from (R)-tert-butyl 3-((5-methylpyrazin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_9H_{14}N_4$, 179.1; Found, 179.1.

Step 3: (R)—N-(4-(3-((5-methylpyrazin-2-yl)amino)pyrrolidine-1-carbonyl)phenyl)acrylamide

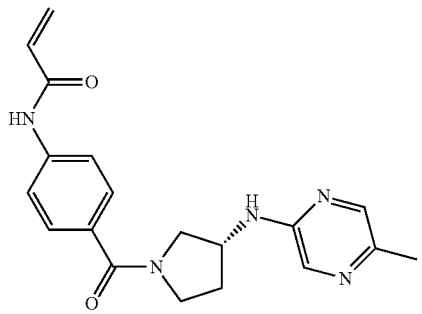 [SMILES: C=CC(=O)Nc1ccc(C(=O)N2CC[C@@H](Nc3cnc(C)cn3)C2)cc1]

The title compound was prepared in 25% yield from (R)-5-methyl-N-(pyrrolidin-3-yl)pyrazin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.88-1.95 (m, 1H), 2.13-2.26 (m, 4H), 3.37-3.41 (m, 1H), 3.52-3.68 (m, 2H), 3.76-3.83 (m, 1H), 4.22-4.36 (m, 1H), 5.78 (d, J=10.4 Hz, 1H), 6.27 (d, J=16.8 Hz, 1H), 6.40-6.47 (m, 1H), 7.04-7.09 (m, 1H), 7.48-7.54 (m, 2H), 7.68-7.76 (m, 2H), 7.83-7.87 (m, 2H), 10.29 (s, 1H). [M+H] Calc'd for C$_{19}$H$_{21}$N$_5$O$_2$, 352.1; Found, 352.1.

Example 62: Synthesis of (R)—N-(4-(3-((5-chloro-4-(methylamino)pyrimidin-2-yl)amino)pyrrolidine-1-carbonyl)phenyl)acrylamide

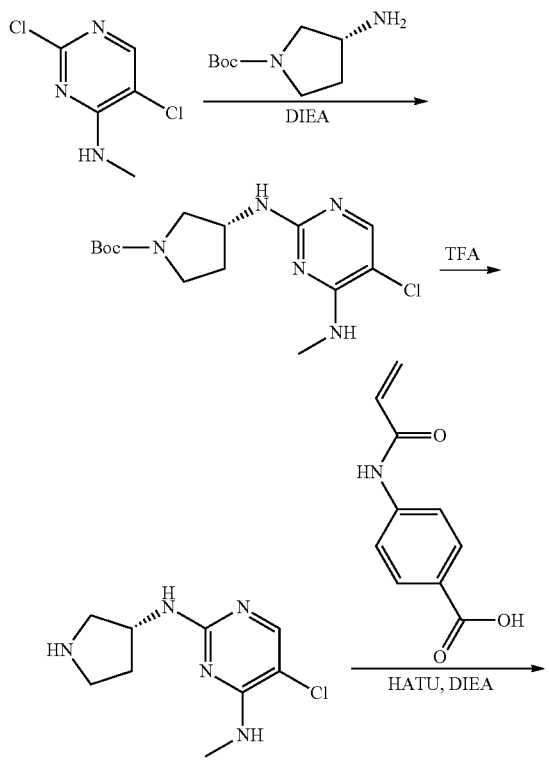

-continued

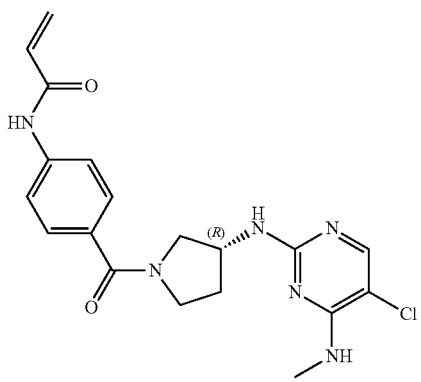

Step 1: (R)-tert-butyl 3-((5-chloro-4-(methylamino)pyrimidin-2-yl)amino)pyrrolidine-1-carboxylate

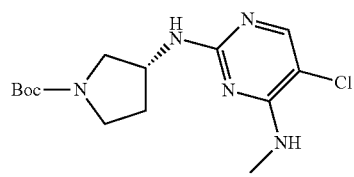 [SMILES: CNc1nc(N[C@@H]2CCN(C(=O)OC(C)(C)C)C2)ncc1Cl]

The title compound was prepared in 39% yield from 2,5-dichloro-N-methylpyrimidin-4-amine using general procedure of (R)-tert-butyl 3-((5-chloro-4-methylpyrimidin-2-yl)amino)pyrrolidine-1-carboxylate. [M+H] Calc'd for C$_{14}$H$_{22}$ClN$_5$O$_2$, 328.1; Found, 328.1.

Step 2: (R)-5-chloro-N4-methyl-N2-(pyrrolidin-3-yl)pyrimidine-2,4-diamine

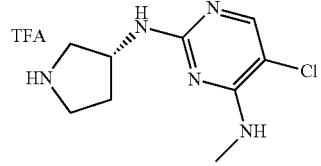

The title compound was prepared in 100% yield from (R)-tert-butyl 3-((5-chloro-4-(methylamino)pyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for C$_9$H$_{14}$ClN$_5$, 228.0; Found, 228.0.

Step 3: (R)—N-(4-(3-((5-chloro-4-(methylamino) pyrimidin-2-yl)amino)pyrrolidine-1-carbonyl)phenyl)acrylamide

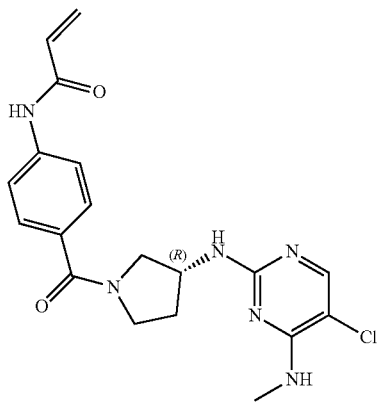

The title compound was prepared in 21% yield from (R)-5-chloro-N⁴-methyl-N²-(pyrrolidin-3-yl)pyrimidine-2,4-diamine 2,2,2-trifluoroacetate using general procedure of (R)—N-(4-(3-((5-chloro-4-methylpyrimidin-2-yl)amino)pyrrolidine-1-carbonyl)phenyl)acrylamide. ¹H NMR (400 MHz, DMSO-d₆): δ 1.86-2.00 (m, 1H), 2.07-2.17 (m, 1H), 2.74 (s, 1.5H), 2.85 (s, 1.5H), 3.39-3.75 (m, 4H), 4.18-4.22 (m, 0.5H), 4.36-4.40 (m, 0.5H), 5.78 (d, J=10.4 Hz, 1H), 6.26-6.30 (m, 1H), 6.41-6.48 (m, 1H), 6.89-7.05 (m, 2H), 7.48-7.54 (m, 2H), 7.69-7.77 (m, 3H), 10.32 (s, 1H). [M+H] Calc'd for C₁₉H₂₁ClN₆O₂, 401.1; Found, 401.1.

Example 63: Synthesis of (R)-1-(7-(3-((5-chloro-4-methoxypyrimidin-2-yl)amino)pyrrolidine-1-carbonyl)-2H-benzo[b][1,4]oxazin-4(3H)-yl)prop-2-en-1-one

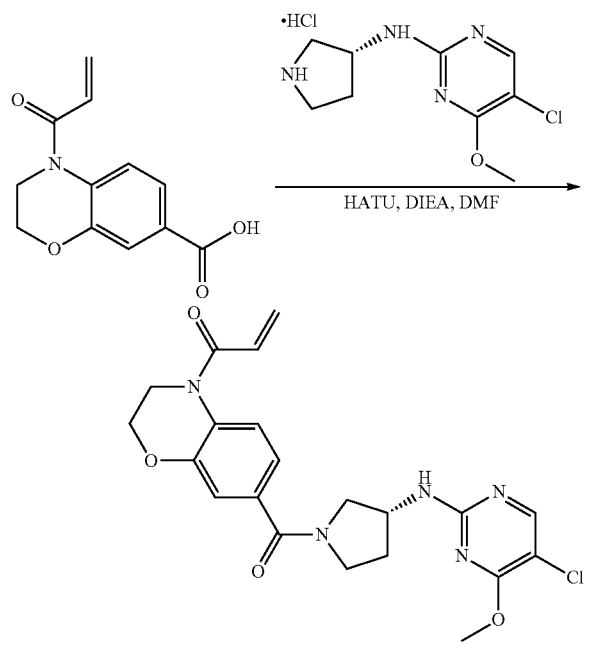

A mixture of 4-acryloyl-3,4-dihydro-2H-benzo[b][1,4]oxazine-7-carboxylic acid (150 mg, 0.64 mmol), (R)-5-chloro-4-methoxy-N-(pyrrolidin-3-yl)pyrimidin-2-amine hydrochloride (232 mg, 0.71 mmol), HATU (292 mg, 0.77 mmol) and DIEA (248 mg, 1.92 mmol) in DMF (20 mL) was stirred at RT overnight. The mixture was diluted with water (20 mL) and extracted with EA (20 mL*3). The combined organic layer was washed with brine (20 mL), dried over Na₂SO₄, filtered and concentrated in vacuo. The residue was purified by prep-HPLC to afford (R)-1-(7-(3-((5-chloro-4-methoxypyrimidin-2-yl)amino)pyrrolidine-1-carbonyl)-2H-benzo[b][1,4]oxazin-4(3H)-yl)prop-2-en-1-one (89.9 mg, 32%) as a white solid. ¹H NMR (400 MHz, DMSO-d₆): δ 1.91-2.13 (m, 2H), 3.50-3.95 (m, 9H), 4.30-4.31 (m, 3H), 5.83-5.85 (m, 1H), 6.25-6.30 (m, 1H), 6.78-6.79 (m, 1H), 7.02-7.08 (m, 2H), 7.49-7.67 (m, 2H), 8.08-8.14 (m, 1H). [M+H] Calc'd for C₂₁H₂₂ClN₅O₄, 444.1; Found, 444.1.

Example 64: Synthesis of (R)—N-(4-(3-((5-chloropyridin-2-yl)amino)pyrrolidine-1-carbonyl)phenyl)acrylamide

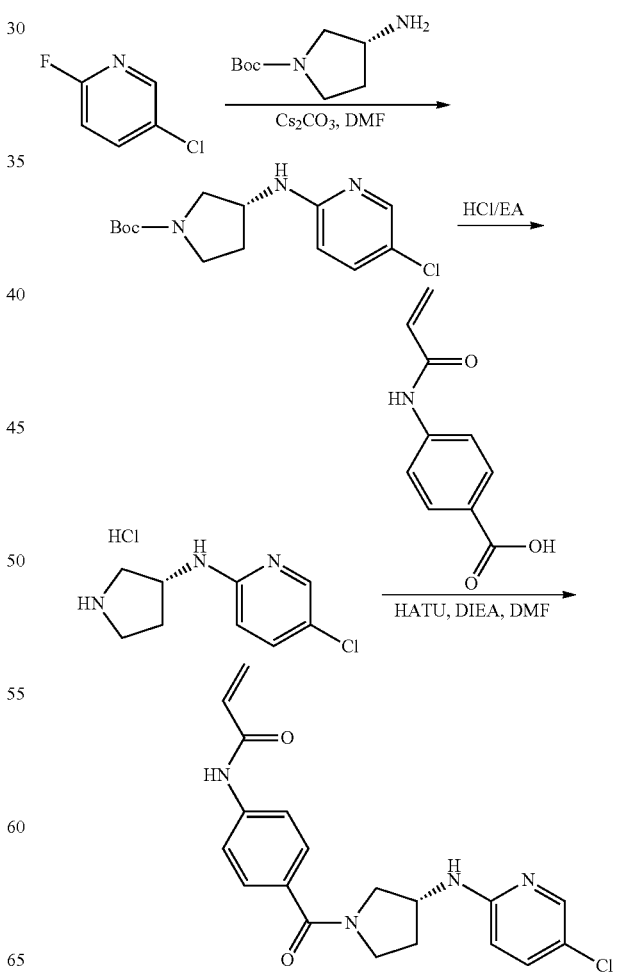

Step 1: (R)-tert-butyl 3-((5-chloropyridin-2-yl)amino)pyrrolidine-1-carboxylate

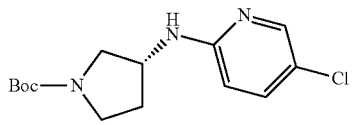 [SMILES: CC(C)(C)OC(=O)N1CC[C@@H](Nc2ccc(Cl)cn2)C1]

A mixture of 5-chloro-2-fluoropyridine (424 mg, 2.28 mmol), (R)-tert-butyl 3-aminopyrrolidine-1-carboxylate (300 mg, 2.28 mmol) and $Cs_2CO_3$ (1486 mg, 4.56 mmol) in DMF (2 mL) was stirred at 120° C. for 14 hours. The mixture was cooled to RT and concentrated. The residue was purified by flash chromatography on silica gel (petroleum ether/EtOAc=5/1) to afford (R)-tert-butyl 3-((5-chloropyridin-2-yl)amino)pyrrolidine-1-carboxylate (150 mg, 22%) as a white solid. [M+H] Calc'd for $C_{14}H_{20}ClN_3O_2$, 298.1; Found, 298.1.

Step 2: (R)-5-chloro-N-(pyrrolidin-3-yl)pyridin-2-amine hydrochloride

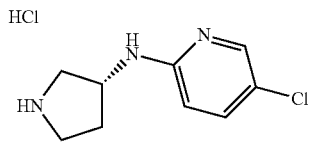 [SMILES: Cl ; Clc1ccc(N[C@@H]2CCNC2)nc1]

The title compound was prepared in 100% yield from (R)-tert-butyl 3-((5-chloropyridin-2-yl)amino)pyrrolidine-1-carboxylate using general procedure of (R)-5-chloro-4-methyl-N-(pyrrolidin-3-yl)pyridin-2-amine hydrochloride. [M+H] Calc'd for $C_9H_{12}ClN_3$, 198.0; Found, 198.0.

Step 3: (R)—N-(4-(3-((5-chloropyridin-2-yl)amino)pyrrolidine-1-carbonyl)phenyl)acrylamide

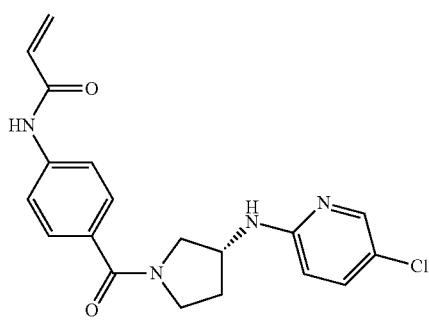 [SMILES: C=CC(=O)Nc1ccc(C(=O)N2CC[C@@H](Nc3ccc(Cl)cn3)C2)cc1]

The title compound was prepared in 11% yield from (R)-5-chloro-N-(pyrrolidin-3-yl)pyridin-2-amine hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, $CDCl_3$): δ 1.96-2.01 (m, 1H), 2.25-2.50 (m, 1H), 3.37-3.96 (m, 4H), 4.34-4.37 (m, 1H), 4.52-4.60 (m, 1H), 5.79 (d, J=10.4 Hz, 1H), 6.24-6.33 (m, 1H), 6.39-6.47 (m, 1H), 7.32-7.40 (m, 1H), 7.43-7.70 (m, 5H), 7.98 (s, 0.5H), 8.05 (s, 0.5H). [M+H] Calc'd for $C_{19}H_9CN_4O_2$, 371.1; Found, 371.1.

Example 65: Synthesis of (R)-1-(6-(3-((5-chloro-4-methoxypyrimidin-2-yl)amino)pyrrolidine-1-carbonyl)-3,4-dihydroquinolin-1(2H)-yl)prop-2-en-1-one

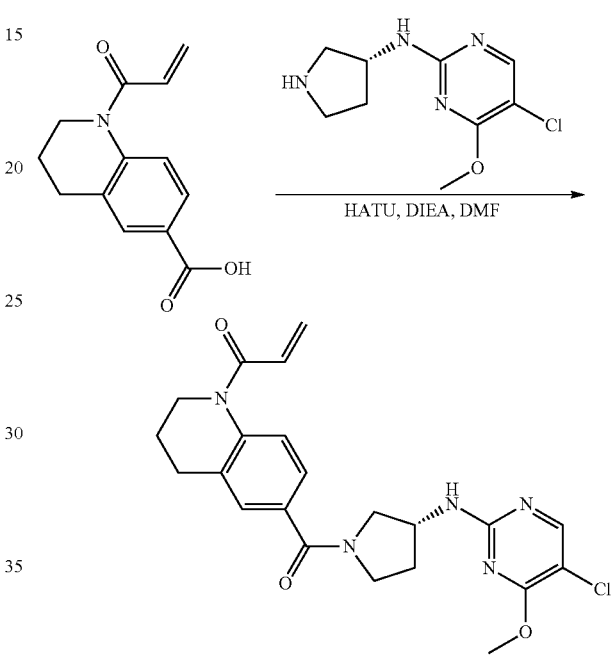

The title compound was prepared in 18% yield from 1-acryloyl-1,2,3,4-tetrahydro-quinoline-6-carboxylic acid using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.88-2.15 (m, 4H), 2.72-2.73 (m, 2H), 3.28-3.94 (m, 9H), 4.29-4.45 (m, 1H), 5.72 (d, J=12.0 Hz, 1H), 6.22 (d, J=8.8 Hz, 1H), 6.57 (d, J=16.8 Hz, 1H), 7.35 (m, 3H), 7.67 (m, 1H), 8.11 (s, 1H). [M+H] Calcd.: 442, Found: 442.

Example 66: Synthesis of (R)—N-(2-chloro-4-(3-((5-chloro-4-methoxypyrimidin-2-yl)amino)pyrrolidine-1-carbonyl)phenyl)acrylamide

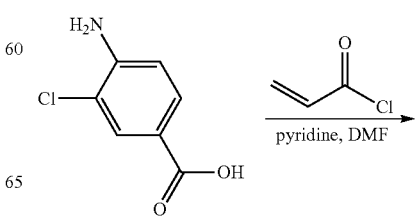

247

-continued

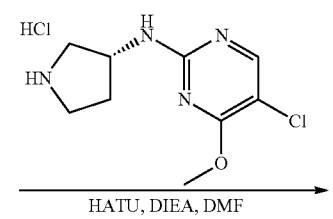

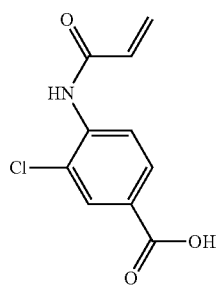 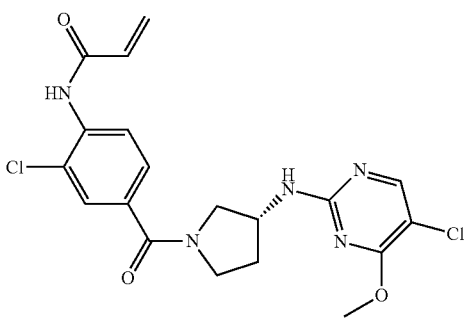

Step 2: (R)—N-(2-chloro-4-(3-((5-chloro-4-methoxypyrimidin-2-yl)amino)pyrrolidine-1-carbonyl)phenyl)acrylamide

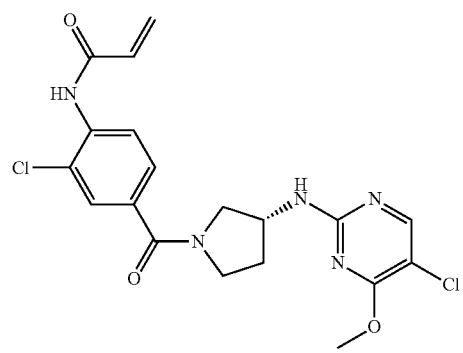

A mixture of 4-acrylamido-3-chlorobenzoic acid (150 mg, 0.67 mmol), (R)-5-chloro-4-methoxy-N-(pyrrolidin-3-yl)pyrimidin-2-amine hydrochloride (235 mg, 0.73 mmol), HATU (305 mg, 0.8 mmol) and DIEA (260 mg, 2.01 mmol) in DMF (15 mL) was stirred at RT overnight. The mixture was concentrated and purified by prep-HPLC to afford (R)—N-(2-chloro-4-(3-((5-chloro-4-methoxypyrimidin-2-yl)amino)pyrrolidine-1-carbonyl)phenyl)acrylamide (130.1 mg, 44%) as a white solid. $^1$H NMR (400 MHz, DMSO-d$_6$): δ 1.90-2.14 (m, 2H), 3.29-3.94 (m, 7H), 4.27-4.44 (m, 1H), 5.80-5.82 (m, 1H), 6.28-6.32 (m, 1H), 6.62-6.69 (m, 1H), 7.50-7.51 (m, 1H), 7.62-7.67 (m, 2H), 7.89-7.91 (m, 1H), 8.08-8.14 (m, 1H), 9.79-9.80 (m, 1H). [M+H] Calc'd for $C_{19}H_9Cl_2N_5O_3$, 436.1; Found, 436.1.

Example 67: Synthesis of (R)—N-(4-(3-((5-chloro-4-methoxypyrimidin-2-yl)amino)pyrrolidine-1-carbonyl)thiazol-2-yl)acrylamide Step 1: 4-acrylamido-3-chlorobenzoic acid

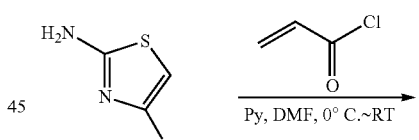


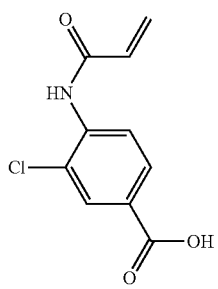

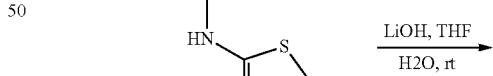

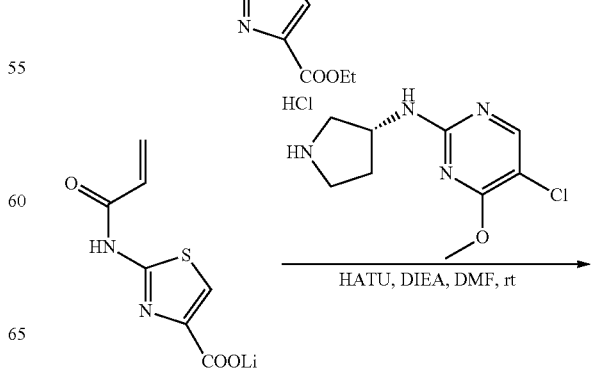

A mixture of 4-amino-3-chlorobenzoic acid (4.0 g, 23.3 mmol) in DMF (30 mL) was added Pyridine (3.6 g, 45.6 mmol) at 0° C. and then acryloyl chloride (2.1 g, 23.2 mmol). The reaction mixture was stirred at RT for 16 h. The mixture was concentrated and added DCM (100 mL), washed with 0.5N HCl (30 mL), dried over Na$_2$SO$_4$, filtered and concentrated in vacuo to afford 4-acrylamido-3-chlorobenzoic acid (770 mg, 11%) as yellow solid. [M+H] Calc'd for $C_{10}H_8ClNO_3$, 226.1; Found, 226.1

249
-continued

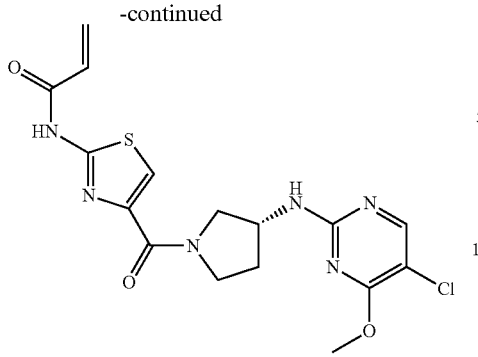

Step 1: ethyl 2-acrylamidothiazole-4-carboxylate

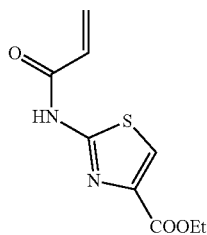

To a solution of ethyl 2-aminothiazole-4-carboxylate (5.0 g, 29.0 mmol) in DMF (35 mL) was added pyridine (2.5 mL) at 0° C. Then to the mixture was added acryloyl chloride (3.5 mL, 43.6 mmol) dropwise over 3 min. The mixture was stirred at RT overnight. The reaction was quenched with water (50 mL) and extracted with EA (50 mL*3). The combined organic layers were washed with water (100 mL*2) and brine (100 mL), dried over $Na_2SO_4$, filtered and concentrated in vacuo. The residue was purified by flash chromatography on silica gel (PE/EA=1/1) to give ethyl 2-acrylamidothiazole-4-carboxylate (1.5 g, 23%). [M+H] Calcd.: 227, Found: 227.

Step 2: 2-acrylamidothiazole-4-carboxylic acid

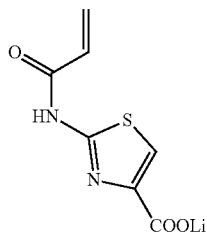

To a solution of 2-acrylamidothiazole-4-carboxylate (500 mg, 2.22 mmol) in THF (15 mL) and water (15 mL) was added $LiOH.H_2O$ (93 mg, 2.22 mmol) at rt. The mixture was stirred at RT overnight. The reaction was concentrated in vacuo to give lithium 2-acrylamidothiazole-4-carboxylate (400 mg, 23%). [M+H] Calcd.: 199, Found: 199.

250

Step 3: (R)—N-(4-(3-((5-chloro-4-methoxypyrimidin-2-yl)amino)pyrrolidine-1-carbonyl)thiazol-2-yl)acrylamide

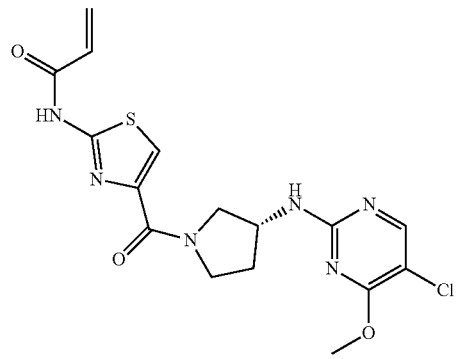 [SMILES: C=CC(=O)Nc1nc(C(=O)N2CC[C@@H](Nc3ncc(Cl)c(OC)n3)C2)cs1]

The title compound was prepared in 14% yield from Lithium salt of 2-Acryloylamino-thiazole-4-carboxylic acid using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.99-2.02 (m, 1H), 2.10-2.15 (m, 1H), 3.67-3.69 (m, 3H), 3.97-4.00 (m, 3H), 4.10-4.40 (m, 2H), 5.89-5.92 (m, 1H), 6.40 (d, J=10.0 Hz, 1H), 6.51-6.52 (m, 1H), 7.67 (s, 1H), 7.75 (s, 1H), 8.12 (d, J=10.0 Hz, 1H), 12.39 (s, 1H). [M+H] Calcd.: 409, Found: 409.

Example 68: Synthesis of (R)—N-(4-(3-((5-chloro-4-methoxypyrimidin-2-yl)amino)pyrrolidine-1-carbonyl)-2-morpholinophenyl)acrylamide

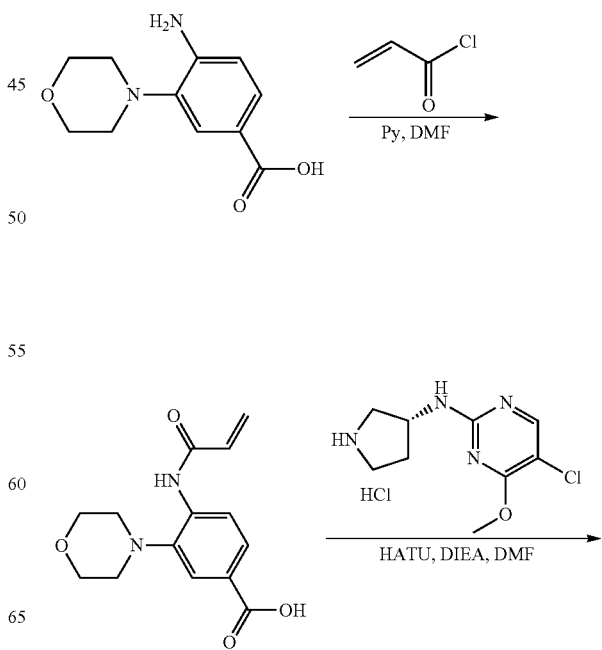

251

-continued

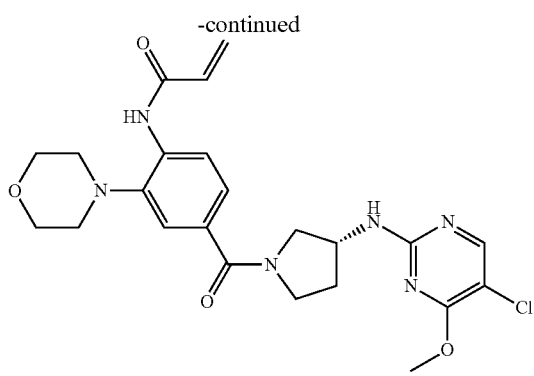

Step 1: 4-acrylamido-3-morpholinobenzoic acid

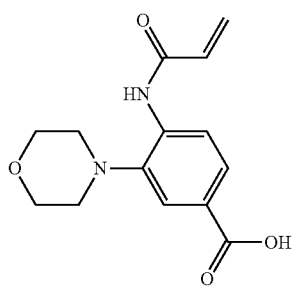 [SMILES: C=CC(=O)Nc1ccc(C(=O)O)cc1N1CCOCC1]

To a mixture of 4-amino-3-morpholinobenzoic acid (500 mg, 2.25 mmol) in DMF (20 mL) was added Pyridine (533 mg, 6.75 mmol) and acryloyl chloride (610 mg, 6.75 mmol) at 0° C. The mixture was stirred at RT for 5 h. The mixture was then concentrated and purified by column to afford 4-acrylamido-3-morpholinobenzoic acid (170 mg, 27%) as a white solid. [M+H] Calc'd for $C_{14}H_{17}N_2O_4$, 277.1; Found, 277.1.

Step 2: (R)—N-(4-(3-((5-chloro-4-methoxypyrimidin-2-yl)amino)pyrrolidine-1-carbonyl)-2-morpholinophenyl)acrylamide

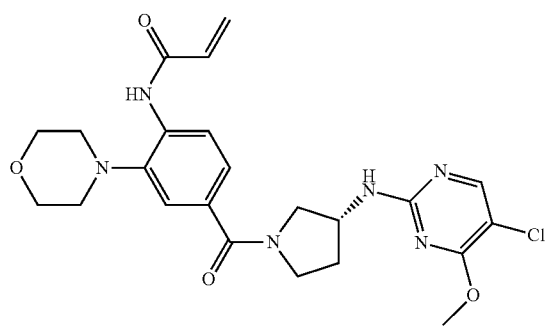 [SMILES: C=CC(=O)Nc1ccc(C(=O)N2CC[C@@H](Nc3ncc(Cl)c(OC)n3)C2)cc1N1CCOCC1]

A mixture of 4-acrylamido-3-morpholinobenzoic acid (150 mg, 0.54 mmol), (R)-5-chloro-4-methoxy-N-(pyrrolidin-3-yl)pyrimidin-2-amine (HCl salt) (193 mg, 0.59 mmol), HATU (246 mg, 0.65 mmol) and DIEA (209 mg, 1.62 mmol) in DMF (10 mL) was stirred at RT overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(4-(3-((5-chloro-4-methoxypyrimidin-2-yl)amino)pyrrolidine-1-carbonyl)-2-morpholinophenyl)acrylamide (101 mg, 38%) as a white solid (TFA salt). $^1$H NMR (400 MHz, DMSO-$d_6$): δ 1.93-2.09 (m, 1H), 2.09-2.31 (m, 1H), 2.78-2.83 (m, 4H), 3.41-3.45 (m, 1H), 3.50-3.55 (m, 1H), 3.62-3.69 (m, 1H), 3.79-3.95 (m, 8H), 4.26-4.30 (m, 1H), 5.79 (d, J=10.4 Hz, 1H), 6.25 (s, 0.5H), 6.29 (s, 0.5H), 6.65-6.73 (m, 1H), 7.25-7.34 (m, 2H), 7.73 (br s, 1H), 8.05-8.15 (m, 2H), 9.20 (s, 0.5H), 9.22 (s, 0.5H). [M+H] Calc'd for $C_{23}H_{28}ClN_6O_4$, 487.1; Found, 487.

Example 69: Synthesis of (R)—N-(4-(3-((5-chloropyrimidin-2-yl)amino)pyrrolidine-1-carbonyl)-2-(1-methyl-1H-pyrazol-4-yl)phenyl)acrylamide

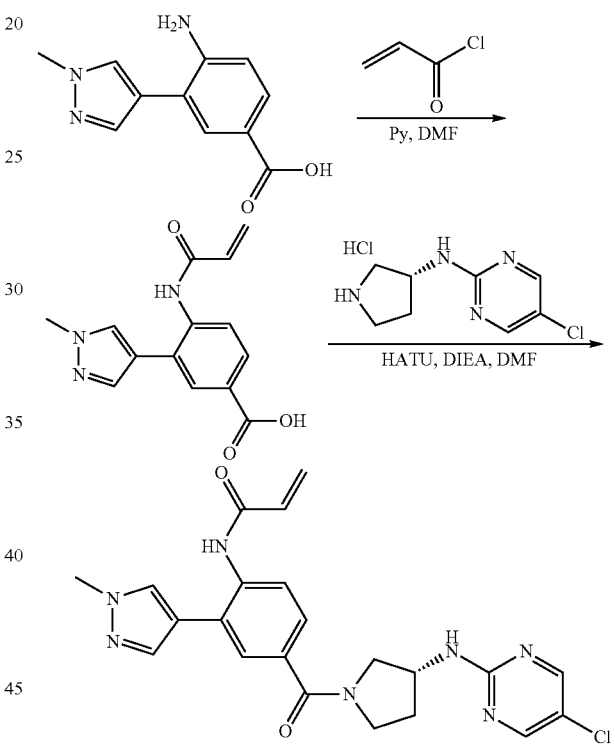

Step 1: 4-acrylamido-3-(1-methyl-1H-pyrazol-4-yl)benzoic Acid

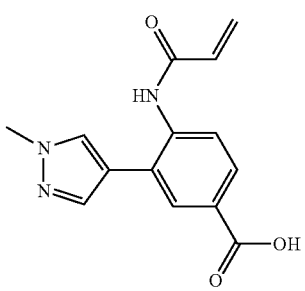 [SMILES: C=CC(=O)Nc1ccc(C(=O)O)cc1-c1cnn(C)c1]

To a mixture of 4-amino-3-(1-methyl-1H-pyrazol-4-yl)benzoic acid (500 mg, 2.30 mmol) in DMF (20 mL) was added Pyridine (545 mg, 6.90 mmol) at 0° C. followed by acryloyl chloride (312 mg, 3.45 mmol). The mixture was allowed to slowly warm to RT and stirred overnight. The mixture was then concentrated and purified by column chromatography to afford 4-acrylamido-3-(1-methyl-1H-pyrazol-4-yl)benzoic acid (150 mg, 24%) as white solid. [M+H] Calc'd for $C_{14}H_{14}N_3O_3$, 272.0; Found, 272.0

Step 2: (R)—N-(4-(3-((5-chloropyrimidin-2-yl)amino)pyrrolidine-1-carbonyl)-2-(1-methyl-1H-pyrazol-4-yl)phenyl)acrylamide

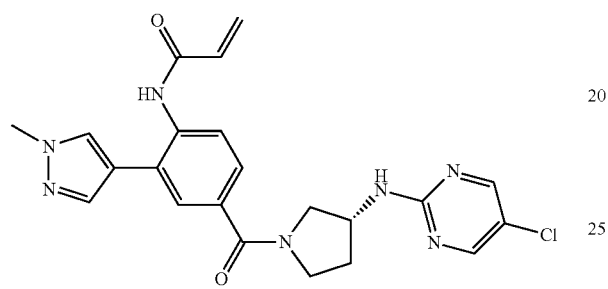

A mixture of 4-acrylamido-3-(1-methyl-1H-pyrazol-4-yl)benzoic acid (150 mg, 0.55 mmol), (R)-5-chloro-N-(pyrrolidin-3-yl)pyrimidin-2-amine (HCl salt) (155 mg, 0.66 mmol), HATU (250 mg, 0.66 mmol) and DIEA (212 mg, 1.65 mmol) in DMF (10 mL) was stirred at RT overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(4-(3-((5-chloropyrimidin-2-yl)amino)pyrrolidine-1-carbonyl)-2-(1-methyl-1H-pyrazol-4-yl)phenyl)acrylamide (96.2 mg, 39%) as a white solid (TFA salt). $^1$H NMR (400 MHz, DMSO-$d_6$): δ 1.88-2.01 (m, 1H), 2.11-2.19 (m, 1H), 3.37-3.46 (m, 1H), 3.64-3.67 (m, 1H), 3.74-3.80 (m, 2H), 3.85-3.88 (m, 3H), 4.21-4.42 (m, 1H), 5.75 (d, J=10.0 Hz, 1H), 6.22 (s, 0.5H), 6.26 (s, 0.5H), 6.48-6.55 (m, 1H), 7.35-7.40 (m, 1H), 7.54-7.68 (m, 3H), 7.81 (br s, 1H), 7.98 (d, J=8.4 Hz, 1H), 8.31 (s, 1H), 8.38 (s, 1H), 9.61 (s, 0.5H), 9.62 (s, 0.5H). [M+H] Calc'd for $C_{22}H_{23}ClN_7O_2$, 452.1; Found, 452.1.

Example 70: Synthesis of (R)—N-(4-(3-((5-cyanopyrimidin-2-yl)amino)pyrrolidine-1-carbonyl)phenyl)-N-methylacrylamide

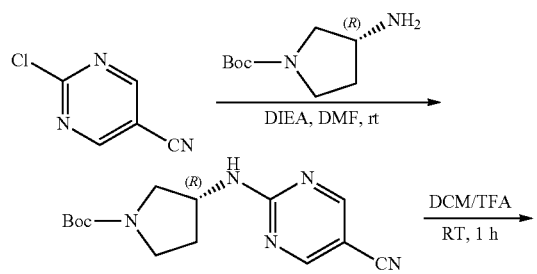

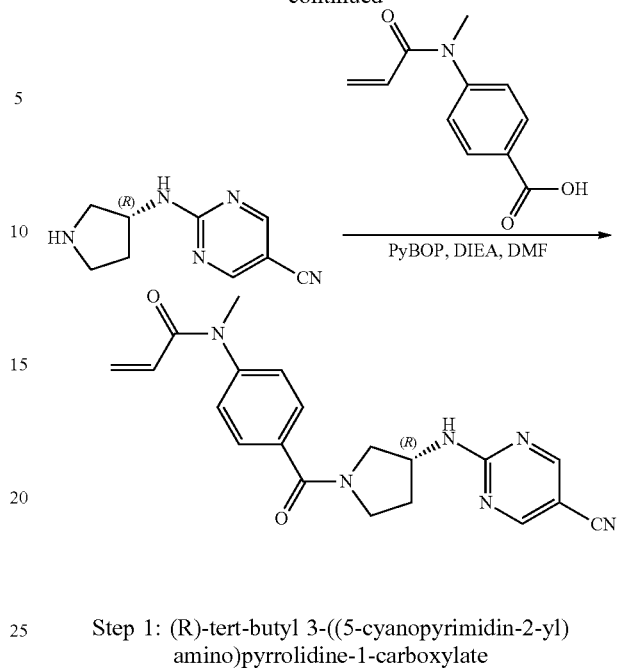

Step 1: (R)-tert-butyl 3-((5-cyanopyrimidin-2-yl)amino)pyrrolidine-1-carboxylate

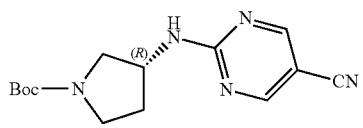

A mixture of 2-chloropyrimidine-5-carbonitrile (2.0 g, 14.3 mmol), (R)-tert-butyl 3-aminopyrrolidine-1-carboxylate (2.7 g, 14.3 mmol) and DIEA (4.6 g, 35.8 mmol) in DMF (20 mL) was stirred at rt overnight. The solution was poured into water (50 mL) and was extracted with DCM (50 mL*2). The combined organic layers were washed with water (100 mL*2) and brine (100 mL), dried over $Na_2SO_4$, concentrated and purified by flash column chromatography (PE:EA=10:1) to give (R)-tert-butyl 3-((5-cyanopyrimidin-2-yl)amino)pyrrolidine-1-carboxylate (4.1 g, 99%) as white solid. [M+H] MS Calc'd: $C_{14}H_9N_5O_2$, 290.2, Found: 290.2.

Step 2: (R)-2-(pyrrolidin-3-ylamino)pyrimidine-5-carbonitrile

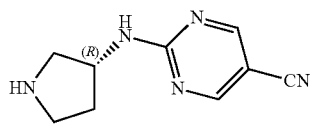

To a solution of (R)-tert-butyl 3-((5-cyanopyrimidin-2-yl)amino)pyrrolidine-1-carboxylate (2.0 g, 6.9 mmol) in DCM (15 mL) was added TFA (5 mL) at rt. The mixture was stirred at rt for 1 h and concentrated in vacuo to give crude product. DCM (20 mL) was added to the crude product and the reaction mixture was washed with sodium carbonate aqueous solution. The organics were dried over anhydrous sodium sulfate, filtered and concentrated in vacuo to give (R)-2-(pyrrolidin-3-ylamino)pyrimidine-5-carbonitrile (1.3 g, 100%) as an off-white solid. [M+H] MS Calc'd: $C_9H_{11}N_5$, 190.1; Found: 190.1.

Step 3: (R)—N-(4-(3-((5-cyanopyrimidin-2-yl)amino)pyrrolidine-1-carbonyl)phenyl)-N-methylacrylamide

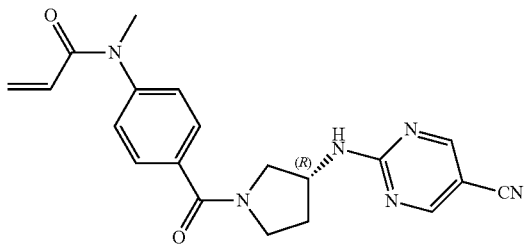

A mixture of 4-(N-methylacrylamido)benzoic acid (196 mg, 0.95 mmol), (R)-2-(pyrrolidin-3-ylamino)pyrimidine-5-carbonitrile (200 mg, 1.06 mmol), PyBOP (551 mg, 1.06 mmol) and DIEA (680 mg, 5.30 mmol) in DMF (15 mL) was stirred at rt for 3 h. The reaction mixture was concentrated in vacuo. The residue was purified by prep-HPLC to give (R)—N-(4-(3-((5-cyanopyrimidin-2-yl)amino)pyrrolidine-1-carbonyl)phenyl)-N-methylacrylamide (161.8 mg, 40.7%) as a white solid. $^1$H NMR (400 MHz, DMSO-$d_6$): 1.94-2.06 (m, 1H), 2.17-2.25 (m, 1H), 3.30 (d, J=4.4 Hz, 3H), 3.39-3.87 (m, 4H), 4.24-4.58 (m, 1H), 5.61-5.65 (m, 1H), 6.13-6.24 (m, 2H), 7.37 (t, J=11.6 Hz, 2H), 7.63 (t, J=10.4 Hz, 2H), 8.67-8.81 (m, 3H). [M+H] Ms Calc'd: $C_{20}H_{20}N_6O_2$, 377.2; Found, 377.1.

Example 71: Synthesis of (R)—N-(4-(3-((4-cyclopropoxy-5-fluoropyrimidin-2-yl)amino)pyrrolidine-1-carbonyl)phenyl)acrylamide

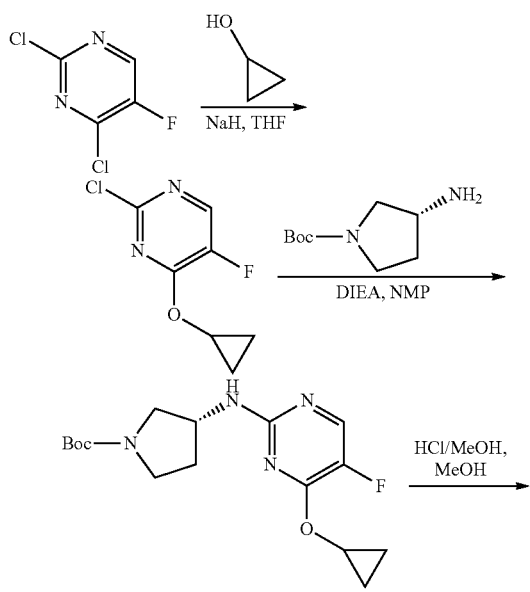

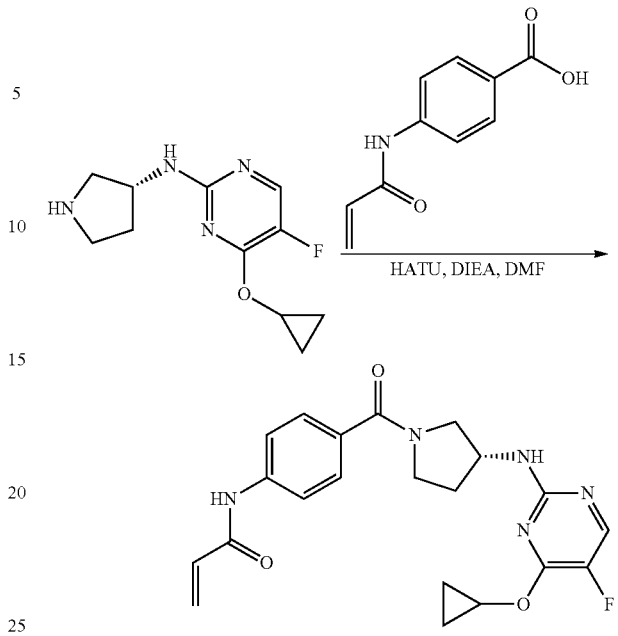

Step 1: 2-chloro-4-cyclopropoxy-5-fluoropyrimidine

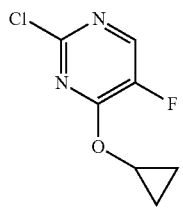 [SMILES: Fc1cnc(Cl)nc1OC1CC1]

The title compound was prepared in 100% yield from 2,4-dichloro-5-fluoropyrimidine using general procedure of 2-chloro-4-cyclopropoxy-5-methylpyrimidine. [M+H] Calc'd for $C_7H_6ClFN_2O$, 189.0; Found, 189.0.

Step 2: (R)-tert-butyl 3-((4-cyclopropoxy-5-fluoropyrimidin-2-yl)amino)pyrrolidine-1-carboxylate

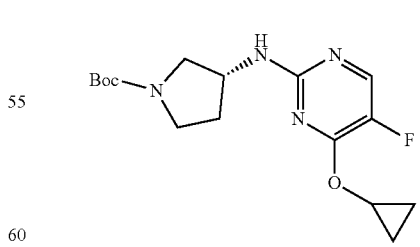

The title compound was prepared in 53% yield from 2-chloro-4-cyclopropoxy-5-fluoropyrimidine using general procedure of (R)-tert-butyl 3-((5-chloro-4-methylpyrimidin-2-yl)amino)pyrrolidine-1-carboxylate. [M+H] Calc'd for $C_{16}H_{23}FN_4O_3$, 339.1; Found, 339.1.

Step 3: (R)-4-cyclopropoxy-5-fluoro-N-(pyrrolidin-3-yl)pyrimidin-2-amine

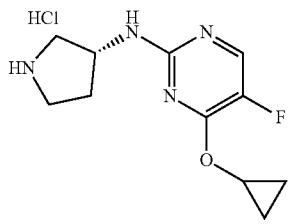 [SMILES: Cl ; Fc1cnc(N[C@@H]2CCNC2)nc1OC1CC1]

The title compound was prepared in 100% yield from (R)-tert-butyl 3-((4-cyclopropoxy-5-fluoropyrimidin-2-yl)amino)pyrrolidine-1-carboxylate using general procedure of (R)-5-chloro-4-cyclopropoxy-N-(pyrrolidin-3-yl)pyrimidin-2-amine hydrochloride. [M+H] Calc'd for $C_{11}H_{15}FN_4O$, 239.1; Found, 239.1.

Step 4: (R)—N-(4-(3-((4-cyclopropoxy-5-fluoropyrimidin-2-yl)amino)pyrrolidine-1-carbonyl)phenyl)acrylamide

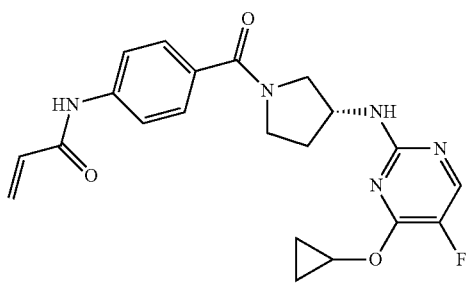 [SMILES: C=CC(=O)Nc1ccc(C(=O)N2CC[C@@H](Nc3ncc(F)c(OC4CC4)n3)C2)cc1]

The title compound was prepared in 21% yield from (R)-4-cyclopropoxy-5-fluoro-N-(pyrrolidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 0.61-0.78 (m, 4H), 1.99-2.07 (m, 1H), 2.13-2.17 (m, 1H), 3.42-3.85 (m, 4H), 4.14-4.40 (m, 2H), 5.77-5.80 (m, 1H), 6.26-6.31 (m, 1H), 6.41-6.48 (m, 1H), 7.46-7.54 (m, 3H), 7.69-7.73 (m, 2H), 8.06 (d, J=2.8 Hz, 0.5H), 8.13 (d, J=2.4 Hz, 0.5H), 10.31 (s, 1H). [M+H] Calc'd for $C_{21}H_{22}FN_5O_3$, 412.1; Found, 412.1.

Example 72: Synthesis of (R)—N-(2-chloro-4-(3-((5-chloropyrimidin-2-yl)amino)pyrrolidine-1-carbonyl)phenyl)acrylamide

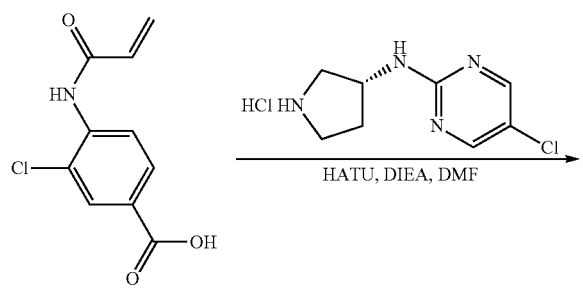

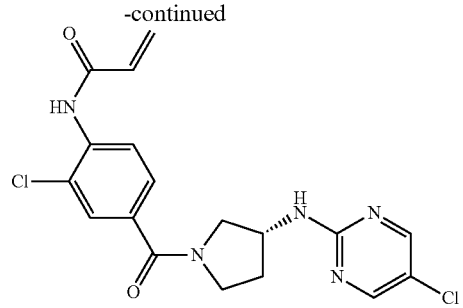

A mixture of 4-acrylamido-3-chlorobenzoic acid (300 mg, 1.34 mmol), (R)-5-chloro-N-(pyrrolidin-3-yl)pyrimidin-2-amine hydrochloride (354 mg, 1.46 mmol), HATU (610 mg, 1.6 mmol) and DIEA (520 mg, 4.02 mmol) in DMF (20 mL) was stirred at RT for overnight. The mixture was concentrated and purified by prep-HPLC to afford (R)—N-(2-chloro-4-(3-((5-chloropyrimidin-2-yl)amino)pyrrolidine-1-carbonyl)phenyl)acrylamide (38.3 mg, 5.5%) as a white solid. $^1$H NMR (400 MHz, DMSO-d$_6$): δ 1.98-2.14 (m, 2H), 3.38-3.74 (m, 4H), 4.27-4.42 (m, 1H), 5.80-5.82 (m, 1H), 6.27-6.32 (m, 1H), 6.64-6.69 (m, 1H), 7.48-7.49 (m, 1H), 7.62-7.66 (m, 2H), 7.82-7.91 (m, 1H), 8.32-8.38 (m, 2H), 9.78-9.80 (m, 1H). [M+H] Calc'd for $C_{18}H_{17}Cl_2N_5O_2$, 406.1; Found, 406.1.

Example 73: Synthesis of (R)—N-(5-(3-((5-chloro-4-methoxypyrimidin-2-yl)amino)pyrrolidine-1-carbonyl)thiazol-2-yl)acrylamide

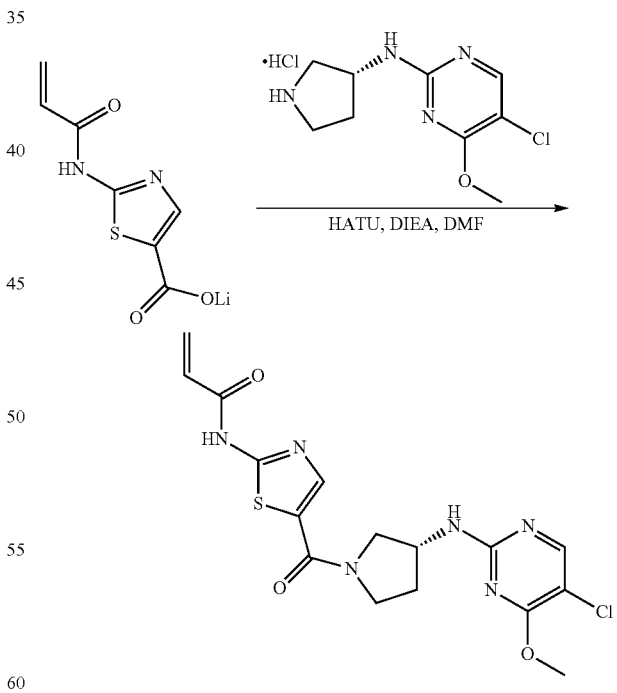

The title compound was prepared in 2% yield from lithium 2-acrylamidothiazole-5-carboxylate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.98-2.25 (m, 2H), 3.52-3.92 (m, 6H), 3.97-4.08 (m, 1H), 4.38-4.43 (m, 1H), 2.93-

5.96 (m, 1H), 6.41-6.53 (m, 2H), 7.75 (brs, 1H), 7.94-7.99 (m, 1H), 8.14 (s, 1H), 12.59 (s, 1H). [M+H] Calcd.: 409.0, Found: 409.0.

Example 74: Synthesis of (R)—N-(4-(3-((5-chloro-4-methoxypyrimidin-2-yl)amino)pyrrolidine-1-carbonyl)-2-(piperidin-1-yl)phenyl)acrylamide

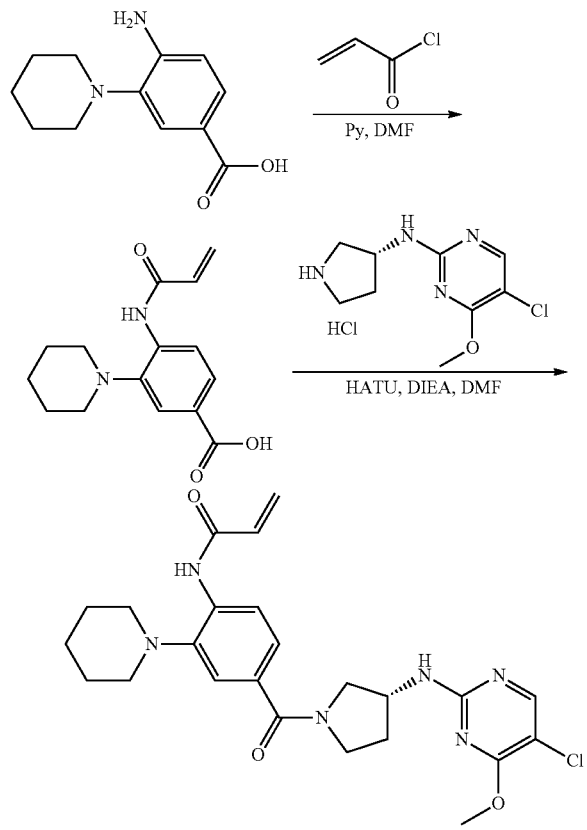

Step 1: 4-acrylamido-3-(piperidin-1-yl)benzoic acid

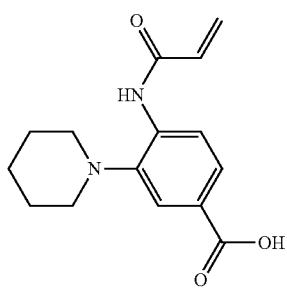 [SMILES: C=CC(=O)Nc1ccc(C(=O)O)cc1N1CCCCC1]

A mixture of 4-amino-3-(piperidin-1-yl)benzoic acid (1.0 g, 4.5 mmol) in DMF (20 mL) was added Pyridine (1.07 g, 13.6 mmol) followed by acryloyl chloride (1.23 g, 13.6 mmol) at 0° C. The mixture was then stirred at RT overnight. The mixture was concentrated and purified by column chromatography to afford 4-acrylamido-3-(piperidin-1-yl) benzoic acid (700 mg, 58%) as yellow oil. [M+H] Calc'd for $C_{15}H_{19}N_2O_3$, 275.1; Found, 275.1

Step 2: (R)—N-(4-(3-((5-chloro-4-methoxypyrimidin-2-yl)amino)pyrrolidine-1-carbonyl)-2-(piperidin-1-yl)phenyl)acrylamide

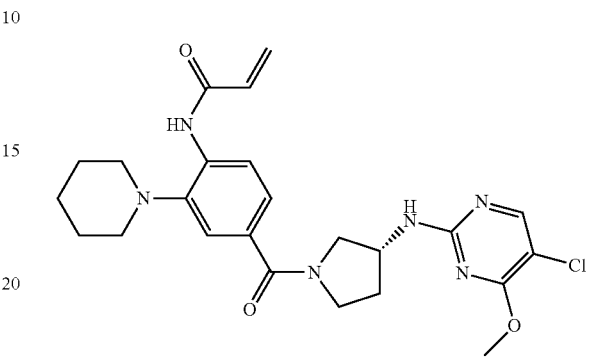

A mixture of 4-acrylamido-3-(piperidin-1-yl)benzoic acid (150 mg, 0.55 mmol), (R)-5-chloro-4-methoxy-N-(pyrrolidin-3-yl)pyrimidin-2-amine (HCl salt) (159 mg, 0.66 mmol), HATU (250 mg, 0.66 mmol) and DIEA (212 mg, 1.65 mmol) in DMF (10 mL) was stirred at RT for overnight. The mixture was diluted with water (10 mL) and extracted with DCM (10 mL*3). The combined organic layer was then washed with brine (20 mL), dried over $Na_2SO_4$, filtered and concentrated in vacuo. The residue was purified by prep-HPLC to afford (R)—N-(4-(3-((5-chloro-4-methoxypyrimidin-2-yl)amino)pyrrolidine-1-carbonyl)-2-(piperidin-1-yl) phenyl)acrylamide (16 mg, 6%) as a white solid (TFA salt). $^1$H NMR (400 MHz, DMSO-$d_6$): δ 1.47-1.55 (m, 2H), 1.66-1.76 (m, 4H), 1.88-2.01 (m, 1H), 2.14-2.18 (m, 1H), 2.67-2.78 (m, 4H), 3.40-3.94 (m, 7H), 4.24-4.43 (m, 1H), 5.79 (d, J=10.0 Hz, 1H), 6.24 (s, 0.5H), 6.28 (s, 0.5H), 6.63-6.71 (m, 1H), 7.21-7.31 (m, 2H), 7.71 (br s, 1H), 8.02-8.15 (m, 2H), 9.09 (s, 0.5H), 9.11 (s, 0.5H). [M+H] Calc'd for $C_{24}H_{30}ClN_6O_3$, 485.2; Found, 485.2.

Example 75: Synthesis of (R)—N-(4-(3-((5-methylpyridin-2-yl)amino)pyrrolidine-1-carbonyl)phenyl)acrylamide

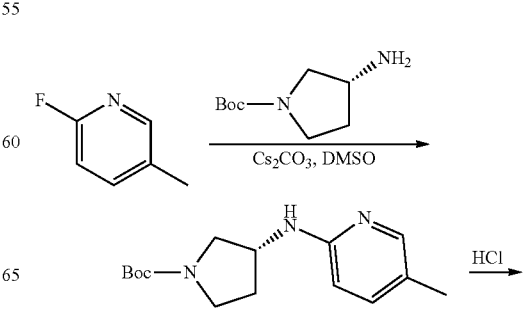

-continued

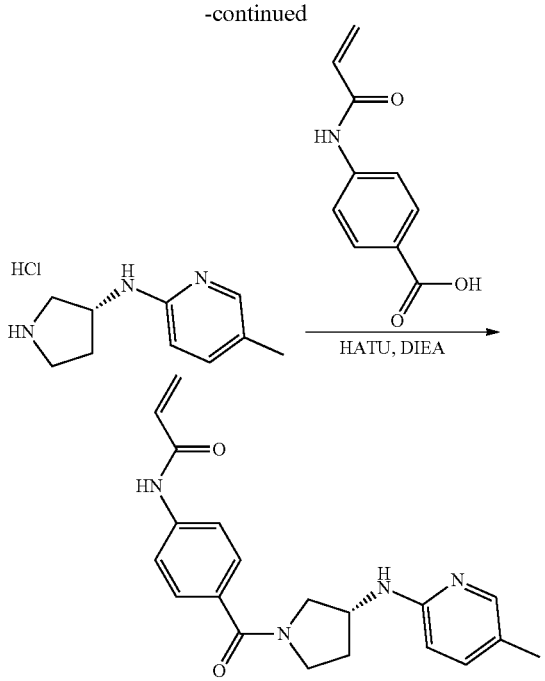

Step 1: (R)-tert-butyl 3-((5-methylpyridin-2-yl)amino)pyrrolidine-1-carboxylate

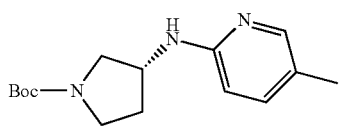 [SMILES: Cc1ccc(N[C@@H]2CCN(C(=O)OC(C)(C)C)C2)nc1]

A mixture of 2-fluoro-5-methylpyridine (1006 mg, 5.4 mmol), (R)-tert-butyl 3-aminopyrrolidine-1-carboxylate (600 mg, 5.4 mmol) and Cs₂CO₃ (3520 mg, 10.8 mmol) in DMSO (2 mL) was stirred at 160° C. for 32 hours. The mixture was cooled to RT, diluted with water (80 mL) and extracted with EtOAc (80 mL*3). The combined organic phase was washed with brine (50 mL), dried over Na₂SO₄, filtered and concentrated in vacuo. The residue was purified by flash chromatography on silica gel (petroleum ether/EtOAc=5/1) to afford (R)-tert-butyl 3-((5-methylpyridin-2-yl)amino)pyrrolidine-1-carboxylate (60 mg, 4%) as a white solid. [M+H] Calc'd for $C_{15}H_{23}N_3O_2$, 278.1; Found, 278.1.

Step 2: (R)-5-methyl-N-(pyrrolidin-3-yl)pyridin-2-amine hydrochloride

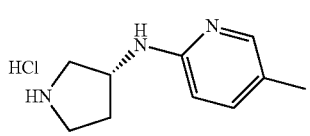

To a mixture of (R)-tert-butyl 3-((5-methylpyridin-2-yl)amino)pyrrolidine-1-carboxylate (60 mg, 0.217 mmol) in EtOAc (2 mL) was added HCl/EtOAc (4M, 2 mL). The mixture was stirred at RT for 2 hours. The mixture was concentrated in vacuo to afford (R)-5-methyl-N-(pyrrolidin-3-yl)pyridin-2-amine hydrochloride (46 mg, crude, 100%) as a yellow solid. [M+H] Calc'd for $C_{10}H_{15}N_3$, 178.1; Found, 178.1.

Step 3: (R)—N-(4-(3-((5-methylpyridin-2-yl)amino)pyrrolidine-1-carbonyl)phenyl)acrylamide

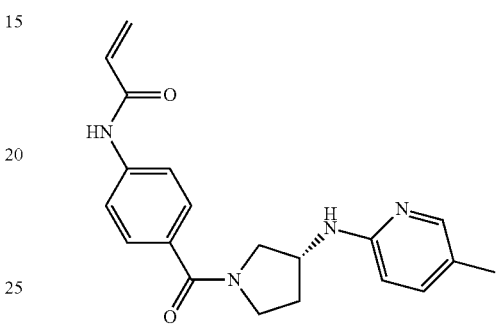

The title compound was prepared in 16% yield from (R)-5-methyl-N-(pyrrolidin-3-yl)pyridin-2-amine hydrochloride using general procedure of (R)—N-(4-(3-((5-chloro-4-methylpyrimidin-2-yl)amino)pyrrolidine-1-carbonyl)phenyl)acrylamide. ¹H NMR (400 MHz, CDCl₃): δ 1.92-2.00 (m, 1H), 2.15-2.25 (m, 3H), 2.31-2.36 (m, 1H), 3.34-3.57 (m, 1H), 3.64-4.04 (m, 3H), 4.32-4.47 (m, 2H), 5.79 (d, J=10.0 Hz, 1H), 6.22-6.30 (m, 2H), 6.37-6.47 (m, 1H), 6.99-7.21 (m, 1H), 7.29-7.60 (m, 4H), 7.86 (s, 0.5H), 7.94 (s, 0.5H). [M+H] Calc'd for $C_{20}H_{22}N_4O_2$, 351.1; Found, 351.1.

Example 76: Synthesis of (R)—N-(4-(3-((5-bromopyrimidin-2-yl)amino)pyrrolidine-1-carbonyl)-2-methylphenyl)acrylamide

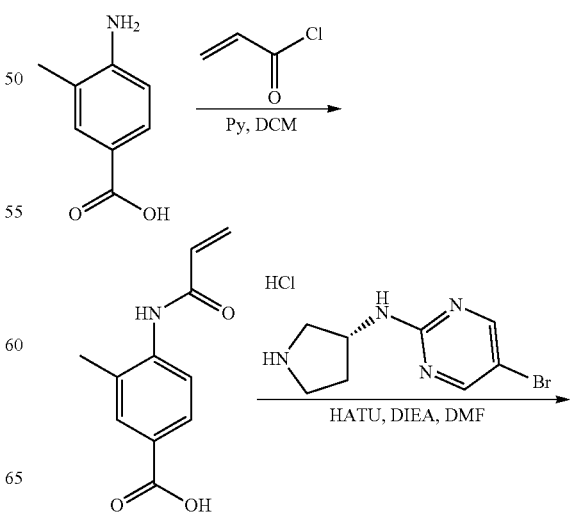

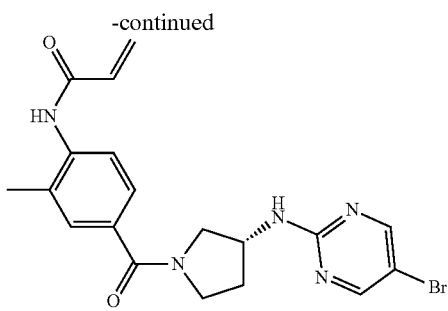

Step 1: 4-acrylamido-3-methylbenzoic acid

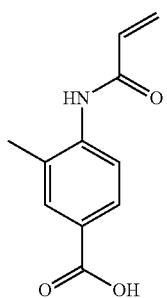

To a solution of 4-amino-3-methylbenzoic acid (10.0 g, 66.0 mmol) and Pyridine (16 mL) in DMF (50 mL) was added acryloyl chloride (6.0 g, 66.0 mmol) dropwise. The mixture was stirred at RT for 3 h. The residue was diluted with water (100 mL) and extracted with DCM (100 mL*3). The combined organic layer was washed with brine (200 mL), dried over $Na_2SO_4$, filtered and concentrated in vacuo. The residue was purified by column chromatography (PE: EA=1:1) to afford 4-acrylamido-3-methylbenzoic acid (800 mg, 6%) as white solid. [M+H] Calc'd for $C_{11}H_{12}NO_3$, 206.0; Found, 206.0

Step 2: (R)—N-(4-(3-((5-bromopyrimidin-2-yl)amino)pyrrolidine-1-carbonyl)-2-methylphenyl)acrylamide

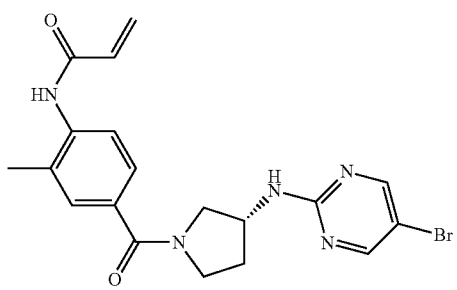 [SMILES: C=CC(=O)Nc1ccc(C(=O)N2CC[C@@H](Nc3ncc(Br)cn3)C2)cc1C]

A mixture of 4-acrylamido-3-methylbenzoic acid (260 mg, 1.76 mmol), (R)-5-bromo-N-(pyrrolidin-3-yl)pyrimidin-2-amine (586 mg, 2.10 mmol), HATU (798 mg, 2.10 mmol) and DIEA (681 mg, 5.28 mmol) in DMF (20 mL) was stirred at RT for overnight. The mixture was diluted with water (20 mL) and extracted with DCM (20 mL*3). The combined organic layer was washed with brine (30 mL), dried over $Na_2SO_4$, filtered and concentrated in-vacuo. The residue was purified by prep-HPLC to afford (R)—N-(4-(3-((5-bromopyrimidin-2-yl)amino)pyrrolidine-1-carbonyl)-2-methylphenyl)acrylamide (233.7 mg, 31%) as white solid. $^1$H NMR (400 MHz, DMSO-$d_6$): δ 1.93-2.08 (m, 1H), 2.20-2.49 (m, 4H), 3.28-3.77 (m, 4H), 4.23-4.39 (m, 1H), 5.76 (d, J=10.4 Hz, 1H), 6.23 (s, 0.5H), 6.28 (s, 0.5H), 6.53-6.60 (m, 1H), 7.30-7.40 (m, 2H), 7.59-7.64 (m, 1H), 7.79-7.82 (m, 1H), 8.36 (s, 1H), 8.42 (s, 1H), 9.51 (s, 0.5H), 9.56 (s, 0.5H). [M+H] Calc'd for $C_{19}H_2BrN_5O_2$, 430.0; Found, 430.0.

Example 77: Synthesis of (R)—N-(6-(3-((5-chloro-4-methoxypyrimidin-2-yl)amino)pyrrolidine-1-carbonyl)pyridin-3-yl)-N-methylacrylamide

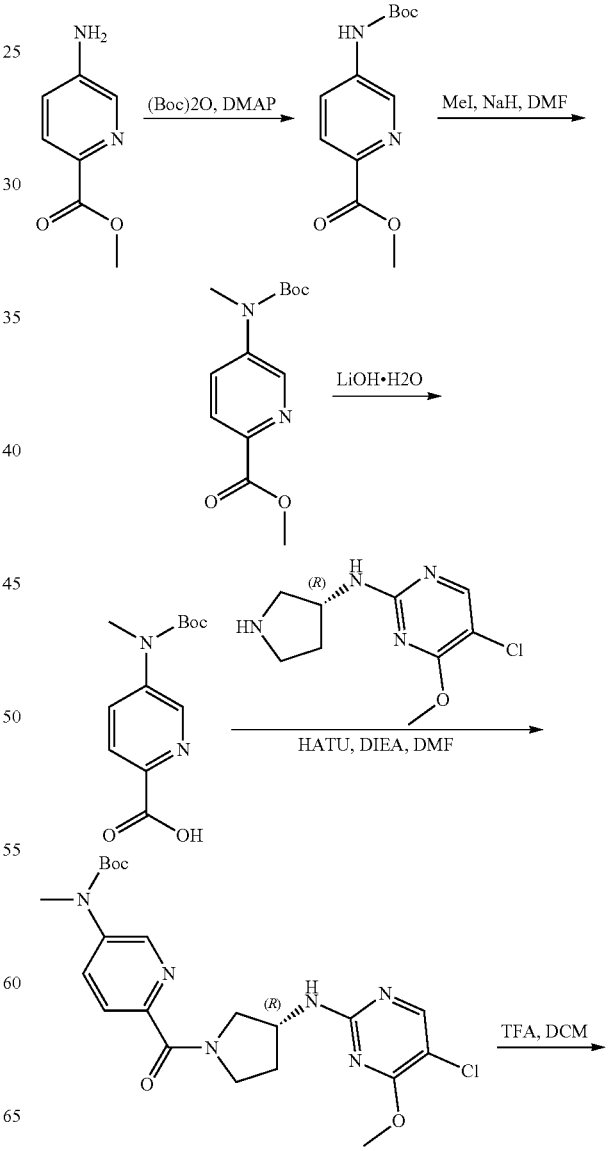

-continued

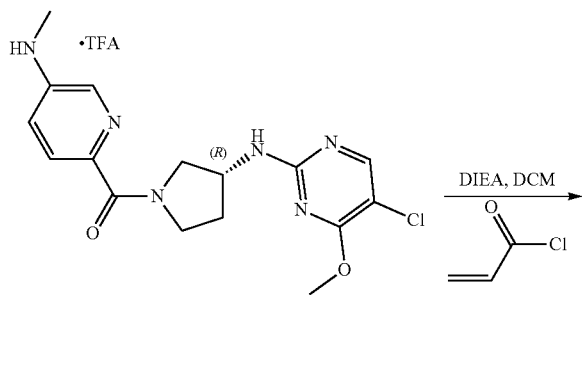

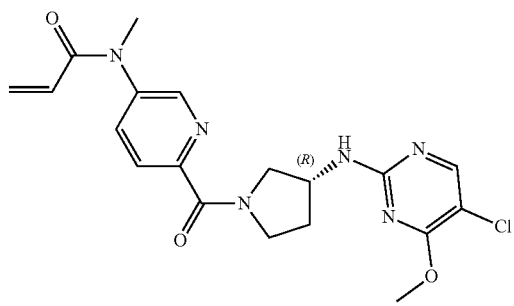

Step 1: methyl 5-((tert-butoxycarbonyl)amino)picolinate

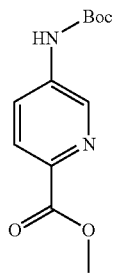

To a solution of 5-Amino-pyridine-2-carboxylic acid methyl ester (1.0 g, 6.6 mmol) in DCM (15 mL) was added DMAP (8 mg, 0.07 mmol) and (Boc)$_2$O (1.6 g, 7.2 mmol) at ice-bath. The mixture was stirred at RT overnight. Then the reaction mixture was diluted with DCM (20 mL) and washed with water (20 mL). The organic phase was separated, dried over Na$_2$SO$_4$, filtered and concentrated in vacuo. The residue was purified by flash chromatography on silica gel (petroleum ether/EtOAc=2/1) to afford product (0.8 g, 48%) as a white solid. [M+H]MS Calcd.: C$_{12}$H$_{16}$N$_2$O$_4$, 253.1, Found: 253.1.

Step 2: methyl 5-((tert-butoxycarbonyl)(methyl)amino)picolinate

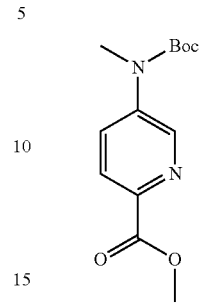

To a solution of methyl 5-((tert-butoxycarbonyl)(methyl) amino)picolinate (700 mg, 0.78 mmol) in DMF (15 mL) was added NaH (200 mg, 60%, 3.33 mmol) at 0° C., and the mixture was stirred at 0° C. for 30 minutes. MeI was added and the mixture was stirred at rt overnight. The mixture was quenched with water (30 mL) and extracted with EA (30 mL*3). The combined organic layers were washed with water (30 mL*2) and brine (30 mL), dried over Na$_2$SO$_4$, filtered and concentrated in vacuo. The residue was purified by flash chromatography on silica gel (petroleum ether/ EtOAc=2/1) to afford product (150 mg, 48%) as a white solid. [M+H]MS Calcd.: C$_{13}$H$_{18}$N$_2$O$_4$, 267.1, Found: 267.1.

Step 3: 5-((tert-butoxycarbonyl)(methyl)amino)picolinic acid

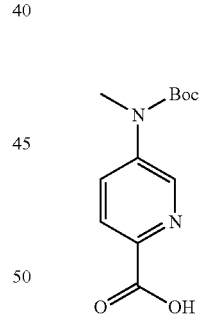

To a solution of 5-(tert-butoxycarbonyl-methyl-amino)-pyridine-2-carboxylic acid methyl ester (150 mg, 0.56 mmol) in MeOH (5 mL) was added LiOH.H$_2$O (71 mg, 1.69 mmol) and water (5 mL) at RT. The mixture was stirred at RT overnight. MeOH was concentrated in vacuo. The residue was acidated with 1 N HCl to pH 6, and extracted with EA (10 mL), the organic layer was dried over Na$_2$SO$_4$, filtered and concentrated in vacuo to afford product (120 mg, 80%) as a white solid. [M+H] MS Calcd.: C$_{12}$H$_{16}$N$_2$O$_4$, 253.1, Found: 253.1.

Step 4: (R)-tert-butyl(6-(3-((5-chloro-4-methoxypyrimidin-2-yl)amino)pyrrolidine-1-carbonyl)pyridin-3-yl)(methyl)carbamate

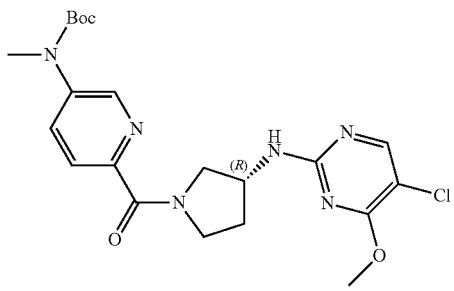

To a solution of 5-(((tert-butoxycarbonyl)(methyl)amino) picolinic acid (120 mg, 0.48 mmol) in DMF (5 mL) was added (R)-5-chloro-4-methoxy-N-(pyrrolidin-3-yl)pyrimidin-2-amine (160 mg, 0.48 mmol) and DIEA (185 mg, 1.43 mmol) at rt. The mixture was stirred at rt 30 minutes and HATU (220 mg, 0.57 mmol) was then added. The mixture was stirred at RT overnight. The reaction was quenched with water (50 mL) and extracted with EA (30 mL*3). The combined organic layers were washed with water (30 mL*2) and brine (30 mL), dried over $Na_2SO_4$, filtered and concentrated in vacuo. The residue was purified by flash chromatography on silica gel (petroleum ether/EtOAc=2/1) to afford the desired product (180 mg, 82%) as a white solid. [M+H]MS Calcd.: $C_{21}H_{27}ClN_6O_4$, 463.1, Found: 463.1.

Step 5: (R)-(3-((5-chloro-4-methoxypyrimidin-2-yl)amino)pyrrolidin-1-yl)(5-(methylamino)pyridin-2-yl)methanone TFA Salt

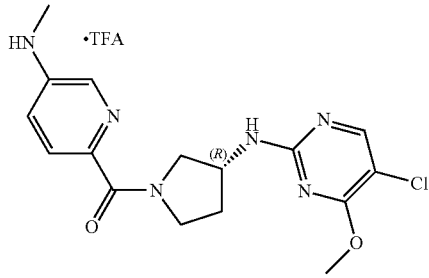

To a solution of (R)-tert-butyl (6-(3-((5-chloro-4-methoxypyrimidin-2-yl)amino)pyrrolidine-1-carbonyl)pyridin-3-yl)(methyl)carbamate (180 mg, 0.39 mmol) in DCM (5 mL) was added TFA (1 mL) at rt. The mixture was stirred at RT for 2 hours. The solvent was removed in vacuo to afford crude product (180 mg, 100%) as an oil. [M+H]MS Calcd.: $C_{16}H_{19}ClN_6O_2$, 363.1, Found: 363.1.

Step 6: (R)—N-(6-(3-((5-chloro-4-methoxypyrimidin-2-yl)amino)pyrrolidine-1-carbonyl)pyridin-3-yl)-N-methylacrylamide

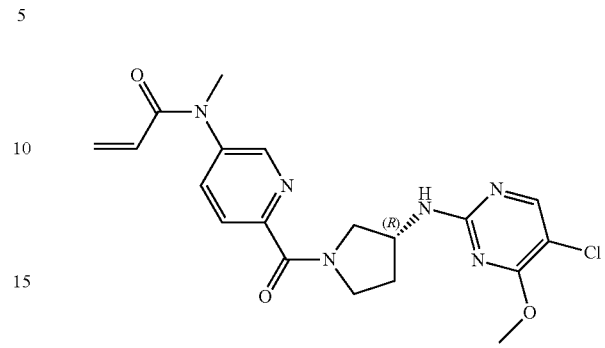

To a solution of (R)-(3-((5-chloro-4-methoxypyrimidin-2-yl)amino)pyrrolidin-1-yl)(5-(methylamino)pyridin-2-yl) methanone TFA salt (150 mg, 0.41 mmol) in DCM (5 mL) was added DIEA (210 mg, 1.64 mmol) at rt and the mixture was stirred at rt 30 minutes. Acryloyl chloride (75 mg, 0.82 mmol) was added dropwise, and the mixture was stirred at RT overnight. The solvent was removed in vacuo and the residue was purified by prep-HPLC to give the desired product (8 mg, 5%) as solid. [M+H]MS Calcd.: $C_{19}H_{21}ClN_6O_3$, 417.2, Found: 417.2.

Example 78: Synthesis of (R)—N-(4-(3-((5-chloro-4-methoxypyrimidin-2-yl)amino)pyrrolidine-1-carbonyl)-2-(4-methylpiperazin-1-yl)phenyl)acrylamide

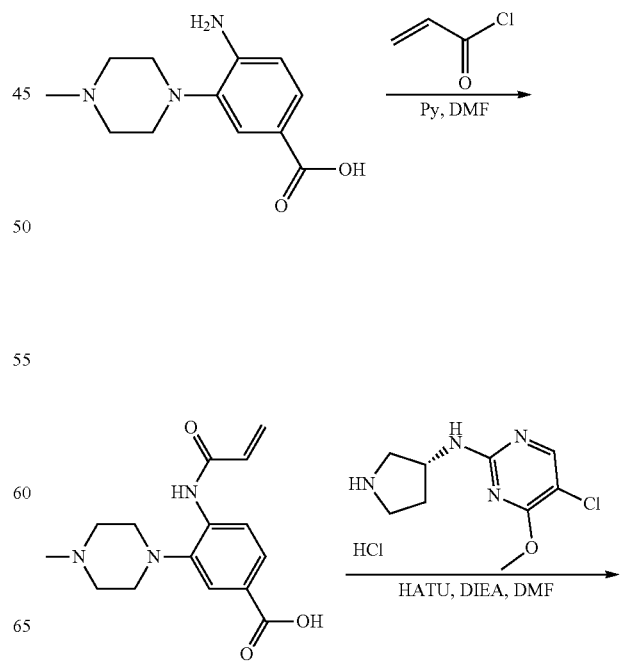

-continued

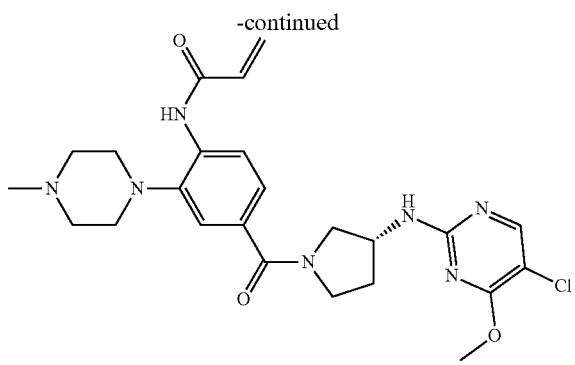

Step 1: 4-acrylamido-3-(4-methylpiperazin-1-yl)benzoic Acid

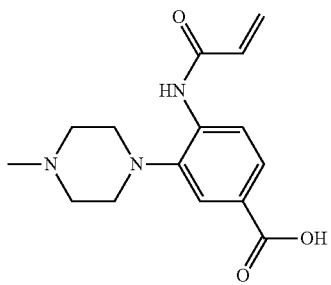 [SMILES: C=CC(=O)Nc1ccc(C(=O)O)cc1N1CCN(C)CC1]

A mixture of 4-amino-3-(4-methylpiperazin-1-yl)benzoic acid (1.3 g, 5.5 mmol) in DMF (20 mL) was added Pyridine (1.3 g, 16.5 mmol) followed by acryloyl chloride (1.25 g, 13.8 mmol) at 0° C. The mixture was stirred at RT overnight. The mixture was concentrated and purified by column chromatography to afford 4-acrylamido-3-(piperidin-1-yl)benzoic acid (650 mg, 40%) as a brown solid. [M+H] Calc'd for $C_{15}H_{20}N_3O_3$, 290.1; Found, 290.1

Step 2: (R)—N-(4-(3-((5-chloro-4-methoxypyrimidin-2-yl)amino)pyrrolidine-1-carbonyl)-2-(4-methylpiperazin-1-yl)phenyl)acrylamide

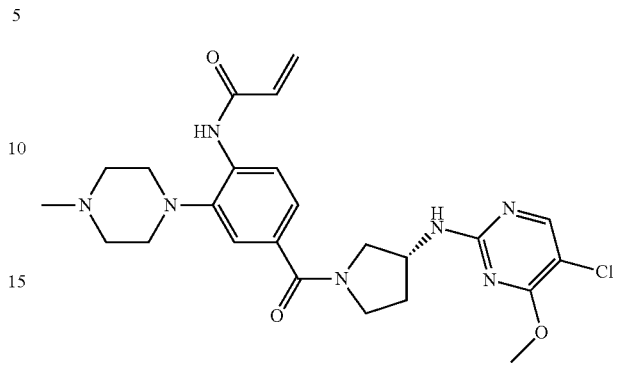

A mixture of 4-acrylamido-3-(piperidin-1-yl)benzoic acid (150 mg, 0.52 mmol), (R)-5-chloro-4-methoxy-N-(pyrrolidin-3-yl)pyrimidin-2-amine (HCl salt) (206 mg, 0.78 mmol), HATU (237 mg, 0.62 mmol) and DIEA (202 mg, 1.56 mmol) in DMF (10 mL) was stirred at RT overnight. The mixture was diluted with water (10 mL) and extracted with DCM (10 mL*3). The combined organic layer was washed with brine (20 mL), dried over $Na_2SO_4$, filtered and concentrated in-vacuo. The residue was purified by prep-HPLC to afford (R)—N-(4-(3-((5-chloro-4-methoxypyrimidin-2-yl)amino)pyrrolidine-1-carbonyl)-2-(4-methylpiperazin-1-yl)phenyl)acrylamide (16.3 mg, 6.3%) as a white solid (TFA salt). $^1$H NMR (400 MHz, DMSO-$d_6$): δ 1.88-2.00 (m, 1H), 2.09-2.20 (m, 1H), 2.25 (s, 3H), 2.50-2.54 (m, 4H), 2.79-2.84 (m, 4H), 3.40-3.94 (m, 7H), 4.24-4.43 (m, 1H), 5.78 (d, J=10.4 Hz, 1H), 6.23 (s, 0.5H), 6.28 (s, 0.5H), 6.60-6.67 (m, 1H), 7.22-7.32 (m, 2H), 7.68 (br s, 1H), 8.00-8.14 (m, 2H), 9.08 (s, 0.5H), 9.10 (s, 0.5H). [M+H] Calc'd for $C_{24}H_{31}ClN_7O_3$, 500.2; Found, 500.2.

Example 79: Synthesis of (R)—N-(2-methyl-4-(3-((5-(trifluoromethyl)pyrimidin-2-yl)amino)pyrrolidine-1-carbonyl)phenyl)acrylamide

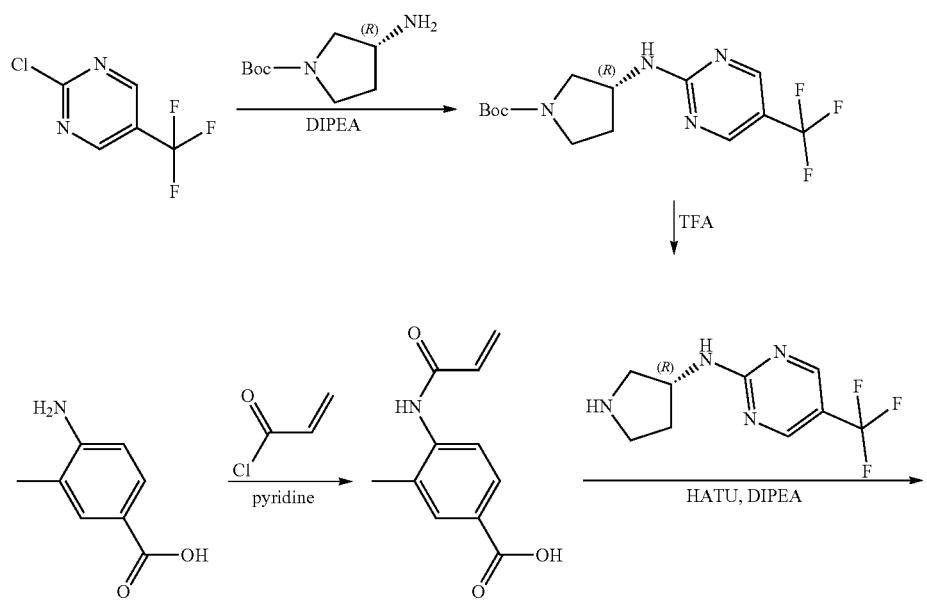

-continued

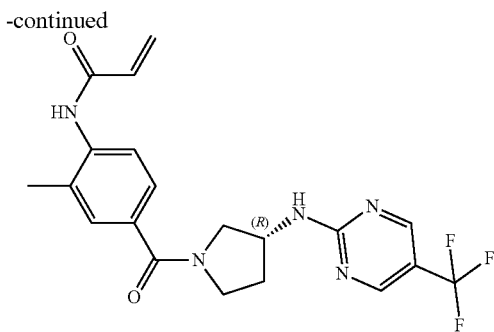

Step 1: (R)-tert-butyl 3-((5-(trifluoromethyl)pyrimidin-2-yl)amino)pyrrolidine-1-carboxylate

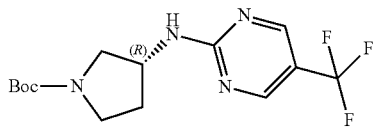

The title compound was prepared in 96% yield from 2-chloro-5-(trifluoromethyl)pyrimidine using general procedure of (R)-tert-butyl 3-((5-chloro-4-methylpyrimidin-2-yl)amino)pyrrolidine-1-carboxylate. [M+H] Calc'd for $C_{14}H_{19}F_3N_4O_2$, 333.1; Found, 333.1.

Step 2: (R)—N-(pyrrolidin-3-yl)-5-(trifluoromethyl)pyrimidin-2-amine 2,2,2-trifluoroacetate

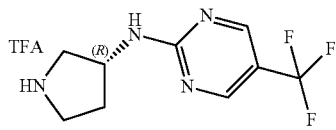

The title compound was prepared in 100% yield from (R)-tert-butyl 3-((5-(trifluoromethyl)pyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_9H_{11}F_3N_4$, 233.0; Found, 233.0.

Step 3: 4-acrylamido-3-methylbenzoic acid

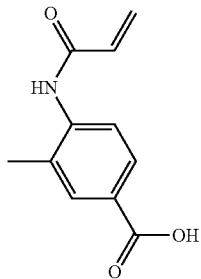

To a solution of 4-amino-3-methylbenzoic acid (13.7 g, 91.0 mmol) and pyridine (5 mL) in DMF (100 mL) was added acryloyl chloride (12.4 g, 136.5 mmol) at 0° C. The mixture was stirred at RT for 4 hours. The mixture was diluted with water (1000 mL) and filtered. The filter cake was washed with water (200 mL*2) and dried to afford 4-acrylamido-3-methylbenzoic acid (15.1 g, 81%) as a white solid. [M+H] Calc'd for $C_{11}H_{11}NO_3$, 206.0; Found, 206.0.

Step 4: (R)—N-(2-methyl-4-(3-((5-(trifluoromethyl)pyrimidin-2-yl)amino)pyrrolidine-1-carbonyl)phenyl)acrylamide The title compound was prepared in 20% yield from 4-acrylamido-3-methylbenzoic acid using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.90-2.07 (m, 1H), 2.16-2.27 (m, 4H), 3.38-3.72 (m, 3H), 3.78-3.82 (m, 1H), 4.35-4.55 (m, 1H), 5.78 (d, J=10.0 Hz, 1H), 6.27 (d, J=17.2 Hz, 1H), 6.54-6.61 (m, 1H), 7.32-7.42 (m, 2H), 7.61-7.66 (m, 1H), 8.41-8.44 (m, 1H), 8.63-8.71 (m, 2H), 9.51 (s, 0.5H), 9.54 (s, 0.5H). [M+H] Calc'd for $C_{20}H_2F_3N_5O_2$, 420.1; Found, 420.1.

Example 80: Synthesis of (R)—N-(4-(3-((5-chloro-4-methylpyrimidin-2-yl)amino)pyrrolidine-1-carbonyl)-2-methylphenyl)acrylamide

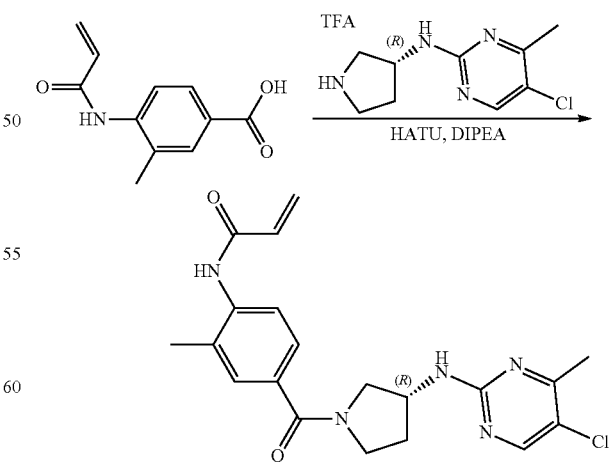

The title compound was prepared in 16% yield from 4-acrylamido-3-methylbenzoic acid using general procedure of (R)—N-(4-(3-((5-chloro-4-methylpyrimidin-2-yl)amino)

pyrrolidine-1-carbonyl)phenyl)acrylamide. $^1$H NMR (400 MHz, DMSO-d$_6$): δ 1.84-1.99 (m, 1H), 2.00-2.36 (m, 7H), 3.48-3.55 (m, 2H), 3.59-3.68 (m, 1H), 3.72-3.76 (m, 1H), 4.25-4.42 (m, 1H), 5.78 (d, J=10.4 Hz, 1H), 6.26 (d, J=16.8 Hz, 1H), 6.53-6.60 (m, 1H), 7.30-7.40 (m, 2H), 7.61 (t, J=8.8 Hz, 1H), 7.70 (s, 1H), 8.19 (s, 0.5H), 8.26 (s, 0.5H), 9.52 (d, J=8.0 Hz, 1H). [M+H] Calc'd for C$_{20}$H$_{22}$ClN$_5$O$_2$, 400.1; Found, 400.1.

Example 81: Synthesis of (R)—N-(4-(3-((4-cyclopropoxy-5-methylpyrimidin-2-yl)amino)pyrrolidine-1-carbonyl)phenyl)acrylamide

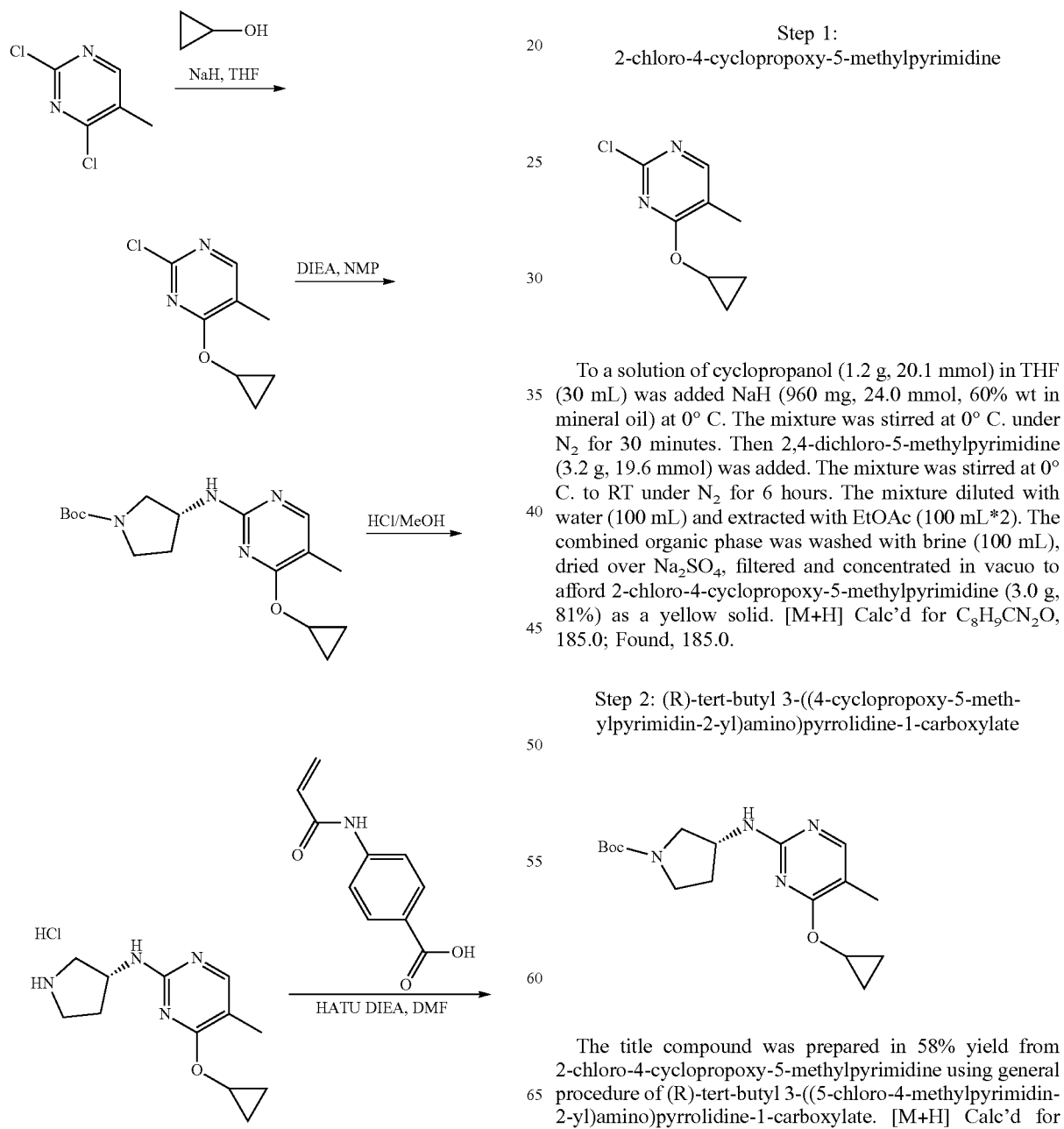

Step 1: 2-chloro-4-cyclopropoxy-5-methylpyrimidine

To a solution of cyclopropanol (1.2 g, 20.1 mmol) in THF (30 mL) was added NaH (960 mg, 24.0 mmol, 60% wt in mineral oil) at 0° C. The mixture was stirred at 0° C. under N$_2$ for 30 minutes. Then 2,4-dichloro-5-methylpyrimidine (3.2 g, 19.6 mmol) was added. The mixture was stirred at 0° C. to RT under N$_2$ for 6 hours. The mixture diluted with water (100 mL) and extracted with EtOAc (100 mL*2). The combined organic phase was washed with brine (100 mL), dried over Na$_2$SO$_4$, filtered and concentrated in vacuo to afford 2-chloro-4-cyclopropoxy-5-methylpyrimidine (3.0 g, 81%) as a yellow solid. [M+H] Calc'd for C$_8$H$_9$ClN$_2$O, 185.0; Found, 185.0.

Step 2: (R)-tert-butyl 3-((4-cyclopropoxy-5-methylpyrimidin-2-yl)amino)pyrrolidine-1-carboxylate The title compound was prepared in 58% yield from 2-chloro-4-cyclopropoxy-5-methylpyrimidine using general procedure of (R)-tert-butyl 3-((5-chloro-4-methylpyrimidin-2-yl)amino)pyrrolidine-1-carboxylate. [M+H] Calc'd for C$_{17}$H$_{26}$N$_4$O$_3$, 335.2; Found, 335.2.

Step 3: (R)-4-cyclopropoxy-5-methyl-N-(pyrrolidin-3-yl)pyrimidin-2-amine hydrochloride

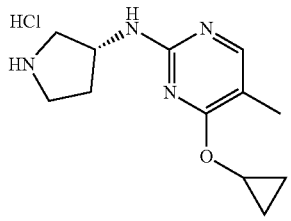 [SMILES: Cl ; Cc1cnc(N[C@@H]2CCNC2)nc1OC1CC1]

The title compound was prepared in 100% yield from (R)-tert-butyl 3-((4-cyclopropoxy-5-methylpyrimidin-2-yl)amino)pyrrolidine-1-carboxylate using general procedure of (R)-5-chloro-4-cyclopropoxy-N-(pyrrolidin-3-yl)pyrimidin-2-amine hydrochloride. [M+H] Calc'd for $C_{12}H_{18}N_4O$, 235.1; Found, 235.1.

Step 4: (R)—N-(4-(3-((4-cyclopropoxy-5-methylpyrimidin-2-yl)amino)pyrrolidine-1-carbonyl)phenyl)acrylamide

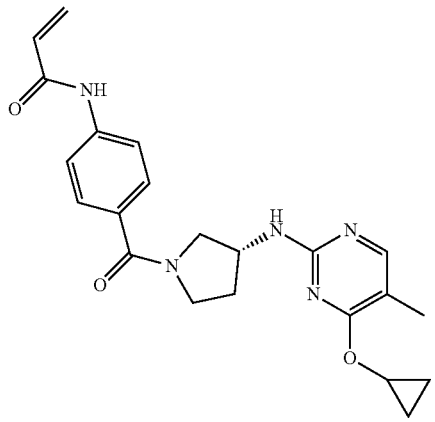 [SMILES: C=CC(=O)Nc1ccc(C(=O)N2CC[C@@H](Nc3ncc(C)c(OC4CC4)n3)C2)cc1]

The title compound was prepared in 21% yield from (R)-4-cyclopropoxy-5-methyl-N-(pyrrolidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. ¹H NMR (400 MHz, DMSO-d₆): δ 0.52-0.78 (m, 4H), 1.80 (s, 1.5H), 1.86 (s, 1.5H), 1.90-2.15 (m, 2H), 3.36-3.86 (m, 4H), 4.14-4.31 (m, 2H), 5.78 (d, J=10.4 Hz, 1H), 6.28 (d, J=16.8 Hz, 1H), 6.41-6.47 (m, 1H), 7.17 (s, 1H), 7.48-7.53 (m, 2H), 7.68-7.72 (m, 2H), 7.80 (s, 0.5H), 7.88 (s, 0.5H), 10.29 (s, 1H). [M+H] Calc'd for $C_{22}H_{25}N_5O_3$, 408.1; Found, 408.1.

Example 82: Synthesis of (R)—N-(4-(3-((5-chloro-4-methoxypyrimidin-2-yl)amino)pyrrolidine-1-carbonyl)-2-(1-methyl-1H-pyrazol-4-yl)phenyl)acrylamide

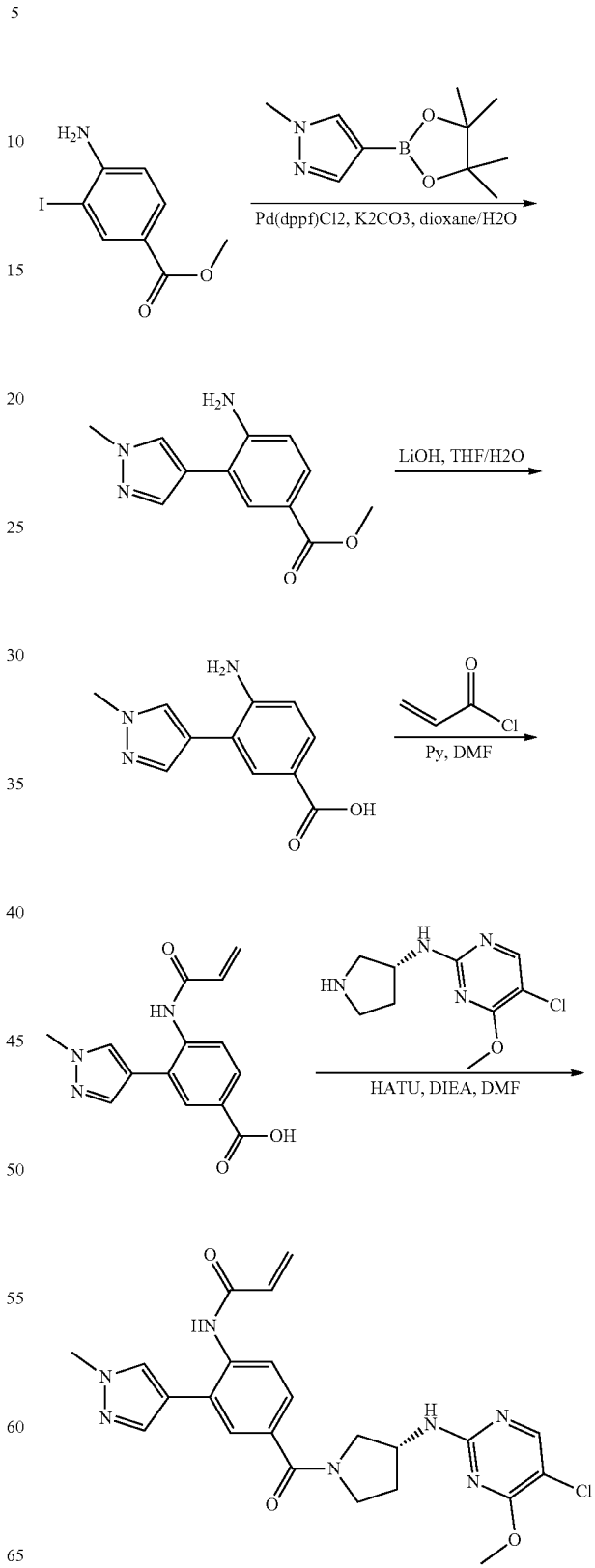

Step 1: methyl 4-amino-3-(1-methyl-1H-pyrazol-4-yl)benzoate

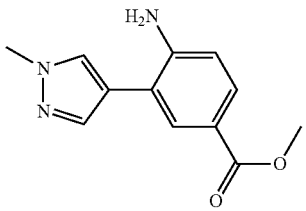

A mixture of methyl 4-amino-3-iodobenzoate (500 mg, 1.81 mmol), 1-methyl-4-(4,4,5,5-tetramethyl-1,3,2-dioxaborolan-2-yl)-1H-pyrazole (563 mg, 2.71 mmol), Pd(dppf)Cl₂ (132 mg, 0.18 mmol) and Cs₂CO₃ (1177 mg, 3.61 mmol) in dioxane/H₂O (10 mL/2 mL) was stirred at 90° C. for 8 h. The mixture was diluted with water (30 mL) and extracted with DCM (10 mL*3). The combined organic layer was washed with brine (50 mL), dried over Na₂SO₄, filtered and concentrated in vacuo. The residue was purified by column (PE:EA=1:1) to afford methyl 4-amino-3-(1-methyl-1H-pyrazol-4-yl)benzoate (400 mg, 96%) as brown solid. [M+H] Calc'd for C₁₂H₁₃N₃O₂, 232.1; Found, 232.1.

Step 2: 4-amino-3-(1-methyl-1H-pyrazol-4-yl)benzoic acid

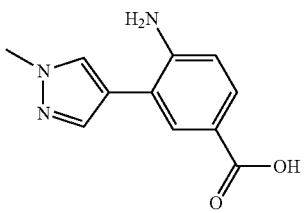 [SMILES: Cn1cc(-c2cc(C(=O)O)ccc2N)cn1]

A mixture of methyl 4-amino-3-(1-methyl-1H-pyrazol-4-yl)benzoate (400 mg, 1.81 mmol) and LiOH (235 mg, 5.60 mmol) in THF/H₂O (20 mL/10 mL) was stirred at 40° C. for 24 h. The mixture was then adjusted to pH=3 and extracted with DCM (10 mL*3). The combined organic layer was washed with brine (50 mL), dried over Na₂SO₄, filtered and concentrated in vacuo to afford 4-amino-3-(1-methyl-1H-pyrazol-4-yl)benzoic acid (300 mg, 76%) as brown solid. [M+H]Calc'd for C₁₁H₁₁N₃O₂, 218.0; Found, 218.0.

Step 3: 4-acrylamido-3-(1-methyl-1H-pyrazol-4-yl)benzoic acid

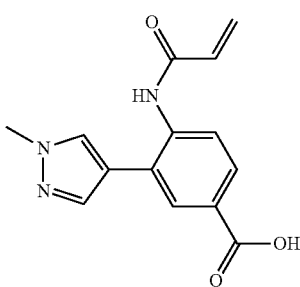 [SMILES: C=CC(=O)Nc1ccc(C(=O)O)cc1-c1cnn(C)c1]

A mixture of 4-amino-3-(1-methyl-1H-pyrazol-4-yl)benzoic acid (300 mg, 1.38 mmol) in DMF (15 mL) was added Pyridine (328 mg) at 0° C. followed by acryloyl chloride (188 mg, 2.08 mmol). The mixture was then stirred at RT for 5 h. The mixture was concentrated and added DCM (20 mL), washed with 0.5N HCl (5 mL), dried over Na₂SO₄, filtered, concentrated in vacuo to afford 4-acrylamido-3-(1-methyl-1H-pyrazol-4-yl)benzoic acid (150 mg, 40%) as brown solid. [M+H]Calc'd for C₁₄H₁₃N₃O₃, 272.1; Found, 272.1

Step 4: (R)—N-(4-(3-((5-chloro-4-methoxypyrimidin-2-yl)amino)pyrrolidine-1-carbonyl)-2-(1-methyl-1H-pyrazol-4-yl)phenyl)acrylamide

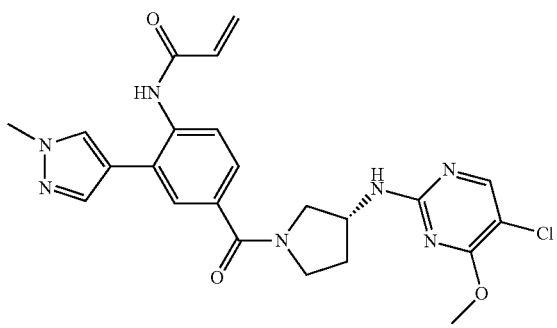 [SMILES: C=CC(=O)Nc1ccc(C(=O)N2CC[C@@H](Nc3ncc(Cl)c(OC)n3)C2)cc1-c1cnn(C)c1]

A mixture of 4-acrylamido-3-(1-methyl-1H-pyrazol-4-yl) benzoic acid (150 mg, 0.55 mmol), (R)-5-chloro-4-methoxy-N-(pyrrolidin-3-yl)pyrimidin-2-amine (HCl salt) (175 mg, 0.66 mmol), HATU (252 mg, 0.66 mmol), DIEA (286 mg, 2.22 mmol) in DMF (10 mL) was stirred at RT for overnight. The mixture was diluted with water (50 mL) and extracted with DCM (50 mL*3). The combined organic layer was washed with brine (20 mL), dried over Na₂SO₄, filtered and concentrated in-vacuo. The residue was then purified by prep-HPLC to afford (R)—N-(4-(3-((5-chloro-4-methoxypyrimidin-2-yl)amino)pyrrolidine-1-carbonyl)-2-(1-methyl-1H-pyrazol-4-yl)phenyl)acrylamide (48.2 mg, 18%) as a white solid (TFA salt). ¹H NMR (400 MHz, DMSO-d₆) δ 1.90-2.03 (m, 1H), 2.14-2.17 (m, 1H), 3.39-3.70 (m, 3H), 3.79-3.95 (m, 7H), 4.24-4.45 (m, 1H), 5.75 (d, J=10.4 Hz, 1H), 6.23 (s, 0.5H), 6.27 (s, 0.5H), 6.48-6.56 (m, 1H), 7.36-7.41 (m, 1H), 7.56-7.73 (m, 4H), 7.97 (s, 0.5H), 7.99 (s, 0.5H), 8.08-8.16 (m, 1H), 9.62 (s, 1H). [M+H] Calc'd for C₂₃H₂₄ClN₇O₃, 482.0; Found, 482.0.

Example 83: Synthesis of (R)—N-(4-(3-((5-chloropyrimidin-2-yl)amino)pyrrolidine-1-carbonyl)phenyl)-2-methylenebutanamide

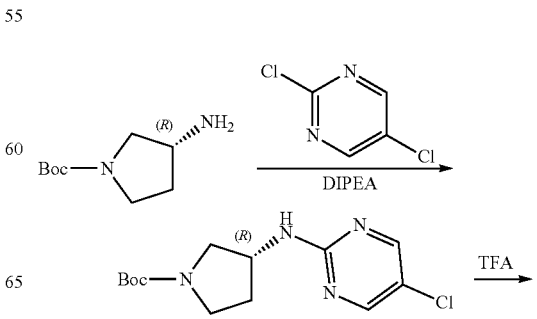

279

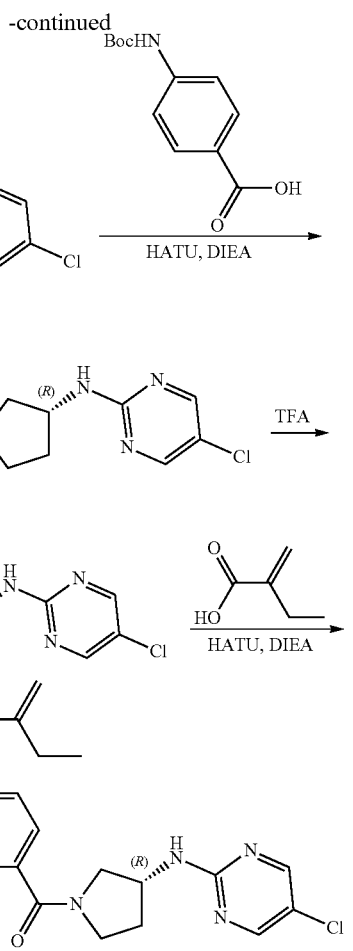

Step 1: 4-((tert-butoxycarbonyl)amino)benzoic acid

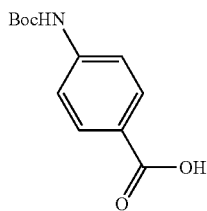 [SMILES: CC(C)(C)OC(=O)Nc1ccc(C(=O)O)cc1]

To a solution of 4-aminobenzoic acid (5.0 g, 36.5 mmol) and TEA (7.4 g, 73 mmol) in dioxane (45 mL) and H₂O (20 mL) was added di-tert-butyl dicarbonate (15.9 g, 73 mmol) at RT. The solution was stirred at RT for overnight. The solution was concentrated to afford 4-((tert-butoxycarbonyl)amino)benzoic acid (7.0 g, 81%) as a white solid. [M+H] Calc'd for C₁₂H₁₅NO₄, 238.1; Found, 238.1.

Step 2: 2-methylenebutanoic Acid

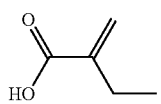

280

To a solution of 2-ethylmalonic acid (1.5 g, 11.4 mmol) in EtOAc (114 mL) was added Paraformaldehyde (680 mg, 22.7 mmol) and diethylamine (1.2 g, 17.0 mmol) at 0° C. The mixture was refluxed for 4 hours. The solution was cooled to R.T and concentrated. The residue was quenched with ice-water and acidified to pH 1.0 with con.HCl. The solution was extracted with DCM (100 mL*3). The combined organic phase was washed with brine (100 mL), dried over Na₂SO₄, filtered and concentrated in vacuo. The residue was purified by flash chromatography on silica gel (petroleum ether/EtOAc=1/1) to afford 2-methylenebutanoic acid (700 mg, 64%) as colorless oil. [M+H] Calc'd for C₅H₈O₂, 101.0; Found, 101.0.

Step 3: (R)-tert-butyl 3-((5-chloropyrimidin-2-yl)amino)pyrrolidine-1-carboxylate

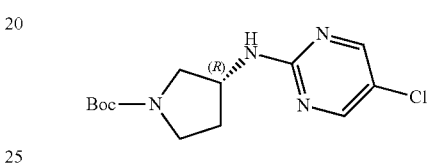

The title compound was prepared in 82% yield from 2,5-dichloropyrimidine using general procedure of (R)-tert-butyl 3-((5-chloro-4-methylpyrimidin-2-yl)amino)pyrrolidine-1-carboxylate. [M+H] Calc'd for C₁₃H₁₉ClN₄O₂, 299.1; Found, 299.1.

Step 4: (R)-5-chloro-N-(pyrrolidin-3-yl)pyrimidin-2-amine 2,2,2-trifluoroacetate

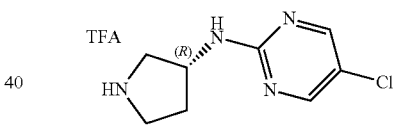

The title compound was prepared in 100% yield from (R)-tert-butyl 3-((5-chloropyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for C₈H₁₁ClN₄, 199.0; Found, 199.0.

Step 5: (R)-tert-butyl (4-(3-((5-chloropyrimidin-2-yl)amino)pyrrolidine-1-carbonyl)phenyl)carbamate

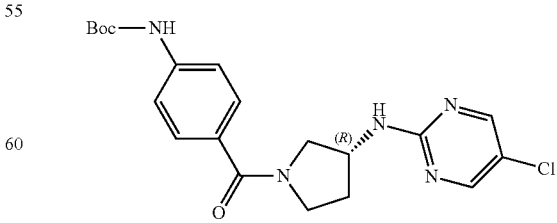

The title compound was prepared in 64% yield from 4-((tert-butoxycarbonyl)amino)benzoic acid using general procedure of (R)—N-(4-(3-((5-chloro-4-methylpyrimidin- 2-yl)amino)pyrrolidine-1-carbonyl)phenyl)acrylamide. [M+H] Calc'd for C20H24ClN5O3, 418.1; Found, 418.1.

Step 6: (R)-(4-aminophenyl)(3-((5-chloropyrimidin-2-yl)amino)pyrrolidin-1-yl)methanone 2,2,2-trifluoroacetate

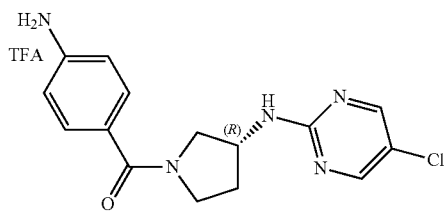

The title compound was prepared in 100% yield from (R)-tert-butyl (4-(3-((5-chloropyrimidin-2-yl)amino)pyrrolidine-1-carbonyl)phenyl)carbamate using general procedure of (R)-5-chloro-4-methyl-N-(pyrrolidin-3-yl)pyrimidin-2-amine 2,2,2-trifluoroacetate. [M+H] Calc'd for C15H16ClN5O, 318.1; Found, 318.1.

Step 7: (R)—N-(4-(3-((5-chloropyrimidin-2-yl)amino)pyrrolidine-1-carbonyl)phenyl)-2-methylenebutanamide

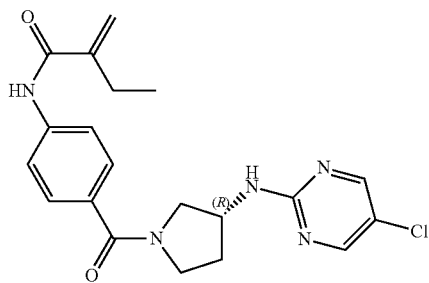

The title compound was prepared in 32% yield from (R)-(4-aminophenyl)(3-((5-chloropyrimidin-2-yl)amino)pyrrolidin-1-yl)methanone 2,2,2-trifluoroacetate using general procedure of (R)—N-(4-(3-((5-chloro-4-methylpyrimidin-2-yl)amino)pyrrolidine-1-carbonyl)phenyl)acrylamide. ¹H NMR (400 MHz, DMSO-d6): δ 1.02 (t, J=7.6 Hz, 3H), 1.87-2.01 (m, 1H), 2.07-2.18 (m, 1H), 2.32-2.36 (m, 2H), 3.40-3.54 (m, 2H), 3.63-3.80 (m, 2H), 4.21-4.40 (m, 1H), 5.47 (s, 1H), 5.76 (d, J=4.0 Hz, 1H), 7.46-7.51 (m, 2H), 7.71-7.76 (m, 2H), 7.81-7.83 (m, 1H), 8.32 (s, 1H), 8.39 (s, 1H), 10.02 (s, 1H). [M+H] Calc'd for C20H22ClN5O2, 400.1; Found, 400.1.

Example 84: Synthesis of (R)—N-(4-(3-((5-chloropyrimidin-2-yl)amino)pyrrolidine-1-carbonyl)phenyl)ethenesulfonamide

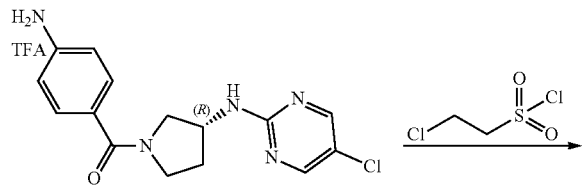

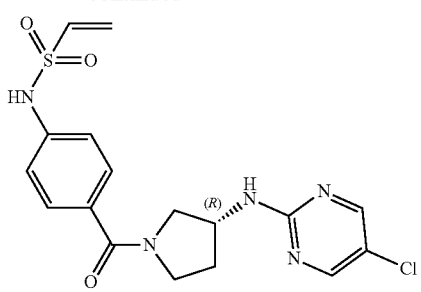

To a solution of (R)-(4-aminophenyl)(3-((5-chloropyrimidin-2-yl)amino)pyrrolidin-1-yl)methanone 2,2,2-trifluoroacetate (91 mg, 0.29 mmol) in DCM (1.5 mL) was added DIEA (176 mg, 1.74 mmol) and 2-chloroethanesulfonyl chloride (47 mg, 0.29 mmol) in DCM (0.5 mL) dropwise at 0° C. The solution was stirred at RT for 5 hours. The solution was concentrated and the residue was purified by prep-HPLC to afford (R)—N-(4-(3-((5-chloropyrimidin-2-yl)amino)pyrrolidine-1-carbonyl)phenyl)ethenesulfonamide (19.8 mg, 17%) as a white solid. ¹H NMR (400 MHz, DMSO-d6): δ 1.84-2.00 (m, 1H), 2.07-2.17 (m, 1H), 3.29-3.31 (m, 1H), 3.40-3.66 (m, 2H), 3.72-3.76 (m, 1H), 4.21-4.40 (m, 1H), 6.07 (dd, J=2.8 Hz, 9.6 Hz, 1H), 6.17 (dd, J=3.6 Hz, 16.4 Hz, 1H), 6.79-6.86 (m, 1H), 7.13-7.18 (m, 2H), 7.45-7.50 (m, 2H), 7.81-7.84 (m, 1H), 8.32 (s, 1H), 8.38 (s, 1H), 10.21 (br s, 1H). [M+H] Calc'd for C17H18ClN5O3S, 408.0; Found, 408.0.

Example 85: Synthesis of (R)—N-(4-(3-((5-cyclopropylpyridin-2-yl)amino)pyrrolidine-1-carbonyl)phenyl)acrylamide

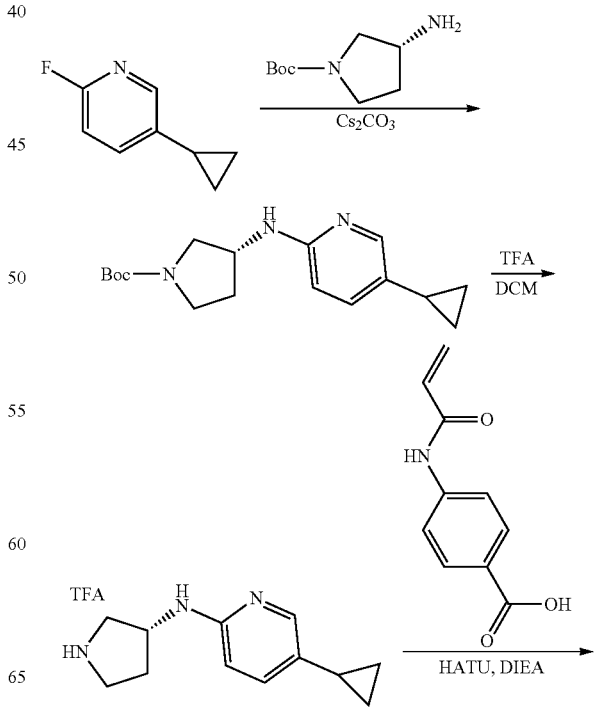

283

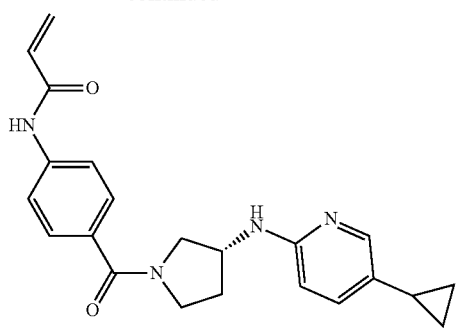

Step 1: (R)-tert-butyl 3-((5-cyclopropylpyridin-2-yl)amino)pyrrolidine-1-carboxylate

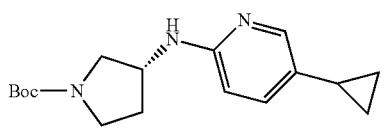 [SMILES: CC(C)(C)OC(=O)N1CC[C@@H](Nc2ccc(C3CC3)cn2)C1]

A mixture of 5-cyclopropyl-2-fluoropyridine (543 mg, 2.92 mmol), (R)-tert-butyl 3-aminopyrrolidine-1-carboxylate (400 mg, 2.92 mmol) and $Cs_2CO_3$ (1904 mg, 5.84 mmol) in DMSO (2 mL) was stirred at 160° C. for 24 hours. The mixture was cooled to RT diluted with water (20 mL) and extracted with EtOAc (20 mL*3). The combined organic phase was concentrated and the residue was purified by flash chromatography on silica gel (PE/EtOAc=2/1) to afford (R)-tert-butyl 3-((5-cyclopropylpyridin-2-yl)amino)pyrrolidine-1-carboxylate (35 mg, 4%) as a yellow solid. [M+H] Calc'd for $C_{17}H_{25}N_3O_2$, 304.1; Found, 304.1.

Step 2: (R)-5-cyclopropyl-N-(pyrrolidin-3-yl)pyridin-2-amine 2,2,2-trifluoroacetate

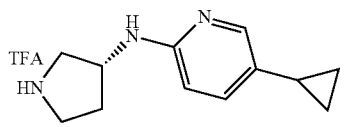 [SMILES: c1cc(N[C@@H]2CCNC2)ncc1C1CC1 ; "TFA"]

The title compound was prepared in 100% yield from (R)-tert-butyl 3-((5-cyclopropylpyridin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{12}H_{17}N_3$, 204.1; Found, 204.1.

284

Step 3: (R)—N-(4-(3-((5-cyclopropylpyridin-2-yl)amino)pyrrolidine-1-carbonyl)phenyl)acrylamide

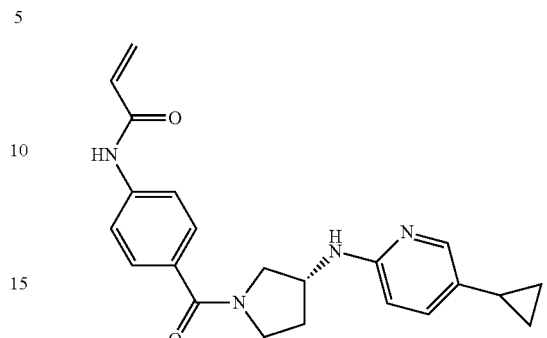

The title compound was prepared in 13% yield from (R)-5-cyclopropyl-N-(pyrrolidin-3-yl)pyridin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 0.47-0.54 (m, 2H), 0.76-0.83 (m, 2H), 1.68-1.92 (m, 2H), 2.07-2.19 (m, 1H), 3.25-3.29 (m, 1H), 3.50-3.66 (m, 2H), 3.74-3.82 (m, 1H), 4.22-4.36 (m, 1H), 5.78 (d, J=10.0 Hz, 1H), 6.25-6.29 (m, 1H), 6.37-6.47 (m, 2H), 6.56-6.60 (m, 1H), 7.03-7.10 (m, 1H), 7.49-7.54 (m, 1H), 7.68-7.85 (m, 3H), 10.32 (br s, 1H). [M+H] Calc'd for $C_{22}H_{24}N_4O_2$, 377.1; Found, 377.1.

Example 86: Synthesis of (R)—N-(4-(3-((5-chloro-4-(dimethylamino)pyrimidin-2-yl)amino)pyrrolidine-1-carbonyl)phenyl)acrylamide

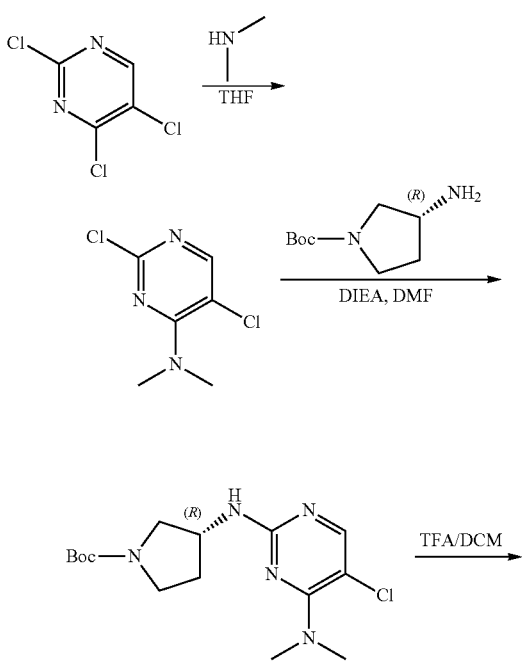

-continued

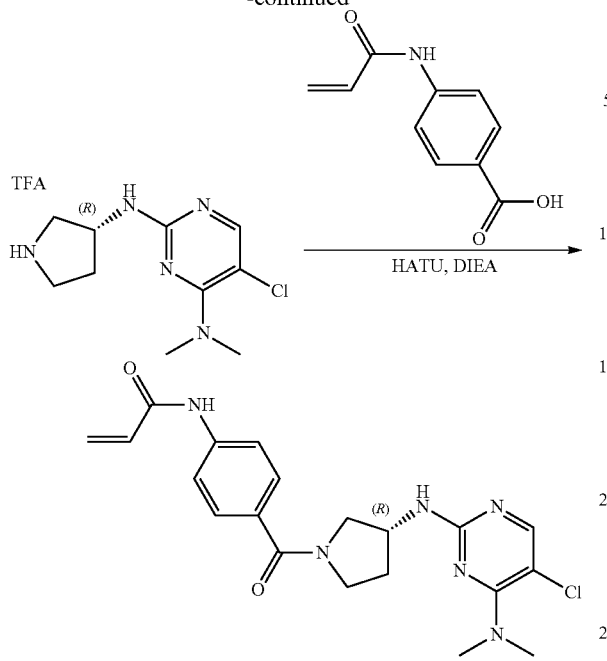

Step 1: 2,5-dichloro-N,N-dimethylpyrimidin-4-amine

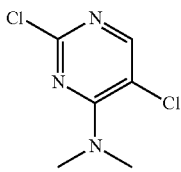

To a mixture of 2,4,5-trichloropyrimidine (400 mg, 2.19 mmol) in THF (4 mL) was added dimethylamine (295 mg, 6.56 mmol) at 0° C. The mixture was stirred at 5° C. for 2 hours. The mixture was diluted with water (10 mL) and extracted with EtOAc (50 mL*3). The combined organic phase was concentrated in vacuo. The residue was purified by reverse column to afford 2,5-dichloro-N,N-dimethylpyrimidin-4-amine (196 mg, 47%) as colorless oil. [M+H] Calc'd for $C_6H_7Cl_2N_3$, 192.0; Found, 192.0.

Step 2: (R)-tert-butyl 3-((5-chloro-4-(dimethylamino)pyrimidin-2-yl)amino)pyrrolidine-1-carboxylate

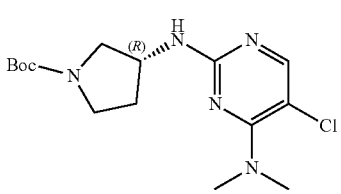

The title compound was prepared in 28% yield from 2,5-dichloro-N,N-dimethylpyrimidin-4-amine using general procedure of (R)-tert-butyl 3-((5-chloro-4-methylpyrimidin-2-yl)amino)pyrrolidine-1-carboxylate. [M+H] Calc'd for $C_{15}H_{24}ClN_5O_2$, 342.1; Found, 342.1.

Step 3: (R)-5-chloro-N4,N4-dimethyl-N2-(pyrrolidin-3-yl)pyrimidine-2,4-diamine 2,2,2-trifluoroacetate

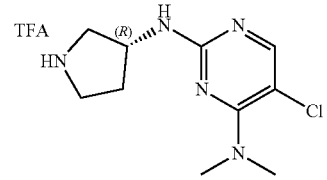

The title compound was prepared in 100% yield from (R)-tert-butyl 3-((5-chloro-4-(dimethylamino)pyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{10}H_{16}ClN_5$, 242.1; Found, 242.1.

Step 4: (R)—N-(4-(3-((5-chloro-4-(dimethylamino)pyrimidin-2-yl)amino)pyrrolidine-1-carbonyl)phenyl)acrylamide

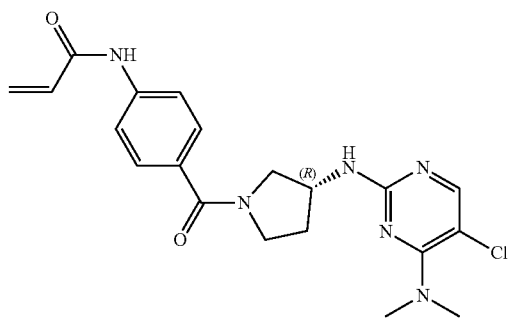

The title compound was prepared in 26% yield from (R)-5-chloro-$N^4$,$N^4$-dimethyl-N-(pyrrolidin-3-yl)pyrimidine-2,4-diamine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.87-1.99 (m, 1H), 2.07-2.15 (m, 1H), 3.02 (s, 3H), 3.10 (s, 3H), 3.42-3.55 (m, 2H), 3.61-3.77 (m, 2H), 4.19-4.36 (m, 1H), 5.78 (d, J=11.2 Hz, 1H), 6.28 (d, J=16.8 Hz, 1H), 6.41-6.48 (m, 1H), 7.16 (br s, 1H), 7.48-7.53 (m, 2H), 7.69-7.73 (m, 2H), 7.80 (s, 0.5H), 7.86 (s, 0.5H), 10.30 (s, 1H). [M+H] Calc'd for $C_{20}H_{23}ClN_6O$, 415.1; Found, 415.1.

Example 87: Synthesis of (R)—N-(4-(3-((5-chloropyrimidin-2-yl)amino)pyrrolidine-1-carbonyl)phenyl)acrylamide

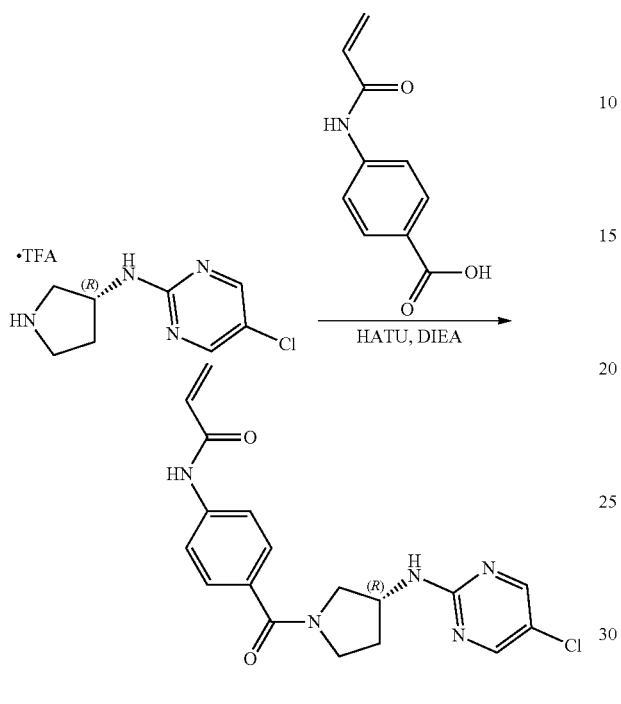

Step 1: (R)—N-(4-(3-((5-chloropyrimidin-2-yl)amino)pyrrolidine-1-carbonyl)phenyl)acrylamide

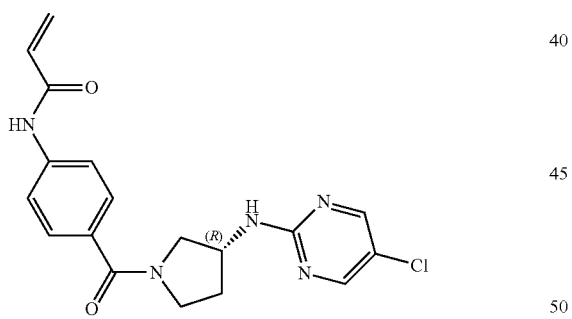

A mixture of (R)-5-chloro-N-(pyrrolidin-3-yl)pyrimidin-2-amine TFA salt (3.8 g, 10.4 mmol), 4-acrylamidobenzoic acid (2.0 g, 10.4 mmol), HATU (4.7 g, 12.5 mmol) and DIPEA (6.7 g, 52.0 mmol) in DMF (5.0 mL) was stirred at RT for 3 hours. The reaction mixture was diluted with $H_2O$ (100 mL) and extracted with EtOAc (100 mL*2). The combined organics were washed with brine (100 mL), dried over $Na_2SO_4$, filtered and concentrated. The residue was purified by prep-HPLC to give (R)—N-(4-(3-((5-chloropyrimidin-2-yl)amino)pyrrolidine-1-carbonyl)phenyl)acrylamide (1.8 g, 47%). $^1H$ NMR (400 MHz, DMSO-$d_6$): δ 1.86-2.02 (m, 1H), 2.07-2.19 (m, 1H), 3.30-3.37 (m, 1H), 3.40-3.48 (m, 1H), 3.51-3.62 (m, 1H), 3.70-3.80 (m, 1H), 4.24-4.26 (m, 0.5H), 4.39-4.41 (m, 0.5H), 5.78 (d, J=10.8 Hz, 1H), 6.28 (d, J=16.8 Hz, 1H), 6.41-6.50 (m, 1H), 7.28-7.31 (m, 2H), 7.48-7.54 (m, 2H), 7.81 (brs, 1H), 8.32 (s, 1H), 8.38 (s, 1H), 10.27 (brs, 1H). [M+H]MS Calcd.: $C_{19}H_{21}ClN_6O_3$, 372.1, Found: 372.1.

Example 88: Synthesis of (R)—N-(4-(3-((5-chloro-4-(2-methoxyethoxy)pyrimidin-2-yl)amino)pyrrolidine-1-carbonyl)phenyl)acrylamide

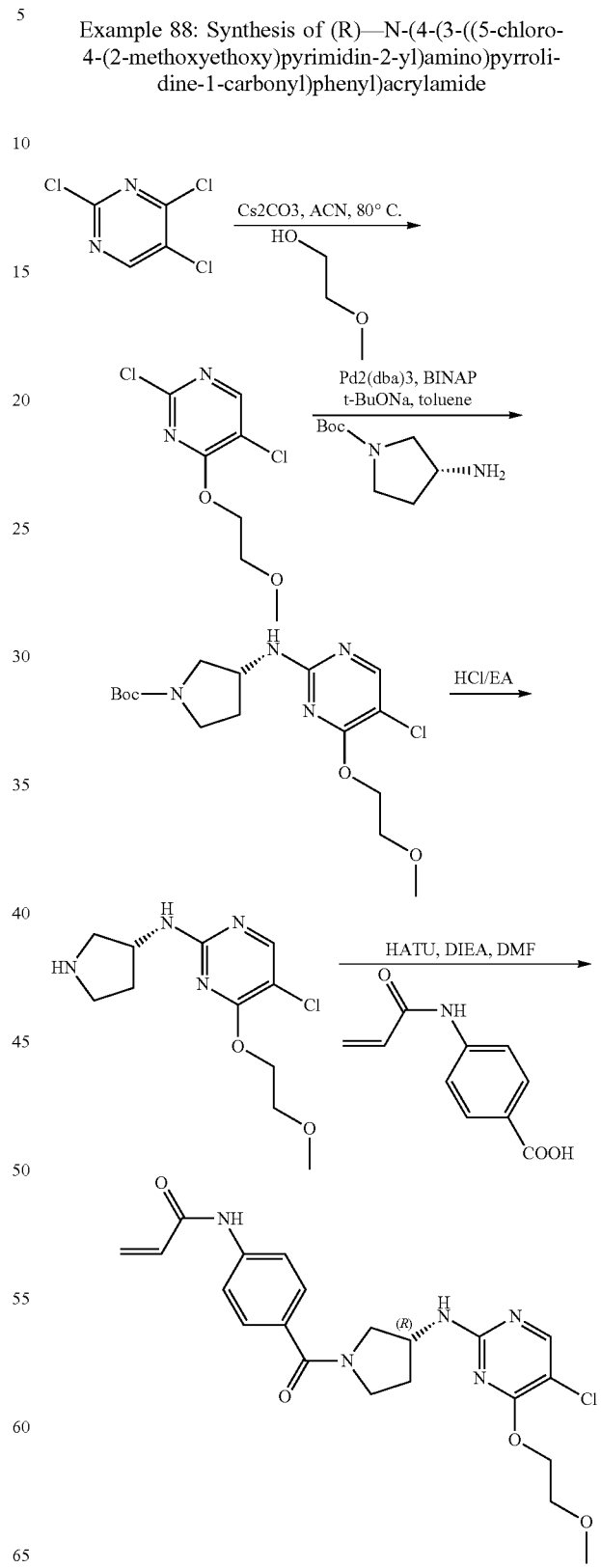

Step 1: 2,5-dichloro-4-(2-methoxyethoxy)pyrimidine

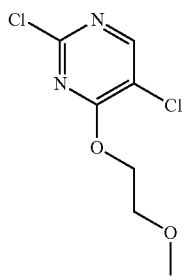

A mixture of 2,4,5-trichloropyrimidine (2.0 g, 10.9 mmol), 2-methoxyethanol (748 mg, 9.8 mmol), $Cs_2CO_3$ (5.3 g, 16.3 mmol) in $CH_3CN$ (30 mL) was stirred at 80° C. for 4 h. The reaction mixture was cooled, added $H_2O$ (40 mL) and extracted with EA (40 mL*2). The combined organic layer was dried over $Na_2SO_4$, concentrated and purified by silica gel chromatography (PE/EA=PE~1/10) to afford 2,5-dichloro-4-(2-methoxyethoxy)pyrimidine (1.2 g, 50%) as colorless oil. [M+H] Calc'd for $C_7H_8Cl_2N_2O_2$, 222.9; Found, 222.9

Step 2: (R)-tert-butyl 3-((5-chloro-4-(2-methoxyethoxy)pyrimidin-2-yl)amino)pyrrolidine-1-carboxylate

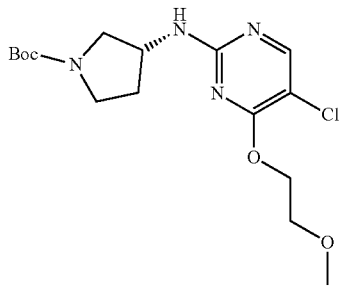

A mixture of 2,5-dichloro-4-(2-methoxyethoxy)pyrimidine (1.2 g, 2.7 mmol), (R)-tert-butyl 3-aminopyrrolidine-1-carboxylate (1.1 g, 2.9 mmol), BINAP (1.3 g, 1.1 mmol), t-BuONa (778 mg, 4.1 mol) and $Pd_2(dba)_3$ (622 mg, 5.4 mmol) in toluene (25 mL) was stirred at 100° C. overnight. The reaction mixture was cooled, filtered and concentrated. The residue was purified by silicagel chromatography (PE/EA=) to afford (R)-tert-butyl 3-((5-chloro-4-(2-methoxyethoxy)pyrimidin-2-yl)amino)pyrrolidine-1-carboxylate (600 mg, 30%) as yellow oil. [M+H] Calc'd for $C_{16}H_{25}ClN_4O_4$, 373.1; Found, 373.1.

Step 3: (R)-5-chloro-4-(2-methoxyethoxy)-N-(pyrrolidin-3-yl)pyrimidin-2-amine

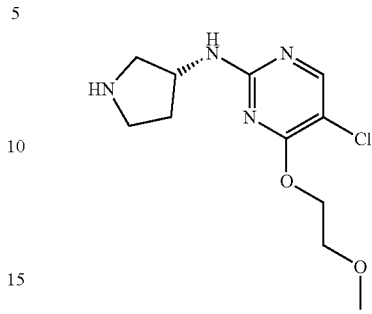

A mixture of (R)-tert-butyl 3-((5-chloro-4-(2-methoxyethoxy)pyrimidin-2-yl)amino)pyrrolidine-1-carboxylate (600 mg, 1.6 mmol) in HCl/EA (15 mL) was stirred at RT for 1 h. The reaction mixture was concentrated to afford (R)-5-chloro-4-(2-methoxyethoxy)-N-(pyrrolidin-3-yl)pyrimidin-2-amine (400 mg, 91%) as yellow oil. [M+H] Calc'd for $C_{11}H_{17}ClN_4O_2$, 273.1; Found, 273.1.

Step 4: (R)—N-(4-(3-((5-chloro-4-(2-methoxyethoxy)pyrimidin-2-yl)amino)pyrrolidine-1-carbonyl)phenyl)acrylamide

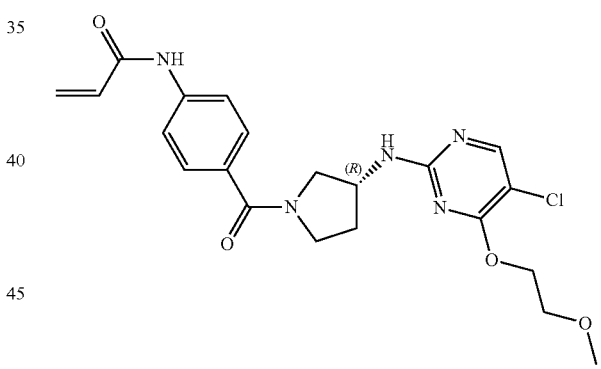

A mixture of (R)-5-chloro-4-(2-methoxyethoxy)-N-(pyrrolidin-3-yl)pyrimidin-2-amine (231 mg, 1.2 mmol), 4-acrylamidobenzoic acid (300 mg, 1.1 mmol), HATU (419 mg, 1.1 mmol) and DIEA (284 mg, 1.2 mmol) in DMF (15 mL) was stirred at RT for overnight. The reaction mixture was added $H_2O$ (40 mL) and extracted with EA (40 mL*3). The combined organic layer was dried over $Na_2SO_4$, filtered and concentrated. The residue was purified by prep-HPLC to afford (R)—N-(4-(3-((5-chloro-4-(2-methoxyethoxy)pyrimidin-2-yl)amino)pyrrolidine-1-carbonyl)phenyl)acrylamide (219.2 mg, 45%) as a yellow solid. $^1$H NMR (400 MHz, DMSO-$d_6$): 1.89-2.15 (m, 2H), 3.23 (s, 1H), 3.31 (s, 2H), 3.52-3.77 (m, 6H), 4.21-4.48 (m, 3H), 5.77-5.79 (d, J=10.0 Hz, 1H), 6.25-6.30 (d, J=17.2 Hz, 1H), 6.40-6.48 (m, 1H), 7.49-7.54 (m, 2H), 7.69-7.73 (m, 2H), 8.08-8.15 (m, 1H), 10.32-10.33 (d, J=4.8 Hz, 1H). [M+H] Calc'd for $C_{21}H_{24}ClN_5O_4$, 446.1; Found, 446.1.

Example 89: Synthesis of (R)—N-(4-(3-((4-(azetidin-1-yl)-5-chloropyrimidin-2-yl)amino)pyrrolidine-1-carbonyl)phenyl)acrylamide

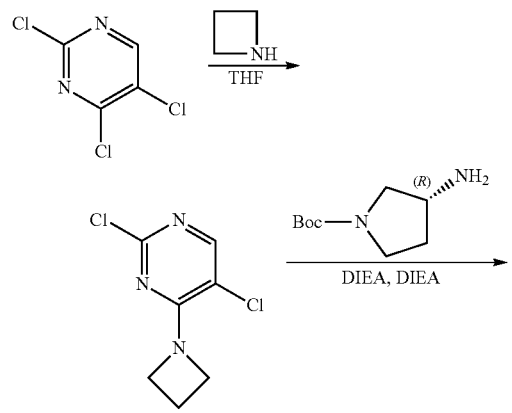

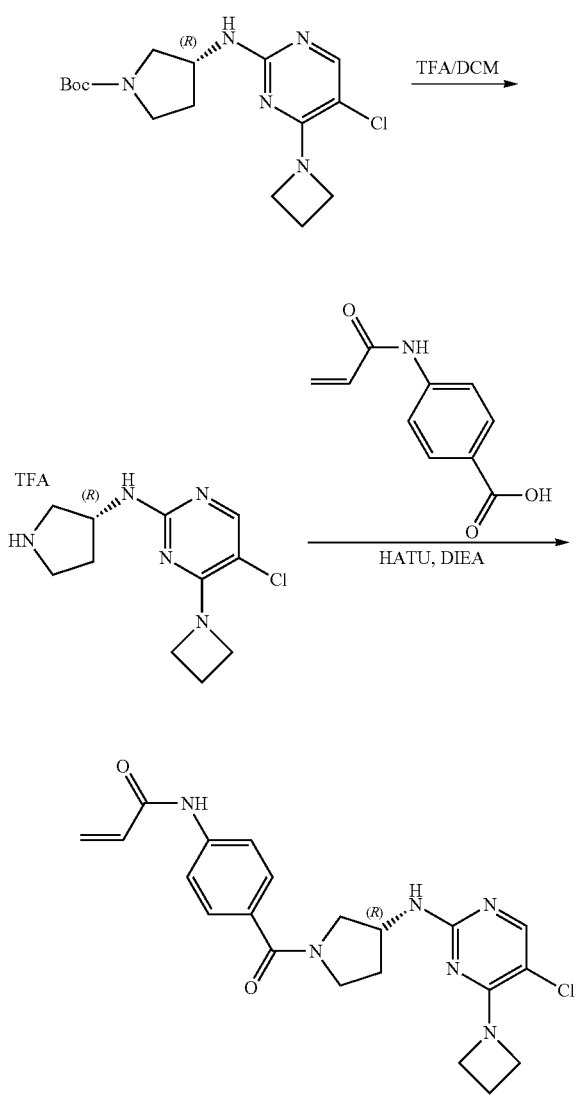

Step 1: 4-(azetidin-1-yl)-2,5-dichloropyrimidine

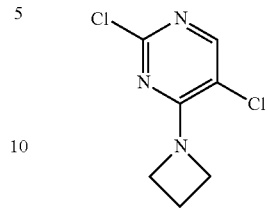

The title compound was prepared in 84% yield from 2,4,5-trichloropyrimidine using general procedure of 2,5-dichloro-N,N-dimethylpyrimidin-4-amine. [M+H] Calc'd for $C_7H_7C_2N_3$, 204.0; Found, 204.0.

Step 2: (R)-tert-butyl 3-((4-(azetidin-1-yl)-5-chloropyrimidin-2-yl)amino)pyrrolidine-1-carboxylate

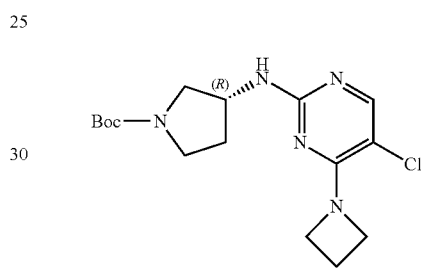

The title compound was prepared in 25% yield from 4-(azetidin-1-yl)-2,5-dichloropyrimidine using general procedure of (R)-tert-butyl 3-((5-chloro-4-methylpyrimidin-2-yl)amino)pyrrolidine-1-carboxylate. [M+H] Calc'd for $C_{16}H_{24}ClN_5O_2$, 354.1; Found, 354.1.

Step 3: (R)-4-(azetidin-1-yl)-5-chloro-N-(pyrrolidin-3-yl)pyrimidin-2-amine 2,2,2-trifluoroacetate

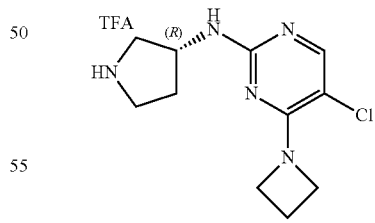

The title compound was prepared in 100% yield from (R)-tert-butyl 3-((4-(azetidin-1-yl)-5-chloropyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_1H_{16}ClN_5$, 254.1; Found, 254.1.

Step 4: (R)—N-(4-(3-((4-(azetidin-1-yl)-5-chloropyrimidin-2-yl)amino)pyrrolidine-1-carbonyl)phenyl)acrylamide

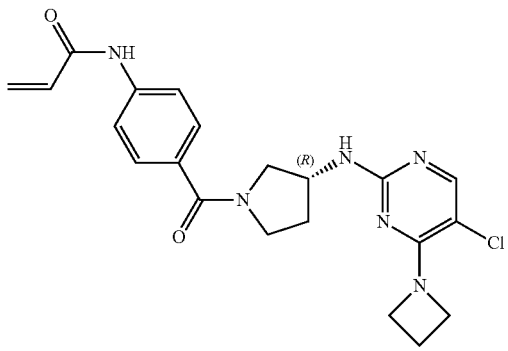

The title compound was prepared in 15% yield from (R)-4-(azetidin-1-yl)-5-chloro-N-(pyrrolidin-3-yl)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.83-2.05 (m, 1H), 2.07-2.11 (m, 1H), 2.18-2.33 (m, 2H), 3.27-3.32 (m, 1H), 3.47-3.77 (m, 3H), 4.14-4.34 (m, 5H), 5.77-5.80 (m, 1H), 6.25-6.30 (m, 1H), 6.41-6.48 (m, 1H), 7.14 (br s, 1H), 7.47-7.53 (m, 2H), 7.69-7.78 (m, 3H), 10.32 (s, 1H). [M+H] Calc'd for $C_{21}H_{23}ClN_6O_2$, 427.1; Found, 427.1.

Example 90: Synthesis of (R)—N-(4-(3-((4-amino-5-chloropyrimidin-2-yl)amino)pyrrolidine-1-carbonyl)phenyl)acrylamide

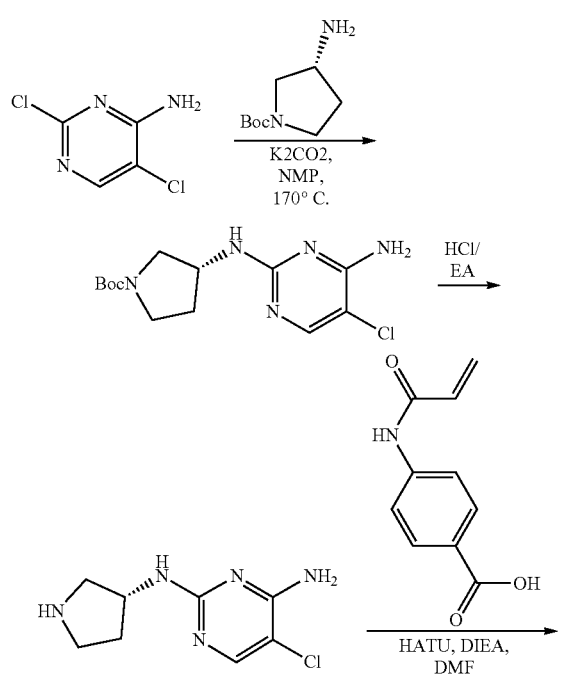

Step 1: (R)-tert-butyl 3-((4-amino-5-chloropyrimidin-2-yl)amino)pyrrolidine-1-carboxylate

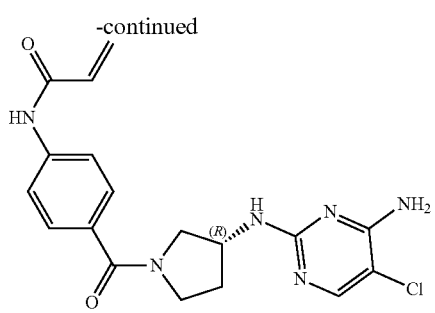

A mixture of 2,5-dichloropyrimidin-4-amine (500 mg, 3.0 mmol) and (R)-tert-butyl 3-aminopyrrolidine-1-carboxylate (1.1 g, 6.0 mmol) in NMP (20 mL) was added K$_2$CO$_3$ (830 mg, 6.0 mmol) at RT. The mixture was stirred at 170° C. for 1.5 h in microwave. The mixture was cooled, diluted with water (10 mL) and extracted with DCM (10 mL*3). The combined organic layer was washed with brine (20 mL), dried over Na$_2$SO$_4$, filtered and concentrated in vacuo. The residue was purified by column (PE:EA=1:1) to afford (R)-tert-butyl 3-((4-amino-5-chloropyrimidin-2-yl)amino)pyrrolidine-1-carboxylate (676 mg, 60%) as a yellow solid. [M+H]Calc'd for $C_{13}H_{21}ClN_5O_2$, 314.1; Found, 314.1

Step 2: (R)-5-chloro-N2-(pyrrolidin-3-yl)pyrimidine-2,4-diamine

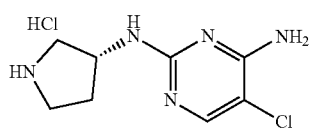 [SMILES: Cl ; Nc1nc(N[C@@H]2CCNC2)ncc1Cl]

A mixture of (R)-tert-butyl 3-((4-amino-5-chloropyrimidin-2-yl)amino)pyrrolidine-1-carboxylate (576 mg, 1.84 mmol) in HCl/EA (10 mL) was stirred at RT for 3 h. The reaction mixture was concentrated to afford (R)-5-chloro-N2-(pyrrolidin-3-yl)pyrimidine-2,4-diamine (600 mg, crude) as a yellow solid. [M+H] Calc'd for $C_8H_{13}ClN_5$, 214.0; Found, 214.0

Step 3: (R)—N-(4-(3-((4-amino-5-chloropyrimidin-2-yl)amino)pyrrolidine-1-carbonyl)phenyl)acrylamide

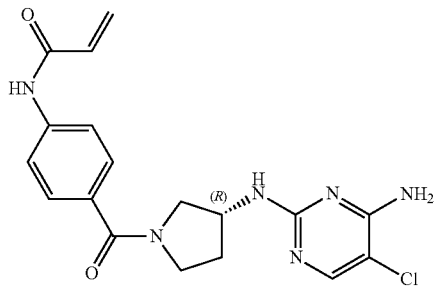

A mixture of 4-acrylamidobenzoic acid (150 mg, 0.78 mmol), (R)-5-chloro-N2-(pyrrolidin-3-yl)pyrimidine-2,4-diamine (HCl salt) (582 mg, 0.78 mmol), HATU (356 mg, 0.94 mmol) and DIEA (503 mg, 3.9 mmol) in DMF (15 mL) was stirred at RT overnight. The mixture was diluted with water (10 mL) and extracted with DCM (10 mL*3). The combined organic layer was washed with brine (20 mL), dried over Na$_2$SO$_4$, filtered and concentrated in-vacuo. The residue was purified by prep-HPLC to afford (R)—N-(4-(3-((4-amino-5-chloropyrimidin-2-yl)amino)pyrrolidine-1-carbonyl)phenyl)acrylamide (34.0 mg, 11%) as a white solid (TFA salt). $^1$H NMR (400 MHz, DMSO-d$_6$): δ 1.95-2.02 (m, 1H), 2.14-2.27 (m, 1H), 3.40-3.82 (m, 3H), 4.25-4.48 (m, 1H), 5.79 (d, J=10.4 Hz, 1H), 6.26 (s, 0.5H), 6.30 (s, 0.5H), 6.41-6.48 (m, 1H), 7.51-7.53 (m, 2H), 7.70-7.75 (m, 2H), 8.00-8.39 (m, 4H), 10.32 (s, 1H). [M+H] Calc'd for C$_{18}$H$_{20}$ClN$_6$O$_2$, 387.1; Found, 387.1

Example 91: Synthesis of (R)—N-(4-(3-((4-amino-5-(trifluoromethyl)pyrimidin-2-yl)amino)pyrrolidine-1-carbonyl)phenyl)acrylamide

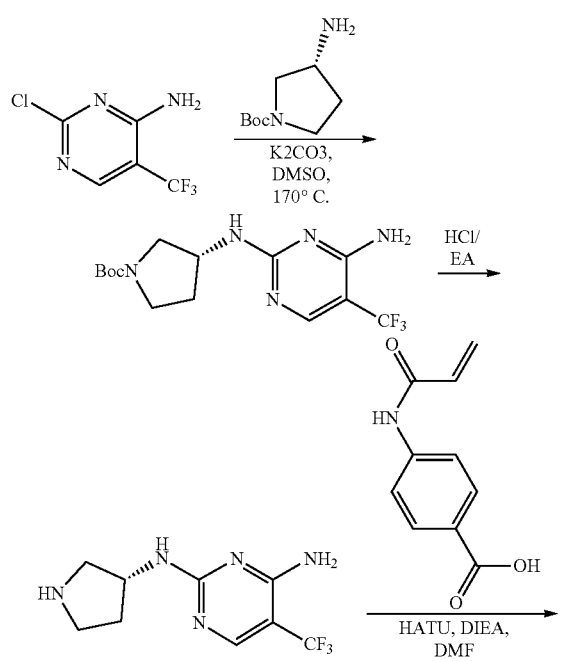

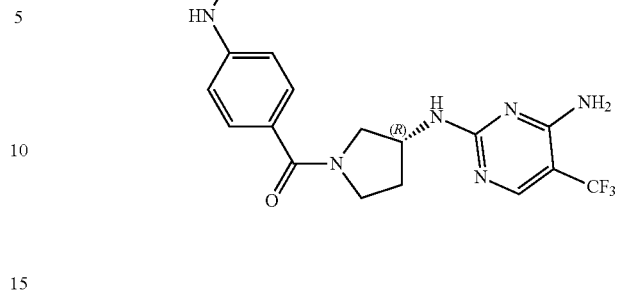

Step 1: (R)-tert-butyl 3-((4-amino-5-(trifluoromethyl)pyrimidin-2-yl)amino)pyrrolidine-1-carboxylate

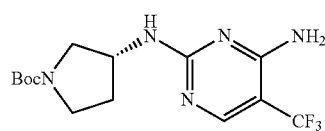 [SMILES: CC(C)(C)OC(=O)N1CC[C@@H](Nc2ncc(C(F)(F)F)c(N)n2)C1]

To a mixture of 2-chloro-5-(trifluoromethyl)pyrimidin-4-amine (500 mg, 2.53 mmol) and (R)-tert-butyl 3-aminopyrrolidine-1-carboxylate (944 mg, 5.07 mmol) in DMSO (20 mL) was added K$_2$CO$_3$ (700 mg, 5.07 mmol). The mixture was stirred at 170° C. for 1.5 h in microwave. The mixture was cooled, diluted with water (10 mL) and extracted with DCM (10 mL*3). The combined organic layer was washed with brine (20 mL), dried over Na$_2$SO$_4$, filtered and concentrated in vacuo. The residue was purified by column (PE:EA=3:1) to afford (R)-tert-butyl 3-((4-amino-5-(trifluoromethyl)pyrimidin-2-yl)amino)pyrrolidine-1-carboxylate (920 mg, 87%) as a white solid. [M+H] Calc'd for C$_{14}$H$_{21}$F$_3$N$_5$O$_2$, 348.1; Found, 348.1

Step 2: (R)—N2-(pyrrolidin-3-yl)-5-(trifluoromethyl)pyrimidine-2,4-diamine (HCl Salt)

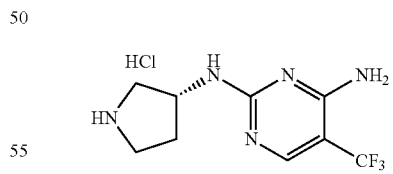

A mixture of (R)-tert-butyl 3-((4-amino-5-(trifluoromethyl)pyrimidin-2-yl)amino)pyrrolidine-1-carboxylate (920 mg, 2.65 mmol) in HCl/EA (15 mL) was stirred at RT for 3 h. The reaction mixture was concentrated in vacuo to afford (R)—N2-(pyrrolidin-3-yl)-5-(trifluoromethyl)pyrimidine-2,4-diamine (HCl salt) (900 mg, >100%) as a white solid. [M+H]Calc'd for C$_9$H$_{12}$F$_3$N$_5$, 248.0; Found, 248.0

Step 3: (R)—N-(4-(3-((4-amino-5-(trifluoromethyl)pyrimidin-2-yl)amino)pyrrolidine-1-carbonyl)phenyl)acrylamide

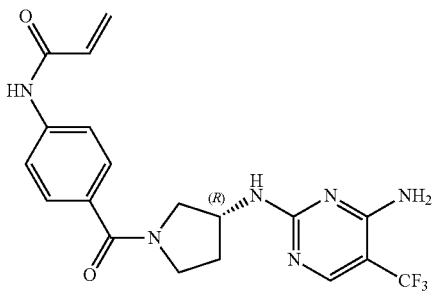

A mixture of 4-acrylamidobenzoic acid (200 mg, 1.05 mmol), (R)—N2-(pyrrolidin-3-yl)-5-(trifluoromethyl)pyrimidine-2,4-diamine (HCl salt) (888 mg, 3.14 mmol), HATU (477 mg, 1.25 mmol) and DIEA (675 mg, 5.23 mmol) in DMF (15 mL) was stirred at RT for overnight. The mixture was diluted with water (10 mL) and extracted with DCM (10 mL*3). The combined organic layer was washed with brine (20 mL), dried over Na$_2$SO$_4$, filtered and concentrated in-vacuo. The residue was purified by prep-HPLC to afford (R)—N-(4-(3-((4-amino-5-(trifluoromethyl)pyrimidin-2-yl)amino)pyrrolidine-1-carbonyl)phenyl)acrylamide (207.0 mg, 47%) as a white solid. $^1$H NMR (400 MHz, DMSO-d$_6$): δ 1.82-2.00 (m, 1H), 2.06-2.16 (m, 1H), 3.34-3.78 (m, 4H), 4.30-4.44 (m, 1H), 5.79 (d, J=10.0 Hz, 1H), 6.26 (s, 0.5H), 6.30 (s, 0.5H), 6.41-6.48 (m, 1H), 6.66-6.86 (m, 2H), 7.35-7.65 (m, 3H), 7.68-7.75 (m, 2H), 8.00-8.14 (m, 1H), 10.32 (s, 1H). [M+H] Calc'd for C$_{19}$H$_{20}$F$_3$N$_6$O$_2$, 421.1; Found, 421.1.

Example 92: Synthesis of (R)—N-(4-(3-((5-chloro-4-(trifluoromethyl)pyrimidin-2-yl)amino)pyrrolidine-1-carbonyl)phenyl)acrylamide

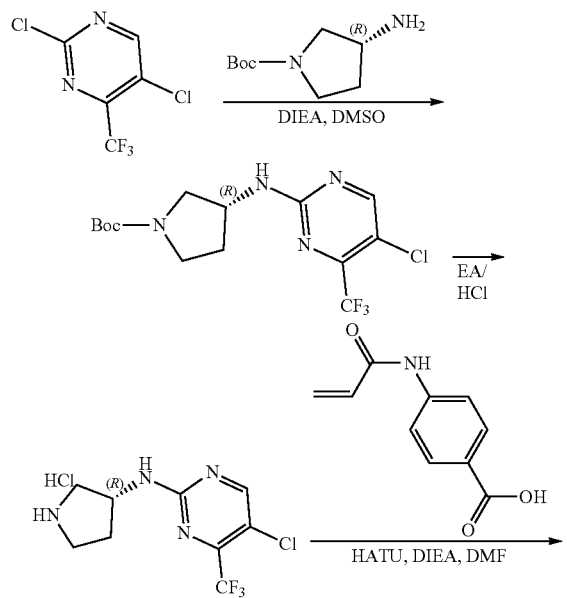

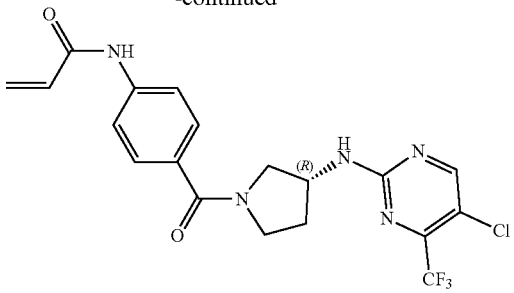

Step 1: (R)-tert-butyl 3-((5-chloro-4-(trifluoromethyl)pyrimidin-2-yl)amino)pyrrolidine-1-carboxylate

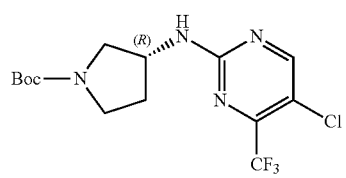

To a mixture of 2,5-dichloro-4-(trifluoromethyl)pyrimidine (500 mg, 2.7 mmol) and (R)-tert-butyl 3-aminopyrrolidine-1-carboxylate (643 mg, 3.5 mmol) in DMSO (10 mL) was added DIEA (593 mg, 4.6 mmol). The reaction mixture was stirred at RT for 16 h. The mixture was diluted with water (10 mL) and extracted with DCM (10 mL*3). The combined organic layer was washed with brine (20 mL), dried over Na$_2$SO$_4$, filtered and concentrated in-vacuo. The residue was purified by column (PE:EA=5:1) to afford (R)-tert-butyl 3-((5-chloro-4-(trifluoromethyl)pyrimidin-2-yl)amino)pyrrolidine-1-carboxylate (860 mg, 87%) as white solid. [M+H] Calc'd for C$_{14}$H$_{18}$ClF$_3$N$_4$O$_2$, 367.1; Found, 367.1

Step 2: (R)-5-chloro-N-(pyrrolidin-3-yl)-4-(trifluoromethyl)pyrimidin-2-amine hydrochloride

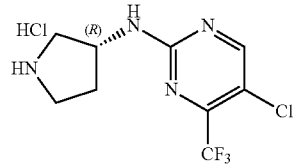

A mixture of (R)-tert-butyl 3-((5-chloro-4-(trifluoromethyl)pyrimidin-2-yl)amino)pyrrolidine-1-carboxylate (400 mg, 1.1 mmol) in HCl/EA (15 mL) was stirred at RT for 2 h. The reaction mixture was concentrated to afford (R)-5-chloro-N-(pyrrolidin-3-yl)-4-(trifluoromethyl)pyrimidin-2-amine hydrochloride (342 mg, >100%) as white solid. [M+H]Calc'd for C$_9$H$_{11}$Cl$_2$F$_3$N$_4$, 267.1; Found, 267.1

Step 3: (R)—N-(4-(3-((5-chloro-4-(trifluoromethyl)pyrimidin-2-yl)amino)pyrrolidine-1-carbonyl)phenyl)acrylamide

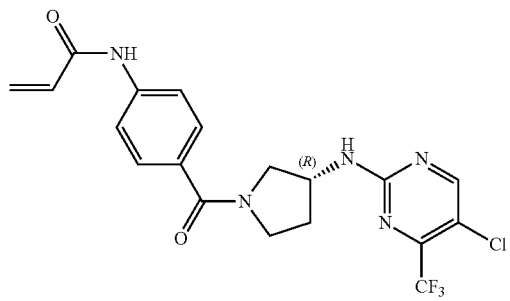

A mixture of 4-acrylamidobenzoic acid (207 mg, 1.1 mmol), (R)-5-chloro-N-(pyrrolidin-3-yl)-4-(trifluoromethyl)pyrimidin-2-amine hydrochloride (342 mg, 1.3 mmol), HATU (627 mg, 1.7 mmol) and DIEA (568 mg, 4.4 mmol) in DMF (10 mL) was stirred at RT for overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(4-(3-((5-chloro-4-(trifluoromethyl)pyrimidin-2-yl)amino)pyrrolidine-1-carbonyl)phenyl)acrylamide (267.8 mg, 47%) as a white solid. $^1$H NMR (400 MHz, DMSO-$d_6$): δ 1.91-2.16 (m, 2H), 3.41-3.81 (m, 4H), 4.30-4.46 (m, 1H), 5.77-5.80 (m, 1H), 6.26-6.30 (m, 1H), 6.41-6.44 (m, 1H), 7.49-7.54 (m, 2H), 7.69-7.73 (m, 2H), 8.46 (s, 1H), 8.62-8.70 (m, 1H), 10.29 (s, 1H). [M+H] Calc'd for $C_{19}H_{17}CF_3N_5O_2$, 440.1; Found, 440.1

Example 93: Synthesis of (R)—N-(4-(3-((5-chloro-4-(trideuteromethoxy)pyrimidin-2-yl)amino)pyrrolidine-1-carbonyl)phenyl)acrylamide

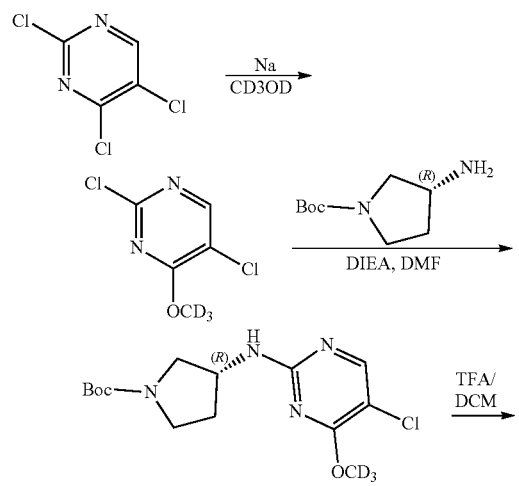

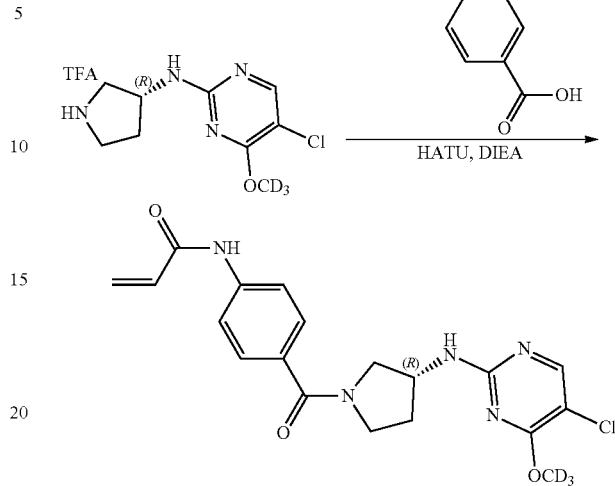

Step 1: 2,5-dichloro-4-(trideuteromethoxy)pyrimidine

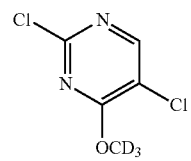

Na (186 mg, 8.07 mmol) was added portionwise into $CD_3OD$ (2.0 mL) at RT. After addition, the mixture was stirred at RT for another 2 hours. Then a solution of 2,4,5-trichloropyrimidine (1.0 g, 5.45 mmol) in THF (10 mL) was added into above mixture and the reaction mixture was stirred at RT for overnight. The mixture was concentrated and the residue was purified by flash chromatography on silica gel (PE) to afford 2,5-dichloro-4-(trideuteromethoxy)pyrimidine (900 mg, 92%) as a white solid. [M+H] Calc'd for $C_5HD_3Cl_2N_2O$, 181.9; Found, 181.9.

Step 2: (R)-tert-butyl 3-((5-chloro-4-(trideuteromethoxy)pyrimidin-2-yl)amino)pyrrolidine-1-carboxylate

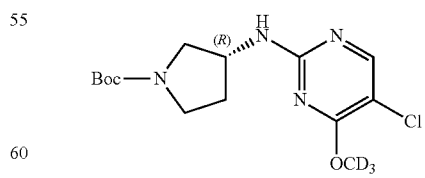

The title compound was prepared in 76% yield from (R)-tert-butyl 3-aminopyrrolidine-1-carboxylate using general procedure of (R)-tert-butyl 3-((5-chloro-4-methylpyrimidin-2-yl)amino)pyrrolidine-1-carboxylate. [M+H] Calc'd for $C_{14}H_{18}D_3ClN_4O_3$, 332.1; Found, 332.1.

Step 3: (R)-5-chloro-N-(pyrrolidin-3-yl)-4-(trichloromethoxy)pyrimidin-2-amine 2,2,2-trifluoroacetate

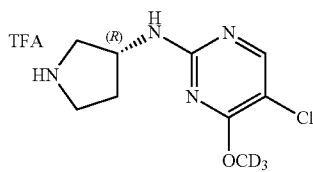

The title compound was prepared in 100% yield from (R)-tert-butyl 3-((5-chloro-4-(trideuteromethoxy)pyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H]Calc'd for $C_9H_{10}D_3ClN_4O$, 232.0; Found, 232.0.

Step 4: (R)—N-(4-(3-((5-chloro-4-(trideuteromethoxy)pyrimidin-2-yl)amino)pyrrolidine-1-carbonyl)phenyl)acrylamide

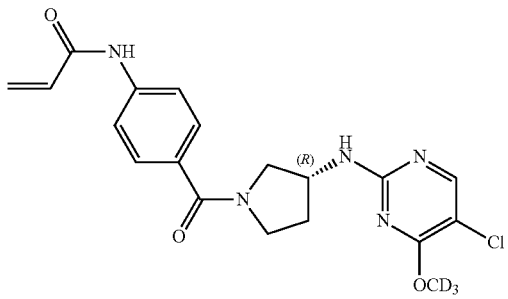

The title compound was prepared in 20% yield from (R)-5-chloro-N-(pyrrolidin-3-yl)-4-(trichloromethoxy)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.85-2.01 (m, 1H), 2.07-2.15 (m, 1H), 3.42-3.79 (m, 4H), 4.26-4.42 (m, 1H), 5.74-5.80 (m, 1H), 6.28 (d, J=16.4 Hz, 1H), 6.45-6.49 (m, 1H), 7.47-7.53 (m, 2H), 7.68-7.73 (m, 3H), 8.07 (s, 0.5H), 8.14 (s, 0.5H) 10.29 (s, 1H). [M+H] Calc'd for $C_{19}H_{17}D_3ClN_5O_3$, 405.1; Found, 405.1.

Example 94: Synthesis of (R)—N-(4-(3-((5-chloropyrimidin-2-yl)amino)pyrrolidine-1-carbonyl)thiazol-2-yl)acrylamide

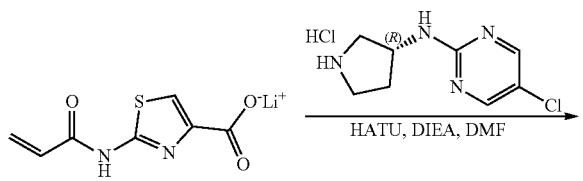

Step 1: (R)—N-(4-(3-((5-chloropyrimidin-2-yl)amino)pyrrolidine-1-carbonyl)thiazol-2-yl)acrylamide

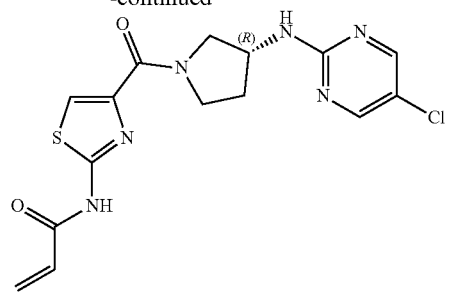

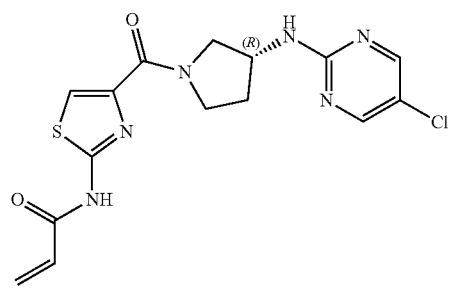

The title compound was prepared in 20% yield from lithium 2-acrylamidothiazole-4-carboxylate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.89-2.00 (m, 1H), 2.07-2.21 (m, 1H), 3.47-3.56 (m, 1H), 3.65-3.71 (m, 1H), 3.74-3.79 (m, 0.5H), 3.92-3.98 (m, 1H), 4.10-4.15 (m, 0.5H), 4.33-4.39 (m, 1H), 5.89-5.94 (m, 1H), 6.37-6.43 (m, 1H), 6.50-6.58 (m, 1H), 7.75 (d, J=2.0 Hz, 1H), 7.83 (d, J=6.4 Hz, 1H), 8.32 (s, 1H), 8.38 (s, 1H), 12.38 (br s, 1H). [M+H] Calc'd for $C_{15}H_{15}ClN_6O_2S$, 379.0; Found, 379.0.

Example 95: Synthesis of (R)—N-(4-(3-((5-chloro-4-phenoxypyrimidin-2-yl)amino)pyrrolidine-1-carbonyl)phenyl)acrylamide

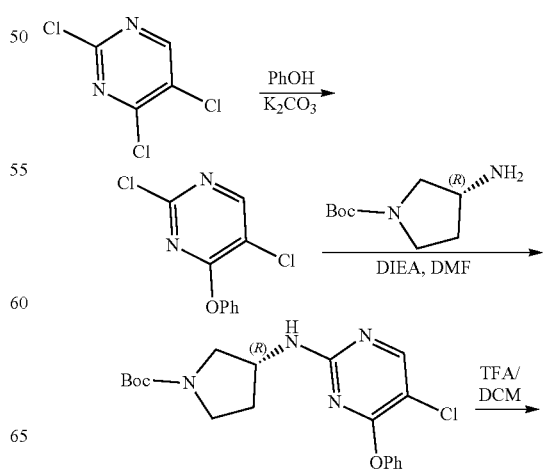

303

-continued

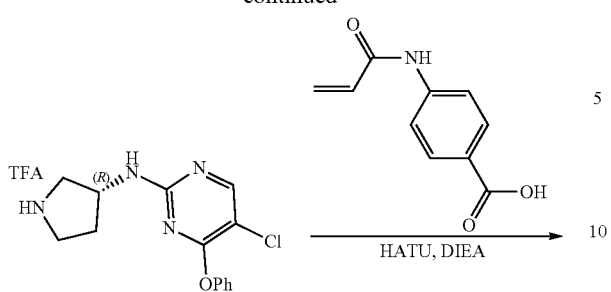

Step 1: 2,5-dichloro-4-phenoxypyrimidine

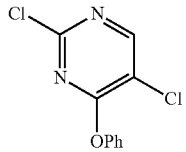 [SMILES: Clc1ncc(Cl)c(Oc2ccccc2)n1]

A solution of 2,4,5-trichloropyrimidine (500 mg, 2.72 mmol), phenol (384 mg, 4.08 mmol) and K$_2$CO$_3$ (750 mg, 5.44 mmol) in DMF (5 mL) was stirred at RT for 4 hours. The mixture was diluted with water (20 mL) and extracted with EtOAc (30 mL*2). The combined organic phase was washed with brine (20 mL), dried over Na$_2$SO$_4$, filtered and concentrated to afford 2,5-dichloro-4-phenoxypyrimidine (700 mg, crude, 100%) as a white solid. [M+H] Calc'd for C$_{10}$H$_6$Cl$_2$N$_2$O, 240.9; Found, 240.9.

Step 2: (R)-tert-butyl 3-((5-chloro-4-phenoxypyrimidin-2-yl)amino)pyrrolidine-1-carboxylate

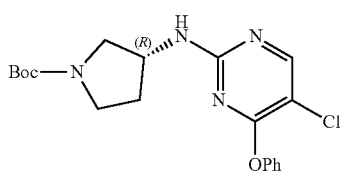

The title compound was prepared in 56% yield from 2,5-dichloro-4-phenoxypyrimidine using general procedure of (R)-tert-butyl 3-((5-chloro-4-methylpyrimidin-2-yl)amino)pyrrolidine-1-carboxylate. [M+H] Calc'd for C$_{19}$H$_{23}$ClN$_4$O$_3$, 391.1; Found, 391.1.

304

Step 3: (R)-5-chloro-4-phenoxy-N-(pyrrolidin-3-yl)pyrimidin-2-amine 2,2,2-trifluoroacetate

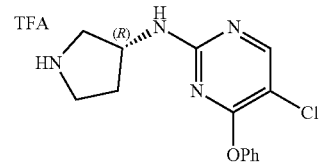

The title compound was prepared in 100% yield from (R)-tert-butyl 3-((5-chloro-4-phenoxypyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for C$_{14}$H$_{15}$ClN$_4$O, 291.0; Found, 291.0.

Step 4: (R)—N-(4-(3-((5-chloro-4-phenoxypyrimidin-2-yl)amino)pyrrolidine-1-carbonyl)phenyl)acrylamide

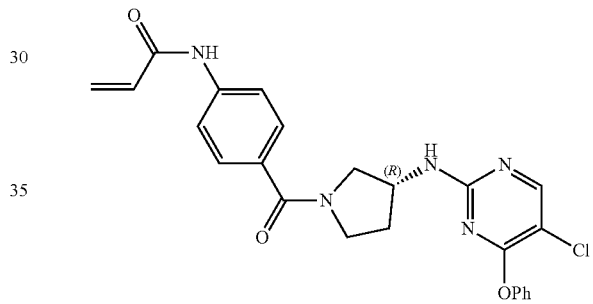

The title compound was prepared in 20% yield from (R)-5-chloro-4-phenoxy-N-(pyrrolidin-3-yl)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.85-2.15 (m, 2H), 3.30-3.32 (m, 1H), 3.36-3.73 (m, 3H), 4.23-4.38 (m, 1H), 5.78 (d, J=1.2 Hz, 1H), 6.26 (s, 0.4H), 6.29 (s, 0.6H), 7.12-7.31 (m, 4H), 7.45-7.46 (m, 3H), 7.48-7.78 (m, 3H), 8.25 (s, 0.6H), 8.27 (s, 0.4H), 10.30 (s, 1H). [M+H] Calc'd for C$_{24}$H$_{22}$ClN$_5$O$_3$, 464.1; Found, 464.1.

Example 96: Synthesis of (R)—N-(4-(3-((5-chloro-4-ethoxypyrimidin-2-yl)amino)pyrrolidine-1-carbonyl)phenyl)acrylamide

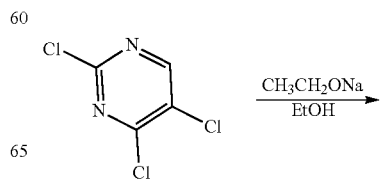

305

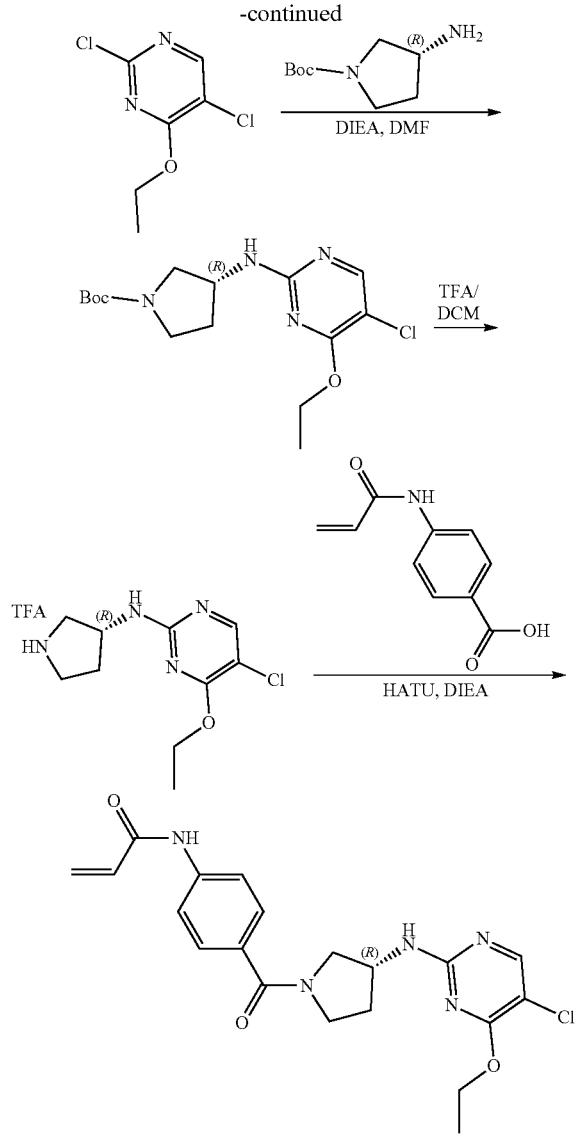

Step 1: 2,5-dichloro-4-ethoxypyrimidine

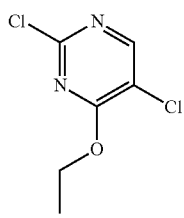

A solution of 2,4,5-trichloropyrimidine (1.00 g, 5.43 mmol) and CH₃CH₂ONa (0.73 g, 10.87 mmol) in EtOH (10 mL) was stirred at RT for 2 hours. The mixture was diluted with water (20 mL) and extracted with EtOAc (30 mL*2). The combined organic phase was washed with brine (30 mL), dried over Na₂SO₄, filtered and concentrated in vacuo. The residue was purified by flash chromatography on silica gel (PE/EtOAc=10/1) to afford 2,5-dichloro-4-ethoxypy-

306 rimidine (0.95 g, 81%) as a white solid. [M+H] Calc'd for $C_6H_6Cl_2N_2O$, 192.9; Found, 192.9.

Step 2: (R)-tert-butyl 3-((5-chloro-4-ethoxypyrimidin-2-yl)amino)pyrrolidine-1-carboxylate

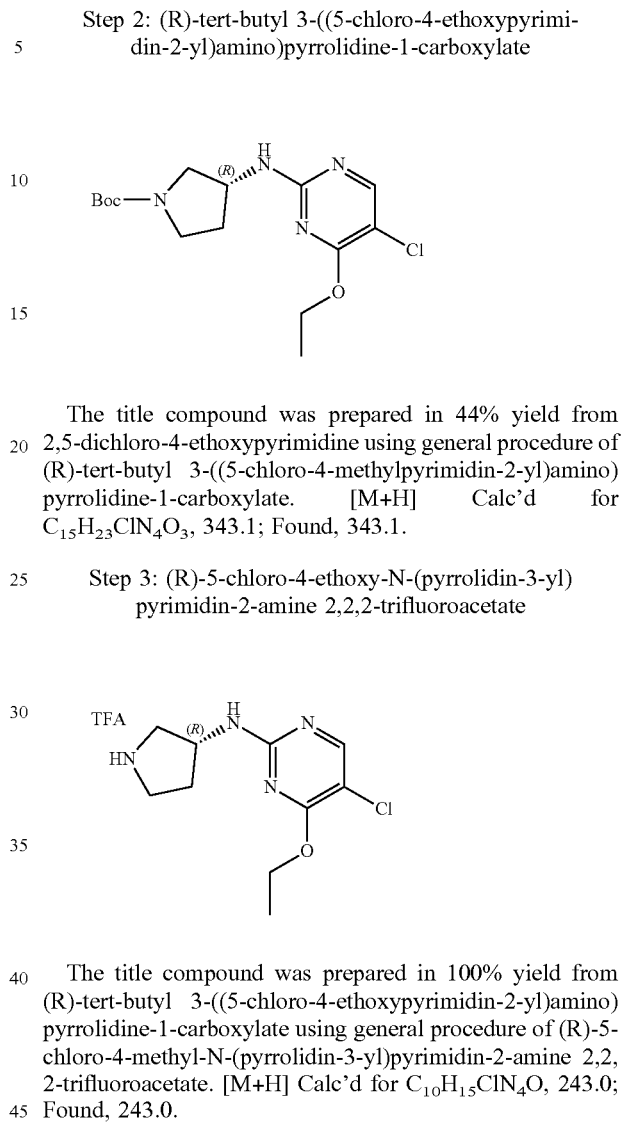

The title compound was prepared in 44% yield from 2,5-dichloro-4-ethoxypyrimidine using general procedure of (R)-tert-butyl 3-((5-chloro-4-methylpyrimidin-2-yl)amino)pyrrolidine-1-carboxylate. [M+H] Calc'd for $C_{15}H_{23}ClN_4O_3$, 343.1; Found, 343.1.

Step 3: (R)-5-chloro-4-ethoxy-N-(pyrrolidin-3-yl)pyrimidin-2-amine 2,2,2-trifluoroacetate

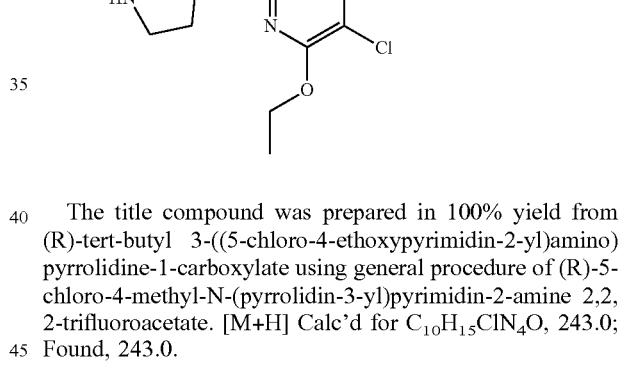

The title compound was prepared in 100% yield from (R)-tert-butyl 3-((5-chloro-4-ethoxypyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{10}H_{15}ClN_4O$, 243.0; Found, 243.0.

Step 4: (R)—N-(4-(3-((5-chloro-4-ethoxypyrimidin-2-yl)amino)pyrrolidine-1-carbonyl)phenyl)acrylamide

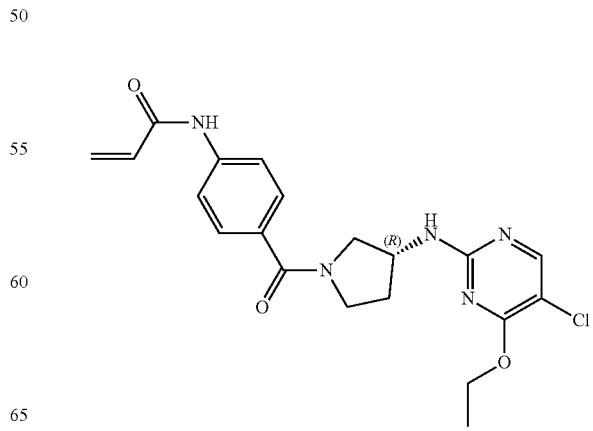

The title compound was prepared in 24% yield from (R)-5-chloro-4-ethoxy-N-(pyrrolidin-3-yl)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.26-1.39 (m, 3H), 1.93-2.17 (m, 2H), 3.41-3.82 (m, 4H), 4.26-4.45 (m, 3H), 5.80 (s, 0.5H), 5.83 (s, 0.5H), 6.28 (s, 0.4H), 6.33 (s, 0.6H), 6.43-6.52 (m, 1H), 7.51-7.57 (m, 2H), 7.71-7.77 (m, 3H), 8.10 (s, 0.6H), 8.17 (s, 0.4H), 10.35 (s, 1H). [M+H] Calc'd for C$_{20}$H$_{22}$ClN$_5$O$_3$, 416.1; Found, 416.1.

Example 97: Synthesis of (R)—N-(4-(3-((5-chloro-4-hydroxypyrimidin-2-yl)amino)pyrrolidine-1-carbonyl)phenyl)acrylamide

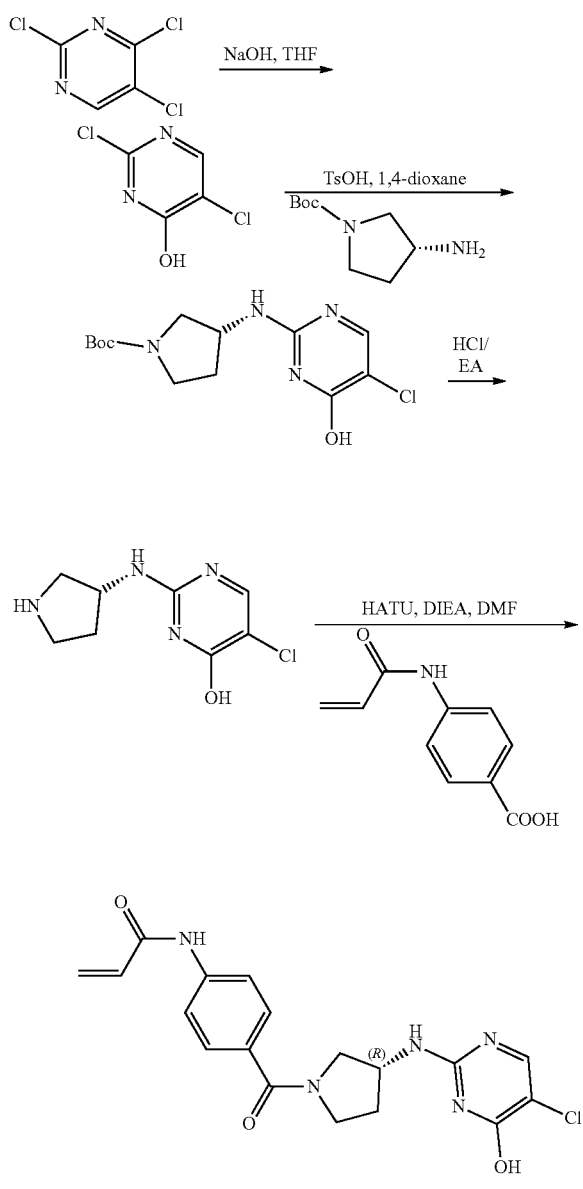

Step 1: 2,5-dichloropyrimidin-4-ol

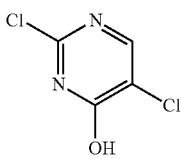

A mixture of 2,4,5-trichloropyrimidine (2.0 g, 10.9 mmol) and NaOH (872 mg, 21.8 mmol) in THF (10 mL) and water (1 mL) was stirred at RT overnight. The reaction mixture was added H$_2$O (40 mL) and extracted with EA (40 mL*2). The combined organic layer was dried over Na$_2$SO$_4$, filtered and concentrated to afford 2,5-dichloropyrimidin-4-ol (1.7 g, 95%) as a yellow solid. [M+H] Calc'd for C$_4$H$_2$Cl$_2$N$_2$O, 164.9; Found, 164.9

Step 2: (R)-tert-butyl 3-((5-chloro-4-hydroxypyrimidin-2-yl)amino)pyrrolidine-1-carboxylate

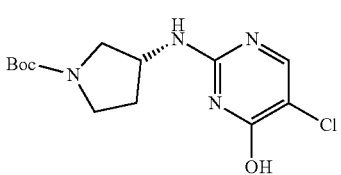

A mixture of 2,5-dichloropyrimidin-4-ol (800 mg, 4.9 mmol), (R)-tert-butyl 3-aminopyrrolidine-1-carboxylate (1.4 g, 7.3 mmol) and TsOH (1.4 g, 7.3 mmol) in 1,4-dioxane (25 mL) was stirred at 105° C. overnight. The reaction mixture was concentrated and purified by prep-HPLC to afford (R)-tert-butyl 3-((5-chloro-4-hydroxypyrimidin-2-yl)amino)pyrrolidine-1-carboxylate (400 mg, 27%) as a white solid. [M+H] Calc'd for C$_{13}$H$_9$CN$_4$O$_3$, 315.1; Found, 315.1

Step 3: (R)-5-chloro-2-(pyrrolidin-3-ylamino)pyrimidin-4-ol

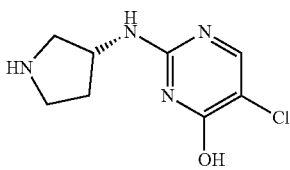

A mixture of (R)-tert-butyl 3-((5-chloro-4-hydroxypyrimidin-2-yl)amino)pyrrolidine-1-carboxylate (100 mg, 0.32 mmol) in HCl/EA (5 mL) was stirred at RT for 1 h. The reaction mixture was concentrated in vacuo to afford (R)-5-chloro-2-(pyrrolidin-3-ylamino)pyrimidin-4-ol (50 mg, 74%) as yellow oil. [M+H] Calc'd for C$_8$H$_{11}$ClN$_4$O, 215.1; Found, 215.1

Step 4: (R)—N-(4-(3-((5-chloro-4-hydroxypyrimidin-2-yl)amino)pyrrolidine-1-carbonyl)phenyl)acrylamide

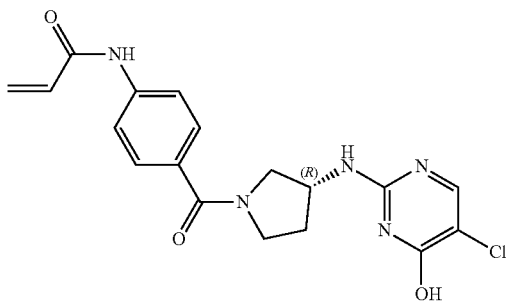

A mixture of (R)-5-chloro-2-(pyrrolidin-3-ylamino)pyrimidin-4-ol (200 mg, 0.93 mmol), 4-acrylamidobenzoic acid (196 mg, 1.0 mmol), HATU (353 mg, 0.93 mmol) and DIEA (241 mg, 1.8 mmol) in DMF (10 mL) was stirred at RT for overnight. To the reaction mixture was added H$_2$O (40 mL) and extracted with EA. The combined organic layer was dried over Na$_2$SO$_4$, filtered and concentrated. The residue was purified by prep-HPLC to afford (R)—N-(4-(3-((5-chloro-4-hydroxypyrimidin-2-yl)amino)pyrrolidine-1-carbonyl)phenyl)acrylamide (10.6 mg, 3%) as a white solid. $^1$H NMR (400 MHz, DMSO-d$_6$): δ 2.00-2.02 (m, 1H), 2.15-2.20 (m, 1H), 3.45-3.70 (m, 4H), 4.54 (s, 1H), 5.77-5.80 (m, 1H), 6.31 (d, J=2.0 Hz, 1H), 6.41-6.43 (m, 1H), 7.73 (d, J=8.8 Hz, 2H), 7.82-7.85 (m, 3H), 8.49 (d, J=6.4 Hz, 1H), 10.38 (s, 1H). [M+H] Calc'd for C$_{18}$H$_{18}$ClN$_5$O$_3$, 387.9; Found, 387.9.

Example 98: Synthesis of (R,E)-N-(4-(3-((5-chloropyrimidin-2-yl)amino)pyrrolidine-1-carbonyl)phenyl)-4-(dimethylamino)but-2-enamide

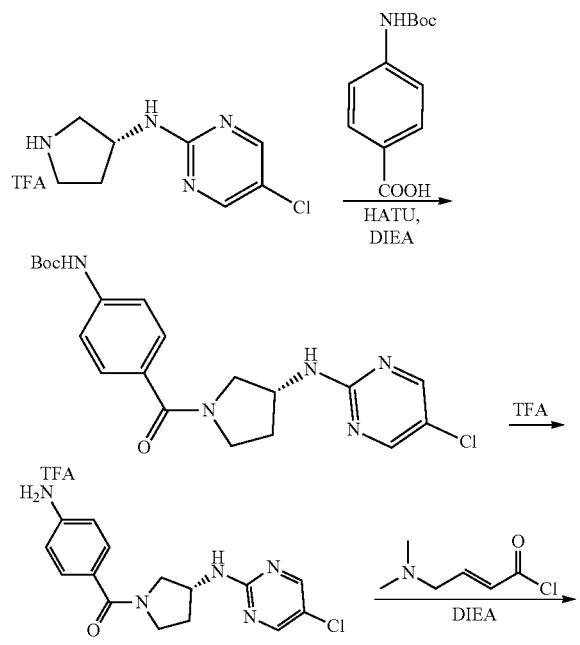

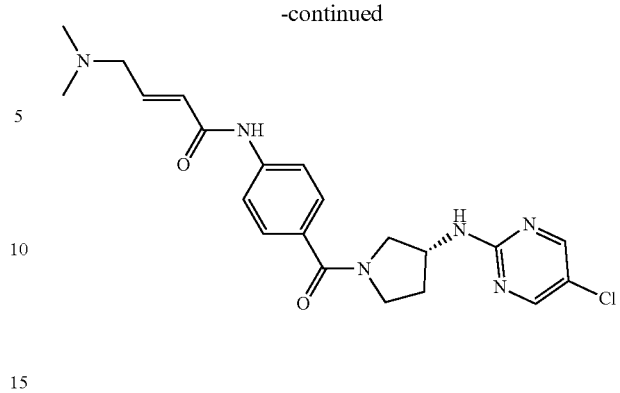

Step 1: (R)-tert-butyl (4-(3-((5-chloropyrimidin-2-yl)amino)pyrrolidine-1-carbonyl)phenyl)carbamate

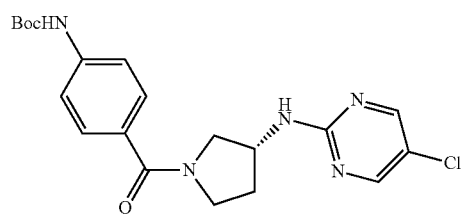 [SMILES: CC(C)(C)OC(=O)Nc1ccc(C(=O)N2CC[C@@H](Nc3ncc(Cl)cn3)C2)cc1]

The title compound was prepared in 74% yield from (R)-5-chloro-N-(pyrrolidin-3-yl)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. [M+H] Calc'd for C$_{20}$H$_{24}$ClN$_5$O$_3$, 418.1; Found, 418.1.

Step 2: (R)-(4-aminophenyl)(3-((5-chloropyrimidin-2-yl)amino)pyrrolidin-1-yl)methanone 2,2,2-trifluoroacetate

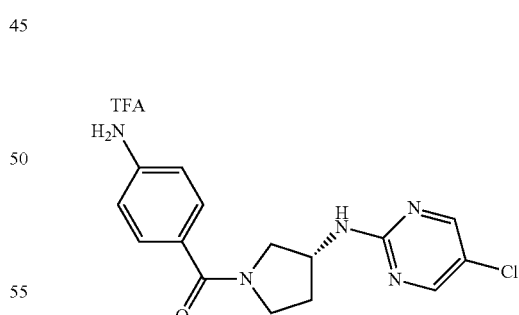

The title compound was prepared in 100% yield from (R)-tert-butyl (4-(3-((5-chloropyrimidin-2-yl)amino)pyrrolidine-1-carbonyl)phenyl)carbamate using general procedure of (R)-5-chloro-4-methyl-N-(pyrrolidin-3-yl)pyrimidin-2-amine 2,2,2-trifluoroacetate. [M+H] Calc'd for C$_{15}$H$_{16}$ClN$_5$O, 318.0; Found, 318.0.

311

Step 3: (R,E)-N-(4-(3-((5-chloropyrimidin-2-yl)amino)pyrrolidine-1-carbonyl)phenyl)-4-(dimethylamino)but-2-enamide

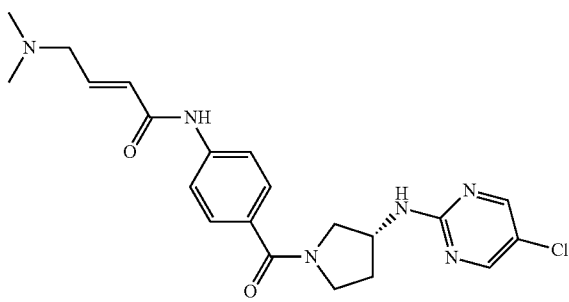 [SMILES: CN(C)C/C=C/C(=O)Nc1ccc(C(=O)N2CC[C@@H](Nc3ncc(Cl)cn3)C2)cc1]

The title compound was prepared in 20% yield from (R)-(4-aminophenyl)(3-((5-chloropyrimidin-2-yl)amino)pyrrolidin-1-yl)methanone general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-$d_6$): δ 1.88-2.01 (m, 1H), 2.10-2.12 (m, 1H), 2.18 (s, 6H), 3.05 (d, J=5.2 Hz, 2H), 3.36-3.45 (m, 1H), 3.51-3.57 (m, 1H), 3.64-3.74 (m, 1H), 3.76-3.78 (m, 1H), 4.24-4.40 (m, 1H), 6.28 (d, J=15.2 Hz, 1H), 6.72-6.78 (m, 1H), 7.47-7.52 (m, 2H), 7.67-7.71 (m, 2H), 7.79-7.81 (m, 1H), 8.31 (s, 1H), 8.38 (s, 1H), 10.21 (s, 1H). [M+H] Calc'd for $C_{21}H_{25}ClN_6O_2$, 429.1; Found, 429.1.

Example 99: Synthesis of (R)—N-(4-(3-((5-cyclopropyl-4-methoxypyrimidin-2-yl)amino)pyrrolidine-1-carbonyl)phenyl)acrylamide

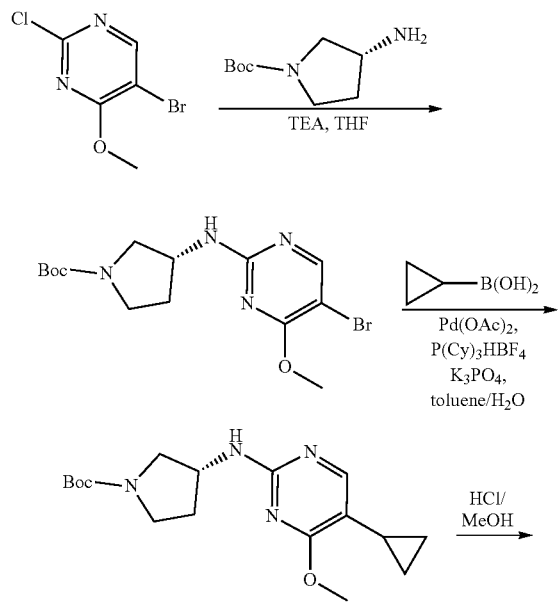

312

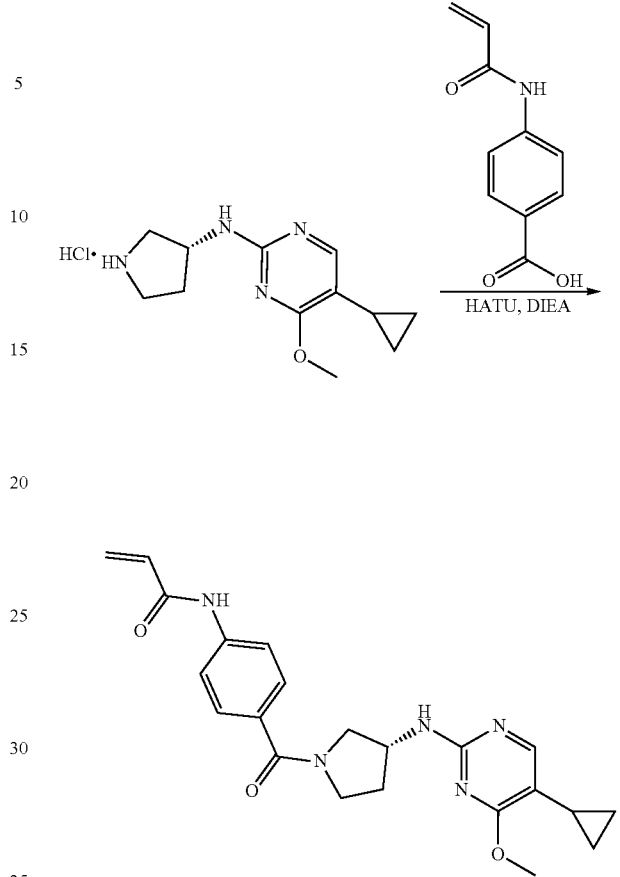

Step 1: (R)-tert-butyl 3-((5-bromo-4-methoxypyrimidin-2-yl)amino)pyrrolidine-1-carboxylate A mixture of 5-bromo-2-chloro-4-methoxypyrimidine (2.5 g, 13.4 mmol), (R)-tert-butyl 3-aminopyrrolidine-1-carboxylate (3.0 g, 13.4 mmol) and TEA (4.0 g, 40.2 mmol) in THF (30 mL) was stirred at 80° C. for 16 hours. The mixture was cooled to RT, diluted with water (50 mL) and extracted with EtOAc (50 mL*3). The combined organic phase was washed with brine (50 mL), dried over $Na_2SO_4$, filtered and concentrated in vacuo. The residue was purified by flash chromatography on silica gel (PE/EtOAc=2/1) to afford (R)-tert-butyl 3-((5-bromo-4-methoxypyrimidin-2-yl)amino)pyrrolidine-1-carboxylate (2.3 g, 46%) as a white solid. [M+H]Calc'd for $C_{14}H_{21}BrN_4O_3$, 373.0; Found, 373.0.

Step 2: (R)-tert-butyl 3-((5-cyclopropyl-4-methoxy-pyrimidin-2-yl)amino)pyrrolidine-1-carboxylate

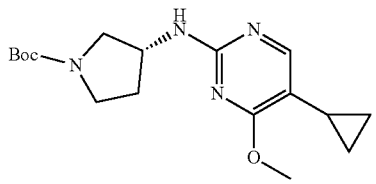 [SMILES: COc1nc(N[C@@H]2CCN(C(=O)OC(C)(C)C)C2)ncc1C1CC1]

A mixture of (R)-tert-butyl 3-((5-bromo-4-methoxypyrimidin-2-yl)amino)pyrrolidine-1-carboxylate (200 mg, 0.54 mmol), cyclopropylboronic acid (230 mg, 2.68 mmol), Pd(OAc)$_2$, (73 mg, 0.32 mmol), P(Cy)$_3$HBF$_4$ (48 mg, 0.13 mmol) and K$_3$PO$_4$ (1.14 g, 5.41 mmol) in toluene/H$_2$O (20 mL/2 mL) was stirred at 100° C. under N$_2$ for 4 hours. The mixture was cooled to RT and filtered over Celite. The filtrate was concentrated in vacuo and the residue was purified by flash chromatography on silica gel (PE/EtOAc=10/1 to PE/EtOAc=3/1) to afford (R)-tert-butyl 3-((5-cyclopropyl-4-methoxypyrimidin-2-yl)amino)pyrrolidine-1-carboxylate (150 mg, 83%) as colorless oil. [M+H] Calc'd for C$_{17}$H$_{26}$N$_4$O$_3$, 335.2; Found, 335.2.

Step 3: (R)-5-cyclopropyl-4-methoxy-N-(pyrrolidin-3-yl)pyrimidin-2-amine

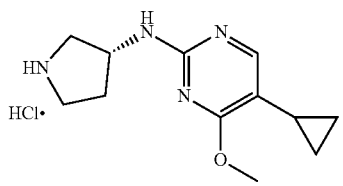

The title compound was prepared in 100% yield from (R)-tert-butyl 3-((5-cyclopropyl-4-methoxypyrimidin-2-yl)amino)pyrrolidine-1-carboxylate using general procedure of (R)-5-chloro-4-methyl-N-(pyrrolidin-3-yl)pyridin-2-amine hydrochloride. [M+H] Calc'd for C$_{12}$H$_{18}$N$_4$O, 235.1; Found, 235.1.

Step 4: (R)—N-(4-(3-((5-cyclopropyl-4-methoxypyrimidin-2-yl)amino)pyrrolidine-1-carbonyl)phenyl)acrylamide

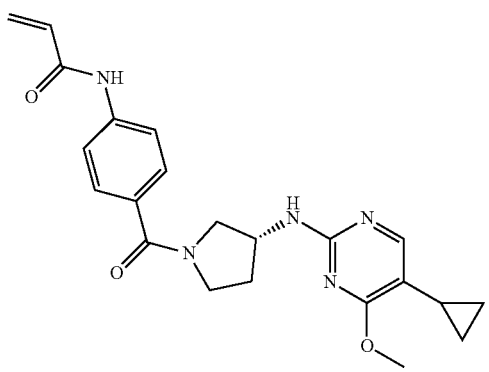 [SMILES: C=CC(=O)Nc1ccc(C(=O)N2CC[C@@H](Nc3ncc(C4CC4)c(OC)n3)C2)cc1]

The title compound was prepared in 13% yield from (R)-5-cyclopropyl-4-methoxy-N-(pyrrolidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 0.50-0.55 (m, 2H), 0.69-0.76 (m, 2H), 1.59-1.68 (m, 1H), 1.86-2.01 (m, 1H), 2.07-2.16 (m, 1H), 3.36-3.43 (m, 1H), 3.46-3.55 (m, 1H), 3.60-3.69 (m, 1H), 3.73-3.75 (m, 1H), 3.80 (s, 1.5H), 3.89 (s, 1.5H), 4.22-4.43 (m, 1H), 5.79 (d, J=10.0 Hz, 1H), 6.28 (d, J=16.8 Hz, 1H), 6.41-6.47 (m, 1H), 7.19-7.23 (m, 1H), 7.48-7.54 (m, 2H), 7.67-7.75 (m, 3H), 10.31 (s, 1H). [M+H] Calc'd for C$_{22}$H$_{25}$N$_5$O$_3$, 408.1; Found, 408.1.

Example 100: Synthesis of (R)—N-(4-(3-((5-(trifluoromethyl)pyrimidin-2-yl)amino)pyrrolidine-1-carbonyl)thiazol-2-yl)acrylamide

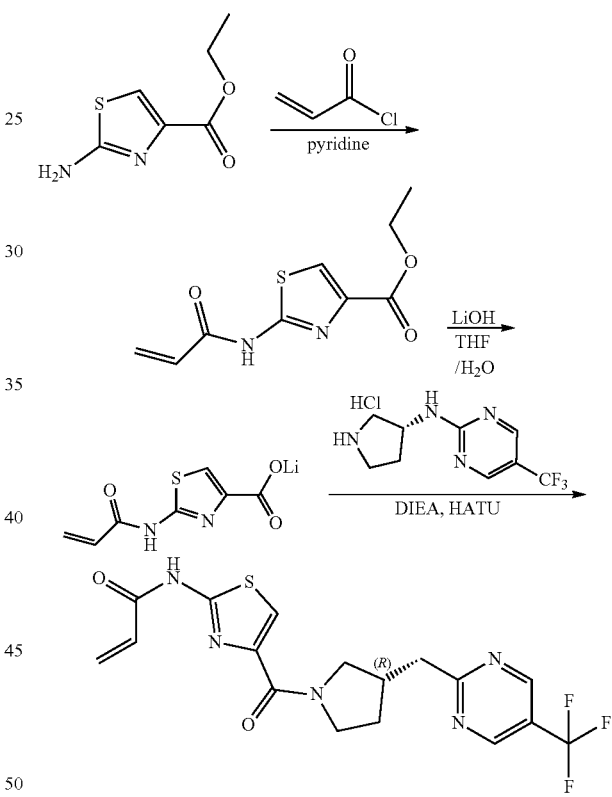

Step 1: ethyl 2-acrylamidothiazole-4-carboxylate

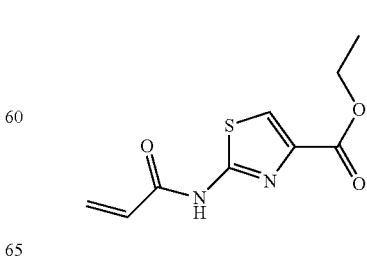

To a solution of ethyl 2-aminothiazole-4-carboxylate (3.0 g, 17.4 mmol) in DMF (20 mL) was added pyridine (1.5 g, 19.1 mmol) and acryloyl chloride (2.4 g, 28.1 mmol) at 0° C. The reaction mixture was stirred at 0° C. for 10 minutes and then at RT for overnight. The mixture was poured into ice-water (30 mL) and extracted with EtOAc (30 mL*5). The combined organic phase was washed with brine (30 mL*2), dried over Na₂SO₄, filtered and concentrated in vacuo. The residue was purified by flash chromatography on silica gel (petroleum ether/EtOAc=3/1) to afford ethyl 2-acrylamidothiazole-4-carboxylate (1.0 g, 25%) as a white solid. [M+H] Calc'd for C₉H₁₀N₂O₃S, 227.0; Found, 227.0.

Step 2: Lithium 2-acrylamidothiazole-4-carboxylate

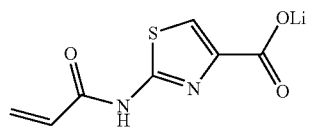

To a solution of ethyl 2-acrylamidothiazole-4-carboxylate (300 mg, 1.6 mmol) in THF/H₂O (4 mL/2 mL) was added LiOH H₂O (56 mg, 1.3 mmol). The mixture was stirred at RT for overnight. Another batch of LiOH H₂O (56 mg, 1.3 mmol) was added. The mixture was stirred at RT for 5 hours. The mixture was concentrated in vacuo to afford lithium 2-acrylamidothiazole-4-carboxylate (326 mg, crude, 100%) as a yellow solid. [M+H] Calc'd for C₇H₅LiN₂O₃S, 199.0; Found, 199.0

Step 3: (R)—N-(4-(3-((5-(trifluoromethyl)pyrimidin-2-yl)amino)pyrrolidine-1-carbonyl)thiazol-2-yl)acrylamide

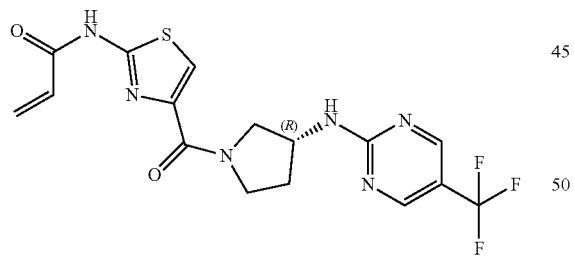

The title compound was prepared in 30% yield from lithium 2-acrylamidothiazole-4-carboxylate using general procedure of (R)—N-(4-(3-((5-chloro-4-methylpyrimidin-2-yl)amino)pyrrolidine-1-carbonyl)phenyl)acrylamide. ¹H NMR (400 MHz, DMSO-d₆): δ 1.99-2.07 (m, 1H), 2.13-2.23 (m, 1H), 3.50-3.58 (m, 1H), 3.68-3.73 (m, 1H), 3.78-3.83 (m, 0.5H), 3.93-3.99 (m, 1H), 4.14-4.18 (m, 0.5H), 4.46-4.52 (m, 1H), 5.89-5.93 (m, 1H), 6.37-6.43 (m, 1H), 6.50-6.58 (m, 1H), 7.75 (s, 1H), 8.40 (d, J=6.4 Hz, 1H), 8.65-8.70 (m, 2H), 12.30 (br s, 1H). [M+H] Calc'd for C₁₆H₁₅F₃N₆O₂S, 413.0; Found, 413.0.

Example 101: Synthesis of (R)—N-(4-(3-((5-chloro-4-methoxypyrimidin-2-yl)amino)piperidine-1-carbonyl)thiazol-2-yl)acrylamide

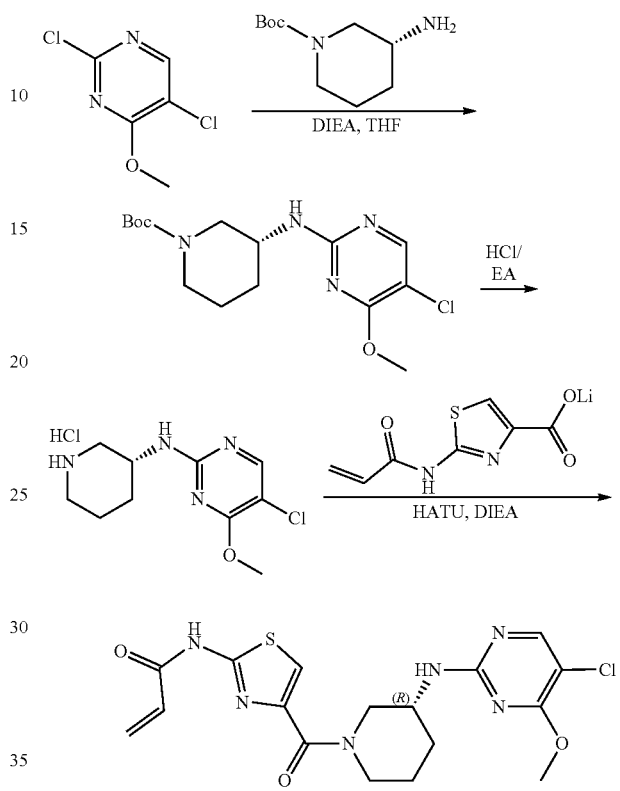

Step 1: (R)-tert-butyl 3-((5-chloro-4-methoxypyrimidin-2-yl)amino)piperidine-1-carboxylate

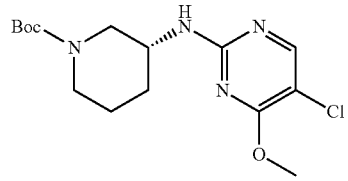 [SMILES: COc1nc(N[C@@H]2CCCN(C(=O)OC(C)(C)C)C2)ncc1Cl]

A mixture of 2,5-dichloro-4-methoxypyrimidine (300 mg, 1.7 mmol), (R)-tert-butyl 3-aminopiperidine-1-carboxylate (340 mg, 1.7 mmol) and DIEA (439 mg, 3.4 mmol) in THF (3 mL) was stirred at 80° C. overnight. The mixture was cooled to RT, diluted with water (10 mL) and extracted with EtOAc (20 mL*3). The combined organic phase was washed with brine (20 mL), dried over Na₂SO₄, filtered and concentrated in vacuo. The residue was purified by flash chromatography on silica gel (petroleum ether/EtOAc=5/1) to afford (R)-tert-butyl 3-((5-choro-4-methoxypyrimidin-2-yl)amino)piperidine-1-carboxylate (188 mg, 33%) as yellow oil. [M+H] Calc'd for C₁₅H₂₃ClN₄O₃, 343.1; Found, 343.1.

Step 2: (R)-5-chloro-4-methoxy-N-(piperidin-3-yl)pyrimidin-2-amine hydrochloride

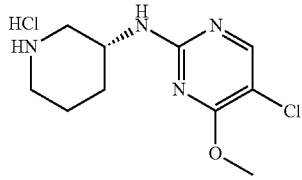 [SMILES: Cl ; COc1nc(N[C@@H]2CCCNC2)ncc1Cl]

The title compound was prepared in 100% yield from (R)-tert-butyl 3-((5-chloro-4-methoxypyrimidin-2-yl)amino)piperidine-1-carboxylate using general procedure of (R)-5-chloro-4-methyl-N-(pyrrolidin-3-yl)pyridin-2-amine hydrochloride. [M+H] Calc'd for $C_{10}H_{15}ClN_4$, 243.0; Found, 243.0.

Step 3: (R)—N-(4-(3-((5-chloro-4-methoxypyrimidin-2-yl)amino)piperidine-1-carbonyl)thiazol-2-yl)acrylamide

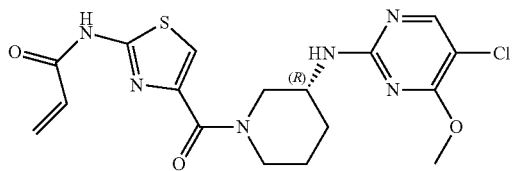

The title compound was prepared in 31% yield from (R)-5-chloro-4-methoxy-N-(piperidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.47-1.96 (m, 4H), 2.07-2.76 (m, 1H), 3.01-3.16 (m, 1H), 3.50-4.01 (m, 6H), 5.91 (d, J=11.6 Hz, 1H), 6.38-6.52 (m, 2H), 7.23-7.44 (m, 2H), 7.93-8.10 (m, 1H), 12.40 (br s, 1H). [M+H] Calc'd for $C_{17}H_{19}ClN_6O_3S$, 423.0; Found, 423.0.

Example 102: Synthesis of (R)—N-(4-(3-((5-chloro-4-(2-cyanoethoxy)pyrimidin-2-yl)amino)pyrrolidine-1-carbonyl)phenyl)acrylamide

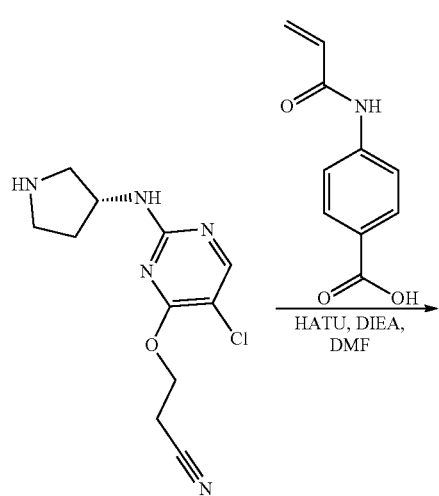

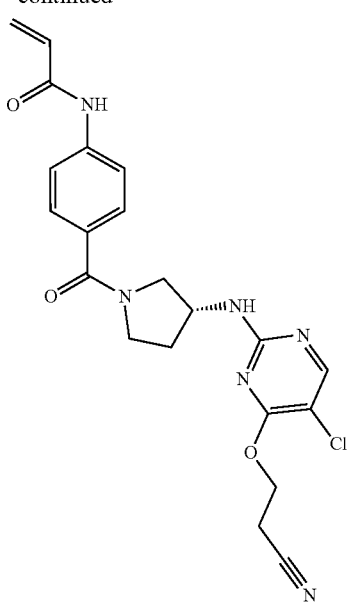

The title compound was prepared in 20% yield from (R)-3-((5-chloro-2-(pyrrolidin-3-ylamino)pyrimidin-4-yl)oxy)propanenitrile TFA salt using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.90-2.01 (m, 1H), 2.07-2.15 (m, 1H), 2.99-3.09 (m, 2H), 3.39-3.45 (m, 1H), 3.51-3.54 (m, 1H), 3.62-3.66 (m, 1H), 3.74-3.79 (m, 1H), 4.27-4.55 (m, 3H), 5.78 (d, J=10.8 Hz, 1H), 6.26-6.30 (m, 1H), 6.41-6.48 (m, 1H), 7.49-7.54 (m, 2H), 7.69-7.73 (m, 3H), 8.13-8.20 (m, 1H), 10.30 (s, 1H). [M+H] Calc'd for $C_{21}H_{21}ClN_6O_3$, 441.1; Found, 441.1.

Example 103: Synthesis of N-(4-((R)-3-((5-chloropyrimidin-2-yl)amino)pyrrolidine-1-carbonyl)-2-((tetrahydrofuran-3-yl)oxy)phenyl)acrylamide

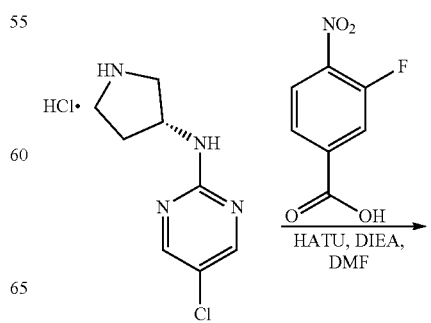

319
-continued

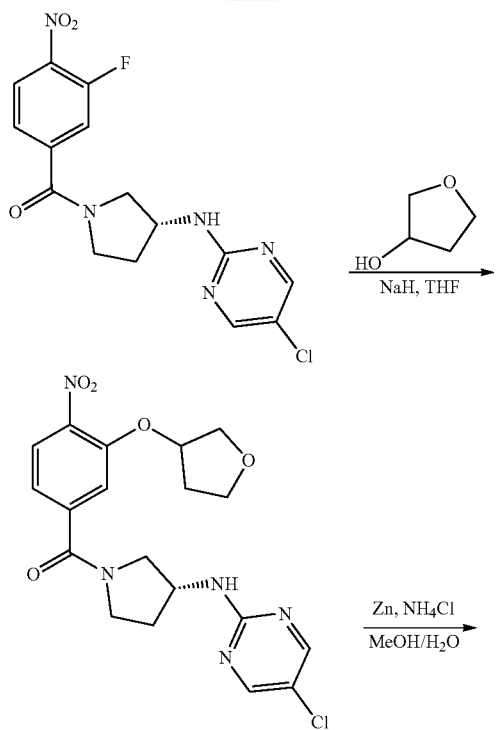

320

Step 1: (R)-(3-((5-chloropyrimidin-2-yl)amino)pyrrolidin-1-yl)(3-fluoro-4-nitrophenyl)methanone

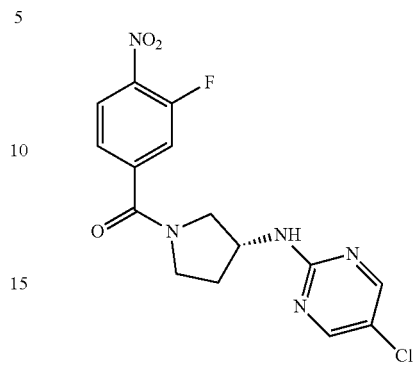

The title compound was prepared in 77% yield from (R)-5-chloro-N-(pyrrolidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. [M+H] Calc'd for $C_{15}H_{13}ClFN_5O_3$, 366.0; Found, 366.0.

Step 2: ((R)-3-((5-chloropyrimidin-2-yl)amino)pyrrolidin-1-yl)(4-nitro-3-((tetrahydrofuran-3-yl)oxy)phenyl)methanone

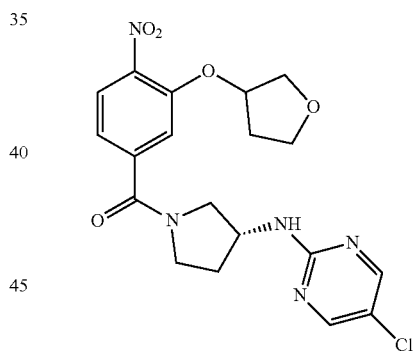

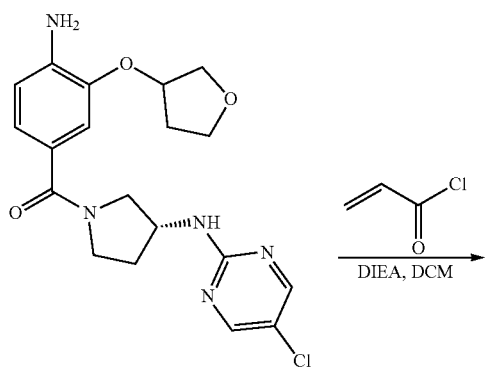

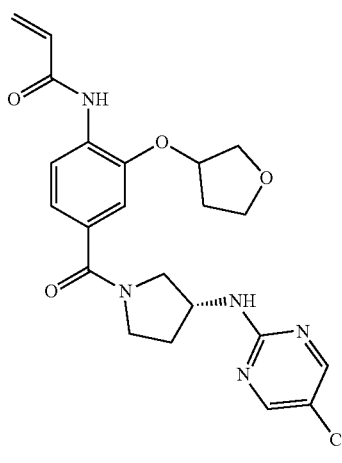

To a solution of tetrahydrofuran-3-ol (24 mg, 0.27 mmol) in THF (5 mL) was added NaH (24 mg, 0.6 mmol, 60% wt in mineral oil) at 0° C. The mixture was stirred at 0° C. under $N_2$ for 30 minutes. Then (R)-(3-((5-chloropyrimidin-2-yl)amino)pyrrolidin-1-yl)(3-fluoro-4-nitrophenyl)methanone (100 mg, 0.27 mmol) was added and the mixture was stirred at 0° C. to RT under $N_2$ overnight. The mixture was diluted with water (10 mL) and extracted with EtOAc (20 mL*2). The combined organic phase was washed with brine (20 mL), dried over $Na_2SO_4$, filtered and concentrated. The residue was purified by flash chromatography on silica gel (PE/EtOAc=1/1) to afford ((R)-3-((5-chloropyrimidin-2-yl)amino)pyrrolidin-1-yl)(4-nitro-3-((tetrahydrofuran-3-yl)oxy)phenyl)methanone (100 mg, 85%) as yellow oil. [M+H] Calc'd for $C_{19}H_{20}ClN_5O_5$, 434.1; Found, 434.1.

Step 3: (4-amino-3-((tetrahydrofuran-3-yl)oxy)phenyl)((R)-3-((5-chloropyrimidin-2-yl)amino)pyrrolidin-1-yl)methanone

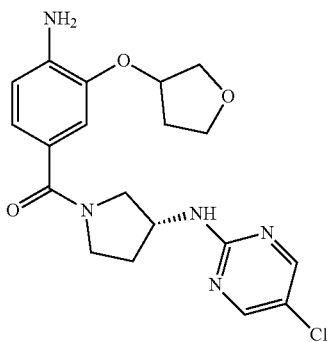 [SMILES: Nc1ccc(C(=O)N2CC[C@@H](Nc3ncc(Cl)cn3)C2)cc1OC1CCOC1]

A mixture of ((R)-3-((5-chloropyrimidin-2-yl)amino)pyrrolidin-1-yl)(4-nitro-3-((tetrahydrofuran-3-yl)oxy)phenyl)methanone (100 mg, 0.23 mmol) and NH$_4$Cl (124 mg, 2.3 mmol) in MeOH (5 mL) and H$_2$O (2 mL) was heated to 50° C. for 10 minutes. Then Zn (150 mg, 2.3 mmol) was added. The mixture was stirred at 70° C. for 3 hours. The mixture was cooled to RT and filtered. The filtrate was concentrated in vacuo. The residue was diluted with water (10 mL) and extracted with EtOAc (20 mL*2). The combined organic phase was washed with brine (20 mL), dried over Na$_2$SO$_4$, filtered and concentrated to afford (4-amino-3-((tetrahydrofuran-3-yl)oxy)phenyl)((R)-3-((5-chloropyrimidin-2-yl)amino)pyrrolidin-1-yl)methanone (80 mg, 86%) as yellow oil. [M+H]Calc'd for C$_{19}$H$_{22}$ClN$_5$O$_3$, 404.1; Found, 404.1.

Step 4: N-(4-((R)-3-((5-chloropyrimidin-2-yl)amino)pyrrolidine-1-carbonyl)-2-((tetrahydrofuran-3-yl)oxy)phenyl)acrylamide

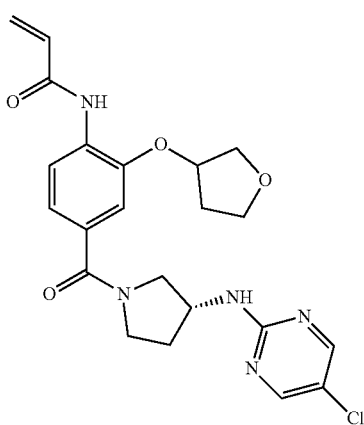 [SMILES: C=CC(=O)Nc1ccc(C(=O)N2CC[C@@H](Nc3ncc(Cl)cn3)C2)cc1OC1CCOC1]

The title compound was prepared in 27% yield from (4-amino-3-((tetrahydrofuran-3-yl)oxy)phenyl)((R)-3-((5-chloropyrimidin-2-yl)amino)pyrrolidin-1-yl)methanone using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-d$_6$): δ 1.87-2.27 (m, 4H), 3.35-3.38 (m, 1H), 3.44-3.79 (m, 4H), 3.85-3.93 (m, 3H), 4.23-4.41 (m, 1H), 5.05-5.10 (m, 1H), 5.76 (d, J=10.4 Hz, 1H), 6.25 (d, J=16.8 Hz, 1H), 6.68-6.76 (m, 1H), 7.08-7.14 (m, 2H), 7.82-7.85 (m, 1H), 8.10-8.16 (m, 1H), 8.32 (s, 1H), 8.39 (s, 1H), 9.22 (s, 0.5H), 9.24 (s, 0.5H). [M+H]Calc'd for C$_{22}$H$_{24}$ClN$_5$O$_4$, 458.1; Found, 458.1.

Example 104: Synthesis of (R)—N-(4-(3-((5-bromopyrimidin-2-yl)amino)pyrrolidine-1-carbonyl)phenyl)-N-methylacrylamide

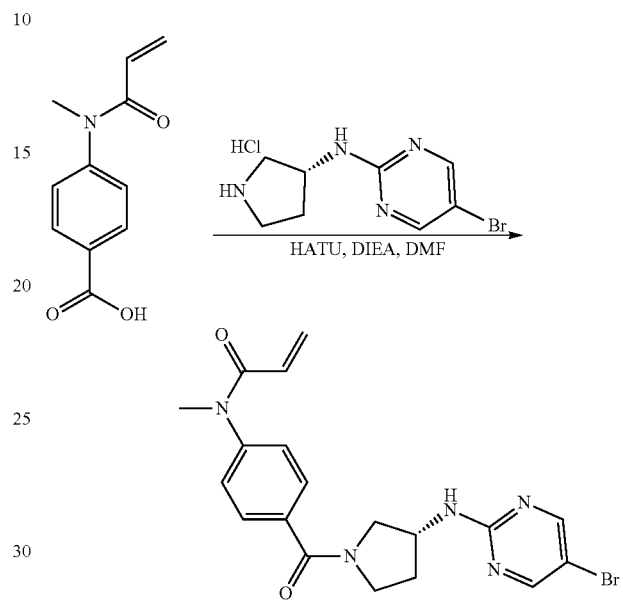

To a solution of 4-(N-methylacrylamido)benzoic acid (100 mg, 0.49 mmol), (R)-5-bromo-N-(pyrrolidin-3-yl)pyrimidin-2-amine, HCl salt (150 mg, 0.54 mmol) and DIEA (189 mg, 1.47 mmol) in DMF (15 mL) was added HATU (205 g, 0.54 mmol) at rt. The mixture was stirred at rt overnight. The mixture was diluted with water (20 mL) and extracted with EtOAc (20 mL*2). The combined organic layers were washed with water (20 mL*2), washed with brine (20 mL), dried over Na$_2$SO$_4$, filtered and concentrated. The residue was purified by prep-HPLC to afford (R)—N-(4-(3-((5-bromopyrimidin-2-yl)amino)pyrrolidine-1-carbonyl)phenyl)-N-methylacrylamide (35.3 mg, 17%). $^1$H NMR (400 MHz, DMSO-d$_6$): δ 1.86-2.01 (m, 1H), 2.11-2.19 (m, 1H), 3.26 (s, 1.5H), 3.28 (s, 1.5H), 3.33-3.80 (m, 4H), 4.26-4.43 (m, 1H), 5.60 (d, J=10.4 Hz, 1H), 6.09-6.19 (m, 2H), 7.31-7.36 (m, 2H), 7.56-7.61 (m, 2H), 7.81-7.84 (m, 1H), 8.36 (s, 1H), 8.43 (s, 1H). [M+H] MS Calcd for C$_{19}$H$_{20}$BrN$_5$O$_2$: 430.1; MS Found: 430.1.

Example 105: Synthesis of (R)—N-(3-(3-((5-chloro-4-methoxypyrimidin-2-yl)amino)pyrrolidine-1-carbonyl)phenyl)acrylamide

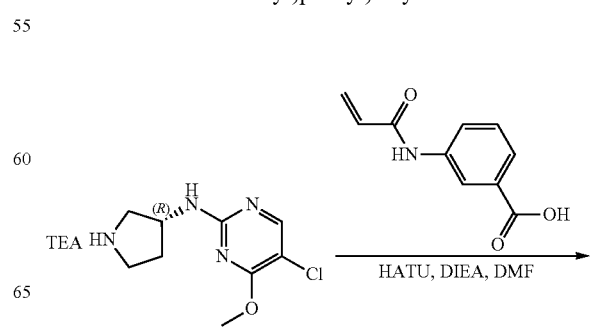

-continued

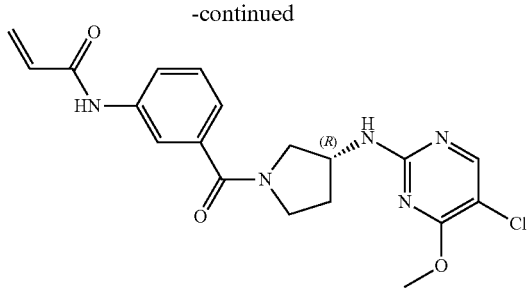

Step 1: (R)—N-(3-(3-((5-chloro-4-methoxypyrimidin-2-yl)amino)pyrrolidine-1-carbonyl)phenyl)acrylamide

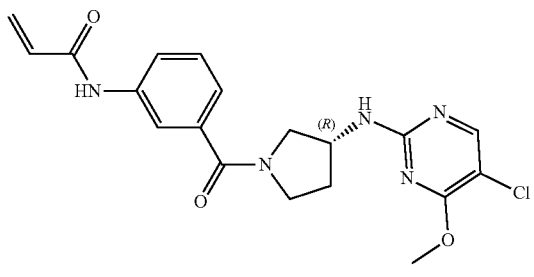

The title compound was prepared in 29% yield from (R)-5-chloro-4-methoxy-N-(pyrrolidin-3-yl)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.90-2.02 (m, 1H), 2.07-2.18 (m, 1H), 3.34-3.75 (m, 4H), 3.85 (s, 1.5H), 3.94 (s, 1.5H), 4.26-4.44 (m, 1H), 5.77 (d, J=12.0 Hz, 1H), 6.23-6.29 (m, 1H), 6.38-6.46 (m, 1H), 7.18-7.23 (m, 1H), 7.34-7.41 (m, 1H), 7.61-7.72 (m, 2H), 7.89-7.92 (m, 1H), 8.06 (s, 0.5H), 8.14 (s, 0.5H), 10.23 (s, 0.5H), 10.26 (s, 0.5H). [M+H] Calc'd for $C_{19}H_{20}ClN_5O_3$, 402.1; Found, 402.1.

Example 106: Synthesis of (R)—N-(3-(3-((5-chloro-4-methoxypyrimidin-2-yl)amino)piperidine-1-carbonyl)phenyl)acrylamide

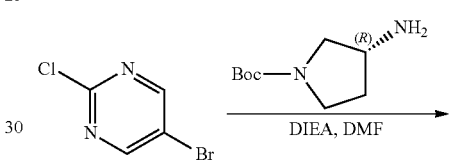

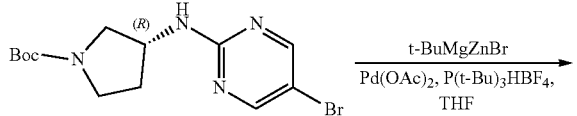

The title compound was prepared in 23% yield from (R)-5-chloro-4-methoxy-N-(piperidin-3-yl)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.49-1.85 (m, 2H), 1.91-2.07 (m, 2H), 2.66-3.02 (m, 1H), 3.21-3.24 (m, 1H), 3.37-3.58 (m, 3H), 3.80-3.94 (m, 3H), 5.75-5.78 (m, 1H), 6.26 (d, J=16.8 Hz, 1H), 6.39-6.47 (m, 1H), 6.95-7.09 (m, 1H), 7.14-7.38 (m, 2H), 7.54-7.77 (m, 2H), 7.95-8.12 (m, 1H), 10.15 (br s, 0.6H), 10.25 (br s, 0.4H). [M+H] Calc'd for $C_{20}H_{22}ClN_5O_3$, 416.1; Found, 416.1.

Example 107: Synthesis of (R)—N-(4-(3-((5-isobutylpyrimidin-2-yl)amino)pyrrolidine-1-carbonyl)phenyl)acrylamide

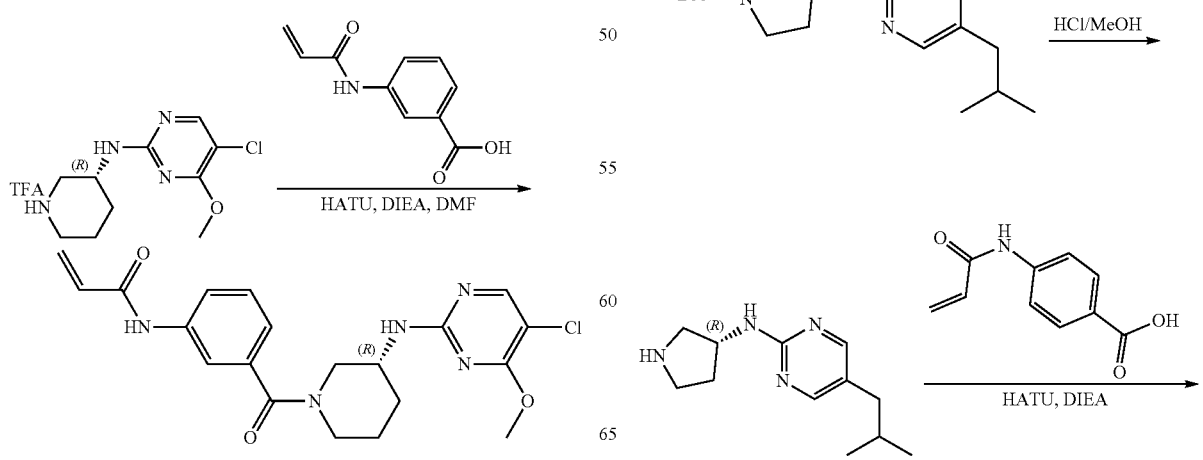

325
-continued

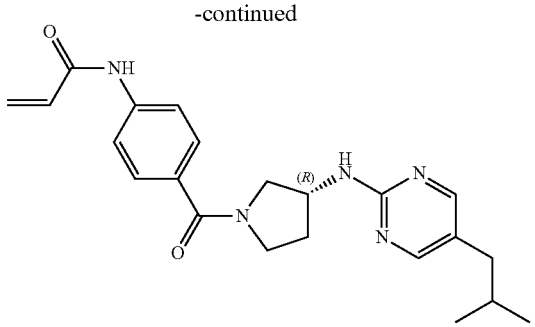

Step 1: (R)-tert-butyl 3-((5-bromopyrimidin-2-yl)amino)pyrrolidine-1-carboxylate

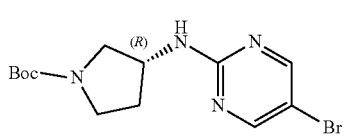

The title compound was prepared in 85% yield from 5-bromo-2-chloropyrimidine using general procedure of (R)-tert-butyl 3-((5-chloro-4-methylpyrimidin-2-yl)amino)pyrrolidine-1-carboxylate. [M+H] Calc'd for $C_{13}H_{19}BrN_4O_2$, 343.0; Found, 343.0

Step 2: (R)-tert-butyl 3-((5-isobutylpyrimidin-2-yl)amino)pyrrolidine-1-carboxylate

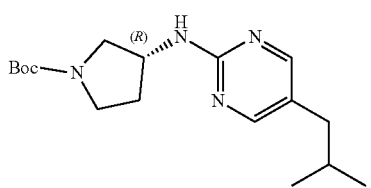

To a mixture of (R)-tert-butyl 3-((5-bromopyrimidin-2-yl)amino)pyrrolidine-1-carboxylate (100 mg, 0.29 mmol), Pd(OAc)$_2$ (13 mg, 0.06 mmol) and P(t-Bu)$_3$HBF$_4$ (33 mg, 0.12 mmol) in THF (3 mL) at 0° C. was added t-BuZnBr (2.6 mL, 0.87 mmol, 0.33 M). The mixture was stirred at RT for 1 hour. The mixture was quenched with water (10 mL) and extracted with EtOAc (20 mL*2). The combined organic phase was concentrated. The residue was purified by flash chromatography on silica gel (petroleum ether/EtOAc=5/1) to afford (R)-tert-butyl 3-((5-isobutylpyrimidin-2-yl)amino)pyrrolidine-1-carboxylate (60 mg, 65%) as a white solid. [M+H]Calc'd for $C_{17}H_{28}N_4O_2$, 321.2; Found, 321.2.

326

Step 3: (R)-5-isobutyl-N-(pyrrolidin-3-yl)pyrimidin-2-amine hydrochloride

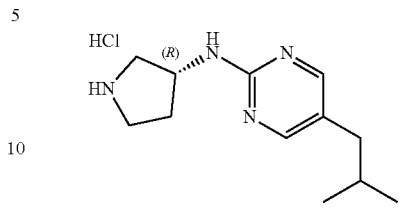

The title compound was prepared in 100% yield from (R)-tert-butyl 3-((5-isobutylpyrimidin-2-yl)amino)pyrrolidine-1-carboxylate using general procedure of (R)-5-chloro-4-methyl-N-(pyrrolidin-3-yl)pyridin-2-amine hydrochloride. [M+H] Calc'd for $C_{12}H_{20}N_4$, 221.1; Found, 221.1.

Step 4: (R)—N-(4-(3-((5-isobutylpyrimidin-2-yl)amino)pyrrolidine-1-carbonyl)phenyl)acrylamide

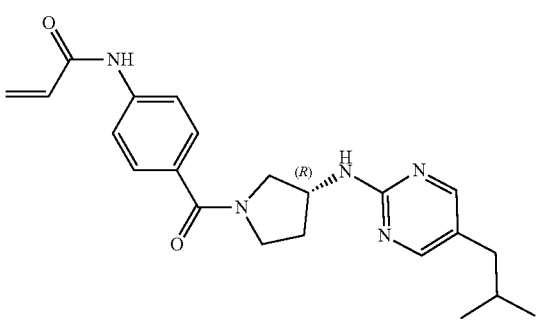

The title compound was prepared in 36% yield from (R)-5-isobutyl-N-(pyrrolidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 0.73-0.86 (m, 6H), 1.67-1.75 (m, 1H), 1.86-2.09 (m, 1H), 2.14-2.27 (m, 3H), 3.33-3.35 (m, 1H), 3.40-3.51 (m, 1H), 3.56-3.69 (m, 1H), 3.73-3.79 (m, 1H), 4.23-4.42 (m, 1H), 5.78 (d, J=10.0 Hz, 1H), 6.27 (d, J=16.8 Hz, 1H), 6.40-6.48 (m, 1H), 7.29-7.33 (m, 1H), 7.48-7.54 (m, 2H), 7.68-7.73 (m, 2H), 8.07 (s, 1H), 8.14 (s, 1H), 10.31 (br s, 1H). [M+H] Calc'd for $C_{22}H_{27}N_5O_2$, 394.2; Found, 394.2.

Example 108 & 109: (S)—N-(4-(3-((5-chloropyrimidin-2-yl)amino)-3-methylpyrrolidine-1-carbonyl)phenyl)acrylamide&(R)—N-(4-(3-((5-chloropyrimidin-2-yl)amino)-3-methylpyrrolidine-1-carbonyl)phenyl)acrylamide

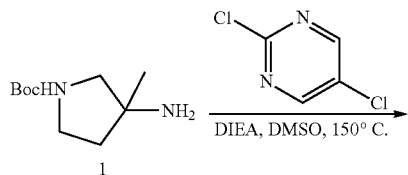

-continued
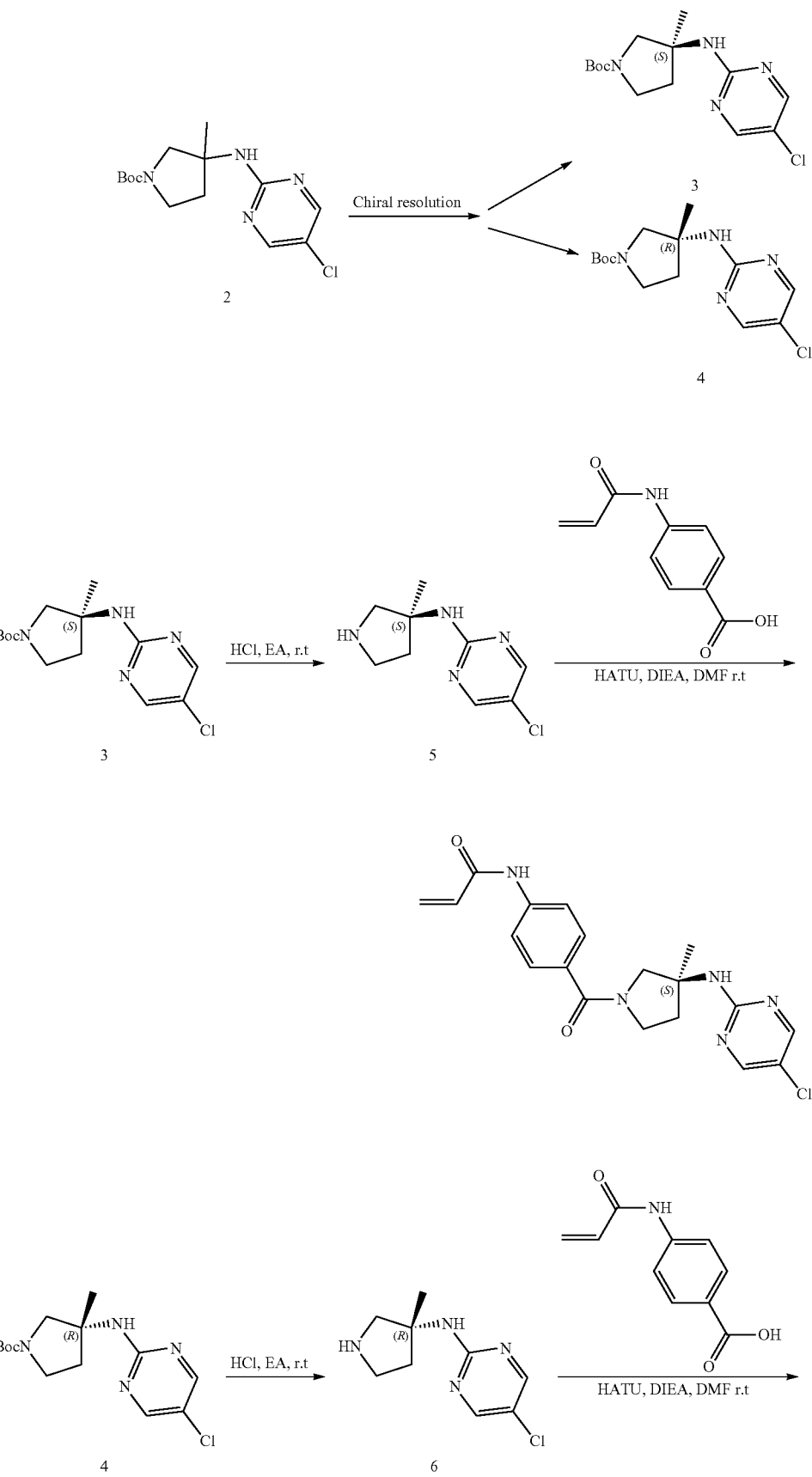

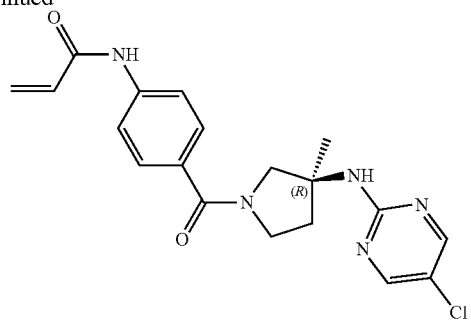

Step 1: (S)-tert-butyl 3-((5-chloropyrimidin-2-yl)amino)-3-methylpyrrolidine-1-carboxylate & (R)-tert-butyl 3-((5-chloropyrimidin-2-yl)amino)-3-methylpyrrolidine-1-carboxylate

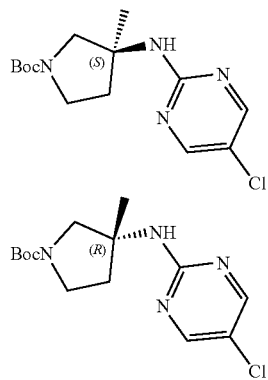

To a solution of tert-butyl 3-amino-3-methylpyrrolidine-1-carboxylate (460 mg, 2.3 mmol) and 2,5-dichloropyrimidine (1.7 g, 11.5 mmol) in DMSO (15 mL) was added DIEA (1.4 g, 11.5 mmol) The mixture was stirred at 150° C. for 1 h. The mixture was cooled, diluted with water (200 mL) and extracted with EA (100 mL). The combined organic layer was washed with brine (100 mL), dried over $Na_2SO_4$ and concentrated in vacuo. The residue was purified by column chromatography (PE:EA from 10:1 to 4:1) to afford 170 mg product as a white solid. Then Chiral separation (IG:Hex: EtOH=80:20) to get (S)-tert-butyl 3-((5-chloropyrimidin-2-yl)amino)-3-methylpyrrolidine-1-carboxylate (50 mg, 11.111 min) and (R)-tert-butyl 3-((5-chloropyrimidin-2-yl)amino)-3-methylpyrrolidine-1-carboxylate (50 mg, 13.614 min). [M+H] Calc'd for $C_9H_{13}CN_4$, 313.1; Found, 313.1.

Step 2: (S)-tert-butyl 3-((5-chloropyrimidin-2-yl)amino)-3-methylpyrrolidine-1-carboxylate

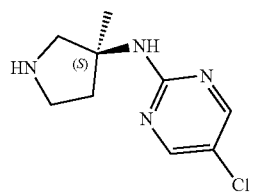

To a solution of (S)-tert-butyl 3-((5-chloropyrimidin-2-yl)amino)-3-methylpyrrolidine-1-carboxylate (50 mg, 0.16 mmol) in EA (10 mL) was added HCl (gas) at −50° C. The reaction mixture was stirred at rt for 3 h. The reaction mixture was concentrated to afford 50 mg crude product as a yellow solid. [M+H] Calc'd for $C_9H_{13}ClN_4$, 213.1; Found, 213.1.

Step 3: (S)—N-(4-(3-((5-chloropyrimidin-2-yl)amino)-3-methylpyrrolidine-1-carbonyl)phenyl)acrylamide

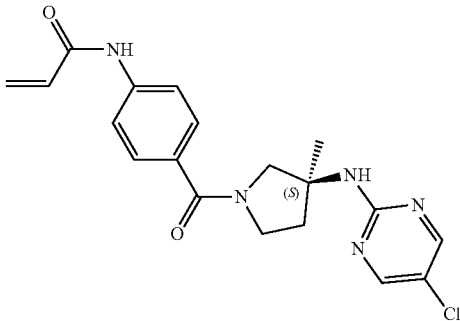

To a solution of (S)-tert-butyl 3-((5-chloropyrimidin-2-yl)amino)-3-methylpyrrolidine-1-carboxylate (50 mg, 0.23 mmol) and 4-acrylamidobenzoic acid (44 mg, 0.23 mmol) in DMF (3 mL) was added HATU (105 mg, 0.27 mmol) and DIEA (90 mg, 0.69 mmol) at RT. The mixture was stirred at rt for 2 h, The reaction mixture was concentrated in vacuo. The residue was purified by prep-HPLC to afford (R)—N-(4-(3-((5-cyanopyrimidin-2-yl)amino)pyrrolidine-1-carbonyl)-2-(2-(dimethylamino)ethoxy)phenyl)acrylamide (25.4 mg, 25.4%) as a white solid. $^1$H NMR (400 MHz, $CD_3OD$): δ 1.50 (s, 2H), 1.63 (s, 1H), 2.07-2.13 (m, 1H), 2.46-2.49 (m, 1H), 3.61-3.82 (m, 3H), 4.16-4.19 (d, J=11.2 Hz, 1H), 5.79-5.83 (m, 1H), 6.37-6.45 (m, 2H), 7.44-7.56 (m, 2H), 7.71-7.87 (m, 2H), 8.19 (s, 1H), 8.30 (s, 1H). [M+H] Calc'd for $C_{19}H_{20}ClN_5O_2$, 386.1; Found, 386.1.

Step 4: (R)—N-(4-(3-((5-cyanopyrimidin-2-yl)amino)pyrrolidine-1-carbonyl)-2-(2-(dimethylamino)ethoxy)phenyl)acrylamide

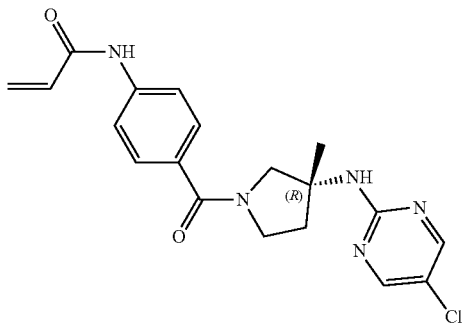

To a solution of (R)-5-chloro-N-(3-methylpyrrolidin-3-yl)pyrimidin-2-amine (50 mg, 0.23 mmol) and 4-acrylamidobenzoic acid (44 mg, 0.23 mmol) in DMF (3 mL) was added HATU (105 mg, 0.27 mmol) and DIEA (90 mg, 0.69 mmol). The reaction mixture was stirred at RT for 2 h. The reaction mixture was concentrated. The residue was purified by prep-HPLC to afford (R)—N-(4-(3-((5-cyanopyrimidin-2-yl)amino)pyrrolidine-1-carbonyl)-2-(2-(dimethylamino)ethoxy)phenyl)acrylamide (37.7 mg, 31%) as a white solid. $^1$H NMR (400 MHz, CD$_3$OD): δ 1.50 (s, 2H), 1.63 (s, 1H), 2.07-2.13 (m, 1H), 2.46-2.49 (m, 1H), 3.61-3.82 (m, 3H), 4.16-4.19 (d, J=11.2 Hz, 1H), 5.79-5.83 (m, 1H), 6.37-6.45 (m, 2H), 7.44-7.56 (m, 2H), 7.71-7.87 (m, 2H), 8.19 (s, 1H), 8.30 (s, 1H). [M+H] Calc'd for C$_{19}$H$_{20}$ClN$_5$O$_2$, 386.1; Found, 386.1.

Example 110: Synthesis of (R)—N-(3-(3-((5-chloropyrimidin-2-yl)amino)pyrrolidine-1-carbonyl)-1-methyl-1H-pyrazol-5-yl)acrylamide

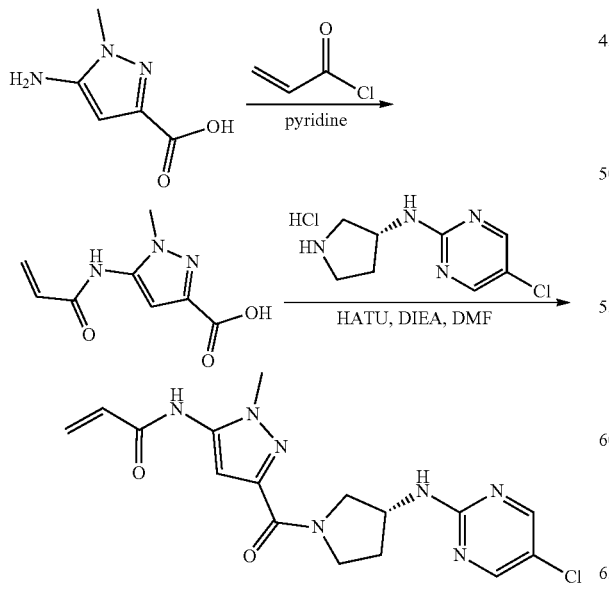

Step 1: 5-acrylamido-1-methyl-1H-pyrazole-3-carboxylic acid

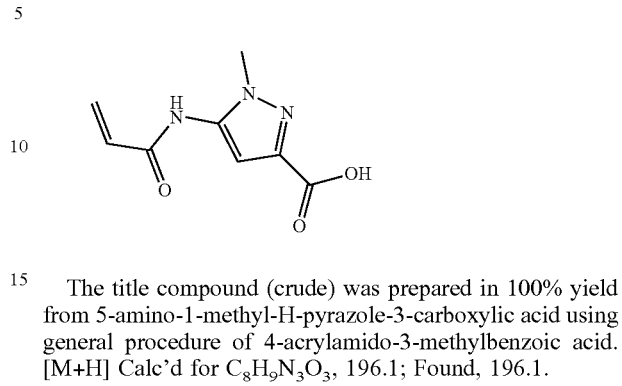

The title compound (crude) was prepared in 100% yield from 5-amino-1-methyl-H-pyrazole-3-carboxylic acid using general procedure of 4-acrylamido-3-methylbenzoic acid. [M+H] Calc'd for C$_8$H$_9$N$_3$O$_3$, 196.1; Found, 196.1.

Step 2: (R)—N-(3-(3-((5-chloropyrimidin-2-yl)amino)pyrrolidine-1-carbonyl)-1-methyl-1H-pyrazol-5-yl)acrylamide

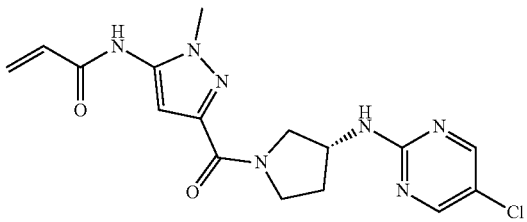 [SMILES: C=CC(=O)Nc1cc(C(=O)N2CC[C@@H](Nc3ncc(Cl)cn3)C2)nn1C]

The title compound was prepared in 20% yield from 5-acrylamido-1-methyl-1H-pyrazole-3-carboxylic acid using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.89-1.98 (m, 1H), 2.09-2.21 (m, 1H), 3.44-3.56 (m, 1H), 3.64-3.69 (m, 0.5H), 3.72-3.77 (m, 4H), 3.91-3.96 (m, 0.5H), 4.00-4.14 (m, 1H), 4.29-4.40 (m, 1H), 5.82-5.85 (m, 1H), 6.28-6.33 (m, 1H), 6.46-6.54 (m, 1H), 6.64 (s, 0.5H), 6.65 (s, 0.5H), 7.78-7.80 (m, 1H), 8.36 (s, 1H), 8.38 (s, 1H), 10.31 (br s, 1H). [M+H] Calc'd for C$_{16}$H$_{18}$ClN$_7$O$_2$, 376.1; Found, 376.1.

Example 111: Synthesis of (R)—N-(4-(3-((5-chloro-4-deutero-6-(methylamino)pyrimidin-2-yl)amino)pyrrolidine-1-carbonyl)phenyl)acrylamide

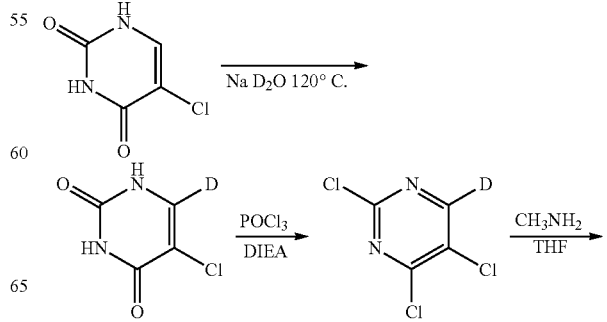

333
-continued

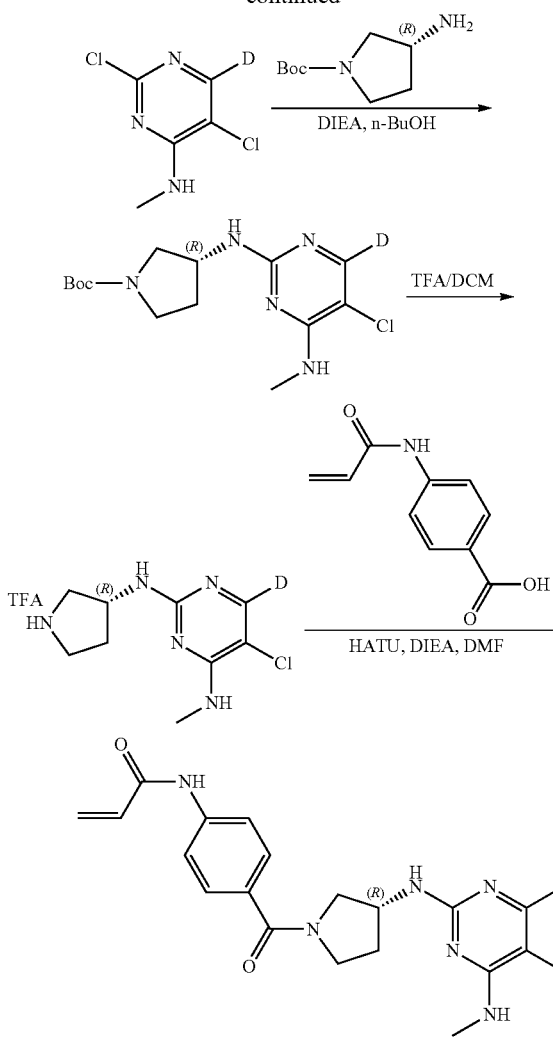

Step 1: 5-chloro-6-deuteropyrimidine-2,4(1H,3H)-dione

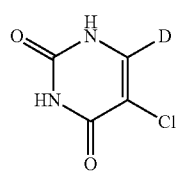

Na (1.0 g, 4.3 mmol) was added to D$_2$O (5 mL) at 0° C. The mixture was used directly in the next step. A mixture of 5-chloropyrimidine-2,4(1H,3H)-dione (2.0 g, 13.7 mmol) and NaOD (1.7 g, 41.1 mmol) in D$_2$O (6 mL) was stirred at 120° C. under N$_2$ overnight. The mixture was cooled to RT and filtered. The filter cake was dried to afford 5-chloro-6-deuteropyrimidine-2,4(1H,3H)-dione (1.5 g, 75%) as a yellow solid. [M+H] Calc'd for C$_4$H$_2$DClN$_2$O$_2$, 147.9; Found, 147.9.

334

Step 2: 2,4,5-trichloro-6-deuteropyrimidine

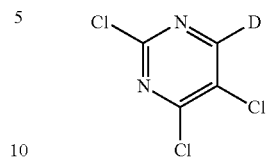

A mixture of 5-chloro-6-deuteropyrimidine-2,4(1H,3H)-dione (240 mg, 1.6 mmol) and DIEA (413 mg, 3.2 mmol) in POCl$_3$ (2.5 g, 16.3 mmol) was stirred at 110° C. for 24 h. The solution was cooled to RT and added to hot water dropwise. Then the reaction mixture was extracted with DCM (30 mL*2). The combined organic phase was concentrated in vacuo to afford 2,4,5-trichloro-6-deuteropyrimidine (360 mg, crude, 100%) as yellow oil. [M+H] Calc'd for C$_4$DCl$_3$N$_2$, 183.9; Found, 183.9.

Step 3: 2,5-dichloro-6-deutero-N-methylpyrimidin-4-amine

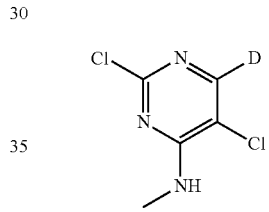

The title compound was prepared in 58% yield from 2,4,5-trichloro-6-deuteropyrimidine using general procedure of 2,5-dichloro-N,N-dimethylpyrimidin-4-amine. [M+H] Calc'd for C$_5$H$_4$DCl$_2$N$_3$, 178.9; Found, 178.9

Step 4: (R)-tert-butyl 3-((5-chloro-4-deutero-6-(methylamino)pyrimidin-2-yl)amino)pyrrolidine-1-carboxylate

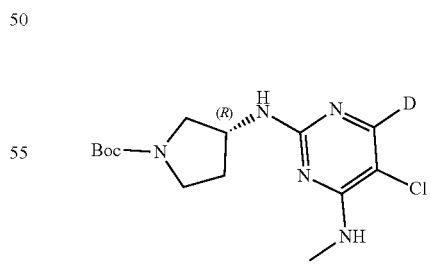

The title compound was prepared in 50% yield from 2,5-dichloro-6-deutero-N-methylpyrimidin-4-amine using general procedure of (R)-tert-butyl 3-((5-chloro-4-methylpyrimidin-2-yl)amino)pyrrolidine-1-carboxylate. [M+H] Calc'd for C$_{14}$H$_{21}$DClN$_5$O$_2$, 329.1; Found, 329.1.

Step 5: (R)-5-chloro-6-deutero-N4-methyl-N2-(pyrrolidin-3-yl)pyrimidine-2,4-diamine 2,2,2-trifluoroacetate

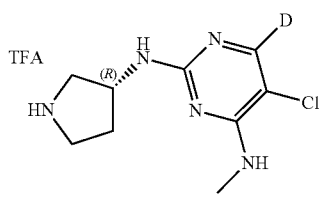

The title compound was prepared in 100% yield from (R)-tert-butyl 3-((5-chloro-4-deutero-6-(methylamino)pyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_9H_{13}DClN_5$, 229.1; Found, 229.1.

Step 6: (R)—N-(4-(3-((5-chloro-4-deutero-6-(methylamino)pyrimidin-2-yl)amino)pyrrolidine-1-carbonyl)phenyl)acrylamide

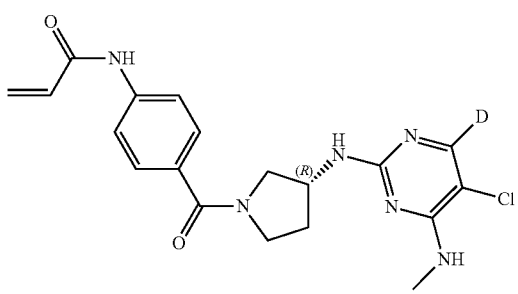

The title compound was prepared in 31% yield from (R)-5-chloro-6-deutero-N4-methyl-N2-(pyrrolidin-3-yl)pyrimidine-2,4-diamine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.96-1.99 (m, 1H), 2.09-2.13 (m, 1H), 2.74 (s, 1.5H), 2.85 (s, 1.5H), 3.42-3.77 (m, 4H), 4.21-4.38 (m, 1H), 5.76-5.79 (m, 1H), 6.28 (d, J=16.8 Hz, 1H), 6.41-6.48 (m, 1H), 6.88-6.92 (m, 1H), 7.02 (br s, 1H), 7.48-7.53 (m, 2H), 7.69-7.73 (m, 2H), 10.30 (s, 1H). [M+H] Calc'd for $C_{19}H_{20}DClN_6O_2$, 402.1; Found, 402.1.

Example 112: Synthesis of (R)—N-(4-(3-((5-chloropyrimidin-2-yl)amino)pyrrolidine-1-carbonyl)-2-(2-(dimethylamino)ethoxy)phenyl)acrylamide

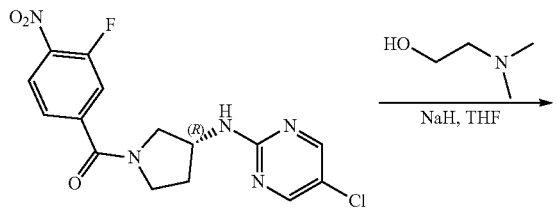

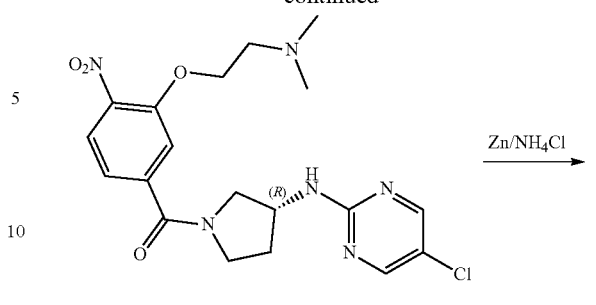

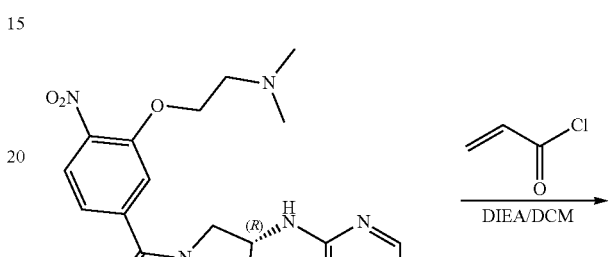

Step 1: (R)-(3-((5-chloropyrimidin-2-yl)amino)pyrrolidin-1-yl)(3-(2-(dimethylamino)ethoxy)-4-nitrophenyl)methanone

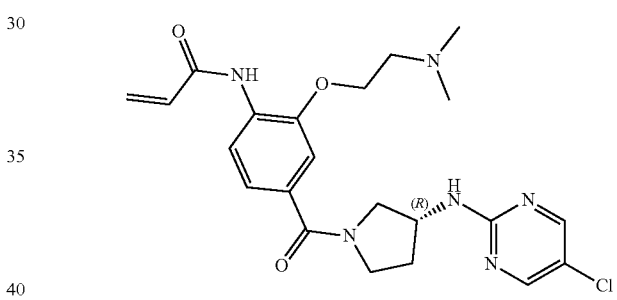

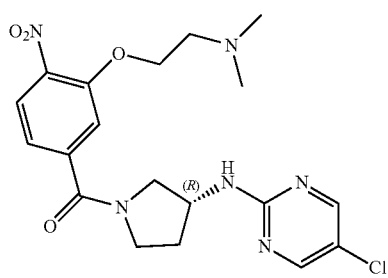

The title compound was prepared in 100% yield from (R)-(3-((5-chloropyrimidin-2-yl)amino)pyrrolidin-1-yl)(3-fluoro-4-nitrophenyl)methanone using general procedure of ((R)-3-((5-chloropyrimidin-2-yl)amino)pyrrolidin-1-yl)(4-nitro-3-((tetrahydrofuran-3-yl)oxy)phenyl)methanone. [M+H] Calc'd for $C_{19}H_{23}ClN_6O_4$, 435.1; Found, 435.1.

Step 2: (R)-(4-amino-3-(2-(dimethylamino)ethoxy)phenyl)(3-((5-chloropyrimidin-2-yl)amino)pyrrolidin-1-yl)methanone

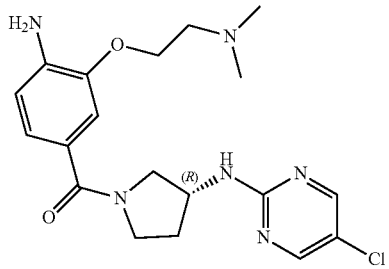

The title compound was prepared in 80% yield from (R)-(3-((5-chloropyrimidin-2-yl)amino)pyrrolidin-1-yl)(3-(2-(dimethylamino)ethoxy)-4-nitrophenyl)methanone using general procedure of (4-amino-3-((tetrahydrofuran-3-yl)oxy)phenyl)((R)-3-((5-chloropyrimidin-2-yl)amino)pyrrolidin-1-yl)methanone. [M+H] Calc'd for $C_{19}H_{25}ClN_6O_2$, 405.1; Found, 405.1.

Step 3: (R)—N-(4-(3-((5-chloropyrimidin-2-yl)amino)pyrrolidine-1-carbonyl)-2-(2-(dimethylamino)ethoxy)phenyl)acrylamide

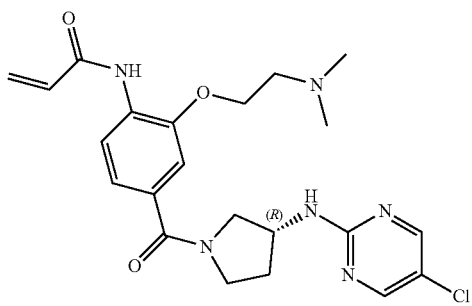

The title compound was prepared in 18% yield from (R)-(4-amino-3-(2-(dimethylamino)ethoxy)phenyl)(3-((5-chloropyrimidin-2-yl)amino)pyrrolidin-1-yl)methanone using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-$d_6$): δ 1.87-2.01 (m, 1H), 3.10-2.19 (m, 1H), 2.22 (s, 3H), 2.24 (s, 3H), 2.60-2.64 (m, 2H), 3.41-3.44 (m, 1H), 3.52-3.57 (m, 1H), 3.64-3.67 (m, 1H), 3.74-3.80 (m, 1H), 4.12-4.18 (m, 2H), 4.22-4.41 (m, 1H), 5.78 (d, J=10.0 Hz, 1H), 6.26 (d, J=16.8 Hz, 1H), 6.52-6.59 (m, 1H), 7.12-7.18 (m, 1H), 7.23 (s, 0.5H), 7.27 (s, 0.5H), 7.83 (br s, 1H), 8.12-8.17 (m, 1H), 8.32 (s, 1H), 8.39 (s, 1H), 9.67 (s, 0.5H), 9.71 (s, 0.5H). [M+H] Calc'd for $C_{22}H_{27}ClN_6O_3$, 459.1; Found, 459.1.

Example 113: Synthesis of (R)—N-(4-(3-((5-ethynylpyrimidin-2-yl)amino)pyrrolidine-1-carbonyl)phenyl)-N-methylacrylamide

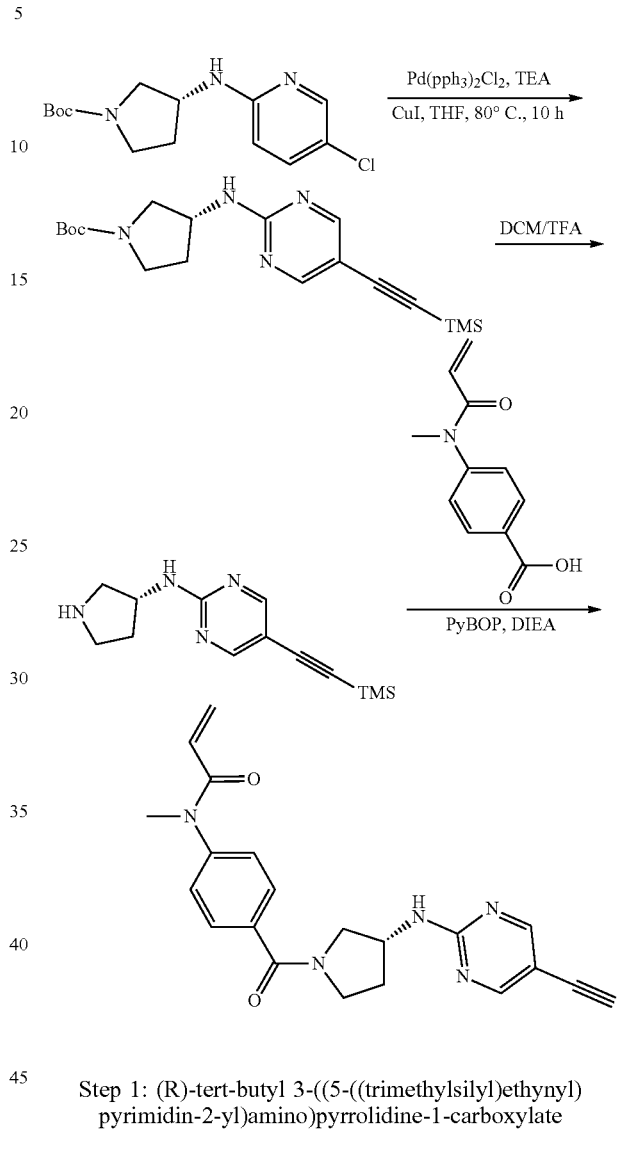

Step 1: (R)-tert-butyl 3-((5-((trimethylsilyl)ethynyl)pyrimidin-2-yl)amino)pyrrolidine-1-carboxylate

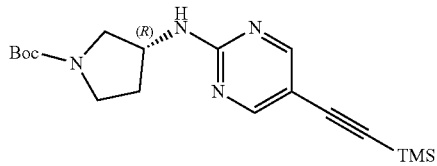

A solution of (R)-tert-butyl 3-((4-bromophenyl)amino)pyrrolidine-1-carboxylate (11.0 g, 32.2 mmol), ethynyl trimethylsilane (12.6 g, 130.0 mmol), CuI (1.8 g, 9.7 mmol) and Pd(PPh$_3$)$_2$Cl$_2$ (2.3 g, 3.2 mmol) in TEA (80 mL) was stirred at 80° C. for 2 h under N$_2$. The reaction mixture was cooled, diluted with water (150 mL) and extracted with EA (200 mL*2). The combined organic layers were washed with brine (150 mL), dried over anhydrous sodium sulfate, filtered and concentrated under reduced pressure. The residue was purified by column chromatography on silica gel (PE/

EA=5/1) to give (R)-tert-butyl 3-((5-((trimethylsilyl)ethynyl)pyrimidin-2-yl)amino)pyrrolidine-1-carboxylate (9.2 g, 79%). [M+H] MS Calc'd $C_{18}H_{28}N_4O_2Si$: 361.2; Found: 361.2.

Step 2: (R)—N-(pyrrolidin-3-yl)-5-((trimethylsilyl)ethynyl)pyrimidin-2-amine

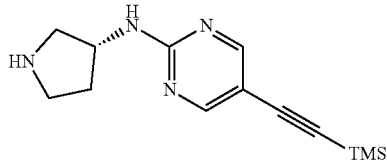 [SMILES: C[Si](C)(C)C#Cc1cnc(N[C@@H]2CCNC2)nc1]

To a solution of (R)-tert-butyl 3-((5-((trimethylsilyl)ethynyl)pyrimidin-2-yl)amino)pyrrolidine-1-carboxylate (400 mg, 1.11 mmol) in DCM (8 mL) was added TFA (8 mL) at rt. DCM (20 mL) was added to the crude product and the reaction mixture was washed with sodium carbonate aqueous solution. The organics were dried over anhydrous sodium sulfate, filtered and concentrated under reduced pressure to give (R)—N-(pyrrolidin-3-yl)-5-((trimethylsilyl)ethynyl)pyrimidin-2-amine (220 mg, 76%) as a brown solid. [M+H] MS Calc'd for $C_{13}H_{20}N_4Si$: 261.1; Found: 261.1.

Step 3: (R)—N-(4-(3-((5-ethynylpyrimidin-2-yl)amino)pyrrolidine-1-carbonyl)phenyl)-N-methylacrylamide

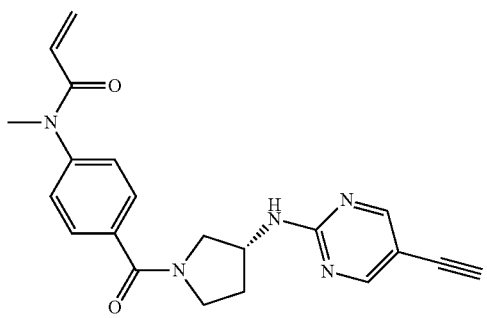 [SMILES: C#Cc1cnc(N[C@@H]2CCN(C(=O)c3ccc(N(C)C(=O)C=C)cc3)C2)nc1]

A mixture of 4-(N-methylacrylamido)benzoic acid (118 mg, 0.57 mmol), (R)—N-(pyrrolidin-3-yl)-5-((trimethylsilyl)ethynyl)pyrimidin-2-amine (120 mg, 0.64 mmol), PyBOP (332 mg, 6.38 mmol) and DIEA (412 mg, 3.19 mmol) in DMF (10 mL) was stirred at rt 3 h. The reaction mixture was concentrated. The residue was purified by prep-HPLC to (R)—N-(4-(3-((5-ethynylpyrimidin-2-yl)amino)pyrrolidine-1-carbonyl)phenyl)acrylamide (108.4 mg, 33.9%) as a white solid. ¹H NMR (400 MHz, DMSO-$d_6$): 1.89-1.99 (m, 1H), 2.14-2.17 (m, 1H), 3.26 (s, 1.5H), 3.29 (s, 1.5H), 3.48-3.78 (m, 4H), 4.24-4.26 (m, 1H), 4.33-4.48 (m, 1H), 5.60 (d, J=7.2 Hz, 1H), 6.14-6.16 (m, 2H), 7.31-7.36 (m, 2H), 7.56-7.61 (m, 2H), 8.01 (t, J=9.2 Hz, 1H), 8.39 (s, 1H), 8.45 (s, 1H). [M+H]Calc'd for $C_{21}H_{21}N_5O_2$: 376.2; Found: 376.2.

Example 114: Synthesis of (R,E)-N-(4-(3-((5-chloro-4-(trideuteromethoxy)pyrimidin-2-yl)amino)pyrrolidine-1-carbonyl)phenyl)-4-(dimethylamino)but-2-enamide

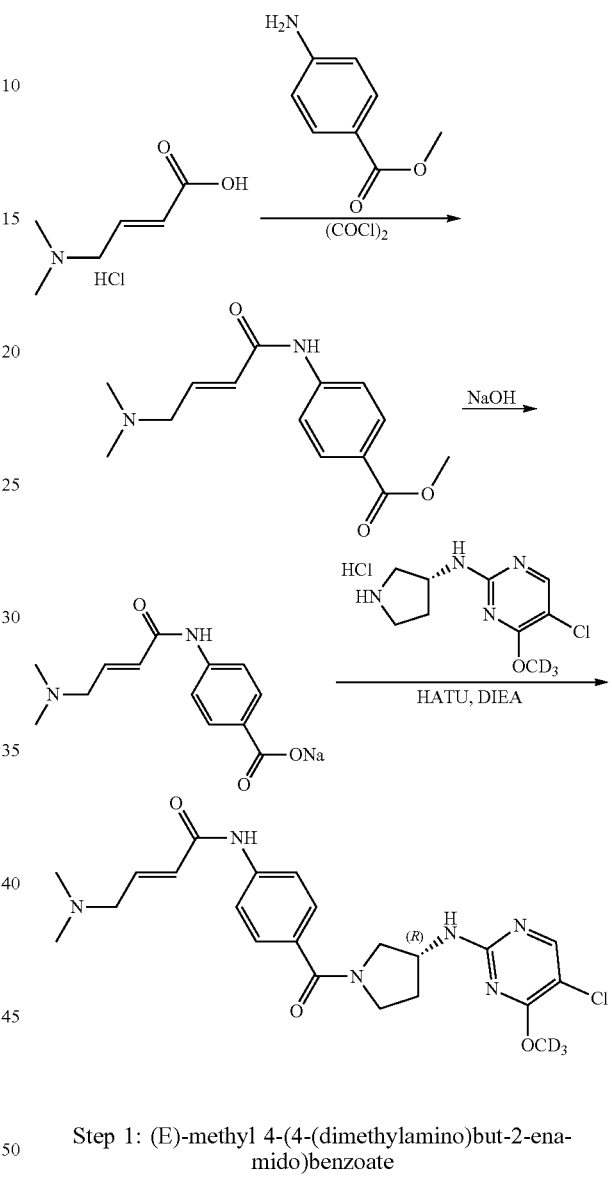

Step 1: (E)-methyl 4-(4-(dimethylamino)but-2-enamido)benzoate

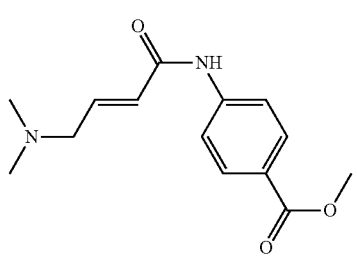

To a solution of (E)-4-(dimethylamino)but-2-enoic acid hydrochloride (1.0 g, 6.0 mmol) in DCM/DMF (15 mL/2 drops) was added oxalyl chloride (1.5 g, 11.8 mmol) dropwise at 0° C. under N₂. The solution was stirred at RT for 2 hours. The mixture was concentrated at 30° C. The residue was dissolved in THF (10 mL) and was added to a mixture of methyl 4-aminobenzoate (453 mg, 3.0 mmol) and DIEA (2.3 g, 18 mmol) in THF (10 mL) at 0° C. The solution was stirred at RT for 2 hours. The solution was concentrated and the residue was diluted with DCM (50 mL), washed with brine (20*3 mL), dried over Na₂SO₄ and filtered. The filtrate was concentrated in vacuo and the residue was purified by flash chromatography on silica gel (DCM/MeOH=20/1) to afford (E)-methyl 4-(4-(dimethylamino)but-2-enamido)benzoate (340 mg, 21%) as a brown solid. [M+H] Calc'd for $C_{14}H_{18}N_2O_3$, 263.1; Found, 263.1.

Step 2: sodium (E)-4-(4-(dimethylamino)but-2-enamido)benzoate

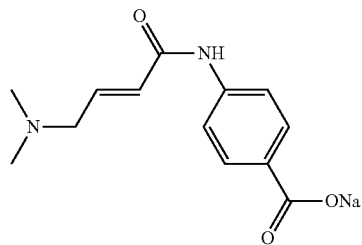

A mixture of (E)-methyl 4-(4-(dimethylamino)but-2-enamido)benzoate (340 mg, 1.3 mmol) in THF/H₂O (3 mL/3 mL) was stirred at 65° C. for 5 hours. The solution was concentrated to afford sodium (E)-4-(4-(dimethylamino)but-2-enamido)benzoate (307 mg, 87%) as a yellow solid. [M+H22] Calc'd for $C_{13}H_{15}N_2NaO_3$, 249.1; Found, 249.1.

Step 3: (R,E)-N-(4-(3-((5-chloro-4-(trideuteromethoxy)pyrimidin-2-yl)amino)pyrrolidine-1-carbonyl)phenyl)-4-(dimethylamino)but-2-enamide

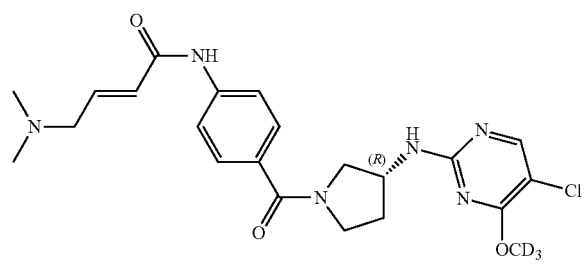

The title compound was prepared in 15% yield from sodium (E)-4-(4-(dimethylamino)but-2-enamido)benzoate using general procedure of (R)—N-(4-(3-((5-chloro-4-methylpyrimidin-2-yl)amino)pyrrolidine-1-carbonyl)phenyl)acrylamide. ¹H NMR (400 MHz, CDCl₃): δ 1.95-2.01 (m, 1H), 2.27 (s, 6H), 2.29-2.38 (m, 1H), 3.10 (d, J=5.6 Hz, 2H), 3.39-3.42 (m, 0.5H), 3.60-3.90 (m, 3H), 3.99-4.03 (m, 0.5H), 4.42-4.54 (m, 1H), 5.15-5.26 (m, 1H), 6.14 (d, J=15.2 Hz, 1H), 6.94-7.00 (m, 1H), 7.45-7.50 (m, 2H), 7.56-7.60 (m, 2H), 7.82-7.85 (m, 1H), 7.96-8.03 (m, 1H). [M+H] Calc'd for $C_{22}H_{24}D_3ClN_6O_3$, 462.2; Found, 462.2.

Example 115: Synthesis of (R,E)-N-(4-(3-((5-chloro-4-methoxypyrimidin-2-yl)amino)pyrrolidine-1-carbonyl)phenyl)-4-(dimethylamino)but-2-enamide

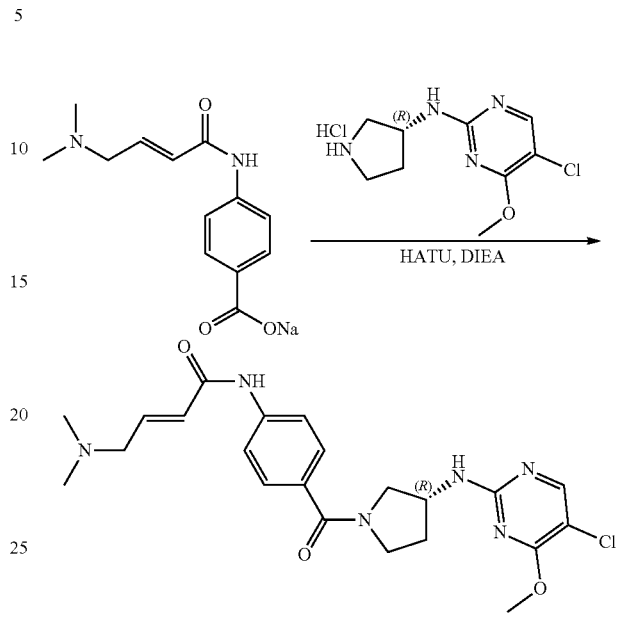

The title compound was prepared in 11% yield from sodium (E)-4-(4-(dimethylamino)but-2-enamido)benzoate using general procedure of (R)—N-(4-(3-((5-chloro-4-methylpyrimidin-2-yl)amino)pyrrolidine-1-carbonyl)phenyl)acrylamide. ¹H NMR (400 MHz, DMSO-d₆): δ 2.00-2.07 (m, 1H), 2.14-2.19 (m, 7H), 3.06 (d, J=5.2 Hz, 2H), 3.35-3.38 (m, 1H), 3.40-3.45 (m, 1H), 3.61-3.65 (m, 1H), 3.75-3.78 (m, 1H), 3.85 (s, 1.5H), 3.94 (s, 1.5H), 4.22-4.45 (m, 1H), 6.27 (d, J=15.2 Hz, 1H), 6.72-6.77 (m, 1H), 7.47-7.52 (m, 2H), 7.67-7.71 (m, 3H), 8.07 (s, 0.5H), 8.14 (s, 0.5H), 10.20 (s, 1H). [M+H] Calc'd for $C_{22}H_{27}ClN_6O_3$, 459.1; Found, 459.1.

Example 116: Synthesis of (R)-1-(3-(3-((5-chloropyrimidin-2-yl)amino)pyrrolidine-1-carbonyl)phenyl)-1H-pyrrole-2,5-dionefuran-2,5-dione

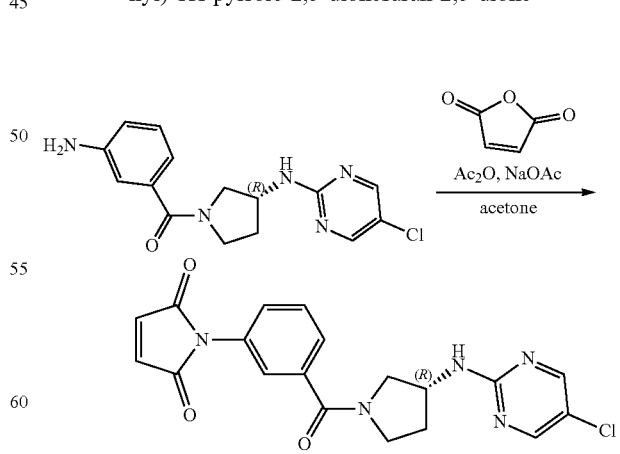

A mixture of (R)-(3-aminophenyl)(3-((5-chloropyrimidin-2-yl)amino)Pyrrolidin-1-yl)methanone (175 mg, 0.55 mmol) and furan-2,5-dione (81.5 mg, 0.83 mmol) in acetone (5 mL) was stirred at 20° C. for 2 hrs. The reaction mixture was concentrated. To the residue was added a solution of sodium acetate (45 mg, 0.55 mmol) and acetic anhydride (112 mg, 1.1 mmol) in DMF (3 mL). The mixture was stirred at 50° C. for 5 hrs. The mixture was cooled, filtered and concentrated. The residue was purified by silica gel chromatography (DCM/MeOH=20/1) to afford (R)-1-(3-(3-((5-chloropyrimidin-2-yl)amino)pyrrolidine-1-carbonyl)phenyl)-1H-pyrrole-2,5-dionefuran-2,5-dione (91.0 mg, 41%) as a yellow solid. $^1$H NMR (400 MHz, CDCl$_3$): 2.00-2.03 (m, 1H), 2.27-2.27 (m, 1H), 3.40-3.62 (m, 2H), 3.63-4.03 (m, 2H), 4.47-4.57 (m, 1H), 5.28-5.36 (m, 1H), 6.86-6.88 (m, 2H), 7.44-7.57 (m, 4H), 8.19 (s, 1H), 8.25 (s, 1H). [M+H] Calc'd for C19H$_{16}$ClN$_5$O$_3$, 398.1; Found, 398.1.

Example 117: Synthesis of (R,E)-N-(4-(3-((5-chloro-4-methoxypyrimidin-2-yl)amino)pyrrolidine-1-carbonyl)-2-methylphenyl)-4-(dimethylamino)but-2-enamide

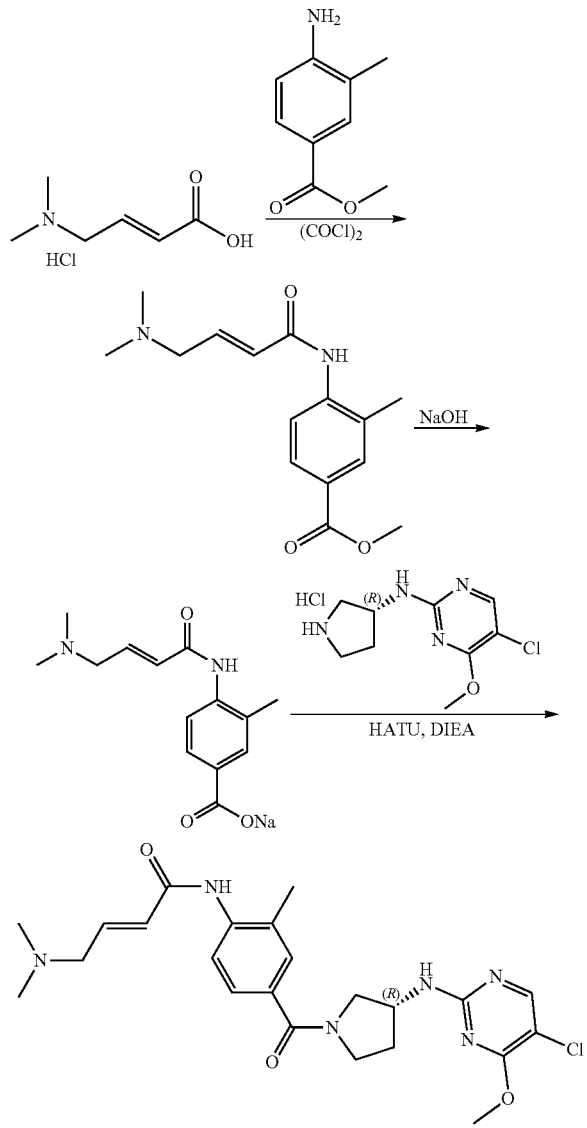

Step 1: (E)-methyl 4-(4-(dimethylamino)but-2-enamido)-3-methylbenzoate

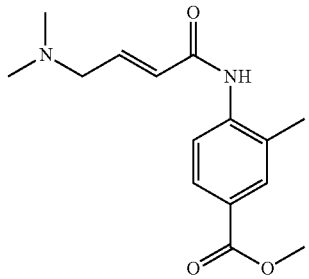

The title compound was prepared in 3.6% yield from (E)-4-(dimethylamino)but-2-enoic acid hydrochloride using general procedure of (E)-methyl 4-(4-(dimethylamino)but-2-enamido)benzoate. [M+H] Calc'd for C$_{15}$H$_{20}$N$_2$O$_3$, 277.1; Found, 277.1.

Step 2: sodium (E)-4-(4-(dimethylamino)but-2-enamido)-3-methylbenzoate

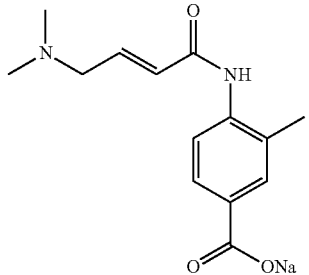

The title compound was prepared in 100% yield from (E)-methyl 4-(4-(dimethylamino)but-2-enamido)-3-methylbenzoate using general procedure of sodium (E)-4-(4-(dimethylamino)but-2-enamido)benzoate. [M+H22] Calc'd for C$_{14}$H$_{17}$N$_2$NaO$_3$, 263.1; Found, 263.1.

Step 3: (R,E)-N-(4-(3-((5-chloro-4-methoxypyrimidin-2-yl)amino)pyrrolidine-1-carbonyl)-2-methylphenyl)-4-(dimethylamino)but-2-enamide

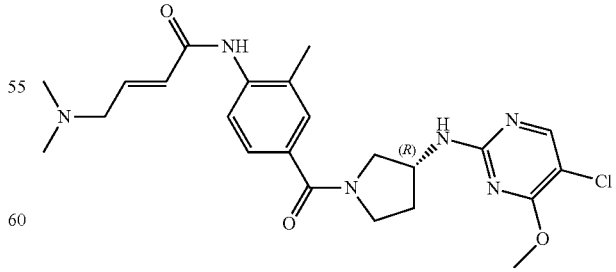

The title compound was prepared in 12% yield from sodium (E)-4-(4-(dimethylamino)but-2-enamido)-3-methylbenzoate using general procedure of (R)—N-(4-(3-((5-chloro-4-methylpyrimidin-2-yl)amino)pyrrolidine-1-carbonyl)phenyl)acrylamide. ¹H NMR (400 MHz, DMSO-d₆): δ 1.89-2.01 (m, 1H), 2.14-2.19 (m, 7H), 2.22 (s, 1.5H), 2.25 (s, 1.5H), 3.06 (d, J=6.0 Hz, 2H), 3.37-3.45 (m, 1H), 3.51-3.54 (m, 1H), 3.62-3.67 (m, 1H), 3.76-3.79 (m, 1H), 3.85 (s, 1.5H), 3.94 (s, 1.5H), 4.24-4.43 (m, 1H), 6.41 (d, J=15.2 Hz, 1H), 6.70-6.77 (m, 1H), 7.30-7.39 (m, 2H), 7.61-7.66 (m, 2H), 8.07 (s, 0.5H), 8.14 (s, 0.5H), 9.40 (s, 1H). [M+H] Calc'd for $C_{23}H_{29}ClN_6O_3$, 473.1; Found, 473.1.

Example 118: (R)—N-(4-(3-((4-(dimethylamino)-5-(trifluoromethyl)pyrimidin-2-yl)amino)pyrrolidine-1-carbonyl)phenyl)acrylamide

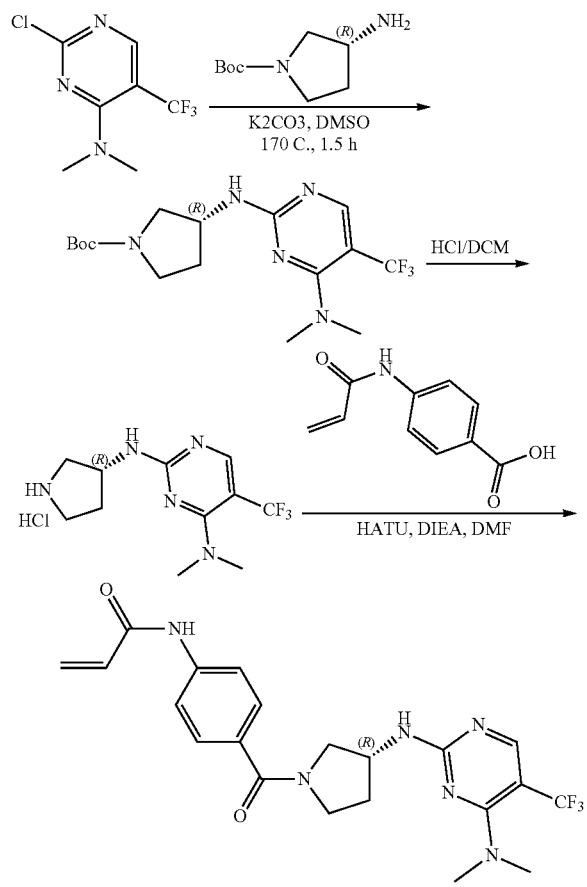

Step 1: (R)-tert-butyl 3-((4-(dimethylamino)-5-(trifluoromethyl)pyrimidin-2-yl)amino)pyrrolidine-1-carboxylate

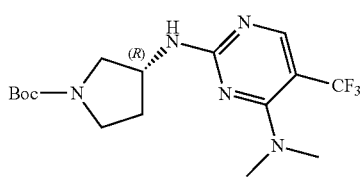

A mixture of 2-chloro-N,N-dimethyl-5-(trifluoromethyl)pyrimidin-4-amine (300 mg, 1.33 mmol), (R)-tert-butyl 3-aminopyrrolidine-1-carboxylate (298 mg, 1.60 mmol) and $K_2CO_3$ (276 mg, 2.00 mmol) in DMSO (3 mL) was stirred at 170° C. for 1.5 h under microwave conditions. The reaction mixture was cooled, added $H_2O$ (20 mL) and extracted with EA (20 mL*2). The combined organic layer was dried over $Na_2SO_4$, filtered and concentrated. The residue was purified by silica gel chromatography (PE/EA=50/1~10/1) to afford (R)-tert-butyl 3-((4-(dimethylamino)-5-(trifluoromethyl)pyrimidin-2-yl)amino)pyrrolidine-1-carboxylate (350 mg, 70%) as a white solid. [M+H] Calc'd for $C_{16}H_{24}F_3N_5O_2$, 376.2; Found, 376.2.

Step 2: (R)—N4,N4-dimethyl-N2-(pyrrolidin-3-yl)-5-(trifluoromethyl)pyrimidine-2,4-diamine (HCl Salt)

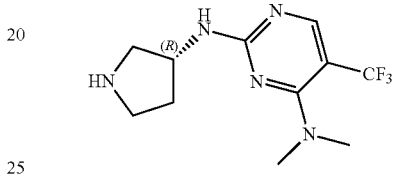

A mixture of (R)-tert-butyl 3-((4-(dimethylamino)-5-(trifluoromethyl)pyrimidin-2-yl)amino)pyrrolidine-1-carboxylate (350 mg, 0.93 mmol) in HCl/DCM (20 mL) was stirred at RT overnight. The reaction mixture was concentrated to afford (R)—N4,N4-dimethyl-N2-(pyrrolidin-3-yl)-5-(trifluoromethyl)pyrimidine-2,4-diamine (290 mg, 100%) as white solid (HCl salt). [M+H] Calc'd for $C_{11}H_{16}F_3N_5$, 276.1; Found, 276.1

Step 3: (R)—N-(4-(3-((4-(dimethylamino)-5-(trifluoromethyl)pyrimidin-2-yl)amino)pyrrolidine-1-carbonyl)phenyl)acrylamide

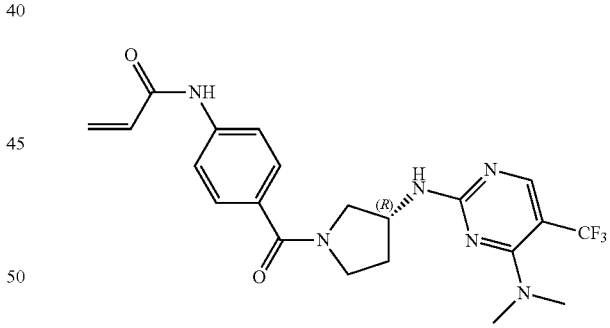

A mixture of (R)—N4,N4-dimethyl-N2-(pyrrolidin-3-yl)-5-(trifluoromethyl)pyrimidine-2,4-diamine (HCl salt) (320 mg, 0.52 mmol), 4-acrylamidobenzoic acid (214 mg, 1.12 mmol), HATU (426 mg, 1.12 mmol) and DIEA (481 mg, 3.73 mmol) in DMF (10 mL) was stirred at RT for overnight. The mixture was diluted with water (50 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(4-(3-((4-(dimethylamino)-5-(trifluoromethyl)pyrimidin-2-yl)amino)pyrrolidine-1-carbonyl) phenyl)acrylamide (293.3 mg, 70%) as a white solid. ¹H NMR (400 MHz, DMSO-d₆): δ 2.07-2.23 (m, 2H), 3.05 (s, 3H), 3.13 (s, 3H), 3.44-3.65 (m, 3H), 3.82-3.87 (m, 1H), 4.60-4.76 (m, 1H), 5.78 (dd, J=1.6 Hz, 8.4 Hz, 1H), 6.26-6.30 (m, 1H), 6.42-6.49 (m, 1H), 6.62-6.69 (m, 1H), 7.49-7.53 (m, 2H), 7.71-7.73 (m, 2H), 8.09-8.13 (m, 1H), 10.3 (s, 1H). [M+H] Calc'd for $C_{21}H_{23}F_3N_6O_2$, 449.2; Found, 449.2

Example 119: Synthesis of (R)—N-(4-(3-((5-chloro-4-ethoxypyrimidin-2-yl)amino)pyrrolidine-1-carbonyl)-2-(4-methylpiperazin-1-yl)phenyl)acrylamide

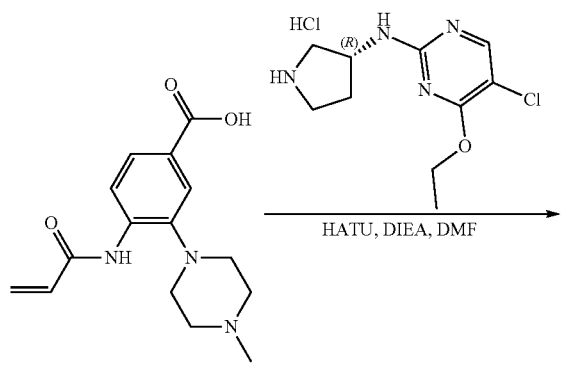

A mixture of 4-acrylamido-3-(4-methylpiperazin-1-yl) benzoic acid (150 mg, 0.52 mmol), (R)-5-chloro-4-ethoxy-N-(pyrrolidin-3-yl)pyrimidin-2-amine (HCl salt) (173 mg, 0.62 mmol), HATU (235 mg, 0.62 mmol) and DIEA (201 mg, 1.56 mmol) in DMF (15 mL) was stirred at RT for overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(4-(3-((5-chloro-4-ethoxypyrimidin-2-yl)amino)pyrrolidine-1-carbonyl)-2-(4-methylpiperazin-1-yl)phenyl)acrylamide (38.5 mg, 14%) as a white solid. $^1$H NMR (400 MHz, DMSO-$d_6$): δ 1.20-1.36 (m, 3H), 1.85-2.03 (m, 1H), 2.06-2.20 (m, 1H), 2.24 (s, 1H), 2.51-2.55 (m, 4H), 2.76-2.86 (m, 4H), 3.40-3.78 (m, 4H), 4.20-4.45 (m, 3H), 5.79 (d, J=10.0 Hz, 1H), 6.23 (s, 0.5H), 6.28 (s, 0.5H), 6.60-6.67 (m, 1H), 7.22-7.32 (m, 2H), 7.64 (br s, 1H), 8.00-8.13 (m, 2H), 9.08 (s, 0.5H), 9.10 (s, 0.5H). [M+H] Calc'd for $C_{25}H_{32}ClN_7O_3$, 514.2; Found, 514.2

Example 120: Synthesis of (R)—N-(4-(3-((4-(methylamino)-5-(trifluoromethyl)pyrimidin-2-yl)amino)pyrrolidine-1-carbonyl)phenyl)acrylamide

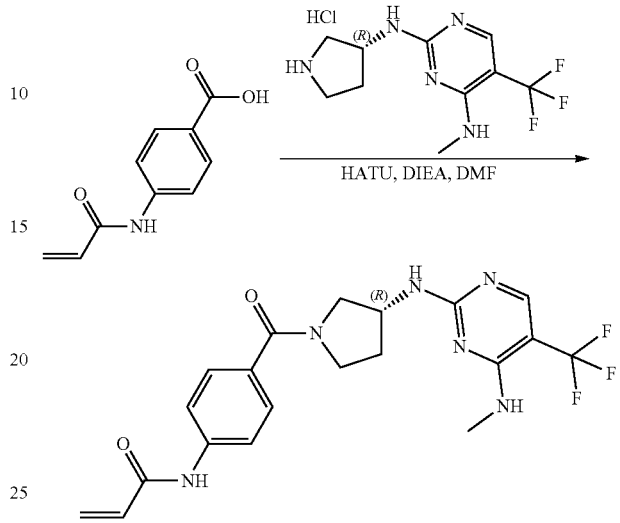

A mixture of 4-acrylamidobenzoic acid (257 mg, 1.34 mmol), (R)—N4-methyl-N2-(pyrrolidin-3-yl)-5-(trifluoromethyl)pyrimidine-2,4-diamine hydrochloride (363 mg, 1.22 mmol), HATU (510 mg, 1.34 mmol) and DIEA (473 mg, 3.66 mmol) in DMF (20 mL) was stirred at RT for overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(4-(3-((4-(methylamino)-5-(trifluoromethyl)pyrimidin-2-yl)amino)pyrrolidine-1-carbonyl)phenyl)acrylamide (235.6 mg, 46%) as a white solid. $^1$H NMR (400 MHz, DMSO-$d_6$): δ 1.91-2.14 (m, 2H), 2.68-2.88 (m, 3H), 3.38-3.42 (m, 1H), 3.53 (s, 1H), 3.63 (d, J=6.8 Hz, 1H), 3.78-3.87 (m, 1H), 4.31 (s, 0.5H), 4.48 (m, 0.5H), 5.79 (d, J=10.0 Hz, 1H), 6.26 (s, 0.5H), 6.31 (s, 0.5H), 6.42-6.49 (m, 1H), 6.83-6.92 (m, 1H), 7.49-7.74 (m, 5H), 7.98-8.07 (m, 1H), 10.31 (s, 1H). [M+H] Calc'd for $C_{25}H_{32}ClN_7O_3$, 435.2; Found, 435.2.

Example 121: Synthesis of (R,E)-N-(4-(3-((5-chloro-4-ethoxypyrimidin-2-yl)amino)pyrrolidine-1-carbonyl)benzyl)-4-(dimethylamino)but-2-enamide

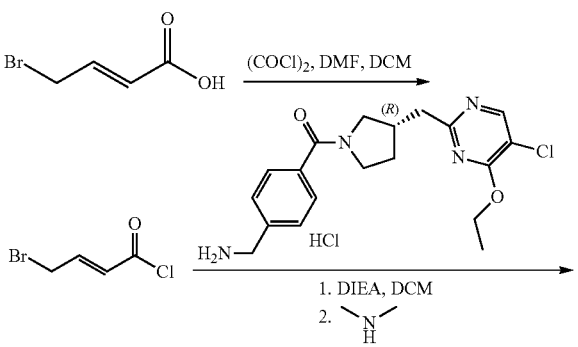

-continued

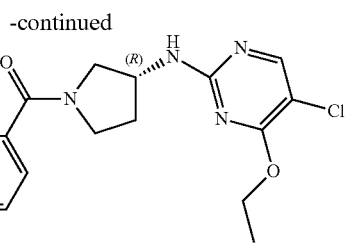

Step 1: (E)-4-bromobut-2-enoyl Chloride

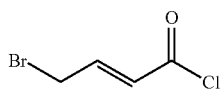

To a mixture of (E)-4-bromobut-2-enoic acid (400 mg, 2.42 mmol) and DMF (¼ drops) in DCM (10 mL) was added (COCl)$_2$ (611 mg, 4.85 mmol) at 0° C. The reaction mixture was stirred at RT overnight. The reaction mixture was concentrated in vacuo to afford (E)-4-bromobut-2-enoyl chloride (445 g, 100%) as yellow oil.

Step 2: (R,E)-N-(4-(3-((5-chloro-4-ethoxypyrimidin-2-yl)amino)pyrrolidine-1-carbonyl)benzyl)-4-(dimethylamino)but-2-enamide

To a mixture of (R)-(4-(aminomethyl)phenyl)(3-((5-chloro-4-ethoxypyrimidin-2-yl)amino)pyrrolidin-1-yl)methanone HCl salt (400 mg, 0.97 mmol) and DIEA (502 mg, 3.89 mmol) in DCM (15 mL) was added (E)-4-bromobut-2-enoyl chloride (400 mg, 2.42 mmol) at 0° C. The reaction mixture was stirred at for 2 h and dimethylamine (0.98 mL, 1.95 mmol) was added. The reaction mixture was stirred at RT overnight, The mixture was diluted with water (10 mL) and extracted with DCM (10 mL*3). The combined organic layer was washed with brine (20 mL), dried over Na$_2$SO$_4$, filtered and concentrated in vacuo. The residue was purified by prep-HPLC to afford (R,E)-N-(4-(3-((5-chloro-4-ethoxypyrimidin-2-yl)amino)pyrrolidine-1-carbonyl)benzyl)-4-(dimethylamino)but-2-enamide (34.5 mg, 7%) as a yellow solid. $^1$H NMR (400 MHz, DMSO-d$_6$): δ 1.18-1336 (m, 3H), 1.87-2.00 (m, 2H), 2.14 (s, 6H), 2.97-3.00 (m, 2H), 3.41-3.59 (m, 3H), 3.74-3.79 (m, 1H), 4.23-4.42 (m, 5H), 6.07-6.12 (m, 1H), 6.57-6.64 (m, 1H), 7.27-7.32 (m, 2H), 7.45-7.50 (m, 2H), 7.64 (br s, 1H), 8.07-8.13 (m, 1H), 8.51-8.56 (m, 1H). [M+H] Calc'd for C$_{24}$H$_{31}$ClN$_6$O$_3$, 487.2; Found, 487.2.

Example 122: Synthesis of (R,E)-N-(4-(3-((5-chloropyrimidin-2-yl)amino)pyrrolidine-1-carbonyl)benzyl)-4-(dimethylamino)but-2-enamide

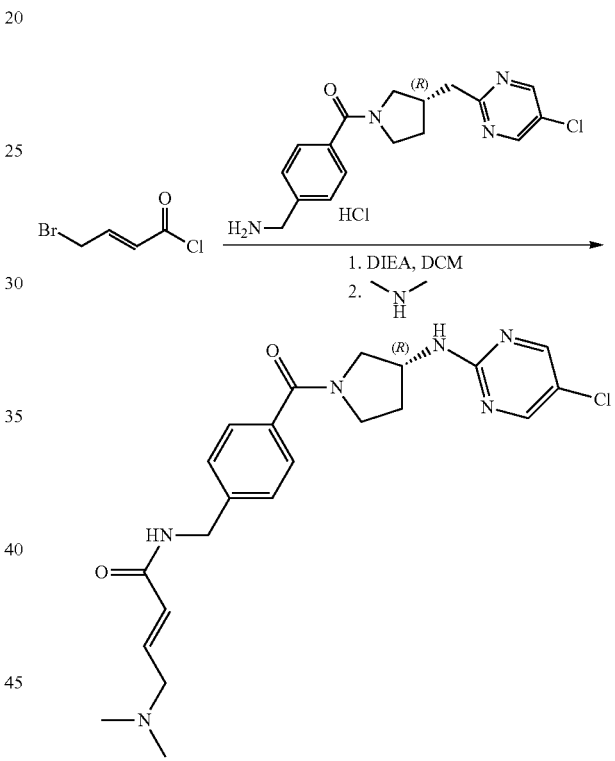

To a mixture of (R)-(4-(aminomethyl)phenyl)(3-((5-chloropyrimidin-2-yl)amino)pyrrolidin-1-yl)methanone HCl salt (350 mg, 0.820 mmol) and DIEA (529 mg, 4.10 mmol) in DCM (10 mL) was added (E)-4-bromobut-2-enoyl chloride (180 mg, 0.984 mmol) at 0° C. The reaction mixture was stirred at for 2 h and dimethylamine (0.84 mL, 1.64 mmol) was added. The reaction mixture was stirred at RT for overnight, The mixture was diluted with water (10 mL) and extracted with DCM (10 mL*3). The combined organic layer was washed with brine (20 mL), dried over Na$_2$SO$_4$, filtered and concentrated in-vacuo. The residue was purified by prep-HPLC to afford (R,E)-N-(4-(3-((5-chloropyrimidin-2-yl)amino)pyrrolidine-1-carbonyl)benzyl)-4-(dimethylamino)but-2-enamide (18.3 mg, 5%) as a yellow solid (TFA salt). $^1$H NMR (400 MHz, CD$_3$OD): δ 1.97-2.35 (m, 2H), 2.90 (s, 6H), 3.37-3.41 (m, 1H), 3.52-3.72 (m, 2H), 3.78-3.85 (m, 1H), 3.90-3.94 (m, 2H), 4.36-4.55 (m, 3H), 6.38-6.43 (m, 1H), 6.70-6.79 (m, 1H), 7.36-7.41 (m, 2H), 7.47-

7.54 (m, 2H), 8.20 (s, 1H), 8.28 (s, 1H). [M+H] Calc'd for $C_{22}H_{27}ClN_6O_2$, 443.2; Found, 443.2.

Example 123: (R)—N-(4-(3-((5-chloro-4-(2-ethoxyethoxy)pyrimidin-2-yl)amino)pyrrolidine-1-carbonyl)-2-(4-methylpiperazin-1-yl)phenyl)acrylamide

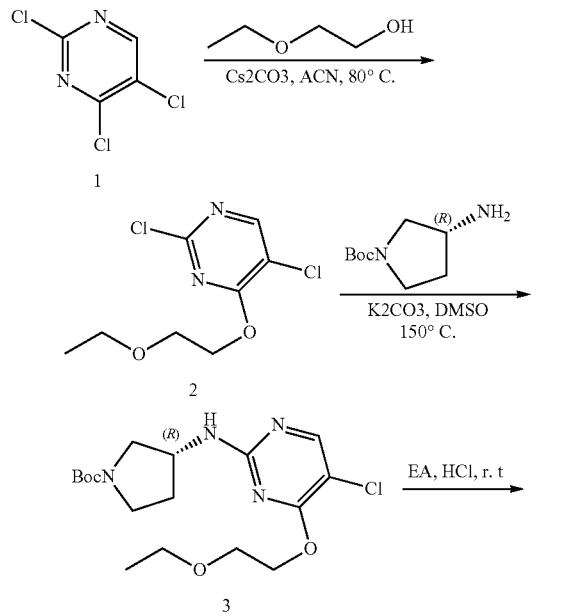

Step 1: 2,5-dichloro-4-(2-ethoxyethoxy)pyrimidine

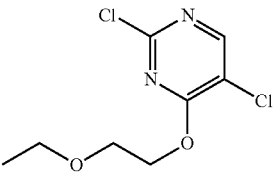

To a solution of 2,4,5-trichloropyrimidine (2.5 g, 13.7 mmol) and 2-ethoxyethanol (1.1 g, 12.3 mmol) in ACN (40 mL) was added $Cs_2CO_3$ (6.6 g, 20.5 mmol) at RT. The mixture was stirred at 80° C. for 4 h. The mixture was cooled, diluted with water (200 mL) and extracted with EA (100 mL*2). The combined organic layer was washed with brine (100 mL), dried over $Na_2SO_4$ and concentrated. The residue was purified by column chromatography to afford 1.8 g crude product as off white solid. [M+H] Calc'd for $C_8H_{10}Cl_2N_2O_2$, 237.1; Found, 237.1.

Step 2: (R)-tert-butyl 3-((5-chloro-4-(2-ethoxyethoxy)pyrimidin-2-yl)amino)pyrrolidine-1-carboxylate

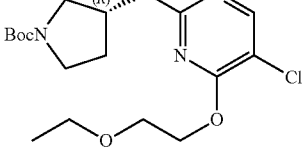

To a solution of 2,5-dichloro-4-(2-ethoxyethoxy)pyrimidine (1.8 g, 7.6 mmol) and (R)-tert-butyl 3-aminopyrrolidine-1-carboxylate (2.8 g, 15.3 mmol) in DMSO (25 mL) was added $K_2CO_3$ (2.1 g, 15.3 mmol). The reaction mixture was stirred at 150° C. for 4 h. The reaction mixture was cooled, added water (50 mL) and extracted with EA (50 mL*2). The combined organic layer was washed with brine (100 mL), dried over $Na_2SO_4$, filtered and concentrated. The residue was purified by column chromatography to afford 1.8 g of product as colorless oil. [M+H] Calc'd for $C_{17}H_{27}ClN_4O_4$, 387.1; Found, 387.1.

Step 3: (R)-5-chloro-4-(2-ethoxyethoxy)-N-(pyrrolidin-3-yl)pyrimidin-2-amine

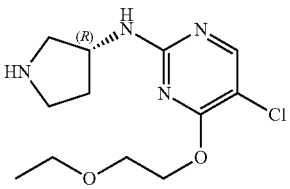

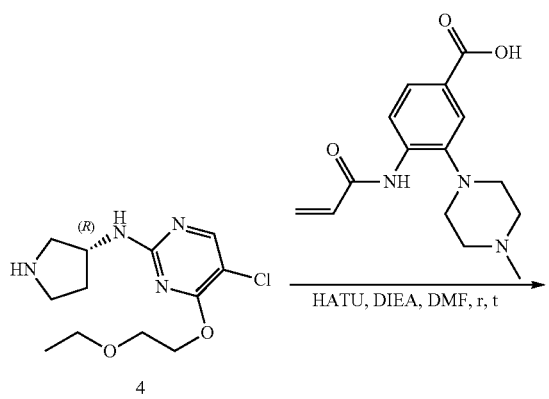

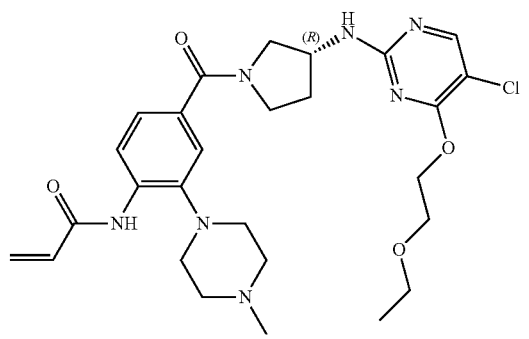

To a solution of (R)-tert-butyl 3-((5-chloro-4-(2-ethoxyethoxy)pyrimidin-2-yl)amino)pyrrolidine-1-carboxylate (1.8 g, 4.7 mmol) in EA (20 mL) was added HCl(gas) at −50° C. The reaction mixture was stirred at rt for 3 h. The reaction mixture was concentrated to afford 1.5 g of product as a yellow solid. [M+H] Calc'd for $C_{12}H_{19}ClN_4O_2$, 287.1; Found, 287.1.

Step 4: (R)—N-(4-(3-((5-chloro-4-(2-ethoxyethoxy)pyrimidin-2-yl)amino)pyrrolidine-1-carbonyl)-2-(4-methylpiperazin-1-yl)phenyl)acrylamide

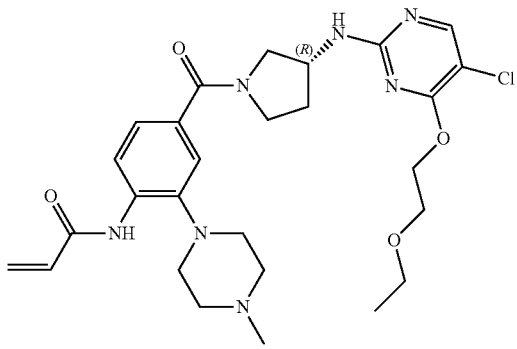

To a solution of (R)-5-chloro-4-(2-ethoxyethoxy)-N-(pyrrolidin-3-yl)pyrimidin-2-amine (200 mg, 0.69 mmol) and 4-acrylamido-3-(4-methylpiperazin-1-yl)benzoic acid (197 mg, 0.69 mmol) in DMF (5 ml) was added HATU (315 mg, 0.83 mmol) and DIEA (267 mg, 2.07 mmol). The reaction mixture was stirred at rt for 2 h. The reaction mixture was concentrated. The residue was purified by prep-HPLC to afford (R)—N-(4-(3-((5-chloro-4-(2-ethoxyethoxy)pyrimidin-2-yl)amino)pyrrolidine-1-carbonyl)-2-(4-methylpiperazin-1-yl)phenyl)acrylamide (11.7 mg, 4%) as a white solid. $^1$H NMR (400 MHz, DMSO-$d_6$): 1.10-1.11 (m, 3H), 1.90-2.12 (m, 2H), 2.24 (s, 2H), 2.77-2.83 (m, 4H), 3.41-3.72 (m, 12H), 4.24-4.47 (m, 3H), 5.77-5.79 (d, J=10.0 Hz, 1H), 6.23 (s, 0.5H), 6.26 (s, 0.5H), 6.60-6.65 (m, 1H), 7.24-7.26 (m, 2H), 7.66 (s, 1H), 8.03-8.15 (m, 2H), 9.05-9.11 (m, 1H); [M+H] Calc'd for $C_{27}H_{36}ClN_7O_4$, 558.2; Found, 558.2.

Example 124: Synthesis of (R)—N-(4-(3-((5-chloro-4-methoxypyrimidin-2-yl)amino)pyrrolidine-1-carbonyl)phenyl)propiolamide

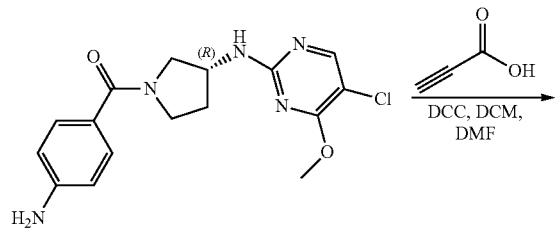

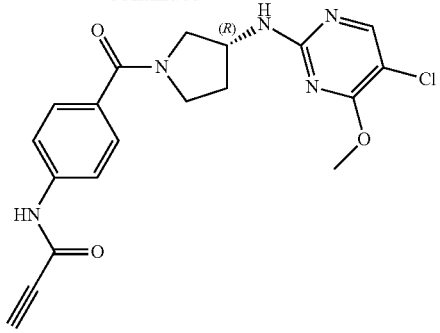

To a solution of propiolic acid (39 mg, 0.56 mmol) in DCM (3 mL) was added DCC (116 mg, 0.56 mmol) slowly at 0° C. under $N_2$. The reaction mixture was stirred at 0° C. for 1 h. Then a solution of (R)-(4-aminophenyl)(3-((5-chloro-4-methoxypyrimidin-2-yl)amino)pyrrolidin-1-yl)methanone (163 mg, 0.47 mmol) in DMF (2 mL) was slowly added. The solution was stirred at 0° C. for 90 minutes. Then the reaction mixture was allowed to warm to RT and stirred for overnight. The solution was diluted with EtOAc and washed with water (3 times). The organic phase was concentrated and the residue was purified by prep-HPLC to afford (R)-(4-aminophenyl)(3-((5-chloro-4-methoxypyrimidin-2-yl)amino)pyrrolidin-1-yl)methanone (45.5 mg, 24%) as a light yellow solid. $^1$H NMR (400 MHz, CDCl$_3$): 1.95-2.06 (m, 1H), 2.19-2.40 (m, 1H), 2.96 (s, 1H), 3.35-3.44 (m, 0.5H), 3.54-3.70 (m, 1.5H), 3.74-4.07 (m, 5H), 4.40-4.60 (m, 1H), 5.06-5.30 (m, 1H), 7.46-7.60 (m, 4H), 7.93-8.09 (m, 2H). [M+H] Calc'd for $C_{19}H_{18}ClN_5O_3$, 400.1; Found, 400.1.

Example 125: Synthesis of (R)—N-(4-(3-((5-chloropyrimidin-2-yl)amino)pyrrolidine-1-carbonyl)phenyl)propiolamide

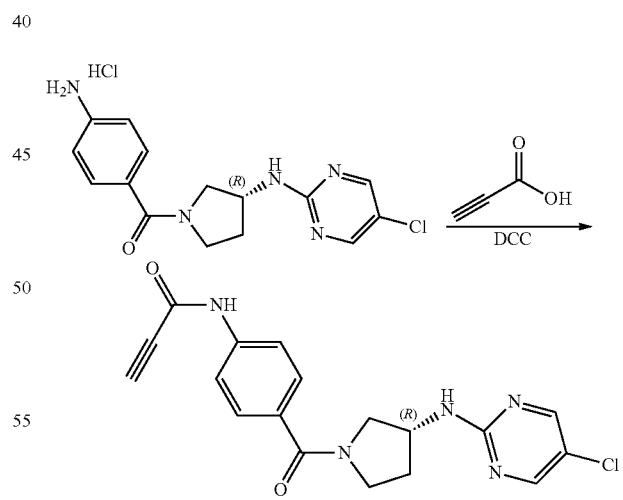

To a solution of DCC (167 mg, 0.81 mmol) in DCM (2.5 mL) was added propiolic acid (57 mg, 0.81 mmol) at 0° C. under $N_2$. The mixture was stirred at 0° C. for 1 hour. Then a solution of (R)-(4-aminophenyl)(3-((5-chloropyrimidin-2-yl)amino)pyrrolidin-1-yl)methanone (235 mg, 0.74 mmol) in DCM (0.5 mL) was added to the reaction mixture. The solution was stirred at 0° C. to RT for 16 hours. The solution was diluted with DCM (60 mL), washed with water (20*3 mL) and brine (20 mL), dried over Na$_2$SO$_4$ filtered and concentrated. The residue was purified by flash chromatography on silica gel (DCM/MeOH=50/1) to afford (169 mg, 62%) as a yellow solid. $^1$H NMR (400 MHz, CDCl$_3$): δ 1.97-2.01 (m, 1H), 2.23-2.38 (m, 1H), 2.95 (s, 1H), 3.35-3.39 (m, 0.5H), 3.58-3.64 (m, 1H), 3.74-3.88 (m, 2H), 3.99-4.03 (m, 0.5H), 4.42-4.58 (m, 1H), 5.37-5.49 (m, 1H), 7.47-7.57 (m, 4H), 8.18 (s, 1H), 8.25 (s, 1H), 8.48 (s, 0.5H), 8.51 (s, 0.5H). [M+H]Calc'd for C$_{18}$H$_{16}$ClN$_5$O$_2$, 370.0; Found, 370.0

Example 126: Synthesis of (R)-1-(4-(3-((5-chloro-4-(trideuteromethoxy)pyrimidin-2-yl)amino)pyrrolidine-1-carbonyl)phenyl)pyrrolidine-2,5-dione

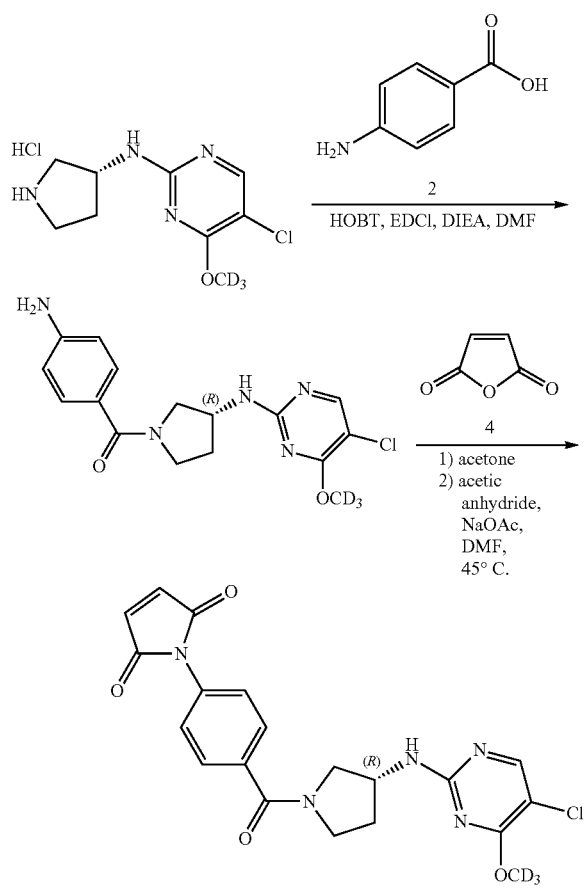

Step 1: (R)-(4-aminophenyl)(3-((5-chloro-4-(trideuteromethoxy)pyrimidin-2-yl)amino)pyrrolidin-1-yl)methanone To a solution of (R)-5-chloro-N-(pyrrolidin-3-yl)-4-(trideuteromethoxy)pyrimidin-2-amine hydrochloride (400 mg, 1.49 mmol) and 4-aminobenzoic acid (205 mg, 1.49 mmol) in DMF (6 mL) was added HOBT (349 mg, 2.24 mmol), EDCI (429 mg, 2.24 mmol) and DIEA (577 mg, 4.47 mmol) in an ice-bath. The mixture was then stirred at RT for 3 hours. After completion of the reaction, the mixture was diluted with water (20 mL) and the mixture was extracted with EA (20 mL*2). The combined organic layer was washed with brine, dried over anhydrous sodium sulfate, filtered and concentrated under reduced pressure. The residue was purified by C18 reversed phase chromatography (20-95% ACN in H$_2$O) to afford (R)-(4-aminophenyl)(3-((5-chloro-4-(trideuteromethoxy)pyrimidin-2-yl)amino)pyrrolidin-1-yl)methanone (3) (310 mg, 59% yield) as a white solid. [M+H] Calc'd: C$_{16}$H$_{15}$D$_3$ClN$_5$O$_2$, 351.1; Found: 351.1.

Step 2: (R)-1-(4-(3-((5-chloro-4-(trideuteromethoxy)pyrimidin-2-yl)amino)pyrrolidine-1-carbonyl)phenyl)pyrrolidine-2,5-dione

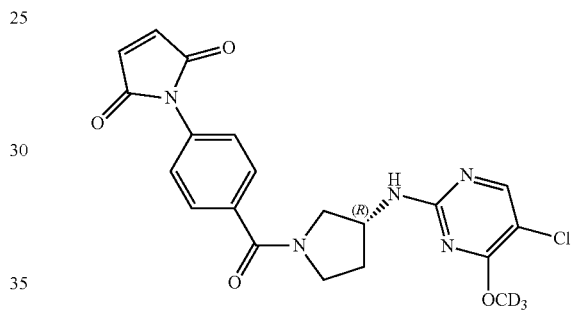

To a solution of furan-2,5-dione (32 mg, 0.32 mmol) in acetone (2 mL) was added (R)-(4-aminophenyl)(3-((5-chloro-4-(trideuteromethoxy)pyrimidin-2-yl)amino)pyrrolidin-1-yl)methanone (75 mg, 0.21 mmol). The mixture was stirred at 0° C. for 20 min. Then the reaction mixture was concentrated under reduced pressure. The residue was dissolved in 2 mL of DMF and heated to 45° C. Acetic anhydride (0.2 mL) and NaOAc (3 mg, 0.04 mmol) were then added with stirring. The mixture was stirred at 45° C. for 2 hours. After completion of the reaction, the mixture was diluted with water and the mixture was extracted with DCM (50 mL×2). The combined organic layer was washed with brine, dried over anhydrous sodium sulfate, filtered, and concentrated under reduced pressure. The residue was purified by column chromatography on silica gel (DCM/MeOH=80/1) to give the product (R)-1-(4-(3-((5-chloro-4-(trideuteromethoxy)pyrimidin-2-yl)amino)pyrrolidine-1-carbonyl)phenyl)pyrrolidine-2,5-dione (20 mg, 22% yield) as a white solid. $^1$H NMR (400 MHz, CDCl$_3$): 2.01-2.02 (m, 1H), 2.24-2.39 (m, 1H), 3.40-3.42 (m 0.5H), 3.59-3.90 (m, 3H), 4.02-4.07 (m, 0.5H), 4.46-4.57 (m, 1H), 5.10-5.22 (m, 1H), 6.88 (s, 2H), 7.42-7.47 (m, 2H), 7.61-7.66 (m, 2H), 7.97 (s, 0.5H), 8.04 (s, 0.5H). [M+H] Calc'd for C$_{20}$H$_{15}$D$_3$ClN$_5$O$_4$, 431.1; Found, 431.2.

Example 127: Synthesis of N-(4-((R)-3-((5-chloropyrimidin-2-yl)amino)pyrrolidine-1-carbonyl)-2-(3-(dimethylamino)pyrrolidin-1-yl)phenyl)acrylamide

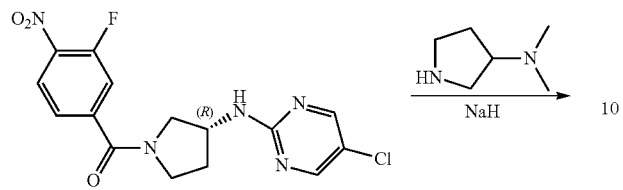

Step 1: ((R)-3-((5-chloropyrimidin-2-yl)amino)pyrrolidin-1-yl)(3-(3-(dimethylamino)pyrrolidin-1-yl)-4-nitrophenyl)methanone

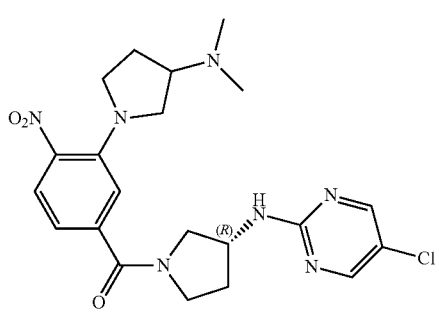

The title compound was prepared in 32% yield from (R)-(3-((5-chloropyrimidin-2-yl)amino)pyrrolidin-1-yl)(3-fluoro-4-nitrophenyl)methanone using general procedure of ((R)-3-((5-chloropyrimidin-2-yl)amino)pyrrolidin-1-yl)(4-nitro-3-((tetrahydrofuran-3-yl)oxy)phenyl)methanone. [M+H] Calc'd for $C_{21}H_{26}ClN_7O_3$, 460.1; Found, 460.1.

Step 2: (4-amino-3-(3-(dimethylamino)pyrrolidin-1-yl)phenyl)((R)-3-((5-chloropyrimidin-2-yl)amino)pyrrolidin-1-yl)methanone

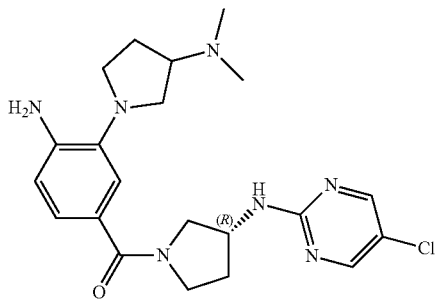

The title compound was prepared in 100% yield from ((R)-3-((5-chloropyrimidin-2-yl)amino)pyrrolidin-1-yl)(3-(3-(dimethylamino)pyrrolidin-1-yl)-4-nitrophenyl)methanone using general procedure of (4-amino-3-((tetrahydrofuran-3-yl)oxy)phenyl)((R)-3-((5-chloropyrimidin-2-yl)amino)pyrrolidin-1-yl)methanone. [M+H] Calc'd for $C_{21}H_{28}ClN_7O$, 430.2; Found, 430.2.

Step 3: N-(4-((R)-3-((5-chloropyrimidin-2-yl)amino)pyrrolidine-1-carbonyl)-2-(3-(dimethylamino)pyrrolidin-1-yl)phenyl)acrylamide

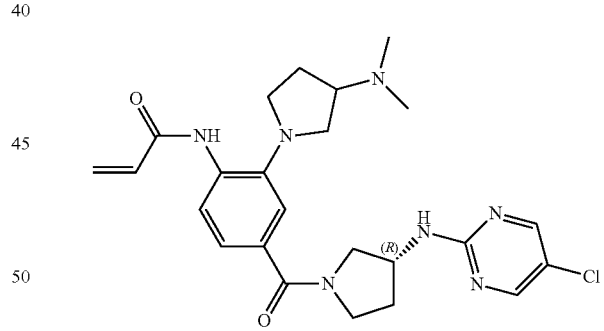

The title compound was prepared in 30% yield from (4-amino-3-(3-(dimethylamino)pyrrolidin-1-yl)phenyl)((R)-3-((5-chloropyrimidin-2-yl)amino)pyrrolidin-1-yl)methanone using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-$d_6$): δ 1.69-1.74 (m, 1H), 1.85-2.00 (m, 1H), 2.02-2.08 (m, 2H), 2.14 (s, 3H), 2.15 (s, 3H), 2.64-2.70 (m, 1H), 3.08-3.77 (m, 8H), 4.23-4.42 (m, 1H), 5.72 (d, J=10.0 Hz, 1H), 6.22 (d, J=16.8 Hz, 1H), 6.48-6.54 (m, 1H), 6.87-6.95 (m, 2H), 7.31-7.37 (m, 1H), 7.80-7.83 (m, 1H), 8.32 (s, 1H), 8.38 (s, 1H), 9.48 (br s, 1H). [M+H] Calc'd for $C_{24}H_{30}ClN_7O_2$, 484.2; Found, 484.2.

Example 128: Synthesis of (R)-1-(3-(3-((5-chloro-4-(trideuteriomethoxy)pyrimidin-2-yl)amino)pyrrolidine-1-carbonyl)phenyl)-1H-pyrrole-2,5-dione

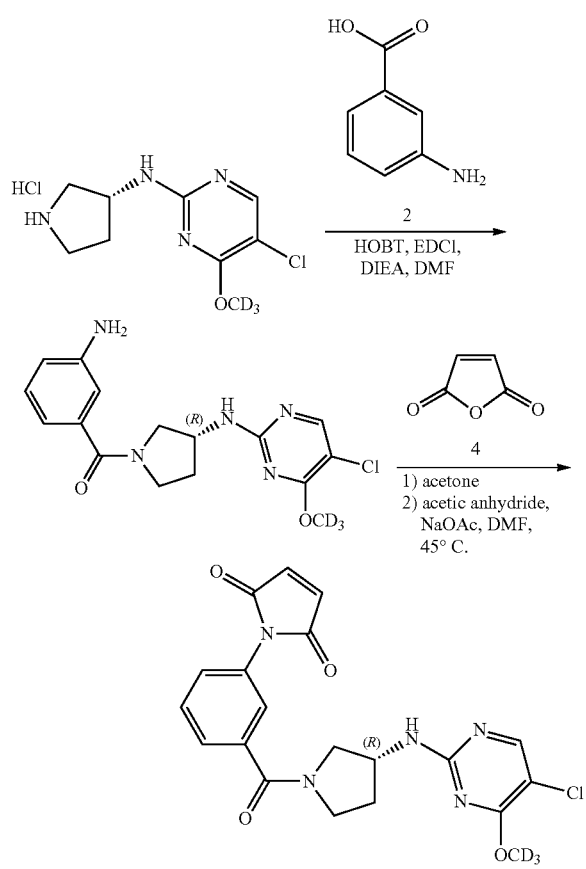

Step 1: (R)-(3-aminophenyl)(3-((5-chloro-4-(trideuteromethoxy)pyrimidin-2-yl)amino)pyrrolidin-1-yl) methanone

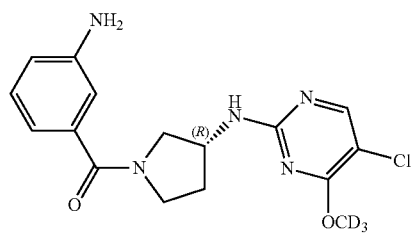

To a solution of (R)-5-chloro-N-(pyrrolidin-3-yl)-4-(trideuteromethoxy)pyrimidin-2-amine hydrochloride (170 mg, 0.63 mmol) and 3-aminobenzoic acid (87 mg, 0.63 mmol) in DMF (4 mL) was added HOBT (147 mg, 0.95 mmol), EDCI (182 mg, 0.95 mmol) and DIEA (244 mg, 1.89 mmol). The mixture was stirred at rt for 3 hours. After completion of the reaction, the mixture was diluted with water (20 mL) and the mixture was extracted with EA (20 mL*2). The combined organic layer was washed with brine, dried over anhydrous sodium sulfate, filtered, and concentrated under reduced pressure. The residue was purified by C18 reversed phase chromatography (20-95% ACN in H$_2$O) to give the product (R)-(3-aminophenyl)(3-((5-chloro-4-(trideuteriomethoxy) pyrimidin-2-yl)amino)pyrrolidin-1-yl)methanone (105 mg, 48% yield) as a pale yellow solid. [M+H] Calc'd: $C_{16}H_{15}D_3ClN_5O_2$, 351.1; Found: 351.1.

Step 2: (R)-1-(3-(3-((5-chloro-4-(trideuteromethoxy) pyrimidin-2-yl)amino)pyrrolidine-1-carbonyl)phenyl)-1H-pyrrole-2,5-dione

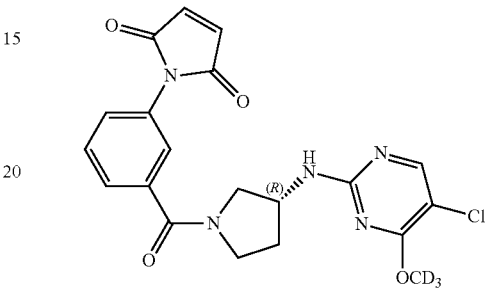

To a solution of furan-2,5-dione (44 mg, 0.45 mmol) in acetone (2 mL) was added (R)-(3-aminophenyl)(3-((5-chloro-4-(trideuteriomethoxy)pyrimidin-2-yl)amino)pyrrolidin-1-yl)methanone (105 mg, 0.3 mmol). The mixture was stirred at 0° C. for 20 min. The reaction mixture was concentrated under reduced pressure. The residue was dissolved in 2 mL of DMF and heated to 45° C. Acetic anhydride (0.2 mL) and NaOAc (5 mg, 0.06 mmol) were then added with stirring. The mixture was stirred at 45° C. for 2 hours. After completion of the reaction, the mixture was diluted with water and extracted with DCM (100 mL*2). The combined organic layer was washed with brine, dried over anhydrous sodium sulfate, filtered and concentrated under reduced pressure. The residue was purified by column chromatography on silica gel (DCM/MeOH=50/1) to afford (R)-1-(3-(3-((5-chloro-4-(trideuteromethoxy)pyrimidin-2-yl)amino)pyrrolidine-1-carbonyl)phenyl)-1H-pyrrole-2,5-dione (80 mg, 62% yield) as pale yellow solid. $^1$H NMR (400 MHz, CDCl$_3$): 1.97-2.05 (m, 1H), 2.25-2.38 (m, 1H), 3.46 (dd, J=10.8 Hz, 5.2 Hz, 0.5H), 3.93-3.60 (m, 3H), 4.04 (dd, J=13.2 Hz, 6.4 Hz, 0.5H), 4.45-4.58 (m, 1H), 5.13-5.22 (m, 1H), 6.87 (d, J=4.8 Hz, 2H), 7.45-7.58 (m, 4H), 7.97 (s, 0.5H), 8.03 (s, 0.5H). [M+H] Calc'd for $C_{20}H_{15}D_3ClN_5O_4$, 431.1; Found, 431.2.

Example 129: Synthesis of (R,E)-1-(8-(3-((5-chloropyrimidin-2-yl)amino)pyrrolidine-1-carbonyl)-2H-benzo[b][1,4]oxazin-4(3H)-yl)-4-(dimethylamino) but-2-en-1-one

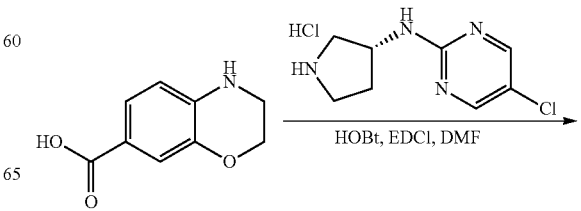

361
-continued

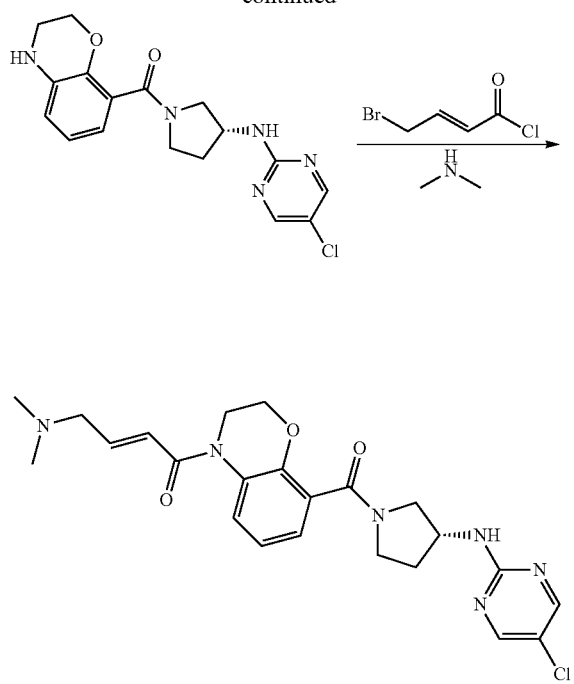

Step 1: (R)-(3-((5-chloropyrimidin-2-yl)amino)pyrrolidin-1-yl)(3,4-dihydro-2H-benzo[b][1,4]oxazin-8-yl)methanone

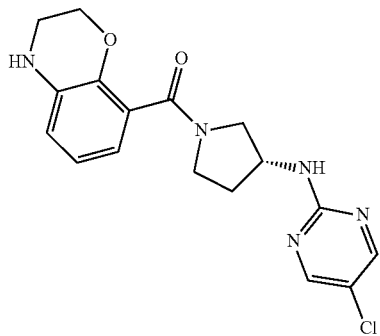 [SMILES: O=C(c1cccc2c1OCCN2)N1CC[C@@H](Nc2ncc(Cl)cn2)C1]

A mixture of 3,4-dihydro-2H-benzo[b][1,4]oxazine-7-carboxylic acid (200 mg, 1.1 mmol), (R)-5-chloro-N-(pyrrolidin-3-yl)pyrimidin-2-amine hydrochloride (258 mg, 1.1 mmol), HOBt (223 mg, 1.7 mmol), EDCI (316 mg, 1.7 mmol) and DIEA (426 mg, 3.3 mmol) in DMF (5 mL) was stirred at RT for 5 hours. The mixture was poured into water (30 mL) and extracted with EtOAc (20 mL*3). The combined organic phase was concentrated and the residue was purified by prep-HPLC to afford (R)-(3-((5-chloropyrimidin-2-yl)amino)pyrrolidin-1-yl)(3,4-dihydro-2H-benzo[b][1,4]oxazin-8-yl)methanone (400 mg, 80%) as a red solid. [M+H] Calc'd for $C_{17}H_{18}ClN_5O_2$, 360.1; Found, 360.1.

362

Step 2: (R,E)-1-(8-(3-((5-chloropyrimidin-2-yl)amino)pyrrolidine-1-carbonyl)-2H-benzo[b][1,4]oxazin-4(3H)-yl)-4-(dimethylamino)but-2-en-1-one

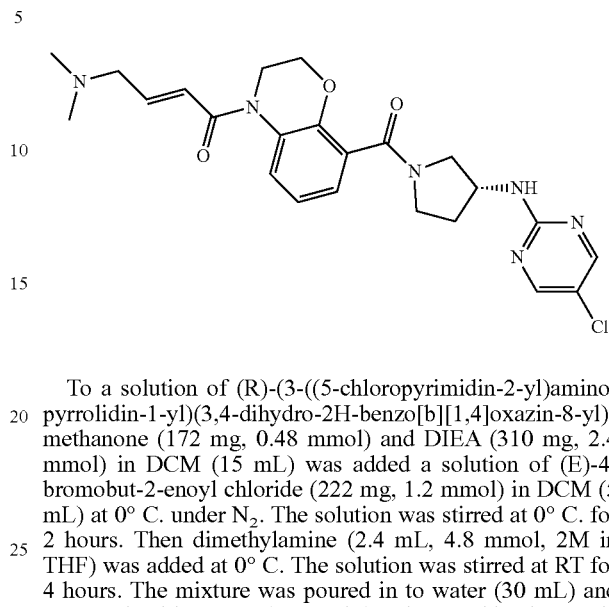

To a solution of (R)-(3-((5-chloropyrimidin-2-yl)amino)pyrrolidin-1-yl)(3,4-dihydro-2H-benzo[b][1,4]oxazin-8-yl)methanone (172 mg, 0.48 mmol) and DIEA (310 mg, 2.4 mmol) in DCM (15 mL) was added a solution of (E)-4-bromobut-2-enoyl chloride (222 mg, 1.2 mmol) in DCM (5 mL) at 0° C. under $N_2$. The solution was stirred at 0° C. for 2 hours. Then dimethylamine (2.4 mL, 4.8 mmol, 2M in THF) was added at 0° C. The solution was stirred at RT for 4 hours. The mixture was poured in to water (30 mL) and extracted with DCM (20 mL*3). The combined organic phase was concentrated and the residue was purified by prep-HPLC to afford (R,E)-1-(8-(3-((5-chloropyrimidin-2-yl)amino)pyrrolidine-1-carbonyl)-2H-benzo[b][1,4]oxazin-4(3H)-yl)-4-(dimethylamino)but-2-en-1-one (44 mg, 19%) as a yellow solid. $^1$H NMR (400 MHz, DMSO-$d_6$): δ 1.86-2.03 (m, 1H), 2.13-2.19 (m, 7H), 3.08-3.40 (m, 2H), 3.40-3.47 (m, 1H), 3.51-3.57 (m, 1H), 3.65-3.71 (m, 1H), 3.74-3.82 (m, 1H), 3.95-3.97 (m, 2H), 4.27-4.46 (m, 3H), 6.57-6.63 (m, 1H), 6.77-6.83 (m, 1H), 7.06-7.10 (m, 2H), 7.52 (br s, 1H), 7.86 (d, J=7.2 Hz, 1H), 8.36 (s, 1H), 8.42 (s, 1H). [M+H] Calc'd for $C_{23}H_{27}ClN_6O_3$, 471.1; Found, 471.1.

Example 130: Synthesis of (R)-1-(7-(3-((5-chloropyrimidin-2-yl)amino)pyrrolidine-1-carbonyl)-3,4-dihydroisoquinolin-2(1H)-yl)prop-2-en-1-one

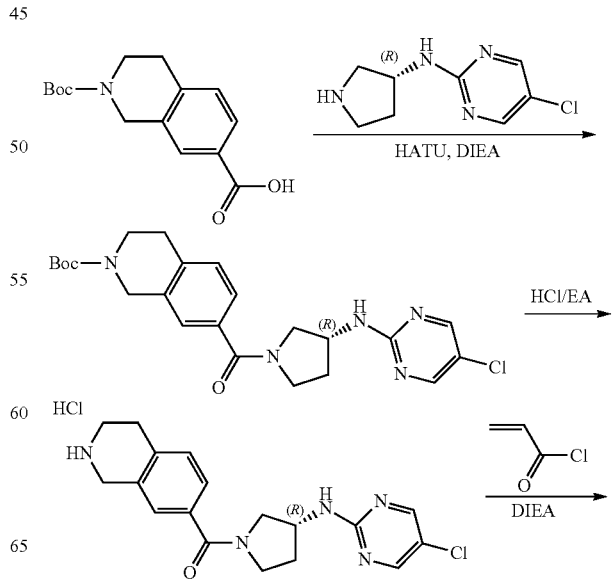

-continued

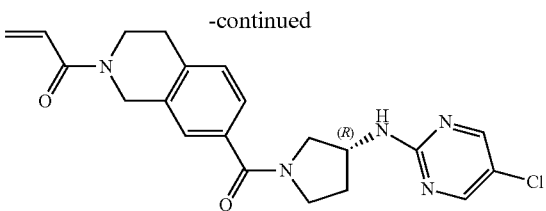

Step 1: (R)-tert-butyl 7-(3-((5-chloropyrimidin-2-yl)amino)pyrrolidine-1-carbonyl)-3,4-dihydroisoquinoline-2(1H)-carboxylate

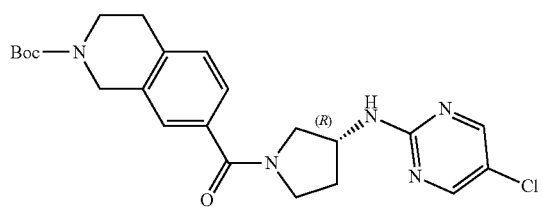

The title compound was prepared in 91% yield from 2-(tert-butoxycarbonyl)-1,2,3,4-tetrahydroisoquinoline-7-carboxylic acid using general procedure of (R)—N-(4-(3-((5-chloro-4-methylpyrimidin-2-yl)amino)pyrrolidine-1-carbonyl)phenyl)acrylamide. [M+H] Calc'd for $C_{23}H_{28}ClN_5O_3$, 458.1; Found, 458.1.

Step 2: (R)-(3-((5-chloropyrimidin-2-yl)amino)pyrrolidin-1-yl)(1,2,3,4-tetrahydroisoquinolin-7-yl)methanone hydrochloride

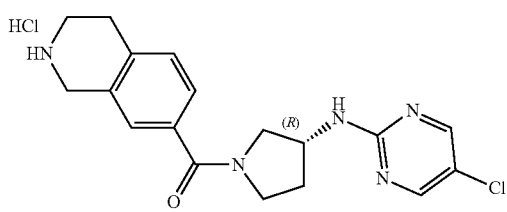

The title compound was prepared in 100% yield from (R)-tert-butyl 7-(3-((5-chloropyrimidin-2-yl)amino)pyrrolidine-1-carbonyl)-3,4-dihydroisoquinoline-2(1H)-carboxylate using general procedure of (R)-5-chloro-4-methyl-N-(pyrrolidin-3-yl)pyridin-2-amine hydrochloride [M+H] Calc'd for $C_{18}H_{20}ClN_5O$, 358.1; Found, 358.1.

Step 3: (R)-1-(7-(3-((5-chloropyrimidin-2-yl)amino)pyrrolidine-1-carbonyl)-3,4-dihydroisoquinolin-2(1H)-yl)prop-2-en-1-one

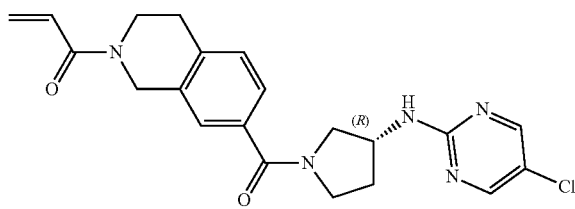

The title compound was prepared in 37% yield from (R)-(3-((5-chloropyrimidin-2-yl)amino)pyrrolidin-1-yl)(1,2,3,4-tetrahydroisoquinolin-7-yl)methanone hydrochloride using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-$d_6$): δ 1.83-2.02 (m, 1H), 2.08-2.20 (m, 1H), 2.76-2.93 (m, 2H), 3.41-3.86 (m, 6H), 4.22-4.44 (m, 1H), 4.61-4.85 (m, 2H), 5.71 (d, J=10.4 Hz, 1H), 6.10-6.17 (m, 1H), 6.84-6.93 (m, 1H), 7.18-7.25 (m, 1H), 7.29-7.41 (m, 2H), 7.80 (br s, 1H), 8.31 (s, 1H), 8.38 (s, 1H). [M+H] Calc'd for $C_{21}H_{22}ClN_5O_2$, 412.1; Found, 412.1.

Example 131: Synthesis of (R,E)-N-(4-(3-((5-chloropyrimidin-2-yl)amino)pyrrolidine-1-carbonyl)phenyl)but-2-enamide

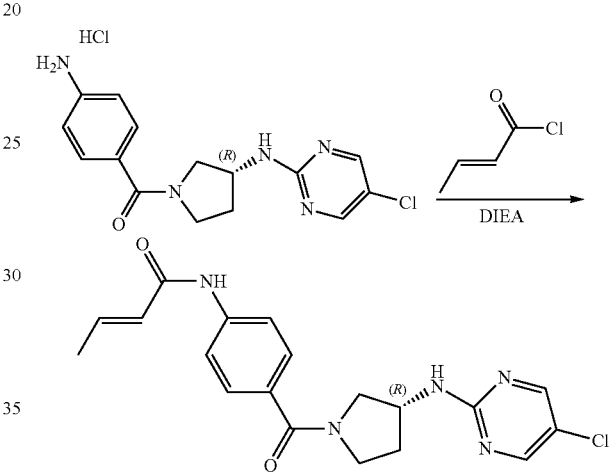

The title compound was prepared in 28% yield from (R)-(4-aminophenyl)(3-((5-chloropyrimidin-2-yl)amino)pyrrolidin-1-yl)methanone hydrochloride using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-$d_6$): δ 1.83-2.00 (m, 1H), 2.07-2.18 (m, 1H), 3.14 (d, J=6.4 Hz, 2H), 3.40-3.78 (m, 4H), 4.23-4.40 (m, 1H), 5.12-5.20 (m, 2H), 5.90-5.99 (m, 1H), 7.45-7.50 (m, 2H), 7.59-7.64 (m, 2H), 7.80 (br s, 1H), 8.31 (s, 1H), 8.38 (s, 1H), 10.11 (s, 1H). [M+H]Calc'd for $C_{19}H_{20}ClN_5O_2$, 386.1; Found, 386.1.

Example 132: Synthesis of (R)-1-(6-(3-((5-chloropyrimidin-2-yl)amino)pyrrolidine-1-carbonyl)-3,4-dihydroisoquinolin-2(1H)-yl)prop-2-en-1-one

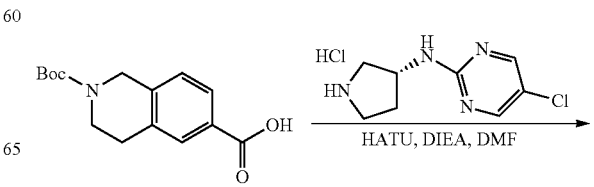

-continued

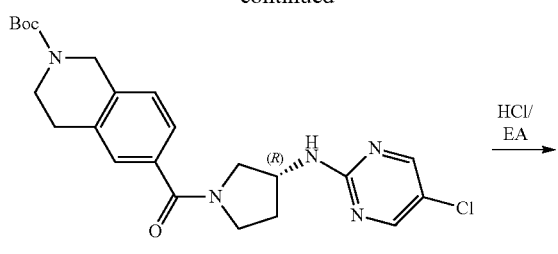

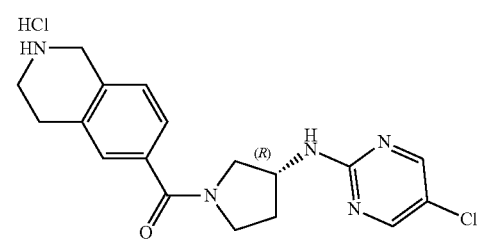

Step 2: (R)-(3-((5-chloropyrimidin-2-yl)amino)pyrrolidin-1-yl)(1,2,3,4-tetrahydroisoquinolin-6-yl)methanone hydrochloride The title compound was prepared in 100% yield from (R)-tert-butyl 7-(3-((5-chloropyrimidin-2-yl)amino)pyrrolidine-1-carbonyl)-3,4-dihydroisoquinoline-2(1H)-carboxylate using general procedure of (R)-5-chloro-4-methyl-N-(pyrrolidin-3-yl)pyridin-2-amine hydrochloride [M+H] Calc'd for $C_{18}H_{20}ClN_5O$, 358.1; Found, 358.1.

Step 3: (R)-1-(6-(3-((5-chloropyrimidin-2-yl)amino)pyrrolidine-1-carbonyl)-3,4-dihydroisoquinolin-2(1H)-yl)prop-2-en-1-one

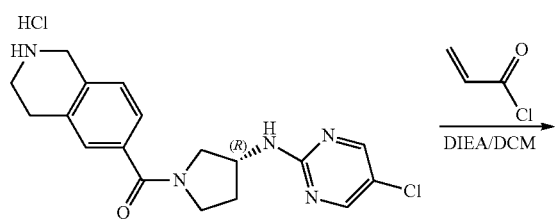

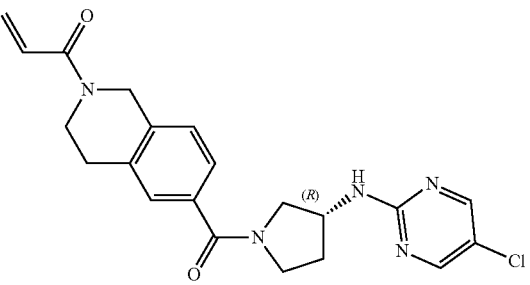

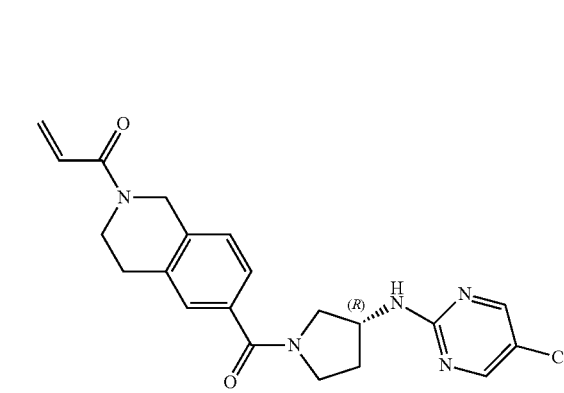

Step 1: (R)-tert-butyl 6-(3-((5-chloropyrimidin-2-yl)amino)pyrrolidine-1-carbonyl)-3,4-dihydroisoquinoline-2(1H)-carboxylate The title compound was prepared in 41% yield from (R)-(3-((5-chloropyrimidin-2-yl)amino)pyrrolidin-1-yl)(1,2,3,4-tetrahydroisoquinolin-6-yl)methanone hydrochloride using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-$d_6$): δ 1.83-2.02 (m, 2H), 2.08-2.20 (m, 2H), 2.81-2.87 (m, 3H), 3.63-3.80 (m, 3H), 4.23-4.42 (m, 1H), 4.68-4.81 (m, 2H), 5.72 (d, J=10.4 Hz, 1H), 6.15 (d, J=16.4 Hz, 1H), 6.84-6.92 (m, 1H), 7.21-7.34 (m, 3H), 7.78-7.82 (m, 1H), 8.31 (s, 1H), 8.38 (s, 1H). [M+H] Calc'd for $C_{21}H_{22}ClN_5O_2$, 412.1; Found, 412.1.

Example 133: Synthesis of (R)—N-(4-(3-((5-chloropyrimidin-2-yl)amino)pyrrolidine-1-carbonyl)phenyl)-2-cyanoacetamide

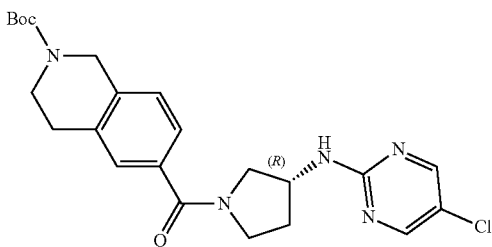

The title compound was prepared in 75% yield from 2-(tert-butoxycarbonyl)-1,2,3,4-tetrahydroisoquinoline-6-carboxylic acid using general procedure of (R)—N-(4-(3-((5-chloro-4-methylpyrimidin-2-yl)amino)pyrrolidine-1-carbonyl)phenyl)acrylamide. [M+H] Calc'd for $C_{23}H_{28}ClN_5O_3$, 458.1; Found, 458.1.

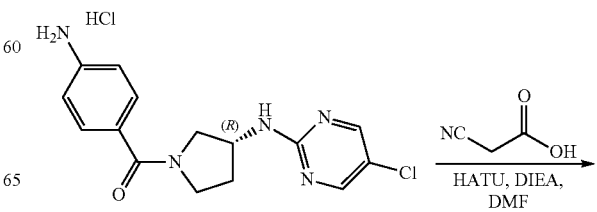

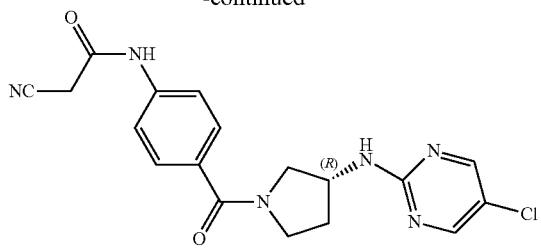

The title compound was prepared in 34% yield from (R)-(4-aminophenyl)(3-((5-chloropyrimidin-2-yl)amino)pyrrolidin-1-yl)methanone hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.88-2.00 (m, 1H), 2.07-2.16 (m, 1H), 3.36-3.74 (m, 4H), 3.92 (s, 2H), 4.23-4.40 (m, 1H), 7.48-7.61 (m, 4H), 7.79-7.82 (m, 1H), 8.31 (s, 1H), 8.38 (s, 1H), 10.45 (s, 1H). [M+H] Calc'd for $C_{18}H_{17}ClN_6O_2$, 385.1; Found, 385.1.

Example 134: Synthesis of (R)—N-(4-(3-((5-chloropyrimidin-2-yl)amino)pyrrolidine-1-carbonyl)phenyl)-2-cyano-3-(dimethylamino)acrylamide

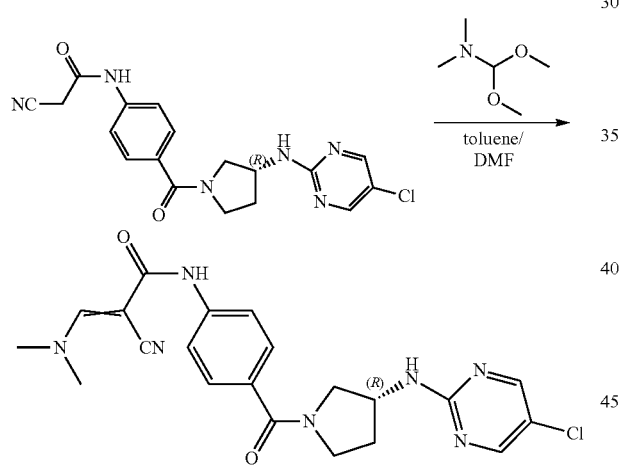

A mixture of (R)—N-(4-(3-((5-chloropyrimidin-2-yl)amino)pyrrolidine-1-carbonyl)phenyl)-2-cyanoacetamide (100 mg, 0.26 mmol) and 1,1-dimethoxy-N,N-dimethylmethanamine (116 mg, 0.52 mmol) in toluene/DMF (1 mL/1 mL) was stirred at 90° C. for 2 hours. The mixture was cooled to RT and concentrated. The residue was purified by prep-HPLC to afford (R)—N-(4-(3-((5-chloropyrimidin-2-yl)amino)pyrrolidine-1-carbonyl)phenyl)-2-cyano-3-(dimethylamino)acrylamide (19.8 mg, 17%) as a white solid. $^1$H NMR (400 MHz, DMSO-$d_6$): δ 1.88-2.00 (m, 1H), 2.12-2.18 (m, 1H), 3.22 (s, 3H), 3.29 (s, 3H), 3.38-3.44 (m, 1H), 3.52-3.56 (m, 1H), 3.63-3.67 (m, 1H), 3.73-3.80 (m, 1H), 4.23-4.40 (m, 1H), 7.43-7.48 (m, 2H), 7.60-7.65 (m, 2H), 7.80-7.83 (m, 2H), 8.31 (s, 1H), 8.38 (s, 1H), 9.24 (s, 1H). [M+H] Calc'd for $C_{21}H_{22}CN_7O_2$, 440.1; Found, 440.1.

Example 135: Synthesis of (R)—N-(3-(3-((5-chloropyrimidin-2-yl)amino)pyrrolidine-1-carbonyl)phenyl)-2-cyano-3-(dimethylamino)acrylamide

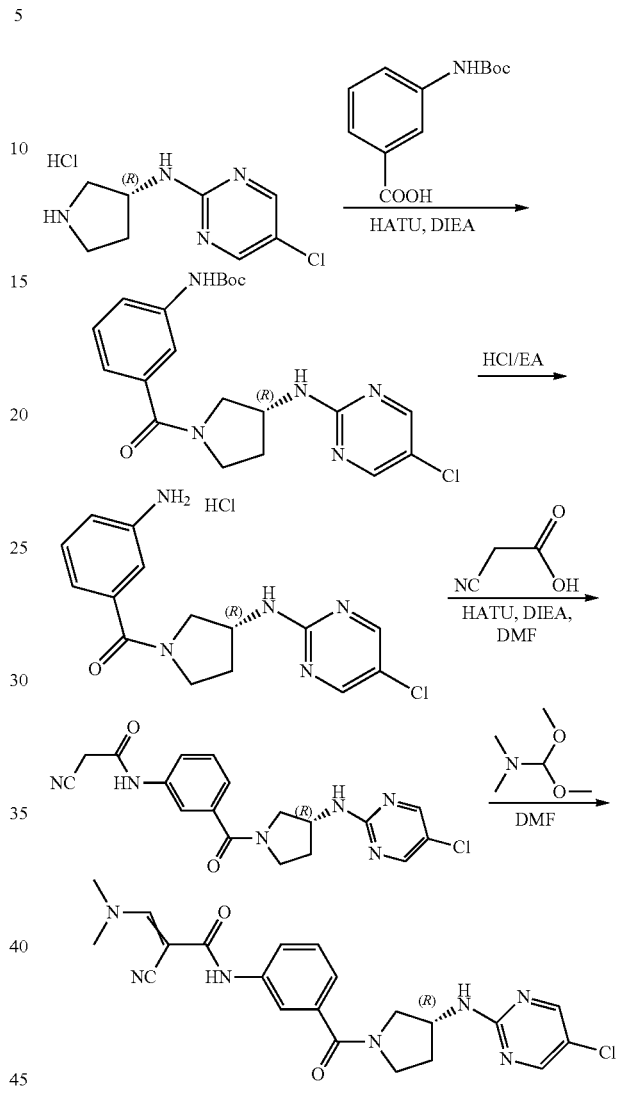

Step 1: (R)-tert-butyl (3-(3-((5-chloropyrimidin-2-yl)amino)pyrrolidine-1-carbonyl)phenyl)carbamate

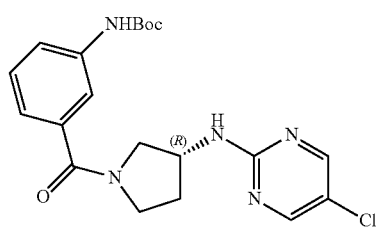

The title compound was prepared in 45% yield from (R)-tert-butyl (3-(3-((5-chloropyrimidin-2-yl)amino)pyrrolidine-1-carbonyl)phenyl)carbamate using general procedure of (R)—N-(4-(3-((5-chloro-4-methylpyrimidin-2-yl)

amino)pyrrolidine-1-carbonyl)phenyl)acrylamide. [M+H] Calc'd for $C_{20}H_{24}ClN_5O_3$, 418.1; Found, 418.1.

Step 2: (R)-(3-aminophenyl)(3-((5-chloropyrimidin-2-yl)amino)pyrrolidin-1-yl)methanone hydrochloride

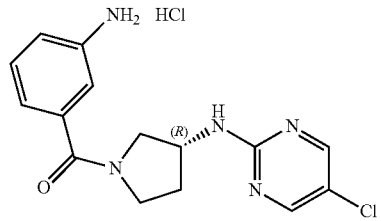

The title compound was prepared in 100% yield from (R)-tert-butyl (3-(3-((5-chloropyrimidin-2-yl)amino)pyrrolidine-1-carbonyl)phenyl)carbamate using general procedure of (R)-5-chloro-4-methyl-N-(pyrrolidin-3-yl)pyridin-2-amine hydrochloride. [M+H] Calc'd for $C_{15}H_{16}ClN_5O$, 318.1; Found, 318.1.

Step 3: (R)—N-(3-(3-((5-chloropyrimidin-2-yl)amino)pyrrolidine-1-carbonyl)phenyl)-2-cyanoacetamide

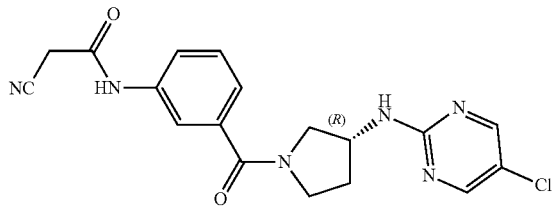

The title compound was prepared in 37% yield from (R)-(3-aminophenyl)(3-((5-chloropyrimidin-2-yl)amino)pyrrolidin-1-yl)methanone hydrochloride using general procedure of (R)—N-(4-(3-((5-chloro-4-methylpyrimidin-2-yl)amino)pyrrolidine-1-carbonyl)phenyl)acrylamide. [M+H] Calc'd for $C_{18}H_{17}ClN_6O_2$, 385.1; Found, 385.1.

Step 4: (R)—N-(3-(3-((5-chloropyrimidin-2-yl)amino)pyrrolidine-1-carbonyl)phenyl)-2-cyano-3-(dimethylamino)acrylamide

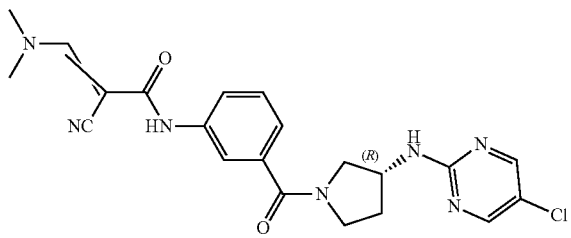

The title compound was prepared in 36% yield from (R)—N-(3-(3-((5-chloropyrimidin-2-yl)amino)pyrrolidine-1-carbonyl)phenyl)-2-cyanoacetamide using general procedure of (R)—N-(4-(3-((5-chloropyrimidin-2-yl)amino)pyrrolidine-1-carbonyl)phenyl)-2-cyano-3-(dimethylamino)acrylamide. $^1$H NMR (400 MHz, DMSO-d$_6$): δ 1.88-2.00 (m, 1H), 2.11-2.18 (m, 1H), 3.21 (s, 3H), 3.28 (s, 3H), 3.42-3.79 (m, 4H), 4.24-4.39 (m, 1H), 7.11-7.17 (m, 1H), 7.28-7.35 (m, 1H), 7.61-7.64 (m, 1H), 7.74-7.84 (m, 3H), 8.31 (s, 1H), 8.38 (s, 1H), 9.19 (s, 0.5H), 9.22 (s, 0.5H). [M+H] Calc'd for $C_{21}H_{22}ClN_7O_2$, 440.1; Found, 440.1.

Example 136: Synthesis of (R)-1-(6-(3-((5-chloropyrimidin-2-yl)amino)pyrrolidine-1-carbonyl)indolin-1-yl)prop-2-en-1-one

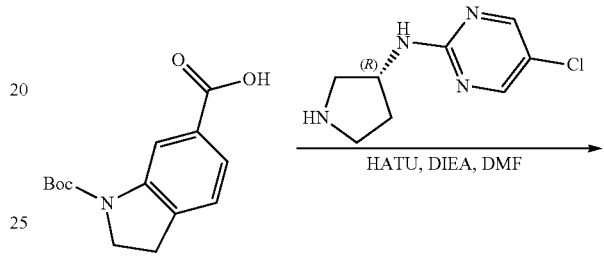

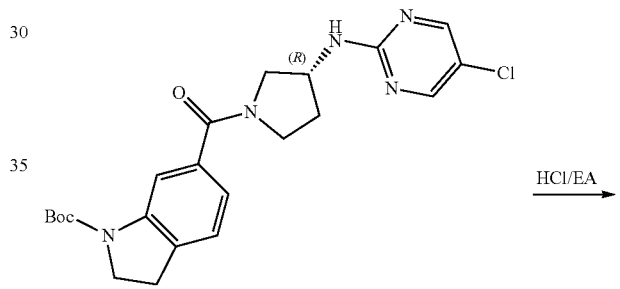

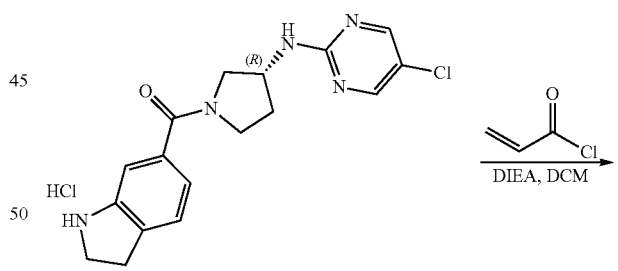

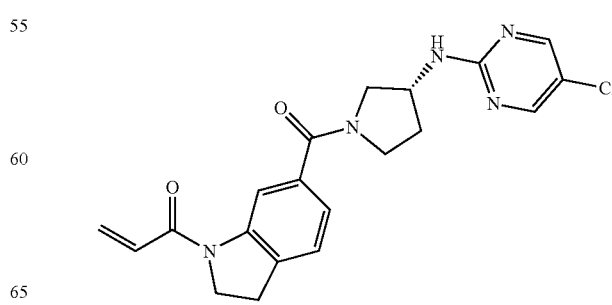

Step 1: (R)-tert-butyl 6-(3-((5-chloropyrimidin-2-yl)amino)pyrrolidine-1-carbonyl)indoline-1-carboxylate

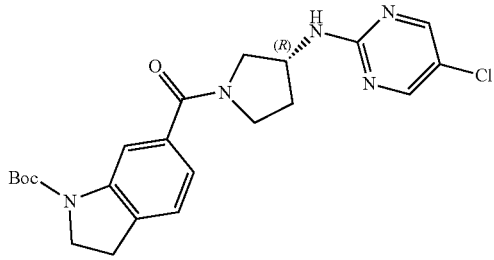

The title compound was prepared in 67% yield from 1-(tert-butoxycarbonyl)indoline-6-carboxylic acid using general procedure of (R)—N-(4-(3-((5-chloro-4-methylpyrimidin-2-yl)amino)pyrrolidine-1-carbonyl)phenyl)acrylamide. [M+H] Calc'd for $C_{22}H_{26}ClN_5O_3$, 444.1; Found, 444.1.

Step 2: (R)-(3-((5-chloropyrimidin-2-yl)amino)pyrrolidin-1-yl)(indolin-6-yl)methanone hydrochloride

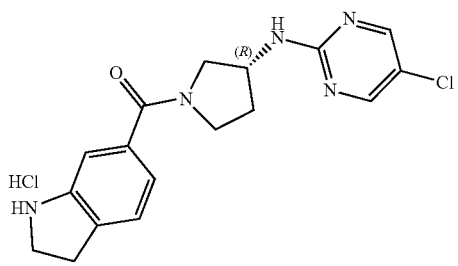

The title compound was prepared in 97% yield from (R)-tert-butyl 6-(3-((5-chloropyrimidin-2-yl)amino)pyrrolidine-1-carbonyl)indoline-1-carboxylate using general procedure of (R)-5-chloro-4-methyl-N-(pyrrolidin-3-yl)pyridin-2-amine hydrochloride [M+H] Calc'd for $C_{17}H_{18}ClN_5O$, 344.1; Found, 344.1.

Step 3: (R)-1-(6-(3-((5-chloropyrimidin-2-yl)amino)pyrrolidine-1-carbonyl)indolin-1-yl)prop-2-en-1-one

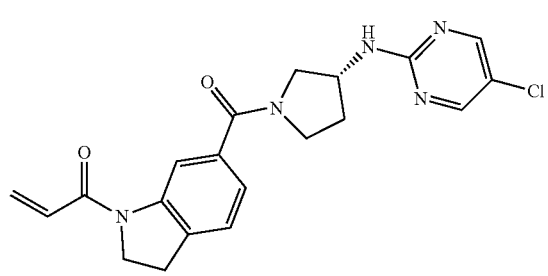 [SMILES: C=CC(=O)N1CCc2ccc(C(=O)N3CC[C@@H](Nc4ncc(Cl)cn4)C3)cc21]

The title compound was prepared in 15% yield from (R)-(3-((5-chloropyrimidin-2-yl)amino)pyrrolidin-1-yl)(indolin-6-yl)methanone hydrochloride using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-d$_6$): δ 1.85-2.02 (m, 1H), 2.07-2.12 (m, 1H), 3.12-3.15 (m, 2H), 3.44-3.79 (m, 4H), 4.21-4.40 (m, 3H), 5.80-5.83 (m, 1H), 6.30 (d, J=16.4 Hz, 1H), 6.70-6.77 (m, 1H), 7.11-7.15 (m, 1H), 7.28-7.31 (m, 1H), 7.80-7.87 (m, 1H), 8.28-8.31 (m, 2H), 8.40 (s, 1H). [M+H] Calc'd for $C_{20}H_{20}ClN_5O_2$, 398.1; Found, 398.1.

Example 137: Synthesis of (R)—N-(4-(3-((5-chloro-4-(2-hydroxyethoxy)pyrimidin-2-yl)amino)pyrrolidine-1-carbonyl)phenyl)acrylamide

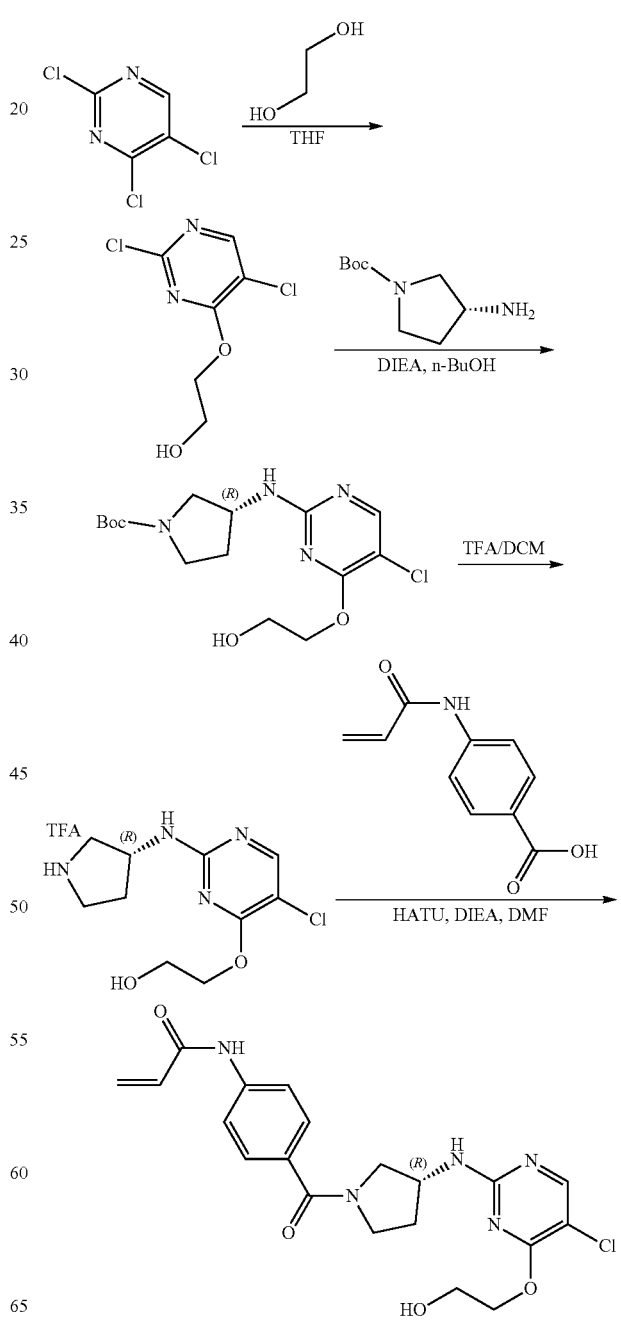

Step 1: 2-((2,5-dichloropyrimidin-4-yl)oxy)ethanol

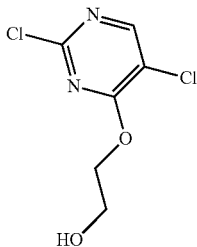 [SMILES: OCCOc1nc(Cl)ncc1Cl]

To a solution of 2,4,5-trichloropyrimidine (500 mg, 2.7 mmol) in THF (5 mL) was added ethane-1,2-diol (226 mg, 2.7 mmol) dropwise at 0° C. The mixture was stirred at 0° C. for 30 minutes. The mixture was purified by flash chromatography on silica gel (petroleum ether/EtOAc=10/1) to afford 2-((2,5-dichloropyrimidin-4-yl)oxy)ethanol (360 mg, 64%) as a white solid. [M+H]Calc'd for $C_6H_6Cl_2N_2O_2$, 208.9; Found, 208.9.

Step 2: (R)-tert-butyl 3-((5-chloro-4-(2-hydroxyethoxy)pyrimidin-2-yl)amino)pyrrolidine-1-carboxylate

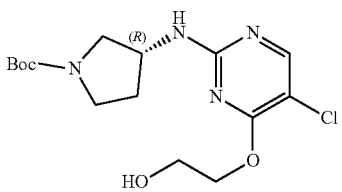

The title compound was prepared in 93% yield from 2-((2,5-dichloropyrimidin-4-yl)oxy)ethanol using general procedure of (R)-tert-butyl 3-((5-chloro-4-methylpyrimidin-2-yl)amino)pyrrolidine-1-carboxylate. [M+H] Calc'd for $C_{15}H_{23}ClN_4O_4$, 359.1; Found, 359.1.

Step 3: (R)-2-((5-chloro-2-(pyrrolidin-3-ylamino)pyrimidin-4-yl)oxy)ethanol 2,2,2-trifluoroacetate

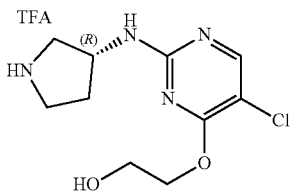

The title compound was prepared in 100% yield from (R)-tert-butyl 3-((5-chloro-4-(2-hydroxyethoxy)pyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{10}H_{15}ClN_4O_2$, 259.0; Found, 259.0.

Step 4: (R)—N-(4-(3-((5-chloro-4-(2-hydroxyethoxy)pyrimidin-2-yl)amino)pyrrolidine-1-carbonyl)phenyl)acrylamide

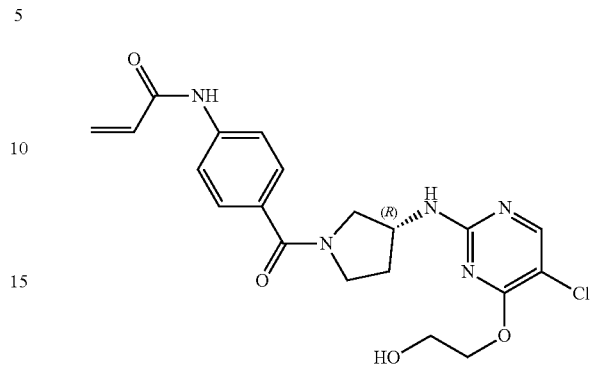

The title compound was prepared in 13% yield from (R)-2-((5-chloro-2-(pyrrolidin-3-ylamino)pyrimidin-4-yl)oxy)ethanol 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, CDCl$_3$): δ 1.88-2.00 (m, 1H), 2.07-2.14 (m, 1H), 3.37-3.78 (m, 6H), 4.24-4.38 (m, 3H), 4.84-4.90 (m, 1H), 5.78 (d, J=10.0 Hz, 1H), 6.28 (d, J=16.8 Hz, 1H), 6.41-6.48 (m, 1H), 7.49-7.54 (m, 2H), 7.61-7.67 (m, 3H), 8.07 (s, 0.5H), 8.14 (s, 0.5H), 10.32 (s, 1H). [M+H] Calc'd for $C_{20}H_{22}ClN_5O_4$, 432.1; Found, 432.1.

Example 138: Synthesis of (R)—N-(4-(3-((5-chloro-4-deutero-6-(trideuteromethoxy)pyrimidin-2-yl)amino)pyrrolidine-1-carbonyl)phenyl)acrylamide

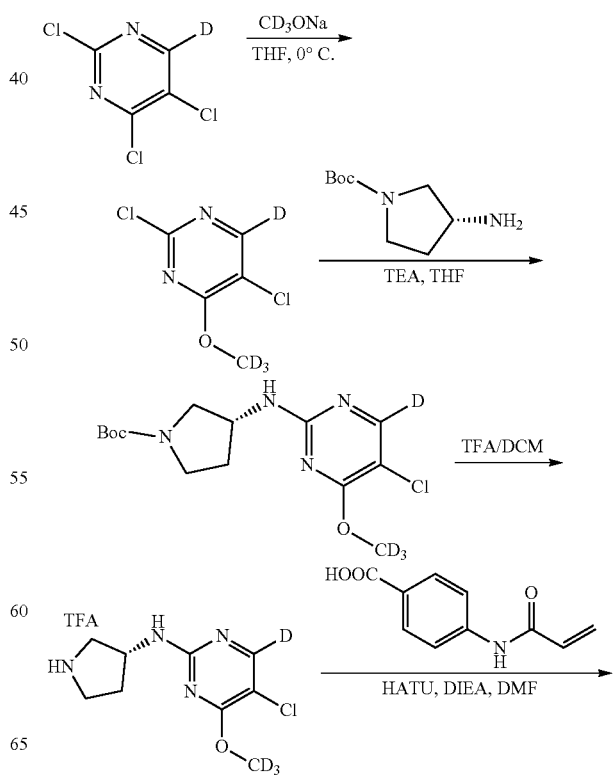

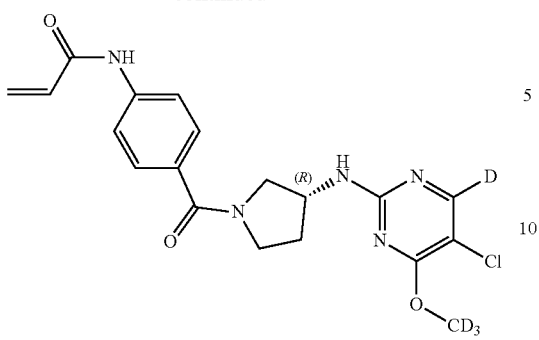

Step 1: 2,5-dichloro-4-deutero-6-(trideuteromethoxy) pyrimidine

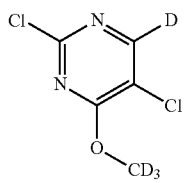

To a solution of 2,4,5-trichloro-6-deuteropyrimidine (200 mg, 1.08 mmol) in THF (2 mL) was added CD$_3$ONa (62 mg, 1.08 mmol) at 0° C. The mixture was stirred at 0° C. for 30 minutes. The mixture was concentrated. The residue was purified by flash chromatography on silica gel (PE) to afford 2,5-dichloro-4-deutero-6-(trideuteromethoxy)pyrimidine (180 mg, 91%) as yellow oil. [M+H] Calc'd for C$_5$D$_4$Cl$_2$N$_2$O, 183.9; Found, 183.9.

Step 2: (R)-tert-butyl 3-((5-chloro-4-deutero-6-(trideuteromethoxy)pyrimidin-2-yl)amino)pyrrolidine-1-carboxylate

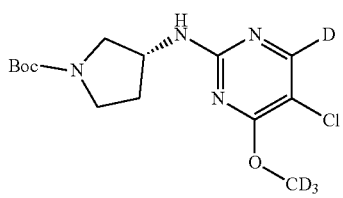 [SMILES: [2H]c1nc(N[C@@H]2CCN(C(=O)OC(C)(C)C)C2)nc(OC([2H])([2H])[2H])c1Cl]

2,5-dichloro-4-deutero-6-(trideuteromethoxy)pyrimidine (180 mg, 1.01 mmol), (R)-tert-butyl 3-aminopyrrolidine-1-carboxylate (186 mg, 1.01 mmol) and TEA (303 mg, 3.0 mmol) in THF (4 mL) were combined at RT. The mixture was then stirred at 75° C. for 30 minutes. The mixture was concentrated and the resultant residue was purified by flash chromatography on silica gel (PE/EA=10/1) to afford (R)-tert-butyl 3-((5-chloro-4-deutero-6-(trideuteromethoxy)pyrimidin-2-yl)amino)pyrrolidine-1-carboxylate (150 mg, 46%) as a white solid. [M+H] Calc'd for C$_{14}$H$_{17}$D$_4$ClN$_4$O$_3$, 333.1; Found, 333.1.

Step 3: (R)-5-chloro-4-deutero-N-(pyrrolidin-3-yl)-6-(deuteromethoxy)pyrimidin-2-amine 2,2,2-trifluoroacetate

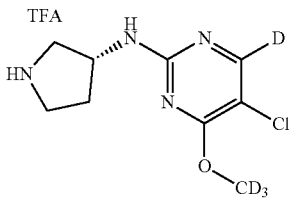 [SMILES: [2H]c1nc(N[C@@H]2CCNC2)nc(OC([2H])([2H])[2H])c1Cl]

The title compound was prepared in 100% yield from (R)-tert-butyl 3-((5-chloro-4-deutero-6-(trideuteromethoxy)pyrimidin-2-yl)amino)pyrrolidine-1-carboxylate using general procedure of (R)-5-chloro-4-methyl-N-(pyrrolidin-3-yl) pyrimidin-2-amine 2,2,2-trifluoroacetate. [M+H]Calc'd for C$_9$H$_9$D$_4$ClN$_4$O, 233.1; Found, 233.1.

Step 4: (R)—N-(4-(3-((5-chloro-4-deutero-6-(trideuteromethoxy)pyrimidin-2-yl)amino)pyrrolidine-1-carbonyl)phenyl)acrylamide

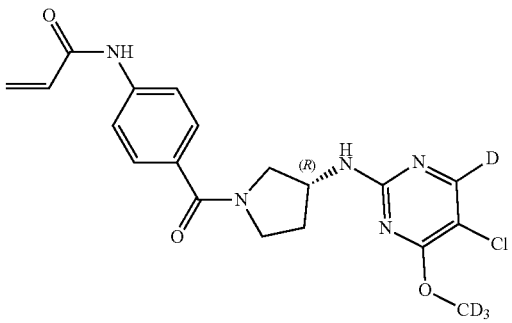

The title compound was prepared in 11% yield from (R)-5-chloro-4-deutero-N-(pyrrolidin-3-yl)-6-(deuteromethoxy)pyrimidin-2-amine 2,2,2-trifluoroacetate using general procedure of (R)—N-(4-(3-((5-chloro-4-methylpyrimidin-2-yl)amino)pyrrolidine-1-carbonyl)phenyl)acrylamide. $^1$H NMR (400 MHz, CDCl$_3$): δ 1.97-2.03 (m, 1H), 2.21-2.37 (m, 1H), 3.39-4.04 (m, 4H), 4.44-4.56 (m, 1H), 5.17-5.41 (m, 1H), 5.79 (d, J=10.0 Hz, 1H), 6.24-6.31 (m, 1H), 6.46 (d, J=16.8 Hz, 1H), 7.47-7.52 (m, 2H), 7.58-7.65 (m, 2H), 7.67-7.72 (m, 1H). [M+H] Calc'd for C$_{19}$H$_{16}$D$_4$ClN$_5$O$_3$, 406.1; Found, 406.1.

Example 139: Synthesis of (R)—N-(4-(3-((5-chloro-4-(dimethylamino)-6-deuteropyrimidin-2-yl)amino)pyrrolidine-1-carbonyl)phenyl)acrylamide

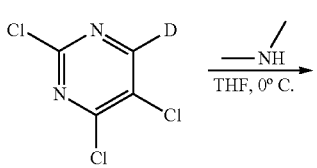

-continued

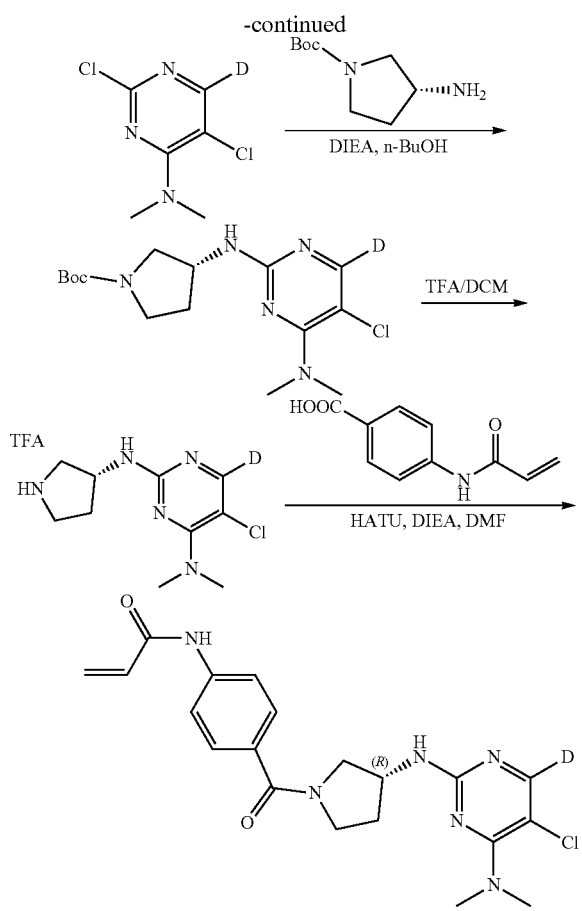

Step 1: 2,5-dichloro-6-deutero-N,N-dimethylpyrimidin-4-amine

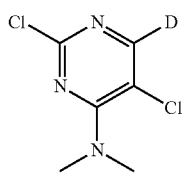

The title compound was prepared in 67% yield from 4,5-trichloro-6-deuteropyrimidine using general procedure of 2,5-dichloro-N,N-dimethylpyrimidin-4-amine. [M+H] Calc'd for $C_6H_6DCl_2N_3$, 193.0; Found, 193.0

Step 2: (R)-tert-butyl 3-((5-chloro-4-(dimethylamino)-6-deuteropyrimidin-2-yl)amino)pyrrolidine-1-carboxylate

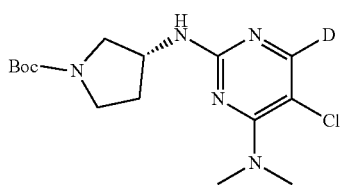 [SMILES: [2H]c1nc(N[C@@H]2CCN(C(=O)OC(C)(C)C)C2)nc(N(C)C)c1Cl]

The title compound was prepared in 31% yield from 2,5-dichloro-6-deutero-N,N-dimethylpyrimidin-4-amine using general procedure of (R)-tert-butyl 3-((5-chloro-4-methylpyrimidin-2-yl)amino)pyrrolidine-1-carboxylate. [M+H] Calc'd for $C_{15}H_{23}DClN_5O_2$, 343.1; Found, 343.1.

Step 3: (R)-5-chloro-6-deutero-N4,N4-dimethyl-N2-(pyrrolidin-3-yl)pyrimidine-2,4-diamine

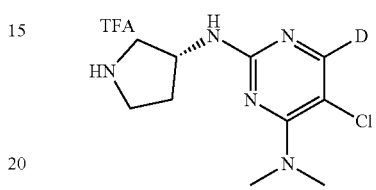

The title compound was prepared in 100% yield from (R)-tert-butyl 3-((5-chloro-4-(dimethylamino)-6-deuteropyrimidin-2-yl)amino)pyrrolidine-1-carboxylate using general procedure of (R)-5-chloro-4-methyl-N-(pyrrolidin-3-yl)pyrimidin-2-amine 2,2,2-trifluoroacetate. [M+H] Calc'd for $C_{10}H_{15}DClN_5$, 243.1; Found, 243.1.

Step 4: (R)—N-(4-(3-((5-chloro-4-(dimethylamino)-6-deuteropyrimidin-2-yl)amino)pyrrolidine-1-carbonyl)phenyl)acrylamide

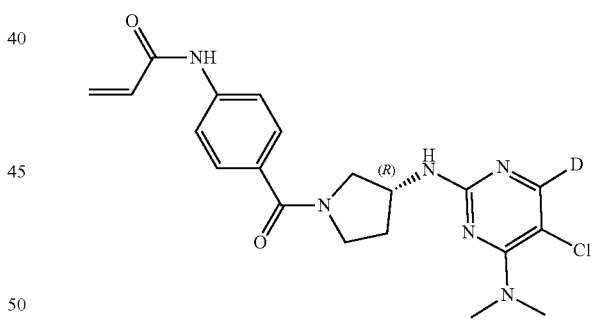

The title compound was prepared in 43% yield from (R)-5-chloro-6-deutero-N4,N4-dimethyl-N2-(pyrrolidin-3-yl)pyrimidine-2,4-diamine using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-$d_6$): δ 1.87-1.98 (m, 1H), 2.12-2.19 (m, 1H), 3.02 (s, 3H), 3.10 (s, 3H), 3.42-3.77 (m, 4H), 4.19-4.36 (m, 1H), 5.78 (d, J=10.0 Hz, 1H), 6.28 (d, J=16.8 Hz, 1H), 6.41-6.48 (m, 1H), 7.16 (br s, 1H), 7.48-7.53 (m, 2H), 7.69-7.73 (m, 2H), 10.30 (s, 1H). [M+H] Calc'd for $C_{20}H_{22}DClN_6O_2$, 416.1; Found, 416.1.

Example 140: Synthesis of (R)-1-(4-(3-((5-chloropyrimidin-2-yl)amino)pyrrolidine-1-carbonyl) phenyl)-1H-pyrrole-2,5-dione

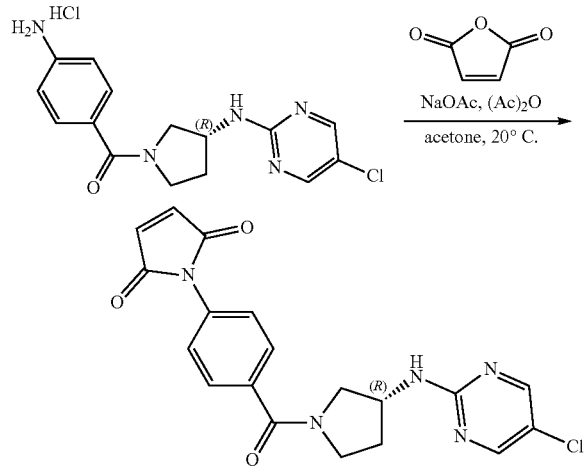

A mixture of (R)-(4-aminophenyl)(3-((5-chloropyrimidin-2-yl)amino)Pyrrolidin-1-yl)methanone (310 mg, 0.87 mmol) and furan-2,5-dione (121.8 mg, 1.74 mmol) in acetone (5 mL) was stirred at 20° C. for 2 hrs. The reaction mixture was concentrated under reduced pressure. To this residue was added a solution of sodium acetate (76.3 mg, 0.87 mmol) and acetic anhydride (177 mg, 1.74 mmol) in DMF (3 mL). The mixture was stirred at 50° C. for 5 hrs. The reaction was filtered and concentrated and the residue was purified by silica gel chromatography (DCM/MeOH=20/1) to afford (R)-1-(4-(3-((5-chloropyrimidin-2-yl)amino)pyrrolidine-1-carbonyl)phenyl)-1H-pyrrole-2,5-dione (142.6 mg, 41%) as a yellow solid. $^1$H NMR (400 MHz, CDCl$_3$): 1.99-2.03 (m, 1H), 2.26-2.40 (m, 1H), 3.36-4.07 (m, 4H), 4.44-4.58 (m, 1H), 5.23-5.33 (m, 1H), 6.72-6.87 (m, 2H), 7.38-7.46 (m, 2H), 7.54-7.65 (m, 2H), 8.19-8.25 (m, 2H); [M+H] Calc'd for C$_{19}$H$_{16}$ClN$_5$O$_3$, 398.1; Found, 398.1.

Example 141: Synthesis of N-(4-((R)-3-((5-chloropyrimidin-2-yl)amino)pyrrolidine-1-carbonyl)phenyl)oxirane-2-carboxamide

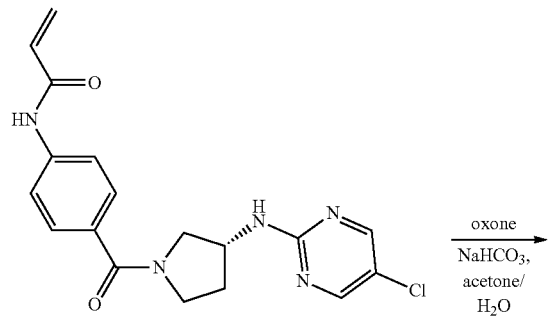

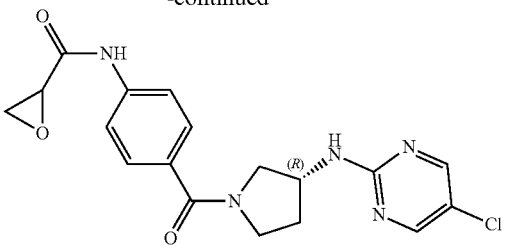

To a mixture of (R)—N-(4-(3-((5-chloropyrimidin-2-yl)amino)pyrrolidine-1-carbonyl)phenyl)acrylamide (300 mg, 0.81 mmol) in acetone/H$_2$O (6 mL/6 mL) was added NaHCO$_3$ (299 mg, 3.56 mmol) and oxone (996 mg, 1.62 mmol) portionwise at 0° C. The mixture was stirred at RT for 3 hours. The mixture was poured to sat. NaHCO$_3$ (15 mL) and extracted with EtOAc (20 mL*2). The combined organic phase was washed with brine (20 mL), dried over Na$_2$SO$_4$, filtered and concentrated. The residue was purified by prep-HPLC to afford N-(4-((R)-3-((5-chloropyrimidin-2-yl)amino)pyrrolidine-1-carbonyl)phenyl)oxirane-2-carboxamide (23.9 mg, 8%) as a yellow solid. $^1$H NMR (400 MHz, DMSO-d$_6$): δ 2.07-2.17 (m, 2H), 3.51-3.56 (m, 2H), 3.62-3.68 (m, 1H), 3.76-3.83 (m, 1H), 4.40-4.53 (m, 1H), 5.76-5.80 (m, 1H), 6.27 (d, J=16.0 Hz, 1H), 6.41-6.47 (m, 1H), 7.49-7.53 (m, 2H), 7.69-7.73 (m, 2H), 7.97 (s, 0.5H), 8.06 (s, 0.5H), 8.26-8.33 (m, 1H), 8.77 (s, 0.5H), 8.81 (s, 0.5H), 10.29 (s, 1H); [M+H] Calc'd for C$_{18}$H$_{18}$ClN$_5$O$_3$: 388.1; Found: 388.1.

Example 142: Synthesis of N-(4-((R)-3-((5-chloro-4-methoxypyrimidin-2-yl)amino)pyrrolidine-1-carbonyl)phenyl)oxirane-2-carboxamide

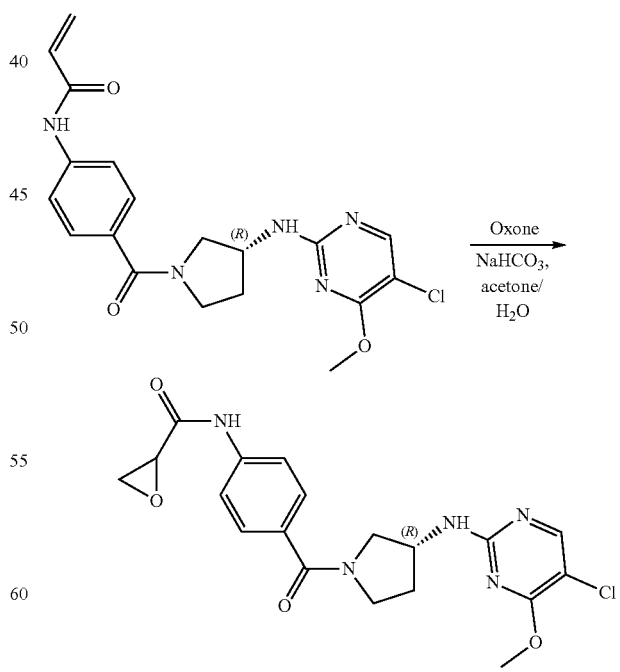

The title compound was prepared in 11% yield from (R)—N-(4-(3-((5-chloro-4-methoxypyrimidin-2-yl)amino)pyrrolidine-1-carbonyl)phenyl)acrylamide using general procedure of N-(4-((R)-3-((5-chloropyrimidin-2-yl)amino)pyrrolidine-1-carbonyl)phenyl)oxirane-2-carboxamide. ¹H NMR (400 MHz, CDCl₃): δ 2.08-2.15 (m, 1H), 2.28-2.42 (m, 1H), 3.48-3.84 (m, 3H), 3.93-4.06 (m, 4H), 4.48-4.57 (m, 1H), 5.79 (s, 0.5H), 5.82 (s, 0.5H), 6.24-6.31 (m, 1H), 6.44 (s, 0.6H), 6.48 (s, 0.4H), 7.34-7.38 (m, 1H), 7.50-7.54 (m, 2H), 7.58-7.62 (m, 2H), 7.72 (s, 1H), 8.21-8.24 (m, 1H). [M+H] Calc'd for C₁₉H₂₀ClN₅O₄, 418.1; Found, 418.1.

Example 143: Synthesis of N-(4-((R)-3-((5-chloro-4-ethoxypyrimidin-2-yl)amino)pyrrolidine-1-carbonyl)-2-((tetrahydrofuran-3-yl)oxy)phenyl)acrylamide

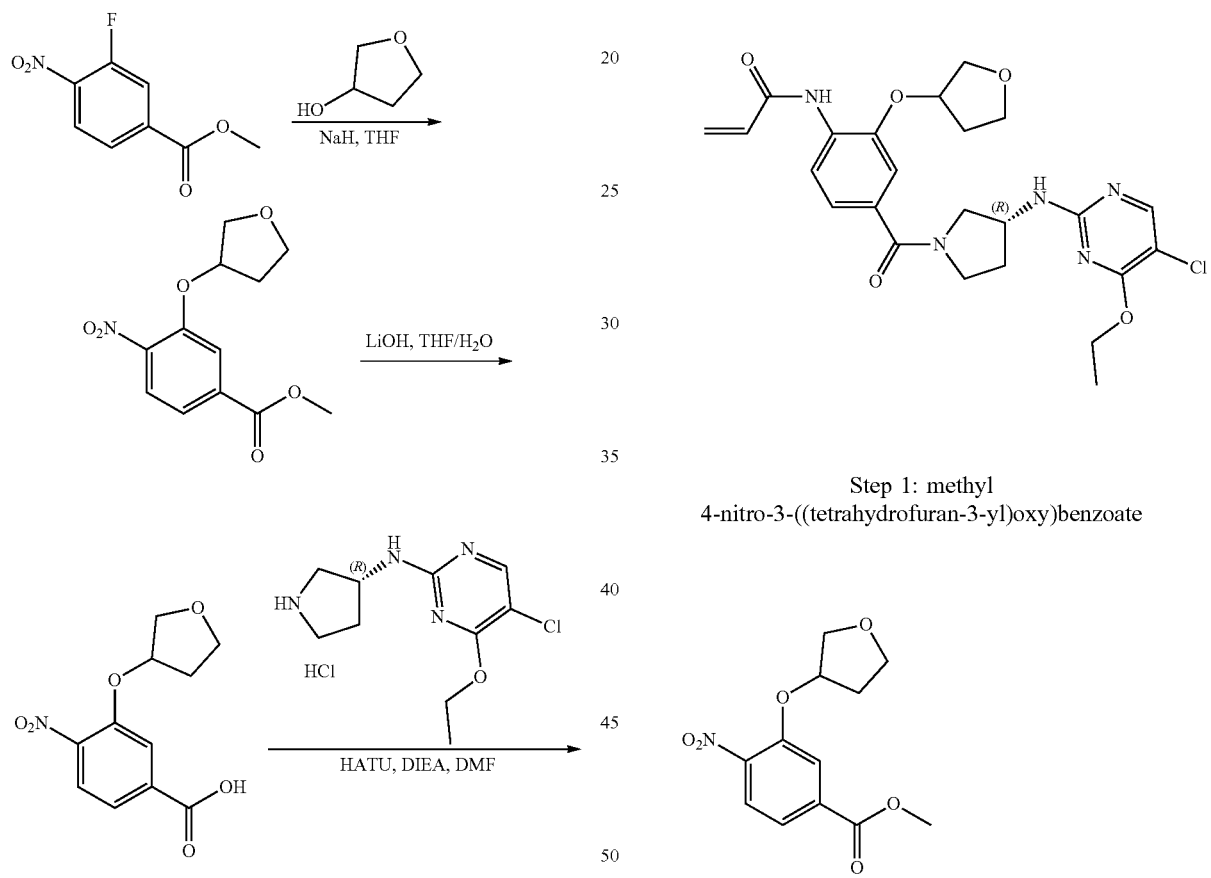

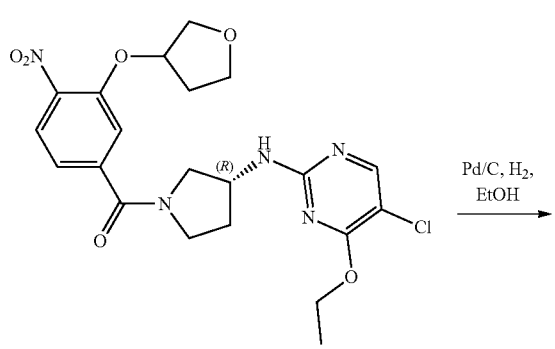

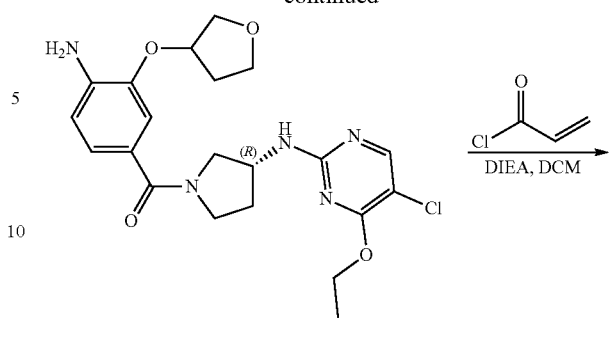

Step 1: methyl 4-nitro-3-((tetrahydrofuran-3-yl)oxy)benzoate

To a mixture of tetrahydrofuran-3-ol (884 mg, 10.0 mmol) in THF (10 mL) was added NaH (884 mg, 11.0 mmol) at 0° C. After the reaction mixture was stirred at for 20 min, methyl 3-fluoro-4-nitrobenzoate (2.0 g, 10.1 mmol) was added. The reaction mixture was then stirred at RT overnight, The mixture was diluted with water (10 mL) and extracted with DCM (10 mL*3). The combined organic layer was washed with brine (20 mL), dried over Na₂SO₄, filtered and concentrated and purified by silica gel chromatography (PE/EA=1~10/1) to afford methyl 4-nitro-3-((tetrahydrofuran-3-yl)oxy)benzoate (717 mg, 27%) as yellow solid. [M+H] Calc'd for C₁₂H₁₃NO₆, 268.1; Found, 268.1

Step 2: 4-nitro-3-((tetrahydrofuran-3-yl)oxy)benzoate

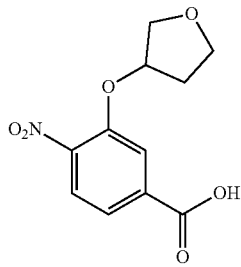 [SMILES: O=C(O)c1ccc([N+](=O)[O-])c(OC2CCOC2)c1]

A mixture of methyl 4-nitro-3-((tetrahydrofuran-3-yl)oxy)benzoate (350 mg, 1.31 mmol) and LiOH (83 mg, 1.97 mmol) in THF/H$_2$O (10 mL/5 mL) was stirred at RT for overnight, The mixture was adjusted to pH 5 and extracted with DCM (10 mL*3). The combined organic layer was washed with brine (20 mL), dried over Na$_2$SO$_4$, filtered and concentrated to afford 4-nitro-3-((tetrahydrofuran-3-yl)oxy) benzoic acid (330 mg, 100%) as a yellow solid. [M+H] Calc'd for C$_{11}$H$_{11}$NO$_6$, 254.0; Found, 254.0

Step 3: ((R)-3-((5-chloro-4-ethoxypyrimidin-2-yl)amino)pyrrolidin-1-yl)(4-nitro-3-((tetrahydrofuran-3-yl)oxy)phenyl)methanone

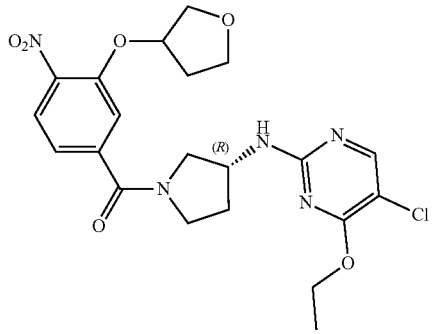

A mixture of 4-nitro-3-((tetrahydrofuran-3-yl)oxy)benzoic acid (330 mg, 1.31 mmol), (R)-5-chloro-4-ethoxy-N-(pyrrolidin-3-yl)pyrimidin-2-amine HCl salt (437 mg, 1.57 mmol), HATU (597 mg, 1.57 mmol) and DIEA (845 mg, 6.55 mmol) in DMF (15 mL) was stirred at RT for overnight. The reaction mixture was extracted by EA/H2O (40/100 mL), dried over Na$_2$SO$_4$, filtered, concentrated and the mixture was purified by silica gel chromatography (PE/EA=1/1~0/1) to afford ((R)-3-((5-chloro-4-ethoxypyrimidin-2-yl)amino)pyrrolidin-1-yl)(4-nitro-3-((tetrahydrofuran-3-yl)oxy)phenyl)methanone (600 mg, 96%) as a yellow solid. [M+H] Calc'd for C$_{21}$H$_{24}$ClN$_5$O$_6$, 478.1; Found, 478.1

Step 4: (4-amino-3-((tetrahydrofuran-3-yl)oxy)phenyl)((R)-3-((5-chloro-4-ethoxypyrimidin-2-yl)amino)pyrrolidin-1-yl)methanone

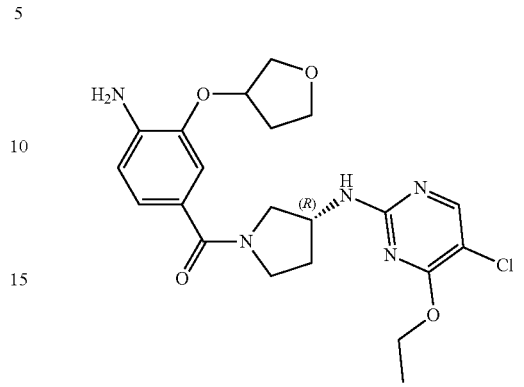

A mixture of ((R)-3-((5-chloro-4-ethoxypyrimidin-2-yl)amino)pyrrolidin-1-yl)(4-nitro-3-((tetrahydrofuran-3-yl)oxy)phenyl)methanone (600 mg, 1.47 mmol) and Pd/C (150 mg, 10%) in EtOH (20 mL) was stirred at 50° C. overnight under 1 atm H$_2$ atmosphere. The reaction mixture was filtered and concentrated to afford (4-amino-3-((tetrahydrofuran-3-yl)oxy)phenyl)((R)-3-((5-chloro-4-ethoxypyrimidin-2-yl)amino)pyrrolidin-1-yl)methanone (650 mg, 99%) as a yellow solid. [M+H] Calc'd for C$_{21}$H$_{26}$ClN$_5$O$_4$, 448.2; Found, 448.2.

Step 5: N-(4-((R)-3-((5-chloro-4-ethoxypyrimidin-2-yl)amino)pyrrolidine-1-carbonyl)-2-((tetrahydrofuran-3-yl)oxy)phenyl)acrylamide

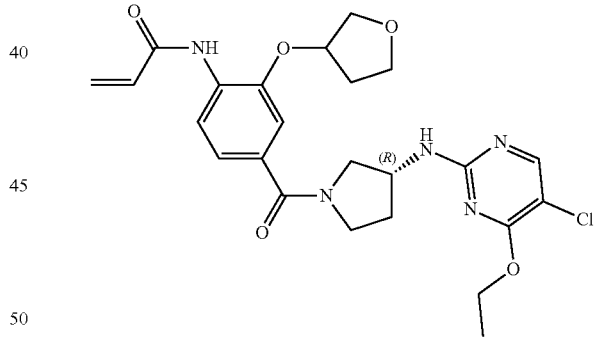

A mixture of (4-amino-3-((tetrahydrofuran-3-yl)oxy)phenyl)((R)-3-((5-chloro-4-ethoxypyrimidin-2-yl)amino)pyrrolidin-1-yl)methanone (550 mg, 1.23 mmol) and DIEA (238 mg, 1.85 mmol) in DCM (25 mL) was stirred at 0° C. under nitrogen atmosphere. Acryloyl chloride (78 mg, 0.86 mmol) in DCM (5 mL) was added dropwise and the mixture was warmed to RT and stirred for overnight. The mixture was concentrated and purified by prep-HPLC to afford N-(4-((R)-3-((5-chloro-4-ethoxypyrimidin-2-yl)amino)pyrrolidine-1-carbonyl)-2-((tetrahydrofuran-3-yl)oxy)phenyl)acrylamide (78.7 mg, 13%) as a white solid. $^1$H NMR (400 MHz, DMSO-d$_6$): δ 1.25-1.36 (m, 3H), 1.91-2.25 (m, 4H), 3.38-3.67 (m, 3H), 3.72-3.80 (m, 2H), 3.90-3.92 (m, 3H), 4.23-4.41 (m, 3H), 5.06-5.10 (m, 1H), 5.75-5.77 (m, 1H), 6.23-6.28 (m, 1H), 6.68-6.75 (m, 1H), 7.08-7.14 (m, 2H), 7.64 (s, 1H), 8.07-8.16 (m, 2H), 9.20-9.21 (m, 1H). [M+H]Calc'd for $C_{24}H_{28}ClN_5O_5$, 502.2; Found, 502.2.

Example 144: Synthesis of (R)—N-(4-(3-((5-chloro-4-ethoxypyrimidin-2-yl)amino)pyrrolidine-1-carbonyl)-2-(2-(dimethylamino)ethoxy)phenyl)acrylamide

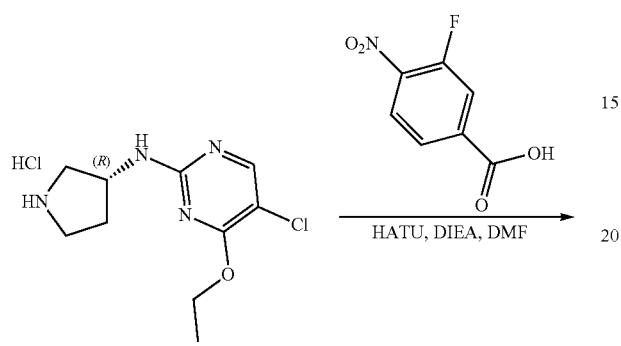

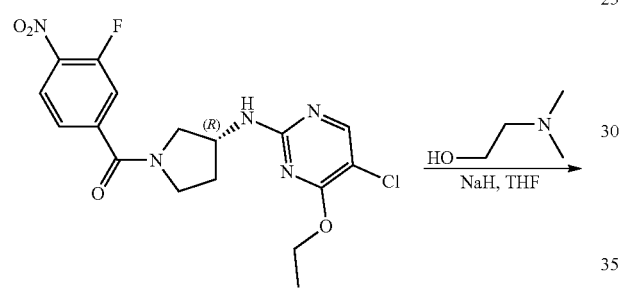

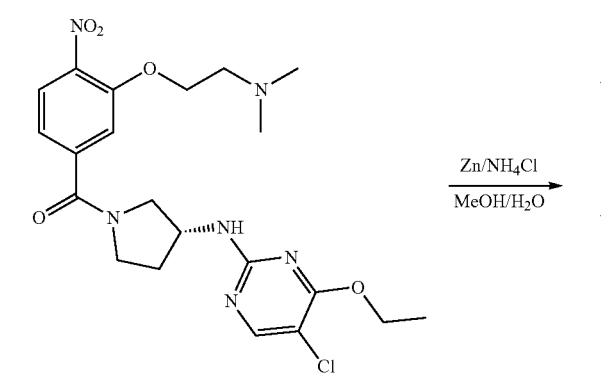

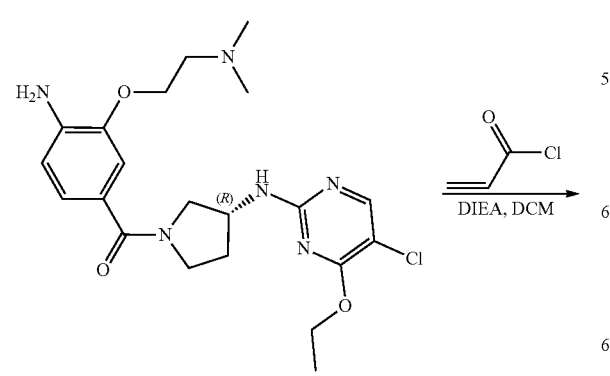

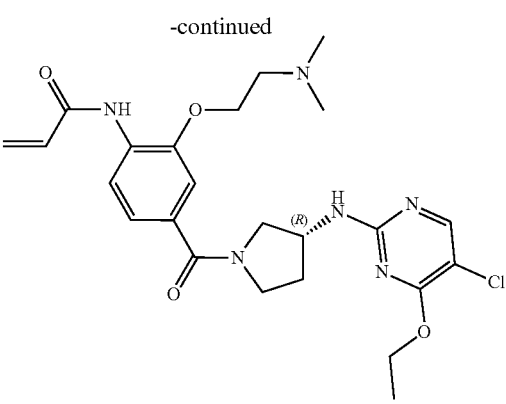

Step 1: (R)-(3-((5-chloro-4-ethoxypyrimidin-2-yl)amino)pyrrolidin-1-yl)(3-fluoro-4-nitrophenyl)methanone

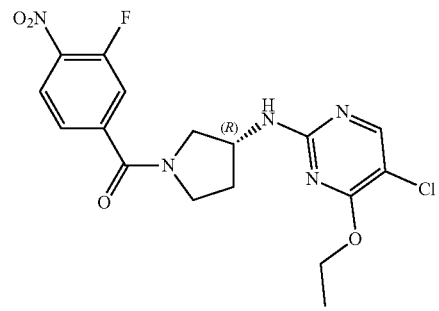

The title compound was prepared in 86% yield from (R)-5-chloro-4-ethoxy-N-(pyrrolidin-3-yl)pyrimidin-2-amine hydrochloride using general procedure of (R)—N-(4-(3-((5-chloro-4-methylpyrimidin-2-yl)amino)pyrrolidine-1-carbonyl)phenyl)acrylamide. [M+H] Calc'd for $C_{17}H_{17}ClFN_5O_4$, 410.0; Found, 410.0.

Step 2: (R)-(3-((5-chloro-4-ethoxypyrimidin-2-yl)amino)pyrrolidin-1-yl)(3-(2-(dimethylamino)ethoxy)-4-nitrophenyl)methanone

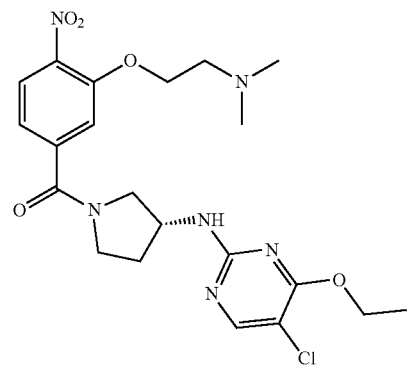 [SMILES: CCOc1nc(N[C@@H]2CCN(C(=O)c3ccc([N+](=O)[O-])c(OCCN(C)C)c3)C2)ncc1Cl]

The title compound was prepared in 64% yield from (R)-(3-((5-chloro-4-ethoxypyrimidin-2-yl)amino)pyrrolidin-1-yl)(3-fluoro-4-nitrophenyl)methanone using general procedure of ((R)-3-((5-chloropyrimidin-2-yl)amino)pyrrolidin-1-yl)(4-nitro-3-((tetrahydrofuran-3-yl)oxy)phenyl)methanone. [M+H] Calc'd for $C_{21}H_{27}ClN_6O_5$, 479.1; Found, 479.1.

Step 3: (R)-(4-amino-3-(2-(dimethylamino)ethoxy)phenyl)(3-((5-chloro-4-ethoxypyrimidin-2-yl)amino)pyrrolidin-1-yl)methanone

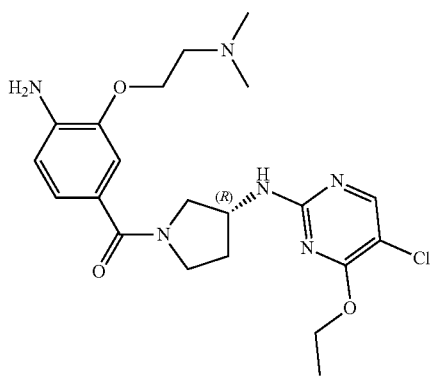

The title compound was prepared in 100% yield from (R)-(3-((5-chloro-4-ethoxypyrimidin-2-yl)amino)pyrrolidin-1-yl)(3-(2-(dimethylamino)ethoxy)-4-nitrophenyl)methanone using general procedure of (4-amino-3-((tetrahydrofuran-3-yl)oxy)phenyl)((R)-3-((5-chloropyrimidin-2-yl)amino)pyrrolidin-1-yl)methanone. [M+H] Calc'd for $C_{21}H_{29}ClN_6O_3$, 449.1; Found, 449.1.

Step 4: (R)—N-(4-(3-((5-chloro-4-ethoxypyrimidin-2-yl)amino)pyrrolidine-1-carbonyl)-2-(2-(dimethylamino)ethoxy)phenyl)acrylamide

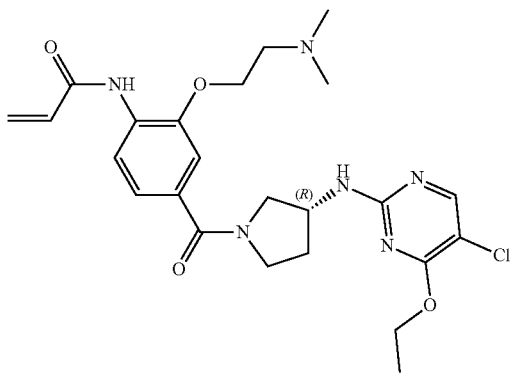

The title compound was prepared in 9% yield from (R)-(4-amino-3-(2-(dimethylamino)ethoxy)phenyl)(3-((5-chloro-4-ethoxypyrimidin-2-yl)amino)pyrrolidin-1-yl)methanone using general procedure of (R)-1-(6-(3-((5-chloro-4-methoxypyrimidin-2-yl)amino)pyrrolidine-1-carbonyl)-2-azaspiro[3.3]heptan-2-yl)prop-2-en-1-one. $^1$H NMR (400 MHz, DMSO-$d_6$): δ 1.23-1.36 (m, 3H), 1.89-2.02 (m, 1H), 2.07-2.15 (m, 1H), 2.22 (s, 3H), 2.25 (s, 3H), 2.59-2.63 (m, 2H), 3.39-3.43 (m, 1H), 3.51-3.55 (m, 1H), 3.61-3.65 (m, 1H), 3.74-3.79 (m, 1H), 4.13-4.40 (m, 5H), 5.78 (d, J=10.4 Hz, 1H), 6.26 (d, J=16.8 Hz, 1H), 6.52-6.59 (m, 1H), 7.12-7.18 (m, 1H), 7.23 (s, 0.5H), 7.27 (s, 0.5H), 7.64 (brs, 1H), 8.07-8.17 (m, 2H), 9.66 (s, 0.5H), 9.69 (s, 0.5H). [M+H] Calc'd for $C_{24}H_{31}ClN_6O_4$, 503.2; Found, 503.2.

Example 145: Synthesis of (R,E)-N-(4-(3-((5-chloro-4-methoxypyrimidin-2-yl)amino)pyrrolidine-1-carbonyl)-2-fluorophenyl)-4-(dimethylamino)but-2-enamide

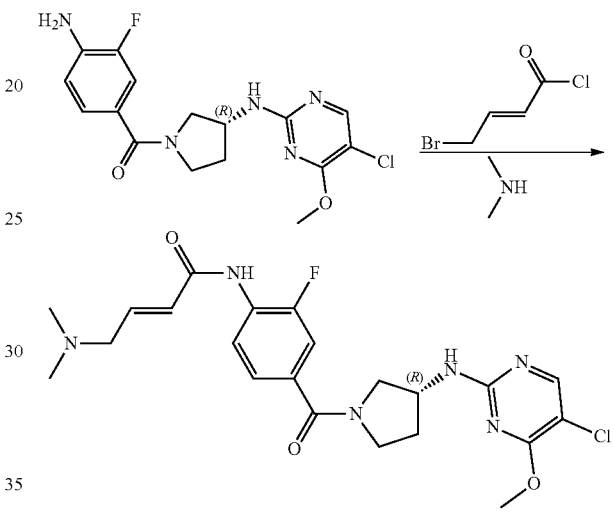

The title compound was prepared in 6% yield from (R)-(4-amino-3-fluorophenyl)(3-((5-chloro-4-methoxypyrimidin-2-yl)amino)pyrrolidin-1-yl)methanone using general procedure of (R,E)-1-(8-(3-((5-chloropyrimidin-2-yl)amino)pyrrolidine-1-carbonyl)-2H-benzo[b][1,4]oxazin-4(3H)-yl)-4-(dimethylamino)but-2-en-1-one. $^1$H NMR (400 MHz, DMSO-$d_6$): δ 1.87-2.04 (m, 1H), 2.13-2.17 (m, 7H), 3.06 (d, J=5.6 Hz, 2H), 3.36-3.48 (m, 1H), 3.51-3.57 (m, 1H), 3.61-3.68 (m, 1H), 3.71-3.79 (m, 1H), 3.86 (s, 1.5H), 3.94 (s, 1.5H), 4.26-4.44 (m, 1H), 6.48 (d, J=15.2 Hz, 1H), 6.73-6.80 (m, 1H), 7.33-7.45 (m, 2H), 7.68 (brs, 1H), 8.08-8.14 (m, 2H), 9.96 (br s, 1H). [M+H]Calc'd for $C_{22}H_{26}ClFN_6O_3$, 477.1; Found, 477.1.

Example 146: Synthesis of (R,E)-1-(6-(3-((5-chloropyrimidin-2-yl)amino)pyrrolidine-1-carbonyl)indolin-1-yl)-4-(dimethylamino)but-2-en-1-one

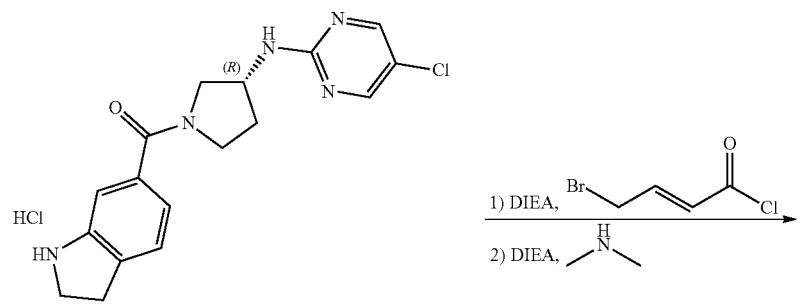

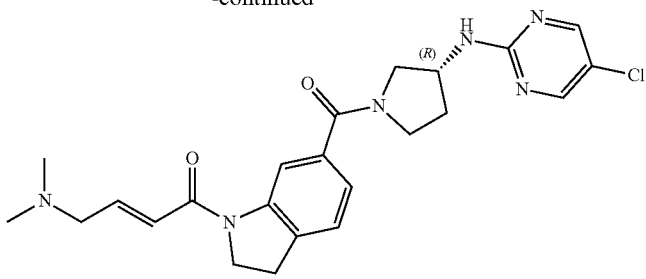

The title compound was prepared in 21% yield from (R)-(3-((5-chloropyrimidin-2-yl)amino)pyrrolidin-1-yl)(indolin-6-yl)methanone hydrochloride using general procedure of (R,E)-1-(8-(3-((5-chloropyrimidin-2-yl)amino)pyrrolidine-1-carbonyl)-2H-benzo[b][1,4]oxazin-4(3H)-yl)-4-(dimethylamino)but-2-en-1-one as a trifluroacetate salt. $^1$H NMR (400 MHz, DMSO-d$_6$): δ 1.84-2.01 (m, 1H), 2.03-2.22 (m, 1H), 2.81 (s, 6H), 3.20-3.30 (m, 3H), 3.42-3.50 (m, 1H), 3.52-3.58 (m, 1H), 3.61-3.79 (m, 2H), 3.95-3.97 (m, 2H), 4.22-4.44 (m, 2H), 6.72-6.86 (m, 2H), 7.14-7.18 (m, 1H), 7.24-7.33 (m, 1H), 7.80-7.86 (m, 1H), 8.25-8.38 (m, 3H), 9.88 (br s, 1H).

Example 147: Synthesis of (R)—N-(4-(3-((5-cyanopyridin-2-yl)amino)pyrrolidine-1-carbonyl)phenyl)acrylamide

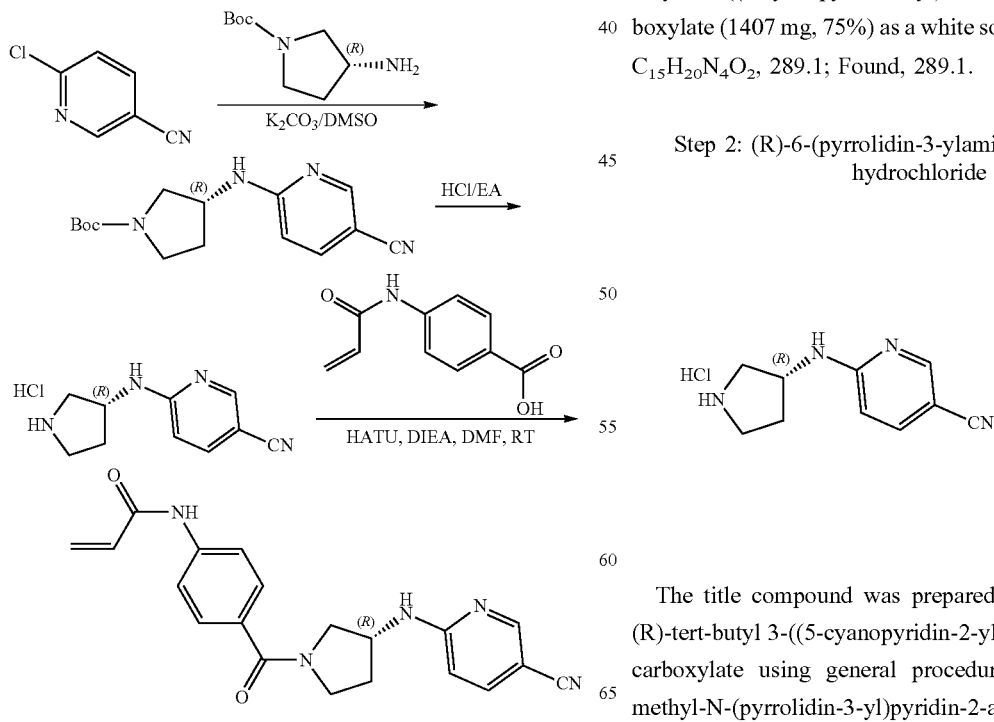

Step 1: (R)-tert-butyl 3-((5-cyanopyridin-2-yl)amino)pyrrolidine-1-carboxylate

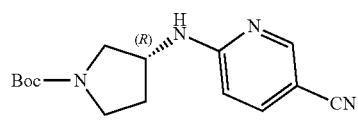

A mixture of 6-chloronicotinonitrile (900 mg, 6.5 mmol), (R)-tert-butyl 3-aminopyrrolidine-1-carboxylate (1931 mg, 10.0 mmol) and K$_2$CO$_3$ (1791 mg, 13.0 mmol) in DMSO (10 mL) was stirred at 90° C. for 2 hours. The mixture was cooled to RT, diluted with water (40 mL) and extracted with EtOAc (30 mL*2). The combined organic phase was washed with brine (30 mL), dried over Na$_2$SO$_4$, filtered and concentrated. The residue was purified by flash chromatography on silica gel (petroleum ether/EtOAc=4/1) to afford (R)-tert-butyl 3-((5-cyanopyridin-2-yl) amino)pyrrolidine-1-carboxylate (1407 mg, 75%) as a white solid. [M+H] Calc'd for C$_{15}$H$_{20}$N$_4$O$_2$, 289.1; Found, 289.1.

Step 2: (R)-6-(pyrrolidin-3-ylamino)nicotinonitrile hydrochloride

The title compound was prepared in 100% yield from (R)-tert-butyl 3-((5-cyanopyridin-2-yl)amino)pyrrolidine-1-carboxylate using general procedure of (R)-5-chloro-4-methyl-N-(pyrrolidin-3-yl)pyridin-2-amine hydrochloride. [M+H] Calc'd for C$_{10}$H$_{12}$N$_4$, 189.1; Found, 189.1.

Step 3: (R)—N-(4-(3-((5-cyanopyridin-2-yl)amino)pyrrolidine-1-carbonyl)phenyl)acrylamide

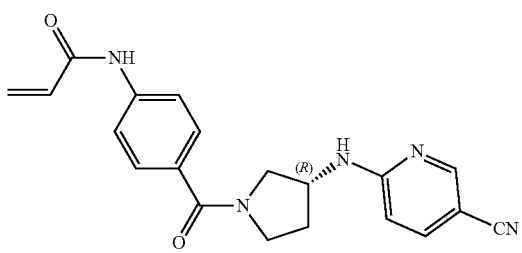

The title compound was prepared in 32% yield from (R)-6-(pyrrolidin-3-ylamino)nicotinonitrile hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.87-1.94 (m, 1H), 2.07-2.23 (m, 1H), 3.43-3.85 (m, 4H), 4.37-4.48 (m, 1H), 5.78 (d, J=10.8 Hz, 1H), 6.28 (d, J=16.8 Hz, 1H), 6.41-6.47 (m, 1H), 6.54-6.61 (m, 1H), 7.50-7.54 (m, 2H), 7.66-7.71 (m, 3H), 7.82-7.90 (m, 1H), 8.34 (s, 0.5H), 8.44 (s, 0.5H), 10.30 (s, 1H). [M+H] Calc'd for C$_{20}$H$_{19}$N$_5$O$_2$, 362.1; Found, 362.1.

Example 148: Synthesis of (R)—N-(4-(3-((5-cyanopyrimidin-2-yl)amino)pyrrolidine-1-carbonyl)phenyl)acrylamide

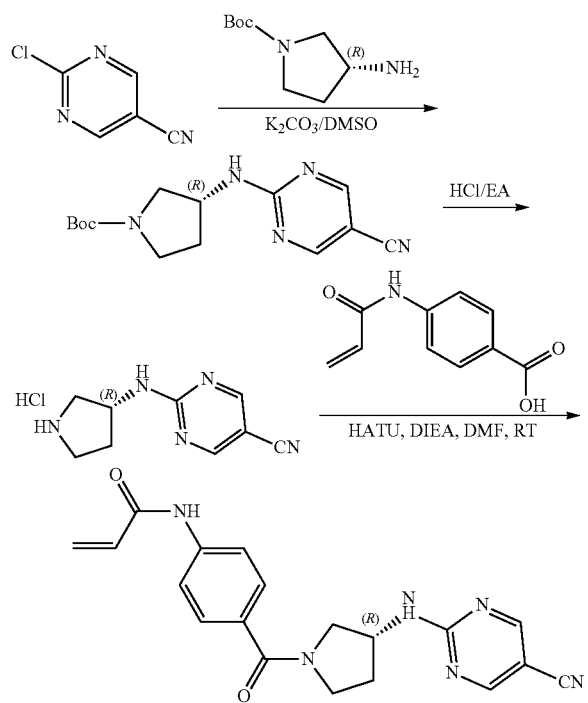

Step 1: (R)-tert-butyl 3-((5-cyanopyrimidin-2-yl)amino)pyrrolidine-1-carboxylate

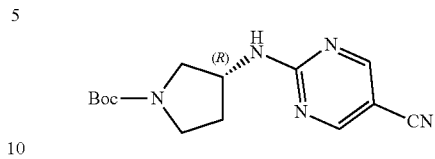

A mixture of 2-chloropyrimidine-5-carbonitrile (600 mg, 4.3 mmol), (R)-tert-butyl 3-aminopyrrolidine-1-carboxylate (1287 mg, 6.9 mmol) and K$_2$CO$_3$ (1194 mg, 8.6 mmol) in DMSO (5 mL) was stirred at 90° C. for 3 hours. The mixture was cooled to RT, diluted with water (30 mL) and extracted with EtOAc (20 mL*2). The combined organic phase was washed with brine (20 mL), dried over Na$_2$SO$_4$, filtered and concentrated in vacuo. The residue was purified by flash chromatography on silica gel (petroleum ether/EtOAc=10/1) to afford (R)-tert-butyl 3-((5-cyanopyrimidin-2-yl)amino)pyrrolidine-1-carboxylate (1.09 g, 88%) as a pink solid. [M+H]Calc'd for C$_{14}$H$_{19}$N$_5$O$_2$, 290.1; Found, 290.1.

Step 2: (R)-2-(pyrrolidin-3-ylamino)pyrimidine-5-carbonitrile hydrochloride

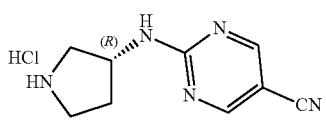

The title compound was prepared in 100% yield from (R)-tert-butyl 3-((5-cyanopyrimidin-2-yl)amino)pyrrolidine-1-carboxylate using general procedure of (R)-5-chloro-4-methyl-N-(pyrrolidin-3-yl)pyridin-2-amine hydrochloride. [M+H] Calc'd for C$_9$H$_{11}$N$_5$, 190.1; Found, 190.1.

Step 3: (R)—N-(4-(3-((5-cyanopyrimidin-2-yl)amino)pyrrolidine-1-carbonyl)phenyl)acrylamide

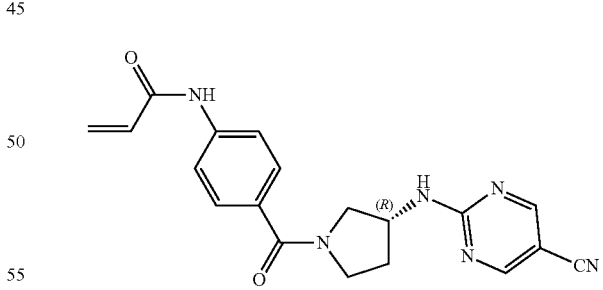

The title compound was prepared in 29% yield from (R)-2-(pyrrolidin-3-ylamino)pyrimidine-5-carbonitrile hydrochloride using general procedure of (R)—N-(4-(3-((5-chloro-4-methylpyrimidin-2-yl)amino)pyrrolidine-1-carbonyl)phenyl)acrylamide. $^1$H NMR (400 MHz, DMSO-d$_6$): δ 1.93-2.07 (m, 1H), 2.12-2.21 (m, 1H), 3.36-3.82 (m, 4H), 4.37-4.48 (m, 1H), 5.79 (d, J=10.0 Hz, 1H), 6.28 (d, J=16.8 Hz, 1H), 6.41-6.47 (m, 1H), 7.49-7.54 (m, 2H), 7.68-7.75 (m, 2H), 8.66-8.78 (m, 3H), 10.31 (s, 1H). [M+H] Calc'd for C$_{19}$H$_{18}$N$_6$O$_2$, 363.1; Found, 363.1.

Example 149: Synthesis of (R,E)-1-(6-(3-((5-chloropyrimidin-2-yl)amino)pyrrolidine-1-carbonyl)-3,4-dihydroisoquinolin-2(1H)-yl)-4-(dimethylamino)but-2-en-1-one

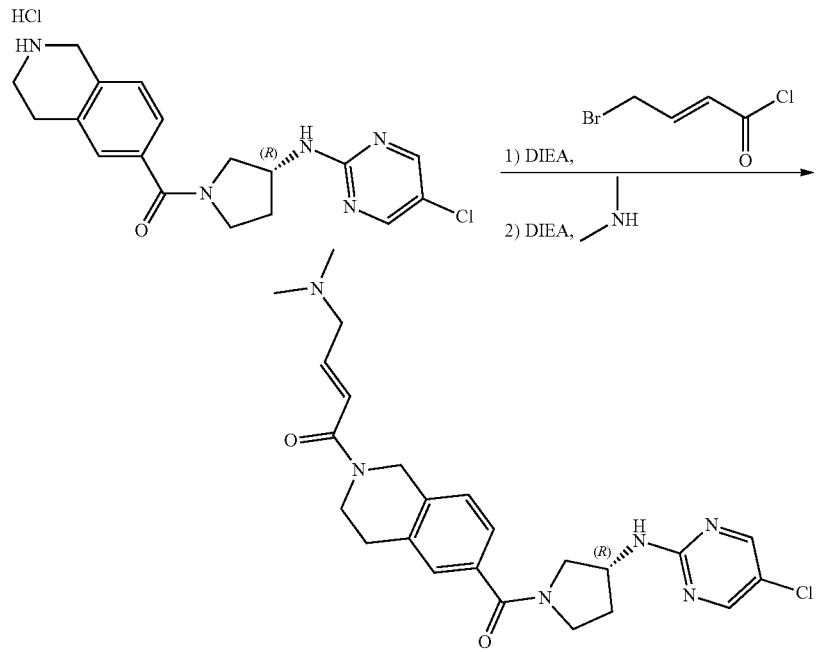

The title compound was prepared in 19% yield from (R)-(3-((5-chloropyrimidin-2-yl)amino)pyrrolidin-1-yl)(1,2,3,4-tetrahydroisoquinolin-6-yl)methanone hydrochloride using general procedure of (R,E)-1-(8-(3-((5-chloropyrimidin-2-yl)amino)pyrrolidine-1-carbonyl)-2H-benzo[b][1,4]oxazin-4(3H)-yl)-4-(dimethylamino)but-2-en-1-one. $^1$H NMR (400 MHz, DMSO-d$_6$): δ 1.86-2.00 (m, 1H), 2.09-2.15 (m, 1H), 2.18 (s, 6H), 2.81-2.86 (m, 2H), 3.04 (d, J=3.6 Hz, 2H), 3.40-3.68 (m, 3H), 3.70-3.78 (m, 3H), 4.23-4.40 (m, 1H), 4.67-4.78 (m, 2H), 6.64-6.67 (m, 2H), 7.24-7.35 (m, 3H), 7.78-7.82 (m, 1H), 8.31 (s, 1H), 8.38 (s, 1H). [M+H] Calc'd for C$_{24}$H$_{29}$ClN$_6$O$_2$, 469.2; Found, 469.2.

Example 150: (R,E)-N-(6-(3-((5-chloro-4-methoxypyrimidin-2-yl)amino)pyrrolidine-1-carbonyl)pyridin-3-yl)but-2-enamide

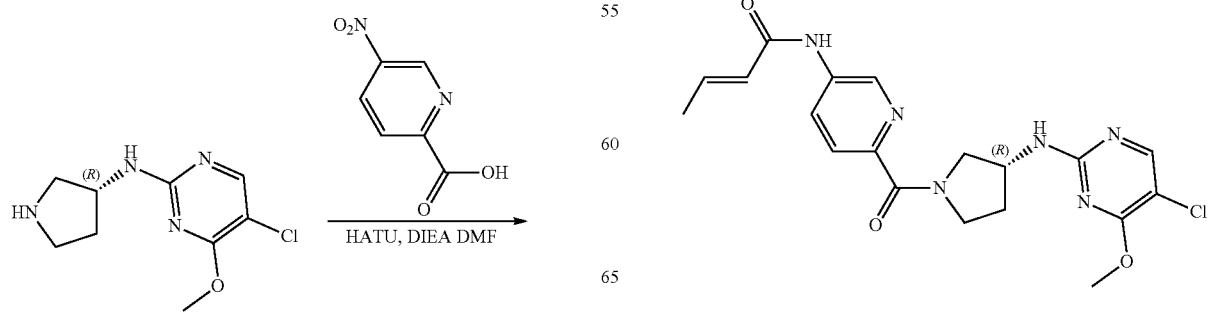

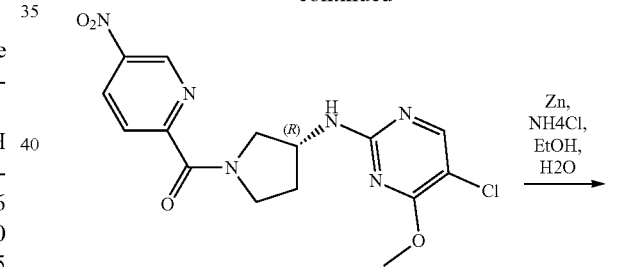

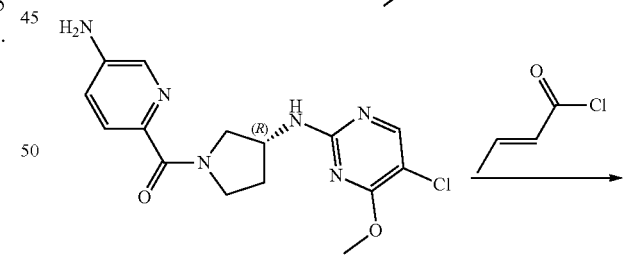

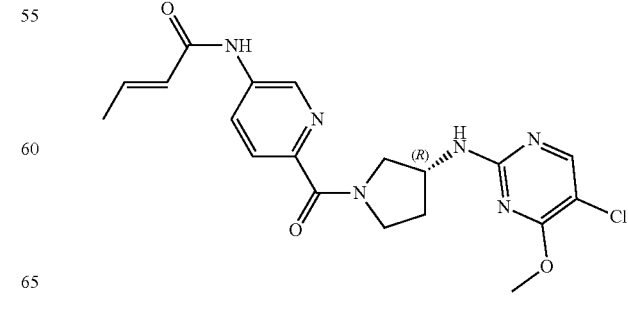

Step 1: (R)-(3-((5-chloro-4-methoxypyrimidin-2-yl)amino)pyrrolidin-1-yl)(5-nitropyridin-2-yl)methanone

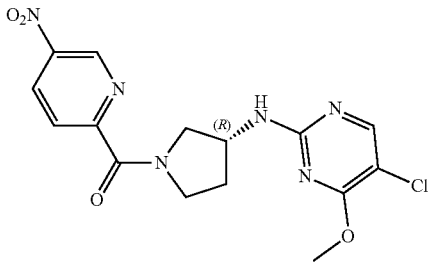

A mixture of (R)-5-chloro-4-methoxy-N-(pyrrolidin-3-yl)pyrimidin-2-amine (2.2 g, 10.0 mmol), 5-nitropicolinic acid (1.7 g, 10.0 mmol), HATU (3.8 g, 10.0 mmol) and DIEA (3.9 g, 30.0 mmol) in DMF (30 mL) was stirred at RT for overnight. The reaction mixture was concentrated to get the crude product (R)-(3-((5-chloro-4-methoxypyrimidin-2-yl)amino)pyrrolidin-1-yl)(5-nitropyridin-2-yl)methanone (3.4 g, 94%) as a yellow solid. [M+H] MS Calc'd: $C_{15}H_{15}ClN_6O_4$, 379.1; Found: 379.1.

Step 2: (R)-(5-aminopyridin-2-yl)(3-((5-chloro-4-methoxypyrimidin-2-yl)amino)pyrrolidin-1-yl)methanone

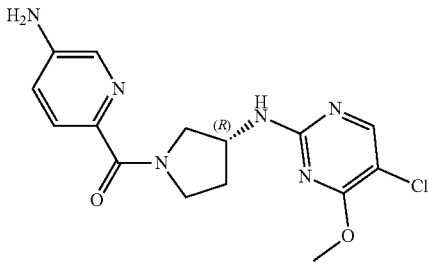

To a solution of (R)-(3-((5-chloro-4-methoxypyrimidin-2-yl)amino)pyrrolidin-1-yl)(5-nitropyridin-2-yl)methanone (3.4 g, 9.0 mmol) in EtOH (150 mL) and $H_2O$ (15 mL) was added Zn (5.9 g, 89.9 mmol) and $NH_4Cl$ (4.8 g, 89.9 mmol). The reaction mixture was stirred at 80° C. for 2 h. The reaction mixture was concentrated and the residue was purified by column chorography on silica gel to get (R)-(5-aminopyridin-2-yl)(3-((5-chloro-4-methoxypyrimidin-2-yl)amino)pyrrolidin-1-yl)methanone (2.0 g, 68%) as a white solid. [M+H] MS Calc'd: $C_{15}H_{17}ClN_6O_2$, 349.1; Found: 349.1.

Step 3: (R,E)-N-(6-(3-((5-chloro-4-methoxypyrimidin-2-yl)amino)pyrrolidine-1-carbonyl)pyridin-3-yl)but-2-enamide

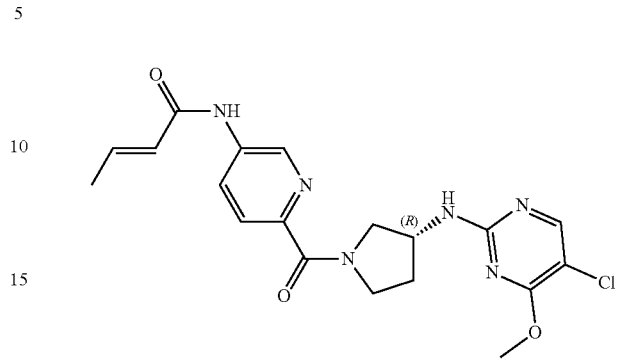

To a solution of (R)-(5-aminopyridin-2-yl)(3-((5-chloro-4-methoxypyrimidin-2-yl)amino)pyrrolidin-1-yl)methanone (400 mg, 1.15 mmol) and DIEA (450 mg, 3.45 mmol) in DCM (20 mL) and DMF (2 mL) was added (E)-but-2-enoyl chloride (143 mg, 1.38 mmol) at ice-bath. The reaction mixture was stirred at RT for 2 h. The reaction mixture was concentrated and the residue was purified by prep-HPLC to afford (R,E)-N-(6-(3-((5-chloro-4-methoxypyrimidin-2-yl)amino)pyrrolidine-1-carbonyl)pyridin-3-yl)but-2-enamide (33.2 mg, 7%) as a white solid. $^1$H NMR (400 MHz, DMSO-$d_6$): 1.89 (d, J=6.8 Hz, 3H), 1.96-2.00 (m, 1H), 2.11-2.13 (m, 1H), 3.48-3.80 (m, 3H), 3.88 (s, 3H), 3.93 (s, 1H), 4.75-4.76 (m, 1H), 6.15-6.16 (s, 1H), 6.84-6.90 (m, 1H), 7.66-7.78 (m, 2H), 8.09-8.19 (m, 2H), 8.77-8.81 (m, 1H), 10.35 (d, J=5.2 Hz, 1H). [M+H]MS Calc'd: $C_{19}H_{21}ClN_6O_3$, 417.1; Found: 417.2.

Example 151: (R)—N-(4-(3-((5-chloro-4-methoxypyrimidin-2-yl)amino)pyrrolidine-1-carbonyl)phenyl)but-2-ynamide

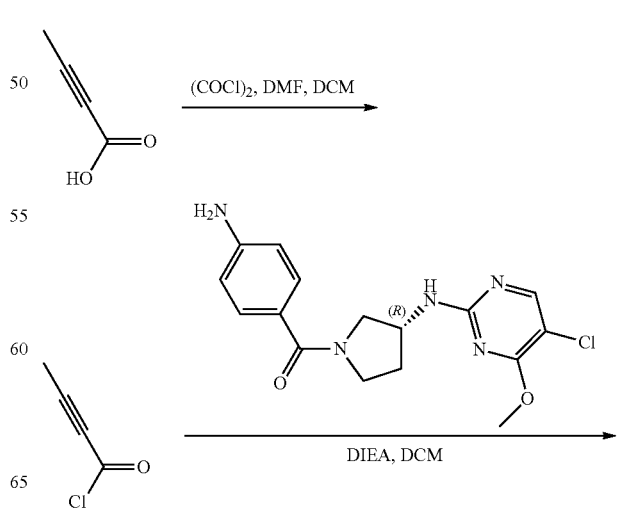

397

-continued

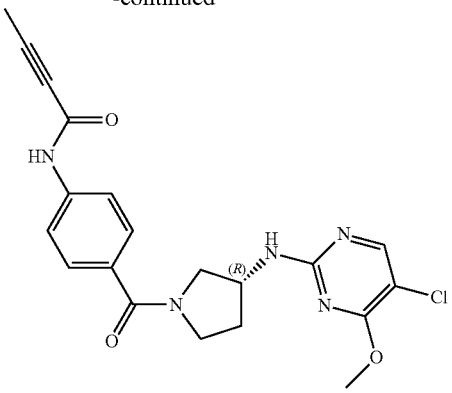

Step 1: but-2-ynoyl chloride

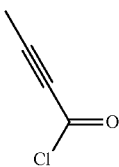

To a solution of but-2-ynoic acid (800 mg, 9.52 mmol) in DCM (5 mL) was added DMF (1 drop) and (COCl)₂ (1.01 g, 9.52 mmol) at 0° C. under N₂ atmosphere and allowed to stir at 0° C. for 5 min. The crude reaction mixture was used directly in the next step without any additional workup or purification.

Step 2: (R)—N-(4-(3-((5-chloro-4-methoxypyrimidin-2-yl)amino)pyrrolidine-1-carbonyl)phenyl)but-2-ynamide

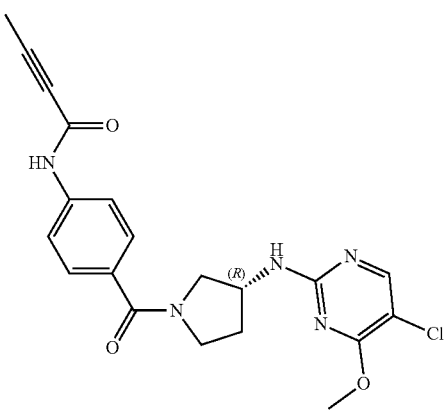

To a solution of (R)-(4-aminophenyl)(3-((5-chloro-4-methoxypyrimidin-2-yl)amino)pyrrolidin-1-yl)methanone hydrochloride (450 mg, 1.17 mmol) and DIEA (1.23 g, 9.52 mmol) in DCM (15 mL) was added but-2-ynoyl chloride (9.52 mmol) dropwise in an ice-bath. The reaction mixture was stirred at 0° C. for 5 min. The reaction mixture was concentrated in-vacuo and the residue was purified by prep-HPLC to afford (R)—N-(4-(3-((5-chloro-4-methoxy-

398 pyrimidin-2-yl)amino)pyrrolidine-1-carbonyl)phenyl)but-2-ynamide (59.4 mg, 12.2%) as a white solid. ¹H NMR (400 MHz, DMSO-d₆): 1.89-2.14 (m, 5H), 3.36-3.79 (m, 4H), 3.86-3.94 (m, 3H), 4.26-4.42 (m, 1H), 7.46-7.65 (m, 5H), 8.07-8.14 (m, 1H), 10.76 (s, 1H). [M+H] MS Calc'd: $C_{20}H_{20}ClN_5O_3$, 414.1; Found: 414.1.

Example 152: Synthesis of (R)—N-(6-(3-((5-chloro-4-ethoxypyrimidin-2-yl)amino)pyrrolidine-1-carbonyl)pyridin-3-yl)acrylamide

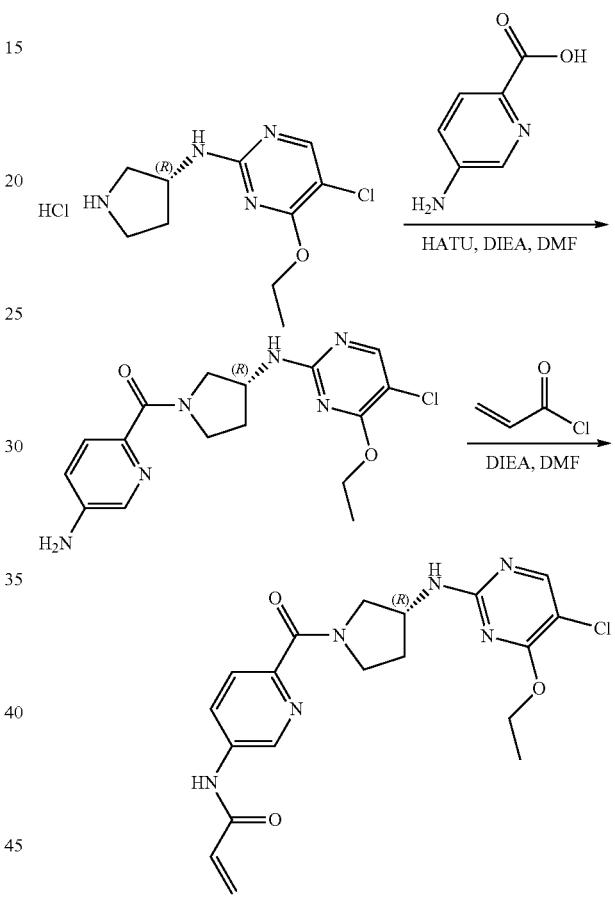

Step 1: (R)-(5-aminopyridin-2-yl)(3-((5-chloro-4-ethoxypyrimidin-2-yl)amino)pyrrolidin-1-yl)methanone

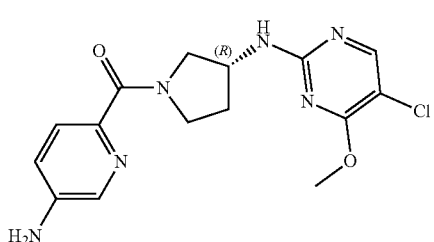

A mixture of (R)-5-chloro-4-ethoxy-N-(pyrrolidin-3-yl)pyrimidin-2-amine HCl salt (1.63 g, 5.84 mmol), 5-aminopicolinic acid (807 mg, 5.85 mmol), HATU (2.66 g, 7.02 mmol) and DIEA (3.02 g, 23.4 mmol) in DMF (25 mL) was stirred at RT for overnight. To the reaction mixture was added H₂O (150 mL) and extracted with Ethyl Acetate. The combined organic layer was dried over Na₂SO₄, filtered and concentrated. The residue was purified by silica gel chromatography (DCM/MeOH=100/1~20/1) to afford (R)-(5-aminopyridin-2-yl)(3-((5-chloro-4-ethoxypyrimidin-2-yl)amino)pyrrolidin-1-yl)methanone (1.0 g, 48%) as a yellow solid. [M+H]Calc'd for C₁₆H₁₉ClN₆O₂, 363.1; Found, 363.1.

Step 2: (R)—N-(6-(3-((5-chloro-4-ethoxypyrimidin-2-yl)amino)pyrrolidine-1-carbonyl)pyridin-3-yl)acrylamide

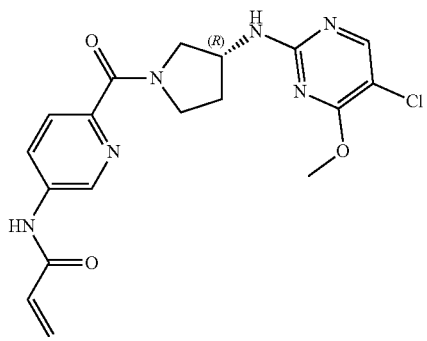

A mixture of (R)-(5-aminopyridin-2-yl)(3-((5-chloro-4-ethoxypyrimidin-2-yl)amino)pyrrolidin-1-yl)methanone (1.0 g, 2.76 mmol) and DIEA (712 mg, 5.52 mmol) in DMF (30 mL) was stirred at 0° C. under nitrogen atmosphere. Acryloyl chloride (275 mg, 3.04 mmol) was added dropwise and the mixture was warmed to RT and stirred for overnight. The mixture was concentrated in vacuo and purified by prep-HPLC to afford (R)—N-(6-(3-((5-chloro-4-ethoxypyrimidin-2-yl)amino)pyrrolidine-1-carbonyl)pyridin-3-yl)acrylamide (287.8 mg, 26%) as a white solid. ¹H NMR (400 MHz, DMSO-d₆): δ 1.27-1.36 (m, 3H), 1.94-2.00 (m, 1H), 2.08-2.19 (m, 1H), 3.49-4.05 (m, 4H), 4.30-4.42 (m, 3H), 5.83-5.86 (m, 1H), 6.30-6.35 (m, 1H), 6.42-6.50 (m, 1H), 7.63 (s, 1H), 7.77-7.80 (m, 1H), 8.09-8.23 (m, 2H), 8.80-8.85 (m, 1H), 10.54-10.56 (m, 1H). [M+H]Calc'd for C₁₉H₂₁ClN₆O₃, 417.1; Found, 417.1.

Example 153: (R)—N-(4-(3-((5-chloro-4-(2-ethoxyethoxy)pyrimidin-2-yl)amino)pyrrolidine-1-carbonyl)phenyl)acrylamide

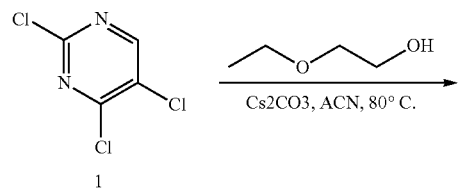

Step 1: 2,5-dichloro-4-(2-ethoxyethoxy)pyrimidine

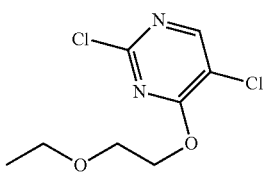

To a solution of 2,4,5-trichloropyrimidine (2.5 g, 13.7 mmol) and 2-ethoxyethanol (1.1 g, 12.3 mmol) in CH₃CN (40 mL) was added Cs₂CO₃ (6.6 g, 20.5 mmol) at RT. The reaction mixture was stirred at 80° C. for 4 h. The mixture was cooled, diluted with water (200 mL) and extracted with Ethyl Acetate (100 mL). The combined organic layer was washed with brine (100 mL), dried over Na₂SO₄ filtered and evaporated. The residue was purified by column chromatography to afford 1.8 g of product as a off white solid. [M+H] Calc'd for C₈H₁₀Cl₂N₂O₂, 237.1; Found, 237.1.

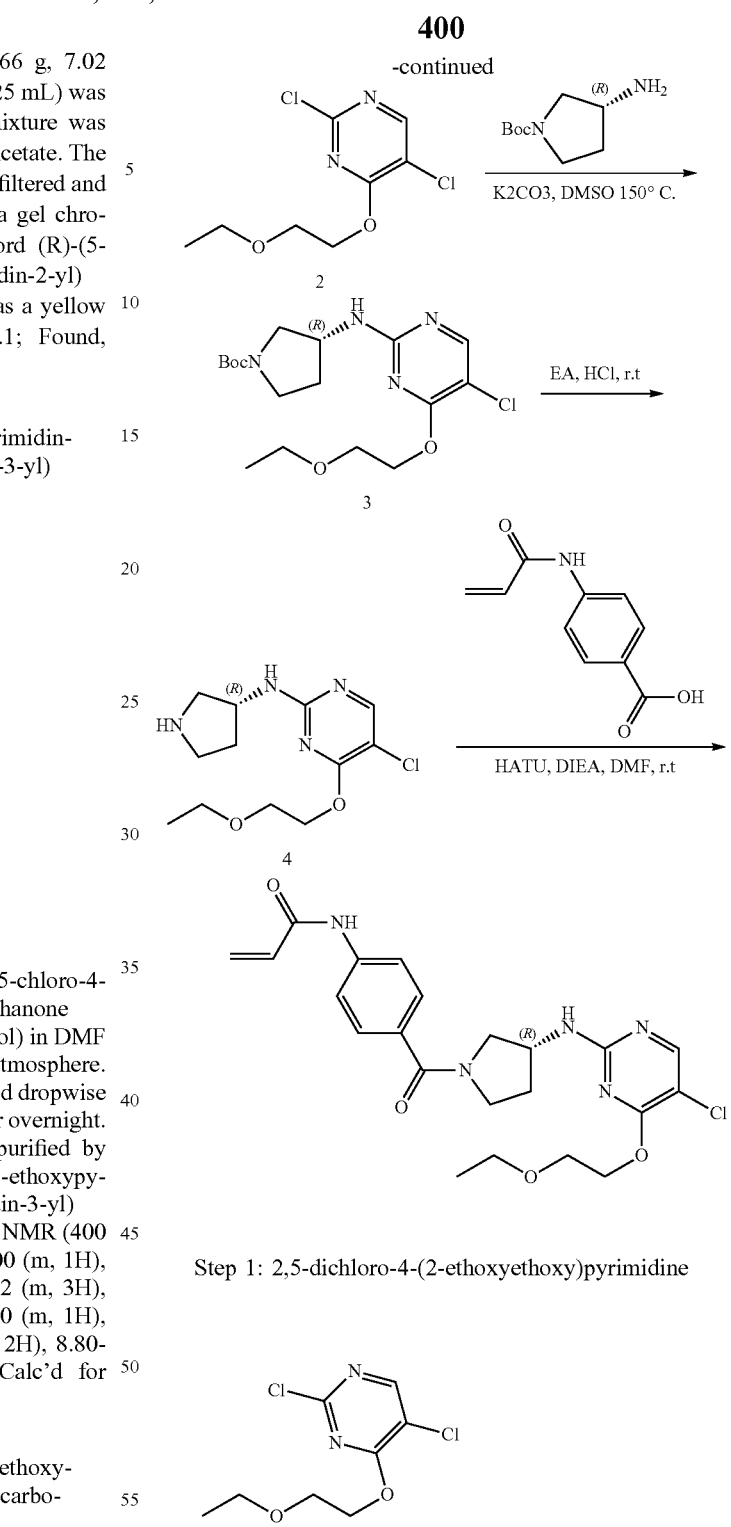

Step 2: (R)-tert-butyl 3-((5-chloro-4-(2-ethoxyethoxy)pyrimidin-2-yl)amino)pyrrolidine-1-carboxylate

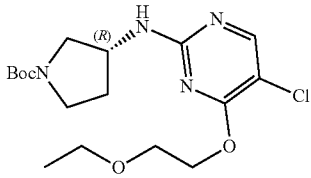

To a solution of 2,5-dichloro-4-(2-ethoxyethoxy)pyrimidine (1.8 g, 7.6 mmol) and (R)-tert-butyl 3-aminopyrrolidine-1-carboxylate (2.8 g, 15.3 mmol) in DMSO (25 mL) was added $K_2CO_3$ (2.1 g, 15.3 mmol) at RT. The reaction mixture was stirred at 150° C. for 4 h. The reaction mixture was cooled, added water and extracted with Ethyl Acetate. The combined organic layer was washed with brine (100 mL), dried over $Na_2SO_4$, filtered and concentrated in vacuo. The residue was purified by column chromatography to afford 1.8 g crude product as colorless oil. [M+H] Calc'd for $C_{17}H_{27}ClN_4O_4$, 387.1; Found, 387.1.

Step 3: (R)-5-chloro-4-(2-ethoxyethoxy)-N-(pyrrolidin-3-yl)pyrimidin-2-amine

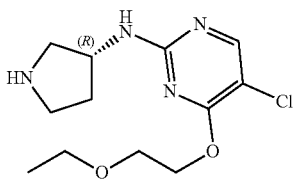

To a solution of (R)-tert-butyl 3-((5-chloro-4-(2-ethoxyethoxy)pyrimidin-2-yl)amino)pyrrolidine-1-carboxylate (1.8 g, 4.66 mmol) in Ethyl Acetate (20 mL) was bubbled HCl (gas) at −50° C. The reaction mixture was stirred at RT for 3 h. The mixture was concentrated in vacuo to afford 1.5 g crude product as a yellow solid. [M+H] Calc'd for $C_{12}H_{19}ClN_4O_2$, 287.1; Found, 287.1

Step 4: (R)—N-(4-(3-((5-chloro-4-(2-ethoxyethoxy)pyrimidin-2-yl)amino)pyrrolidine-1-carbonyl)phenyl)acrylamide

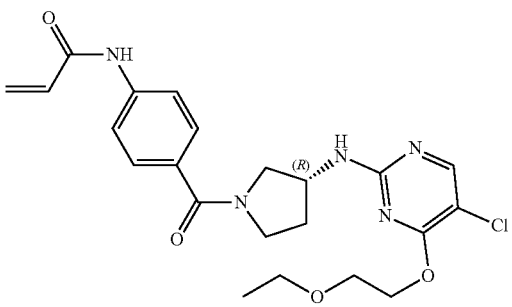

To a solution of (R)-5-chloro-4-(2-ethoxyethoxy)-N-(pyrrolidin-3-yl)pyrimidin-2-amine (150 mg, 0.5 mmol) and 4-acrylamidobenzoic acid (100 mg, 0.5 mmol) in DMF (3 ml) was added HATU (228 mg, 0.6 mmol) and DIEA (193 mg, 1.5 mmol) at RT. The reaction mixture was stirred at RT for 2 h. The reaction mixture was concentrated in vacuo. The residue was purified by prep-HPLC to afford (R)—N-(4-(3-((5-chloro-4-(2-ethoxyethoxy)pyrimidin-2-yl)amino)pyrrolidine-1-carbonyl)phenyl)acrylamide (17.4 mg, 8%) as a white solid. $^1H$ NMR (400 MHz, DMSO-$d_6$): 1.05-1.13 (m, 3H), 1.90-2.16 (m, 2H), 3.48-3.71 (m, 8H), 4.21-4.47 (m, 3H), 5.77-5.79 (d, J=10.4 Hz, 1H), 6.25 (s, 0.5H), 6.29 (s, 0.5H), 6.40-6.43 (m, 1H), 7.48-7.53 (m, 2H), 7.69-7.72 (m, 3H), 8.08-8.15 (m, 1H), 10.29 (s, 1H). [M+H] Calc'd for $C_{22}H_{26}ClN_5O_4$, 460.1; Found, 460.1.

Example 154: Synthesis of (R)—N-(4-(3-((5-chloro-4-(trideuteromethoxy)pyrimidin-2-yl)amino)pyrrolidine-1-carbonyl)phenyl)propiolamide

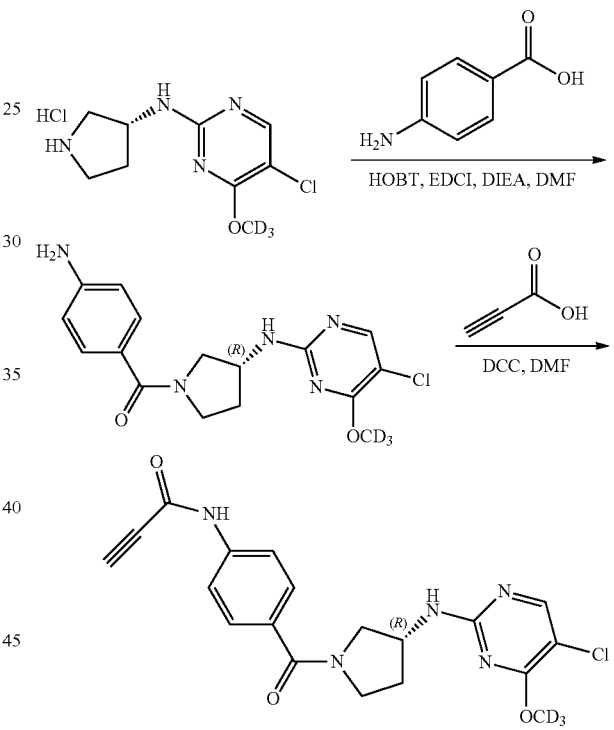

Step 1: (R)-(4-aminophenyl)(3-((5-chloro-4-(trideuteromethoxy)pyrimidin-2-yl)amino)pyrrolidin-1-yl)methanone

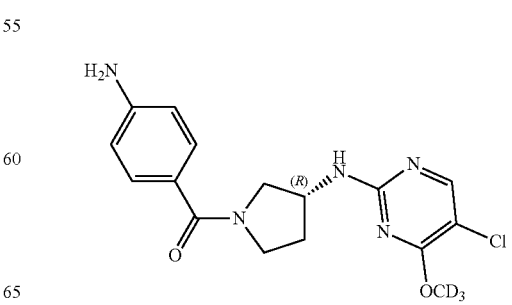

To a solution of (R)-5-chloro-N-(pyrrolidin-3-yl)-4-(trideuteromethoxy)pyrimidin-2-amine hydrochloride (400 mg, 1.49 mmol) and 4-aminobenzoic acid (205 mg, 1.49 mmol) in DMF (6 mL) was added HOBt (349 mg, 2.24 mmol), EDCI (429 mg, 2.24 mmol) and DIEA (577 mg, 4.47 mmol) at ice-bath. The reaction mixture was stirred at RT for 3 hours. After completion of the reaction, the mixture was diluted with water (20 mL) and extracted with EtOAc (20 mL*2). The combined organic layer was washed with brine, dried over anhydrous sodium sulfate, filtered and concentrated under reduced pressure. The residue was purified by C18 reversed phase chromatography (20-95% ACN in $H_2O$) to give (R)-(4-aminophenyl)(3-((5-chloro-4-(trideuteromethoxy)pyrimidin-2-yl)amino)pyrrolidin-1-yl)methanone (310 mg, 59% yield) as a white solid. [M+H] Calc'd: $C_{16}H_{15}D_3ClN_5O_2$, 351.1; Found: 351.1.

Step 2: (R)—N-(4-(3-((5-chloro-4-(trideuteromethoxy)pyrimidin-2-yl)amino)pyrrolidine-1-carbonyl)phenyl)propiolamide

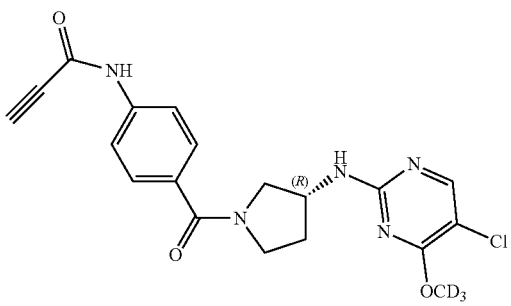

To a solution of DCC (56 mg, 0.27 mmol) in DMF (2 mL) was added propiolic acid (16 mg, 0.22 mmol) slowly at 0° C. under $N_2$ and the mixture was stirred at 0° C. for 1 h before the addition of (R)-(4-aminophenyl)(3-((5-chloro-4-(trideuteriomethoxy)pyrimidin-2-yl)amino)pyrrolidin-1-yl)methanone (65 mg, 0.18 mmol) in DMF (2 mL). The mixture was stirred at 0° C. for 1.5 h, then warmed to room temperature for overnight. After completion of the reaction, the mixture was diluted with water and the mixture was extracted with DCM (50 mL*2), combined the extracts and washed with brine (50 mL), dried over anhydrous sodium sulfate, filtered, and concentrated under reduced pressure. The residue was purified by C18 reversed phase chromatography (20-95% ACN in $H_2O$) to give (R)—N-(4-(3-((5-chloro-4-(trideuteriomethoxy)pyrimidin-2-yl)amino)pyrrolidine-1-carbonyl)phenyl)propiolamide (5 mg, 7% yield) as pale yellow solid. $^1$H NMR (400 MHz, $CDCl_3$): 1.98-2.03 (m, 1H), 2.23-2.36 (m, 1H), 2.97 (s, 1H), 3.38-3.41 (m, 0.5H), 3.56-3.90 (m, 3H), 4.00-4.03 (m, 0.5H), 4.44-4.56 (m, 1H), 5.09-5.21 (m, 0.5H), 7.51-7.56 (m, 4H), 7.86 (s, 1H), 7.97 (s, 0.5H), 8.03 (s, 0.5H). [M+H] Calc'd for $C_{19}H_{15}D_3ClN_5O_3$, 403.1; Found, 403.1.

Example 155: Synthesis of (S)—N-(4-(3-((5-chloropyrimidin-2-yl)amino)pyrrolidine-1-carbonyl)phenyl)acrylamide

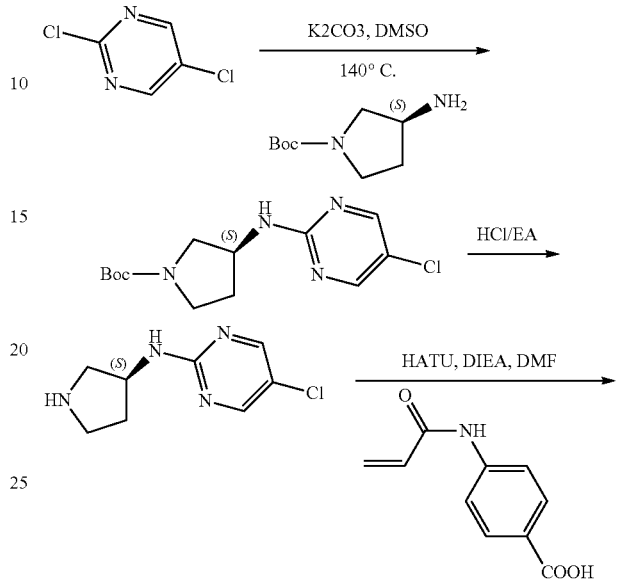

Step 1: (S)-tert-butyl 3-((5-chloropyrimidin-2-yl)amino)pyrrolidine-1-carboxylate

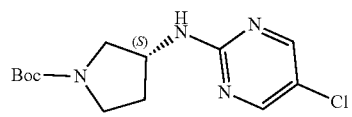

A mixture of 2,5-dichloropyrimidine (2.0 g, 6.7 mmol), (S)-tert-butyl 3-aminopyrrolidine-1-carboxylate (3.0 g, 8.1 mmol) and $K_2CO_3$ (3.7 g, 26.8 mmol) in DMSO (20 mL) was stirred at 140° C. for 4 h. The reaction mixture was cooled, added $H_2O$ (100 mL) and extracted with Ethyl Acetate (100 mL*2), washed with brine (100 mL), dried over $Na_2SO_4$, filtered and concentrated. The residue was purified by silica gel chromatography (PE/EA=1/5 to 1/3) to afford (S)-tert-butyl 3-((5-chloropyrimidin-2-yl)amino)pyrrolidine-1-carboxylate (2.5 g, 63%) as a yellow solid. [M+H] Calc'd for $C_{13}H_{19}ClN_4O_2$, 299.1; Found, 299.1.

Step 2: (S)-5-chloro-N-(pyrrolidin-3-yl)pyrimidin-2-amine

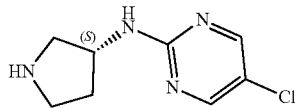

A mixture of (S)-tert-butyl 3-((5-chloropyrimidin-2-yl)amino)pyrrolidine-1-carboxylate (2.5 g, 84 mmol) in HCl/EA (10 mL) was stirred at RT for 1 h. The reaction mixture was concentrated to afford (S)-5-chloro-N-(pyrrolidin-3-yl)pyrimidin-2-amine (2.5 g, 100%) as a yellow solid. [M+H] Calc'd for $C_{18}H_{18}ClN_4$, 199.1; Found, 199.1

Step 3: (S)—N-(4-(3-((5-chloropyrimidin-2-yl)amino)pyrrolidine-1-carbonyl) phenyl)acryl amide

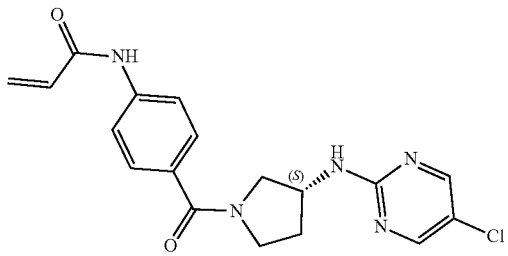

A mixture of (S)-5-chloro-N-(pyrrolidin-3-yl)pyrimidin-2-amine (700 mg, 3.7 mmol), 4-acrylamidobenzoic acid (802 mg, 4.0 mmol), HATU (1.39 g, 3.7 mmol) and DIEA (946 mg, 7.3 mmol) in DMF (25 mL) was stirred at RT for 4 h. To this reaction mixture was added $H_2O$ (100 mL) and extracted with EA (100 mL*2), washed with brine (100 mL). The organic layer was dried over $Na_2SO_4$, filtered and concentrated. The residue was purified by prep-HPLC to afford (S)—N-(4-(3-((5-chloropyrimidin-2-yl)amino)pyrrolidine-1-carbonyl)phenyl)acrylamide (358 mg, 27%) as a white solid. $^1$H NMR (400 MHz, DMSO-$d_6$): 1.90-1.99 (m, 1H), 2.12-2.17 (m, 1H), 3.28-3.82 (m, 4H), 4.24-4.39 (m, 1H), 5.76-5.79 (d, J=11.2 Hz, 1H), 6.25-6.30 (d, J=16.8 Hz, 1H), 6.41-6.47 (m, 1H), 7.48-7.53 (m, 2H), 7.68-7.72 (m, 2H), 7.79-7.83 (m, 1H), 8.31 (s, 1H), 8.38 (s, 1H), 10.29 (s, 1H). [M+H] Calc'd for $C_{18}H_{18}ClN_5O_2$, 372.1; Found, 372.1.

Example 156: Synthesis of (R)—N-(4-(3-((5-bromopyrimidin-2-yl)amino)pyrrolidine-1-carbonyl)-2-(2-morpholinoethoxy)phenyl)acrylamide

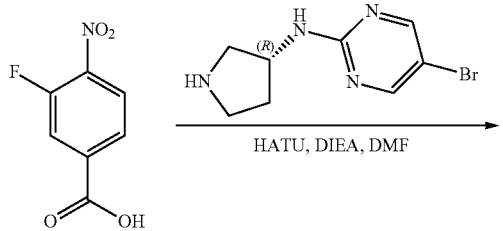

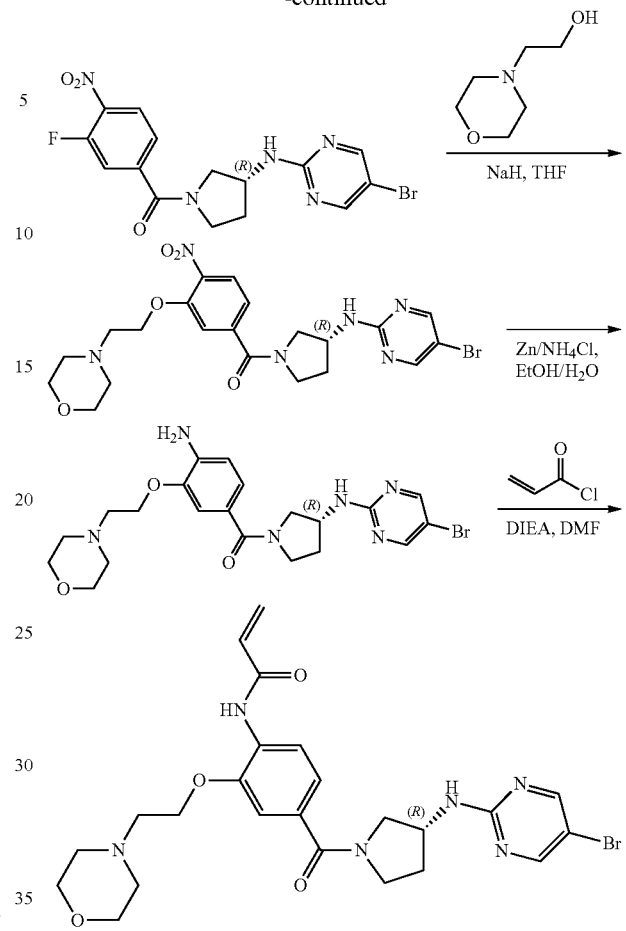

Step 1: (R)-(3-((5-bromopyrimidin-2-yl)amino)pyrrolidin-1-yl)(3-fluoro-4-nitrophenyl)methanone

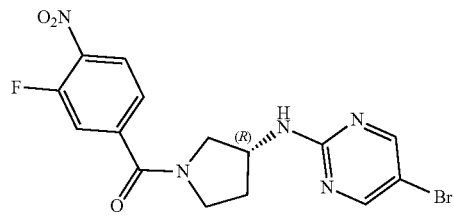

A mixture of 3-fluoro-4-nitrobenzoic acid (5.0 g, 27.0 mmol), (R)-5-bromo-N-(pyrrolidin-3-yl)pyrimidin-2-amine (7.8 g, 32.4 min), HATU (15.4 g, 40 mmol) and DIEA (7.0 g, 54 mmol) in DMF (70 mL) was stirred at RT for 16 hrs. The mixture was diluted with $H_2$ (10 mL) and extracted with EA (200 mL*2). The combined organic layer was dried over $Na_2SO_4$, filtered and concentrated. The residue was purified by silica gel chromatography to give (R)-(3-((5-bromopyrimidin-2-yl)amino)pyrrolidin-1-yl)(3-fluoro-4-nitrophenyl)methanone (7.0 g, 640) as yellow oil. [M+H] Calc'd for $C_{15}H_{13}BrFN_5O_3$, 410.0; Found, 410.0.

Step 2: (R)-(3-((5-bromopyrimidin-2-yl)amino)pyrrolidin-1-yl)(3-(2-morpholinoethoxy)-4-nitrophenyl)methanone

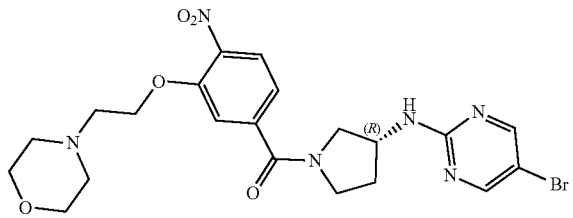

A mixture of 2-morpholinoethanol (192 mg, 1.5 mmol) in THF (20 mL) was stirred at 0° C. NaH (132 mg, 3.4 mmol, 600%) was added. The reaction mixture was stirred at RT for 20 min and then (R)-(3-((5-bromopyrimidin-2-yl)amino)pyrrolidin-1-yl)(3-fluoro-4-nitrophenyl)methanone (600 mg, 1.5 mmol) was added. The reaction mixture was then stirred at RT overnight. The mixture was diluted with water (20 mL) and extracted with EA (20 mL*3). The combined organic layer was washed with brine (20 mL), dried over $Na_2SO_4$, filtered and concentrated and purified by silica gel chromatography to afford (R)-(3-((5-bromopyrimidin-2-yl)amino)pyrrolidin-1-yl)(3-(2-morpholinoethoxy)-4-nitrophenyl)methanone (466 mg, 60%) as yellow solid. [M+H] Calc'd for $C_{21}H_{25}BrN_6O_5$, 521.1; Found, 521.1

Step 3: (R)-(4-amino-3-(2-morpholinoethoxy)phenyl)(3-((5-bromopyrimidin-2-yl)amino)pyrrolidin-1-yl)methanone

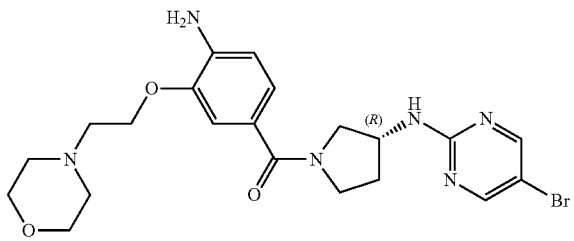

A mixture of (R)-(3-((5-bromopyrimidin-2-yl)amino)pyrrolidin-1-yl)(3-(2-morpholinoethoxy)-4-nitrophenyl)methanone (260 mg, 0.5 mmol) and $NH_4Cl$ (268 mg, 5.0 mmol) in $MeOH/H_2O$ (10 mL/2 mL) was stirred at 50° C. for 1 h. Zn (325 mg, 5 mmol) was added to the mixture at RT and then warmed to 70° C. for 3 h. The mixture was filtered and concentrated to afford (R)-(4-amino-3-(2-morpholinoethoxy)phenyl)(3-((5-bromopyrimidin-2-yl)amino)pyrrolidin-1-yl)methanone (200 mg, 84%) as a yellow solid. [M+H] Calc'd for $C_{21}H_{27}BrN_6O_3$, 491.1; Found, 491.1.

Step 4: (R)—N-(4-(3-((5-bromopyrimidin-2-yl)amino)pyrrolidine-1-carbonyl)-2-(2-morpholinoethoxy)phenyl)acrylamide

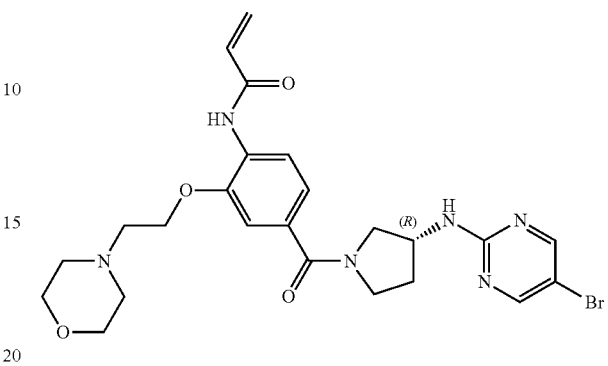

A mixture of (R)-(4-amino-3-(2-morpholinoethoxy)phenyl)(3-((5-bromopyrimidin-2-yl)amino)pyrrolidin-1-yl)methanone (200 mg, 0.41 mmol) and DIEA (129 mg, 1 mmol) in DCM (10 mL) was stirred at 0° C. under nitrogen atmosphere. Acryloyl chloride (37 mg, 0.41 mmol) was added dropwise and the mixture was warmed to RT and stirred for 1 h. The mixture was concentrated and purified by prep-HPLC to afford (R)—N-(4-(3-((5-bromopyrimidin-2-yl)amino)pyrrolidine-1-carbonyl)-2-(2-morpholinoethoxy)phenyl)acrylamide (129.7 mg, 58%) as a white solid. 1H NMR (400 MHz, DMSO-$d_6$): δ 1.90-2.16 (m, 2H), 2.44-2.51 (m, 4H), 2.70-2.76 (m, 2H), 3.34-3.37 (m, 1H), 3.54-3.55 (m, 5H), 3.64-3.77 (m, 2H), 4.18-4.39 (m, 3H), 5.75-5.78 (m, 1H), 6.23-6.27 (m, 1H), 6.62-6.65 (m, 1H), 7.10-7.24 (m, 2H), 7.80-8.08 (m, 2H), 8.36-8.42 (m, 1H), 9.26 (s, 1H). [M+H] Calc'd for $C_{24}H_{29}BrN_6O_4$, 545.1; Found, 545.1.

Example 157: Synthesis of (R)—N-(4-(3-((5-chloropyrimidin-2-yl)amino)pyrrolidin-1-yl)quinazolin-7-yl)acrylamide

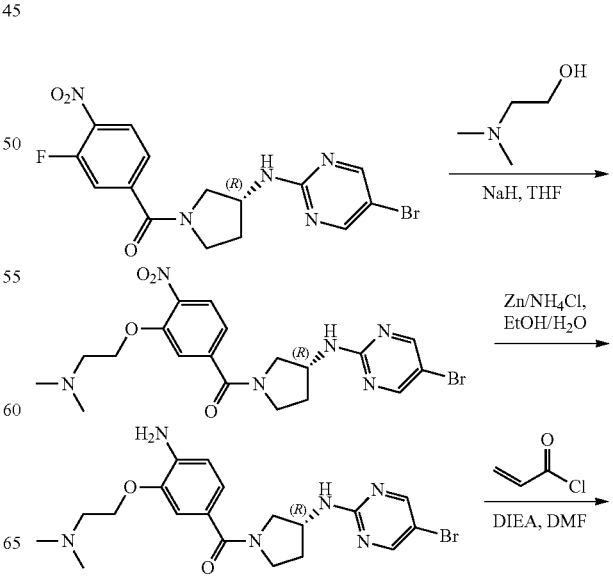

Step 1: (R)-(3-((5-bromopyrimidin-2-yl)amino)pyrrolidin-1-yl)(3-(2-(dimethylamino)ethoxy)-4-nitrophenyl)methanone

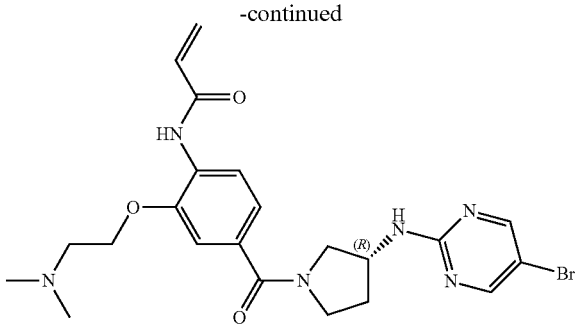

To a mixture of 2-(dimethylamino)ethanol (174 mg, 1.9 mmol) in THF (60 mL) was added NaH (156 mg, 3.9 mmol, 60%) at 0° C. and the reaction mixture was stirred at 0° C. for 15 min. Then added (R)-(3-((5-bromopyrimidin-2-yl)amino)pyrrolidin-1-yl)(3-fluoro-4-nitrophenyl)methanone (800 mg, 1.9 mmol) to the mixture and stirred at RT for overnight. The reaction was quenched with H₂O (10 mL) and the mixture was concentrated. The residue was purified by silica gel chromatography (DCM/MeOH=20/1) to afford (R)-(3-((5-bromopyrimidin-2-yl)amino)pyrrolidin-1-yl)(3-(2-(dimethylamino)ethoxy)-4-nitrophenyl)methanone (700 mg, 75%) as a yellow solid. [M+H] Calc'd for $C_{19}H_{23}BrN_6O_4$, 479.1; Found, 479.1.

Step 2: (R)-(4-amino-3-(2-(dimethylamino)ethoxy)phenyl)(3-((5-bromopyrimidin-2-yl)amino)pyrrolidin-1-yl)methanone

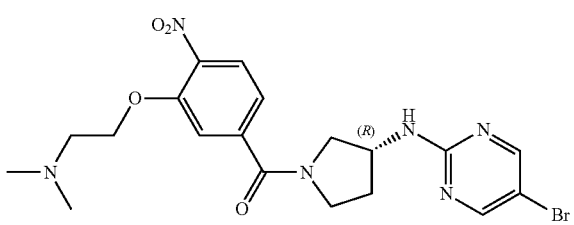

To a mixture of (R)-(3-((5-bromopyrimidin-2-yl)amino)pyrrolidin-1-yl)(3-(2-(dim ethylamino)ethoxy)-4-nitrophenyl)methanone (700 mg, 1.5 mmol) in MeOH/H₂O (20/5 mL) was added NH₄Cl (791 mg, 0.15 mmol) and Zn (952 mg, 0.15 mmol). The reaction mixture was stirred at 70° C. for 2 h. The mixture was cooled, filtered and concentrated in vacuo. The residue was purified by silica gel chromatography (DCM/MeOH=20/1) to afford (R)-(4-amino-3-(2-(dimethylamino)ethoxy)phenyl)(3-((5-bromopyrimidin-2-yl)amino)pyrrolidin-1-yl)methanone (400 mg, 61%) as yellow solid. [M+H] Calc'd for $C_{19}H_{25}BrN_6O_2$, 449.1; Found, 449.1.

Step 3: (R)—N-(4-(3-((5-bromopyrimidin-2-yl)amino)pyrrolidine-1-carbonyl)-2-(2-(dimethylamino)ethoxy)phenyl)acrylamide

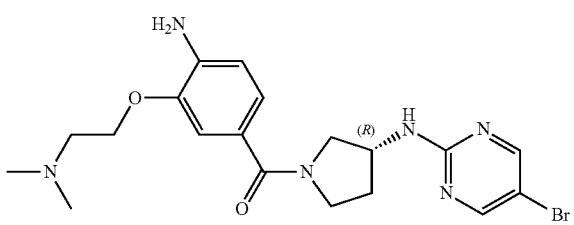

A mixture of (R)-(4-amino-3-(2-(dimethylamino)ethoxy)phenyl)(3-((5-bromopyrimidin-2-yl)amino)pyrrolidin-1-yl)methanone (400 mg, 1.5 mmol) in DCM (20/5 mL) was added DIEA (230 mg, 1.8 mmol) and Acryloyl chloride (81 mg, 0.89 mmol) in an ice-bath. The reaction was then allowed to warm and stirred at RT for 2 h. The mixture was concentrated in vacuo and purified by prep-HPLC to afford (R)—N-(4-(3-((5-bromopyrimidin-2-yl)amino)pyrrolidine-1-carbonyl)-2-(2-(dimethylamino)ethoxy)phenyl)acrylamide (66.9 mg, 15%) as white solid. ¹H NMR (400 MHz, DMSO-d₆): 1.89-1.99 (m, 1H), 2.15-2.22 (m, 1H), 2.23 (d, J=8.4 Hz, 6H), 2.60-2.63 (m, 2H), 3.35-3.44 (m, 1H), 3.52-3.56 (m, 1H), 3.63-3.67 (m, 1H), 3.74-3.78 (m, 1H), 4.12-4.18 (m, 2H), 4.21-4.40 (m, 1H), 5.78 (d, J=10.0 Hz, 1H), 6.24-6.28 (m, 6H), 6.52-6.58 (m, 1H), 7.12-7.17 (m, 1H), 7.23-7.27 (m, 1H), 7.80 (d, J=4.8 Hz, 1H), 8.12-8.17 (m, 1H), 8.36 (s, 1H), 8.42 (s, 1H), 9.66 (d, J=12.4 Hz, 1H). [M+H] Calc'd for $C_{22}H_{27}BrN_6O_3$, 503.1; Found, 503.1.

Example 158: (R)—N-(4-(3-((5-bromopyrimidin-2-yl)amino)pyrrolidine-1-carbonyl)-2-(4-dimethylamino)piperidin-1-yl)phenyl)acrylamide

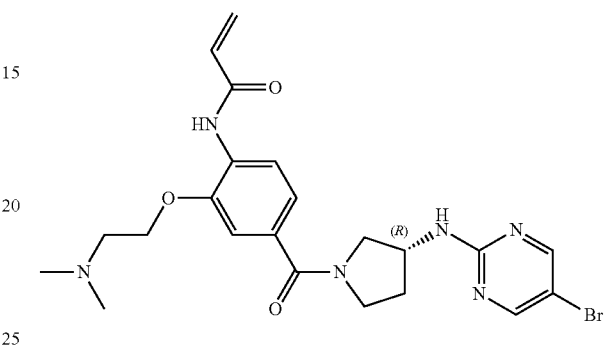

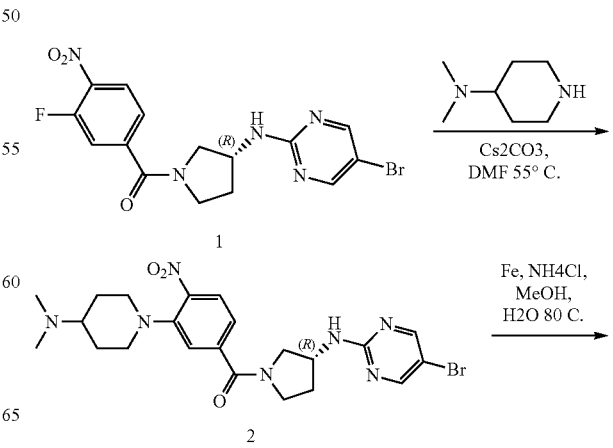

Step 1: (R)-(3-((5-bromopyrimidin-2-yl)amino)pyr-rolidin-1-yl)(3-(4-(dimethylamino)piperidin-1-yl)-4-nitrophenyl)methanone

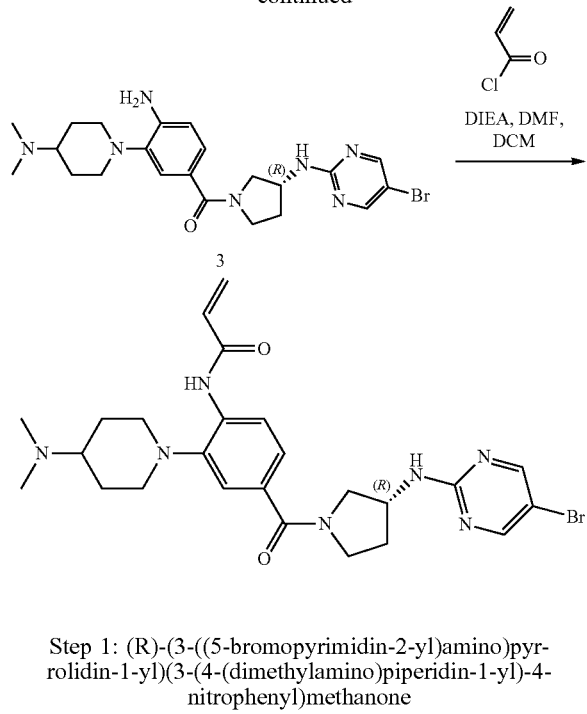

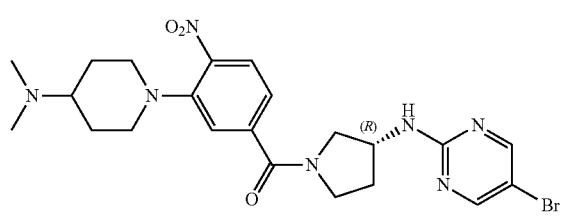

To a solution of (R)-(3-((5-bromopyrimidin-2-yl)amino)pyrrolidin-1-yl)(3-fluoro-4-nitrophenyl)methanone (1.0 g, 2.5 mmol) and N,N-dimethylpiperidin-4-amin (320 mg, 2.5 mmol) in DMF (50 mL) was added $Cs_2CO_3$ (3.3 g, 10 mmol) at RT. The mixture was then stirred at 55° C. for 2 h. The mixture was cooled, diluted with water (200 mL) and extracted with EA (100 mL). The organic layer was washed with brine (100 mL), dried over $Na_2SO_4$, filtered and concentrated to afford 1.0 g of product as a yellow solid. [M+H] Calc'd for $C_{22}H_{28}BrN_7O_3$, 518.1; Found, 518.1

Step 2: (R)-(4-amino-3-(4-(dimethylamino)piperidin-1-yl)phenyl)(3-((5-bromopyrimidin-2-yl)amino)pyrrolidin-1-yl)methanone

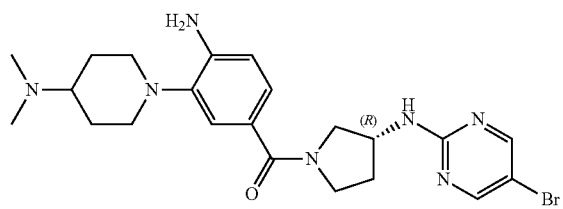

To a solution of (R)-(3-((5-bromopyrimidin-2-yl)amino)pyrrolidin-1-yl)(3-(4-(dimethylamino)piperidin-1-yl)-4-nitrophenyl)methanone (1.0 g, 2.0 mmol) in ethanol (40 mL) and water (40 mL) was added Fe (2.2 g, 40.0 mmol) and $NH_4Cl$ (2.1 g, 40.0 mmol) at RT. The mixture was then stirred at 80° C. for 2 h. The reaction mixture was concentrated in vacuo. The residue was purified by reversed phase chromatography (ACN in water 30%-70%) to afford 500 mg of product as a yellow solid. [M+H] Calc'd for $C_{20}H_{30}N_4O_6$, 488.1; Found, 488.1.

Step 3: (R)—N-(4-(3-((5-bromopyrimidin-2-yl)amino)pyrrolidine-1-carbonyl)-2-(4-(dimethylamino)piperidin-1-yl)phenyl)acrylamide

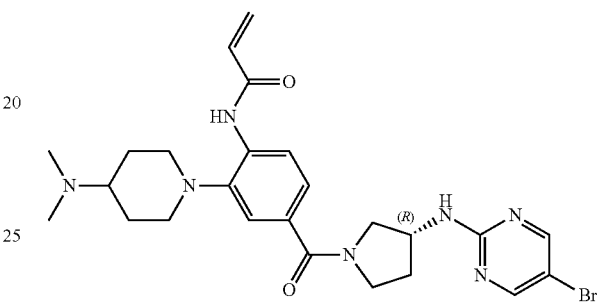

To a solution of (R)-(4-amino-3-(4-(dimethylamino)piperidin-1-yl)phenyl)(3-((5-bromopyrimidin-2-yl)amino)pyrrolidin-1-yl)methanone (400 mg, 0.82 mmol) and DIEA (210 mg, 1.6 mmol) in DCM (20 mL) and DMF (2 mL) was added acryloyl chloride (81 mg, 0.9 mmol) in an ice-bath. The reaction mixture was then stirred at RT for 2 h, The reaction mixture was concentrated in vacuo and the residue was purified by prep-HPLC to afford (R)—N-(4-(3-((5-bromopyrimidin-2-yl)amino)pyrrolidine-1-carbonyl)-2-(4-(dimethylamino)piperidin-1-yl)phenyl)acrylamide (63.8 mg, 14.5%) as a white solid. $^1$H NMR (400 MHz, DMSO-$d_6$): 1.67-1.96 (m, 5H), 2.14-2.21 (m, 8H), 2.54-2.63 (m, 2H), 2.9-3.1 (m, 2H), 3.31-3.65 (m, 4H), 4.22 (s, 0.5H), 4.37 (s, 0.5H), 5.77-5.79 (d, J=10.0 Hz, 1H), 6.24 (s, 0.5H), 6.28 (s, 0.5H), 6.70-6.77 (m, 1H), 7.19-7.30 (m, 2H), 7.81-7.82 (d, J=5.2 Hz, 1H), 8.03-8.04 (m, 1H), 8.36 (s, 1H), 8.42 (s, 1H), 9.09-9.11 (d, J=8.4 Hz, 1H). [M+H] Calc'd for $C_{25}H_{32}BrN_7O_2$, 542.1; Found, 542.1.

Example 159: Synthesis of (R)—N-(4-(3-((5-bromopyrimidin-2-yl)amino)pyrrolidine-1-carbonyl)-2-((2-(dimethylamino)ethyl)(methyl)amino)phenyl)acrylamide

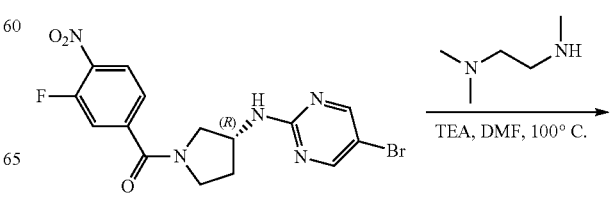

413

-continued

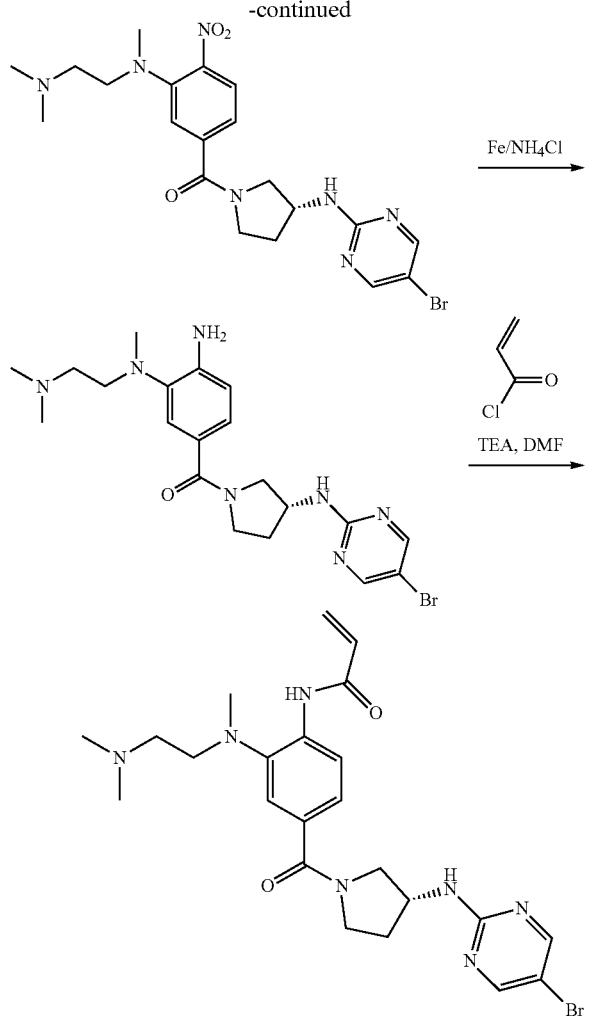

Step 1: (R)-(3-((5-bromopyrimidin-2-yl)amino)pyr-rolidin-1-yl)(3-((2-(dimethylamino)ethyl) (methyl) amino)-4-nitrophenyl)methanone A mixture of (R)-(3-((5-bromopyrimidin-2-yl)amino)pyr-rolidin-1-yl)(3-fluoro-4-nitrophenyl)methanone (1.0 g, 2.44 mmol), N1,N1,N2-trimethylethane-1,2-diamine (324 mg, 3.18 mmol) and TEA (985 mg, 9.76 mmol) in DMF (10 mL) was stirred at 100° C. for 16 h. The solution was concen-

414 trated and purified by silica gel chromatography (DCM/MeOH=7/1) to afford (R)-(3-((5-bromopyrimidin-2-yl) amino)pyrrolidin-1-yl)(3-((2-(dimethylamino)ethyl) (methyl)amino)-4-nitrophenyl)methanone (666 mg, 56%) as brown glutinous oil. [M+H] Calc'd for $C_{20}H_{26}BrN_7O_3$, 492.1, Found, 492.3

Step 2: (R)-(4-amino-3-((2-(dimethylamino)ethyl) (methyl)amino)phenyl)(3-((5-bromo pyrimidin-2-yl) amino)pyrrolidin-1-yl)methanone

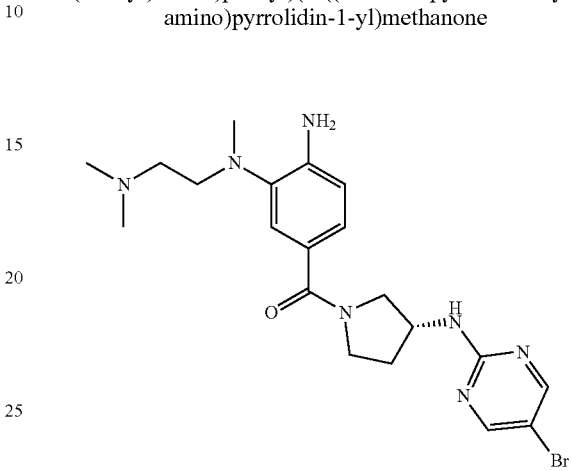

To a mixture of (R)-(3-((5-bromopyrimidin-2-yl)amino) pyrrolidin-1-yl)(3-((2-(dimethylamino)ethyl)(methyl) amino)-4-nitrophenyl)methanone (500 mg, 0.84 mmol) in EtOH/H$_2$O (10/10 mL) was added NH$_4$Cl (454 mg, 8.4 mmol) and Fe (467 mg, 8.4 mmol) at RT. The reaction mixture was stirred at 80° C. for 5 h. The mixture was filtered and concentrated. The residue was purified by silica gel chromatography (DCM/MeOH=7/1) to afford (R)-(4-amino-3-((2-(dimethylamino)ethyl)(methyl)amino)phenyl) (3-((5-bromopyrimidin-2-yl)amino)pyrrolidin-1-yl)metha-none (410 mg, 100%) as a brown solid. [M+H] Calc'd for $C_{20}H_{28}BrN_7O$, 462.2; Found, 462.1

Step 3: (R)—N-(4-(3-((5-bromopyrimidin-2-yl) amino)pyrrolidine-1-carbonyl)-2-((2-(dimethyl ami-no)ethyl)(methyl)amino)phenyl)acrylamide

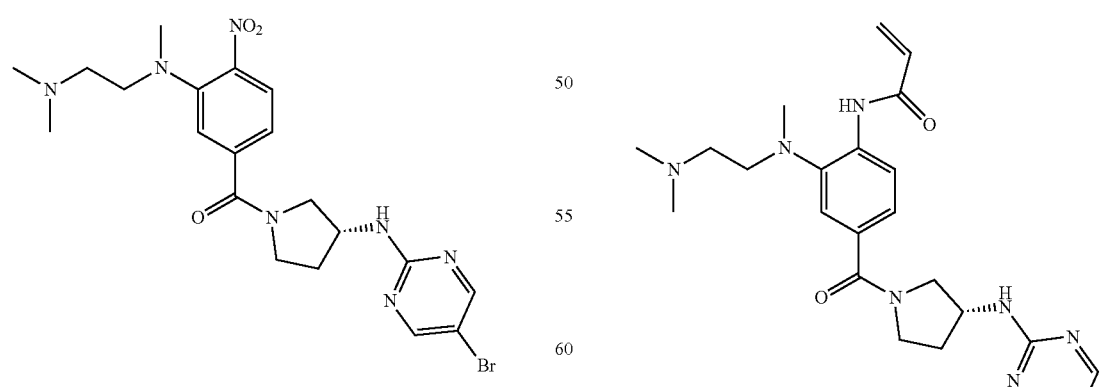

To a mixture of (R)-(4-amino-3-((2-(dimethylamino) ethyl)(methyl)amino)phenyl)(3-((5-bromopyrimidin-2-yl)

amino)pyrrolidin-1-yl)methanone (419 mg, 0.91 mmol) in DMF (5 mL) was added TEA (184 mg, 1.8 mmol) and Acryloyl chloride (73 mg, 0.91 mmol) in an ice-bath. After stirring at RT for 2 h, the mixture was concentrated and purified by prep-HPLC to afford (R)—N-(4-(3-((5-bromopyrimidin-2-yl)amino)pyrrolidine-1-carbonyl)-2-((2-(dimethylamino)ethyl)(methyl)amino)phenyl)acrylamide (30 mg, 6%) as white solid. $^1$H NMR (400 MHz, DMSO-d$_6$): 1.86-2.02 (m, 1H), 2.17-2.20 (m, 7H), 2.26-2.33 (m, 2H), 2.59-2.70 (m, 3H), 2.78-2.81 (m, 2H), 3.35-3.78 (m, 4H), 4.23-4.40 (m, 1H), 5.81 (d, J=10.4 Hz, 1H), 6.25-6.45 (m, 2H), 7.25-7.31 (m, 1H), 7.40-7.46 (m, 1H), 7.81 (d, J=5.6 Hz, 1H), 8.29-8.43 (m, 3H) 10.21-10.26 (m, 1H). [M+H] Calc'd for C$_{23}$H$_{30}$BrN$_7$O$_2$, 516.2; Found, 516.2

Example 160: Synthesis of (R)—N-(4-(3-((5-bromopyrimidin-2-yl)amino)pyrrolidine-1-carbonyl)-2-((2-(dimethylamino)ethyl)(methyl)amino)phenyl) acrylamide Step 1: (R)-tert-butyl 3-((5-cyano-4-methoxypyrimidin-2-yl)amino)pyrrolidine-1-carboxylate

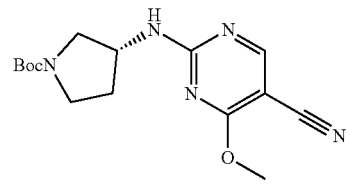 [SMILES: COc1nc(N[C@@H]2CCN(C(=O)OC(C)(C)C)C2)ncc1C#N]

A mixture of 2,4-dichloropyrimidine-5-carbonitrile (900 mg, 5.33 mmol), (R)-tert-butyl 3-aminopyrrolidine-1-carboxylate (1.24 g, 6.66 mmol) and DIEA (1.38 g, 10.66 mmol) in DMSO (10 mL) was stirred at 140° C. for 3 h. The reaction was cooled, quenched with H$_2$O (100 mL) and extracted with DCM (50 mL*2). The combined organic layer was concentrated and purified by silica gel chromatography (PE/EA=3/1) to afford (R)-tert-butyl 3-((5-cyano-4-methoxypyrimidin-2-yl)amino)pyrrolidine-1-carboxylate (280 mg, 18%) as brown solid. [M+H]Calc'd for C$_{15}$H$_{21}$N$_5$O$_3$, 320.2; Found, 320.3

Step 2: (R)-4-methoxy-2-(pyrrolidin-3-ylamino) pyrimidine-5-carbonitrile 2,2,2-trifluoroacetate

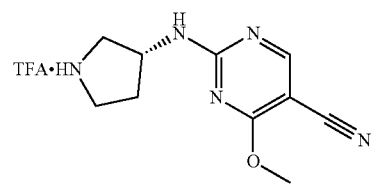

A mixture of (R)-tert-butyl 3-((5-cyano-4-methoxypyrimidin-2-yl)amino)pyrrolidine-1-carboxylate (98 mg, 0.31 mmol) in DCM/TFA (2/1 mL) was stirred at RT for 30 min. The mixture was concentrated to afford (R)-4-methoxy-2-(pyrrolidin-3-ylamino)pyrimidine-5-carbonitrile 2,2,2-trifluoroacetate (190 mg of crude) as brown glutinous oil. [M+H] Calc'd for C$_{10}$H$_{14}$ClN$_5$O, 220.1; Found, 220.1

Step 3: (R)—N-(4-(3-((5-cyano-4-methoxypyrimidin-2-yl)amino)pyrrolidine-1-carbonyl)phenyl)acrylamide

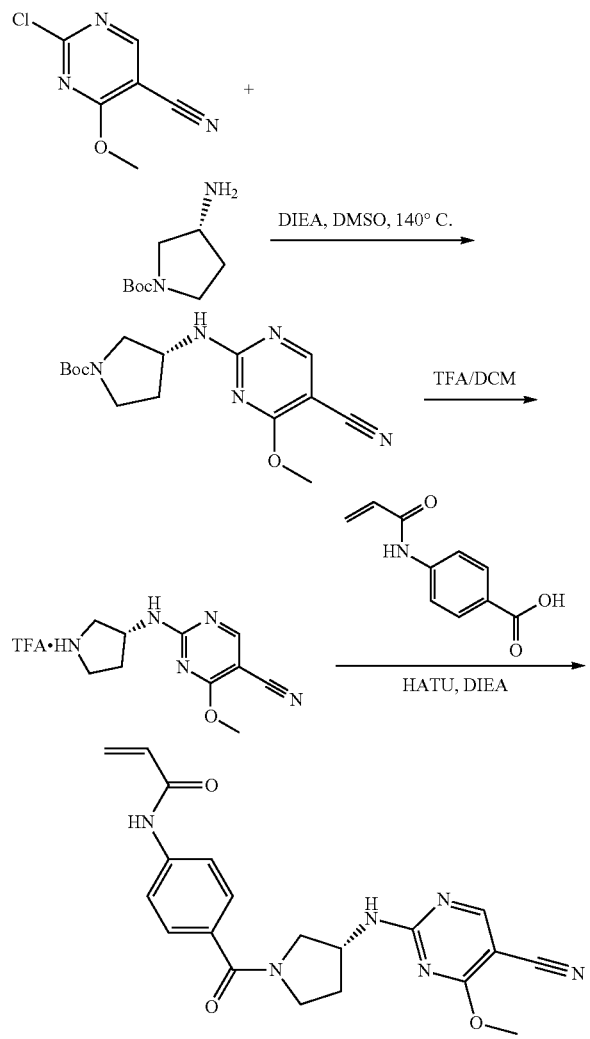

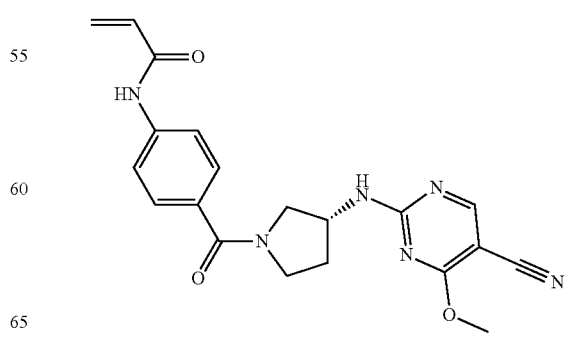

417

To a mixture of (R)-4-methoxy-2-(pyrrolidin-3-ylamino) pyrimidine-5-carbonitrile 2,2,2-trifluoroacetate (190 mg, 0.87 mmol), DIEA (337 mg, 2.61 mmol) and HATU (397 mg, 1.04 mmol) in DCM (5 mL) was added 4-acrylamidobenzoic acid (165 mg, 0.87 mmol). After stirring at RT for 1 h, the mixture was concentrated and purified by prep-HPLC to afford (R)—N-(4-(3-((5-cyano-4-methoxypyrimidin-2-yl)amino)pyrrolidine-1-carbonyl)phenyl)acrylamide (55.6 mg, 45%) as white solid. $^1$H NMR (400 MHz, DMSO-$d_6$): 2.01-2.22 (m, 2H), 3.29-3.34 (m, 3H), 3.46-3.84 (m, 4H), 4.57-4.68 (m, 1H), 5.78 (dd, J=2.0, 10.0 Hz, 1H), 6.26-6.30 (m, 1H), 6.41-6.48 (m, 1H), 7.51-7.54 (m, 2H), 7.71-7.74 (m, 2H), 8.23-8.31 (m, 1H), 10.31 (s, 1H). [M+H] Calc'd for $C_{20}H_{20}N_6O_3$, 393.2; Found, 393.2.

Example 161: Synthesis of (N-(4-((3R)-3-((4-bromophenyl)amino)cyclopentanecarbonyl)-2-(2-(3,3-difluoropiperidin-1-yl)ethoxy)phenyl)acrylamide

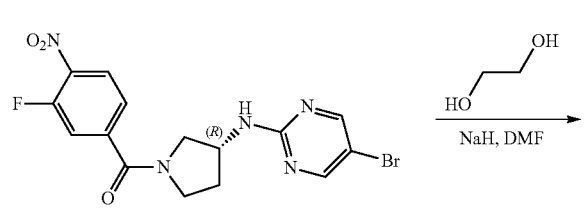

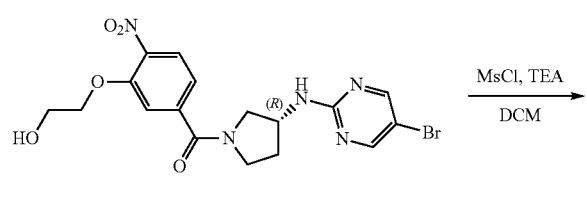

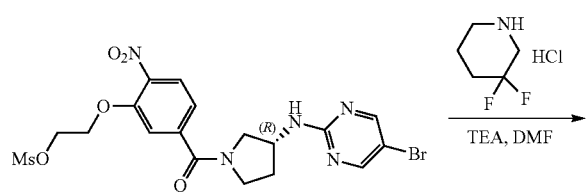

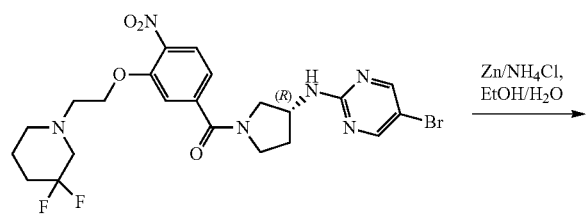

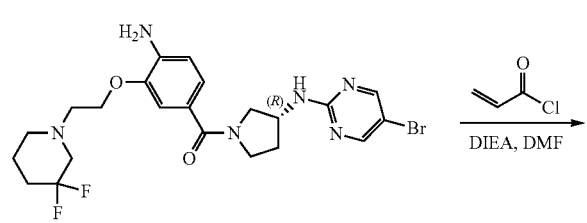

418

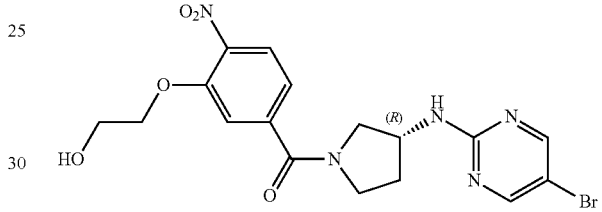

Step 1: (R)-(3-((5-bromopyrimidin-2-yl)amino)pyrrolidin-1-yl)(3-(2-hydroxyethoxy)-4-nitrophenyl) methanone

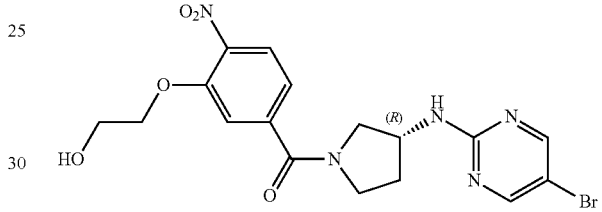

To a mixture of ethane-1,2-diol (3.60 mL, 64.7 mmol) in THF (30 mL) was added NaH (282 mg, 7.04 mmol, 60%) at ice-bath. The reaction mixture was stirred at for 20 min. Then (R)-(3-((5-bromopyrimidin-2-yl)amino)pyrrolidin-1-yl)(3-fluoro-4-nitrophenyl)methanone (2.0 g, 6.40 mmol) was added. The reaction mixture was stirred at RT overnight, The mixture was diluted with water (30 mL) and extracted with EtOAc (30 mL*3). The combined organic layer was washed with brine (30 mL), dried over Na$_2$SO$_4$, filtered and concentrated and purified by silica gel chromatography (DCM:MeOH=20:1) to afford (R)-(3-((5-bromopyrimidin-2-yl)amino)pyrrolidin-1-yl)(3-(2-hydroxyethoxy)-4-nitrophenyl)methanone (1.3 g, 44%) as a brown solid. [M+H] Calc'd for $C_{17}H_{18}BrN_5O_5$, 452.2; Found, 452.2

Step 2: (R)-2-(5-(3-((5-bromopyrimidin-2-yl)amino) pyrrolidine-1-carbonyl)-2-nitrophenoxy)ethyl methanesulfonate To a solution of (R)-(3-((5-bromopyrimidin-2-yl)amino) pyrrolidin-1-yl)(3-(2-hydroxyethoxy)-4-nitrophenyl)methanone (600 mg, 1.32 mmol) in DCM (20 mL) was added TEA (201 mg, 1.99 mmol) in an ice-bath. Then a solution of methanesulfonyl chloride (167.1 mg, 1.46 mmol) in DCM (2 mL) was added dropwise at 0° C. The solution was stirred at 0° C. for 2 hours. The solution was concentrated to afford (R)-2-(5-(3-((5-bromopyrimidin-2-yl)amino)pyrrolidine-1-carbonyl)-2-nitrophenoxy)ethyl methanesulfonate (650 mg, 92%) as a yellow solid which was used to the next step directly. [M+H] Calc'd for $C_{18}H_{20}BrN_5O_7S$, 530.3; Found, 530.3

Step 3: (R)-(3-((5-bromopyrimidin-2-yl)amino)pyrrolidin-1-yl)(3-(2-(3,3-difluoropiperidin-1-yl)ethoxy)-4-nitrophenyl)methanone

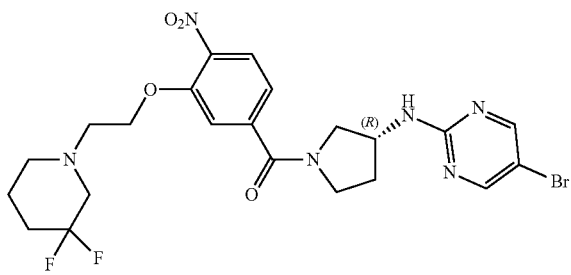

A mixture of (R)-2-(5-(3-((5-bromopyrimidin-2-yl)amino)pyrrolidine-1-carbonyl)-2-nitrophenoxy)ethyl methanesulfonate (650 mg, 1.22 mmol), 3,3-difluoropiperidine hydrochloride (347.6 mg, 2.20 mmol) and TEA (372 mg, 3.67 mmol) in DMF (20 mL) was stirred at 80° C. for 16 h under $N_2$ balloon conditions. The reaction mixture was extracted with EtOAc (30 mL*3). The combined organic layer was washed with brine (30 mL), dried over $Na_2SO_4$, filtered and concentrated and purified by silica gel chromatography (DCM:MeOH=20:1) to afford (R)-(3-((5-bromopyrimidin-2-yl)amino)pyrrolidin-1-yl)(3-(2-(3,3-difluoropiperidin-1-yl)ethoxy)-4-nitrophenyl)methanone (150 mg, 22%) as brown solid. [M+H] Calc'd for $C_{22}H_{25}BrF_2N_6O_4$, 555.3; Found, 555.3

Step 4: (R)-(4-amino-3-(2-(3,3-difluoropiperidin-1-yl)ethoxy)phenyl)(3-((5-bromopyrimidin-2-yl)amino)pyrrolidin-1-yl)methanone

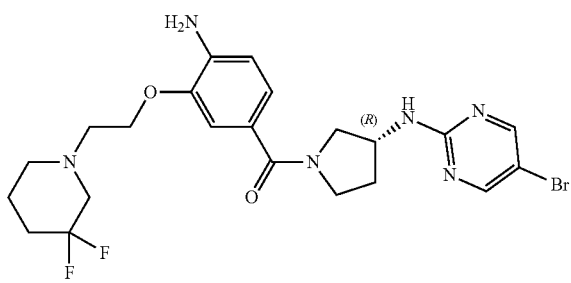

To a mixture of (R)-(3-((5-bromopyrimidin-2-yl)amino)pyrrolidin-1-yl)(3-(2-(3,3-difluoropiperidin-1-yl)ethoxy)-4-nitrophenyl)methanone (150 mg, 0.27 mmol) in MeOH/$H_2O$ (20/5 mL) was added $NH_4Cl$ (146 mg, 2.70 mmol) at RT. The reaction mixture was stirred at 70° C. for 1 h. Then added Zn (175 mg, 2.70 mmol) to reaction mixture and stirred at 70° C. for 2 h. The mixture was cooled, filtered and concentrated. The residue was purified by silica gel chromatography (DCM/MeOH=20/1) to afford (R)-(4-amino-3-(2-(3,3-difluoropiperidin-1-yl)ethoxy)phenyl)(3-((5-bromopyrimidin-2-yl)amino)pyrrolidin-1-yl)methanone (100 mg, 70%) as a brown solid. [M+H] Calc'd for $C_{22}H_{27}BrF_2N_6O_2$, 525.3; Found, 525.3

Step 5: (R)—N-(4-(3-((5-bromopyrimidin-2-yl)amino)pyrrolidine-1-carbonyl)-2-(2-(3,3-difluoropiperidin-1-yl)ethoxy)phenyl)acrylamide

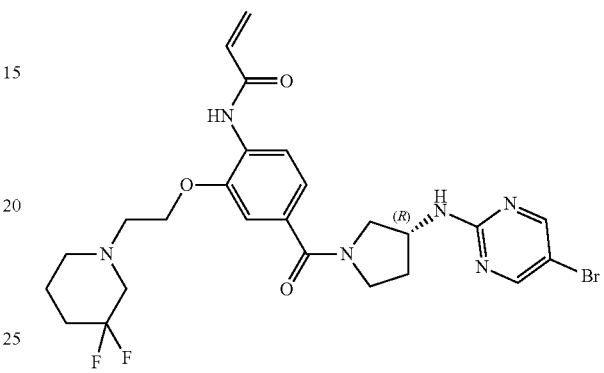

To a mixture of (R)-(4-amino-3-(2-(3,3-difluoropiperidin-1-yl)ethoxy)phenyl)(3-((5-bromopyrimidin-2-yl)amino)pyrrolidin-1-yl)methanone (100 mg, 0.19 mmol) in DCM (10 mL) was added DIEA (49.1 mg, 0.38 mmol) and Acryloyl chloride (17.2 mg, 0.19 mmol) at ice-bath. The reaction mixture was stirred at 0° C. for 1 h. The mixture was concentrated and purified by prep-HPLC to afford (R)—N-(4-(3-((5-bromopyrimidin-2-yl)amino)pyrrolidine-1-carbonyl)-2-(2-(3,3-difluoropiperidin-1-yl)ethoxy)phenyl)acrylamide (3.9 mg, 3.5%) as a white solid. $^1$H NMR (400 MHz, DMSO-$d_6$): 1.61-1.62 (m, 2H), 1.80-2.13 (m, 5H), 2.29-2.32 (m, 1H), 2.75-2.89 (m, 4H), 3.24-3.28 (m, 1H), 3.53-3.79 (m, 3H), 4.17-4.18 (m, 3H), 5.74-5.77 (d, J=10.0 Hz, 1H), 6.24-6.26 (d, J=10.0 Hz, 1H), 6.63-6.68 (m, 1H), 7.08-7.23 (m, 2H), 7.82 (s, 1H), 8.08-8.10 (m, 1H), 8.36-8.42 (m, 2H), 9.22-9.23 (m, 1H). [M+H] Calc'd for $C_{25}H_{29}BrF_2N_6O_3$, 579.4; Found, 579.4

Example 162: Synthesis of (R)—N-(4-(3-((5-bromopyrimidin-2-yl)amino)pyrrolidine-1-carbonyl)-2-(2-(4,4-difluoropiperidin-1-yl)ethoxy)phenyl)acrylamide

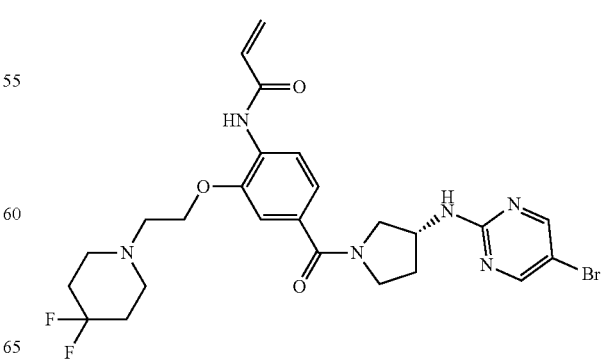

The title compound was prepared in 14.3% yield from {4-Amino-3-[2-(4,4-difluoro-piperidin-1-yl)-ethoxy]-phenyl}-[3-(5-bromo-pyrimidin-2-ylamino)-pyrrolidin-1-yl]-methanone using general procedure of (R)—N-(4-(3-((5-bromopyrimidin-2-yl)amino)pyrrolidine-1-carbonyl)-2-(2-(3,3-difluoropiperidin-1-yl)ethoxy)phenyl)acrylamide (55.1 mg, 14.3%) as brown solid. $^1$H NMR (400 MHz, DMSO-d6): 1.88-1.93 (m, 5H), 2.14-2.41 (m, 1H), 2.56-2.59 (m, 4H), 2.84-2.86 (m, 2H), 3.33-3.79 (m, 4H), 4.19-4.21 (m, 3H), 5.75-5.77 (d, J=10.0 Hz, 1H), 6.23-6.27 (d, J=10.0 Hz, 1H), 6.63-6.65 (m, 1H), 7.08-7.24 (m, 2H), 7.83 (s, 1H), 8.08-8.17 (m, 1H), 8.36-8.43 (m, 2H), 9.28-9.29 (m, 1H). [M+H] Calc'd for $C_{25}H_{29}BrF_2N_6O_3$, 579.4; Found, 579.4.

Example 163 & 164: Synthesis of N-(4-((R)-3-((5-bromopyrimidin-2-yl)amino)pyrrolidine-1-carbonyl)-2-(((R)-1-methylpyrrolidin-3-yl)oxy)phenyl)acrylamide

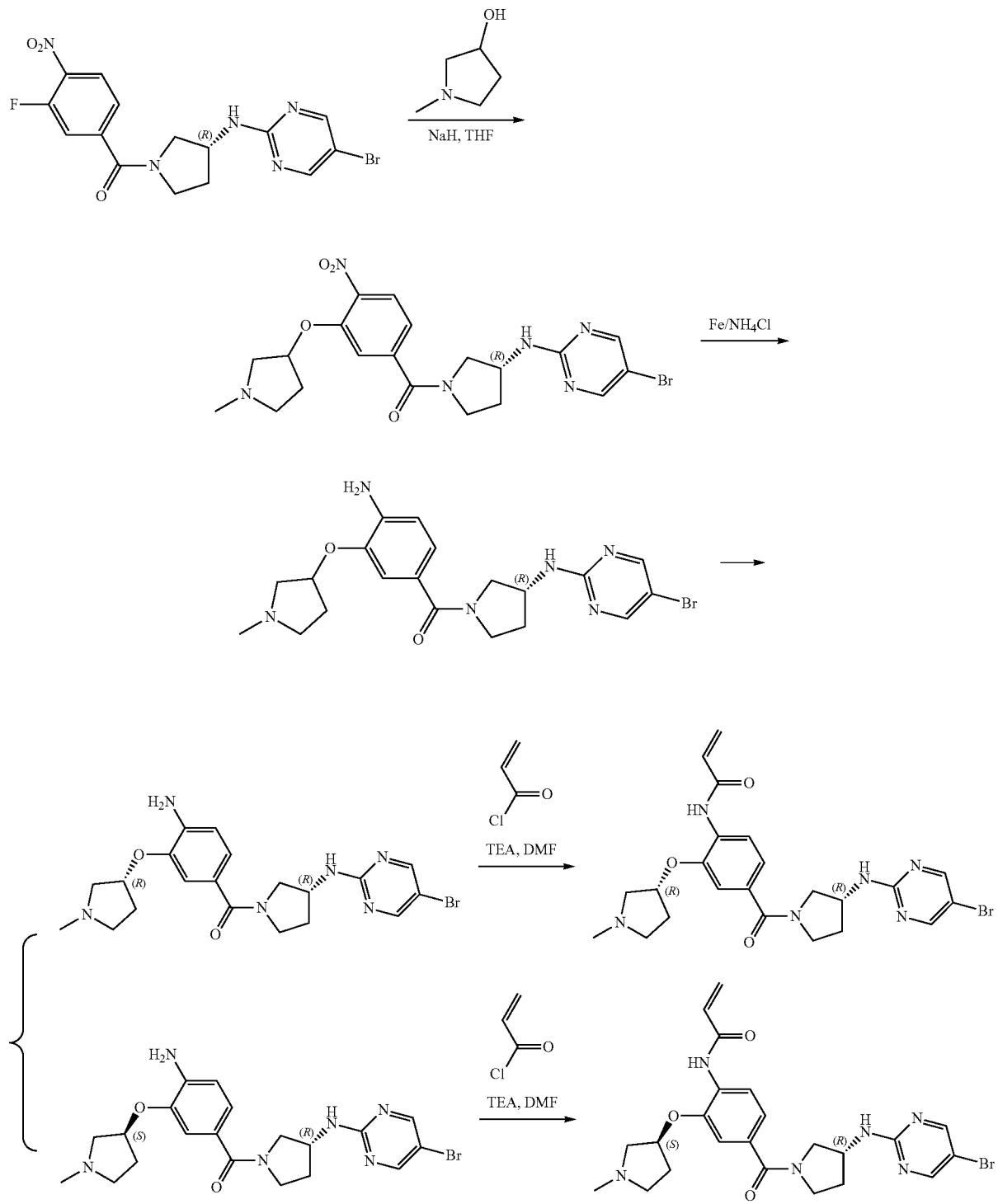

Step 1: ((R)-3-((5-bromopyrimidin-2-yl)amino)pyrrolidin-1-yl)(3-((1-methylpyrrolidin-3-yl)oxy)-4-nitrophenyl)methanone

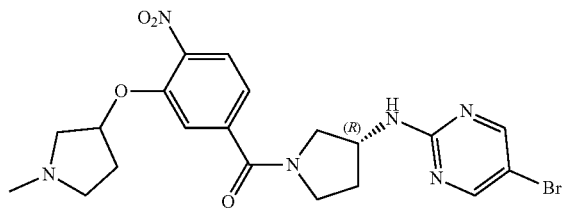

To a mixture of 1-methylpyrrolidin-3-ol (247 mg, 2.44 mmol) in THF (10 mL) was added NaH (117 mg, 4.88 mmol, 60%) at 0° C. and the reaction mixture was stirred at 0° C. for 15 min. Then to the mixture was added (R)-(3-((5-bromopyrimidin-2-yl)amino)pyrrolidin-1-yl)(3-fluoro-4-nitrophenyl)methanone (1.0 g, 2.44 mmol) and the mixture was stirred at 0° C. for 1 h. The reaction was quenched with H₂O (10 mL) and concentrated. The residue was purified by silica gel chromatography (MeOH/EA=3/7) to afford ((R)-3-((5-bromopyrimidin-2-yl)amino)pyrrolidin-1-yl)(3-((1-methylpyrrolidin-3-yl)oxy)-4-nitrophenyl)methanone (873 mg, 73%) as a brown solid. [M+H] Calc'd for $C_{20}H_{23}BrN_6O_4$, 491.1; Found, 491.1.

Step 2: (4-amino-3-((1-methylpyrrolidin-3-yl)oxy)phenyl)((R)-3-((5-bromopyrimidin-2-yl)amino)pyrrolidin-1-yl)methanone

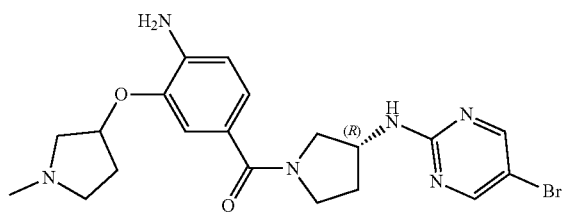

To a mixture of ((R)-3-((5-bromopyrimidin-2-yl)amino)pyrrolidin-1-yl)(3-((1-methylpyrrolidin-3-yl)oxy)-4-nitrophenyl)methanone (784 mg, 1.6 mmol) in EtOH/H₂O (10 mL/10 mL) was added NH₄Cl (864 mg, 16.0 mmol) and Fe (896 mg, 16.0 mmol) at RT. The reaction mixture was stirred at 80° C. for 5 h. The mixture was cooled, filtered and concentrated. The residue was purified by silica gel chromatography (DCM/MeOH=7/1) to afford a racemic mixture of (4-amino-3-((1-methylpyrrolidin-3-yl)oxy)phenyl)((R)-3-((5-bromopyrimidin-2-yl)amino)pyrrolidin-1-yl)methanone (566 mg, 77%) as a white solid. [M+H] Calc'd for $C_{20}H_{25}BrN_6O_2$, 461.1; Found, 461.1.

Step 3: (4-amino-3-(((R)-1-methylpyrrolidin-3-yl)oxy)phenyl)((R)-3-((5-bromopyrimidin-2-yl)amino)pyrrolidin-1-yl)methanone and (4-amino-3-(((S)-1-methylpyrrolidin-3-yl)oxy)phenyl)((R)-3-((5-bromopyrimidin-2-yl)amino)pyrrolidin-1-yl)methanone

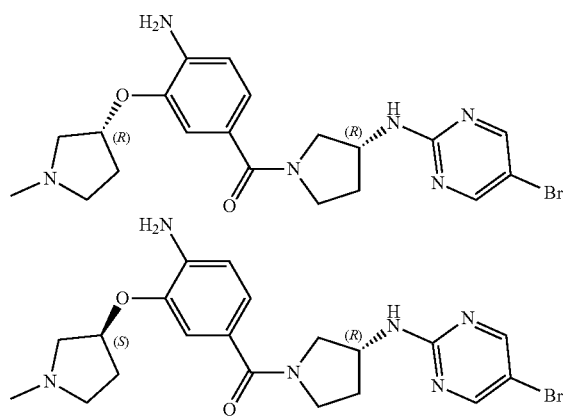

A racemic mixture of (4-amino-3-((1-methylpyrrolidin-3-yl)oxy)phenyl)((R)-3-((5-bromopyrimidin-2-yl)amino)pyrrolidin-1-yl)methanone (566 mg) was purified by chiral separation (IC:Hex:EtOH/DEA=40:60:0.3, 12 mL/min, 254 nm) to give (4-amino-3-(((R)-1-methylpyrrolidin-3-yl)oxy)phenyl)((R)-3-((5-bromopyrimidin-2-yl)amino)pyrrolidin-1-yl)methanone (208 mg, 12.05 min) and (4-amino-3-(((S)-1-methylpyrrolidin-3-yl)oxy)phenyl)((R)-3-((5-bromopyrimidin-2-yl)amino)pyrrolidin-1-yl)methanone (116 mg, 14.19 min) as a white solid.

Step 4: N-(4-((R)-3-((5-bromopyrimidin-2-yl)amino)pyrrolidine-1-carbonyl)-2-(((R)-1-methylpyrrolidin-3-yl)oxy)phenyl)acrylamide

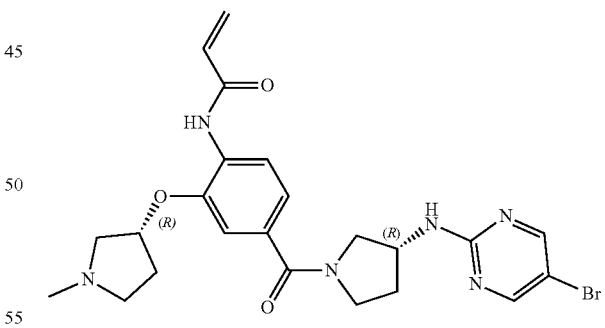

To a mixture of (4-amino-3-(((R)-1-methylpyrrolidin-3-yl)oxy)phenyl)((R)-3-((5-bromopyrimidin-2-yl)amino)pyrrolidin-1-yl)methanone (208 mg, 0.45 mmol) in DCM/DMF (5 mL/2 mL) was added DIEA (116 mg, 0.90 mmol) and Acryloyl chloride (36 mg, 0.45 mmol) in an ice-bath. It was stirred at 0° C. for 1 h. The mixture was concentrated and purified by prep-HPLC to afford N-(4-((R)-3-((5-bromopyrimidin-2-yl)amino)pyrrolidine-1-carbonyl)-2-(((R)-1-methylpyrrolidin-3-yl)oxy)phenyl)acrylamide (37.8 mg, 16%) as white solid. ¹H NMR (400 MHz, DMSO-d₆): 1.89-2.19 (m, 4H), 2.24-2.34 (m, 3.5H), 2.63-2.78 (m, 3.5H), 3.51-3.79 (m, 4H), 4.22-4.41 (m, 1H), 4.87-4.92 (m, 1H), 5.77 (d, J=10.0 Hz, 1H), 6.23-6.28 (m, 1H), 6.65-6.72 (m, 1H), 7.05-7.09 (m, 2H), 7.82 (s, 1H), 8.12-8.17 (m, 1H), 8.36 (s, 1H), 8.43 (s, 1H), 9.34-9.36 (m, 1H). [M+H] Calc'd for C$_{23}$H$_{27}$BrN$_6$O$_3$, 515.1; Found, 515.1.

Step 5: N-(4-((R)-3-((5-bromopyrimidin-2-yl)amino)pyrrolidine-1-carbonyl)-2-(((S)-1-methylpyrrolidin-3-yl)oxy)phenyl)acrylamide To a mixture of (4-amino-3-(((S)-1-methylpyrrolidin-3-yl)oxy)phenyl)((R)-3-((5-bromopyrimidin-2-yl)amino)pyrrolidin-1-yl)methanone (190 mg, 0.41 mmol) in DCM/DMF (5 mL/2 mL) was added DIEA (106 mg, 0.82 mmol) and Acryloyl chloride (33 mg, 0.41 mmol) in an ice-bath and the reaction mixture was stirred at 0° C. for 1 h. The mixture was concentrated and purified by prep-HPLC to afford N-(4-((R)-3-((5-bromopyrimidin-2-yl)amino)pyrrolidine-1-carbonyl)-2-(((S)-1-methylpyrrolidin-3-yl)oxy)phenyl)acrylamide (27.4 mg, 13%) as white solid. $^1$H NMR (400 MHz, DMSO-d$_6$): 1.85-1.94 (m, 2H), 2.10-2.32 (m, 5H), 2.59-2.75 (m, 4H), 3.49-3.78 (m, 4H), 4.21-4.41 (m, 1H), 4.85-4.92 (m, 1H), 5.77 (d, J=10.0 Hz, 1H), 6.65-6.72 (m, 1H), 7.03-7.13 (m, 1H), 7.82 (s, 1H), 8.12-8.17 (m, 1H), 8.36 (s, 1H), 8.43 (s, 1H), 9.32-9.33 (m, 1H). [M+H] Calc'd for C$_{23}$H$_{27}$BrN$_6$O$_3$, 515.1; Found, 515.1

Example 165: Synthesis of (R)—N-(4-(3-((5-cyano-4-methoxypyrimidin-2-yl)amino)pyrrolidine-1-carbonyl)-2-(2-(dimethylamino)ethoxy)phenyl)acrylamide

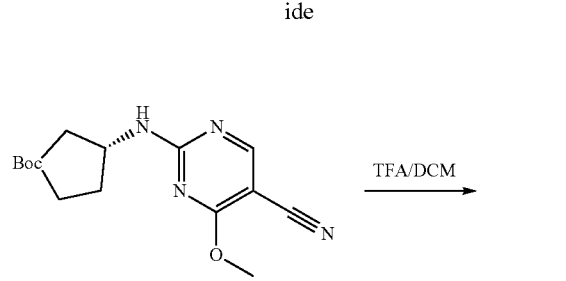

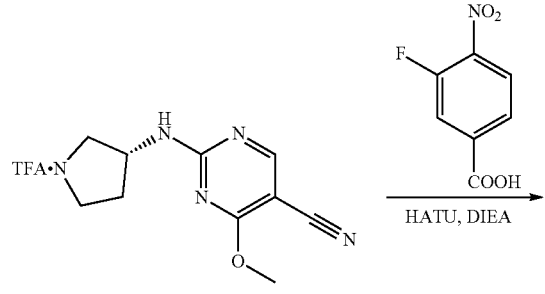

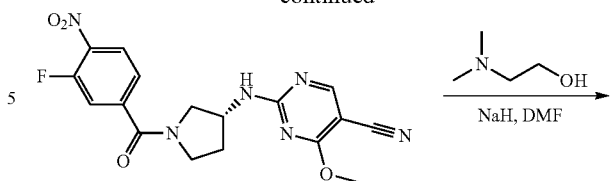

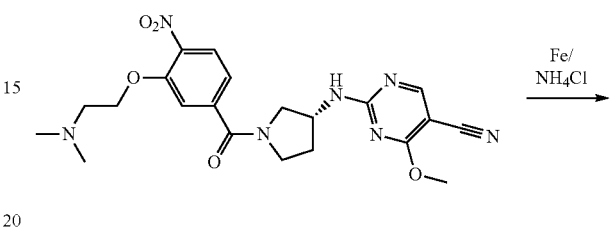

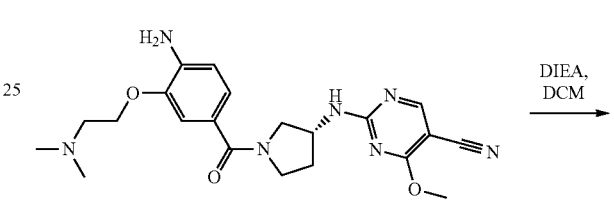

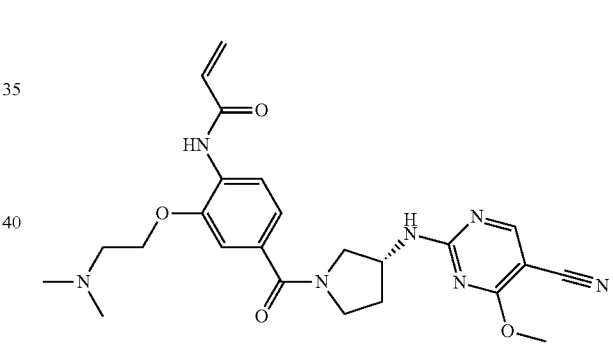

Step 1: (R)-4-methoxy-2-(pyrrolidin-3-ylamino)pyrimidine-5-carbonitrile hydrochloride

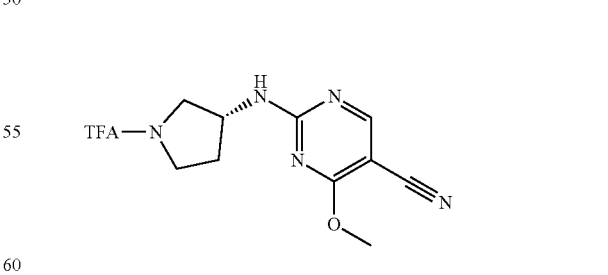

The title compound was prepared in 100% yield from (R)-tert-butyl 3-((5-cyano-4-methoxypyrimidin-2-yl)amino)pyrrolidine-1-carboxylate using general procedure of (R)-4-methoxy-2-(pyrrolidin-3-ylamino)pyrimidine-5-carbonitrile 2,2,2-trifluoroacetate. [M+H] Calc'd for C$_{12}$H$_{12}$F$_3$N$_5$O$_2$ 316.1; Found, 316.3

427

Step 2: (R)-2-((1-(3-fluoro-4-nitrobenzoyl)pyrrolidin-3-yl)amino)-4-methoxypyrimidine-5-carbonitrile

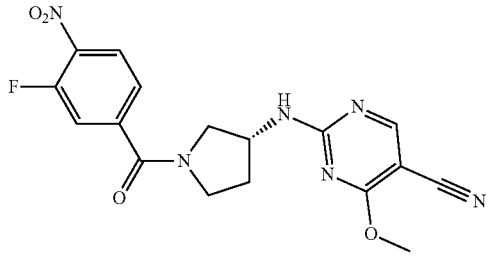 [SMILES: COc1nc(N[C@@H]2CCN(C(=O)c3ccc([N+](=O)[O-])c(F)c3)C2)ncc1C#N]

To a mixture of (R)-4-methoxy-2-(pyrrolidin-3-ylamino)pyrimidine-5-carbonitrile 2,2,2-trifluoroacetate (214 mg, 0.98 mmol), DIEA (379 mg, 2.94 mmol) and HATU (447 mg, 1.18 mmol) in DCM (5 mL) was added 3-fluoro-4-nitrobenzoic acid (181 mg, 0.98 mmol) in an ice-bath. After stirring at RT for 1 h, the mixture was concentrated and purified by flash (DCM/MeOH=10/1) to afford (R)-2-((1-(3-fluoro-4-nitrobenzoyl)pyrrolidin-3-yl)amino)-4-methoxypyrimidine-5-carbonitrile (590 mg, 100%) as yellow oil. [M+H] Calc'd for $C_{17}H_{15}FN_6O_4$ 387.1; Found, 387.3

Step 3: (R)-2-((1-(3-(2-(dimethylamino)ethoxy)-4-nitrobenzoyl)pyrrolidin-3-yl)amino)-4-methoxypyrimidine-5-carbonitrile

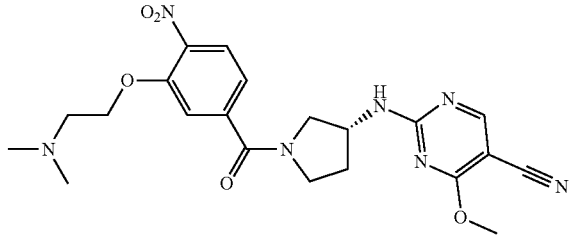 [SMILES: COc1nc(N[C@@H]2CCN(C(=O)c3ccc(N)c(OCCN(C)C)c3)C2)ncc1C#N]

To a mixture of 2-(dimethylamino)ethanol (133 mg, 1.5 mmol) in DMF (2 mL) was added NaH (60 mg, 1.5 mmol, 60%) at 0° C. and the reaction mixture was stirred at 0° C. for 15 min. To the mixture was added (R)-2-((1-(3-fluoro-4-nitrobenzoyl)pyrrolidin-3-yl)amino)-4-methoxypyrimidine-5-carbonitrile (590 mg, 1.5 mmol) and the mixture was stirred at RT for overnight. The reaction was quenched with H₂O (10 mL) and concentrated. The residue was purified by silica gel chromatography (DCM/MeOH=10/1) to afford (R)-2-((1-(3-(2-(dimethylamino)ethoxy)-4-nitrobenzoyl)pyrrolidin-3-yl)amino)-4-methoxypyrimidine-5-carbonitrile (332 mg, 84%) as yellow oil. [M+H] Calc'd for $C_{21}H_{25}N_7O_5$, 456.2; Found, 456.1

428

Step 4: (R)-2-((1-(4-amino-3-(2-(dimethylamino)ethoxy)benzoyl)pyrrolidin-3-yl)amino)-4-methoxypyrimidine-5-carbonitrile

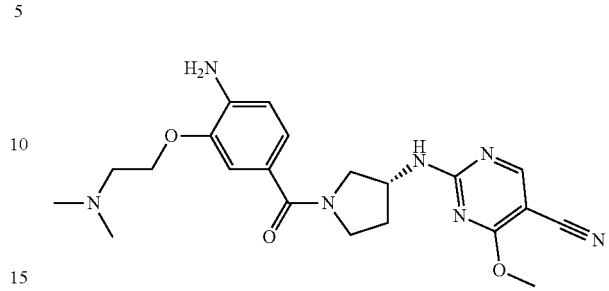

To a mixture of (R)-2-((1-(3-(2-(dimethylamino)ethoxy)-4-nitrobenzoyl)pyrrolidin-3-yl)amino)-4-methoxypyrimidine-5-carbonitrile (330 mg, 0.73 mmol) in EtOH/H₂O (10 mL/10 mL) was added NH₄Cl (394 mg, 7.3 mmol) and Fe (409 mg, 7.3 mmol) at RT. The reaction mixture was stirred at 80° C. for 5 h. The mixture was cooled, filtered and concentrated. The residue was purified by flash (DCM/MeOH=10/1) to afford (R)-2-((1-(4-amino-3-(2-(dimethylamino)ethoxy)benzoyl)pyrrolidin-3-yl)amino)-4-methoxypyrimidine-5-carbonitrile (123 mg, 40%) as a brown solid. [M+H] Calc'd for $C_{21}H_{27}N_7O_3$, 426.2; Found, 426.1

Step 5:(R)—N-(4-(3-((5-cyano-4-methoxypyrimidin-2-yl)amino)pyrrolidine-1-carbonyl)-2-(2-(dimethylamino)ethoxy)phenyl)acrylamide

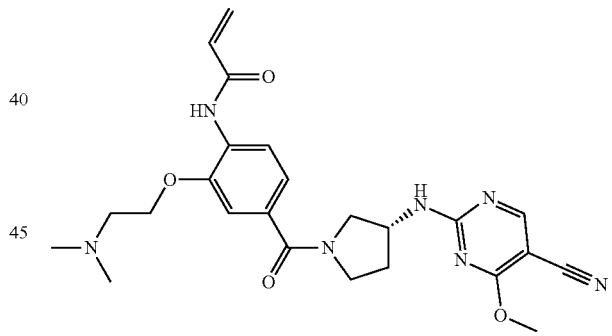

To a mixture of (R)-2-((1-(4-amino-3-(2-(dimethylamino)ethoxy)benzoyl)pyrrolidin-3-yl)amino)-4-methoxypyrimidine-5-carbonitrile (123 mg, 0.29 mmol) in DCM/DMF (5 mL/2 mL) was added DIEA (75 mg, 0.58 mmol) and Acryloyl chloride (23 mg, 0.29 mmol) in an ice-bath and the reaction mixture was stirred at 0° C. for 1 h. The mixture was concentrated and purified by prep-HPLC to afford (R)—N-(4-(3-((5-cyano-4-methoxypyrimidin-2-yl)amino)pyrrolidine-1-carbonyl)-2-(2-(dimethylamino)ethoxy)phenyl)acrylamide (29.6 mg, 21%) as a white solid. ¹H NMR (400 MHz, DMSO-d₆): 1.92-2.03 (m, 1H), 2.13-2.24 (m, 7H), 2.61-2.62 (m, 2H), 3.39-3.84 (m, 4H), 3.88-4.01 (m, 3H), 4.14-4.17 (m, 2H), 4.38-4.56 (m, 1H), 5.78 (d, J=11.2 Hz, 1H), 6.24-6.28 (m, 1H), 6.52-6.59 (m, 1H), 7.14-7.27 (m, 2H), 8.13-8.18 (m, 1H) 8.47-8.65 (m, 2H), 9.67-9.69 (m, 1H). [M+H] Calc'd for $C_{24}H_{29}N_7O_4$, 480.2; Found, 480.2

429

Example 166: (R)—N-(4-(3-((5-cyanopyrimidin-2-yl)amino)pyrrolidine-1-carbonyl)-2-(2-(dimethylamino)ethoxy)phenyl)acrylamide

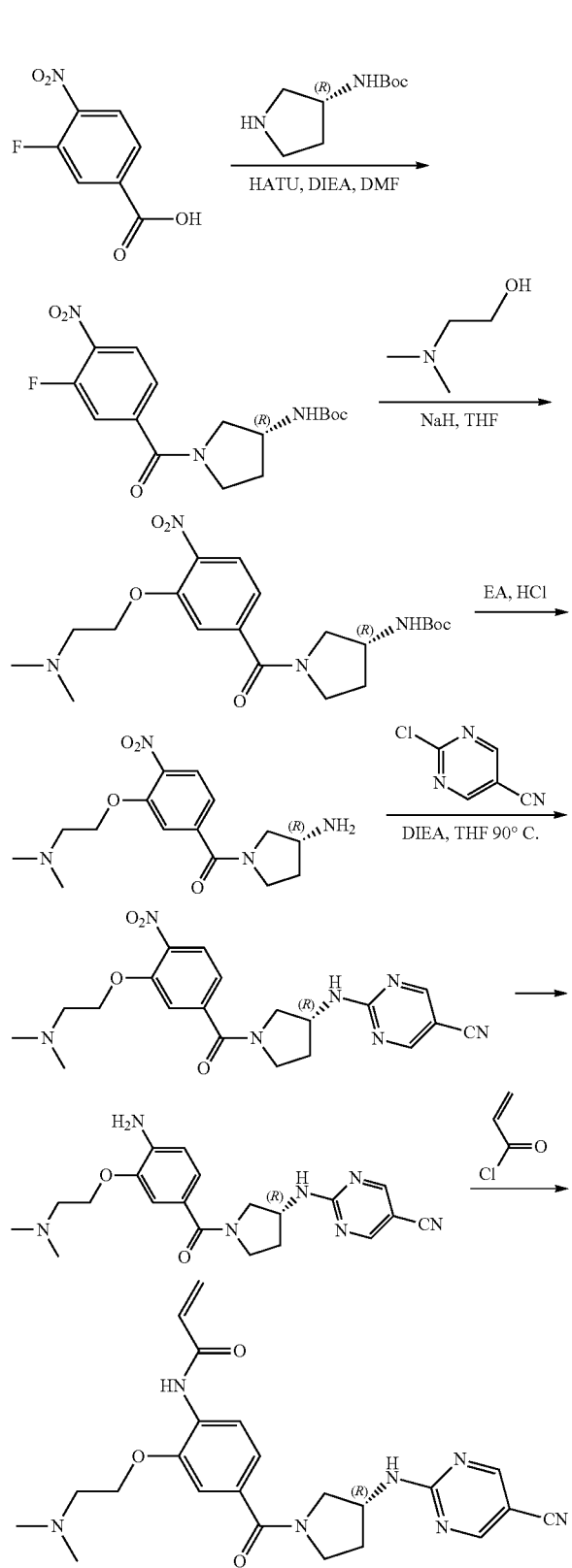

430

Step 1: (R)-tert-butyl (1-(3-fluoro-4-nitrobenzoyl)pyrrolidin-3-yl)carbamate

To a solution of 3-fluoro-4-nitrobenzoic acid (3.0 g, 16.2 mmol) and (R)-tert-butyl pyrrolidin-3-ylcarbamate (3.1 g, 14.6 mmol) in DMF (60 mL) was added HATU (6.7 g, 17.8 mmol) and DIEA (6.2 g, 48.6 mmol) at ice-bath. The mixture was stirred at RT for 2 h. The mixture was diluted with water (200 mL) and extracted with EA (100 mL*2). The combined organic layer was washed with brine (100 mL), dried over $Na_2SO_4$, filtered and ether evaporated. The residue was purified by column chromatography to afford 5 g of product as a yellow solid. [M+H] Calc'd for $C_{16}H_{20}FN_3O_5$, 354.1; Found, 354.1

Step 2: (R)-tert-butyl (1-(3-(2-(dimethylamino)ethoxy)-4-nitrobenzoyl)pyrrolidin-3-yl)carbamate To a solution of 2-(dimethylamino)ethanol (1.5 g, 17.0 mmol) in THF (80 mL) was added NaH (680 mg, 17.0 mmol, 60%) in an ice-bath. The reaction mixture was then stirred at RT for 0.5 h. Then (R)-tert-butyl (1-(3-fluoro-4-nitrobenzoyl)pyrrolidin-3-yl)carbamate (5.0 g, 14.1 mmol) was added and the mixture was stirred at RT for 2 h. The mixture was concentrated in-vacuo and to the residue was added water and extracted with EA. The combined organic layer was washed with brine (100 mL), dried over $Na_2SO_4$, filtered and ether evaporated. The residue was purified by column chromatography to afford 3.6 g of product as a yellow solid. [M+H] Calc'd for $C_{20}H_{30}N_4O_6$, 423.2; Found, 423.2

Step 3: (R)-(3-aminopyrrolidin-1-yl)(3-(2-(dimethylamino)ethoxy)-4-nitrophenyl)methanone

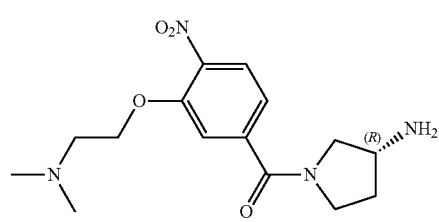

To a solution of (R)-tert-butyl (1-(3-(2-(dimethylamino)ethoxy)-4-nitrobenzoyl)pyrrolidin-3-yl)carbamate (3.6 g, 8.5 mmol) in EA (50 mL) was bubbled HCl (gas) at −50° C. and the reaction mixture was stirred at RT for 3 h. The mixture was concentrated to afford 2.4 g crude product as a yellow solid. [M+H] Calc'd for $C_2H_{30}N_4O_6$, 323.2; Found, 323.2

Step 4: (R)-2-((1-(3-(2-(dimethylamino)ethoxy)-4-nitrobenzoyl)pyrrolidin-3-yl)amino)pyrimidine-5-carbonitrile

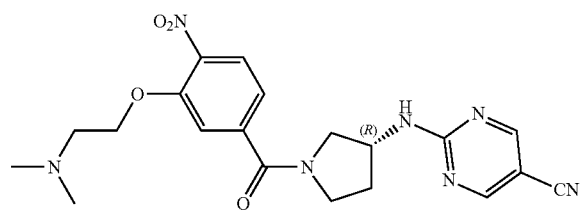

To a solution of (R)-(3-aminopyrrolidin-1-yl)(3-(2-(dimethylamino)ethoxy)-4-nitrophenyl)methanone (1.0 g, 3.1 mmol) and DIEA (1.2 g, 9.3 mmol) in DMA (15 mL) was added a solution of 2-chloropyrimidine-5-carbonitrile (640 mg, 2.8 mmol) in an ice-bath and the reaction mixture was warmed to RT and stirred for 2 h. Then to the mixture was added water (20 mL) which was used directly in the next step. [M+H] Calc'd for $C_{20}H_{23}N_7O_4$, 426.1; Found, 426.1

Step 5: (R)-2-((1-(4-amino-3-(2-(dimethylamino)ethoxy)benzoyl)pyrrolidin-3-yl)amino)pyrimidine-5-carbonitrile

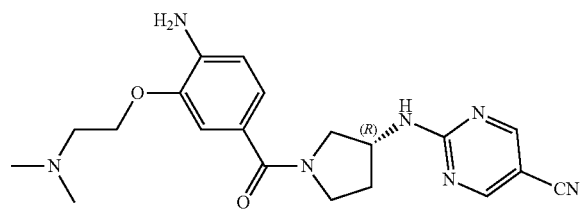

To a solution of (R)-2-((1-(3-(2-(dimethylamino)ethoxy)-4-nitrobenzoyl)pyrrolidin-3-yl)amino)pyrimidine-5-carbonitrile (1.0 g, 2.3 mmol) in ethanol (60 mL) and water (20 mL) was added $NH_4Cl$ (1.2 g, 23.5 mmol) and Fe (1.3 g, 23.5 mmol) at RT. The reaction mixture was then stirred at 80° C. for 2 h. The mixture was filtered and concentrated and the residue was purified by column chromatography to afford 700 mg crude product as a yellow solid. [M+H] Calc'd for $C_{20}H3N_4O_6$, 396.2; Found, 396.2

Step 6: (R)—N-(4-(3-((5-cyanopyrimidin-2-yl)amino)pyrrolidine-1-carbonyl)-2-(2-(dimethylamino)ethoxy)phenyl)acrylamide

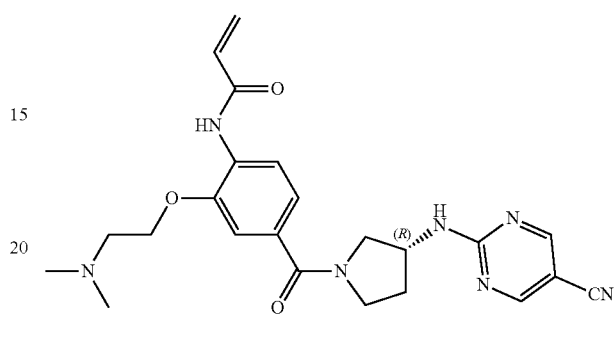

To a solution of (R)-2-((1-(4-amino-3-(2-(dimethylamino)ethoxy)benzoyl)pyrrolidin-3-yl)amino)pyrimidine-5-carbonitrile (700 mg, 1.77 mmol) and DIEA (687 mg, 5.31 mmol) in DCM (30 mL) and DMF (3 mL) was added acryloyl chloride (238 mg, 2.65 mmol) in an ice-bath. The reaction mixture was then warmed to RT and stirred for 2 h. The reaction mixture was concentrated and the residue was purified by prep-HPLC to afford (R)—N-(4-(3-((5-cyanopyrimidin-2-yl)amino)pyrrolidine-1-carbonyl)-2-(2-(dimethylamino)ethoxy)phenyl)acrylamide (152.5 mg, 19%) as a white solid. $^1H$ NMR (400 MHz, DMSO-$d_6$): 1.89-2.03 (m, 1H), 2.03-2.21 (m, 1H), 2.22-2.24 (d, J=6.4 Hz, 6H), 2.60-2.62 (m, 2H), 3.31-3.65 (m, 4H), 4.13-4.17 (m, 2H), 4.39 (s, 0.5H), 4.52 (s, 0.5H), 5.76-5.79 (d, J=10 Hz, 1H), 6.24-6.28 (d, J=16.8 Hz, 1H), 6.52-6.59 (m, 1H), 7.14-7.15 (t, J=14.0 Hz, 1H), 7.23-7.27 (d, J=14.0 Hz, 1H), 8.14-8.17 (t, J=14.0 Hz, 1H), 8.64-8.78 (m, 3H), 9.65-9.68 (d, J=12.4 Hz, 1H). [M+H] Calc'd for $C_{23}H_{27}N_7O_3$, 450.2; Found, 450.2

Example 167: Synthesis of (E)-N-(4-((R)-3-((5-chloro-4-methoxypyrimidin-2-yl)amino)pyrrolidine-1-carbonyl)phenyl)-4-((R)-3-fluoropyrrolidin-1-yl)but-2-enamide

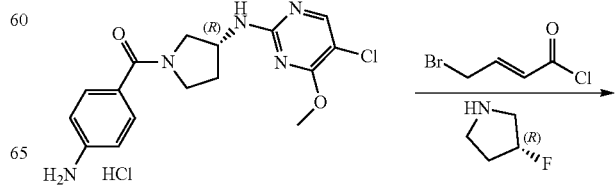

433

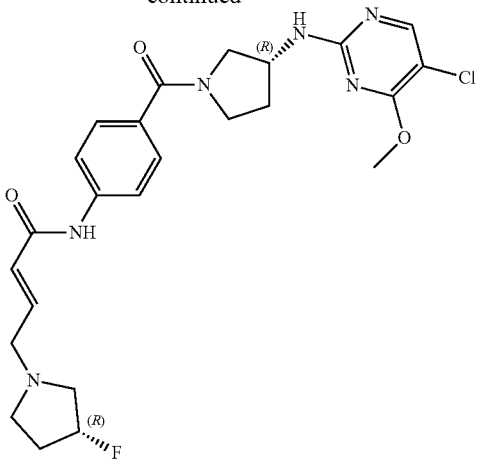

To a solution of (R)-(4-aminophenyl)(3-((5-chloro-4-methoxypyrimidin-2-yl)amino)pyrrolidin-1-yl)methanone hydrochloride (174 mg, 0.5 mmol) and DIEA (194 mg, 1.5 mmol) in DCM (10 mL) was added a solution of (E)-4-bromobut-2-enoyl chloride (184 mg, 1.0 mmol) in DCM (5 mL) in an ice-bath. The mixture was stirred in the ice-bath for 1 h and then (R)-3-fluoropyrrolidine (53 mg, 0.6 mmol) was added to the mixture and the mixture was stirred at RT for 5 h. The mixture was concentrated and purified by prep-HPLC to afford (E)-N-(4-((R)-3-((5-chloro-4-methoxypyrimidin-2-yl)amino)pyrrolidine-1-carbonyl)phenyl)-4-((R)-3-fluoropyrrolidin-1-yl)but-2-enamide (23 mg, 9%) as a yellow solid. $^1$H NMR (400 MHz, DMSO-d$_6$): δ 1.89-1.90 (m, 2H), 1.97-2.16 (m, 2H), 2.33-2.40 (m, 2H), 2.58-2.68 (m, 2H), 2.84-2.87 (m, 2H), 3.28-3.64 (m, 4H), 3.77-3.93 (m, 3H), 4.26-4.40 (m, 1H), 5.14-5.28 (m, 1H), 6.28-6.32 (m, 1H), 6.77-6.81 (m, 1H), 7.47-7.52 (m, 2H), 7.67-7.72 (m, 3H), 8.07-8.14 (m, 1H), 10.24 (s, 1H). [M+H] Calc'd for C$_{24}$H$_{28}$ClFN$_6$O$_3$, 503.1; Found, 503.1

Example 168: Synthesis of (R,E)-N-(4-(3-((5-chloro-4-methoxypyrimidin-2-yl)amino)pyrrolidine-1-carbonyl)phenyl)-4-morpholinobut-2-enamide

434

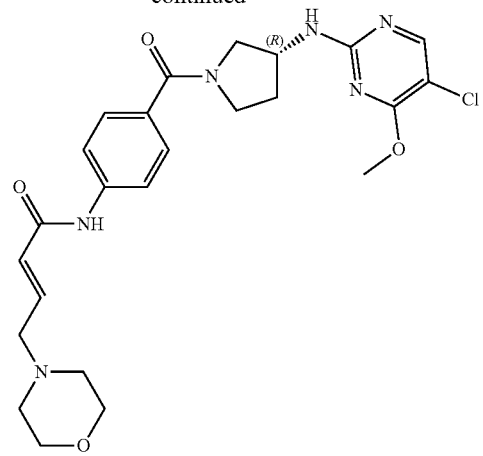

To a solution of (R)-(4-aminophenyl)(3-((5-chloro-4-methoxypyrimidin-2-yl)amino)pyrrolidin-1-yl)methanone (400 mg, 1.15 mmol) and DIEA (593 mg, 4.6 mmol) in DCM (10 mL) was added (E)-4-bromobut-2-enoyl chloride (423 mg, 2.3 mmol) in an ice-bath. The mixture was stirred at RT for 1 h. Morpholine (200 mg, 2.3 mmol) was added to the mixture and stirred at RT for overnight. The mixture was concentrated and purified by prep-HPLC to afford (R,E)-N-(4-(3-((5-chloro-4-methoxypyrimidin-2-yl)amino)pyrrolidine-1-carbonyl)phenyl)-4-morpholinobut-2-enamide (66.5 mg, 12%) as a white solid. $^1$H NMR (400 MHz, DMSO-d$_6$): 1.90-2.15 (m, 2H), 2.39 (s, 4H), 3.12 (d, J=4.4 Hz, 2H), 3.38-3.64 (m, 7H), 3.78-3.94 (m, 4H), 4.25 (s, 0.5H), 4.42 (s, 0.5H), 6.27 (s, 0.5H), 6.31 (s, 0.5H), 6.73-6.77 (m, 1H), 7.50 (t, J=8.4 Hz, 2H), 7.70 (t, J=8.4 Hz, 3H), 8.07 (s, 0.5H), 8.15 (s, 0.5H), 10.23 (s, 1H). [M+H] Calc'd for C$_{24}$H$_{29}$ClN$_6$O$_4$, 501.2 Found, 501.2

Example 169: (R)—N-(4-(3-((5-bromopyrimidin-2-yl)amino)pyrrolidine-1-carbonyl)-2-(4-(dimethylamino)piperidin-1-yl)phenyl)acrylamide

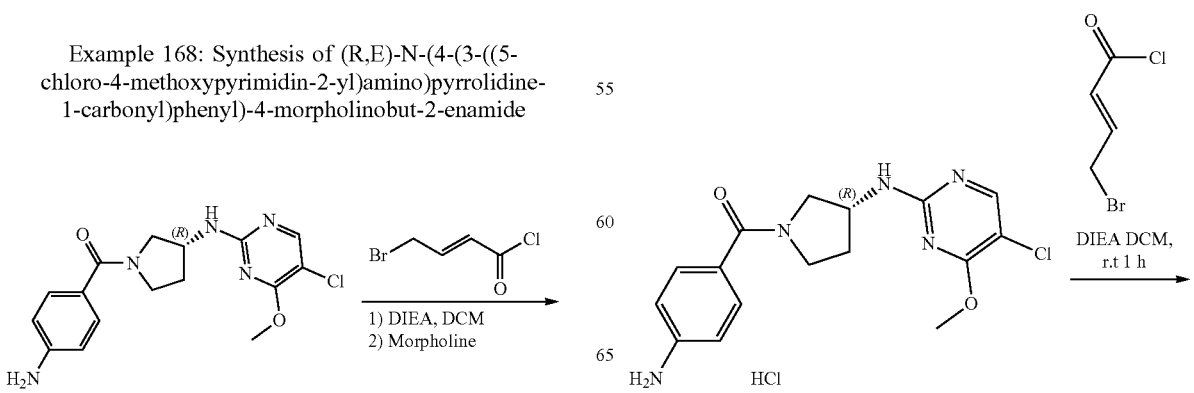

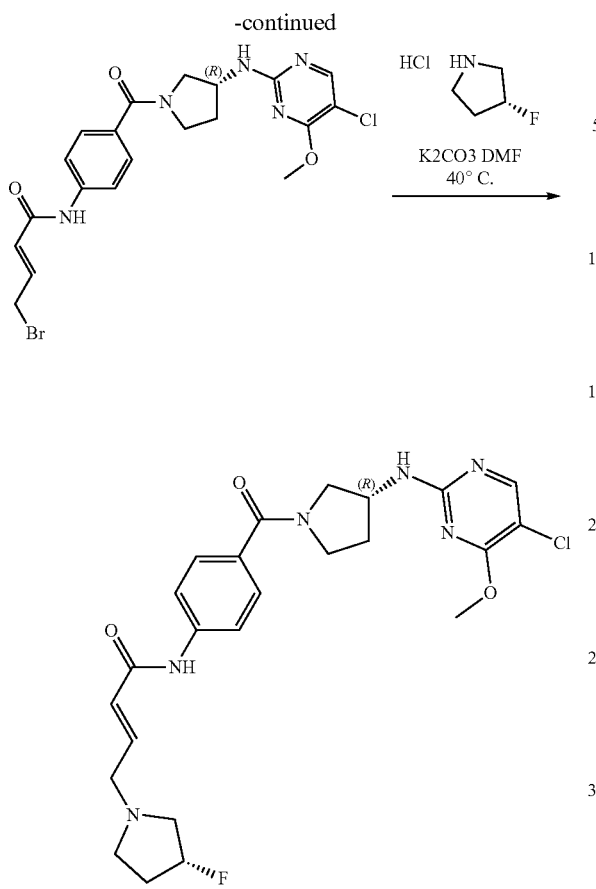

Step 1: (R,E)-4-bromo-N-(4-(3-((5-chloro-4-methoxypyrimidin-2-yl)amino)pyrrolidine-1-carbonyl)phenyl)but-2-enamide

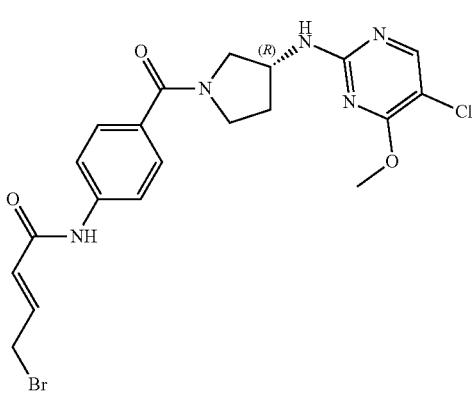

To a solution of (R)-(4-aminophenyl)(3-((5-chloro-4-methoxypyrimidin-2-yl)amino)pyrrolidin-1-yl)methanone (2.0 g, 5.8 mmol) and DIEA (3.7 g, 28.8 mmol) in DCM (50 mL) was added (E)-4-bromobut-2-enoyl chloride (2.1 g, 11.5 mmol) at ice-bath. The mixture was stirred at RT for 2 h. The mixture was concentrated and columned to afford 800 mg crude product as a yellow solid. [M+H] Calc'd for $C_{20}H_{21}BrClN_5O_3$: 496.1 Found: 496.1

Step 2: (E)-N-(4-((R)-3-((5-chloro-4-methoxypyrimidin-2-yl)amino)pyrrolidine-1-carbonyl)phenyl)-4-((S)-3-fluoropyrrolidin-1-yl)but-2-enamide

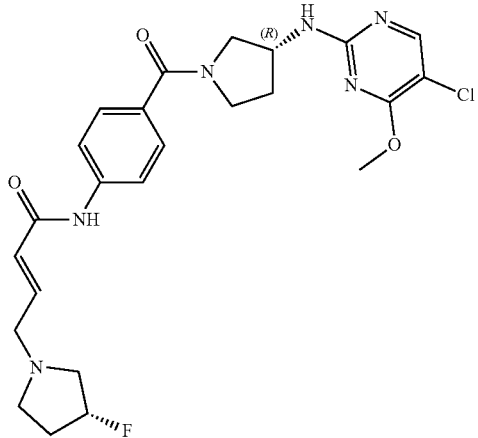

To a solution of (R,E)-4-bromo-N-(4-(3-((5-chloro-4-methoxypyrimidin-2-yl)amino)pyrrolidine-1-carbonyl)phenyl)but-2-enamide (200 mg, 0.4 mmol) and (S)-3-fluoropyrrolidine hydrochloride (71 mg, 0.8 mmol) in DMF (3 mL) was added $K_2CO_3$ (165 mg, 1.2 mmol) at RT. The reaction mixture was stirred at 50° C. for 2 h. The reaction mixture was cooled, filtered and concentrated. The residue was purified by prep-HPLC to afford (E)-N-(4-((R)-3-((5-chloro-4-methoxypyrimidin-2-yl)amino)pyrrolidine-1-carbonyl)phenyl)-4-((S)-3-fluoropyrrolidin-1-yl)but-2-enamide (12.7 mg, 6%) as a white solid. $^1$H NMR (400 MHz, DMSO-d$_6$): 1.87-2.15 (m, 4H), 2.33-2.34 (m, 1H), 2.83-2.87 (m, 2H), 3.27-3.78 (m, 6H), 3.85 (s, 1.5H), 3.94 (s, 1.5H), 4.27 (s, 0.5H), 4.41 (s, 0.5H), 5.14-5.28 (m, 1H), 6.28 (s, 0.5H), 6.32 (s, 0.5H), 6.77-6.81 (m, 1H), 7.47-7.52 (t, J=10.8 Hz, 2H), 7.67-7.71 (m, 3H), 8.07 (s, 0.5H), 8.14 (s, 0.5H), 10.22 (s, 1H). [M+H]Calc'd for $C_{24}H_{28}ClFN_6O_3$, 503.1 Found, 503.1

Example 170: Synthesis of (E)-N-(6-((R)-3-((5-chloro-4-methoxypyrimidin-2-yl)amino)pyrrolidine-1-carbonyl)pyridin-3-yl)-4-((R)-3-fluoropyrrolidin-1-yl)but-2-enamide

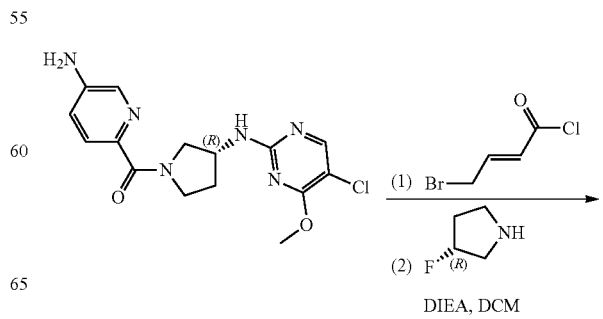

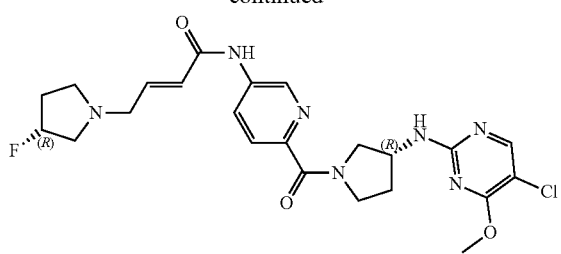

To a solution of (R)-(5-aminopyridin-2-yl)(3-((5-chloro-4-methoxypyrimidin-2-yl)amino)pyrrolidin-1-yl)methanone (200 mg, 0.57 mmol) and DIEA (220 mg, 1.71 mmol) in DCM (20 mL) was added (E)-4-bromobut-2-enoyl chloride (184 mg, 1.00 mmol) in DCM (5 mL) at ice-bath, after 1 h, (R)-3-fluoropyrrolidine (101 mg, 1.14 mmol) was added to the mixture and stirred at RT for 5 h. The mixture was concentrated in vacuo and purified by prep-HPLC to afford (E)-N-(6-((R)-3-((5-chloro-4-methoxypyrimidin-2-yl)amino)pyrrolidine-1-carbonyl)pyridin-3-yl)-4-((R)-3-fluoropyrrolidin-1-yl)but-2-enamide (39.4 mg, 14%) as a white solid. $^1$H NMR (400 MHz, DMSO-$d_6$): δ 1.93-1.97 (m, 2H), 2.11-2.17 (m, 2H), 2.32-2.37 (m, 2H), 2.58-2.66 (m, 2H), 2.82-2.88 (m, 2H), 3.32-3.81 (m, 4H), 3.89-3.93 (m, 3H), 4.34-4.36 (m, 1H), 5.13-5.30 (m, 1H), 6.30-6.34 (m, 1H), 6.82-6.86 (m, 1H), 7.69-7.79 (m, 2H), 8.09-8.21 (m, 2H), 8.78-8.82 (m, 1H), 10.49-10.50 (m, 1H). [M+H] Calc'd for $C_{23}H_{27}ClFN_7O_3$, 504.2; Found, 504.2

Example 171: Synthesis of (E)-N-(6-((R)-3-((5-chloro-4-methoxypyrimidin-2-yl)amino)pyrrolidine-1-carbonyl)pyridin-3-yl)-4-((S)-3-fluoropyrrolidin-1-yl)but-2-enamide Step 1: (R,E)-4-bromo-N-(6-(3-((5-chloro-4-methoxypyrimidin-2-yl)amino)pyrrolidine-1-carbonyl)pyridin-3-yl)but-2-enamide

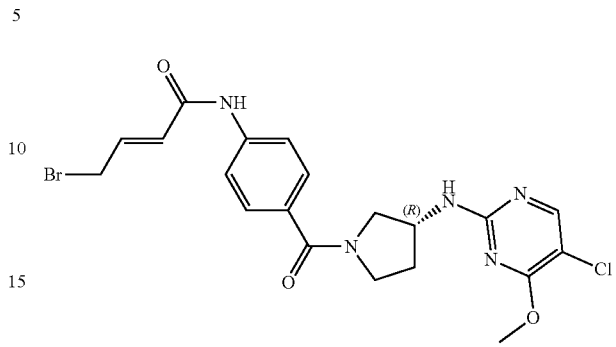

To a solution of (R)-(5-aminopyridin-2-yl)(3-((5-chloro-4-methoxypyrimidin-2-yl)amino)pyrrolidin-1-yl)methanone (500 mg, 1.40 mmol) and DIEA (722 mg, 1.71 mmol) in DCM (20 mL) was added (E)-4-bromobut-2-enoyl chloride (528 mg, 2.80 mmol) in DCM (10 mL) in an ice-bath. The reaction mixture was filtered and concentrated in vacuo. The residue was purified by silica gel chromatography to afford (R,E)-4-bromo-N-(6-(3-((5-chloro-4-methoxypyrimidin-2-yl)amino)pyrrolidine-1-carbonyl)pyridin-3-yl)but-2-enamide (270 mg, 200%) as yellow solid. [M+H] Calc'd for $C_{19}H_{20}BrClN_6O_3$, 495.0; Found, 495.0

Step 2: Synthesis of (E)-N-(6-((R)-3-((5-chloro-4-methoxypyrimidin-2-yl)amino)pyrrolidine-1-carbonyl)pyridin-3-yl)-4-((S)-3-fluoropyrrolidin-1-yl)but-2-enamide

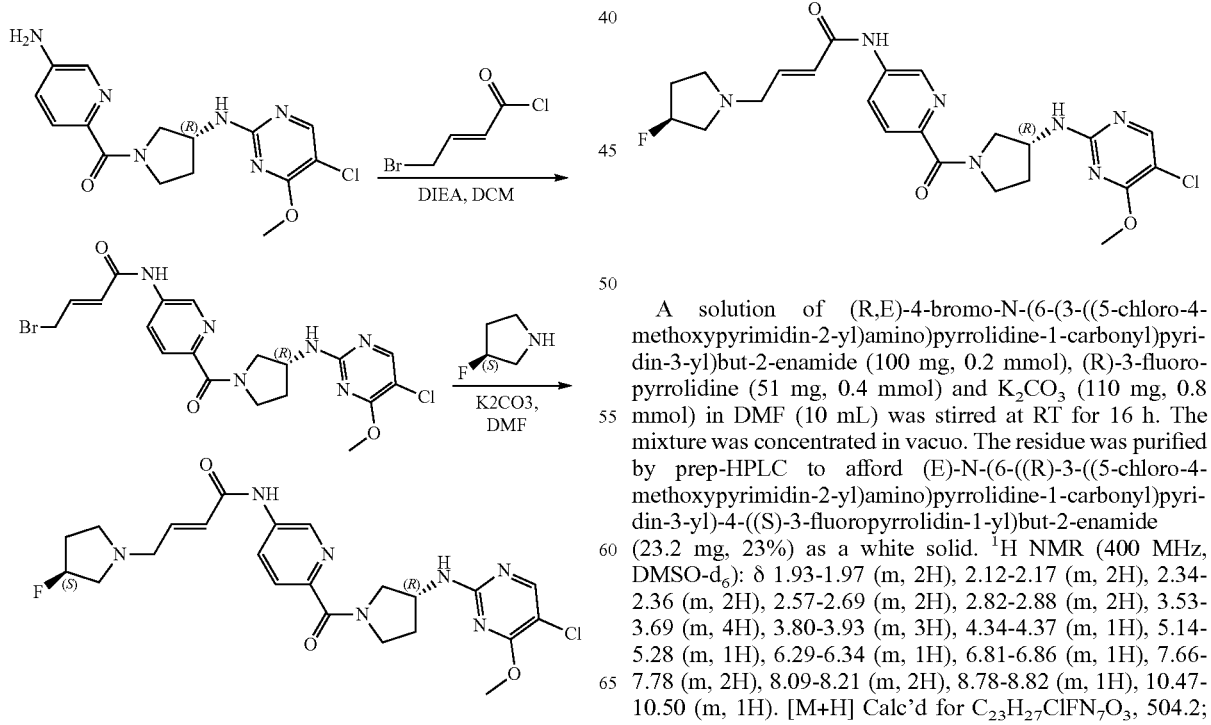

A solution of (R,E)-4-bromo-N-(6-(3-((5-chloro-4-methoxypyrimidin-2-yl)amino)pyrrolidine-1-carbonyl)pyridin-3-yl)but-2-enamide (100 mg, 0.2 mmol), (R)-3-fluoropyrrolidine (51 mg, 0.4 mmol) and $K_2CO_3$ (110 mg, 0.8 mmol) in DMF (10 mL) was stirred at RT for 16 h. The mixture was concentrated in vacuo. The residue was purified by prep-HPLC to afford (E)-N-(6-((R)-3-((5-chloro-4-methoxypyrimidin-2-yl)amino)pyrrolidine-1-carbonyl)pyridin-3-yl)-4-((S)-3-fluoropyrrolidin-1-yl)but-2-enamide (23.2 mg, 23%) as a white solid. $^1$H NMR (400 MHz, DMSO-$d_6$): δ 1.93-1.97 (m, 2H), 2.12-2.17 (m, 2H), 2.34-2.36 (m, 2H), 2.57-2.69 (m, 2H), 2.82-2.88 (m, 2H), 3.53-3.69 (m, 4H), 3.80-3.93 (m, 3H), 4.34-4.37 (m, 1H), 5.14-5.28 (m, 1H), 6.29-6.34 (m, 1H), 6.81-6.86 (m, 1H), 7.66-7.78 (m, 2H), 8.09-8.21 (m, 2H), 8.78-8.82 (m, 1H), 10.47-10.50 (m, 1H). [M+H] Calc'd for $C_{23}H_{27}ClFN_7O_3$, 504.2; Found, 504.2.

Example 172: Synthesis of (R,E)-N-(6-(3-((5-chloro-4-methoxypyrimidin-2-yl)amino)pyrrolidine-1-carbonyl)pyridin-3-yl)-4-(3,3-difluoropiperidin-1-yl)but-2-enamide

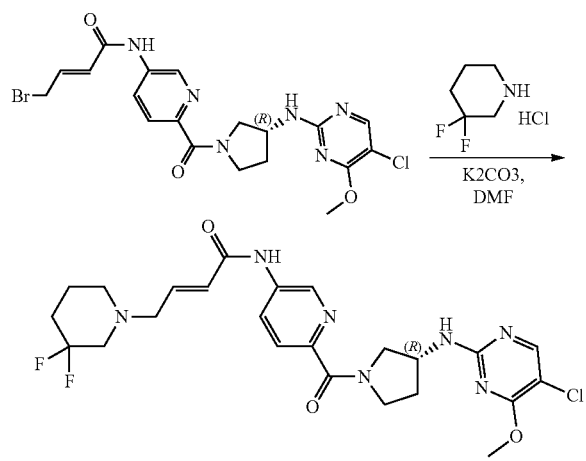

To a mixture of (R,E)-4-bromo-N-(6-(3-((5-chloro-4-methoxypyrimidin-2-yl)amino)pyrrolidine-1-carbonyl)pyridin-3-yl)but-2-enamide (70 mg, 0.2 mmol) and 3,3-difluoropiperidine (45 mg, 0.3 mmol) in DMF (10 mL) was added $K_2CO_3$ (97 mg, 0.6 mmol) at 0° C. The reaction mixture was stirred at 25° C. for 5 h. The reaction was quenched with $H_2O$ (10 mL) and extracted with EA (50 mL×3). The combined organic layer was concentrated in vacuo and purified by prep-HPLC ($NH_4CO_3$ 20%~50%) to afford (R,E)-N-(6-(3-((5-chloro-4-methoxypyrimidin-2-yl)amino)pyrrolidine-1-carbonyl)pyridin-3-yl)-4-(3,3-difluoropiperidin-1-yl)but-2-enamide (11 mg, 15%) as a white solid. $^1$H NMR (400 MHz, DMSO-$d_6$): 1.70-1.75 (m, 2H), 1.87-2.17 (m, 4H), 2.46-2.52 (m, 2H), 2.52-2.75 (m, 2H), 3.26-3.28 (d, J=8.0 Hz, 2H), 3.54-3.83 (m, 4H), 3.90-3.96 (m, 3H), 4.35-4.39 (m, 1H), 6.30-6.35 (m, 1H), 6.79-6.84 (m, 1H), 7.79-7.82 (m, 2H), 8.12-8.24 (m, 2H), 8.81-8.85 (m, 1H), 10.52-10.54 (m, 1H). [M+H] Calc'd for $C_{24}H_{28}ClF_2N_7O_3$, 536.1; Found, 536.2.

Example 173: (R,E)-N-(4-(3-((5-chloro-4-methoxypyrimidin-2-yl)amino)pyrrolidine-1-carbonyl)phenyl)-4-(3,3-difluoropiperidin-1-yl)but-2-enamide

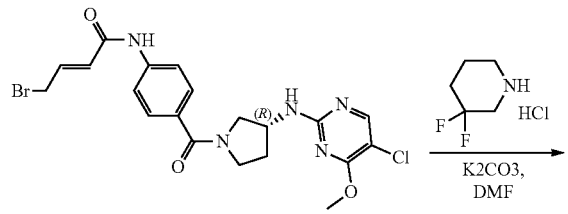

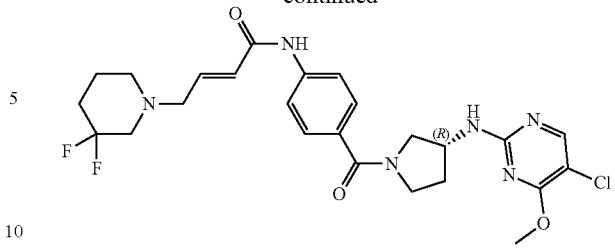

To a mixture of (R)-(4-aminophenyl)(3-((5-chloro-4-methoxypyrimidin-2-yl)amino)pyrrolidin-1-yl)methanone (150 mg, 0.3 mmol) and 3,3-difluoropiperidine (45 mg, 0.3 mmol) in DMF (10 mL) was added $K_2CO_3$ (207 mg, 1.5 mmol) at 0° C. The reaction mixture was then stirred at 40° C. for 13 h. The reaction was cooled, quenched with $H_2O$ (10 mL) and extracted with EA (50 mL*3). The combined organic layer was concentrated in vacuo and purified by prep-HPLC (HCOOH 10%~50%) to afford (R,E)-N-(4-(3-((5-chloro-4-methoxypyrimidin-2-yl)amino)pyrrolidine-1-carbonyl)phenyl)-4-(3,3-difluoropiperidin-1-yl)but-2-enamide (28 mg, 18%) as a white solid. $^1$H NMR (400 MHz, DMSO-$d_6$): 1.64-1.69 (m, 2H), 1.85-2.15 (m, 4H), 2.43-2.49 (m, 2H), 2.65-2.70 (m, 2H), 3.22-3.24 (d, J=8.0 Hz, 2H), 3.35-3.79 (m, 4H), 3.85-3.94 (m, 3H), 4.26-4.27 (m, 1H), 6.26-6.30 (m, 1H), 6.73-6.78 (m, 1H), 7.49-7.52 (m, 2H), 7.68-7.72 (m, 3H), 8.07-8.14 (m, 1H), 10.24 (s, 1H). [M+H] Calc'd for $C_{25}H_{29}ClF_2N_6O_3$, 535.2; Found, 535.2.

Example 174: Synthesis of (R,E)-N-(6-(3-((5-chloro-4-methoxypyrimidin-2-yl)amino)pyrrolidine-1-carbonyl)pyridin-3-yl)-4-morpholinobut-2-enamide

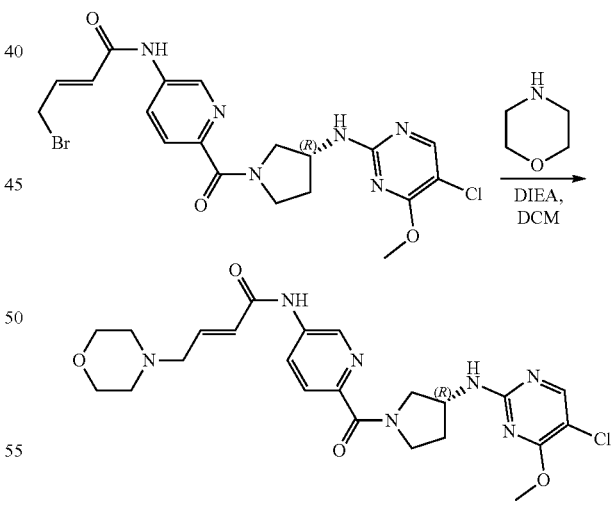

A solution of (R,E)-4-bromo-N-(6-(3-((5-chloro-4-methoxypyrimidin-2-yl)amino)pyrrolidine-1-carbonyl)pyridin-3-yl)but-2-enamide (90 mg, 0.18 mmol), morpholine (32 mg, 0.36 mmol) and DIEA (94 mg, 0.73 mmol) in DCM (5 mL) was stirred at RT for 16 h. The mixture was concentrated and the residue was purified by prep-HPLC to afford (R,E)-N-(6-(3-((5-chloro-4-methoxypyrimidin-2-yl)amino)pyrrolidine-1-carbonyl)pyridin-3-yl)-4-morpholinobut-2-enamide (6.8 mg, 8%) as a brown solid. $^1$H NMR (400 MHz, DMSO-d$_6$): δ 1.93-1.99 (m, 1H), 2.12-2.19 (m, 1H), 2.36-2.40 (m, 4H), 3.14-3.15 (m, 4H), 3.49-3.61 (m, 4H), 3.64-3.82 (m, 2H), 3.88-3.94 (m, 3H), 4.32-4.38 (m, 1H), 6.28-6.33 (m, 1H), 6.76-6.84 (m, 1H), 7.65-7.77 (m, 2H), 8.09-8.20 (m, 2H), 8.80 (dd, J=2.4, 16.4 Hz, 1H), 10.47 (d, J=6.0 Hz, 1H). [M+H] Calc'd for C$_{46}$H$_{57}$BrCl$_2$N$_{14}$O$_8$, 502.2; Found, 502.2.

Example 175 & 176: Synthesis of (E)-N-(6-((R)-3-((5-chloro-4-methoxypyrimidin-2-yl)amino)pyrrolidine-1-carbonyl)pyridin-3-yl)-4-((S)-3-fluoropiperidin-1-yl)but-2-enamide & (E)-N-(6-((R)-3-((5-chloro-4-methoxypyrimidin-2-yl)amino)pyrrolidine-1-carbonyl)pyridin-3-yl)-4-((R)-3-fluoropiperidin-1-yl)but-2-enamide

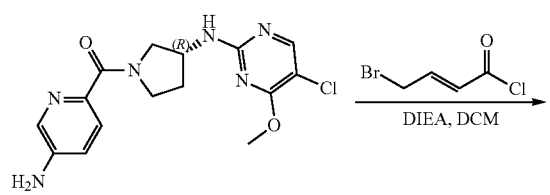

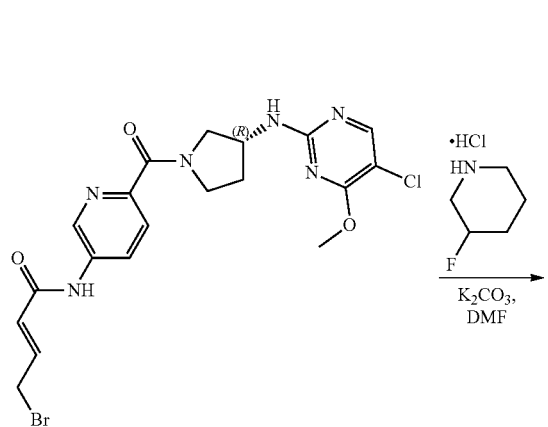

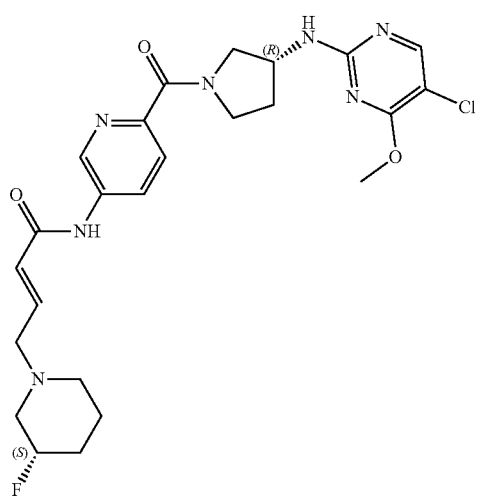

Step 1: (R,E)-4-bromo-N-(6-(3-((5-chloro-4-methoxypyrimidin-2-yl)amino)pyrrolidine-1-carbonyl)pyridin-3-yl)but-2-enamide

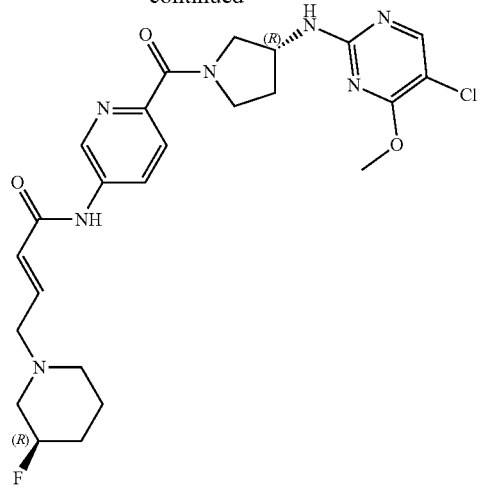

To a solution of (R)-(5-aminopyridin-2-yl)(3-((5-chloro-4-methoxypyrimidin-2-yl)amino)pyrrolidin-1-yl)methanone (1.0 g, 2.9 mmol) and DIEA (1.1 g, 8.7 mmol) in DCM (50 mL) was added a solution of (E)-4-bromobut-2-enoyl chloride (1.1 g, 5.8 mmol) in DCM (10 mL) in an ice-bath and the reaction mixture was stirred at 0° C. for 10 min. The reaction mixture was filtered and concentrated and the residue was purified by silica gel chromatography (PE:EA=1:1) to afford (R,E)-4-bromo-N-(6-(3-((5-chloro-4-methoxypyrimidin-2-yl)amino)pyrrolidine-1-carbonyl)pyridin-3-yl)but-2-enamide (500 mg, 36%) as a white solid. [M+H] Calc'd for C$_{19}$H$_{20}$BrClN$_6$O$_3$, 495.0; Found, 495.0.

Step 2: Synthesis of (E)-N-(6-((R)-3-((5-chloro-4-methoxypyrimidin-2-yl)amino)pyrrolidine-1-carbonyl)pyridin-3-yl)-4-((S)-3-fluoropiperidin-1-yl)but-2-enamide and (E)-N-(6-((R)-3-((5-chloro-4-methoxypyrimidin-2-yl)amino)pyrrolidine-1-carbonyl)pyridin-3-yl)-4-((R)-3-fluoropiperidin-1-yl)but-2-enamide

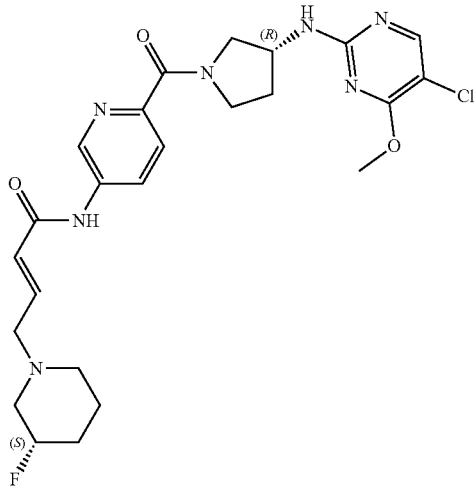

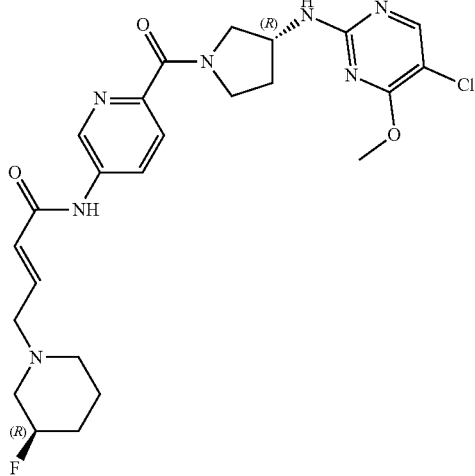

A solution of (R,E)-4-bromo-N-(6-(3-((5-chloro-4-methoxypyrimidin-2-yl)amino)pyrrolidine-1-carbonyl)pyridin-3-yl)but-2-enamide (200 mg, 0.4 mmol), 3-fluoropiperidine HCl salt (225 mg, 1.6 mmol) and K$_2$CO$_3$ (442 mg, 3.2 mmol) in DMF (20 mL) was stirred at RT for 16 h. The mixture was concentrated in vacuo and the residue was purified by prep-HPLC (120 mg, 58%) and chiral separation (IE: 4.6 mm*250 mm 5 um; Method Filename: MeOH-DCM-DEA=80-20-0.2) to afford (E)-N-(6-((R)-3-((5-chloro-4-methoxypyrimidin-2-yl)amino)pyrrolidine-1-carbonyl)pyridin-3-yl)-4-((S)-3-fluoropiperidin-1-yl)but-2-enamide (56.9 mg, Rt=10.227 min) and (E)-N-(6-((R)-3-((5-chloro-4-methoxypyrimidin-2-yl)amino)pyrrolidine-1-carbonyl)pyridin-3-yl)-4-((R)-3-fluoropiperidin-1-yl)but-2-enamide (40.5 mg, Rt=16.573 min) as a white solid.

Rt=10.227 min: $^1$H NMR (400 MHz, DMSO-d$_6$): δ 1.51-1.52 (m, 2H), 1.72-1.94 (m, 4H), 2.13-2.43 (m, 3H), 2.66-2.71 (m, 1H), 3.17-3.19 (m, 2H), 3.48-3.69 (m, 3H), 3.77-4.02 (m, 4H), 4.35-4.37 (m, 1H), 4.58-4.71 (m, 1H), 6.26-6.30 (m, 1H), 6.78-6.81 (m, 1H), 7.70-7.79 (m, 2H), 8.09-8.21 (m, 2H), 8.78-8.82 (m, 1H), 10.48-10.50 (m, 1H). [M+H] Calc'd for C$_{24}$H$_{29}$ClFN$_7$O$_3$, 518.2; Found, 518.2.

Rt=16.573 min: $^1$H NMR (400 MHz, DMSO-d$_6$): δ 1.49-1.51 (m, 2H), 1.74-1.96 (m, 4H), 2.13-2.43 (m, 3H), 2.66-2.69 (m, 1H), 3.17-3.19 (m, 2H), 3.52-3.69 (m, 3H), 3.77-3.93 (m, 4H), 4.35-4.37 (m, 1H), 4.60-4.72 (m, 1H), 6.27-6.31 (m, 1H), 6.77-6.81 (m, 1H), 7.67-7.79 (m, 2H), 8.09-8.21 (m, 2H), 8.78-8.83 (m, 1H), 10.48-10.50 (m, 1H). [M+H] Calc'd for C$_{24}$H$_{29}$ClFN$_7$O$_3$, 518.2; Found, 518.2.

Example 177 & 178: Synthesis of (E)-N-(4-((R)-3-((5-chloro-4-methoxypyrimidin-2-yl)amino)pyrrolidine-1-carbonyl)phenyl)-4-((S)-3-fluoropiperidin-1-yl)but-2-enamide & (E)-N-(4-((R)-3-((5-chloro-4-methoxypyrimidin-2-yl)amino)pyrrolidine-1-carbonyl)phenyl)-4-((R)-3-fluoropiperidin-1-yl)but-2-enamide

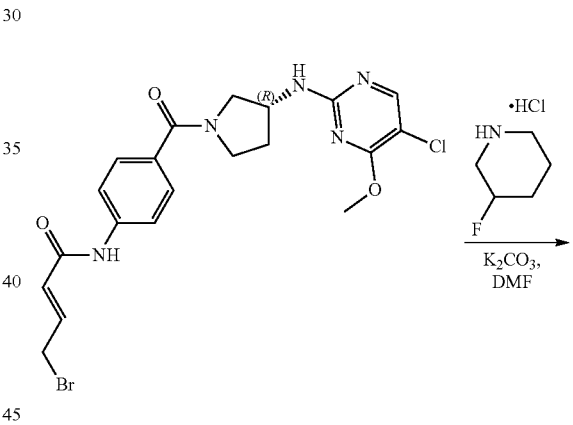

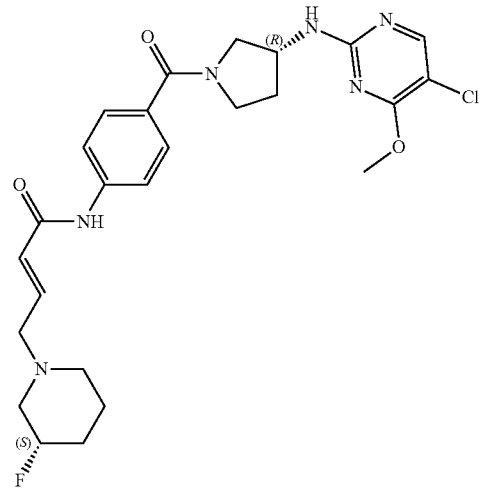

-continued

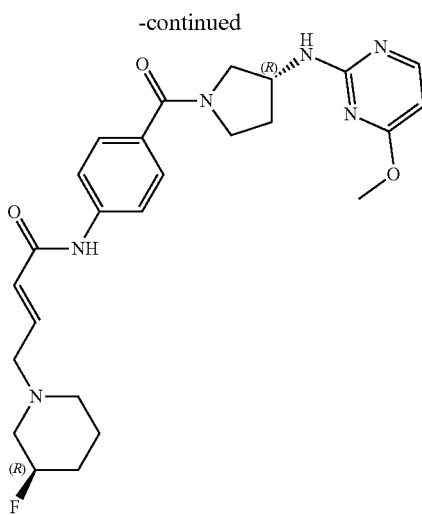

Step 1: (E)-N-(4-((R)-3-((5-chloro-4-methoxypyrimidin-2-yl)amino)pyrrolidine-1-carbonyl)phenyl)-4-((S)-3-fluoropiperidin-1-yl)but-2-enamide & (E)-N-(4-((R)-3-((5-chloro-4-methoxypyrimidin-2-yl)amino)pyrrolidine-1-carbonyl)phenyl)-4-((R)-3-fluoropiperidin-1-yl)but-2-enamide

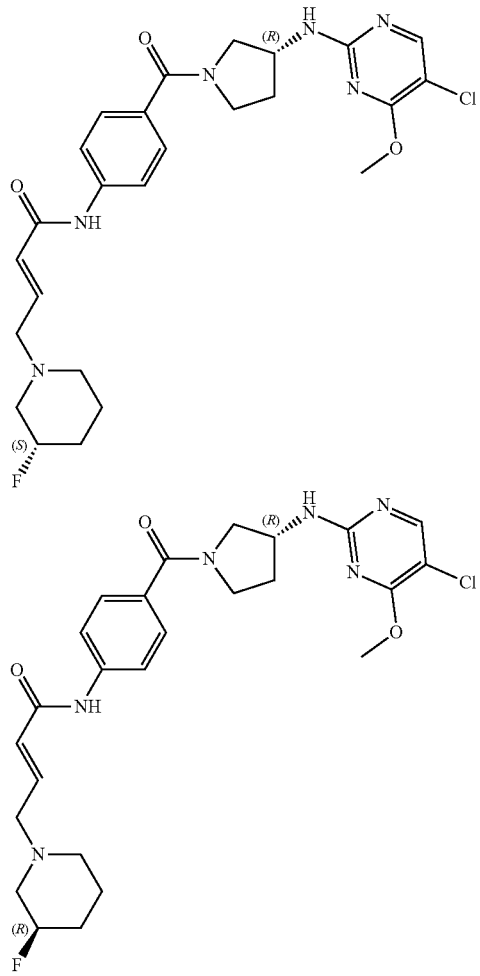

A solution of (R,E)-4-bromo-N-(4-(3-((5-chloro-4-methoxypyrimidin-2-yl)amino)pyrrolidine-1-carbonyl)phenyl)but-2-enamide (400 mg, 0.8 mmol), 3-fluoropiperidine HCl salt (445 mg, 3.2 mmol) and $K_2CO_3$ (883 mg, 6.4 mmol) in DMF (20 mL) was stirred at RT for 16 h. The mixture was concentrated and the residue was purified by prep-HPLC (60 mg, 14%) and chiral separation (IG: 4.6 mm*250 mm 5 um; Method Filename: MeOH-DCM-DEA=85-15-0.2) to afford (E)-N-(4-((R)-3-((5-chloro-4-methoxypyrimidin-2-yl)amino)pyrrolidine-1-carbonyl)phenyl)-4-((S)-3-fluoropiperidin-1-yl)but-2-enamide (19.7 mg, Rt=10.249 min) and (E)-N-(4-((R)-3-((5-chloro-4-methoxypyrimidin-2-yl)amino)pyrrolidine-1-carbonyl)phenyl)-4-((R)-3-fluoropiperidin-1-yl)but-2-enamide (19 mg, Rt=17.114 min) as a white solid.

Rt=10.249 min: $^1$H NMR (400 MHz, DMSO-$d_6$): δ 1.51-1.52 (m, 2H), 1.72-1.94 (m, 4H), 2.10-2.41 (m, 3H), 2.67-2.69 (m, 1H), 3.15-3.17 (m, 2H), 3.34-3.62 (m, 4H), 3.77-3.93 (m, 3H), 4.24-4.40 (m, 1H), 4.59-4.71 (m, 1H), 6.25-6.29 (m, 1H), 6.73-6.76 (m, 1H), 7.47-7.50 (m, 2H), 7.67-7.72 (m, 3H), 8.07-8.15 (m, 1H), 10.24-10.25 (m, 1H). [M+H] Calc'd for $C_{25}H_{30}ClFN_6O_3$, 517.2; Found, 517.2.

Rt=17.114 min: $^1$H NMR (400 MHz, DMSO-$d_6$): δ 1.48-1.51 (m, 2H), 1.71-1.96 (m, 4H), 2.13-2.43 (m, 3H), 2.67-2.69 (m, 1H), 3.15-3.17 (m, 2H), 3.33-3.62 (m, 4H), 3.77-3.93 (m, 3H), 4.26-4.40 (m, 1H), 4.61-4.71 (m, 1H), 6.25-6.29 (m, 1H), 6.73-6.75 (m, 1H), 7.47-7.53 (m, 2H), 7.67-7.72 (m, 3H), 8.07-8.16 (m, 1H), 10.24-10.25 (m, 1H). [M+H] Calc'd for $C_{25}H_{30}ClFN_6O_3$, 517.2; Found, 517.2.

Example 179: Synthesis of (E)-N-(5-((R)-3-((5-chloro-4-methoxypyrimidin-2-yl)amino)pyrrolidine-1-carbonyl)pyridin-2-yl)-4-((R)-3-fluoropyrrolidin-1-yl)but-2-enamide

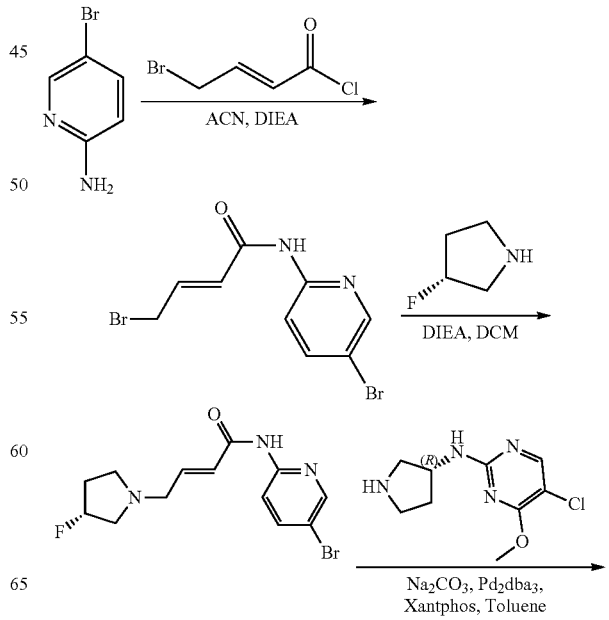

447

-continued

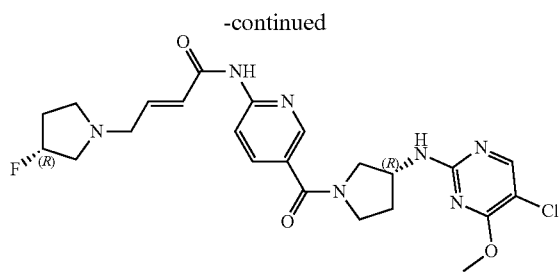

Step 1: (E)-4-bromo-N-(5-bromopyridin-2-yl)but-2-enamide

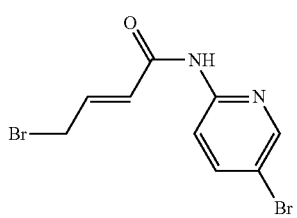 [SMILES: O=C(/C=C/CBr)Nc1ccc(Br)cn1]

To a solution of 5-bromopyridin-2-amine (346 mg, 2.0 mmol) and DIEA (774 mg, 6.0 mmol) in CH$_3$CN (10 mL) was added (E)-4-bromobut-2-enoyl chloride (550 mg, 3.0 mmol) in an ice-bath and the reaction mixture was stirred at 0° C. for 10 min. The reaction mixture was filtered and concentrated. The residue was purified by silica gel chromatography (PE:EA=5:1) to afford (E)-4-bromo-N-(5-bromopyridin-2-yl)but-2-enamide (280 mg, 44%) as white solid. [M+H] Calc'd for C$_9$H$_8$Br$_2$N$_2$O, 318.9; Found, 318.9.

Step 2: Synthesis of (R,E)-N-(5-bromopyridin-2-yl)-4-(3-fluoropyrrolidin-1-yl)but-2-enamide

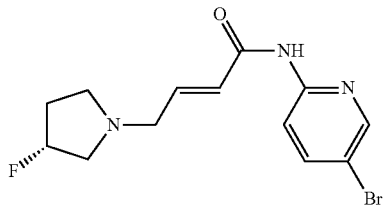 [SMILES: O=C(/C=C/CN1CC[C@@H](F)C1)Nc1ccc(Br)cn1]

To a solution of (E)-4-bromo-N-(5-bromopyridin-2-yl)but-2-enamide (280 mg, 0.88 mmol) and (R)-3-fluoropyrrolidine (156 mg, 1.75 mmol) in DCM (20 mL) was added DIEA (340 mg, 2.64 mmol) in an ice-bath. The reaction mixture was filtered and concentrated and the residue was purified by silica gel chromatography (PE:EA=5:1) to afford (R,E)-N-(5-bromopyridin-2-yl)-4-(3-fluoropyrrolidin-1-yl)but-2-enamide (180 mg, 60%) as a yellow solid. [M+H] Calc'd for C$_{13}$H$_{15}$BrFN$_3$O, 328.0; Found, 328.0.

448

Step 3: (E)-N-(5-((R)-3-((5-chloro-4-methoxypyrimidin-2-yl)amino)pyrrolidine-1-carbonyl)pyridin-2-yl)-4-((R)-3-fluoropyrrolidin-1-yl)but-2-enamide

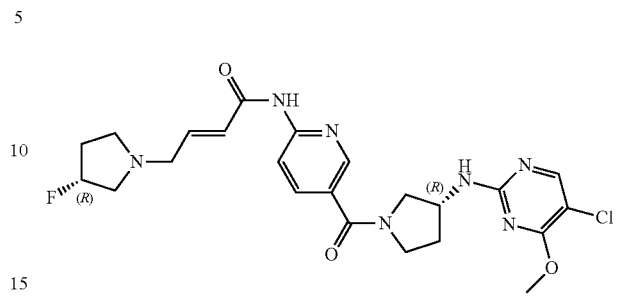

A solution of (R,E)-N-(5-bromopyridin-2-yl)-4-(3-fluoropyrrolidin-1-yl)but-2-enamide (70 mg, 0.2 mmol), (R)-5-chloro-4-methoxy-N-(pyrrolidin-3-yl)pyrimidin-2-amine (73 mg, 0.3 mmol), Na$_2$CO$_3$ (64 mg, 0.6 mmol), Pd$_2$dba$_3$ (73 mg, 0.08 mmol) and Xantphos (46 mg, 0.08 mmol) in toluene (10 mL) was stirred at 110° C. for 16 h under CO. The mixture was concentrated. The residue was purified by prep-HPLC to afford HCOOH salt of (E)-N-(5-((R)-3-((5-chloro-4-methoxypyrimidin-2-yl)amino)pyrrolidine-1-carbonyl)pyridin-2-yl)-4-((R)-3-fluoropyrrolidin-1-yl)but-2-enamide (5.5 mg, 6%) as a yellow solid. $^1$H NMR (400 MHz, DMSO-d$_6$): δ 1.87-1.91 (m, 2H), 2.13-2.16 (m, 2H), 2.33-2.34 (m, 1H), 2.60-2.67 (m, 1H), 2.81-2.83 (m, 2H), 3.53-3.69 (m, 6H), 3.86-3.93 (m, 3H), 4.30-4.43 (m, 1H), 5.14-5.28 (m, 1H), 6.46-6.49 (m, 1H), 6.81-6.86 (m, 1H), 7.71-7.73 (m, 1H), 7.95-7.99 (m, 1H), 8.08-8.24 (m, 2H), 8.30-8.32 (m, 1H), 8.50-8.52 (m, 1H), 10.82-10.84 (m, 1H). [M+H] Calc'd for C$_{23}$H$_{27}$ClFN$_7$O$_3$, 504.2; Found, 504.2.

Example 180: Synthesis of N-(4-((2S,4R)-4-((5-chloro-4-methoxypyrimidin-2-yl)amino)-2-methylpyrrolidine-1-carbonyl)phenyl)acrylamide

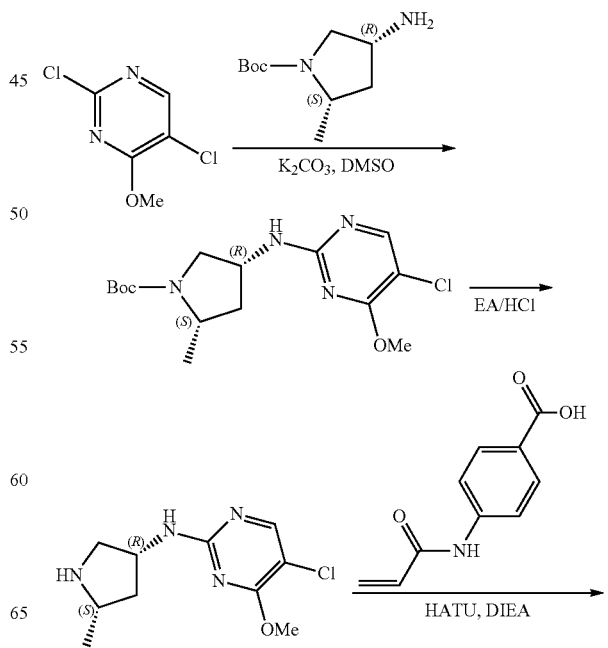

-continued

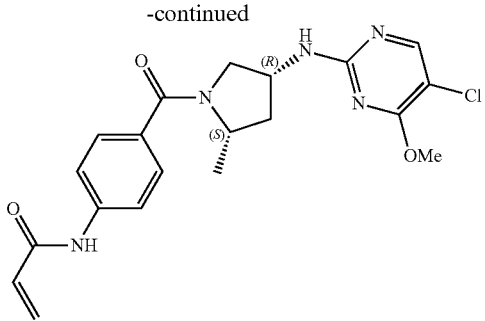

Step 1: (2S,4R)-tert-butyl 4-((5-chloro-4-methoxy-pyrimidin-2-yl)amino)-2-methylpyrrolidine-1-carboxylate

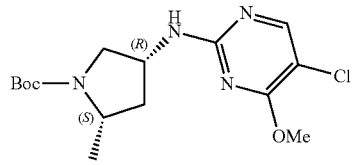

A solution of (2S,4R)-tert-butyl 4-amino-2-methylpyrrolidine-1-carboxylate (200 mg, 1.0 mmol), 2,5-dichloro-4-methoxypyrimidine (358 mg, 2.0 mmol) and $K_2CO_3$ (226 mg, 2.0 mmol) in DMSO (10 mL) was stirred at RT for 2 hrs. The reaction mixture was diluted with water (30 mL) and extracted with EA (20 mL*3). The combined organic layers were washed with water (50 mL) and brine (50 mL), dried over $Na_2SO_4$, filtered and concentrated in vacuo. The residue was purified by silica gel chromatography (PE:EA=1:1) to afford (2S,4R)-tert-butyl 4-((5-chloro-4-methoxypyrimidin-2-yl)amino)-2-methylpyrrolidine-1-carboxylate (100 mg, 30%) as a white solid. [M+H] Calc'd for $C_{15}H_{23}ClN_4O_3$, 343.1; Found, 343.1

Step 2: Synthesis of 5-chloro-4-methoxy-N-((3R,5S)-5-methylpyrrolidin-3-yl)pyrimidin-2-amine

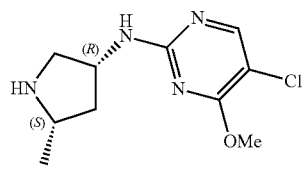

A solution of (2S,4R)-tert-butyl 4-((5-chloro-4-methoxy-pyrimidin-2-yl)amino)-2-methylpyrrolidine-1-carboxylate (100 mg, 0.3 mmol) in EA/HCl (10 mL, 3 M) was stirred at RT for 2 hrs. The reaction mixture was concentrated to afford 5-chloro-4-methoxy-N-((3R,5S)-5-methylpyrrolidin-3-yl)pyrimidin-2-amine (73 mg, 100%) as a white solid. [M+H] Calc'd for $C_{10}H_{15}ClN_4O$, 243.1; Found, 243.1

Step 3: N-(4-((2S,4R)-4-((5-chloro-4-methoxypyrimidin-2-yl)amino)-2-methylpyrrolidine-1-carbonyl)phenyl)acrylamide

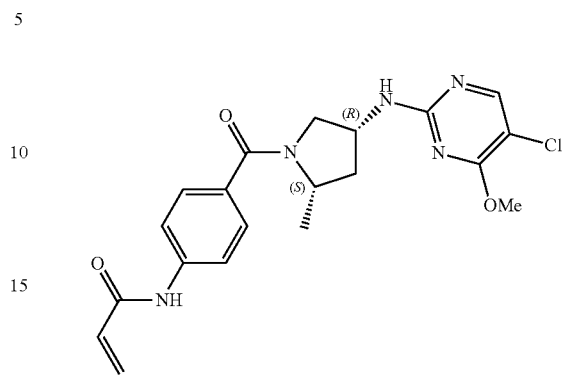

A solution of 5-chloro-4-methoxy-N-((3R,5S)-5-methylpyrrolidin-3-yl)pyrimidin-2-amine (73 mg, 0.3 mmol), 4-acrylamidobenzoic acid (58 mg, 0.3 mmol), HATU (125 mg, 0.33 mmol) and DIEA (116 mg, 0.9 mmol) in DMF (10 mL) was stirred at RT for 16 h. The mixture was concentrated and purified by prep-HPLC to afford N-(4-((2S,4R)-4-((5-chloro-4-methoxypyrimidin-2-yl)amino)-2-methylpyrrolidine-1-carbonyl)phenyl)acrylamide (10.1 mg, 8%) as a white solid. $^1$H NMR (400 MHz, DMSO-$d_6$): δ 1.29-1.31 (m, 3H), 1.65-1.67 (m, 1H), 2.45-2.46 (m, 1H), 3.70-3.83 (m, 5H), 4.08-4.17 (m, 2H), 5.79 (dd, J=1.6, 10.0 Hz, 1H), 6.25-6.30 (m, 1H), 6.41-6.48 (m, 1H), 7.49-7.51 (m, 2H), 7.70-7.72 (m, 3H), 8.07 (s, 1H), 10.33 (s, 1H). [M+H] Calc'd for $C_{20}H_{22}ClN_5O_3$, 416.1; Found, 416.1.

Example 181: (R)—N-(4-(3-((5-ethynylpyrimidin-2-yl)amino)pyrrolidine-1-carbonyl)phenyl)acrylamide

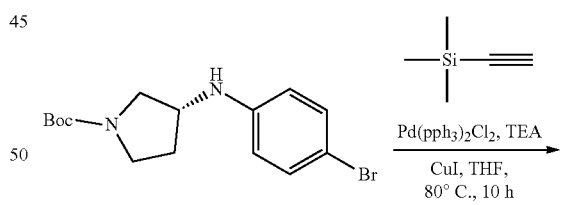

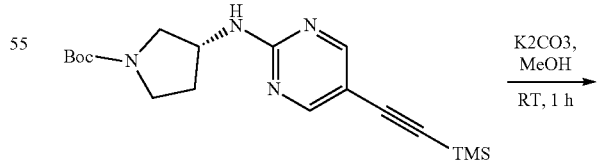

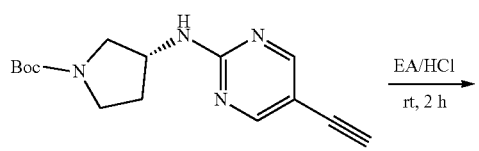

-continued

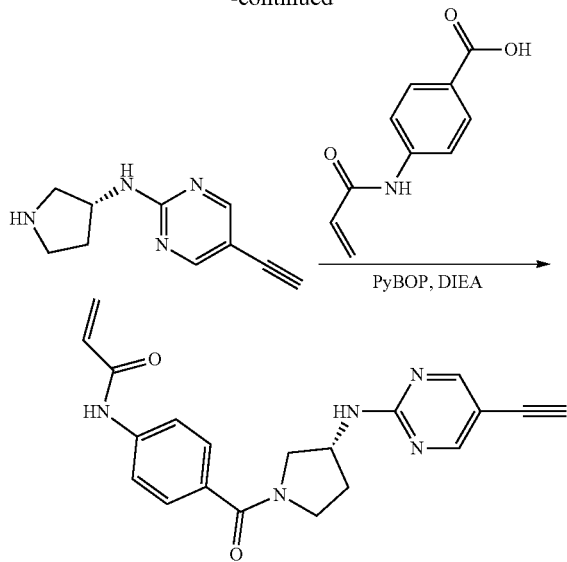

Step 1: (R)-tert-butyl 3-((5-((trimethylsilyl)ethynyl)pyrimidin-2-yl)amino)pyrrolidine-1-carboxylate

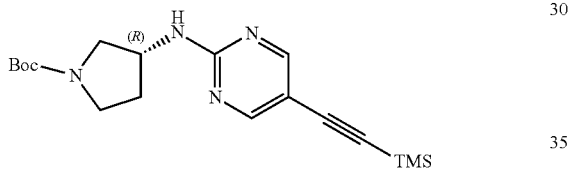

A solution of (R)-tert-butyl 3-((4-bromophenyl)amino)pyrrolidine-1-carboxylate (2.0 g, 5.8 mmol), ethynyl trimethylsilane (1.1 g, 11.7 mmol), CuI (33 mg, 0.2 mmol) and Pd(PPh$_3$)$_2$Cl$_2$ (205 mg, 0.3 mmol) in TEA (20 mL) and THF (20 mL) was stirred at 80° C. for 10 h under N$_2$. The reaction mixture was cooled, diluted with water (50 mL) and extracted with EA (100 mL*2). The combined organic layers were washed with brine (50 mL), dried over anhydrous sodium sulfate, filtered and concentrated under reduced pressure. The residue was purified by column chromatography on silica gel (PE/EA=5/1) to give (R)-tert-butyl 3-((5-((trimethylsilyl)ethynyl)pyrimidin-2-yl)amino)pyrrolidine-1-carboxylate (1.0 g, 47%). [M+H]MS Calc'd C$_{18}$H$_{28}$N$_4$O$_2$Si, 361.1; Found: 361.1.

Step 2: (R)-tert-butyl 3-((5-ethynylpyrimidin-2-yl)amino)pyrrolidine-1-carboxylate

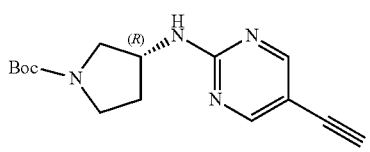

To a solution of (R)-tert-butyl 3-((5-((trimethylsilyl)ethynyl)pyrimidin-2-yl)amino)pyrrolidine-1-carboxylate (1.0 g, 2.8 mmol) in MeOH (20 mL) was added K$_2$CO$_3$ (766 mg 5.5 mmol) in an ice-bath and the mixture was stirred at RT for 1 h. Filtered and concentrated in vacuo to give (R)-tert-butyl 3-((5-ethynylpyrimidin-2-yl)amino)pyrrolidine-1-carboxylate (435 mg, 54%) as a white solid. [M+H] MS Calc'd: C$_{15}$H$_{20}$N$_4$O$_2$, 289.1; Found: 289.1.

Step 3: (R)-5-ethynyl-N-(pyrrolidin-3-yl)pyrimidin-2-amine

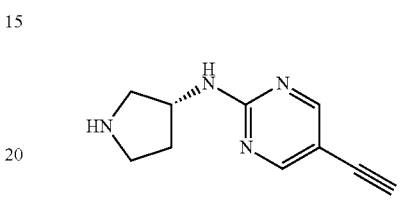

A solution of (R)-tert-butyl 3-((5-ethynylpyrimidin-2-yl)amino)pyrrolidine-1-carboxylate (435 mg, 1.51 mmol) in HCl/EA (15 mL, 3 M) was stirred at RT for 1 h. The mixture was concentrated in vacuo to give (R)-5-ethynyl-N-(pyrrolidin-3-yl)pyrimidin-2-amine HCl salt (283 mg, crude) as brown thick liquid. [M+H] MS Calc'd: C$_{10}$H$_{12}$N$_4$, 189.1; Found: 189.1.

Step 4: (R)—N-(4-(3-((5-ethynylpyrimidin-2-yl)amino)pyrrolidine-1-carbonyl)phenyl)acrylamide

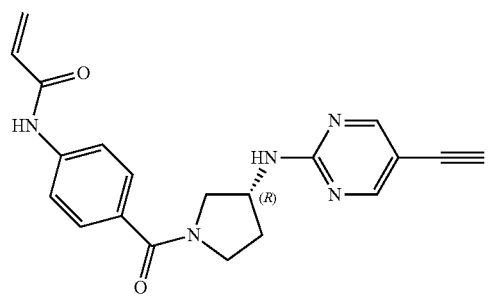

A mixture of (R)-5-ethynyl-N-(pyrrolidin-3-yl)pyrimidin-2-amine HCl salt (260 mg, 1.35 mmol), 4-acrylamidobenzoic acid (281 mg, 1.49 mmol), PyBOP (777 mg, 1.49 mmol) and DIEA (871 mg, 6.75 mmol) in DMF (15 mL) was stirred at RT overnight. The reaction mixture was concentrated and the residue was purified by prep-HPLC to afford (R)—N-(4-(3-((5-ethynylpyrimidin-2-yl)amino)pyrrolidine-1-carbonyl)phenyl)acrylamide (28.9 mg, 5.8%) as a white solid. $^1$H NMR (400 MHz, DMSO-d$_6$): 1.89-1.99 (m, 1H), 2.14-2.16 (m, 1H), 3.43-3.53 (m, 2H), 3.64-3.80 (m, 2H), 4.22-4.49 (m, 2H), 5.78 (d, J=10.0 Hz, 1H), 6.25-6.30 (m, 1H), 6.43-6.45 (m, 1H), 7.50 (t, J=9.2 Hz, 2H), 7.70 (t, J=9.2 Hz, 2H), 7.98-8.00 (m, 1H), 8.38-8.44 (m, 2H), 10.29 (s, 1H). [M+H] Calc'd for C$_{20}$H$_{19}$N$_5$O$_2$, 362.1; Found, 362.1.

Example 182: (R)-tert-butyl (R)—N-(4-(3-((5-ethynyl-4-methoxypyrimidin-2-yl)amino)pyrrolidine-1-carbonyl)phenyl)acrylamide

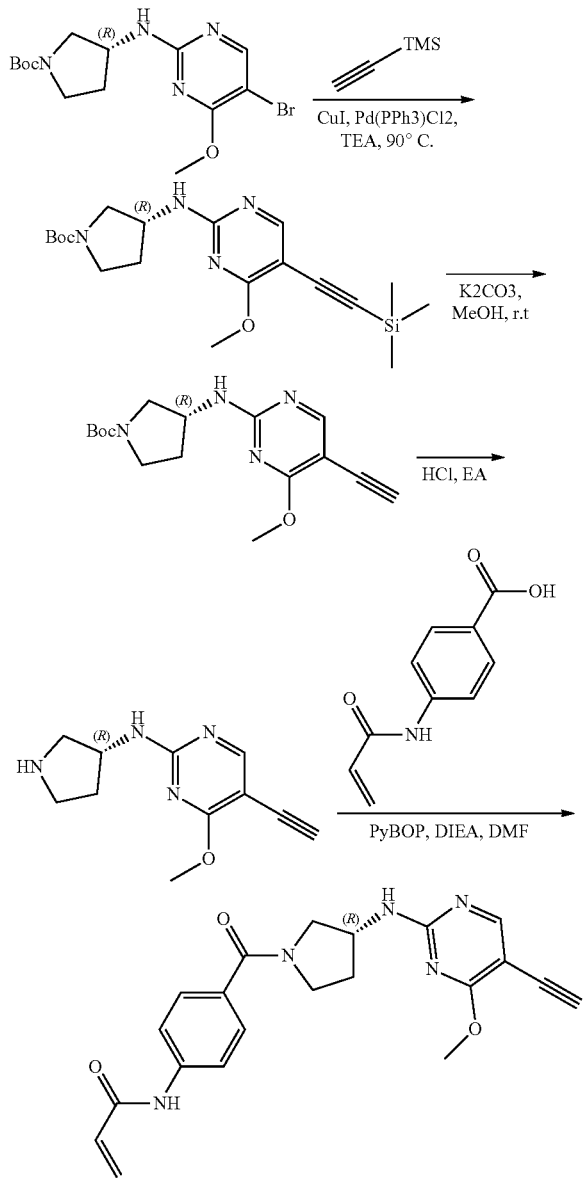

Step 1: (R)-tert-butyl 3-((4-methoxy-5-((trimethylsilyl)ethynyl)pyrimidin-2-yl)amino)pyrrolidine-1-carboxylateboxylate

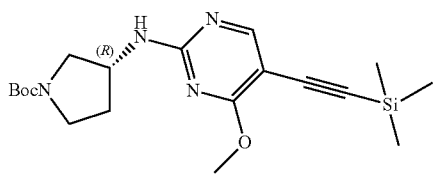

A solution of (R)-tert-butyl 3-((5-bromo-4-methoxypyrimidin-2-yl)amino)pyrrolidine-1-carboxylate (1.0 g, 2.7 mmol), ethynyltrimethylsilane(1.1 g, 10.7 mmol), CuI (152 mg, 0.8 mmol), Pd(PPh$_3$)Cl$_2$ (180 mg, 0.3 mmol) in TEA (20 mL) was stirred at 90° C. for 2 h. The mixture was cooled, diluted with water (50 mL) and extracted with EA (50 mL*2). The combined organic layers were washed with brine (50 mL), dried over anhydrous sodium sulfate, filtered and concentrated under reduced pressure. The residue was purified by column chromatography on silica gel (PE/EA=2/1) to give (R)-tert-butyl 3-((4-methoxy-5-((trimethylsilyl)ethynyl)pyrimidin-2-yl)amino)pyrrolidine-1-carboxylateboxylate (500 mg, 47%). [M+H] MS Calc'd C$_{19}$H$_{30}$N$_4$O$_3$Si, 391.2; Found: 391.2.

Step 2: (R)-tert-butyl 3-((5-ethynyl-4-methoxypyrimidin-2-yl)amino)pyrrolidine-1-carboxylate

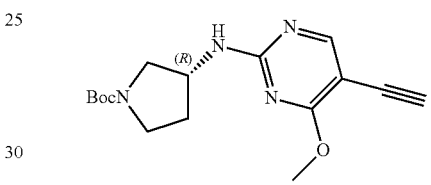

A solution of (R)-tert-butyl 3-((4-methoxy-5-((trimethylsilyl)ethynyl)pyrimidin-2-yl)amino)pyrrolidine-1-carboxylateboxylate (500 mg, 2.5 mmol) and K$_2$CO$_3$ (690 mg, 5.0 mmol) in MeOH (30 mL) was stirred at RT for 3 h. The reaction mixture was filtered and concentrated under vacuum to give (R)-tert-butyl 3-((5-ethynyl-4-methoxypyrimidin-2-yl)amino)pyrrolidine-1-carboxylate (200 mg, 66%) as a yellow solid. [M+H] MS Calc'd: C$_{16}$H$_{22}$N$_4$O$_3$ 319.1; Found: 319.1.

Step 3: (R)-5-ethynyl-4-methoxy-N-(pyrrolidin-3-yl)pyrimidin-2-amine

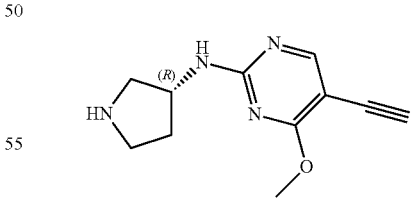

A solution of (R)-tert-butyl 3-((5-ethynyl-4-methoxypyrimidin-2-yl)amino)pyrrolidine-1-carboxylate (180 mg, 0.45 mmol) in HCl/EA (15 mL, 3M) was stirred at rt for 3 h. The reaction mixture was then concentrated under vacuum to give product (R)-5-ethynyl-4-methoxy-N-(pyrrolidin-3-yl)pyrimidin-2-amine (100 mg, 75%) as a yellow solid. [M+H] MS Calc'd: C$_{11}$H$_{14}$N$_4$O, 219.1; Found: 219.1.

Step 4: (R)—N-(4-(3-((5-ethynyl-4-methoxypyrimidin-2-yl)amino)pyrrolidine-1-carbonyl)phenyl)acrylamide

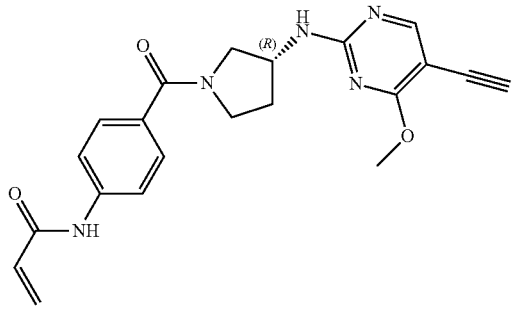

A mixture of (R)-5-ethynyl-4-methoxy-N-(pyrrolidin-3-yl)pyrimidin-2-amine HCl salt (100 mg, 0.34 mmol), 4-acrylamidobenzoic acid (78 mg, 0.41 mmol), PyBOP (213 mg, 0.41 mmol) and DIEA (131 mg, 1.02 mmol) in DMF (15 mL) was stirred at RT for overnight. The reaction mixture was concentrated and the residue was purified by prep-HPLC to afford (R)—N-(4-(3-((5-ethynyl-4-methoxypyrimidin-2-yl)amino)pyrrolidine-1-carbonyl)phenyl)acrylamide (4.5 mg, 3%) as a white solid. $^1$H NMR (400 MHz, DMSO-$d_6$): 1.90-2.13 (m, 2H), 3.31-3.90 (m, 7H), 4.18 (d, J=13.2 Hz, 1H), 4.32 (s, 0.5H), 4.85 (s, 0.5H), 5.78 (d, J=10.0 Hz, 1H), 6.25 (s, 0.5H), 6.30 (s, 0.5H), 6.36-6.41 (m, 1H), 7.50 (t, J=8.8 Hz, 2H), 7.71 (t, J=8.8 Hz, 2H), 7.84-8.00 (m, 1H), 8.15-8.16 (m, 1H), 10.29 (s, 1H). [M+H] Calc'd for $C_{21}H_{21}N_5O_3$, 392.2; Found, 392.2.

Example 183: N-(4-((2R,4R)-4-((5-chloro-4-methoxypyrimidin-2-yl)amino)-2-methylpyrrolidine-1-carbonyl)phenyl)acrylamide

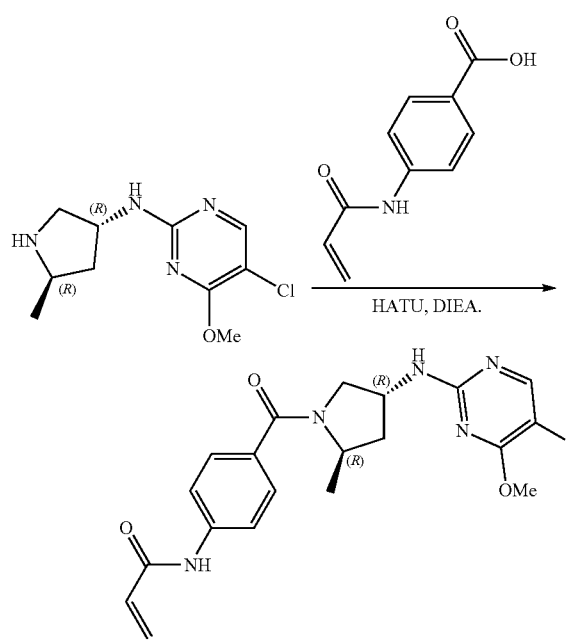

A mixture of 5-chloro-4-methoxy-N-((3R,5R)-5-methylpyrrolidin-3-yl)pyrimidin-2-amine TFA salt (400 mg, 1.65 mmol), 4-acrylamidobenzoic acid (315 mg, 1.65 mmol), HATU (760 mg, 1.98 mmol) and DIEA (660 mg, 5 mmol) in DMF (10 mL) was stirred at RT for overnight. The reaction mixture was concentrated and the residue was purified by prep-HPLC to afford N-(4-((2R,4R)-4-((5-chloro-4-methoxypyrimidin-2-yl)amino)-2-methylpyrrolidine-1-carbonyl)phenyl)acrylamide (3.8 mg, 0.5%) as a white solid. $^1$H NMR (400 MHz, DMSO-$d_6$): 1.30-1.32 (m, 3H), 1.85-1.87 (m, 1H), 2.16-2.14 (m, 1H), 3.37-3.38 (m, 1H), 3.89 (s, 4H), 4.26-4.37 (m, 2H) 5.79-5.83 (m, 1H), 6.32-6.46 (m, 2H), 7.49 (d, J=11.2 Hz, 2H), 7.70-7.73 (m, 3H), 8.09 (s, 1H), 10.34 (s, 1H). [M+H] Calc'd for $C_{20}H_{22}ClN_5O_3$, 416.1; Found, 416.1.

Example 184: Synthesis of (R)—N-(4-(3-((5-(trifluoromethyl)pyrimidin-2-yl)amino)pyrrolidine-1-carbonyl)phenyl)acrylamide

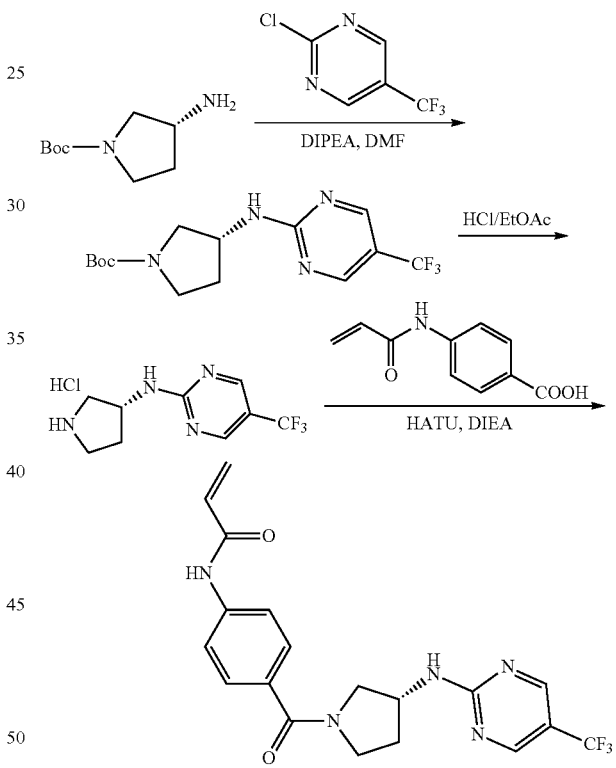

Step 1: (R)-tert-butyl 3-((5-(trifluoromethyl)pyrimidin-2-yl)amino)pyrrolidine-1-carboxylate A mixture of 2-chloro-5-(trifluoromethyl)pyrimidine (293 mg, 1.61 mmol), (R)-tert-butyl 3-aminopyrrolidine-1-carboxylate (300 mg, 1.61 mmol) and DIPEA (623 mg, 4.83 mmol) in DMF (3.0 mL) was stirred at 40° C. for 2.5 hours. The reaction mixture was diluted with H$_2$O (30 mL) and extracted with EtOAc (30 mL*2). The combined organic phases were washed with water (40 mL*2), brine (40 mL), dried over Na$_2$SO$_4$, filtered and concentrated. The residue was purified by silica gel column (petroleum ether/EtOAc=5/1) to give (R)-tert-butyl 3-((5-(trifluoromethyl)pyrimidin-2-yl)amino)pyrrolidine-1-carboxylate (502 mg, 94%). [M+H] MS Calc'd C$_{14}$H$_{19}$F$_3$N$_4$O$_2$, 333.2; Found: 333.2.

Step 2: (R)—N-(pyrrolidin-3-yl)-5-(trifluoromethyl)pyrimidin-2-amine

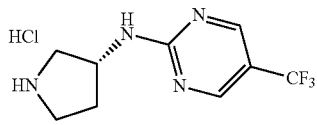

A mixture of (R)-tert-butyl 3-((5-(trifluoromethyl)pyrimidin-2-yl)amino)pyrrolidine-1-carboxylate (502 mg, 1.51 mmol) in HCl/EtOAc (10.0 mL, 4M in EtOAc) was stirred at RT for 1 hour. The reaction mixture was concentrated under reduced pressure to afford the crude product (R)—N-(pyrrolidin-3-yl)-5-(trifluoromethyl)pyrimidin-2-amine hydrochloride HCl salt (390 mg, 95%) which was used in the next step without any further purification. [M+H] MS Calc'd C$_9$H$_{19}$F$_3$N$_4$, 233.1; Found: 233.1.

Step 3: (R)—N-(4-(3-((5-(trifluoromethyl)pyrimidin-2-yl)amino)pyrrolidine-1-carbonyl)phenyl)acrylamide

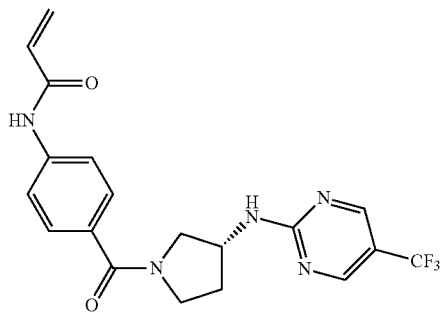

To a mixture of (R)—N-(pyrrolidin-3-yl)-5-(trifluoromethyl)pyrimidin-2-amine HCl salt (195 mg, 0.73 mmol), 4-propionamidobenzoic acid (139 mg, 0.73 mmol) and DIPEA (471 mg, 3.65 mmol) in DMF (5.0 mL) was added HATU (334 mg, 0.88 mmol) slowly and the mixture was stirred at RT overnight. The mixture was diluted with H$_2$O (30 mL), then extracted with EtOAc (30 mL*2). The organic phases were washed with water (30 mL*2) and brine (30 mL), dried over Na$_2$SO$_4$, filtered and concentrated in vacuo. The residue was purified by Prep-HPLC to give (R)—N-(4-(3-((5-(trifluoromethyl)pyrimidin-2-yl)amino)pyrrolidine-1-carbonyl)phenyl)acrylamide (43.5 mg, 15%). $^1$H NMR (400 MHz, DMSO-d$_6$): δ 1.89-2.04 (m, 1H), 2.16-2.21 (m, 1H), 3.36-3.83 (m, 4H), 4.36-4.53 (m, 1H), 5.78 (d, J=10.0 Hz, 1H), 6.28 (d, J=16.9 Hz, 1H), 6.41-6.48 (m, 1H), 7.49-7.54 (m, 2H), 7.68-7.74 (m, 2H), 8.41 (s, 1H), 8.61-8.70 (m, 2H), 10.30 (brs, 1H). [M+H]MS Calc'd C$_{19}$H$_{18}$F$_3$N$_5$O$_2$, 406.1; Found: 406.0.

II. Biological Evaluation

Example 1—Assay Condition a (Thiol Containing Conditions)

Objective: The IC$_{50}$ profile of test compounds was determined using three protein kinases. IC$_{50}$ values were measured by testing 10 concentrations (1×10$^{-04}$M, 3×10$^{-05}$M, 1×10$^{-05}$M, 3×10$^{-06}$M, 1×10$^{-06}$M, 3×10$^{-07}$M, 1×10$^{-07}$M, 3×10$^{-08}$M, 1×10$^{-08}$M, and 3×10$^{-09}$M) of each compound in singlicate.

Test compounds: The compounds were provided as pre-weighed powders in vials. The compounds were dissolved to 1×10$^{-02}$M by adding DMSO. 100 μl of each of the resulting stock solutions were transferred into column 2 of four 96 well "master plates".

Prior to testing, the 1×10$^{-02}$M stock solutions in column 2 of the master plates were subjected to a serial, semi-logarithmic dilution using 100% DMSO as a solvent. This resulted in 10 distinct concentrations, with a dilution end-point of 3×10$^{-07}$M/100% DMSO in column 12. Column 1 and 7 were filled with 100% DMSO as controls. Subsequently, 2×10 μl from each well of the serial diluted copy plates were aliquoted with a 96 channel pipettor into two identical sets of "compound dilution plates".

In the process, 90 μl H$_2$O were added to each well of a set of compound dilution plates. To minimize potential precipitation, the H$_2$O was added to each plate only a few minutes before the transfer of the compound solutions into the assay plates. Each plate was shaken thoroughly, resulting in a "compound dilution plate/10% DMSO".

For the assays, 5 μl solution from each well of the compound dilution plates/10% DMSO were transferred into the assay plates. The final volume of the assay was 50 μl. All compounds were tested at 10 final assay concentrations in the range from 1×10$^{-04}$M to 3×10$^{-09}$M, in singlicate. The final DMSO concentration in the reaction cocktails was 1% in all cases.

Recombinant protein kinases: All protein kinases were expressed in Sf9 insect cells or in E. coli as recombinant GST-fusion proteins or His-tagged proteins, either as full-length or enzymatically active fragments. All kinases were produced from human cDNAs and purified by either GSH-affinity chromatography or immobilized metal. Affinity tags were removed from a number of kinases during purification. The purity of the protein kinases was examined by SDS-PAGE/Coomassie staining, the identity was checked by mass spectroscopy.

Protein kinase assay: A radiometric protein kinase assay ($^{33}$PanQinase® Activity Assay) was used for measuring the kinase activity of the three protein kinases. All kinase assays were performed in 96-well FlashPlates™ from PerkinElmer (Boston, Mass., USA) in a 50 μl reaction volume. The reaction cocktail was pipetted in four steps in the following order:

20 μl of assay buffer (standard buffer)
5 μl of ATP solution (in H$_2$O)
5 μl of test compound (in 10% DMSO)
20 μl enzyme/substrate mix The assay for all protein kinases contained 70 mM HEPES-NaOH pH 7.5, 3 mM MgCl$_2$, 3 mM MnCl$_2$, 3 μM Na-orthovanadate, 1.2 mM DTT, 50 μg/ml PEG$_{20000}$, ATP (variable concentrations, corresponding to the apparent ATP-K$_m$ of the respective kinase), [γ-$^{33}$P]-ATP (approx.

9×10$^{05}$ cpm per well), protein kinase (variable amounts), and substrate (variable amounts).

The following amounts of enzyme and substrate were used per well:

| Kinase Name | Kinase Conc. ng/50 µl | Kinase Conc. nM * | ATP Conc. µM | Substrate Name | Substrate Lot | Substrate µg/50 µl |
|---|---|---|---|---|---|---|
| CDK12 wt/ CycK | 100 | 14.7 | 0.3 | RBER-IRStide | 036 | 2 |

* Maximal molar enzyme assay concentrations, implying enzyme preparations exclusively containing 100% active enzyme The reaction cocktails were incubated at 30° C. for 60 minutes. The reaction was stopped with 50 µl of 2% (v/v) H$_3$PO$_4$, plates were aspirated and washed two times with 200 µl 0.9% (w/v) NaCl. Incorporation of $^{33}$Pi was determined with a microplate scintillation counter (Microbeta, Wallac). All assays were performed with a BeckmanCoulter/ SAGIAN™ Core System.

Evaluation of raw data: The median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was taken as 100% activity.

As part of the data evaluation the low control value from a particular plate was subtracted from the high control value as well as from all 80 "compound values" of the corresponding plate. The residual activity (in %) for each well of a particular plate was calculated by using the following formula:

Res. Activity (%)=100×[(cpm of compound−low control)/(high control−low control)]

The residual activities for each concentration and the compound IC$_{50}$ values were calculated using Quattro Workflow V3.1.1 (Quattro Research GmbH, Munich, Germany). The fitting model for the IC$_{50}$ determinations was "Sigmoidal response (variable slope)" with parameters "top" fixed at 100% and "bottom" at 0%. The fitting method used was a least-squares fit.

Results: The IC$_{50}$ values for all compounds are compiled in Table 1. This table shows all IC$_{50}$ values calculated, as well as the Hill slopes of the corresponding curves. All IC$_{50}$ values that were out of range of the tested concentrations (<3×10$^{−09}$ M; >1×10$^{−04}$M) are marked grey. A Hill slope higher than −0.4 is indicative that the curve is not sigmoidal, very flat or not descending.

Example 2—Assay Condition B (Thiol-Free Conditions)

The IC$_{50}$ profile of compounds was determined using one protein kinase in a customized, thiol free assay. IC$_{50}$ values were measured by testing 10 concentrations (1×10$^{−05}$ M to 3×10$^{−10}$ M) of each test compound in singlicate against each kinase of interest. Prior to testing, the 1×10$^{−03}$ M stock solutions in column 2 of the master plates were subjected to a serial, semi-logarithmic dilution using 100% DMSO as a solvent. This resulted in 10 distinct concentrations, with a dilution endpoint of 3×10$^{−08}$M/100% DMSO in column 12. Column 1 and 7 were filled with 100% DMSO as controls.

Subsequently, 2×10 microliter from each well of the serial diluted copy plates were aliquoted with a 96 channel pipettor into two identical sets of "compound dilution plates". All plates were barcoded for automated identification and tracking purposes. IC$_{50}$ values were measured by testing 10 concentrations (1×10$^{−05}$ M to 3×10$^{−10}$ M) of each compound in singlicate. All compounds were stored as powder until being solubilized in DMSO. Solubilized compounds were stored as 1×10$^{−02}$ M/100% DMSO stock solutions. Prior to the assay process, 90 microliters of H$_2$O were added to each well of a set of compound dilution plates. To minimize potential precipitation, the H$_2$O was added to each plate only a few minutes before the transfer of the compound solutions into the assay plates. Each plate was shaken thoroughly, resulting in compound dilution plates with a final of 10% DMSO. For each assay, 5 microliters of solution from each well of the compound dilution plates/10% DMSO were transferred into the assay plate. The final volume of the assay was 50 µl. All compounds were tested at 10 final assay concentrations in the range from 1×10$^{−05}$ M to 3×10$^{−10}$ M, in singlicate. The final DMSO concentration in the reaction cocktails was 1% in all cases. A radiometric protein kinase assay (33PanQinase® Activity Assay) was used for measuring the kinase activity of the protein kinase. All kinase assays were performed in 96-well FlashPlates™ from PerkinElmer (Boston, Mass., USA) in a 50 microliter reaction volume. The reaction cocktail was pipetted in four steps in the following order: 20 microliter of assay buffer (standard buffer)•5 microliter of ATP solution (in H$_2$O)•5 microliter of test compound (in 10% DMSO)•20 microliter enzyme/ substrate mix. Each assay for the protein kinase contained 70 mM HEPES-NaOH pH 7.5, 3 mM MgCl$_2$, 3 mM MnCl$_2$, 3 microM Na-orthovanadate, 1 mM TCEP, 50 µg/ml PEG20000, ATP (corresponding to the apparent ATP-Km of the kinase, see Table A), [gamma-33P]-ATP (approx. 6×10× E5 cpm per well), with the protein kinase and relevant substrate being used in pre-determined amounts, depending on the kinase in question. For all experiments labeled as "Thiol-free", all glutathione was exchanged from protein preparations so as to be removed from the assay and final buffer conditions contained no thiol-containing reagents. This was done so there would be no interference with the key cysteines in the proteins of interest.

For data analysis, the median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was taken as 100% activity. As part of the data evaluation the low control value from a particular plate was subtracted from the high control value as well as from all 80 "compound values" of the corresponding plate. The residual activity (in %) for each well of a particular plate was calculated by using the following formula:

Res. Activity (%)=100×[(cpm of compound−low control)/(high control−low control)]

The residual activities for each concentration and the compound IC$_{50}$ values were calculated using Quattro Workflow V3.1.1 (Quattro Research GmbH, Munich, Germany; www.quattro-research.com). The fitting model for the IC$_{50}$ determinations was "Sigmoidal response (variable slope)" with parameters "top" fixed at 100% and "bottom" at 0%. The fitting method used was a least-squares fit. As a parameter for assay quality, the Z'-factor (Zhang et al., J. Biomol. Screen. 2: 67-73, 1999) for the low and high controls of each assay plate (n=8) was used. ProQinase's criterion for repetition of an assay plate is a Z'-factor below 0.4 (Iversen et al., J. Biomol. Screen. 3: 247-252, 2006).

Representative data for exemplary compounds disclosed herein are presented in the following Table 6.

TABLE 6

| Synthetic Chemistry Example | CDK12 IC$_{50}$ Condition A | CDk12 IC$_{50}$ Condition B |
|---|---|---|
| 1 | — | A |
| 2 | — | B |
| 3 | — | A |
| 4 | — | B |
| 5 | — | A |
| 6 | — | A |
| 7 | — | A |
| 8 | — | B |
| 9 | — | A |
| 10 | — | A |
| 11 | — | A |
| 12 | — | B |
| 13 | — | C |
| 14 | A | A |
| 15 | — | B |
| 16 | — | C |
| 17 | B | B |
| 18 | — | B |
| 19 | A | A |
| 20 | A | A |
| 21 | — | A |
| 22 | — | B |
| 23 | — | B |
| 24 | — | A |
| 25 | A | A |
| 26 | A | A |
| 27 | — | A |
| 28 | B | B |
| 29 | B | A |
| 30 | — | A |
| 31 | — | A |
| 32 | — | B |
| 33 | — | C |
| 34 | — | B |
| 35 | — | E |
| 36 | — | E |
| 37 | — | C |
| 38 | — | D |
| 39 | — | E |
| 40 | — | D |
| 41 | — | E |
| 42 | — | E |
| 43 | — | C |
| 44 | — | B |
| 45 | — | B |
| 46 | — | C |
| 47 | A | A |
| 48 | — | B |
| 49 | — | A |
| 50 | — | A |
| 51 | — | B |
| 52 | B | A |
| 53 | B | B |
| 54 | A | A |
| 55 | B | A |
| 56 | — | A |
| 57 | — | B |
| 58 | B | A |
| 59 | C | B |
| 60 | — | B |
| 61 | — | C |
| 62 | A | A |
| 63 | — | B |
| 64 | — | B |
| 65 | — | A |
| 66 | — | A |
| 67 | — | A |
| 68 | — | A |
| 69 | — | B |
| 70 | B | — |
| 71 | — | B |
| 72 | — | A |
| 73 | — | B |
| 74 | — | A |
| 75 | — | C |
| 76 | — | A |
| 77 | B | — |
| 78 | — | A |
| 79 | — | A |
| 80 | — | B |
| 81 | — | B |
| 82 | — | B |
| 83 | — | B |
| 84 | — | B |
| 85 | — | B |
| 86 | A | — |
| 87 | B | — |
| 88 | A | — |
| 89 | B | — |
| 90 | A | — |
| 91 | A | — |
| 92 | A | — |
| 93 | A | — |
| 94 | B | — |
| 95 | A | — |
| 96 | A | — |
| 97 | E | — |
| 98 | C | — |
| 99 | B | — |
| 100 | B | — |
| 101 | B | — |
| 102 | A | — |
| 103 | B | — |
| 104 | A | — |
| 105 | B | — |
| 106 | D | — |
| 107 | C | — |
| 108 | E | — |
| 109 | D | — |
| 110 | C | — |
| 111 | A | — |
| 112 | B | — |
| 113 | — | B |
| 114 | B | — |
| 115 | B | — |
| 116 | C | — |
| 117 | B | — |
| 118 | D | — |
| 119 | B | — |
| 120 | A | — |
| 121 | C | — |
| 122 | D | — |
| 123 | B | — |
| 124 | A | — |
| 125 | A | — |
| 126 | B | — |
| 127 | B | — |
| 128 | C | — |
| 129 | B | — |
| 130 | B | — |
| 131 | B | — |
| 132 | C | — |
| 133 | B | — |
| 134 | B | — |
| 135 | C | — |
| 136 | B | — |
| 137 | A | — |
| 138 | A | — |
| 139 | A | — |
| 140 | C | — |
| 141 | C | — |
| 142 | C | — |
| 143 | A | — |
| 144 | A | — |

TABLE 6-continued

| Synthetic Chemistry Example | CDK12 IC$_{50}$ Condition A | CDk12 IC$_{50}$ Condition B |
|---|---|---|
| 145 | B | — |
| 146 | C | — |
| 147 | B | — |
| 148 | B | — |
| 149 | C | — |
| 150 | B | — |
| 151 | A | — |
| 152 | A | — |
| 153 | B | — |
| 154 | A | — |
| 155 | D | — |
| 156 | B | — |
| 157 | A | — |
| 158 | B | — |
| 159 | C | — |
| 160 | D | — |
| 161 | — | — |
| 162 | B | — |
| 163 | A | — |
| 164 | A | — |
| 165 | A | — |
| 166 | B | — |
| 167 | A | — |
| 168 | B | — |
| 169 | A | — |
| 170 | B | — |
| 171 | B | — |
| 172 | B | — |
| 173 | B | — |
| 174 | B | — |
| 175 | B | — |
| 176 | B | — |
| 177 | B | — |
| 178 | B | — |
| 179 | B | — |
| 180 | A | — |
| 181 | A | — |
| 182 | A | — |
| 183 | A | — |
| 184 | A | — |

Note:
Biochemical assay IC$_{50}$ data are designated within the following ranges:
A: ≤0.10 µM
B: >0.10 µM to ≤1.0 µM
C: >1.0 µM to ≤10 µM
D: >10 µM to ≤30 µM
E: >30 µM to ≤100 µM

III. Preparation of Pharmaceutical Dosage Forms

Example 1: Oral Capsule

The active ingredient is a compound of Table 1, or a pharmaceutically acceptable salt thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:
1. A compound, or pharmaceutically acceptable salt or solvate thereof, selected from the group consisting of:
- (R)—N-(4-(3-((5-chloro-4-methoxypyrimidin-2-yl)amino)pyrrolidine-1-carbonyl)-2-methoxyphenyl)acrylamide;
- (R)—N-(4-(3-((5-chloro-4-methoxypyrimidin-2-yl)amino)pyrrolidine-1-carbonyl)-2-(1-methyl-1H-pyrazol-4-yl)phenyl)acrylamide;
- (R)—N-(2-chloro-4-(3-((5-chloro-4-methoxypyrimidin-2-yl)amino)pyrrolidine-1-carbonyl)phenyl)acrylamide;
- (R)—N-(2-chloro-4-(3-((5-chloropyrimidin-2-yl)amino)pyrrolidine-1-carbonyl)phenyl)acrylamide;
- (R)—N-(4-(3-((5-chloro-4-methoxypyrimidin-2-yl)amino)pyrrolidine-1-carbonyl)-2-(4-methylpiperazin-1-yl)phenyl)acrylamide;
- (R)—N-(4-(3-((5-chloro-4-methoxypyrimidin-2-yl)amino)pyrrolidine-1-carbonyl)-2-morpholinophenyl)acrylamide;
- (R)—N-(4-(3-((5-chloro-4-methoxypyrimidin-2-yl)amino)pyrrolidine-1-carbonyl)-2-(piperidin-1-yl)phenyl)acrylamide;
- (R)—N-(4-(3-((5-chloropyrimidin-2-yl)amino)pyrrolidine-1-carbonyl)-2-(1-methyl-1H-pyrazol-4-yl)phenyl)acrylamide;
- (R)—N-(4-(3-((5-bromopyrimidin-2-yl)amino)pyrrolidine-1-carbonyl)phenyl)acrylamide;
- (R)—N-(4-(3-((5-bromo-4-methoxypyrimidin-2-yl)amino)pyrrolidine-1-carbonyl)phenyl)acrylamide;
- (R)—N-(4-(3-((5-chloro-4-cyclopropoxypyrimidin-2-yl)amino)pyrrolidine-1-carbonyl)phenyl)acrylamide;
- (R)—N-(4-(3-((4-cyclopropoxy-5-methylpyrimidin-2-yl)amino)pyrrolidine-1-carbonyl)phenyl)acrylamide;
- (R)—N-(4-(3-((4-cyclopropoxy-5-fluoropyrimidin-2-yl)amino)pyrrolidine-1-carbonyl)phenyl)acrylamide;
- (R)—N-(4-(3-((5-chloro-4-(2,2,2-trifluoroethoxy)pyrimidin-2-yl)amino)pyrrolidine-1-carbonyl)phenyl)acrylamide;
- (R)—N-(4-(3-((5-chloro-4-methoxypyrimidin-2-yl)amino)pyrrolidine-1-carbonyl)phenyl)-N-methylacrylamide;
- (R)—N-(4-(3-((5-chloro-4-methoxypyrimidin-2-yl)amino)pyrrolidine-1-carbonyl)-2-methylphenyl)acrylamide;
- (R)—N-(4-(3-((5-chloropyrimidin-2-yl)amino)pyrrolidine-1-carbonyl)phenyl)-N-methylacrylamide;
- (R)—N-(4-(3-((5-chloropyrimidin-2-yl)amino)pyrrolidine-1-carbonyl)-2-methylphenyl)acrylamide;
- (R)—N-(4-(3-((5-chloropyrimidin-2-yl)amino)pyrrolidine-1-carbonyl)-2-methoxyphenyl)acrylamide;
- (R)—N-(4-(3-((5-chloropyrimidin-2-yl)amino)pyrrolidine-1-carbonyl)-3-methylphenyl)acrylamide;
- (R)—N-(4-(3-((5-chloropyrimidin-2-yl)amino)pyrrolidine-1-carbonyl)-2,6-dimethylphenyl)acrylamide;
- (R)—N-(4-(3-((4-(1-methyl-1H-pyrazol-5-yl)pyrimidin-2-yl)amino)piperidine-1-carbonyl)phenyl)acrylamide;
- (R)—N-(4-(3-((4-morpholinopyrimidin-2-yl)amino)piperidine-1-carbonyl)phenyl)acrylamide;
- (R)—N-(4-(3-((4-methoxypyrimidin-2-yl)amino)piperidine-1-carbonyl)phenyl)acrylamide;
- (R)—N-(4-(3-((5-chloropyrazin-2-yl)amino)piperidine-1-carbonyl)phenyl)acrylamide;
- (R)—N-(4-(3-((4-(1-methyl-1H-pyrazol-4-yl)pyrimidin-2-yl)amino)piperidine-1-carbonyl)phenyl)acrylamide;
- (R)—N-(4-(3-((4-(cyclopentyloxy)pyrimidin-2-yl)amino)piperidine-1-carbonyl)phenyl)acrylamide;
- (R)—N-(4-(3-((4-(1H-pyrazol-4-yl)pyrimidin-2-yl)amino)pyrrolidine-1-carbonyl)phenyl)acrylamide;
- (R)—N-(4-(3-((4-(cyclopentyloxy)pyrimidin-2-yl)amino)pyrrolidine-1-carbonyl)phenyl)acrylamide;
- (R)—N-(4-(3-((4-((1-methyl-1H-pyrazol-4-yl)oxy)pyrimidin-2-yl)amino)pyrrolidine-1-carbonyl)phenyl)acrylamide;
- (R)—N-(4-(3-((5-chloro-4-methoxypyrimidin-2-yl)amino)pyrrolidine-1-carbonyl)phenyl)acrylamide;
- (R)—N-(4-(3-((4-(thiazol-5-yl)pyrimidin-2-yl)amino)pyrrolidine-1-carbonyl)phenyl)acrylamide;
- (R)—N-(4-(3-((5-chloro-4-methylpyrimidin-2-yl)amino)pyrrolidine-1-carbonyl)phenyl)acrylamide;
- (R)—N-(4-(3-((5-chloropyrazin-2-yl)amino)pyrrolidine-1-carbonyl)phenyl)acrylamide;
- (R)—N-(4-(3-((5-chloro-4-methoxypyridin-2-yl)amino)pyrrolidine-1-carbonyl)phenyl)acrylamide;
- (R)—N-(4-(3-((5-chloro-4-methylpyridin-2-yl)amino)pyrrolidine-1-carbonyl)phenyl)acrylamide;
- (R)—N-(4-(3-((5-chloro-4-cyclopropoxypyrimidin-2-yl)amino)pyrrolidine-1-carbonyl)phenyl)acrylamide;
- (R)—N-(4-(3-((5-methylpyrimidin-2-yl)amino)pyrrolidine-1-carbonyl)phenyl)acrylamide;
- (R)—N-(4-(3-((5-cyclopropylpyrimidin-2-yl)amino)pyrrolidine-1-carbonyl)phenyl)acrylamide;
- (R)—N-(4-(3-((5-fluoro-4-methoxypyrimidin-2-yl)amino)pyrrolidine-1-carbonyl)phenyl)acrylamide;
- (R)—N-(4-(3-((5-(trifluoromethyl)pyrazin-2-yl)amino)pyrrolidine-1-carbonyl)phenyl)acrylamide;
- (R)—N-(4-(3-((5-methylpyrazin-2-yl)amino)pyrrolidine-1-carbonyl)phenyl)acrylamide;
- (R)—N-(4-(3-((5-chloro-4-(methylamino)pyrimidin-2-yl)amino)pyrrolidine-1-carbonyl)phenyl)acrylamide;
- (R)—N-(4-(3-((5-chloropyridin-2-yl)amino)pyrrolidine-1-carbonyl)phenyl)acrylamide;
- (R)—N-(2-chloro-4-(3-((5-chloro-4-methoxypyrimidin-2-yl)amino)pyrrolidine-1-carbonyl)phenyl)acrylamide;
- (R)—N-(4-(3-((5-chloro-4-methoxypyrimidin-2-yl)amino)pyrrolidine-1-carbonyl)-2-morpholinophenyl)acrylamide;
- (R)—N-(4-(3-((5-chloropyrimidin-2-yl)amino)pyrrolidine-1-carbonyl)-2-(1-methyl-1H-pyrazol-4-yl)phenyl)acrylamide;
- (R)—N-(4-(3-((5-cyanopyrimidin-2-yl)amino)pyrrolidine-1-carbonyl)phenyl)-N-methylacrylamide;
- (R)—N-(4-(3-((4-cyclopropoxy-5-fluoropyrimidin-2-yl)amino)pyrrolidine-1-carbonyl)phenyl)acrylamide;
- (R)—N-(2-chloro-4-(3-((5-chloropyrimidin-2-yl)amino)pyrrolidine-1-carbonyl)phenyl)acrylamide;
- (R)—N-(4-(3-((5-chloro-4-methoxypyrimidin-2-yl)amino)pyrrolidine-1-carbonyl)-2-(piperidin-1-yl)phenyl)acrylamide;
- (R)—N-(4-(3-((5-methylpyridin-2-yl)amino)pyrrolidine-1-carbonyl)phenyl)acrylamide;
- (R)—N-(4-(3-((5-bromopyrimidin-2-yl)amino)pyrrolidine-1-carbonyl)-2-methylphenyl)acrylamide;
- (R)—N-(4-(3-((5-chloro-4-methoxypyrimidin-2-yl)amino)pyrrolidine-1-carbonyl)-2-(4-methylpiperazin-1-yl)phenyl)acrylamide;
- (R)—N-(2-methyl-4-(3-((5-(trifluoromethyl)pyrimidin-2-yl)amino)pyrrolidine-1-carbonyl)phenyl)acrylamide;
- (R)—N-(4-(3-((5-chloro-4-methylpyrimidin-2-yl)amino)pyrrolidine-1-carbonyl)-2-methylphenyl)acrylamide;
- (R)—N-(4-(3-((4-cyclopropoxy-5-methylpyrimidin-2-yl)amino)pyrrolidine-1-carbonyl)phenyl)acrylamide;

(R)—N-(4-(3-((5-chloro-4-methoxypyrimidin-2-yl)amino)pyrrolidine-1-carbonyl)-2-(1-methyl-1H-pyrazol-4-yl)phenyl)acrylamide;
(R)—N-(4-(3-((5-chloropyrimidin-2-yl)amino)pyrrolidine-1-carbonyl)phenyl)-2-methylenebutanamide;
(R)—N-(4-(3-((5-chloropyrimidin-2-yl)amino)pyrrolidine-1-carbonyl)phenyl)ethenesulfonamide;
(R)—N-(4-(3-((5-cyclopropylpyridin-2-yl)amino)pyrrolidine-1-carbonyl)phenyl)acrylamide;
(R)—N-(4-(3-((5-chloro-4-(dimethylamino)pyrimidin-2-yl)amino)pyrrolidine-1-carbonyl)phenyl)acrylamide;
(R)—N-(4-(3-((5-chloropyrimidin-2-yl)amino)pyrrolidine-1-carbonyl)phenyl)acrylamide;
(R)—N-(4-(3-((5-chloro-4-(2-methoxyethoxy)pyrimidin-2-yl)amino)pyrrolidine-1-carbonyl)phenyl)acrylamide;
(R)—N-(4-(3-((4-(azetidin-1-yl)-5-chloropyrimidin-2-yl)amino)pyrrolidine-1-carbonyl)phenyl)acrylamide;
(R)—N-(4-(3-((4-amino-5-chloropyrimidin-2-yl)amino)pyrrolidine-1-carbonyl)phenyl)acrylamide;
(R)—N-(4-(3-((4-amino-5-(trifluoromethyl)pyrimidin-2-yl)amino)pyrrolidine-1-carbonyl)phenyl)acrylamide;
(R)—N-(4-(3-((5-chloro-4-(trifluoromethyl)pyrimidin-2-yl)amino)pyrrolidine-1-carbonyl)phenyl)acrylamide;
(R)—N-(4-(3-((5-chloro-4-(trideuteromethoxy)pyrimidin-2-yl)amino)pyrrolidine-1-carbonyl)phenyl)acrylamide;
(R)—N-(4-(3-((5-chloro-4-phenoxypyrimidin-2-yl)amino)pyrrolidine-1-carbonyl)phenyl)acrylamide;
(R)—N-(4-(3-((5-chloro-4-ethoxypyrimidin-2-yl)amino)pyrrolidine-1-carbonyl)phenyl)acrylamide;
(R)—N-(4-(3-((5-chloro-4-hydroxypyrimidin-2-yl)amino)pyrrolidine-1-carbonyl)phenyl)acrylamide;
(R,E)-N-(4-(3-((5-chloropyrimidin-2-yl)amino)pyrrolidine-1-carbonyl)phenyl)-4-(dimethylamino)but-2-enamide;
(R)—N-(4-(3-((5-cyclopropyl-4-methoxypyrimidin-2-yl)amino)pyrrolidine-1-carbonyl)phenyl)acrylamide;
(R)—N-(4-(3-((5-chloro-4-(2-cyanoethoxy)pyrimidin-2-yl)amino)pyrrolidine-1-carbonyl)phenyl)acrylamide;
(R)—N-(4-(3-((5-bromopyrimidin-2-yl)amino)pyrrolidine-1-carbonyl)phenyl)-N-methylacrylamide;
(R)—N-(3-(3-((5-chloro-4-methoxypyrimidin-2-yl)amino)pyrrolidine-1-carbonyl)phenyl)acrylamide;
(R)—N-(3-(3-((5-chloro-4-methoxypyrimidin-2-yl)amino)piperidine-1-carbonyl)phenyl)acrylamide;
(R)—N-(4-(3-((5-isobutylpyrimidin-2-yl)amino)pyrrolidine-1-carbonyl)phenyl)acrylamide;
(S)—N-(4-(3-((5-chloropyrimidin-2-yl)amino)-3-methylpyrrolidine-1-carbonyl)phenyl)acrylamide;
(R)—N-(4-(3-((5-cyanopyrimidin-2-yl)amino)pyrrolidine-1-carbonyl)-2-(2-(dimethylamino)ethoxy)phenyl)acrylamide;
(R)—N-(4-(3-((4-deutero-5-chloro-6-(methylamino)pyrimidin-2-yl)amino)pyrrolidine-1-carbonyl)phenyl)acrylamide;
(R)—N-(4-(3-((5-chloropyrimidin-2-yl)amino)pyrrolidine-1-carbonyl)-2-(2-(dimethylamino)ethoxy)phenyl)acrylamide;
(R)—N-(4-(3-((5-ethynylpyrimidin-2-yl)amino)pyrrolidine-1-carbonyl)phenyl)-N-methylacrylamide;
(R,E)-N-(4-(3-((5-chloro-4-(trideuteromethoxy)pyrimidin-2-yl)amino)pyrrolidine-1-carbonyl)phenyl)-4-(dimethylamino)but-2-enamide;
(R,E)-N-(4-(3-((5-chloro-4-methoxypyrimidin-2-yl)amino)pyrrolidine-1-carbonyl)phenyl)-4-(dimethylamino)but-2-enamide;
(R)-1-(3-(3-((5-chloropyrimidin-2-yl)amino)pyrrolidine-1-carbonyl)phenyl)-1H-pyrrole-2,5-dione;
(R,E)-N-(4-(3-((5-chloro-4-methoxypyrimidin-2-yl)amino)pyrrolidine-1-carbonyl)-2-methylphenyl)-4-(dimethylamino)but-2-enamide;
(R)—N-(4-(3-((4-(dimethylamino)-5-(trifluoromethyl)pyrimidin-2-yl)amino)pyrrolidine-1-carbonyl)phenyl)acrylamide;
(R)—N-(4-(3-((5-chloro-4-ethoxypyrimidin-2-yl)amino)pyrrolidine-1-carbonyl)-2-(4-methylpiperazin-1-yl)phenyl)acrylamide;
(R)—N-(4-(3-((4-(methylamino)-5-(trifluoromethyl)pyrimidin-2-yl)amino)pyrrolidine-1-carbonyl)phenyl)acrylamide;
(R,E)-N-(4-(3-((5-chloro-4-ethoxypyrimidin-2-yl)amino)pyrrolidine-1-carbonyl)benzyl)-4-(dimethylamino)but-2-enamide;
(R,E)-N-(4-(3-((5-chloropyrimidin-2-yl)amino)pyrrolidine-1-carbonyl)benzyl)-4-(dimethylamino)but-2-enamide;
(R)—N-(4-(3-((5-chloro-4-(2-ethoxyethoxy)pyrimidin-2-yl)amino)pyrrolidine-1-carbonyl)-2-(4-methylpiperazin-1-yl)phenyl)acrylamide;
(R)—N-(4-(3-((5-chloro-4-methoxypyrimidin-2-yl)amino)pyrrolidine-1-carbonyl)phenyl)propiolamide;
(R)—N-(4-(3-((5-chloropyrimidin-2-yl)amino)pyrrolidine-1-carbonyl)phenyl)propiolamide;
(R)-1-(4-(3-((5-chloro-4-(trideuteromethoxy)pyrimidin-2-yl)amino)pyrrolidine-1-carbonyl)phenyl)-1H-pyrrole-2,5-dione;
N-(4-((R)-3-((5-chloropyrimidin-2-yl)amino)pyrrolidine-1-carbonyl)-2-(3-(dimethylamino)pyrrolidin-1-yl)phenyl)acrylamide;
(R)-1-(3-(3-((5-chloro-4-(trideuteriomethoxy)pyrimidin-2-yl)amino)pyrrolidine-1-carbonyl)phenyl)-1H-pyrrole-2,5-dione;
(R,E)-N-(4-(3-((5-chloropyrimidin-2-yl)amino)pyrrolidine-1-carbonyl)phenyl)but-2-enamide;
(R)—N-(4-(3-((5-chloropyrimidin-2-yl)amino)pyrrolidine-1-carbonyl)phenyl)-2-cyanoacetamide;
(R)—N-(4-(3-((5-chloropyrimidin-2-yl)amino)pyrrolidine-1-carbonyl)phenyl)-2-cyano-3-(dimethylamino)acrylamide;
(R)—N-(3-(3-((5-chloropyrimidin-2-yl)amino)pyrrolidine-1-carbonyl)phenyl)-2-cyano-3-(dimethylamino)acrylamide;
(R)—N-(4-(3-((5-chloro-4-(2-hydroxyethoxy)pyrimidin-2-yl)amino)pyrrolidine-1-carbonyl)phenyl)acrylamide;
(R)—N-(4-(3-((4-deutero-5-chloro-6-(trideuteromethoxy)pyrimidin-2-yl)amino)pyrrolidine-1-carbonyl)phenyl)acrylamide;
(R)—N-(4-(3-((4-deutero-5-chloro-6-(dimethylamino)pyrimidin-2-yl)amino)pyrrolidine-1-carbonyl)phenyl)acrylamide;
(R)-1-(4-(3-((5-chloropyrimidin-2-yl)amino)pyrrolidine-1-carbonyl)phenyl)-1H-pyrrole-2,5-dione;
N-(4-((R)-3-((5-chloropyrimidin-2-yl)amino)pyrrolidine-1-carbonyl)phenyl)oxirane-2-carboxamide;
N-(4-((R)-3-((5-chloro-4-methoxypyrimidin-2-yl)amino)pyrrolidine-1-carbonyl)phenyl)oxirane-2-carboxamide;
(R)—N-(4-(3-((5-chloro-4-ethoxypyrimidin-2-yl)amino)pyrrolidine-1-carbonyl)-2-(2-(dimethylamino)ethoxy)phenyl)acrylamide;
(R,E)-N-(4-(3-((5-chloro-4-methoxypyrimidin-2-yl)amino)pyrrolidine-1-carbonyl)-2-fluorophenyl)-4-(dimethylamino)but-2-enamide;

(R)—N-(4-(3-((5-cyanopyridin-2-yl)amino)pyrrolidine-1-carbonyl)phenyl)acrylamide;

(R)—N-(4-(3-((5-cyanopyrimidin-2-yl)amino)pyrrolidine-1-carbonyl)phenyl)acrylamide;

(R)—N-(4-(3-((5-chloro-4-methoxypyrimidin-2-yl)amino)pyrrolidine-1-carbonyl)phenyl)but-2-ynamide;

(R)—N-(4-(3-((5-chloro-4-(2-ethoxyethoxy)pyrimidin-2-yl)amino)pyrrolidine-1-carbonyl)phenyl)acrylamide;

(R)—N-(4-(3-((5-chloro-4-(trideuteromethoxy)pyrimidin-2-yl)amino)pyrrolidine-1-carbonyl)phenyl)propiolamide;

(S)—N-(4-(3-((5-chloropyrimidin-2-yl)amino)pyrrolidine-1-carbonyl)phenyl)acrylamide;

(R)—N-(4-(3-((5-bromopyrimidin-2-yl)amino)pyrrolidine-1-carbonyl)-2-(2-(dimethylamino)ethoxy)phenyl)acrylamide;

(R)—N-(4-(3-((5-bromopyrimidin-2-yl)amino)pyrrolidine-1-carbonyl)-2-(4-(dimethylamino)piperidin-1-yl)phenyl)acrylamide;

(R)—N-(4-(3-((5-bromopyrimidin-2-yl)amino)pyrrolidine-1-carbonyl)-2-((2-(dimethylamino)ethyl)(methyl)amino)phenyl)acrylamide;

(R)—N-(4-(3-((5-cyano-4-methoxypyrimidin-2-yl)amino)pyrrolidine-1-carbonyl)phenyl)acrylamide;

(R)—N-(4-(3-((5-cyano-4-methoxypyrimidin-2-yl)amino)pyrrolidine-1-carbonyl)-2-(2-(dimethylamino)ethoxy)phenyl)acrylamide;

(R)—N-(4-(3-((5-cyanopyrimidin-2-yl)amino)pyrrolidine-1-carbonyl)-2-(2-(dimethylamino)ethoxy)phenyl)acrylamide;

(E)-N-(4-((R)-3-((5-chloro-4-methoxypyrimidin-2-yl)amino)pyrrolidine-1-carbonyl)phenyl)-4-((R)-3-fluoropyrrolidin-1-yl)but-2-enamide;

(R,E)-N-(4-(3-((5-chloro-4-methoxypyrimidin-2-yl)amino)pyrrolidine-1-carbonyl)phenyl)-4-morpholinobut-2-enamide;

(E)-N-(4-((R)-3-((5-chloro-4-methoxypyrimidin-2-yl)amino)pyrrolidine-1-carbonyl)phenyl)-4-((S)-3-fluoropyrrolidin-1-yl)but-2-enamide;

(R,E)-N-(4-(3-((5-chloro-4-methoxypyrimidin-2-yl)amino)pyrrolidine-1-carbonyl)phenyl)-4-(3,3-difluoropiperidin-1-yl)but-2-enamide;

(E)-N-(4-((R)-3-((5-chloro-4-methoxypyrimidin-2-yl)amino)pyrrolidine-1-carbonyl)phenyl)-4-((S)-3-fluoropiperidin-1-yl)but-2-enamide;

(E)-N-(4-((R)-3-((5-chloro-4-methoxypyrimidin-2-yl)amino)pyrrolidine-1-carbonyl)phenyl)-4-((R)-3-fluoropiperidin-1-yl)but-2-enamide;

N-(4-((2S,4R)-4-((5-chloro-4-methoxypyrimidin-2-yl)amino)-2-methylpyrrolidine-1-carbonyl)phenyl)acrylamide;

(R)—N-(4-(3-((5-ethynylpyrimidin-2-yl)amino)pyrrolidine-1-carbonyl)phenyl)acrylamide;

(R)—N-(4-(3-((5-ethynyl-4-methoxypyrimidin-2-yl)amino)pyrrolidine-1-carbonyl)phenyl)acrylamide;

N-(4-((2R,4R)-4-((5-chloro-4-methoxypyrimidin-2-yl)amino)-2-methylpyrrolidine-1-carbonyl)phenyl)acrylamide; and (R)—N-(4-(3-((5-(trifluoromethyl)pyrimidin-2-yl)amino)pyrrolidine-1-carbonyl)phenyl)acrylamide.

2. The compound of claim 1, or pharmaceutically acceptable salt or solvate thereof, wherein the compound is: (R)—N-(4-(3-((5-chloro-4-methoxypyrimidin-2-yl)amino)pyrrolidine-1-carbonyl)phenyl)-N-methylacrylamide.

3. The compound of claim 1, or pharmaceutically acceptable salt or solvate thereof, wherein the compound is: (R)—N-(4-(3-((5-chloro-4-methoxypyrimidin-2-yl)amino)pyrrolidine-1-carbonyl)phenyl)acrylamide.

4. The compound of claim 1, or pharmaceutically acceptable salt or solvate thereof, wherein the compound is: (R)—N-(4-(3-((5-chloropyrimidin-2-yl)amino)pyrrolidine-1-carbonyl)phenyl)acrylamide.

5. The compound of claim 1, or pharmaceutically acceptable salt or solvate thereof, wherein the compound is: (R)—N-(4-(3-((5-cyanopyrimidin-2-yl)amino)pyrrolidine-1-carbonyl)phenyl)acrylamide.

6. The compound of claim 1, or pharmaceutically acceptable salt or solvate thereof, wherein the compound is: (R)—N-(4-(3-((5-ethynylpyrimidin-2-yl)amino)pyrrolidine-1-carbonyl)phenyl)acrylamide.

7. The compound of claim 1, or pharmaceutically acceptable salt or solvate thereof, wherein the compound is: N-(4-((2R,4R)-4-((5-chloro-4-methoxypyrimidin-2-yl)amino)-2-methylpyrrolidine-1-carbonyl)phenyl)acrylamide.

8. The compound of claim 1, or pharmaceutically acceptable salt or solvate thereof, wherein the compound is: (R)—N-(4-(3-((5-chloro-4-(trideuteromethoxy)pyrimidin-2-yl)amino)pyrrolidine-1-carbonyl)phenyl)acrylamide.

9. The compound of claim 1, or pharmaceutically acceptable salt or solvate thereof, wherein the compound is: (R)—N-(4-(3-((5-bromo-4-methoxypyrimidin-2-yl)amino)pyrrolidine-1-carbonyl)phenyl)acrylamide.

10. A pharmaceutical composition comprising a compound of claim 1, or pharmaceutically acceptable salt or solvate thereof, and at least one pharmaceutically acceptable excipient.

11. The pharmaceutical composition of claim 10, wherein the compound is (R)—N-(4-(3-((5-chloro-4-methoxypyrimidin-2-yl)amino)pyrrolidine-1-carbonyl)phenyl)-N-methylacrylamide, or pharmaceutically acceptable salt or solvate thereof.

12. The pharmaceutical composition of claim 10, wherein the compound is (R)—N-(4-(3-((5-chloro-4-methoxypyrimidin-2-yl)amino)pyrrolidine-1-carbonyl)phenyl)acrylamide, or pharmaceutically acceptable salt or solvate thereof.

13. The pharmaceutical composition of claim 10, wherein the compound is (R)—N-(4-(3-((5-chloropyrimidin-2-yl)amino)pyrrolidine-1-carbonyl)phenyl)acrylamide, or pharmaceutically acceptable salt or solvate thereof.

14. The pharmaceutical composition of claim 10, wherein the compound is (R)—N-(4-(3-((5-cyanopyrimidin-2-yl)amino)pyrrolidine-1-carbonyl)phenyl)acrylamide, or pharmaceutically acceptable salt or solvate thereof.

15. The pharmaceutical composition of claim 10, wherein the compound is (R)—N-(4-(3-((5-ethynylpyrimidin-2-yl)amino)pyrrolidine-1-carbonyl)phenyl)acrylamide, or pharmaceutically acceptable salt or solvate thereof.

16. The pharmaceutical composition of claim 10, wherein the compound is N-(4-((2R,4R)-4-((5-chloro-4-methoxypyrimidin-2-yl)amino)-2-methylpyrrolidine-1-carbonyl)phenyl)acrylamide, or pharmaceutically acceptable salt or solvate thereof.

17. The pharmaceutical composition of claim 10, wherein the compound is (R)—N-(4-(3-((5-chloro-4-(trideuteromethoxy)pyrimidin-2-yl)amino)pyrrolidine-1-carbonyl)phenyl)acrylamide, or pharmaceutically acceptable salt or solvate thereof.

18. The pharmaceutical composition of claim 10, wherein the compound is (R)—N-(4-(3-((5-bromo-4-methoxypyrimidin-2-yl)amino)pyrrolidine-1-carbonyl)phenyl)acrylamide, or pharmaceutically acceptable salt or solvate thereof.

19. The pharmaceutical composition of claim 10, wherein the composition is suitable for oral administration.

20. The pharmaceutical composition of claim 10, wherein the composition is suitable for intravenous administration.

* * * * *